(12) United States Patent
Levin et al.

(10) Patent No.: US 7,420,001 B2
(45) Date of Patent: *Sep. 2, 2008

(54) BIARYL SULFONAMIDES AND METHODS FOR USING SAME

(75) Inventors: Jeremy Ian Levin, New City, NY (US); Thomas Saltmarsh Rush, III, Lexington, MA (US); Frank Lovering, Acton, MA (US); Yonghan Hu, Burlington, MA (US); Jianchang Li, Carlisle, MA (US); Wei Li, Acton, MA (US); Jun Jun Wu, Arlington, MA (US); Rajeev Hotchandani, Somerville, MA (US); Jason Shaoyun Xiang, Winchester, MA (US); Xuemei Du, Valley Cottage, NY (US); Derek Cecil Cole, New City, NY (US); Steve Yikkai Tam, Wellesley, MA (US)

(73) Assignee: Wyeth, Madison, NJ (US)

( * ) Notice: Subject to any disclaimer, the term of this patent is extended or adjusted under 35 U.S.C. 154(b) by 525 days.

This patent is subject to a terminal disclaimer.

(21) Appl. No.: 11/001,589

(22) Filed: Dec. 1, 2004

(65) Prior Publication Data
US 2005/0143422 A1    Jun. 30, 2005

Related U.S. Application Data

(60) Provisional application No. 60/526,840, filed on Dec. 4, 2003.

(51) Int. Cl.
*A61K 31/343* (2006.01)
*C07D 307/81* (2006.01)
(52) U.S. Cl. .................. 514/469; 514/470; 549/466; 549/467
(58) Field of Classification Search ................. 549/466, 549/467; 514/469, 470
See application file for complete search history.

(56) References Cited

U.S. PATENT DOCUMENTS 7,268,135 B2 *  9/2007  Xiang et al. ............... 514/247

FOREIGN PATENT DOCUMENTS

| EP | 0 950 656 A1 | 10/1999 |
|---|---|---|
| WO | 00/51993 A2 | 9/2000 |
| WO | 00/51993 A3 | 9/2000 |
| WO | 01/27084 A1 | 4/2001 |

OTHER PUBLICATIONS

U.S. Appl. No. 11/000,711, filed Dec. 1, 2004, Xiang et al.
Tamura, Y. et al., "Highly Selective and Orally Active Inhibitors of Type IV Collagenase (MMP-9 and MMP-2): N-Sulfonylamino Acid Derivatives," *J Med Chem*, 1998, 41:640-649.
Tang, B. L., "ADAMTS: a novel family of extracellular matrix proteases,", *Int J Biochem Cell Biol*, 2001, 33:33-44.
Abbaszade I. et al., "Cloning and Characterization of ADAMTS11, an Aggrecanase from the ADAMTS family," *J Biol Chem*, Aug. 13, 1999, 274(33): 23443-23450.
Colige, A. et al., "cDNA cloning and expression of bovine procollagen I N-proteinase: A new member of the superfamily of zinc-metalloproteinases with binding sites for cells and other matrix components," *Proc Natl Acad Sci USA*, Mar. 1997, 94, 2374-2379.
Vázquez F. et al., "METH-1, a Human Orgholog of ADAMTS-1, and METH-2 Are Members of a New Family of Proteins with Angio-inhibitory Activity," *J Biol Chem*, Aug. 13, 1999, 274(33): 23349-23357.
Masui T., et al., "An Alu-linked Repetitive Sequence Corresponding to 280 Amino Acids Is Expressed in a Novel Bovine Protein, but Not in Its Human Homologue," *J Biol Chem*, Jan. 31, 1997, 272(5), 2801-2807.
Kuno, K. et al., "Molecular Cloning of a Gene Encoding a New Type of Metalloproteinase-disintegrin Family Protein with Thrombospondin Motifs as an Inflammation Associated Gene," *J Biol Chem*, Jan. 3, 1997, 272(1), 556-562.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).
Widder, et al. (ed.), *Methods in Enzymology*, vol. 112, Academic Press (1985), pp. 309-396.
Krogsgaard-Larsen, et al., (ed). *Design and Application of Prodrugs, Textbook of Drug Design and Development*, Chapter 5, 113-191, 1991.
Bundgaard, H., "Means to enhance penetration; Prodrugs as a means to improve the delivery of peptide drugs," *Advanced Drug Deliver Reviews*, 1992, 8, 1-38.
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4):285-298.
Higuchi and Stella (eds.), *Prodrugs as Novel Drug Delivery Systems*, American Chemical Society (1975), pp. 1-115 and 196-223.
Laemmli, U. K., "Cleavage of Structural Proteins during the Assembly of the Head of Bacteriophage T4," *Nature*, Aug. 15, 1970, 227:680-685.
Oaklet, B. R. et al., "A Simplified Ultrasensitive Silver Stain for Detecting Proteins in Polyacrylamide Gels," *Anal. Biochem*, 1980, 105:361-363.
Towbin, H. et al., "Electrophoretic transfer of proteins from polyacrylamide gels to nitrocellulose sheets: Procedure and some applications," *Proc. Natl. Acad. Sci. USA*, Sep. 1979, 76(9), 4350-4354.
Hughes, C. E. et al., "Monoclonal antibodies that specifically recognize neoepitope sequences generated by 'aggrecanase' and matrix metalloproteinase cleavage of aggrecan: application to catabolism in situ and in vitro, " *Biochem J*, Feb. 1, 1995, 305(3), 799-804.
Romero, D. L. et al, "Discovery, Synthesis, and Bioactivity of Bis(heteroaryl)piperazines. 1. A Novel Class of Non-Nucleoside HIV-1 Reverse Transcriptase Inhibitors," *J. Med. Chem.* 1994, 37, 999-1014.
Emmott, P. et al., "Preparation of Some Naphthofurans," *J. Chem. Soc.* (Jul. 1957) pp. 3144-3148.

(Continued)

*Primary Examiner*—Patricia L Morris
(74) *Attorney, Agent, or Firm*—Woodcock Washburn LLP

(57) ABSTRACT

The present invention relates to biaryl sulfonamides and their use as, for example, metalloproteinase inhibitors.

16 Claims, No Drawings

OTHER PUBLICATIONS

Evans, D. A. et al., "Synthesis of Diaryl Ethers through the Copper-Promoted Arylation of Phenols with Arylboronic Acids. An Expedient Synthesis of Thyroxine," *Tetrahedron Lett.*, May 7, 1998, 39(19):2937-2940.

Bencze, W. L. et. al., "The Absolute Configuration of a Hypolipidemic 1-Aryl Tetralin, Nafenopin," *Tetrahedron* 1970, 26:5407-5414.

Werner, A. W. et al., "Porphyrins with Four Azole Substituents in meso Positions: X-Ray Crystal Structure of Meso-tetrakis-(1-benzylpyrazol-4-yl)-porphyrin at 200 K," *Tetrahedron*, Apr. 17, 1995, 51(16): 4779-4800.

Burtner, R.R. et al., "Antispasmodics. I. Basic Esters of Some Arylacetic Acids," *J. Am. Chem. Soc.*, 1943, 65:262-267.

Abramov, M. A. et al., "Nucleophilic Intramolecular Cyclization Reactions of Alkylnechalcogenolates," *Tetrahedron*, Jun. 9, 2000, 56(24): 3933-3940.

Knight, C.G. et al., "A novel coumarin-labelled peptide for sensitive continuous assays of the matrix metalloproteinases," *FEBS Lett.* (Jan. 1992) 296(3):263-266.

*Remington's Pharmaceutical Sciences*, 17th Ed.; Gennaro, A. R. (Ed.), Mack Publishing Company, Easton, PA (1985) pp. 1409-1677.

* cited by examiner

BIARYL SULFONAMIDES AND METHODS FOR USING SAME

CROSS REFERENCE TO RELATED APPLICATIONS

This application claims benefit to U.S. Provisional Application No. 60/526,840, filed Dec. 4, 2003, the entirety of which is incorporated by reference herein.

FIELD OF THE INVENTION

The present invention relates to biaryl sulfonamides and their use as, for example, metalloproteinase inhibitors.

BACKGROUND OF THE INVENTION

Metalloproteinases, including matrix metalloproteinases and aggrecanases, are known to have a role in the breakdown of connective tissue. Matrix metalloproteinases ("MMPs") constitute a superfamily of proteolytic enzymes that are genetically related and capable of degrading almost all the constituents of extracellular matrix and basement membrane that restrict cell movement. Aggrecanases, members of the ADAMTS (A disintegrin and metalloproteinase with thrombospondin motifs) family of proteins, cleave aggrecan, a cartilage component also known as the large aggregating chondroitin sulphate proteoglycan.

MMPs and aggrecanases can degrade various components of connective tissue, including collagen and proteoglycan. In the absence of natural checks on this activity, a variety of pathologies and undesirable effects can occur. In fact, MMPs and aggrecanases are known to play a role in many disorders in which extracellular protein degradation/destruction occurs, such as cancer, osteoarthritis, rheumatoid arthritis, asthma, chronic obstructive pulmonary disease ("COPD"), atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases.

Therefore, metalloproteinase inhibitors are needed, including inhibitors of MMPs and aggrecanases. Additionally, selective inhibitors directed to specific MMPs and aggrecanases are valuable to avoid potential side effects.

SUMMARY OF THE INVENTION

In one embodiment, the present invention provides novel biaryl sulfonamide compounds. Preferred compounds of the invention are those of the formula 1:

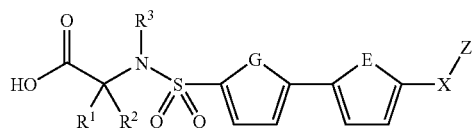

wherein:
$R^1$ and $R^2$ are, independently, H, $CH(OH)R^4$, phenyl, heteroaryl, or C1-C6 alkyl, with the proviso that when $R^1$ or $R^2$ is $CH(OH)R^4$, then Z is substituted with $NR^4SO_2R^5$, $SO_2NR^4R^5$, heterocycloalkyl, heteroaryl, or C3-C6 cycloalkyl;
$R^3$ is H or C1-C6 alkyl;
$R^4$ and $R^5$ are, independently with respect to each occurrence, a bond to the other, H, C1-C6 alkyl, or phenyl;
G and E are, independently, S, O, $N(R^4)$, $C(R^6)=C(R^6)$, or $N=C(R^6)$;
$R^6$ is, independently with respect to each occurrence, H, halogen, $NR^4R^5$, $N[(CH_2)_2]_2O$, $N[(CH_2)_2]_2NR^4$, $NR^4SO_2R^5$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, CN, phenyl, heteroaryl, C1-C6 alkyl, C2-C6 alkenyl, or C2-C6 alkynyl;
X is $N(R^3)C(=O)$, $OC(=O)$, $OS(O)_2$, NHSO2, $OCH_2$, $CH_2S(O)$, or $CH_2S(O)_2$; and
Z is at least one heteroaryl moiety.

In another aspect, the present invention provides methods for using biaryl sulfonamide compounds to modulate and, preferably, inhibit metalloproteinases. Preferred methods involve in vitro and in vivo contacting of the metalloproteinase with a biaryl sulfonamide. Preferred methods of this type are ones in which the activity of the metalloproteinase is determined before or after such contacting and, optionally, the determination is used to assess the extent to which the compound modulates the activity of the enzyme.

DETAILED DESCRIPTION OF THE INVENTION

In accordance with the present invention it has been discovered that biaryl sulfonamide compounds of the present invention are useful in inhibiting metalloproteinases. Moreover, some compounds so great specifity for certain metalloproteinases. Such compounds can be useful in the treatment of cancer, osteoarthritis, rheumatoid arthritis, asthma, COPD, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and periodontal diseases. The metalloproteinase is preferably, Gelatinase A (MMP-2), Macrophage metalloelastase (MMP-12), Collagenase-3 (MMP-13), or Aggrecanase-1 (ADAMTS4). More preferably, the metalloproteinase is MMP-13.

Preferred compounds of the invention are those of the formula 1:

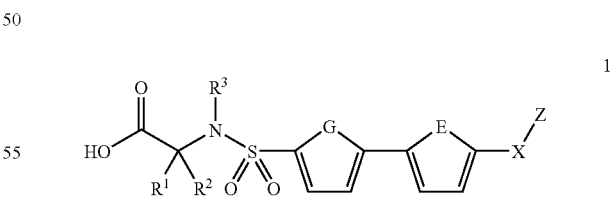

wherein:
$R^1$ and $R^2$ are, independently, H, $CH(OH)R^4$, phenyl, heteroaryl, or C1-C6 alkyl, with the proviso that when $R^1$ or $R^2$ is $CH(OH)R^4$, then Z is substituted with $NR^4SO_2R^5$, $SO_2NR^4R^5$, heterocycloalkyl, heteroaryl, or C3-C6 cycloalkyl;
$R^3$ is H or C1-C6 alkyl;
$R^4$ and $R^5$ are, independently with respect to each occurrence, a bond to the other, H, C1-C6 alkyl, or phenyl;

G and E are, independently, S, O, N($R^4$), C($R^6$)=C($R^6$), or N=C($R^6$);

$R^6$ is, independently with respect to each occurrence, H, halogen, $NR^4R^5$, N[$(CH_2)_2$]$_2$O, N[$(CH_2)_2$]$_2NR^4$, $NR^4SO_2R^5$, $NR^4C(=O)R^5$, NHC(=O)$OR^4$, $NO_2$, $SO_2NR^4R^5$, $SO_2R^4$, $OR^4$, C(=O)$R^4$, $COOR^4$, $CONR^4R^5$, CN, phenyl, heteroaryl, C1-C6 alkyl, C2-C6 alkenyl, or C2-C6 alkynyl;

X is N($R^3$)C(=O), OC(=O), OS(O)$_2$, NHSO$_2$, OCH$_2$, CH$_2$S(O), or CH$_2$S(O)$_2$; and Z is at least one heteroaryl moiety.

When other than H, $R^1$ may be optionally substituted with halogen, $CO_2R^4$, C(=O)$NR^4R^5$, phenyl, or heteroaryl.

When other than H, $R^3$ may be optionally substituted with $NR^4R^5$, N[$(CH_2)_2$]$_2$O, N[$(CH_2)_2$]$_2NR^4$, $NR^4SO_2R^5$, $NR^4C(=O)R^5$, NHC(=O)$OR^4$, $NO_2$, $SO_2NR^4R^5$, $SO_2R^4$, $OR^4$, C(=O)$R^4$, $COOR^4$, $CONR^4R^5$, CN, cycloalkyl, heterocycloalkyl, phenyl, or heteroaryl.

In one embodiment, $R^6$ is each optionally substituted with $NR^4R^5$, N[$(CH_2)_2$]$_2$O, N[$(CH_2)_2$]$_2NR^4$, $NR^4SO_2R^5$, $NR^4C(=O)R^5$, $NR^4C(=O)OR^4$, $NO_2$, $SO_2NR^4R^5$, $SO_2R^4$, $OR^4$, C(=O)$R^4$, $COOR^4$, $CONR^4R^5$, CN, phenyl, or heteroaryl.

In one embodiment, Z is a 5 membered ring. In another embodiment, Z is bicyclic. In yet another embodiment, Z is furan, thiophene, pyrrole, pyrazole, imidazole, oxazole, isoxazole, isothiazole, thiazole, 1,2,5-thiadiazole, 1,2,3-triazole, 1,3,4-thiadiazole, 1,2,3-thiadiazole, 1,2,4-thiadiazole, 1,2,4-triazole, 1,2,4-oxadiazole, 1,3,4-oxadiazole, and furazan, or

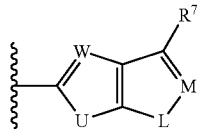

wherein:

U is selected from S, O, and N($R^4$);
W is selected from C($R^6$) and N;
M is selected from C($R^6$), and N;
L is selected from C($R^6$)=C($R^6$), C($R^6$)=N, and N($R^4$);
$R^7$ is selected from a bond to $R^6$, H, halogen, $NR^4R^5$, N[$(CH_2)_2$]$_2$O, N[$(CH_2)_2$]$_2NR^4$, $NHSO_2R^4$, $NR^4C(=O)R^5$, NHC(=O)$OR^4$, $NO_2$, $SO_2NR^4R^5$, $SO_2R^4$, $OR^4$, C(=O)$R^4$, $COOR^4$, $CONR^4R^5$, CN, phenyl, heteroaryl, and C1-C6 alkyl, C2-C6 alkenyl, and C2-C6 alkynyl, each optionally substituted with $NR^4R^5$, N[$(CH_2)_2$]$_2$O, N[$(CH_2)_2$]$_2NR^4$, $NHSO_2R^4$, $NR^4C(=O)R^5$, NHC(=O)$OR^4$, $NO_2$, $SO_2NR^4R^5$, $SO_2R^4$, $OR^8$, C(=O)$R^4$, $COOR^4$, $CONR^4R^5$, CN, cycloalkyl, heterocycloalkyl, phenyl, or heteroaryl; and $R^8$ is selected from H, phenyl, heteroaryl, and C1-C6 alkyl, optionally substituted with $NR^4R^5$, N[$(CH_2)_2$]$_2$O, N[$(CH_2)_2$]$_2$ $NR^4$, $NR^4SO_2R^5$, $NR^4C(=O)R^5$, NHC(=O)$OR^4$, $NO_2$, $SO_2NR^4R^5$, $SO_2R^4$, C(=O)$R^4$, $COOR^4$, $CONR^4R^5$, CN, cycloalkyl, heterocycloalkyl, phenyl, or heteroaryl.

Preferably, Z is:

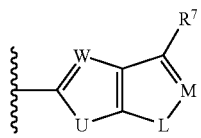

wherein:

U is selected from S, O, and N($R^4$);
W is selected from C($R^6$), and N;
M is selected from C($R^6$), and N;
L is selected from C($R^6$)=C($R^6$), C($R^6$)=N, and N($R^4$);
$R^7$ is selected from a bond to $R^6$, H, halogen, $NR^4R^5$, N[$(CH_2)_2$]$_2$O, N[$(CH_2)_2$]$_2NR^4$, $NHSO_2R^4$, $NR^4C(=O)R^5$, NHC(=O)$OR^4$, $NO_2$, $SO_2NR^4R^5$, $SO_2R^4$, $OR^4$, C(=O)$R^4$, $COOR^4$, $CONR^4R^5$, CN, phenyl, heteroaryl, and C1-C6 alkyl, C2-C6 alkenyl, and C2-C6 alkynyl, each optionally substituted with $NR^4R^5$, N[$(CH_2)_2$]$_2$O, N[$(CH_2)_2$]$_2NR^4$, $NHSO_2R^4$, $NR^4C(=O)R^5$, NHC(=O)$OR^4$, $NO_2$, $SO_2NR^4R^5$, $SO_2R^4$, $OR^8$, C(=O)$R^4$, $COOR^4$, $CONR^4R^5$, CN, cycloalkyl, heterocycloalkyl, phenyl, or heteroaryl; and $R^8$ is selected from H, phenyl, heteroaryl, and C1-C6 alkyl, optionally substituted with $NR^4R^5$, N[$(CH_2)_2$]$_2$O, N[$(CH_2)_2$]$_2$ $NR^4$, $NR^4SO_2R^5$, $NR^4C(=O)R^5$, NHC(=O)$OR^4$, $NO_2$, $SO_2NR^4R^5$, $SO_2R^4$, C(=O)$R^4$, $COOR^4$, $CONR^4R^5$, CN, cycloalkyl, heterocycloalkyl, phenyl, or heteroaryl.

In another embodiment:

$R^3$ is H;
G is C(H)=C(H);
E is C(H)=C(H) or N=C(H);
X is NHC(=O), or OCH$_2$; and

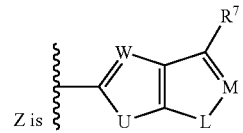

wherein:

U is selected from S, O, and N($R^4$);
W is selected from C($R^6$) and N;
M is selected from C($R^6$), and N;
L is selected from C($R^6$)=C($R^6$), C($R^6$)=N, and N($R^4$);
$R^7$ is selected from a bond to $R^6$, H, halogen, $NR^4R^5$, N[$(CH_2)_2$]$_2$O, N[$(CH_2)_2$]$_2NR^4$, $NHSO_2R^4$, $NR^4C(=O)R^5$, NHC(=O)$OR^4$, $NO_2$, $SO_2NR^4R^5$, $SO_2R^4$, $OR^4$, C(=O)$R^4$, $COOR^4$, $CONR^4R^5$, CN, phenyl, heteroaryl, and C1-C6 alkyl, C2-C6 alkenyl, and C2-C6 alkynyl, each optionally substituted with $NR^4R^5$, N[$(CH_2)_2$]$_2$O, N[$(CH_2)_2$]$_2NR^4$, $NHSO_2R^4$, $NR^4C(=O)R^5$, NHC(=O)$OR^4$, $NO_2$, $SO_2NR^4R^5$, $SO_2R^4$, $OR^8$, C(=O)$R^4$, $COOR^4$, $CONR^4R^5$, CN cycloalkyl, heterocycloalkyl, phenyl, or heteroaryl; and $R^8$ is selected from H, phenyl, heteroaryl, and C1-C6 alkyl, optionally substituted with $NR^4R^5$, N[$(CH_2)_2$]$_2$O, N[$(CH_2)_2$]$_2$ $NR^4$, $NR^4SO_2R^5$, $NR^4C(=O)R^5$, NHC(=O)$OR^4$, $NO_2$, $SO_2NR^4R^5$, $SO_2R^4$, C(=O)$R^4$, $COOR^4$, $CONR^4R^5$, CN, cycloalkyl, heterocycloalkyl, phenyl, or heteroaryl.

Preferably:

E is C(H)=C(H);
U is O;
W is C(H), or C(CH$_3$);
M is C($R^9$), wherein $R^9$ is H, halogen, C1-C6 alkyl, or CN; and
L is C(H)=C(H).

Preferred among the above noted $R^1$ and $R^2$ groups are C1-C6 alkyl, including embodiments wherein at least one of $R^1$ or $R^2$ is C1-C6 alkyl.

Preferred among the above noted $R^3$ groups is H.

Preferred among the above noted $R^4$ and $R^5$ groups are C1-C6 alkyl.

Preferred among the above noted G and E groups are C(H)=C(H).

Preferred among the above noted U groups are O and S.

Preferred among the above noted W groups are C(H) and C(CH$_3$).

Preferred among the above noted M groups are CR$^6$.

Preferred among the above noted L groups are CH=CH.

Preferred among the above noted R$^7$ groups are those other than H.

The following compounds are preferred:

N-({4'-[(1-benzofuran-2-ylcarbonyl)amino]-1,1'-biphenyl-4-yl}sulfonyl)glycine;

L-2-{4'-[(Benzofuran-2-carbonyl)-amino]-biphenyl-4-sulfonylamino}-3-methyl-butyric acid;

N-({4'-[(1H-indol-2-ylcarbonyl)amino]-1,1'-biphenyl-4-yl}sulfonyl)glycine;

(4'-{[(5-chloro-1-benzofuran-2-yl)carbonyl]amino}-1,1'-biphenyl-4-yl)sulfonyl]-L-valine;

N-[(4'-{[(7-methoxy-1-benzofuran-2-yl)carbonyl]amino}-1,1'-biphenyl-4-yl)sulfonyl]-L-valine;

N-[(4'-{[(5-nitro-1-benzofuran-2-yl)carbonyl]amino}-1,1'-biphenyl-4-yl)sulfonyl]-L-valine;

N-[(4'-{[(5-amino-1-benzofuran-2-yl)carbonyl]amino}-1,1'-biphenyl-4-yl)sulfonyl]-L-valine;

N-({4'-[({5-[(methylsulfonyl)amino]-1-benzofuran-2-yl}carbonyl)amino]-1,1'-biphenyl-4-yl}sulfonyl)-L-valine;

N-{[4'-({[5-(acetylamino)-1-benzofuran-2-yl]carbonyl}amino)-1,1'-biphenyl-4-yl]sulfonyl}-L-valine;

4'-[(5-Benzenesulfonylamino-benzofuran-2-carbonyl)-amino]-biphenyl-4-sulfonyl-L-valine;

N-[(4'-{[(4-methoxy-1-benzofuran-2-yl)carbonyl]amino}-1,1'-biphenyl-4-yl)sulfonyl]-L-valine;

4'-[(Benzo[β]thiophene-2-carbonyl)-amino]-biphenyl-4-sulfonyl-L-valine;

4'-[(4-Benzyloxy-benzofuran-2-carbonyl)-amino]-biphenyl-4-sulfonyl-L-valine;

4'-{[4-(1-Carboxy-ethoxy)-benzofuran-2-carbonyl]-amino}-biphenyl-4-sulfonyl-L-valine;

N-({4'-[(1-Benzofuran-2-ylcarbonyl)amino]-1,1'-biphenyl-4-yl}sulfonyl)-L-Asparagine;

L-2-{4'-[(Benzofuran-2-carbonyl)-amino]-biphenyl-4-sulfonylamino}-3-methyl-butyric acid;

N-({4'-[(1-Benzofuran-2-ylcarbonyl)amino]-1,1'-biphenyl-4-yl}sulfonyl)-L-Histidine;

N-({4'-[(1-Benzofuran-2-ylcarbonyl)amino]-1,1'-biphenyl-4-yl}sulfonyl)-L-leucine;

L-2-{4'-[(Benzofuran-2-carbonyl)-amino]-biphenyl-4-sulfonylamino}-3-methyl-butyric acid;

L-2-{4'-[(4-Cyano-3-methyl-benzofuran-2-carbonyl)-amino]-biphenyl-4-sulfonylamino}-3-methyl-butyric acid;

L-3-Methyl-2-{4'-[(3-methyl-4-prop-1-ynyl-benzofuran-2-carbonyl)-amino]-biphenyl-4-sulfonylamino}-butyric acid;

L-2-(4'-{[4-(3-Methoxy-prop-1-ynyl)-3-methyl-benzofuran-2-carbonyl]-amino}-biphenyl-4-sulfonylamino)-3-methyl-butyric acid;

2-{4'-[(4-Cyclopropylethynyl-3-methyl-benzofuran-2-carbonyl)-amino]-biphenyl-4-sulfonylamino}-3-methyl-butyric acid;

L-2-(4'-{[4-(2-Cyclopropyl-ethyl)-3-methyl-benzofuran-2-carbonyl]-amino}-biphenyl-4-sulfonylamino)-3-methyl-butyric acid;

L-2-(4'-{[4-(3-Methoxy-Z-propenyl)-3-methyl-benzofuran-2-carbonyl]-amino}-biphenyl-4-sulfonylamino)-3-methyl-butyric acid;

L-2-(4'-{[4-(3-Hydroxy-prop-1-ynyl)-3-methyl-benzofuran-2-carbonyl]-amino}-biphenyl-4-sulfonylamino)-3-methyl-butyric acid;

L-2-(4'-{[4-(3-Hydroxy-propyl)-3-methyl-benzofuran-2-carbonyl]-amino}-biphenyl-4-sulfonylamino)-3-methyl-butyric acid;

L-3-Methyl-2-(4'-{[3-methyl-4-(4-methyl-pent-1-ynyl)-benzofuran-2-carbonyl]-amino}-biphenyl-4-sulfonylamino)-butyric acid;

L-3-Methyl-2-(4'-{[3-methyl-4-(4-methyl-pentyl)-benzofuran-2-carbonyl]-amino}-biphenyl-4-sulfonylamino)-butyric acid;

L-2-(4'-{[4-(3-Methoxy-propyl)-3-methyl-benzofuran-2-carbonyl]-amino}-biphenyl-4-sulfonylamino)-3-methyl-butyric acid;

L-2-(4'-{[4-(3-Dimethylamino-prop-1-ynyl)-3-methyl-benzofuran-2-carbonyl]-amino}-biphenyl-4-sulfonylamino)-3-methyl-butyric acid;

L-2-(4'-{[4-(3-Dimethylamino-propyl)-3-methyl-benzofuran-2-carbonyl]-amino}-biphenyl-4-sulfonylamino)-3-methyl-butyric acid;

L-2-{4'-[(4-Ethynyl-3-methyl-benzofuran-2-carbonyl)-amino]-biphenyl-4-sulfonylamino}-3-methyl-butyric acid;

L-2-(4'-{[4-(3,3-Dimethyl-but-1-ynyl)-3-methyl-benzofuran-2-carbonyl]-amino}-biphenyl-4-sulfonylamino)-3-methyl-butyric acid;

L-3-Methyl-2-(4'-{[3-methyl-4-(3-methyl-isoxazol-5-yl)-benzofuran-2-carbonyl]-amino}-biphenyl-4-sulfonylamino)-butyric acid;

L-2-{4'-[(4-Methanesulfonylamino-3-methyl-benzofuran-2-carbonyl)-amino]-biphenyl-4-sulfonylamino}-3-methyl-butyric acid;

L-2-(4'-{[4-(Methanesulfonyl-methyl-amino)-3-methyl-benzofuran-2-carbonyl]-amino}-biphenyl-4-sulfonylamino)-3-methyl-butyric acid;

L-3-Hydroxy-2-(4-{5-[(4-methanesulfonylamino-3-methyl-benzofuran-2-carbonyl)-amino]-pyridin-2-yl}-benzenesulfonylamino)-butyric acid;

L-2-(4-{5-[(4-Methanesulfonylamino-3-methyl-benzofuran-2-carbonyl)-amino]-pyridin-2-yl}-benzenesulfonylamino)-3-methyl-butyric acid;

L-2-(4-{5-[(4-Cyano-3-methyl-benzofuran-2-carbonyl)-amino]-pyridin-2-yl}-benzenesulfonylamino)-3-methyl-butyric acid;

D-2-{4'-[(4-Methanesulfonylamino-3-methyl-benzofuran-2-carbonyl)-amino]-biphenyl-4-sulfonylamino}-3-methyl-butyric acid;

L-2-({4'-[(4-Cyano-3-methyl-benzofuran-2-carbonyl)-amino]-biphenyl-4-sulfonyl}-methyl-amino)-3-methyl-butyric acid;

(L-3-Methyl-2-{4'-[(3-methyl-4-methylcarbamoyl-benzofuran-2-carbonyl)-amino]-biphenyl-4-sulfonylamino}-butyric acid triethylamine salt;

2-{4'-[(4-Dimethylcarbamoyl-3-methyl-benzofuran-2-carbonyl)-amino]-biphenyl-4-sulfonylamino}-3-methyl-butyric acid triethylamine salt L-2-{4'-[(4,6-Dimethoxy-3,7-dimethyl-benzofuran-2-carbonyl)-amino]-biphenyl-4-sulfonylamino}-3-methyl-butyric acid;

2-{4'-[(5-Bromo-3-methyl-benzofuran-2-carbonyl)-amino]-biphenyl-4-sulfonylamino}-3-methyl-butyric acid;

L-2-{4'-[(4-Carbamoyl-3-methyl-benzofuran-2-carbonyl)-amino]-biphenyl-4-sulfonylamino}-3-methyl-butyric acid;

L-2-(4'-{[4-(Cyclopropanecarbonyl-amino)-3-methyl-benzofuran-2-carbonyl]-amino}-biphenyl-4-sulfonylamino)-3-methyl-butyric acid;

L-2-{4'-[(4-Acetylamino-3-methyl-benzofuran-2-carbonyl)-amino]-biphenyl-4-sulfonylamino}-3-methyl-butyric acid;

L-3-Methyl-2-{4'-[(3-methyl-4-propionylamino-benzofuran-2-carbonyl)-amino]-biphenyl-4-sulfonylamino}-butyric acid;

L-2-{4'-[(4-Isobutyrylamino-3-methyl-benzofuran-2-carbonyl)-amino]-biphenyl-4-sulfonylamino}-3-methyl-butyric acid;

L-2-{4'-[(4-Cyclopropylmethoxy-3-methyl-benzofuran-2-carbonyl)-amino]-biphenyl-4-sulfonylamino}-3-methyl-butyric acid;

L-2-{4'-[(1H-Benzoimidazole-2-carbonyl)-amino]-biphenyl-4-sulfonylamino}-3-methyl-butyric acid;

L-2-{4'-[(4-sec-Butoxy-3-methyl-benzofuran-2-carbonyl)-amino]-biphenyl-4-sulfonylamino}-3-methyl-butyric acid;

L-3-Methyl-2-{4,-[(3-phenyl-benzofuran-2-carbonyl)-amino]-biphenyl-4-sulfonylamino}-butyric acid;

L-2-(4'-{[4-(Acetyl-methyl-amino)-3-methyl-benzofuran-2-carbonyl]-amino}-biphenyl-4-sulfonylamino)-3-methyl-butyric acid;

L-3-Methyl-2-(4'-{[3-methyl-4-(2H-tetrazol-5-yl)-benzofuran-2-carbonyl]-amino}-biphenyl-4-sulfonylamino)-butyric acid;

L-2-(4'-{[4-(3,3-Dimethyl-butyl)-3-methyl-benzofuran-2-carbonyl]-amino}-biphenyl-4-sulfonylamino)-3-methyl-butyric acid;

L-2-{4'-[(3-Ethyl-benzofuran-2-carbonyl)-amino]-biphenyl-4-sulfonylamino}-3-methyl-butyric acid;

L-2-{4'-[(4-tert-Butoxycarbonylamino-3-methyl-benzofuran-2-carbonyl)-amino]-biphenyl-4-sulfonylamino}-3-methyl-butyric acid;

L-3-Methyl-2-{4'-[(3-methyl-4-methylamino-benzofuran-2-carbonyl)-amino]-biphenyl-4-sulfonylamino}-butyric acid;

L-2-{4'-[(4-Amino-3-methyl-benzofuran-2-carbonyl)-amino]-biphenyl-4-sulfonylamino}-3-methyl-butyric acid;

L-2-{4'-[(4-Dimethylamino-3-methyl-benzofuran-2-carbonyl)-amino]-biphenyl-4-sulfonylamino}-3-methyl-butyric acid;

L-3-Methyl-2-{4'-[(3-methyl-4-pyrrolidin-1-yl-benzofuran-2-carbonyl)-amino]-biphenyl-4-sulfonylamino}-butyric acid;

L-2-({4'-[(4-Methanesulfonylamino-3-methyl-benzofuran-2-carbonyl)-amino]-biphenyl-4-sulfonyl}-methyl-amino)-3-methyl-butyric acid;

L-3-Hydroxy-2-{4'-[(4-methanesulfonylamino-3-methyl-benzofuran-2-carbonyl)-amino]-biphenyl-4-sulfonylamino}-butyric acid;

(S)-3-Methyl-2-(4'-{[4-methyl-2-(4-trifluoromethyl-phenyl)-thiazole-5-carbonyl]-amino}-biphenyl-4-sulfonylamino)-butyric acid;

L-3-Methyl-2-(4'-{[3-methyl-4-(2,2,2-trifluoro-acetylamino)-benzofuran-2-carbonyl]-amino}-biphenyl-4-sulfonylamino)-butyric acid;

L-2-{4'-[(4-Ethanesulfonylamino-3-methyl-benzofuran-2-carbonyl)-amino]-biphenyl-4-sulfonylamino}-3-methyl-butyric acid;

L-3-Methyl-2-(4'-{[3-methyl-4-(propane-2-sulfonylamino)-benzofuran-2-carbonyl]-amino}-biphenyl-4-sulfonylamino)-butyric acid;

L-2-(4'-{[4-(Ethanesulfonyl-methyl-amino)-3-methyl-benzofuran-2-carbonyl]-amino}-biphenyl-4-sulfonylamino)-3-methyl-butyric acid;

L-2-{4'-[(4-Benzenesulfonylamino-3-methyl-benzofuran-2-carbonyl)-amino]-biphenyl-4-sulfonylamino}-3-methyl-butyric acid;

L-3-Methyl-2-(4'-{[3-methyl-4-(thiophene-2-sulfonylamino)-benzofuran-2-carbonyl]-amino}-biphenyl-4-sulfonylamino)-butyric acid;

L-2-(4'-{[4-(1,1-Dioxo-1□6-isothiazolidin-2-yl)-3-methyl-benzofuran-2-carbonyl]-amino}-biphenyl-4-sulfonylamino)-3-methyl-butyric acid;

D-3-Methyl-2-{4'-[(3-methyl-benzofuran-2-carbonyl)-amino]-biphenyl-4-sulfonylamino}-butyric acid;

D-2-{4'-[(Benzofuran-2-carbonyl)-methyl-amino]-biphenyl-4-sulfonylamino}-3-methyl-butyric acid;

4-{5-[(Benzofuran-2-carbonyl)-amino]-pyridin-2-yl}-benzenesulfonyl-L-valine;

N-({4'-[(1-benzofuran-2-ylcarbonyl)amino]-1,1'-biphenyl-4-yl}sulfonyl)-N-methyl-D-valine;

N-({4'-[(1-Benzofuran-2-ylcarbonyl)amino]-1,1'-biphenyl-4-yl}sulfonyl)-N-methyl-L-valine;

N-({4'-[(1-Benzofuran-2-ylcarbonyl)amino]-1,1'-biphenyl-4-yl}sulfonyl)-N-methylglycine;

(S)-2-{4'-[(1,3-Dimethyl-1H-thieno[2,3-c]pyrazole-5-carbonyl)-amino]-biphenyl-4-sulfonylamino}-3-methyl-butyric acid;

N-({4'-[(1-Benzofuran-2-ylcarbonyl)amino]-1,1'-biphenyl-4-yl}sulfonyl)-N-(pyridin-3-ylmethyl)-L-valine;

N-({4'-[(1-Benzofuran-2-ylcarbonyl)amino]-1,1'-biphenyl-4-yl}sulfonyl)-N-(2-morpholin-4-ylethyl)-L-valine;

N-[(4'-{[(3-Methyl-1-benzofuran-2-yl)carbonyl]amino}-1,1'-biphenyl-4-yl)sulfonyl]-L-valine;

N-[(4'-{[(5-Bromo-1-benzofuran-2-yl)carbonyl]amino}-1,1'-biphenyl-4-yl)sulfonyl]-L-valine;

N-[(4'-{[(4-Methyl-3,4,5,6-tetrahydrofuro[4,3,2-ef [3]benzazepin-2-yl)carbonyl]amino}-1,1'-biphenyl-4-yl)sulfonyl]-L-valine;

N-[(4'-{[(5-Ethyl-4-methoxy-3-methyl-1-benzofuran-2-yl)carbonyl]amino}-1,1'-biphenyl-4-yl)sulfonyl]-L-valine;

N-[(4'-{[(4-Ethyl-3-methyl-1-benzofuran-2-yl)carbonyl]amino}-1,1'-biphenyl-4-yl)sulfonyl]-L-valine;

N-[(4'-{[(5-Ethyl-4-isopropoxy-3-methyl-1-benzofuran-2-yl)carbonyl]amino}-1,1'-biphenyl-4-yl)sulfonyl]-L-valine;

N-{[4'-({[4-(Benzyloxy)-5-ethyl-3-methyl-1-benzofuran-2-yl]carbonyl}amino)-1,1'-biphenyl-4-yl]sulfonyl}-L-valine;

N-[(4'-{[(5-Ethyl-4-hydroxy-3-methyl-1-benzofuran-2-yl)carbonyl]amino}-1,1'-biphenyl-4-yl)sulfonyl]-L-valine;

N-{[4'-({[4-(2,2-Dimethyl-1,3-dioxolan-4-yl)-3-methyl-1-benzofuran-2-yl]carbonyl}amino)-1,1'-biphenyl-4-yl]sulfonyl}-L-valine;

N-{[4'-({[4-(Hydroxymethyl)-3-methyl-1-benzofuran-2-yl]carbonyl}amino)-1,1'-biphenyl-4-yl]sulfonyl}-L-valine;

N-[(4'-{[(3,4-Dimethyl-1-benzofuran-2-yl)carbonyl]amino}-1,1'-biphenyl-4-yl)sulfonyl]-L-valine;

N-[(4'-{[(4-Acetyl-3-methyl-1-benzofuran-2-yl)carbonyl]amino}-1,1'-biphenyl-4-yl)sulfonyl]-L-valine;

N-{[4'-({[4-(1-Hydroxyethyl)-3-methyl-1-benzofuran-2-yl]carbonyl}amino)-1,1'-biphenyl-4-yl]sulfonyl}-L-valine;

N-[(4'-{[(3-methyl-4-vinyl-1-benzofuran-2-yl)carbonyl]amino}-1,1'-biphenyl-4-yl)sulfonyl]-L-valine;

N-{[4'-({[4-(1,2-dihydroxyethyl)-3-methyl-1-benzofuran-2-yl]carbonyl}amino)-1,1'-biphenyl-4-yl]sulfonyl}-L-valine;

N-methyl-N-[(4'-{[(3-methyl4-vinyl-1-benzofuran-2-yl)carbonyl]amino}-1,1'-biphenyl-4-yl)sulfonyl]-L-valine;

N-{[4'-({[4-(1,2-dihydroxyethyl)-3-methyl-1-benzofuran-2-yl]carbonyl}amino)-1,1'-biphenyl-4-yl]sulfonyl}-N-methyl-L-valine;
N-{[4'-({[4-(methoxymethyl)-3-methyl-1-benzofuran-2-yl]carbonyl}amino)-1,1'-biphenyl-4-yl]sulfonyl}-L-valine;
N-{[4'-({[4-(1-methoxyethyl)-3-methyl-1-benzofuran-2-yl]carbonyl}amino)-1,1'-biphenyl-4-yl]sulfonyl}-L-valine;
N-{[4'-({[4-(2-methoxyethyl)-3-methyl-1-benzofuran-2-yl]carbonyl}amino)-1,1'-biphenyl-4-yl]sulfonyl}-L-valine;
N-[(4'-{[(4-Isopropoxy-1-benzofuran-2-yl)carbonyl]amino}-1,1'-biphenyl-4-yl)sulfonyl]-L-valine;
N-[(4'-{[(5-methoxy-1-benzofuran-2-yl)carbonyl]amino}-1,1'-biphenyl-4-yl)sulfonyl]-L-valine;
(S)-2-{4'-[(4-Methoxy-3-methyl-benzofuran-2-carbonyl)-amino]-biphenyl-4-sulfonylamino}-3-methyl-butyric acid;
(S)-2-{4'-[(4-ethoxy-3-methyl-benzofuran-2-carbonyl)-amino]-biphenyl-4-sulfonylamino}-3-methyl-butyric acid;
(S)-3-Methyl-2-{4'-[(3-methyl-4-propoxy-benzofuran-2-carbonyl)-amino]-biphenyl-4-sulfonylamino}-butyric acid;
(S)-2-{4'-[(4-Isopropoxy-3-methyl-benzofuran-2-carbonyl)-amino]-biphenyl-4-sulfonylamino}-3-methyl-butyric acid;
(S)-3-Methyl-2-{4'-[(3-methyl-4-phenyl-benzofuran-2-carbonyl)-amino]-biphenyl-4-sulfonylamino}-butyric acid;
(S)-3-Methyl-2-(4'-{[3-methyl-4-(3-nitro-phenyl)-benzofuran-2-carbonyl]-amino}-biphenyl-4-sulfonylamino)-butyric acid;
(S)-3-methyl-2-{4'-[(3-methyl-4-pyridin-3-yl-benzofuran-2-carbonyl)-amino]-biphenyl-4-sulfonylamino}-butyric acid;
(S)-3-Methyl-2-{4'-[(3-methyl-4-pyridin-4-yl-benzofuran-2-carbonyl)-amino]-biphenyl-4-sulfonylamino}-butyric acid;
(S)-2-{4'-[(4-Furan-3-yl-3-methyl-benzofuran-2-carbonyl)-amino]-biphenyl-4-sulfonylamino}-3-methyl-butyric acid;
(S)-3-methyl-2-{4'-[(3-methyl-4-morpholin-4-yl-benzofuran-2-carbonyl)-amino]-biphenyl-4-sulfonylamino}-butyric acid;
(S)-2-{4'-[(5-Chloro-4-isopropoxy-3-methyl-benzofuran-2-carbonyl)-amino]-biphenyl-4-sulfonylamino}-3-methyl-butyric acid;
(S)-2-{4'-[(5-Chloro-4-methoxy-3-methyl-benzofuran-2-carbonyl)-amino]-biphenyl-4-sulfonylamino}-3-methyl-butyric acid;
(S)-2-{4'-[(5,7-Dichloro-4-methoxy-3-methyl-benzofuran-2-carbonyl)-amino]-biphenyl-4-sulfonylamino}-3-methyl-butyric acid;
(S)-2-{4'-[(5-bromo-4-methoxy-3-methyl-benzofuran-2-carbonyl)-amino]-biphenyl-4-sulfonylamino}-3-methyl-butyric acid;
(R)-2-{4'-[(5-Bromo-4-methoxy-3-methyl-benzofuran-2-carbonyl)-amino]-biphenyl-4-sulfonylamino}-3-methyl-butyric acid;
(S)-2-{4'-[(5-Iodo-4-methoxy-3-methyl-benzofuran-2-carbonyl)-amino]-biphenyl-4-sulfonylamino}-3-methyl-butyric acid;
(S)-2-{4'-[(5-Acetyl-4-methoxy-3-methyl-benzofuran-2-carbonyl)-amino]-biphenyl-4-sulfonylamino}-3-methyl-butyric acid;
S)-2-(4'-{[5-(1-Chloro-vinyl)-4-methoxy-3-methyl-benzofuran-2-carbonyl]-amino}-biphenyl-4-sulfonylamino)-3-methyl-butyric acid;
(S)-2-{4'-[(5-Acetyl-4-hydroxy-3-methyl-benzofuran-2-carbonyl)-amino]-biphenyl-4-sulfonylamino}-3-methyl-butyric acid;
(S)-2-{4'-[(5-Cyano-4-methoxy-3-methyl-benzofuran-2-carbonyl)-amino]-biphenyl-4-sulfonylamino}-3-methyl-butyric acid;
(S)-2-{4'-[(5-Methyl-4-methoxy-3-methyl-benzofuran-2-carbonyl)-amino]-biphenyl-4-sulfonylamino}-3-methyl-butyric acid;
(S)-2-{4'-[(5-Hydroxymethyl-4-methoxy-3-methyl-benzofuran-2-carbonyl)-amino]-biphenyl-4-sulfonylamino}-3-methyl-butyric acid;
(S)-3-Methyl-2-{4'-[(benzooxazole-2-carbonyl)-amino]-biphenyl-4-sulfonylamino}-butyric acid;
(S)-3-Methyl-2-{4'-[(4-methyl-benzooxazole-2-carbonyl)-amino]-biphenyl-4-sulfonylamino}-butyric acid;
(S)-3-Methyl-2-{4'-[(5-methyl-benzooxazole-2-carbonyl)-amino]-biphenyl-4-sulfonylamino}-butyric acid;
(S)-3-Methyl-2-{4'-[(5-chloro-benzothiazole-2-carbonyl)-amino]-biphenyl-4-sulfonylamino}-butyric acid;
(S)-3-Methyl-2-{4'-[(5-trifluoromethyl-benzothiazole-2-carbonyl)-amino]-biphenyl-4-sulfonylamino}-butyric acid;
D-3-Methyl-benzofuran-2-carboxylic acid 4'-(1-carboxy-2-methyl-propylsulfamoyl)-3,5-dimethyl-biphenyl-4-yl ester;
D-Benzofuran-2-carboxylic acid 4'-(1-carboxy-2-methyl-propylsulfamoyl)-3,5-dimethyl-biphenyl-4-yl ester;
D-3-Methyl-benzofuran-2-carboxylic acid 4'-(1-carboxy-2-methyl-propylsulfamoyl)-biphenyl-4-yl ester;
Benzofuran-2-carboxylic acid 4'-(1-carboxy-2-methyl-propylsulfamoyl)-biphenyl-4-yl ester;
D-2-[4'-(5-Bromo-4-methoxy-3-methyl-benzofuran-2-ylmethoxy)-biphenyl-4-sulfonylamino]-3-methyl-butyricacid;
D-2-[4'-(Benzothiazol-2-ylmethoxy)-biphenyl-4-sulfonylamino]-3-methyl-butyric acid;
D-3-Methyl-2-[4'-(1-methyl-1H-benzoimidazol-2-ylmethoxy)-biphenyl-4-sulfonylamino]-butyric acid;
D-3-Methyl-2-[4'-(3-methyl-benzofuran-2-ylmethoxy)-biphenyl-4-sulfonylamino]-butyric acid;
D-2-[4'-(Benzofuran-2-ylmethoxy)-3'-methoxy-biphenyl-4-sulfonylamino]-3-methyl-butyric acid;
D-2-[4'-(Benzofuran-2-ylmethoxy)-biphenyl-4-sulfonylamino]-3-methyl-butyric acid;
L-2-[4'-(5-Chloro-4-methoxy-3-methyl benzofuran-2-ylmethoxy)-biphenyl-4-sulfonylamino]-3-methyl-butyric acid;
L-2-[4'-(5-Cyano-4-methoxy-3-methyl benzofuran-2-ylmethoxy)-biphenyl-4-sulfonylamino]-3-methyl-butyric acid;
N-{[4'-(2-Furoyloxy)-1,1'-biphenyl-4-yl]sulfonyl}-D-valine;
N-{[4'-(3-Furoyloxy)-1,1'-biphenyl-4-yl]sulfonyl}-D-valine;
L-2-[4'-(4-Ethyl-3-methyl benzofuran-2-ylmethoxy)-biphenyl-4-sulfonylamino]-3-methyl-butyric acid;
N-[(4'-{[4-(3-methoxypropyl)-3-methyl-1-benzofuran-2-yl]methoxy}-1,1'-biphenyl-4-yl)sulfonyl]-L-valine;
N-({4'-[(5-Bromo-4-methoxy-3-methyl-1-benzofuran-2-yl)methoxy]-1,1'-biphenyl-4-yl}sulfonyl)-L-valine;
N-({4'-[(5-Bromo-4-isopropoxy-3-methyl-1-benzofuran-2-yl)methoxy]-1,1'-biphenyl-4-yl}sulfonyl)-D-valine;
N-[(4'-{[(5-bromo-4-methoxy-3-methyl-1-benzofuran-2-yl)methyl]amino}-1,1'-biphenyl-4-yl)sulfonyl]-L-valine;
L-2-{4'-[(Benzothiazole-2-carbonyl)-amino]-biphenyl-4-sulfonylamino}-3-methyl-butyric acid;

D-2-{4'-[(Benzothiazole-2-carbonyl)-amino]-biphenyl-4-sulfonylamino}-3-methyl-butyric acid;
L-3-Methyl-2-{4'-[(naphtho[2,1-b]furan-2-carbonyl)-amino]-biphenyl-4-sulfonylamino}-butyric acid;
L-3-Methyl-2-{4'-[(1-methyl-naphtho[2,1-b]furan-2-carbonyl)-amino]-biphenyl-4-sulfonylamino}-butyric acid;
L-3-Methyl-2-{4'-[(3-methyl-4-phenoxy-benzofuran-2-carbonyl)-amino]-biphenyl-4-sulfonylamino}-butyric acid;
L-2-(4'-{[4-(1-Methoxycarbonyl-1-methyl-ethoxy)-3-methyl-benzofuran-2-carbonyl]-amino}-biphenyl-4-sulfonylamino)-3-methyl-butyric acid;
L-2-{4'-[(4-Ethoxycarbonylmethoxy-3-methyl-benzofuran-2-carbonyl)-amino]-biphenyl-4-sulfonylamino}-3-methyl-butyric acid;
L-2-{4'-[(4-Methoxycarbonylmethoxy-3-methyl-benzofuran-2-carbonyl)-amino]-biphenyl-4-sulfonylamino}-3-methyl-butyric acid;
L-2-{4'-[(4-Carboxymethoxy-3-methyl-benzofuran-2-carbonyl)-amino]-biphenyl-4-sulfonylamino}-3-methyl-butyric acid;
L-3-Methyl-2-(4'-{[3-methyl-4-(pyridin-3-ylmethoxy)-benzofuran-2-carbonyl]-amino}-biphenyl-4-sulfonylamino)-butyric acid;
L-2-{4'-[(4-Hydroxy-3-methyl-benzofuran-2-carbonyl)-amino]-biphenyl-4-sulfonylamino}-3-methyl-butyric acid;
L-2-(4-{5-[(1-Ethyl-1H-benzimidazole-2-carbonyl)-amino]-pyridin-2-yl}-benzenesulfonylamino)-3-methyl-butyric acid;
N-({4'-[(1,2,3-thiadiazol-4-ylcarbonyl)amino]-1,1'-biphenyl-4-yl}sulfonyl)-L-valine;
D-2-[4'-(Benzofuran-2-sulfonylmethyl)-biphenyl-4-sulfonylamino]-3-methyl-butyric acid;
D-2-[4'-(Benzofuran-2-sulfonylmethyl)-biphenyl-4-sulfonylamino]-3-methyl-butyric acid;
(S)-2-(4'-{[3-(4-Chloro-phenyl)-isoxazole-5-carbonyl]-amino}-biphenyl-4-sulfonylamino)-3-methyl-butyric acid;
(S)-3-Methyl-2-{4'-[(1-methyl-3-phenyl-1H-thieno[2,3-c]pyrazole-5-carbonyl)-amino]-biphenyl-4-sulfonylamino}-butyric acid;
(S)-3-Methyl-2-{4'-[(5-methyl-1-phenyl-1H-pyrazole-3-carbonyl)-amino]-biphenyl-4-sulfonylamino}-butyric acid;
(S)-3-Methyl-2-{4'-[(2-pyridin-4-yl-thiazole-4-carbonyl)-amino]-biphenyl-4-sulfonylamino}-butyric acid;
(S)-3-Methyl-2-[4'-(thiophene-2-sulfonylamino)-biphenyl-4-sulfonylamino]-butyric acid;
(R)-3-Methyl-2-[4'-(thiophene-2-sulfonylamino)-biphenyl-4-sulfonylamino]-butyric acid;
(R)-2-{4'-[(Furan-2-carbonyl)-amino]-biphenyl-4-sulfonylamino}-3-methyl-butyric acid;
(R)-3-Methyl-2-{4'-[(thiophene-2-carbonyl)-amino]-biphenyl-4-sulfonylamino}-butyric acid;
(S)-3-Methyl-2-{4'-[(thiophene-2-carbonyl)-amino]-biphenyl-4-sulfonylamino}-butyric acid;
(S)-2-{4'-[(Furan-2-carbonyl)-amino]-biphenyl-4-sulfonylamino}-3-methyl-butyric acid;
(S)-2-{4'-[(4-Dimethylcarbamoylmethoxy-3-methyl-benzofuran-2-carbonyl)-amino]-biphenyl-4-sulfonylamino}-3-methyl-butyric acid;
(S)-2-(4'-{[4-(2-tert-Butoxycarbonylamino-ethoxy)-3-methyl-benzofuran-2-carbonyl]-amino}-biphenyl-4-sulfonylamino)-3-methyl-butyric acid;
(S)-3-Methyl-2-(4'-{[3-methyl-4-(pyridin-2-ylmethoxy)-benzofuran-2-carbonyl]-amino}-biphenyl-4-sulfonylamino)-butyric acid;
(S)-3-Methyl-2-(4'-{[3-methyl-4-(pyridin-4-ylmethoxy)-benzofuran-2-carbonyl]-amino}-biphenyl-4-sulfonylamino)-butyric acid;
(S)-2-{4'-[(4-Carbamoylmethoxy-3-methyl-benzofuran-2-carbonyl)-amino]-biphenyl-4-sulfonylamino}-3-methyl-butyric acid;
(S)-2-(4'-{[4-(2-Amino-ethoxy)-3-methyl-benzofuran-2-carbonyl]-amino}-biphenyl-4-sulfonylamino)-3-methyl-butyric acid;
(S)-2-(4'-{[4-(2-Dimethylamino-ethoxy)-3-methyl-benzofuran-2-carbonyl]-amino}-biphenyl-4-sulfonylamino)-3-methyl-butyric acid;
N-[(4'-{[(5-Chloro-1-benzofuran-2-yl)carbonyl]amino}-1,1'-biphenyl-4-yl)sulfonyl]-L-valine;
N-({4'-[(5-Bromo-2-furoyl)amino]-1,1'-biphenyl-4-yl}sulfonyl)-L-valine;
N-[(4'-{[(7-Nitro-1H-indol-2-yl)carbonyl]amino}-1,1'-biphenyl-4-yl)sulfonyl]-L-valine;
N-[(4'-{[(2-Pyridin-4-yl-1,3-thiazol-5-yl)carbonyl]amino}-1,1'-biphenyl-4-yl)sulfonyl]-L-valine;
N-[(4'-{[5-(2-Nitrophenyl)-2-furoyl]amino}-1,1'-biphenyl-4-yl)sulfonyl]-L-valine;
N-{[4'-({[2-(2,3-Dihydro-1,4-benzodioxin-2-yl)-1,3-thiazol-4-yl]carbonyl}amino)1,1'-biphenyl-4-yl]sulfonyl}-L-valine;
N-[(4'-{[(5-Methyl-3-phenylisoxazol-4-yl)carbonyl]amino}-1,1'-biphenyl-4-yl)sulfonyl]-L-valine;
N-[(4'-{[(4-Methyl-1,2,3-thiadiazol-5-yl)carbonyl]amino}-1,1'-biphenyl-4-yl)sulfonyl]-L-valine;
N-[(4'-{[(1-tert-Butyl-3-methyl-1H-pyrazol-5-yl)carbonyl]amino}-1,1'-biphenyl-4-yl)sulfonyl]-L-valine;
N-[(4'-{[(3-Chloro-1-benzothien-2-yl)carbonyl]amino}-1,1'-biphenyl-4-yl)sulfonyl]-L-valine;
N-{[4'-({[3-(2-Chlorophenyl)-5-methylisoxazol-4-yl]carbonyl}amino)-1,1'-biphenyl-4-yl]sulfonyl}-L-valine;
N-({4'-[(1-Benzofuran-2-ylcarbonyl)amino]-1,1'-biphenyl-4-yl}sulfonyl)-D-alanine;
N-({4'-[(1-Benzofuran-2-ylcarbonyl)amino]-1,1'-biphenyl-4-yl}sulfonyl)-L-valine;
N-({4'-[(1-Benzofuran-2-ylcarbonyl)amino]-1,1'-biphenyl-4-yl}sulfonyl)-D-valine;
N-({4'-[(1-Benzofuran-2-ylcarbonyl)amino]-1,1'-biphenyl-4-yl}sulfonyl)-L-norvaline;
N-({4'-[(1-Benzofuran-2-ylcarbonyl)amino]-1,1'-biphenyl-4-yl}sulfonyl)-D-norvaline;
N-({4'-[(1-Benzofuran-2-ylcarbonyl)amino]-1,1'-biphenyl-4-yl}sulfonyl)-L-aspartic acid;
N-({4'-[(1-Benzofuran-2-ylcarbonyl)amino]-1,1'-biphenyl-4-yl}sulfonyl)-D-aspartic acid;
N-2-({4'-[(1-Benzofuran-2-ylcarbonyl)amino]-1,1'-biphenyl-4-yl}sulfonyl)-L-glutamine;
N-2-({4'-[(1-Benzofuran-2-ylcarbonyl)amino]-1,1'-biphenyl-4-yl}sulfonyl)-D-glutamine;
N-({4'-[(1-Benzofuran-2-ylcarbonyl)amino]-1,1'-biphenyl-4-yl}sulfonyl)-L-histidine;
N-({4'-[(1-Benzofuran-2-ylcarbonyl)amino]-1,1'-biphenyl-4-yl}sulfonyl)-D-histidine;
N-({4'-[(1-Benzofuran-2-ylcarbonyl)amino]-1,1'-biphenyl-4-yl}sulfonyl)-L-isoleucine;
N-({4'-[(1-Benzofuran-2-ylcarbonyl)amino]-1,1'-biphenyl-4-yl}sulfonyl)-D-isoleucine;
N-({4'-[(1-Benzofuran-2-ylcarbonyl)amino]-1,1'-biphenyl-4-yl}sulfonyl)-L-leucine;
N-({4'-[(1-Benzofuran-2-ylcarbonyl)amino]-1,1'-biphenyl-4-yl}sulfonyl)-D-leucine;
N-({4'-[(1-Benzofuran-2-ylcarbonyl)amino]-1,1'-biphenyl-4-yl}sulfonyl)-L-norleucine;

N-({4'-[(1-Benzofuran-2-ylcarbonyl)amino]-1,1'-biphenyl-4-yl}sulfonyl)-D-norleucine;
N-({4'-[(1-Benzofuran-2-ylcarbonyl)amino]-1,1'-biphenyl-4-yl}sulfonyl)-L-phenylalanine;
N-({4'-[(1-Benzofuran-2-ylcarbonyl)amino]-1,1'-biphenyl-4-yl}sulfonyl)-D-phenylalanine;
1-({4'-[(1-Benzofuran-2-ylcarbonyl)amino]-1,1'-biphenyl-4-yl}sulfonyl)-L-proline;
1-({4'-[(1-Benzofuran-2-ylcarbonyl)amino]-1,1'-biphenyl-4-yl}sulfonyl)-D-proline;
N-({4'-[(1-Benzofuran-2-ylcarbonyl)amino]-1,1'-biphenyl-4-yl}sulfonyl)-L-tryptophan;
N-({4'-[(1-Benzofuran-2-ylcarbonyl)amino]-1,1'-biphenyl-4-yl}sulfonyl)-D-tryptophan;
N-({4'-[(1-Benzofuran-2-ylcarbonyl)amino]-1,1'-biphenyl-4-yl}sulfonyl)-N-methylglycine;
N-({4'-[(1-Benzofuran-2-ylcarbonyl)amino]-1,1'-biphenyl-4-yl}sulfonyl)-2-methylalanine;
N-({4'-[(1-Benzofuran-2-ylcarbonyl)amino]-1,1'-biphenyl-4-yl}sulfonyl)-N-methyl-L-alanine;
1-[({4'-[(1-Benzofuran-2-ylcarbonyl)amino]-1,1'-biphenyl-4-yl}sulfonyl)amino]cyclopentanecarboxylic acid;
N-({4'-[(1-Benzofuran-2-ylcarbonyl)amino]-1,1'-biphenyl-4-yl}sulfonyl)-N-methylvaline;
N-({4'-[(1-Benzofuran-2-ylcarbonyl)amino]-1,1'-biphenyl-4-yl}sulfonyl)-3-methyl-L-valine;
N-({4'-[(1-Benzofuran-2-ylcarbonyl)amino]-1,1'-biphenyl-4-yl}sulfonyl)-2-methylleucine;
N-({4'-[(1-Benzofuran-2-ylcarbonyl)amino]-1,1'-biphenyl-4-yl}sulfonyl)-D-glutamic acid;
(2R)-[({4'-[(1-Benzofuran-2-ylcarbonyl)amino]-1,1'-biphenyl-4-yl}sulfonyl)amino (phenyl)acetic acid;
[({4'-[(1-Benzofuran-2-ylcarbonyl)amino]-1,1'-biphenyl-4-yl}sulfonyl)amino](thien-2-yl)acetic acid;
(2S)-2-[({4'-[(1-Benzofuran-2-ylcarbonyl)amino]-1,1'-biphenyl-4-yl}sulfonyl)amino]-5-methoxy-5-oxopentanoic acid;
3-[({4'-[(1-Benzofuran-2-ylcarbonyl)amino]-1,1'-biphenyl-4-yl}sulfonyl)amino]-3-phenylpropanoic acid;
2-[({4'-[(1-Benzofuran-2-ylcarbonyl)amino]-1,1'-biphenyl-4-yl}sulfonyl)amino]-4-phenylbutanoic acid;
N-({4'-[(1-Benzofuran-2-ylcarbonyl)amino]-1,1'-biphenyl-4-yl}sulfonyl)-L-tyrosine;
N-({4'-[(1-Benzofuran-2-ylcarbonyl)amino]-1,1'-biphenyl-4-yl}sulfonyl)-D-tyrosine;
(2S)-2-[({4'-[(1-Benzofuran-2-ylcarbonyl)amino]-1,1'-biphenyl-4-yl}sulfonyl)amino]-4-tert-butoxy-4-oxobutanoic acid;
(2R)-2-[({4'-[(1-Benzofuran-2-ylcarbonyl)amino]-1,1'-biphenyl-4-yl}sulfonyl)amino]-4-tert-butoxy-4-oxobutanoic acid;
(2S)-[({4'-[(1-Benzofuran-2-ylcarbonyl)amino]-1,1'-biphenyl4-yl}sulfonyl)amino](2,3-dihydro-1H-inden-2-yl)acetic acid;
N-({4'-[(1-Benzofuran-2-ylcarbonyl)amino]-1,1'-biphenyl-4-yl}sulfonyl)-O-methyl-L-tyrosine;
[({4'-[(1-Benzofuran-2-ylcarbonyl)amino]-1,1'-biphenyl-4-yl}sulfonyl)amino (1-methyl-1H-indol-5-yl)acetic acid;
[({4'-[(1-Benzofuran-2-ylcarbonyl)amino]-1,1'-biphenyl-4-yl}sulfonyl)amino](1-benzothien-5-yl)acetic acid;
N-({4'-[(1-Benzofuran-2-ylcarbonyl)amino]-1,1'-biphenyl-4-yl}sulfonyl)-4-nitro-L-phenylalanine;
N-({4'-[(1-Benzofuran-2-ylcarbonyl)amino]-1,1'-biphenyl-4-yl}sulfonyl)-3-(2-naphthyl)alanine;
N-({4'-[(1-Benzofuran-2-ylcarbonyl)amino]-1,1'-biphenyl-4-yl}sulfonyl)-beta-methylphenylalanine;
N-({4'-[(1-Benzofuran-2-ylcarbonyl)amino]-1,1'-biphenyl-4-yl}sulfonyl)-N-methyl-L-tryptophan;
N-2-({4'-[(1-Benzofuran-2-ylcarbonyl)amino]-1,1'-biphenyl-4-yl}sulfonyl)-N~5~-phenylglutamine;
N-({4'-[(1-Benzofuran-2-ylcarbonyl)amino]-1,1'-biphenyl-4-yl}sulfonyl)-4,4,4,4',4',4'-hexafluorovaline;
4-Amino-N-({4'-[(1-benzofuran-2-ylcarbonyl)amino]-1,1'-biphenyl-4-yl}sulfonyl)-L-phenylalanine;
(2R)-2-[({4'-[(1-Benzofuran-2-ylcarbonyl)amino]-1,1'-biphenyl-4-yl}sulfonyl)amino]-5-(benzyloxy)-5-oxopentanoic acid;
N-({4'-[(1-Benzofuran-2-ylcarbonyl)amino]-1,1'-biphenyl-4-yl}sulfonyl)-1-benzyl-L-histidine; and
N-({4'-[(1-Benzofuran-2-ylcarbonyl)amino]-1,1'-biphenyl-4-yl}sulfonyl)-O-benzyl-L-tyrosine.

Particularly preferred compounds are:
L-2-(4'-{[4-(3-Methoxy-propyl)-3-methyl-benzofuran-2-carbonyl]-amino}-biphenyl-4-sulfonylamino)-3-methyl-butyric acid;
L-3-Methyl-2-(4'-{[3-methyl-4-(3-methyl-isoxazol-5-yl)-benzofuran-2-carbonyl]-amino}-biphenyl-4-sulfonylamino)-butyric acid;
D-2-{4'-[(4-Methanesulfonylamino-3-methyl-benzofuran-2-carbonyl)-amino]-biphenyl-4-sulfonylamino}-3-methyl-butyric acid;
L-2-{4[(4-Cyclopropylmethoxy-3-methyl-benzofuran-2-carbonyl)-amino]-biphenyl-4-sulfonylamino}-3-methyl-butyric acid;
L-3-Methyl-2-(4'-{[3-methyl4-(2H-tetrazol-5-yl)-benzofuran-2-carbonyl]-amino}-biphenyl-4-sulfonylamino)-butyric acid;
L-2-{4'-[(4-Dimethylamino-3-methyl-benzofuran-2-carbonyl)-amino]-biphenyl-4-sulfonylamino}-3-methyl-butyric acid;
L-2-{4'-[(4-Benzenesulfonylamino-3-methyl-benzofuran-2-carbonyl)-amino]-biphenyl-4-sulfonylamino}-3-methyl-butyric acid;
L-3-Methyl-2-(4'-{[3-methyl-4-(thiophene-2-sulfonylamino)-benzofuran-2-carbonyl]-amino}-biphenyl-4-sulfonylamino)-butyric acid;
N-[(4'-{[(5-Ethyl-4-methoxy-3-methyl-1-benzofuran-2-yl)carbonyl]amino}-1,1'-biphenyl-4-yl)sulfonyl]-L-valine;
N-[(4'-{[(4-Ethyl-3-methyl-1-benzofuran-2-yl)carbonyl]amino}-1,1'-biphenyl-4-yl)sulfonyl]]-L-valine;
N-[(4'-{[(5-Ethyl-4-hydroxy-3-methyl-1-benzofuran-2-yl)carbonyl]amino}-1,1-biphenyl-4-yl)sulfonyl]-L-valine;
N-{[4'-({[4-(2,2-Dimethyl -1,3-dioxolan-4-yl)-3-methyl-1-benzofuran-2-yl]carbonyl}amino)-1,1'-biphenyl-4-yl]sulfonyl}-L-valine;
N-[(4'-{[(3,4-Dimethyl-1-benzofuran-2-yl)carbonyl]amino}-1,1'-biphenyl-4-yl)sulfonyl]-L-valine;
N-[(4'-{[(4-Acetyl-3-methyl-1-benzofuran-2-yl)carbonyl]amino}-1,1'-biphenyl-4-yl)sulfonyl]]-L-valine;
N-{[4'-({[4-(1-Hydroxyethyl)-3-methyl-1-benzofuran-2-yl]carbonyl}amino)-1,1'-biphenyl-4-yl]sulfonyl}-L-valine;
N-[(4'-{[(3-methyl-4-vinyl-1-benzofuran-2-yl)carbonyl]amino}-1,1'-biphenyl-4-yl)sulfonyl]-L-valine;
N-{[4'-({[4-(methoxymethyl)-3-methyl-1-benzofuran-2-yl]carbonyl}amino)-1,1'-biphenyl-4-yl]sulfonyl}-L-valine;
N-{[4'-({[4-(1-methoxyethyl)-3-methyl-1-benzofuran-2-yl]carbonyl}amino)-1,1'-biphenyl-4-yl]sulfonyl}-L-valine;
N-{[4'-({[4-(2-methoxyethyl)-3-methyl-1-benzofuran-2-yl]carbonyl}amino)-1,1'-biphenyl-4-yl]sulfonyl}-L-valinate;
(S)-2-{4'-[(4-ethoxy-3-methyl-benzofuran-2-carbonyl)-amino]-biphenyl-4-sulfonylamino}-3-methyl-butyric acid;

(S)-3-methyl-2-{4'-[(3-methyl-4-pyridin-3-yl-benzofuran-2-carbonyl)-amino]-biphenyl-4-sulfonylamino}-butyric acid;

(S)-3-Methyl-2-{4'-[(3-methyl-4-pyridin-4-yl-benzofuran-2-carbonyl)-amino]-biphenyl-4-sulfonylamino}-butyric acid;

(S)-2-{4'-[(4-Furan-3-yl-3-methyl-benzofuran-2-carbonyl)-amino]-biphenyl-4-sulfonylamino}-3-methyl-butyric acid;

(S)-2-{4'-[(5-Chloro-4-methoxy-3-methyl-benzofuran-2-carbonyl)-amino]-biphenyl-4-sulfonylamino}-3-methyl-butyric acid;

(S)-2-{4'-[(5-bromo-4-methoxy-3-methyl-benzofuran-2-carbonyl)-amino]-biphenyl-4-sulfonylamino}-3-methyl-butyric acid;

(R)-2-{4'-[(5-Bromo-4-methoxy-3-methyl-benzofuran-2-carbonyl)-amino]-biphenyl-4-sulfonylamino}-3-methyl-butyric acid;

(S)-2-{4'-[(5-Iodo-4-methoxy-3-methyl-benzofuran-2-carbonyl)-amino]-biphenyl-4-sulfonylamino}-3-methyl-butyric acid;

(S)-2-{4'-[(5-Cyano-4-methoxy-3-methyl-benzofuran-2-carbonyl)-amino]-biphenyl-4-sulfonylamino}-3-methyl-butyric acid;

(S)-2-{4'-[(5-Methyl-4-methoxy-3-methyl-benzofuran-2-carbonyl)-amino]-biphenyl-4-sulfonylamino}-3-methyl-butyric acid;

(S)-3-Methyl-2-{4'-[(5-methyl-benzooxazole-2-carbonyl)-amino]-biphenyl-4-sulfonylamino}-butyric acid;

D-2-[4'-(5-Bromo-4-methoxy-3-methyl-benzofuran-2-yl-methoxy)-biphenyl-4-sulfonylamino]-3-methyl-butyric acid;

L-2-{4'-[(4-Ethoxycarbonylmethoxy-3-methyl-benzofuran-2-carbonyl)-amino]-biphenyl-4-sulfonylamino}-3-methyl-butyric acid;

L-2-{4'-[(4-Carboxymethoxy-3-methyl-benzofuran-2-carbonyl)-amino]-biphenyl-4-sulfonylamino}-3-methyl-butyric acid;

L-3-Methyl-2-(4'-{[3-methyl-4-(pyridin-3-ylmethoxy)-benzofuran-2-carbonyl]-amino}-biphenyl-4-sulfonylamino)-butyric acid;

(S)-3-Methyl-2-{4'-[(1-methyl-3-phenyl-1H-thieno[2,3-c]pyrazole-5-carbonyl)-amino]-biphenyl-4-sulfonylamino}-butyric acid; and (S)-3-Methyl-2-(4,-{[3-methyl-4-(pyridin-4-ylmethoxy)-benzofuran-2-carbonyl]-amino}-biphenyl-4-sulfonylamino)-butyric acid.

Definitions

The term "alkyl", as used herein, whether used alone or as part of another group, refers to a substituted or unsubstituted aliphatic hydrocarbon chain and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." C1-C6 alkyl includes straight and branched chain aliphatic groups having from 1 to 6 carbons. Specifically included within the definition of "alkyl" are those aliphatic hydrocarbon chains that are optionally substituted.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted hydrocarbon chain and includes, but is not limited to, straight and branched chains having 2 to 8 carbon atoms and containing at least one double bond. Preferably, the alkenyl moiety has 1 or 2 double bonds. Such alkenyl moieties may exist in the E or Z conformations and the compounds of this invention include both conformations. C2-C6 alkenyl includes a 1 to 6 carbon straight or branched chain having at least one carbon-carbon double bond. Specifically included within the definition of "alkenyl" are those aliphatic hydrocarbon chains that are optionally substituted. Heteroatoms, such as O, S or $NR^4R^5$, attached to an alkenyl should not be attached to a carbon atom that is bonded to a double bond.

The term "alkynyl" refers to a hydrocarbon moiety containing at least one carbon-carbon triple bond. C2-C6 alkynyl includes a 2 to 6 carbon straight or branched chain having at least one carbon-carbon triple bond.

The term "cycloalkyl" refers to a monocyclic, bicyclic, tricyclic, fused, bridged, or spiro monovalent saturated hydrocarbon moiety, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like. C3-C6 cycloalkyl includes monocyclic, saturated rings of 3 to 6 carbons, optionally substituted with $R^6$.

"Heteroaryl" refers to a 5 to 6 membered aromatic heterocyclic ring which contains from 1 to 4 heteroatoms selected from the group consisting of oxygen, nitrogen, and sulfur atoms in the ring and may be fused with a carbocyclic or heterocyclic ring at any possible position.

"Heterocycloalkyl" refers to a 5 to 7-membered saturated ring containing carbon atoms and from 1 to 2 heteroatoms selected from N, O, and S.

The term "phenyl", as used herein, whether used alone or as part of another group, refers to a substituted or unsubstituted phenyl group.

An optionally substituted moiety may be substituted with one or more substituents. Suitable substituents for moieties, including alkyl, phenyl, or heteroaryl, may be selected independently from H, halogen, C1-C6 alkyl, C2-C6 alkenyl, C2-C6 alkynyl, $NR^4R^5$, $N[(CH_2)_2]_2O$, $N[(CH_2)_2]_2NR^4$, $NHSO_2R^4$, $NR^4C(=O)R^5$, $NHC(=O)OR^4$, $NO_2$, $SO_2NR^4R^5$, $SO_2R^4$, $OR^4$, $C(=O)R^4$, $COOR^4$, $CONR^4R^5$, and CN.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, when L is $C(R^6)=C(R^6)$, both carbon atoms form a part of the ring in order to satisfy their respective valences. Likewise, when divalent substituents are presented, it is understood that they are not limited to the order listed, for example, as used in this specification "$OCH_2$" encompasses $CH_2O$ and $OCH_2$.

The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50% of the other, more preferably less than about 75%, and even more preferably less than about 90%.

The terms "effective amount", "therapeutically effective amount" and "effective dosage" as used herein, refer to the amount of a compound, that, when administered to a patient, is effective to at least partially ameliorate (and, in preferred embodiments, cure) a condition form which the patient is suspected to suffer.

Pharmaceuticals

Biaryl sulfonamide compounds have been found to act as metalloproteinase inhibitors. They are therefore useful in the treatment of cancer, osteoarthritis, rheumatoid arthritis, asthma, COPD, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia, and/or periodontal diseases. The present invention thus provides pharmaceutical compositions comprising at least one biaryl sulfonamide compound and one or more pharmaceutically acceptable carriers, excipients, or diluents.

Examples of such carriers are well known to those skilled in the art and are prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of biaryl sulfonamide compounds. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

Methods of Making

The compounds of the invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecules.

In Scheme 1 the compounds of the invention, 1, are prepared by hydrolysis of the corresponding esters, 2, where $R^{10}$ is an alkyl ester such as methyl, ethyl or t-butyl, or a linker to a Wang resin for solid phase synthesis. Methyl and ethyl esters can be cleaved with aqueous base, including sodium or lithium hydroxide. t-Butyl esters and esters linked to resin can be cleaved using trifluoroacetic acid or hydrochloric acid. In addition, lithium iodide in ethyl acetate can be used to cleave methyl esters of general structure 2.

Scheme 1:

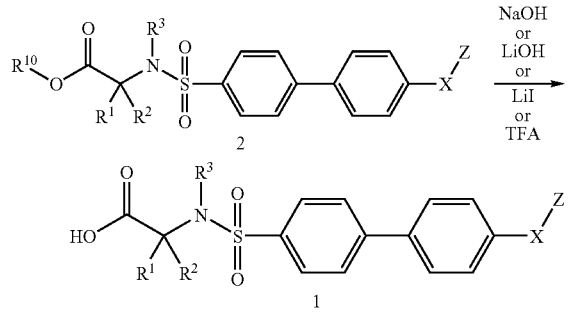

Routes to compounds of structure 2 are shown in Scheme 2. 4-Nitrobiphenyl, 3, is converted into sulfonyl chloride 4 in two steps with chlorosulfonic acid, followed by thionyl chloride or oxalyl chloride with catalytic DMF. Sulfonylation of an (x-amino acid derivative, 5, with sulfonyl chloride 4 provides sulfonamide 6. Sulfonamide 6 may optionally be alkylated with an alkyl halide, tosylate, mesylate or triflate ($R^{11}$=I, Br, Cl, Ots, Oms, OTf) to give the corresponding N—$R^3$ alkyl sulfonamide. The $R^3$ side chain can be further functionalized at any point in the synthesis. The NH or N—$R^3$ sulfonamide is reduced with tin (II) chloride, or hydrogenated over palladium on carbon, or via transfer hydrogenation, to give aniline 7. Aniline 7 is then derivatized to provide 2 by acylation with an acid chloride, or with a carboxylic acid using a peptide coupling reagent such as EDCI, or BOP in the presence of a tertiary amine in a polar aprotic solvent. Sulfonamides 2 are provided by the reaction of aniline 7 with heteroarylsulfonyl chlorides and a tertiary amine base. Secondary anilines 2 are formed by reductive amination of 7 with a heteroaryl aldehyde in the presence of a reducing agent such as sodium cyanoborohydride or preferably sodium triacetoxyborohydride.

Scheme 2:

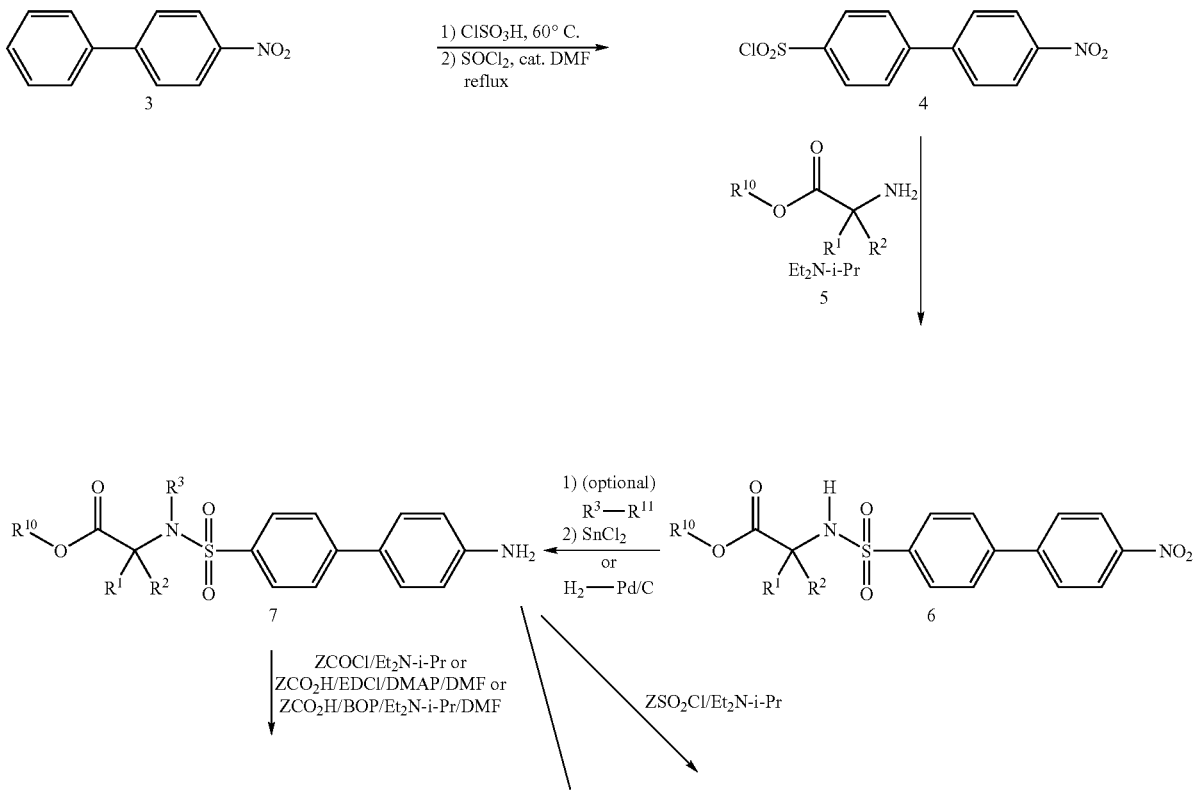

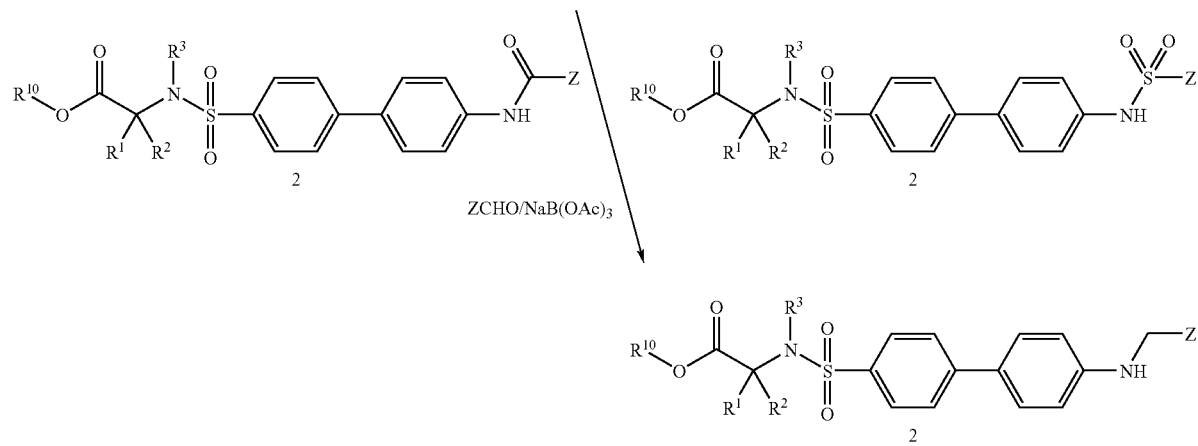

An alternative route to amides 2 is shown in Scheme 3. Commercially available sulfonyl fluoride 8 is acylated with acid chlorides to give amide derivatives 9. The analogous sulfonyl chlorides are available from via nitrobiphenyl 10 through reduction to aniline 11, acylation to give 12 and conversion of the sulfonic acid to the sulfonyl chloride 13. Reaction of amino acids or amino esters, 5, with 9 or 12 in the presence of a tertiary amine base provides compounds 2.

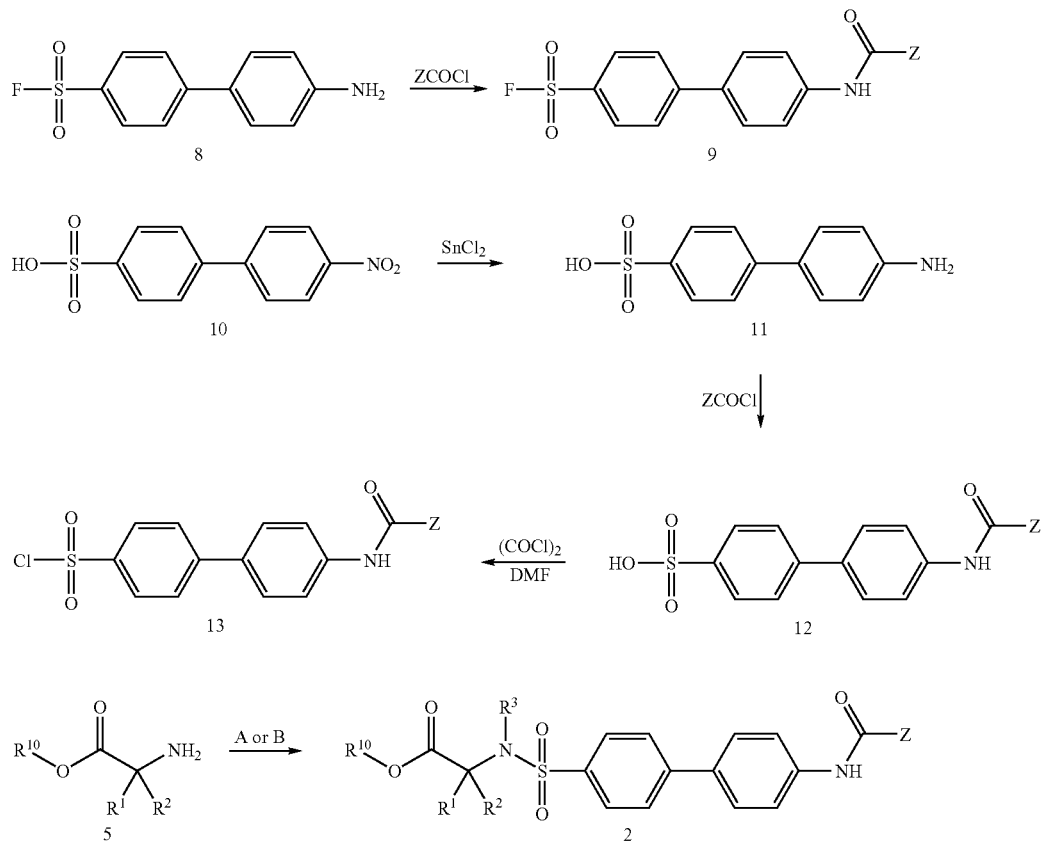

In Scheme 4 amino acid 5 is reacted with 4-bromobenzenesulfonyl chloride to give sulfonamide 14. Palladium catalyzed coupling of 14 with commercially available boronate esters 15 or 16 provides biphenyl sulfonamides 17, where $R^{12}$ is —OH or —NH$_2$. Functionalization of the phenol or aniline affords 2. Pyridyl analogs of the biphenyls are prepared by palladium catalyzed conversion of bromophenylsulfonamide 14 to the corresponding boronate ester, 18, followed by palladium coupling with 2-bromo-5-nitropyridine to afford 19. Hydrogenation of 19 gives aniline 20 which can be functionalized to give 2. Similar routes are available to additional heteroaryl analogs of the biphenyl sulfonamides claimed in the invention.

Thioethers of the invention are prepared according to Scheme 5 starting from the commercially available benzylic bromide 21. Displacement of the bromide with heteroaryl thiols in the presence of an acid scavenger provides thioethers 22 which are coupled to bromoaryl 14 using palladium (0) and a base such as potassium carbonate or sodium carbonate to give 23. Ester cleavage of 23 provides thioether compounds of the invention.

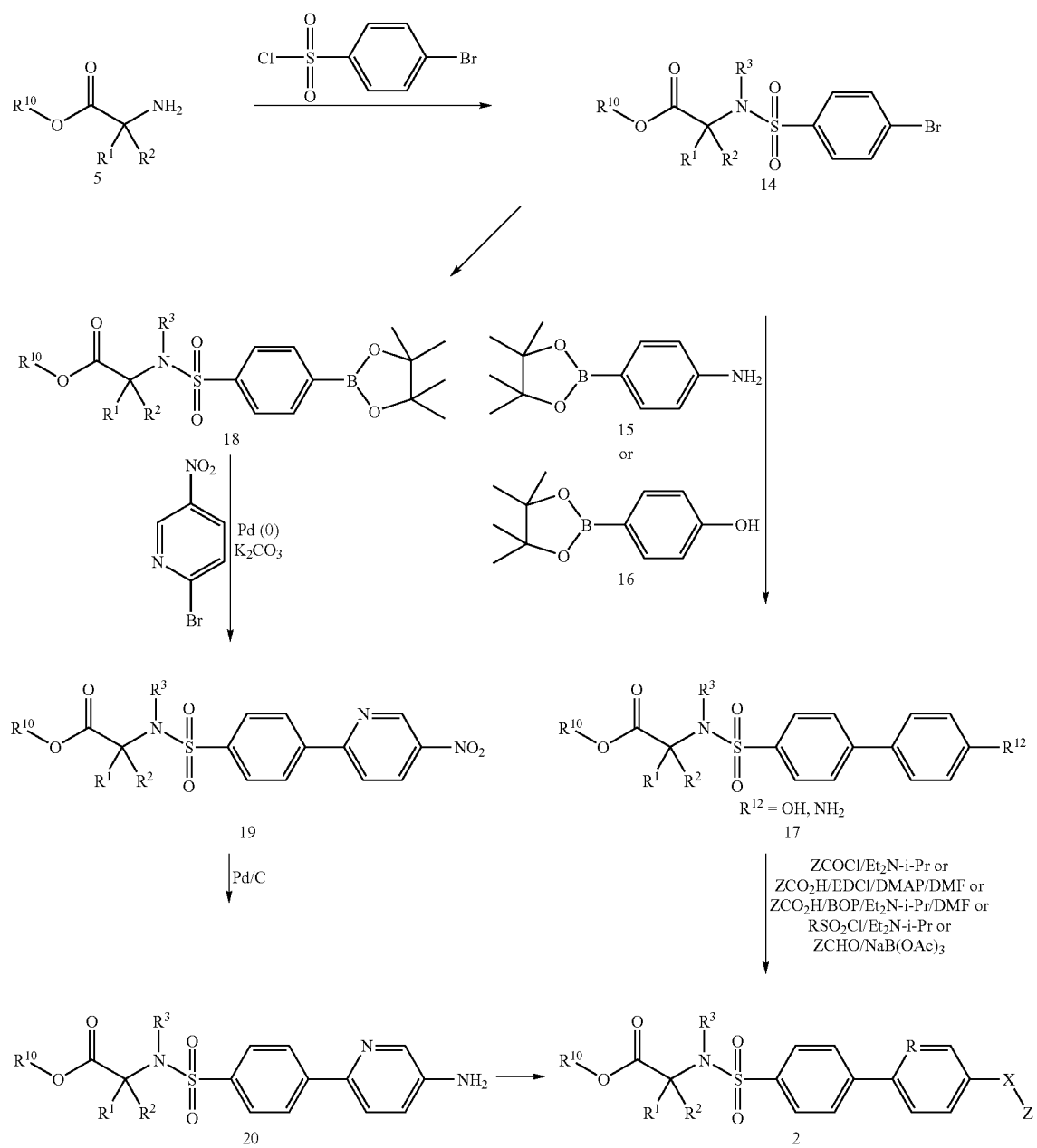

Scheme 5:

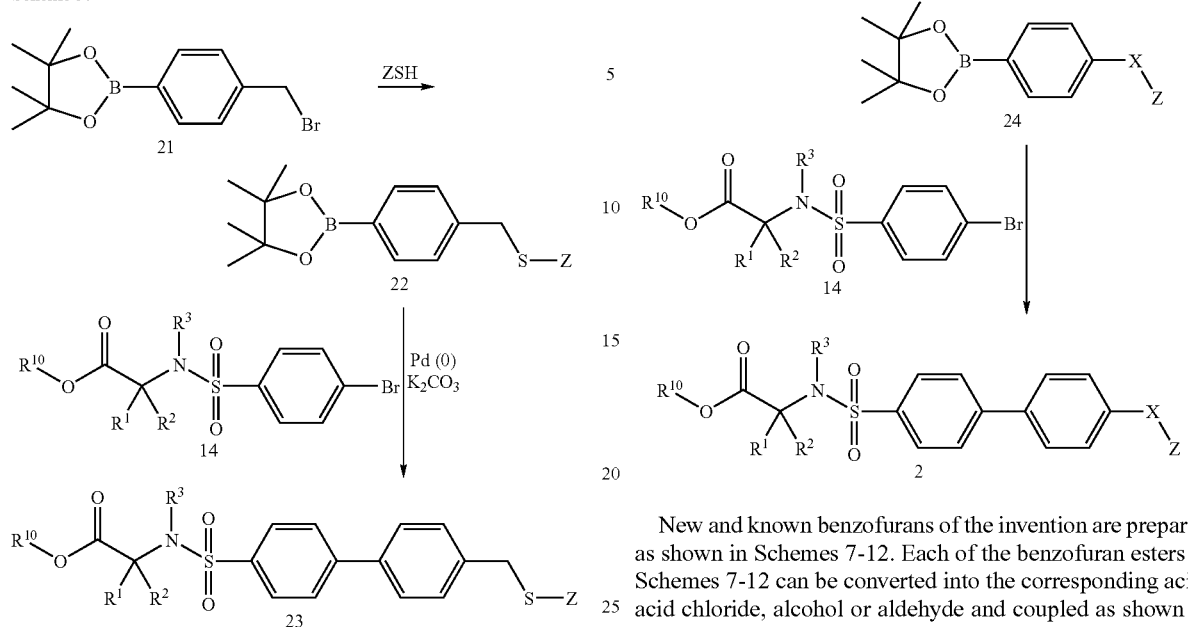

The biphenylsulfonamides of the invention can also be prepared by the route shown in Scheme 6. Boronate esters 15 and 16 can be functionalized to the corresponding amides, sulfonamides, amines, esters, or ethers prior to palladium catalyzed coupling with bromosulfonamide 14 to give analogs 2. Ester hydrolysis of 2 provides the compounds of the invention. Furthermore, it is understood that the methods shown in Schemes 1-6 for the construction of biphenylsulfonamides are applicable to heteroaryl analogs of biphenyl claimed in the invention.

Scheme 6:

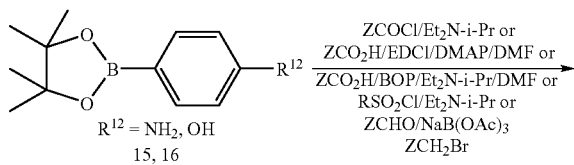

New and known benzofurans of the invention are prepared as shown in Schemes 7-12. Each of the benzofuran esters in Schemes 7-12 can be converted into the corresponding acid, acid chloride, alcohol or aldehyde and coupled as shown in schemes 2-6. It is understood that some of the methodology used for the construction and derivatization of the benzofurans shown is applicable to other heteroaryl ring systems of the invention.

In Scheme 7 salicyladehydes and ketones 25, bearing a variety of substituents $R^7$, are alkylated with α-bromoacetic acid esters to give 26 which is next cyclized in the presence of an alkoxide base in alcohol or potassium carbonate in DMF to afford the substituted benzofurans 27. Esters 27 are hydrolyzed with aqueous hydroxide, or TFA (for $R^{10}$=t-butyl) to give the carboxylic acids 28, which can in turn be converted into the acid chlorides, 29, with oxalyl or thionyl chloride and catalytic DMF. Reduction of esters 28 with diisobutylaluminum hydride or lithium aluminum hydride gives alcohols 30. The alcohols can be oxidized, preferably with Dess-Martin reagent to give the corresponding aldehydes 31. Alternatively, alcohols 30 can be converted into the corresponding chloride or bromide, 32, with thionyl chloride, phosphorus tribromide, carbon tetrabromide-triphenylphosphine or other known method.

Scheme 7:

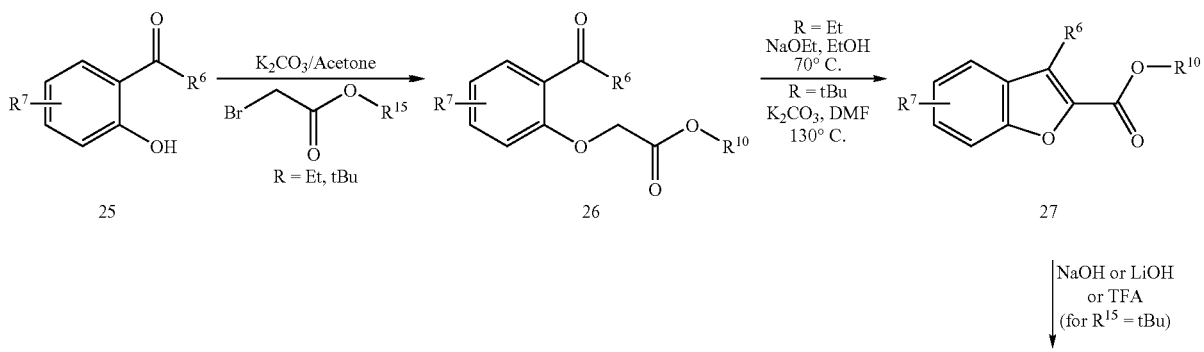

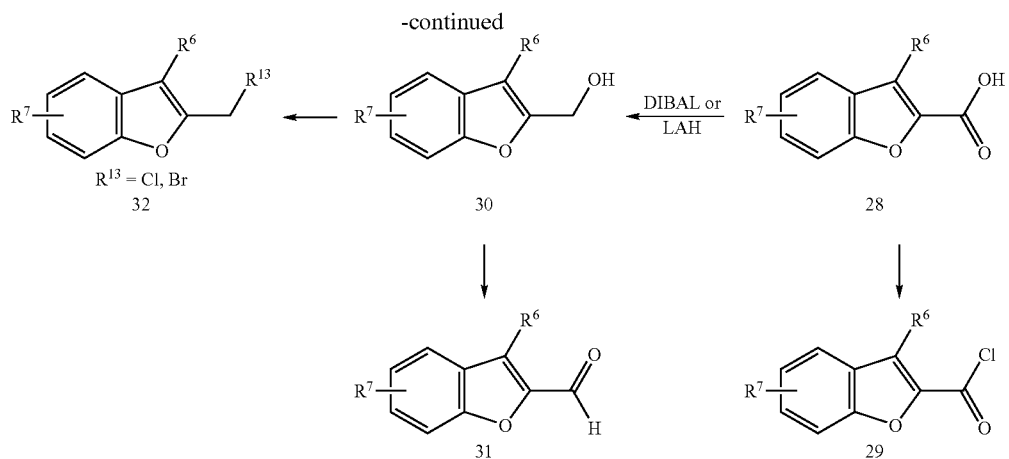

Functionalization of the benzofuran core is shown in Scheme 8. Although only 2-, 3-, and 4-substituents are shown on the benzofuran, the methodology shown in the scheme can accommodate additional substituents and the hydroxy group of 33 can be placed at other positions on the benzofuran. The 4-hydroxybenzofurans, 33, prepared according to Scheme 7, are converted into the corresponding triflates, 34, with trifluormethanesulfonic anhydride an a tertiary amine, pyridine or lutidine. Palladium catalyzed reaction of 34 with zinc cyanide gives nitriles 35. The nitriles can be hydrolyzed in the presence of H peroxide to give amide 36, which can optionally be alkylated with alkyl halides in the presence of sodium hydride or other strong base. Triflates 34 can also undergo stille coupling with tributylvinyltin, or other alkenyl tin reagent, to provide the styrenes 37. Similarly, triflates 34 can be coupled with alkyne derivatives to provide benzofurans 38-40 where $R^{14}$ is an alkyl or aryl group. Although not shown in the Scheme, the alkynes can be partially hydrogenated to provide olefins, or saturated to give the corresponding alkanes. The alkynes can also be substrates in [3+2 or [4+2] cycloadditions to afford, for example, isoxazoles such as 41.

Scheme 8:

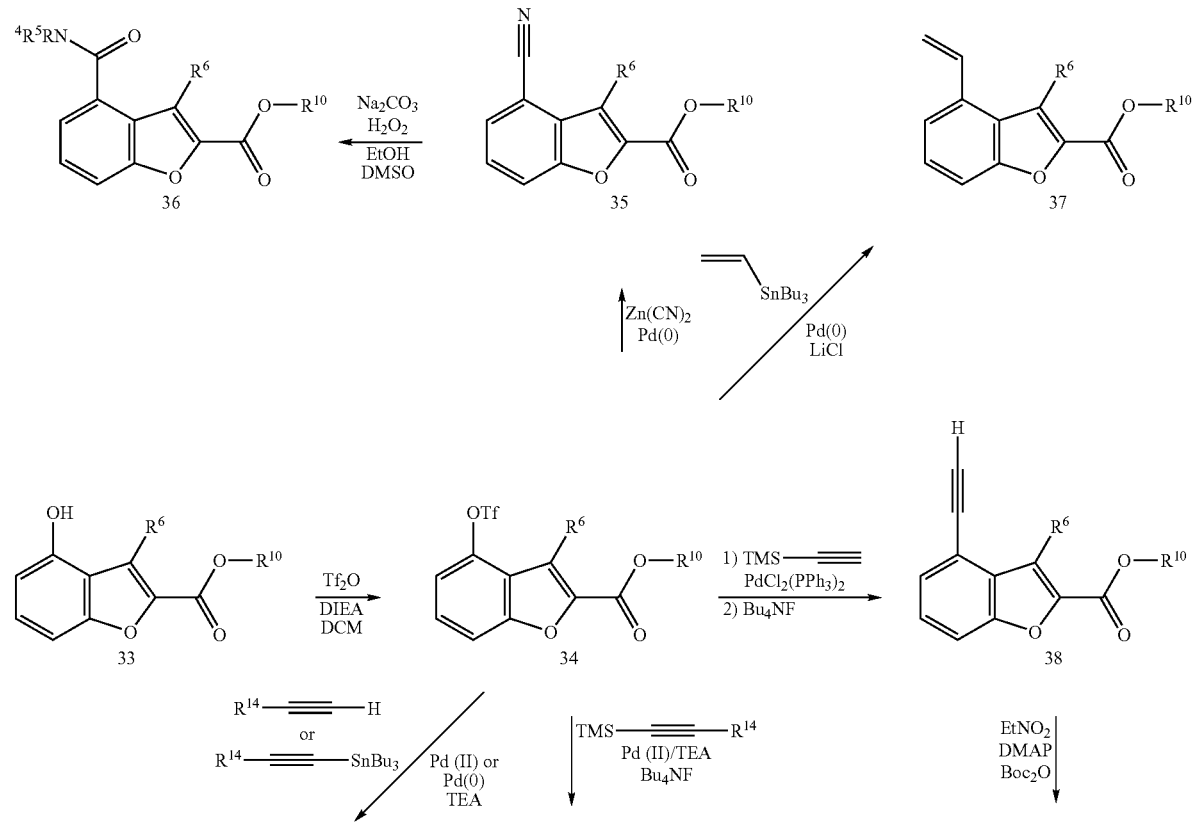

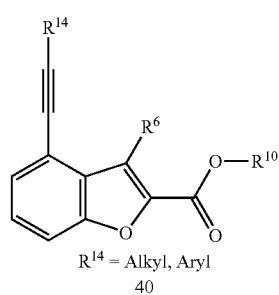

40
R¹⁴ = Alkyl, Aryl

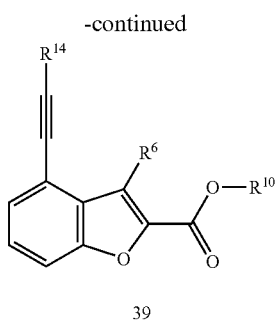

39

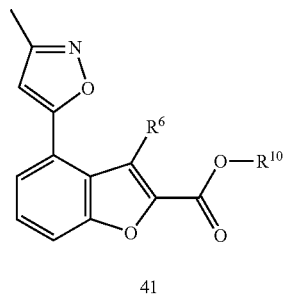

41

Olefin 37 can be derivatized according to the methods shown in Scheme 9. Dihydroxylation with osmium tetroxide and N-methylmorpholine N-oxide affords diols 42 which can in turn be converted into dioxolanes 43 through the acid catalyzed reaction with acetone or other ketone or aldehyde. Oxidative cleavage of the olefin of 37 with osmium tetroxide and sodium periodate gives aldehydes 44. The aldehydes can be reduced with sodium borohydride in methanol or ethanol to give alcohols 45, which may in turn be alkylated with an alkyl halide in the presence of silver oxide, sodium hydride or other base. Conversion of 45 to the corresponding bromide with carbon tetrabromide and triphenylphosphine, followed by reduction with sodium borohydride in DMSO, or other known method for the reduction of benzylic alcohols, provides the methyl-substituted benzofurans 46. Hydrogenation of olefins 37 on palladium on carbon gives the ethyl-substituted-benzofurans 47.

Scheme 9:

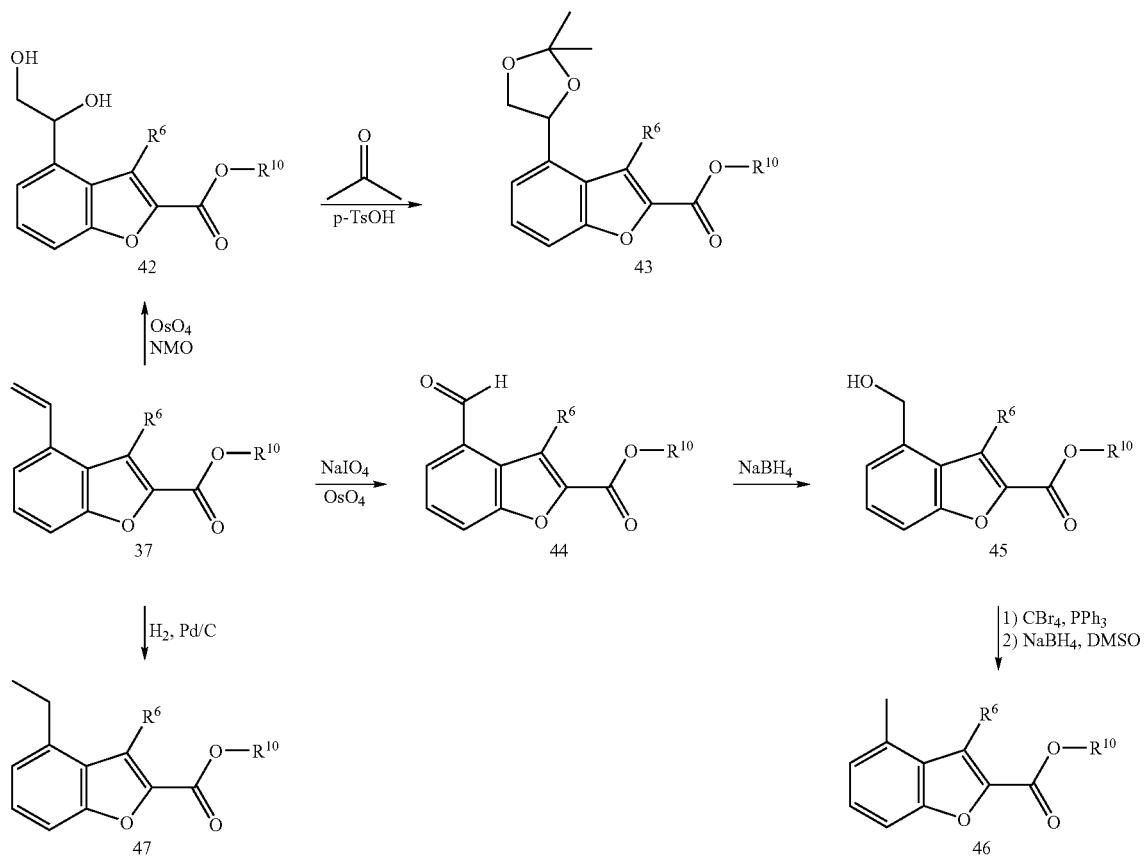

Additional transformations of triflates such as 34 are shown in Scheme 10. Palladium catalyzed reactions with amines, amides, sulfonamides or carbamates provide derivatives 48-50, each of which can then be further functionalized by alkylation of the newly installed nitrogen with an alkyl halide and base such as sodium hydride. Carbamate 50 can be deprotected by exposure to TFA or HCl to give primary aniline 51. This aniline may be mono- or di-alkylated with an alkyl halide in the presence of potassium carbonate in a polar aprotic solvent to give 48, or acylated or sulfonylated to give 49. Palladium catalyzed Suzuki coupling of triflates 34 with aryl or heteroaryl boronic acids or boronate esters provides 52.

Scheme 10:

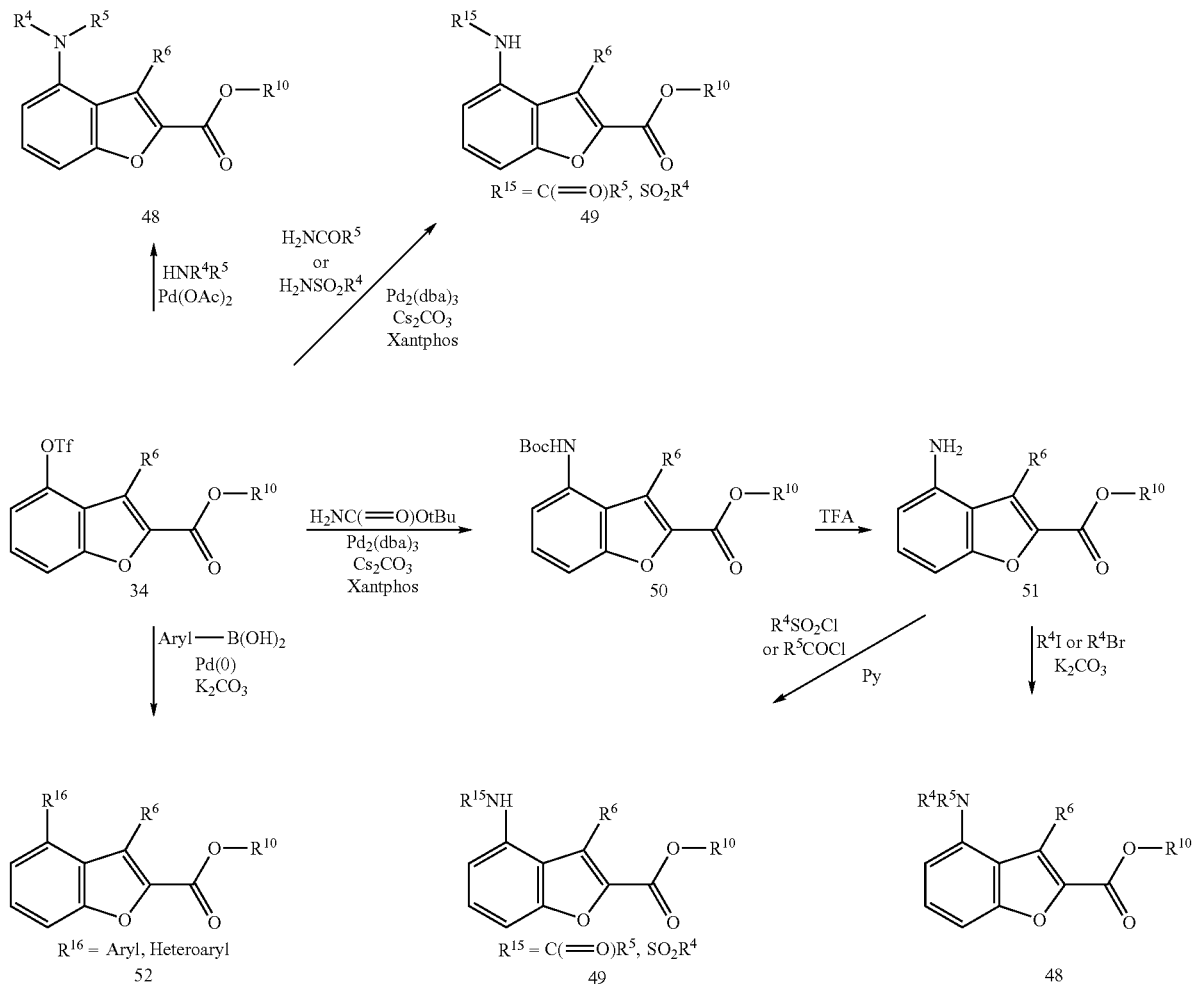

The synthesis of acetyl-benzofurans is shown in Scheme 11. Palladium catalyzed coupling of triflate 34 with butyl vinyl ether followed by hydrolysis in aqueous acid gives methyl ketone 53. Reduction of the methyl ketone provides the secondary alcohols, 54, which may in turn be alkylated with an alkyl halide in the presence of silver oxide, sodium hydride or other base.

Scheme 11:

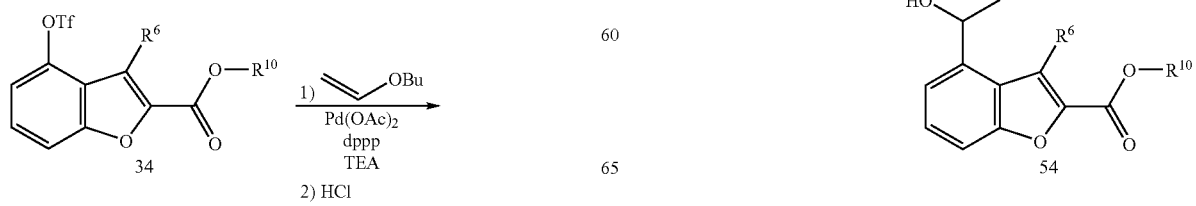

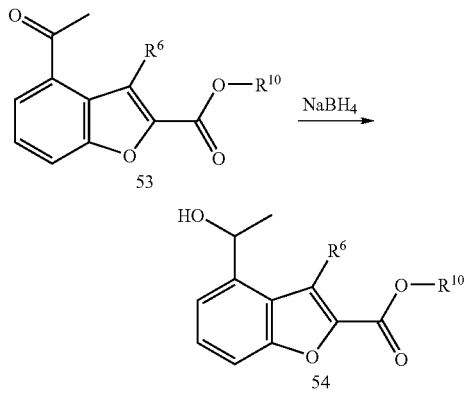

The synthesis of selected 2,4,5-trisubstituted benzofurans ($R^6$=H) and 2,3,4,5-tetrasubstituted benzofurans is shown in Scheme 12. Hydroxybenzofuran 33 can be converted into aryl or heteroaryl ethers, 55, by the reaction with aryl/heteroaryl boronic acids in the presenece of copper acetate. Alkyl ether derivatives, 56, are synthesized by alkylation of 33 with alkyl halides in the presence of sodium hydride or potassium carbonate in a polar aprotic solvent such as DMF or THF. Compounds of structure 33 are readily halogenated with N-halogen succinimides to provide compounds 61, which may in turn be alkylated to give ethers 62. Phenols 33, and their O-alkylated derivatives undergo ortho-acylation with acetyl chloride and titanium tetrachloride to give acetophenones 59, which may in turn be converted into the vinyl chlorides, 60, in the presence of oxalyl chloride and catalytic DMF. Reaction of 33 with magnesium methoxide followed by paraformaldehyde produces the ortho-formyl phenol 57, which can be reduced to the 5-methyl benzofuran 58. The phenol of 58 can subsequently be etherified by raction with an alkyl halide in the presence of sodiumhydride or potassium carbonate.

Certain N-alkyl benzimidazoles of the invention are available as shown in Scheme 13. Thus, 2-methylbenzimidazole, 63, is N-alkylated with an alkyl halide and sodium hydride to give 64, followed by selenium dioxide oxidation to provide the aldehyde, 65. Oxidation of the aldehyde to the carboxylic acid, 66, may be accomplished with silver nitrate. The aldehyde and carboxylate may be coupled with the compounds of Schemes 2-6.

Scheme 13:

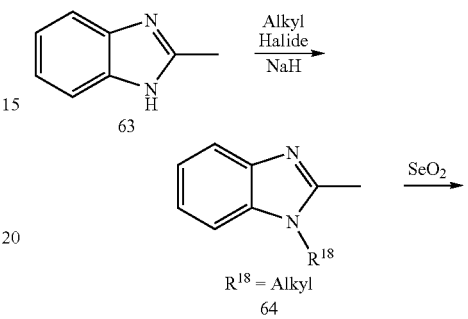

Scheme 12:

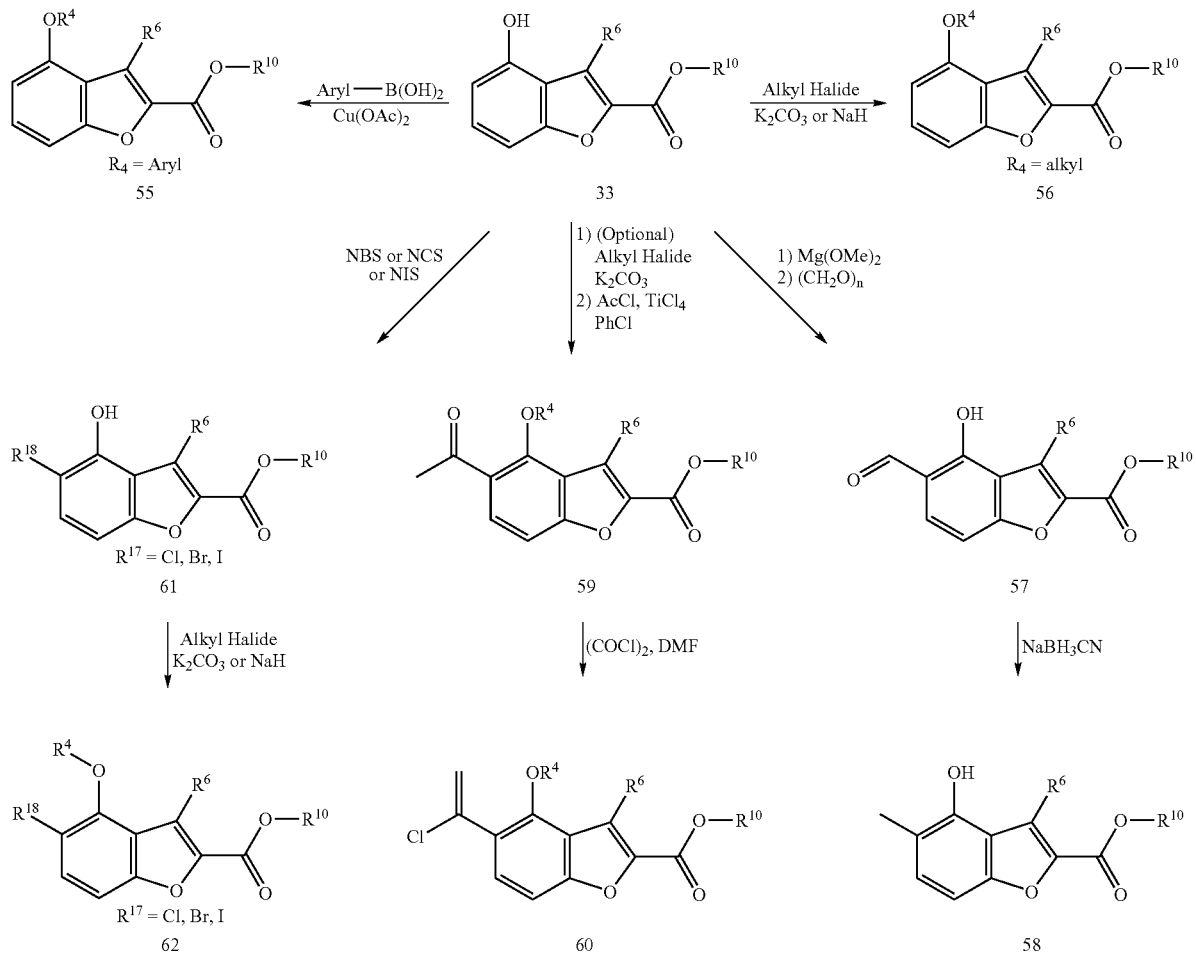

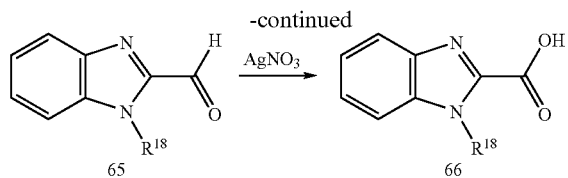

The present invention is further described in the following examples.

EXAMPLES

The following abbreviations are used throughout the experimental section:
DMSO=dimethyl sulfoxide
TFA=trifluoroacetic acid
DMF=N,N-dimethylformamide
MeOH=methanol
THF=tetrahydrofuran The term "work-up" denotes dilution of the reaction mixture with ethyl acetate, washing the combined organics over water and brine, drying over magnesium sulfate or sodium sulfate, filtration and concentration of the filtrate in vacuo.

Example 1

N-({4'-[(1-benzofuran-2-ylcarbonyl)amino]-1,1'-biphenyl-4-yl}sulfonyl)glycine

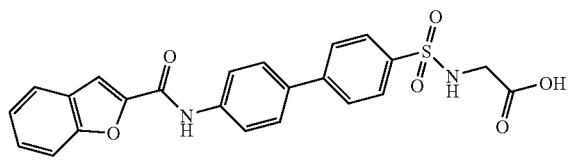

Step 1: To a flame-dried flask was added 4-aminobiphenyl-sulfonyl fluoride (0.75 g, 3 mmol) and methylene chloride (20 mL). The solution was cooled with an ice bath. Benzofuran-2-carbonyl chloride (0.54 g, 3 mmol) was added after the addition of N,N—N,N-diisopropylethylamine (1.50 equiv.). The ice bath was removed and the reaction mixture was allowed to warm to room temperature. The reaction proceeded at room temperature for 5 h. The reaction mixture was diluted with aqueous ammonium chloride solution (15 mL) and the precipitate was filtered and washed with aqueous ammonium chloride solution twice and water twice. The resulting solid was dried over vacuum and 1.05 g of N-{4'-[(1-benzofuran-2-ylcarbonyl)amino]-1,1'-biphenyl-4-yl}sulfonyl fluoride was obtained (Yield 89%).

Step 2: To a 10 ml round-bottom flask was added N-{4'-[(1-benzofuran-2-ylcarbonyl)amino]-1,1'-biphenyl-4-yl}sulfonyl fluoride (0.118 g, 0.3 mmol) and DMSO (2 mL), followed by the addition of glycine t-butyl ester hydrochloride (5.0 equiv.), N,N—N,N-diisopropylethylamine (10 equiv.), 4-(dimethylamino)pyridine (0.3 mmol) and sodium iodide (cat.). The mixture was heated to 120° C. for 5 h, cooled to room temperature and diluted with aqueous ammonium chloride solution (5 mL) and ethyl acetate (15 mL). The aqueous layer was extracted with ethyl acetate (10 mL×2). The combined organic layers were washed with brine twice, dried with anhydrous sodium sulfate and filtered. After concentration, the crude product (110 mg) was purified by flash chromatography to give N-({4'-[(1-benzofuran-2-ylcarbo-nyl)amino]-1,1'-biphenyl-4-yl}sulfonyl)glycine t-butyl ester (75 mg).

Step 3: N-({4'-[(1-benzofuran-2-ylcarbonyl)amino]-1,1'-biphenyl-4-yl}sulfonyl)glycine t-butyl ester (75 mg) was dissolved in a 95% solution of TFA in methylene chloride (5 mL). The solution was stirred at room temperature for 4 h and the solvent was removed under vacuum. The crude product was triturated with hexane/ethyl acetate (95:5) three times. The product was lyophilized with benzene to give 56 mg of N-({4'-[(1-benzofuran-2-ylcarbonyl)amino]-1,1'-biphenyl-4-yl}sulfonyl)glycine. LCMS MH$^+$ (m/z) 451. $^1$H NMR (300 MHz, DMSO-d$_6$): δ 10.54 ppm (s, 1H), 7.95-7.54 ppm (m, 11H), 7.34 ppm (dd, 1H, J$_1$=7.5 Hz, J$_2$=7.5 Hz), 7.20 ppm (dd, 1H, J$_1$=7.5 Hz, J$_2$=7.5 Hz), 3.42 ppm (d, 2H J=6.3 Hz).

Example 2

L-2-{4'-[(Benzofuran-2-carbonyl)-amino]-biphenyl-4-sulfonylamino}-3-methyl-butyric acid

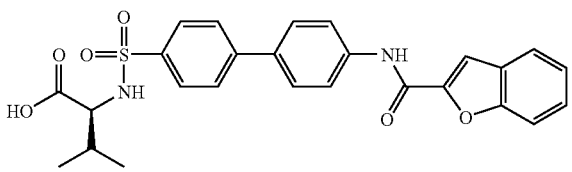

Step 1: To a 10 mL round-bottom flask was added N-{4'-[(1-benzofuran-2-ylcarbonyl)amino]-1,1'-biphenyl-4-yl}sulfonyl fluoride (0.118 g, 0.3 mmol) and DMSO (2 mL), followed by the addition of L-Valine t-butyl ester hydrochloride (5.0 equiv.), N,N-diisopropylethylamine (10 equiv.), 4-(dimethylamino)pyridine (0.3 mmol) and sodium iodide (cat.). The mixture was heated to 120° C. for 6 h and was diluted with aqueous ammonium chloride solution (5 mL) and ethyl acetate (15 mL). The aqueous layer was extracted with ethyl acetate (10 mL×2). The combined organic layers were washed with brine twice, dried with anhydrous sodium sulfate. After concentration, the crude product (110 mg) was purified with flash chromatography to give N-({4'-[(1-benzofuran-2-ylcarbonyl)amino]-1,1'-biphenyl-4-yl}sulfonyl)gly-cine t-butyl ester (65 mg).

Step 2: N-({4'-[(1-benzofuran-2-ylcarbonyl)amino]-1,1'-biphenyl-4-yl}sulfonyl)-L-valine t-butyl ester (60 mg) was dissolved in a 95% solution of TFA in methylene chloride (5 mL). The solution was stirred at room temperature for 4 h and the solvent was removed under vacuum. The crude product was triturated with hexane/ethyl acetate (95:5) three times. The product was lyophilized with benzene to give 36 mg of N-({4'-[(1-benzofuran-2-ylcarbonyl)amino]-1,1'-biphenyl-4-yl}sulfonyl)glycine. LCMS MH$^+$ (m/z) 493. $^1$H NMR (300 MHz, DMSO-d$_6$): δ 10.53 ppm (s, 1H), 7.81-7.54 ppm (m, 11H), 7.34 ppm (dd, 1H, J$_1$=8.4 Hz, J$_2$=8.4 Hz), 7.20 ppm (dd, 1H, J$_1$=8.4 Hz, J$_2$=8.4 Hz), 3.35 ppm (d, 1H J=6.0 Hz), 1.79 ppm (m, 1H), 0.63 ppm (dd, 6H, J$_1$=13.8 Hz, J$_2$=6.6 Hz).

Example 3

N-({4'-[(1H-indol-2-ylcarbonyl)amino]-1,1'-biphenyl-4-yl}sulfonyl)glycine

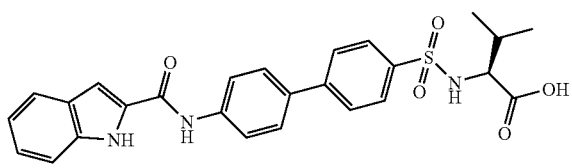

N-({4'-[(1H-indol-2-ylcarbonyl)amino]-1,1'-biphenyl-4-yl}sulfonyl)glycine was prepared according to the procedure of Example 1, using indole-2-carbonyl chloride and 4-aminobiphenylsulfonyl fluoride in Step 1, and L-valine-t-butyl ester hydrochloride in Step 2. LCMS MH+ (m/z) 492. $^1$H NMR (300 MHz, DMSO-d$_6$): δ 11.62 ppm (s, 1H), 10.20 ppm (s, 1H), 7.95-7.22 ppm (m, 11H), 7.04 ppm (dd, 1H, $J_1$=7.2 Hz, $J_2$=7.5 Hz), 6.8 ppm (dd, 1H, $J_1$=7.2 Hz, $J_2$=7.5 Hz), 3.43 ppm (d, 2H J=5.8 Hz).

Example 4

(4'-{[(5-chloro-1-benzofuran-2-yl)carbonyl]animo}-1,1'-biphenyl-4-yl)sulfonyl]-L-valine

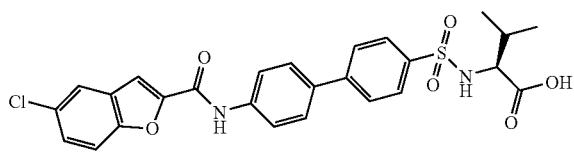

Step 1: To a 120 mL shaking vessel was added Fmoc-L-Valine-Wang resin (10 g, 0.9 mmol/g) purchased from Advanced ChemTech. The resin was rinsed with DMF (60 mL×2). A 20% solution of piperidine in DMF was added and the mixture was shaken for 20 min. The solvent was filtered and the resin washed with DMF (2×), methanol (1×) and methylene chloride (5×).

Step 2: To the resin product of Step 1 was then added anhydrous methylene chloride (60 mL), N,N-diisopropylethylamine (40.5 mmol) and 4-nitrobiphenylsulfonyl chloride (27 mmol). The mixture was shaken at room temperature for 4 h before filtration. The resin was washed with methanol followed with methylene chloride (3×).

Step 3: The resin product of Step 2 resin was rinsed with DMF (2×) and then treated with a 2 M DMF solution of tin chloride (60 mL). The mixture was shaken at room temperature overnight and the solvent and reagent were removed by filtration. The resin was washed with DMF (2×), methanol followed with methylene chloride (5×).

Step 4: The resin product of Step 3 (0.25 g) was treated with anhydrous methylene chloride (5 mL), N,N-diisopropylethylamine (1.0 mmol) and 5-chlorobenzofuran-2-carbonyl chloride (0.67 mmol). The mixture was shaken at room temperature for 2 h before filtration. The resin was washed with methylene chloride (2×), and methanol, followed by methylene chloride (3×).

Step 5: The resin product of Step 4 was then treated with a 95% solution of TFA in methylene chloride and agitated at room temperature for 2 h. The solution was collected by filtration and the solvent was removed under vacuum. The crude product was then purified by flash chromatography to give 4'-{[(5-chloro-1-benzofuran-2-yl)carbonyl]amino}-1,1'-biphenyl-4-yl)sulfonyl]-L-valine. LCMS MH+ (m/z) 528. $^1$H NMR (300 MHz, DMSO-d$_6$): δ 10.58 ppm (s, 1H), 7.80-7.59 ppm (m, 11H), 7.36 ppm (dd, 1H, $J_1$=7.2 Hz, $J_2$=1.8 Hz), 3.35 ppm (d, 1H J=6.0 Hz), 1.75 ppm (m, 1H), 0.63 ppm (dd, 6H, $J_1$=10.2 Hz, $J_2$=6.6 Hz).

Example 5

N-[(4'-{[(7-methoxy-1-benzofuran-2-yl)carbonyl]amino}-1,1'-biphenyl-4-yl)sulfonyl]-L-valine

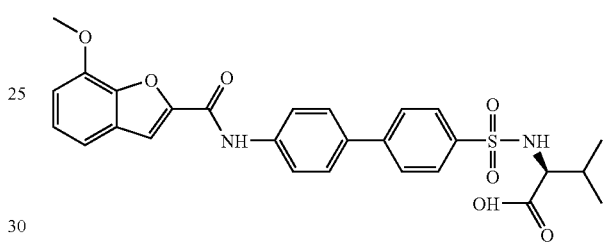

According to the procedure of Example 4, using 7-methoxybenzofurancarbonyl chloride, N-[(4'-{[(7-methoxy-1-benzofuran-2-yl)carbonyl]amino}-1,1'-biphenyl-4-yl)sulfonyl]-L-valine was prepared. LCMS MH+(m/z) 523. $^1$H NMR (300 MHz, DMSO-d$_6$): δ 10.45 ppm (s, 1H), 7.79-7.62 ppm (m, 10H), 7.14 ppm (d, 1H, J=21.0 Hz), 6.94 ppm (d, 1H, J=5.0 Hz), 3.81 ppm (s, 1H), 3.36 ppm (d, 1H J=6.0 Hz), 1.75 ppm (m, 1H), 0.63 ppm (m, 6H).

Example 6

N-[(4'-{[(5-nitro-1-benzofuran-2-yl)carbonyl]amino}-1,1'-biphenyl-4-yl)sulfonyl]-L-valine

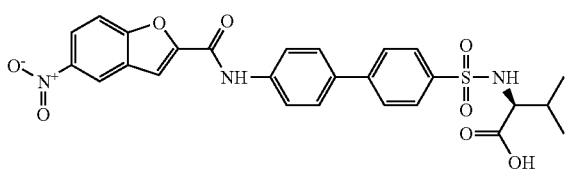

According to the procedure of Example 4, using 5-nitrobenzofurancarbonyl chloride, N-[(4'-{[(5-nitro-1-benzofuran-2-yl)carbonyl]amino}-1,1'-biphenyl-4-yl)sulfonyl]-L-valine was prepared. LCMS MH+(m/z) 538. $^1$H NMR (300 MHz, DMSO-d$_6$): δ 10.71 ppm (s, 1H), 8.69 ppm (s, 1H), 8.21 ppm (d, 1H, J=7.0 Hz), 7.84-7.61 ppm (m, 1OH), 3.38 ppm (d, 1H J=6.0 Hz), 1.75 ppm (m, 1H), 0.64 ppm (dd, 6H, $J_1$=8.7 Hz, $J_2$=6.6 Hz).

Example 7

N-[(4'-{[(5-amino-1-benzofuran-2-yl)carbonyl]amino}-1,1'-biphenyl-4-yl)sulfonyl]-L-valine

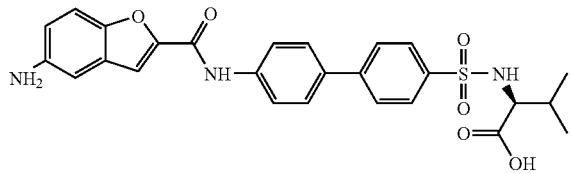

Step 1: To a 120 mL shaking vessel was added Fmoc-L-Val-Wang resin (10 g, 0.9 mmol/g) purchased from Advanced ChemTech. The resin was rinsed with DMF (60 mL×2). A 20% piperidine solution in DMF was added and the mixture was shaken for 20 min. The solvent was filtered and the resin washed with DMF (2×), methanol (1×) and methylene chloride (5×).

Step 2: To the resin was then added with anhydrous methylene chloride (60 mL), N,N-diisopropylethylamine (40.5 mmol) and 4-nitrobiphenylsulfonyl chloride (27 mmol). The mixture was shaken at room temperature for 4 h before filtration. The resin was washed with methanol followed with methylene chloride (3×).

Step 3: The obtained resin was rinsed with DMF (2×) and then treated with a 2 M DMF solution of tin chloride (60 mL). The mixture was shaken at room temperature overnight and the solvent and reagent were removed by filtration. The resin was washed with DMF (2×), methanol followed with methylene chloride (5×).

Step 4: The resin (0.6 g) was treated with anhydrous methylene chloride (10 mL), N,N-diisopropylethylamine (2.2.0 mmol) and 5-nitrobenzofuran-2-carbonyl chloride (1.50 mmol). The mixture was shaken at room temperature for 2 h before filtration. The resin was washed with methylene chloride (2×), methanol followed by methylene chloride (2×). The resin was added with tin (II) chloride solution in DMF (2 M, 12 mL) and shaken at room temperature overnight. The reagent was removed by filtration and the resin was washed with DMF (2×), methanol, and methylene chloride (5×).

Step 5: The above-obtained resin was divided into two portions of 0.3 g of resin. One portion of the resin was treated with a 95% solution of TFA in methylene chloride (5 mL) and agitated at room temperature for 2 h. The solution was collected by filtration and the solvent was removed under vacuum. The crude product was then purified by flash chromatography to give N-[(4'-{[(5-amino-1-benzofuran-2-yl)carbonyl]amino}-1,1'-biphenyl-4-yl)sulfonyl]-L-valine. LCMS MH+ (m/z) 508. $^1$H NMR (300 MHz, DMSO-$d_6$): δ 10.56 ppm (s, 1H), 7.80-7.30 ppm (m, 12H), 3.50 ppm (m, 1H), 1.90 ppm (m, 1H), 0.63 ppm (m, 6H).

Example 8

N-({4'-[({5-[(methylsulfonyl)amino]-1-benzofuran-2-yl}carbonyl)amino]-1,1'-biphenyl-4-yl}sulfonyl)-L-valine

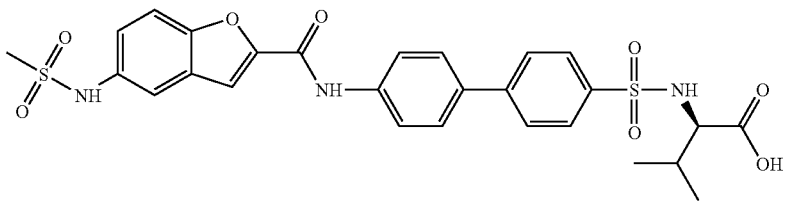

N-[(4'-{[(5-amino-1-benzofuran-2-yl)carbonyl]amino}-1,1'-biphenyl-4-yl)sulfonyl]-L-valine-Wang resin (0.3 g), from Example 7, was suspended in methylene chloride (6 mL). To the suspension was added with N,N-diisopropylethylamine (6.0 equiv.) and methanesulfonyl chloride (3.0 equiv.). The reaction was allowed to proceed at room temperature for 1 h and the reagent was removed by filtration. The resin was washed with methylene chloride (2×), methanol and methylene chloride (2×) before being treated with a 95% solution of TFA in methylene chloride (5 mL) and agitated at room temperature for 2 h. The solution was collected by filtration and the solvent was removed via vacuum. The crude product was then purified by flash chromatography to give N-({4'-[({5-[(methylsulfonyl)amino]-1-benzofuran-2-yl}carbonyl)amino]-1,1'-biphenyl-4-yl}sulfonyl)-L-valine LCMS MH+ (m/z) 586. $^1$H NMR (300 MHz, DMSO-$d_6$): δ 10.53 ppm (s, 1H), 9.59 ppm (s, 1H), 7.78-7.16 ppm (m, 12H), 3.30 ppm (m, 1H), 1.87 ppm (m, 1H), 0.63 ppm (m, 6H).

Example 9

N-{[4'-({[5-(acetylamino)-1-benzofuran-2-yl]carbonyl}amino)-1,1'-biphenyl-4-yl]sulfonyl}-L-valine

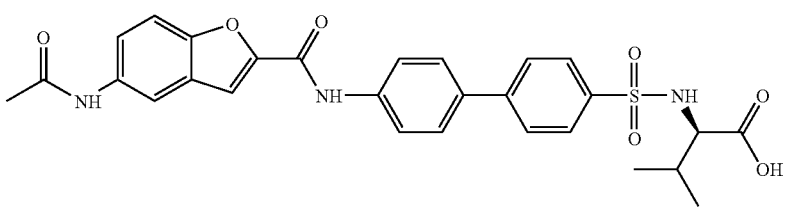

N-[(4'-{[(5-amino-1-benzofuran-2-yl)carbonyl]amino}-1,1'-biphenyl-4-yl)sulfonyl]-L-valine-Wang resin (0.3 g), from Example 7, was suspended in methylene chloride (6 mL). To the suspension was added N,N-diisopropylethylamine (6.0 equiv.) and acetyl chloride (3.0 equiv.). The reaction was allowed to proceed at room temperature for 0. h and the reagent was removed by filtration. The resin was washed with methylene chloride (2×), methanol and methylene chloride (2×) before being treated with a 95% solution of TFA in methylene chloride (5 mL) and agitated at room temperature for 2 h. The solution was collected by filtration and the solvent was removed via vacuum. The crude product was then purified by flash chromatography to give N-{[4'-({[5-(acetylamino)-1-benzofuran-2-yl]carbonyl}amino)-1,1'-biphenyl-4-yl]sulfonyl}-L-valine. LCMS MH$^+$ (m/z) 550. $^1$H NMR (300 MHz, DMSO-d$_6$): δ 10.50 ppm (s, 1H), 9.92 ppm (s, 1H), 8.00-7.34 ppm (m, 12H), 3.33 ppm (m, 1H), 1.89 ppm (s, 3 H), 1.76 ppm (m, 1H), 0.63 ppm (m, 6H).

Example 10

4'-[(5-Benzenesulfonylamino-benzofuran-2-carbonyl)-amino]-biphenyl-4-sulfonyl-L-valine

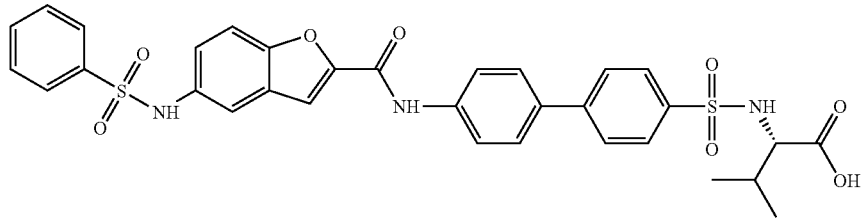

N-[(4'-{[(5-amino-1-benzofuran-2-yl)carbonyl]amino}-1,1'-biphenyl-4-yl)sulfonyl]-L-valine-Wang resin (0.3 g), from Example 7, was sulfonylated with benzenesulfonyl chloride according to the procedure of Example 8 followed by cleavage from the resin to provide 4'-[(5-benzenesulfonylamino-benzofuran-2-carbonyl)-amino]-biphenyl-4-sulfonyl-L-valine. LCMS MH$^+$ (m/z) 648. $^1$H NMR (300 MHz, CD$_3$OD): δ 7.92-7.69 ppm (m, 9H), 7.58-7.43 ppm (m, 6H), 7.22-7.18 ppm (dd, 2H, J$_1$=9.0 Hz, J$_2$=2.5 Hz), 3.64 ppm (d, 1H, J=5.0 Hz), 2.09-2.01 ppm (m, 1H), 0.97 ppm (d, 3H, J=7.0 Hz), 0.90 ppm (d, 3H, J=7.0 Hz).

Example 11

N-[(4'-{[(4-methoxy-1-benzofuran-2-yl)carbonyl]amino}-1,1'-biphenyl-4-yl)sulfonyl]-L-valine

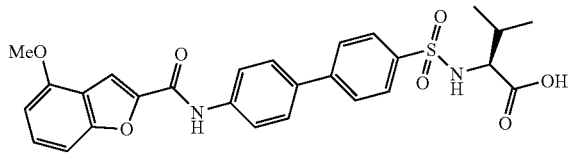

According to the procedure of Example 4, N-[(4'-{[(4-methoxy-1-benzofuran-2-yl)carbonyl]amino}-1,1'-biphenyl-4-yl)sulfonyl]-L-valine was prepared starting from Fmoc-L-Val-Wang resin and using 4-methoxybenzofuran-2-carbonyl chloride. LCMS MH$^+$ (m/z) 523. $^1$H NMR (300 MHz, DMSO-d$_6$): δ 10.62 ppm (s, 1H), 8.19-7.79 ppm (m, 9H), 7.47 ppm (dd, 1H, J$_1$=8.1 Hz, J$_2$=8.1 Hz), 7.32 ppm (d, 1H, J=8.4 Hz), 6.90 ppm (d, 1H, J=8.1 Hz), 3.96 ppm (s, 3H), 1.97 ppm (m, 1H), 0.82 ppm (dd, 6H, J$_1$=18.0 Hz, J$_2$=6.9 Hz).

Example 12

4'-[(Benzo[β]thiophene-2-carbonyl)-amino]-biphenyl-4-sulfonyl-L-valine

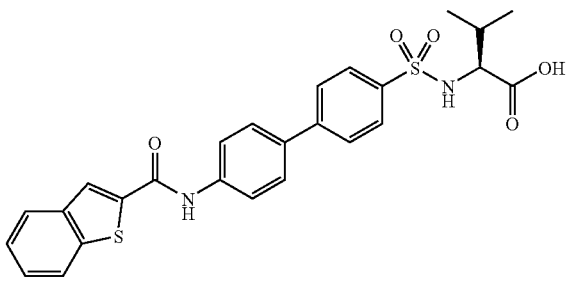

According to the procedure of Example 4, 4'-[(benzo[β]thiophene-2-carbonyl)-amino]-biphenyl-4-sulfonyl-L-valine was prepared starting from Fmoc-L-Val-Wang resin and using benzothiophenecarbonyl chloride. LCMS MH$^+$ (m/z) 509. $^1$H NMR (300 MHz, CD$_3$OD): δ 10.68 ppm (s, 1H), 8.41 ppm (s, 1H), 8.09-7.80 ppm (m, 12H), 7.54-7.47 ppm (m, 1H), 1.99-1.94 ppm (m, 1H), 0.86-0.80 ppm (m, 6H).

Example 13

4'-[(4-Benzyloxy-benzofuran-2-carbonyl)-amino]-biphenyl-4-sulfonyl-L-valine

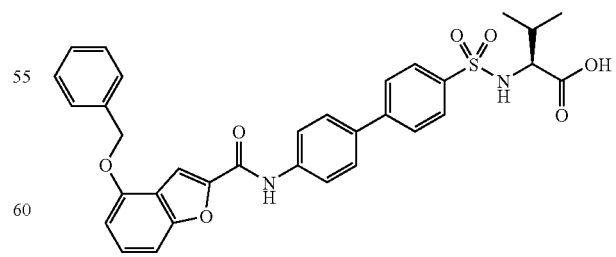

Step 1: 4-Benzyloxy-benzofuran-2-carbonyl chloride (0.61 mmol) was added to a solution of the product of Example 2A-Step 4, L-2-(4'-amino-biphenyl-4-sulfonylamino)-3-methyl-butyric acid methyl ester (0.55 mmol), and N,N-diisopropylethylamine (1.4 mmol) in 2 mL of $CH_2Cl_2$ maintained at 0° C. The reaction was allowed to warm to room temperature and stirred for 5 h. The mixture was diluted with ethyl acetate and washed with brine (3×). The organic layer was separated and dried over anhydrous sodium sulfate, filtered and then concentrated to give 350 mg of 2-{4'-[(4-benzyloxy-benzofuran-2-carbonyl)-amino]-biphenyl-4-sulfonyl}-L-valine methyl ester.

Step 2: 2-{4'-[(4-Benzyloxy-benzofuran-2-carbonyl)-amino]-biphenyl-4-sulfonyl}-L-valine methyl ester (0.24 mmol) was dissolved in THF and MeOH (2:1) (0.6 mL). A 5 M solution of LiOH in water (5.0 equiv.) was then added. The reaction was stirred at room temperature overnight. The reaction was diluted with ethyl acetate and acidified with 1N hydrochloric acid. The organic layer was washed with brine (2×), dried (magnesium sulfate), filtered and concentrated to afford 55 mg of the pure 2-{4'-[(4-benzyloxy-benzofuran-2-carbonyl)-amino]-biphenyl-4-sulfonyl}-L-valine. LCMS $MH^+$ (m/z) 599. $^1H$ NMR (300 MHz, DMSO-$d_6$): δ 10.55 ppm (s, 1H), 8.08 ppm (d, 1H, J=9.2 Hz), 7.97-7.76 ppm (m, 8 H), 7.58-7.28 ppm (m, 7H), 7.02 ppm (d, 1H, J=8.0 Hz), 5.31 ppm (s, 2H), 3.94 ppm (s, 2H), 3.58-3.52 ppm (m, 1H), 1.96-1.90 ppm (m, 1H), 0.84 ppm (d, 3H, J=7.0 Hz), 0.81 ppm (d, 3H, J=7.0 Hz).

Example 14

4'-{[4-(1-Carboxy-ethoxy)-benzofuran-2-carbonyl]-amino}-biphenyl-4-sulfonyl-L-valine

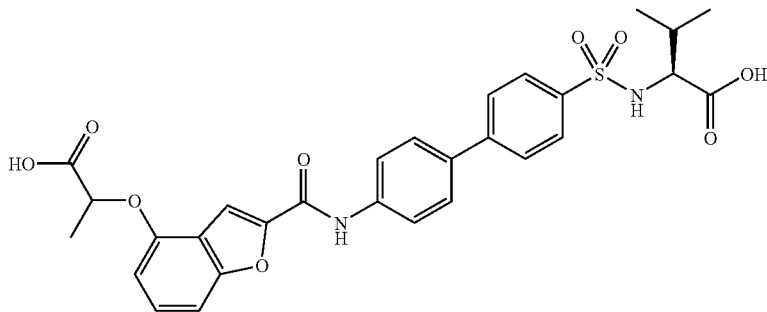

The product of Example 13-Step 1, 4'-[(4-benzyloxy-benzofuran-2-carbonyl)-amino]-biphenyl-4-sulfonyl-L-valine methyl ester (0.32 mmol), was dissolved in 3 mL of ethyl acetate-MeOH (2:1) and 10% Pd/C (20 mg) was added. The reaction was stirred under a hydrogen atmosphere for 5 h. The reaction mixture was filtered through celite and then concentrated to give 4'-[(4-hydroxy-benzofuran-2-carbonyl)-amino]-biphenyl-4-sulfonyl-L-valine methyl ester in 80% yield. The product (0.13 mmol) was dissolved in anhydrous DMF (1 mL), and $Cs_2CO_3$ (0.26 mmol) was added, followed by 2-bromo-propionic acid ethyl ester (0.13 mmol). After the reaction was complete by TLC the reaction was diluted with ethyl acetate and acidified with 1N hydrochloric acid. The organic layer was washed with brine (2×), dried (magnesium sulfate), filtered and concentrated to afford 79 mg of 4'-{[4-(1-ethoxycarbonyl-ethoxy)-benzofuran-2-carbonyl]-amino}-biphenyl-4-sulfonyl-L-valine methyl ester. The ester was taken up in THF:MeOH (2:1, 2 mL) and treated with NaOH (5N, 5 eq). The reaction was stirred overnight, diluted with ethyl acetate and acidified with 1N HCl. The organic layer was isolated and washed with brine (2×), dried (magnesium sulfate), filtered and concentrated to afford 4'-{[4-(1-carboxy-ethoxy)-benzofuran-2-carbonyl]-amino}-biphenyl-4-sulfonyl-L-valine. LCMS $MH^+$ (m/z) 581. $^1H$ NMR (300 MHz, $CD_3OD$): δ 7.91-7.68 ppm (m, 6H), 7.40-7.09 ppm (m, 3H), 6.70 ppm (d, 1H, J=8 Hz), 4.99 ppm (q, 1H, J=13 Hz), 3.69 ppm (d, 1H, J=5.8 Hz), 2.08-2.00 ppm (m, 1H), 1.69 ppm (d, 3H, J=6.9 Hz), 0.97 ppm (d, 3H, J=7.0 Hz), 0.96 ppm (d, 3H, J=7.0 Hz).

Example 15

N2-({4'-[(1-Benzofuran-2-ylcarbonyl)animo]-1,1'-biphenyl-4-yl}sulfonyl)-L-Asparagine

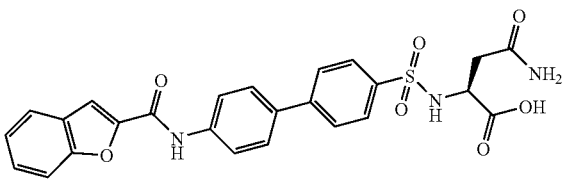

According to the procedure of Example 4, N-2-({4'-[(1-benzofuran-2-ylcarbonyl)amino]-1,1'-biphenyl-4-yl}sulfonyl)-L-asparagine was prepared from Fmoc-L-asparagine-Wang resin. LCMS $MH^+$ (m/z) 508. $^1H$ NMR (300 MHz, DMSO-$d_6$): δ 10.71 ppm (s, 1H), 8.16-7.50 ppm (m, 12H), 7.39 ppm (dd, 1H, $J_1$=7.5 Hz, $J_2$=7.5 Hz), 3.95 ppm (m, 1H), 2.34 ppm (d, 2H, J=6.0 Hz ).

Example 16

L-2-{4'-[(Benzofuran-2-carbonyl)-amino]-biphenyl-4-sulfonylamino}-3-methyl-butyric acid

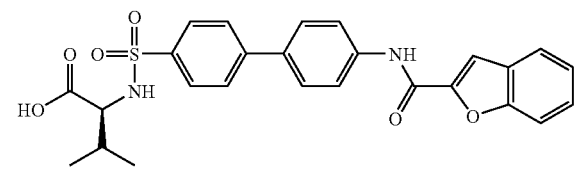

Step 1: To a stirred solution of 4-nitrobiphenyl (50.00 g, 0.25 mol) in chloroform (750 mL) was added dropwise at room temperature chlorosulfonic acid (17 mL, 0.3 mol). The reaction mixture was stirred at 60° C. for 6 h. The white precipitate formed was collected by filtration and washed with cold chloroform. The product was air dried to give 31.00 g of 4-nitrobiphenylsulfonic acid (Yield 61%).

Step 2: The crude 4-nitrobiphenylsulfonic acid obtained above (31.00 g, 0.11 mol) was diluted with thionyl chloride (100 mL) and treated with a catalytic amount of DMF (0.1 mL). The reaction mixture was refluxed for 4 h, cooled to room temperature, and concentrated under vacuum. To remove the residual thionyl chloride, toluene was added and was concentrated to give 29.00 g (yield 84%) of the desired product, 4'-nitro-biphenyl-4-sulfonyl chloride.

Step 3: To a dry round-bottomed flask was added 4'-nitro-biphenyl-4-sulfonyl chloride (5.09 g), anhydrous dichloromethane (50 mL), and L-valine methyl ester hydrochloride (1.10 equiv.). The mixture was cooled with an ice bath before the addition of N,N-diisopropylethylamine (2.50 equiv.). The ice bath was removed and the reaction mixture was warmed up to room temperature and stirred at room temperature for 2 h. The reaction was then diluted with ethyl acetate (100 mL) and saturated ammonium chloride solution (20 mL). The organic layer and aqueous layer were separated and the aqueous layer was extracted with ethyl acetate (30 mL×2). The combined organic layers were washed with brine and dried over anhydrous sodium sulfate, filtered and evaporated under vacuum to provide 6.31 g of product, L-3-methyl-2-(4'-nitro-biphenyl-4-sulfonylamino)-butyric acid methyl ester (yield 95%).

Step 4: The product obtained in Step 3 above was dissolved in ethyl acetate (120 mL). To the solution was added $SnCl_2$ dihydrate (4.0 equiv.). The reaction was allowed to proceed at room temperature for 6 h. The reaction mixture was cooled with a water bath, and 2 M sodium carbonate solution (30 mL) and ethyl acetate (100 mL) were added. The mixture was transferred to a centrifuge bottle and centrifuged for 20 min. The supernatant was separated and washed with water and brine and dried over anhydrous sodium sulfate. After filtration and concentration, 5.52 g of product L-2-(4'-amino-biphenyl-4-sulfonylamino)-3-methyl-butyric acid methyl ester was obtained.

Step 5: To an oven-dried flask was added L-2-(4'-amino-biphenyl-4-sulfonylamino)-3-methyl-butyric acid methyl ester (5.52 g), anhydrous methylene chloride (100 mL), and N,N-diisopropylethylamine (2.0 equiv.). The solution was cooled with an ice bath and 2-benzofurancarbonyl chloride (1.0 equiv.) was then added. The reaction proceeded at 0° C. for 4 h. Water was added and the precipitate was filtrated and washed with cold ether. After drying in vacuo, the product L-2-{4'-[(benzofuran-2-carbonyl)-amino]-biphenyl-4-sulfonylamino}-3-methyl-butyric acid methyl ester was obtained as a white solid (6.98 g, yield 90%).

Step 6: The methyl ester product of Step 5 above was dissolved in THF (150 mL). Methanol (100 mL) and water (100 mL) were added followed by lithium hydroxide monohydrate (3.60 g). The reaction mixture was stirred at room temperature until no starting material remained. The reaction mixture was cooled in an ice bath and acidified with concentrated hydrochloric acid to ~pH 3. The resulting precipitate was filtered and washed with cold water and cold ether to provide 5.65 g of L-2-{4'-[(benzofuran-2-carbonyl)-amino]-biphenyl-4-sulfonylamino}-3-methyl-butyric acid.

Example 17

N-({4'-[(1-Benzofuran-2-ylcarbonyl)amino]-1,1'-biphenyl-4-yl}sulfonyl)-L-Histidine

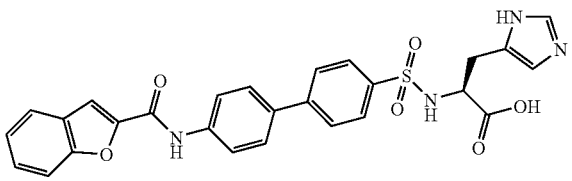

According to the procedure of Example 4, N-({4'-[(1-benzofuran-2-ylcarbonyl)amino]-1,1'-biphenyl-4-yl}sulfonyl)-L-histidine was prepared from Fmoc-N-Boc-L-histidine-Wang resin. LCMS MH$^+$ (m/z) 531. $^1$H NMR (300 MHz, DMSO-d$_6$): δ 10.72 ppm (s, 1H), 8.25 (s, 1H), 7.98 ppm (d, 1H, J=9.3 Hz), 7.86-7.73 ppm (m, 10H), 7.44 ppm (dd, 1H, J$_1$=9.6 Hz, J$_2$=7.8 Hz), 7.38 ppm (dd, 1H, J$_1$=7.2 Hz, J$_2$=7.2 Hz), 6.68 ppm (s, 1H), 6.54 ppm (s, 1 H), 2.85 ppm (d, 2H, J=5.1 Hz).

Example 18

N-({4'-[(1-Benzofuran-2-ylcarbonyl)amino]-1,1'-biphenyl-4-yl}sulfonyl)-L-leucine

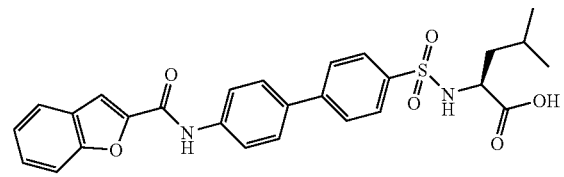

According to the procedure of Example 4, N-({4'-[(1-benzofuran-2-ylcarbonyl)amino]-1,1'-biphenyl-4-yl}sulfonyl)-L-leucine was prepared from Fmoc-L-leucine-Wang resin. LCMS MH$^+$ (m/z) 507. $^1$H NMR (300 MHz, DMSO-$_6$): δ 10.75 ppm (s, 1H), 8.33 (s, 1H), 7.98 ppm (d, 1H, J=9.3 Hz), 7.84-7.73 ppm (m, 10H), 7.52 ppm (dd, 1H, J$_1$=7.2 Hz, J$_2$=7.2 Hz), 7.38 ppm (dd, 1H, J$_1$=7.5 Hz, J$_2$=7.5 Hz), 3.23 ppm (m, 1H), 1.45 (m, 2H), 0.81 (m, 7H).

Example 19

L-2-{4'-[(Benzofuran-2-carbonyl)-amino]-biphenyl-4-sulfonylamino}-3-methyl-butyric acid

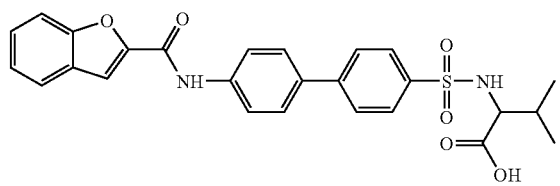

Step 1: To 0.838 g of L-valine methyl ester hydrochloride in 15 mL of dichloromethane, cooled in an ice bath, 1.34 g of 4-bromobenzenesulfonyl chloride was added followed by 2.79 mL of triethylamine. The mixture was stirred at room temperature overnight and then diluted with dichloromethane. The dichloromethane was washed with water and brine, dried over Na₂SO₄, filtered, and concentrated in vacuo to provide 1.77 g of methyl N-[(4-bromophenyl)sulfonyl]-L-valinate as a colorless solid. Yield ~100%. m.p. 88-90° C.; MS: 348.2 (M–H)⁻.

Step 2: A mixture of 0.175 g (0.5 mmol) of methyl N-[(4-bromophenyl)sulfonyl]-L-valinate, 0.25 g (1.5 mmol) of 4-nitrophenylboronic acid, 0.087 g of tetrakis(triphenylphosphine)palladium and 8 mL of saturated sodium bicarbonate in 8 mL of ethylene glycol dimethyl ether were refluxed for 2 h, then cooled to room temperature. To the reaction was added 50 mL of ethyl acetate and 40 mL of water. The water layer was extracted with ethyl acetate. The combined ethyl acetate layers was dried over Na₂SO₄, filtered, and concentrated in vacuo. The crude product was purified by column chromatography, eluting with hexane:ethyl acetate (2:1) to provide 0.159 g of methyl N-[(4'-nitro-1,1'-biphenyl-4-yl)sulfonyl]-L-valinate as a yellow solid. Yield 81%. m.p. 144-146° C.; MS: 391.0(M–H)⁻.

Step 3: To 1.72 g of 4-bromoaniline was added to 1.89 g of benzofuran-2-carboxylic acid chloride in 35 mL of dichloromethane cooled in ice bath, followed by the addition of 4.9 mL of triethylamine. The reaction was stirred at room temperature overnight and then diluted with dichloromethane. The dichloromethane layer was washed with water, 1N HCl, water and brine, dried over Na₂SO₄, filtered, and concentrated in vacuo to provide 2.61 g of N-(4-bromophenyl)-1-benzofuran-2-carboxamide as a yellow solid. Yield 72%. m.p. 178-180° C.; MS: 314.1(M–H)⁻.

Step 4: A mixture of 0.74 g of N-[(4-bromophenyl)-1-benzofuran-2-carboxamide, 0.653 g of bis(pinacolato)diboron, 0.689 g of potassium acetate and 0.096 g of bis(diphenyl phoshino)ferrocene] dichloropalladium (II) dichloromethane complex in 15 mL of DMSO were heated at ~80° C. for 2 h, then cooled to room temperature. Then 20 mL of toluene, 40 mL of ethyl acetate and 40 mL of water were added to the reaction. The water layer was extracted with 30 mL of ethyl acetate. The combined organic layers were filtered and washed 4 times with 40 mL of water, dried over Na₂SO₄, filtered and concentrated in vacuo to obtain 0.34 g of the boronate ester as a black oily compound.

To the above product, 0.273 g of methyl N-[(4-bromophenyl)sulfonyl]-L-valinate, 0.13 g of tetrakis(triphenylphosphine)palladium, 7.5 mL saturated sodium bicarbonate and 12 mL of ethylene glycol dimethyl ether were added and the resulting mixture was refluxed for 2 h. The reaction was then cooled to room temperature. Ethyl acetate and water were added to the reaction and the mixture was filtered. The organic layer was washed with water and brine, dried over Na₂SO₄, filtered and concentrated in vacuo. The product was purified by column chromatography, eluting with hexane: ethyl acetate (2:1) to provide 0.112 g of methyl N-({4'-[(1-benzofuran-2-ylcarbonyl)amino]-1,1'-biphenyl-4-yl}sulfonyl)-L-valinate as a white solid. Yield 28.4%. m.p. 195-200° C.; MS: 507.1(M+H)⁺.

Step 5: According to the procedure of Example 2A, Step 6, methyl N-({4'-[(1-benzofuran-2-ylcarbonyl)amino]-1,1'-biphenyl-4-yl}sulfonyl)-L-valinate was converted into L-2-{4'-[(benzofuran-2-carbonyl)-amino]-biphenyl-4-sulfonylamino}-3-methyl-butyric acid.

Example 20

L-2-{4'-[(4-Cyano-3-methyl-benzofuran-2-carbonyl)-amino]-biphenyl-4-sulfonylamino}-3-methyl-butyric acid

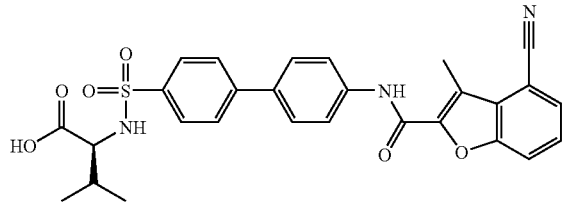

Step 1: To 4-hydroxy-3-methyl-benzofuran-2-carboxylic acid ethyl ester (6.336 g, 28.8 mmol, 1 eq) in methylene chloride (120 mL) in a round bottom flask under nitrogen was added N,N-diisopropylethylamine (12.54 mL, 72.0 mmol, 2.5 eq). The mixture was cooled to 0° C. and trifluoromethanesulfonic anhydride (7.27 mL, 43.2 mmol, 1.5 eq) was added dropwise. After stirring for one hour, the mixture was diluted with methylene chloride (350 mL), and washed with water twice. The organic layer was dried and evaporated in vacuo to give 3-methyl-4-trifluoromethanesulfonyloxy-benzofuran-2-carboxylic acid ethyl ester suitable for use without purification. ¹H NMR (400 MHz, CDCl₃) δ ppm 1.5 (t, J=7.1 Hz, 3 H) 2.8 (s, 3 H) 4.5 (q, J=7.2 Hz, 2 H) 7.2 (d, J=9.6 Hz, 1 H) 7.5 (t, J=8.2 Hz, 1 H) 7.6 (d, J=8.3 Hz, 1 H).

Step 2: To 3-methyl-4-trifluoromethanesulfonyloxy-benzofuran-2-carboxylic acid ethyl ester (721 mg, 2.0 mmol, 1 eq) in 10 mL of DMF under nitrogen was added 322 mg of Zn(CN)₂ (2.74 mmol, 1.37 eq), and 123 mg of Pd(PPh₃)₄ (0.1 mmol, 0.05 eq). The reaction mixture was heated to 85° C. The reaction was complete in 2.5 h by TLC. After work up and column chromatography eluting with 5% ethyl acetate/hexane, 4-cyano-3-methyl-benzofuran-2-carboxylic acid ethyl ester was obtained in 80% yield (367 mg). ¹H NMR (400 MHz, CD₃OD) δ ppm 1.6 (t, J=7.1 Hz, 3 H) 3.0 (s, 3 H) 4.6 (q, J=7.2 Hz, 2 H) 7.8 (dd, J=8.3, 7.6 Hz, 1 H) 7.9(m, 1 H) 8.1 (dd, J=8.3, 1.0 Hz, 1 H).

Step 3: To 550 mg of 4-cyano-3-methyl-benzofuran-2-carboxylic acid ethyl ester (2.4 mmol) in 15 mL of THF was added 5 mL of MeOH and 5 mL of 1N LiOH. The reaction was complete in 2 h. After quenching with 5 mL of 1 N HCl and work up, 4-cyano-3-methyl-benzofuran-2-carboxylic acid was obtained in quantitative yield. ¹H NMR (400 MHz, DMSO-d₆) δ ppm 2.7 (s, 3 H) 7.7 (m, 1 H) 7.9 (d, J=7.3 Hz, 1 H) 8.1 (m, 1 H).

Step 4: To a mixture of 4-cyano-3-methyl-benzofuran-2-carboxylic acid (525 mg, 2.6 mmol, 1 eq), 1-(3-dimethylaminopropyl)-3-ethylcarbodiimide hydrochloride (EDCI, 752 mg, 3.9 mmol, 1.5 eq), and 4-(dimethylamino)pyridine,(335 mg, 2.7 mmol, 1 eq) in 15 mL of DMF under nitrogen was added L-2-(4'-amino-biphenyl-4-sulfonylamino)-3-methyl-butyric acid methyl ester, the product of Example 2A, Step 4. The mixture was stirred at 100° C. for 8 h. After work up and column chromatography (20% ethyl acetate/hexane), L-2-{4'-[(4-cyano-3-methyl-benzofuran-2-carbonyl)-amino]-biphenyl-4-sulfonylamino}-3-methyl-butyric acid methyl ester was obtained (643 mg, 1.18 mmol) in 45% yield. ¹H NMR (400 MHz, DMSO-d₆) δ ppm 0.8 (dd, J=14.7, 6.8 Hz, 6 H) 1.9 (m, 1 H) 2.8 (s, 3 H) 3.3 (s, 3 H) 3.6 (dd, J=9.3, 7.1 Hz, 1 H)

7.7 (dd, J=8.3, 7.6 Hz, 1 H) 7.8 (dd, J=8.8, 3.3 Hz, 4 H) 7.9 (m, 3 H) 8.0 (d, J=8.8 Hz, 2 H) 8.1 (m, 1 H) 8.3 (d, J=9.6 Hz, 1 H) 10.8 (s, 1 H).

Step 5: The methyl ester obtained in Step 4 (183 mg) was dissolved in THF (8 mL) and methanol (3 mL) and 1N LiOH (1 mL) were added. The reaction mixture was stirred at room temperature until the reaction was complete (~1-2 days). The reaction mixture was then acidified with 1N hydrochloric acid to ~pH 4. The resulting mixture was extracted with ethyl acetate and the combined organic layers were dried, filtered and concentrated in vacuo to provide 2-{4'-[(4-cyano-3-methyl-benzofuran-2-carbonyl)-amino]-biphenyl-4-sulfonylamino}-3-methyl-butyric acid in quantitative yield. $^1$H NMR (400 MHz, DMSO-$_6$) δ ppm 0.8 (dd, J=29.7, 6.7 Hz, 6 H) 2.0 (m, 1 H) 2.8 (s, 3 H) 3.3 (s, 1 H) 7.7 (m, 1 H) 7.8 (m, 6 H) 7.9 (d, J=7.1 Hz, 1 H) 8.0 (d, J=8.8 Hz, 2 H) 8.1 (d, J=8.6 Hz, 1 H) 10.8 (s, 1 H).

Example 21

L-3-Methyl-2-{4'-[(3-methyl-4-prop-1-ynyl-benzofuran-2-carbonyl)-amino]-biphenyl-4-sulfonylamino}-butyric acid

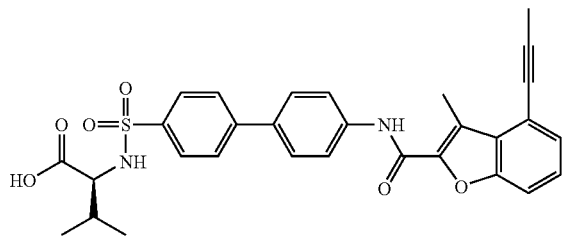

Step 1: To 3-methyl-4-trifluoromethanesulfonyloxy-benzofuran-2-carboxylic acid ethyl ester (550 mg, 1.6 mmol, 1 eq), the product of Example 20, Step 1, in 5 mL of toluene under nitrogen was added 60 mg of Pd(PPh$_3$)$_4$ (0.05 mmol, 0.03 eq) and tributyl-prop-1-ynyl-stannane (0.55 mL, 1.8 mmol, 1.13 eq). The resulting reaction mixture was heated to reflux for 18 h. After work up and column chromatography (3% ethyl acetate/hexane), 3-methyl-4-prop-1-ynyl-benzofuran-2-carboxylic acid ethyl ester was obtained in 14% yield (56 mg). $^1$H NMR (400 MHz, CDCl$_3$) δ ppm 1.4 (t, J=7.1 Hz, 3 H) 2.1 (s, 3 H) 2.8 (s, 3 H) 4.5 (q, J=7.1 Hz, 2 H) 7.3 (m, 2 H) 7.5 (dd, J=7.6, 1.8 Hz, 1 H).

Step 2: According to the procedure of Example 20, Step 3, 3-methyl-4-prop-1-ynyl-benzofuran-2-carboxylic acid ethyl ester was hydrolyzed to give 3-methyl-4-prop-1-ynyl-benzofuran-2-carboxylic acid in 99% yield. $^1$H NMR (400 MHz, CDCl$_3$) δ ppm 2.2 (s, 3 H) 2.9 (s, 3 H) 7.3 (m, 2 H) 7.5 (m, 1 H).

Step 3: To a mixture of 3-methyl-4-prop-1-ynyl-benzofuran-2-carboxylic acid (46 mg, 0.21 mmol, 1 eq), was added L-2-(4'-amino-biphenyl-4-sulfonylamino)-3-methyl-butyric acid methyl ester (79 mg, 0.22 mmol, 1 eq), the product of Example 2A, Step 4, and benzotriazol-1-yloxytris(dimethylamino)phosphonium hexafluorophosphate (BOP, 127 mg, 0.29 mmol, 1.4 eq) in 5 mL DMF under nitrogen was added 0.05 mL of N,N-diisopropylethylamine (0.29 mmol, 1.4 eq). The reaction mixture was stirred at room temperature for 18 h. After work up and column chromatography (25% ethyl acetate/hexane), L-3-methyl-2-{4'-[(3-methyl-4-prop-1-ynyl-benzofuran-2-carbonyl)-amino]-biphenyl-4-sulfonylamino}-butyric acid methyl ester was obtained in 45% yield (55 mg). $^1$H NMR (400 MHz, DMSO-d$_6$) δ ppm 0.8 (dd, J=14.8, 6.7 Hz, 6 H) 1.9 (m, 1 H) 2.2 (dd, 3 H) 2.8 (s, 3 H) 3.3 (s, 3 H) 3.6 (dd, J=9.3, 7.1 Hz, 1 H) 7.4 (d, J=7.1 Hz, 1 H) 7.5 (m, 1 H) 7.7 (d, J=7.6 Hz, 1 H) 7.8 (t, J=8.8 Hz, 4 H) 7.9 (m, 2 H) 8.0 (d, J=8.8 Hz, 2 H) 8.3 (d, J=9.6 Hz, 1 H) 10.6 (s, 1 H).

Step 4: According to the procedure of Example 20, Step 5, L-3-methyl-2-{4'-[(3-methyl-4-prop-1-ynyl-benzofuran-2-carbonyl)-amino]-biphenyl-4-sulfonylamino}-butyric acid methyl ester was hydrolyzed to give L-3-methyl-2-{4'-[(3-methyl-4-prop-1-ynyl-benzofuran-2-carbonyl)-amino]-biphenyl-4-sulfonylamino}-butyric acid in quantitative yield. $^1$H NMR (400 MHz, DMSO-d$_6$) δ ppm 0.8 (dd, J=12.4, 6.8 Hz, 6 H) 1.9 (m, 1 H) 2.2 (s, 3 H) 2.8 (s, 3 H) 3.6 (dd, J=9.3, 6.1 Hz, 1 H) 7.4 (d, J=6.8 Hz, 1 H) 7.5 (m, 1 H) 7.7 (d, J=8.3 Hz, 1 H) 7.8 (d, J=8.8 Hz, 2 H) 7.9 (m, 4 H) 8.0 (d, J=8.8 Hz, 2 H) 8.1 (d, J=9.6 Hz, 1 H) 10.6 (s, 1 H).

Example 22

L-2-(4'-{[4-(3-Methoxy-prop-1-ynyl)-3-methyl-benzofuran-2-carbonyl]-amino}-biphenyl-4-sulfonylamino)-3-methyl-butyric acid

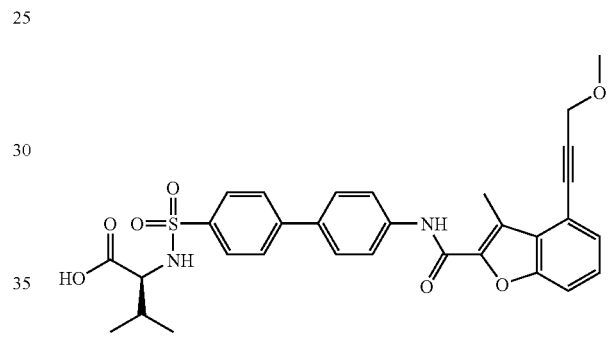

Step 1: To the product of Example 20, Step 1, 3-methyl-4-trifluoromethanesulfonyloxy-benzofuran-2-carboxylic acid ethyl ester (860 mg, 2.4 mmol, 1 eq), in 7 mL of DMF under nitrogen was added 98 mg of PdCl$_2$(PPh$_3$)$_2$ (0.14 mmol, 0.06 eq), 0.42 mL of 3-methoxy-propyne (5.0 mmol, 2.1 eq) and 1.36 mL of triethylamine (9.7 mmol, 4.0 eq). The reaction mixture was heated to 90° C. for 18 h. After work up and column chromatography (4% ethyl acetate/hexane), 4-(3-methoxy-prop-1-ynyl)-3-methyl-benzofuran-2-carboxylic acid ethyl ester was obtained in 53% yield (343 mg). $^1$H NMR (400 MHz, CDCl$_3$) δ ppm 1.4 (t, J=7.2 Hz, 3 H) 2.8 (t, 3 H) 3.5 (s, 3 H) 4.4 (s, 2 H) 4.5 (q, J=7.2 Hz, 2 H) 7.4 (m, 2 H) 7.5 (dd, J=7.7, 1.6 Hz, 1 H)

Step 2: According to the procedure of Example 20, Step 3, 4-(3-methoxy-prop-1-ynyl)-3-methyl-benzofuran-2-carboxylic acid ethyl ester was hydrolyzed to give 4-(3-methoxy-prop-1-ynyl)-3-methyl-benzofuran-2-carboxylic acid in 100% yield. $^1$H NMR (400 MHz, CD$_3$OD) δ ppm 2.7 (s, 3 H) 3.4 (s, 3 H) 4.3 (s, 2 H) 7.3 (m, 2 H) 7.4 (dd, J=7.8, 1.5 Hz, 1 H)

Step 3: According to the procedure of Example 21, Step 3, 4-(3-methoxy-prop-1-ynyl)-3-methyl-benzofuran-2-carboxylic acid was coupled with L-2-(4'-amino-biphenyl-4-sulfonylamino)-3-methyl-butyric acid methyl ester to give L-2-(4'-{[4-(3-methoxy-prop-1-ynyl)-3-methyl-benzofuran-2-carbonyl]-amino}-biphenyl-4-sulfonylamino)-3-methyl-butyric acid methyl ester in 88% yield. $^1$H NMR (400 MHz, CDCl$_3$) δ ppm 0.9 (dd, J=32.5, 6.7 Hz, 6 H) 2.1 (m, 1 H) 2.9 (s, 3 H) 3.4 (s, 3 H) 3.5 (s, 3 H) 3.8 (dd, J=10.1, 5.1 Hz, 1 H)

4.4 (s, 2 H) 5.1 (d, J=10.1 Hz, 1 H) 7.4 (m, 2 H) 7.5 (m, 1 H) 7.6 (d, J=8.6 Hz, 2 H) 7.7 (d, J=8.6 Hz, 2 H) 7.9 (dd, J=17.8, 8.7 Hz, 4 H) 8.4 (s, 1 H).

Step 4: According to the procedure of Example 20, Step 5, L-2-(4'-{[4-(3-methoxy-prop-1-ynyl)-3-methyl-benzofuran-2-carbonyl]-amino}-biphenyl-4-sulfonylamino)-3-methyl-butyric acid methyl ester was hydrolyzed to give L-2-(4'-{[4-(3-methoxy-prop-1-ynyl)-3-methyl-benzofuran-2-carbonyl]-amino}-biphenyl-4-sulfonylamino)-3-methyl-butyric acid in 100% yield. $^1$H NMR (400 MHz, DMSO-$d_6$) δ ppm 0.8 (dd, J=12.0, 6.4 Hz, 6 H) 2.0 (dd, J=13.4, 8.1 Hz, 1 H) 2.8 (s, 3 H) 3.4 (s, 3 H) 3.6 (m, 1 H) 4.4 (s, 2 H) 7.5 (m, 2 H) 7.8 (m, 7 H) 8.0 (m, 3 H) 10.6 (s, 1 H) 12.6 (s, 1 H).

Example 23

2-{4'-[(4-Cyclopropylethynyl-3-methyl-benzofuran-2-carbonyl)-amino]-biphenyl-4-sulfonylamino}-3-methyl-butyric acid

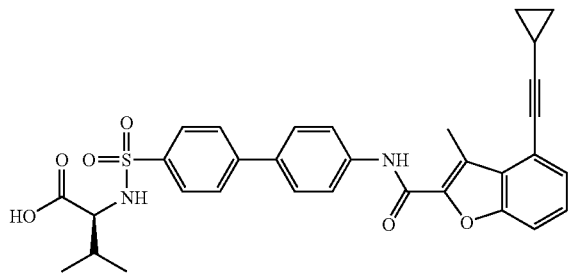

Step 1: To the product of Example 20, Step 1, 3-methyl-4-trifluoromethanesulfonyloxy-benzofuran-2-carboxylic acid ethyl ester (1.8 g, 5.1 mmol, 1 eq), in 2 mL of DMF under nitrogen was added 200 mg of PdCl$_2$(PPh$_3$)$_2$ (0.28 mmol, 0.05 eq), Et$_3$N (2.85 mL, 20.4 mmol, 4 eq), cyclopropylethynyl-trimethylsilane (1 g, 7.2 mmol, 1.4 eq), and tetrabutylammonium fluoride (5.1 mL, 1.0 M in THF, 5.1 mmol, 1 eq). The reaction mixture was sealed and heated to 80° C. for 12 h. After workup and column chromatography (2% ethyl acetate/hexane), 4-cyclopropylethynyl-3-methyl-benzofuran-2-carboxylic acid ethyl ester was obtained in 15% yield (202.6 mg). $^1$H NMR (400 MHz, CD$_3$OD) δ ppm 0.7 (m, 2 H) 0.9 (m, 2 H) 1.3 (t, J=7.1 Hz, 3 H) 1.5 (m, 1 H) 2.7 (s, 3 H) 4.3 (q, J=7.2 Hz, 2 H) 7.2 (m, 1 H) 7.3 (dd, J=8.3, 7.3 Hz, 1 H) 7.4 (m, 1 H).

Step 2: According to the procedure of Example 20, Step 3, 4-cyclopropylethynyl-3-methyl-benzofuran-2-carboxylic acid ethyl ester was hydrolyzed to give 4-cyclopropylethynyl-3-methyl-benzofuran-2-carboxylic acid in quantitative yield. $^1$H NMR (400 MHz, DMSO-$d_6$) δ ppm 0.8 (m, 2 H) 0.9 (m, 2 H) 1.6 (m, 1 H) 2.7 (s, 3 H) 7.3 (dd, J=7.6, 1.0 Hz, 1 H) 7.4 (m, 1 H) 7.6 (dd, J=8.3, 1.0 Hz, 1 H).

Step 3: According to the procedure of Example 21, Step 3, coupling of 4-cyclopropylethynyl-3-methyl-benzofuran-2-carboxylic acid with L-2-(4'-amino-biphenyl-4-sulfonylamino)-3-methyl-butyric acid methyl ester gave L-2-{4'-[(4-cyclopropylethynyl-3-methyl-benzofuran-2-carbonyl)-amino]-biphenyl-4-sulfonylamino}-3-methyl-butyric acid methyl ester in 54% yield. $^1$H NMR (400 MHz, CDCl$_3$) δ ppm 0.9 (m, 10 H) 1.6 (m, 1 H) 2.1 (m, 1 H) 2.9 (s, 3 H) 3.4 (s, 3 H) 3.8 (dd, J=10.1, 5.1 Hz, 1 H) 5.1 (d, J=10.1Hz, 1 H) 7.3 (m, 2 H) 7.4 (m, 1 H) 7.6 (d, J=8.8 Hz, 2 H) 7.7 (d, J=8.6 Hz, 2 H) 7.9 (dd, J=18.8, 8.7 Hz, 4 H) 8.4 (s, 1 H).

Step 4: According to the procedure of Example 20, Step 5, L-2-{4'-[(4-cyclopropylethynyl-3-methyl-benzofuran-2-carbonyl)-amino]-biphenyl-4-sulfonylamino}-3-methyl-butyric acid methyl ester was hydrolyzed in quantitative yield to provide L-2-{4'-[(4-cyclopropylethynyl-3-methyl-benzofuran-2-carbonyl)-amino]-biphenyl-4-sulfonylamino}-3-methyl-butyric acid. $^1$H NMR (400 MHz, DMSO-$d_6$) δ ppm 0.8 (m, J=12.6, 6.6 Hz, 8 H) 1.0 (m, 2 H) 1.7 (m, 1 H) 2.0 (m, 1 H) 2.8 (s, 3 H) 3.6 (dd, J=9.1, 5.8 Hz, 1 H) 7.3 (dd, J7.6, 0.8 Hz, 1 H) 7.5 (m, 1 H) 7.6 (d, J=7.3 Hz, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.6 (s, 1 H) 12.6 (s, 1 H).

Example 24

L-2-(4'-{[4-(2-Cyclopropyl-ethyl)-3-methyl-benzofuran-2-carbonyl]-amino}-biphenyl-4-sulfonylamino)-3-methyl-butyric acid

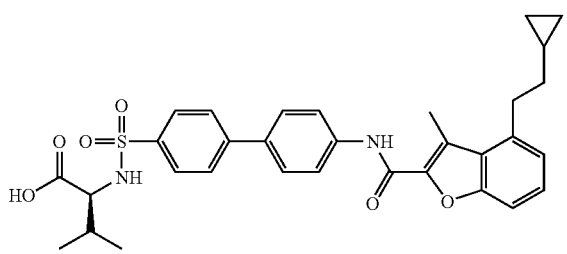

Step 1: To a solution of the product of Example 23, Step 3, L-2-{4'-[(4-cyclopropylethynyl-3-methyl-benzofuran-2-carbonyl)-amino]-biphenyl-4-sulfonylamino}-3-methyl-butyric acid methyl ester (132 mg, 0.23 mmol), in 10 mL of THF under nitrogen was added 5% Pd/C (32 mg). A balloon of hydrogen was attached to the reaction mixture. After 36 h the reaction was filtered through celite, and the filtrate was concentrated in vacuo. The crude product was purified using preparative HPLC to give L-2-(4'-{[4-(2-cyclopropyl-ethyl)-3-methyl-benzofuran-2-carbonyl]-amino}-biphenyl-4-sulfonylamino)-3-methyl-butyric acid methyl ester in 56% yield. $^1$H NMR (400 MHz, DMSO-$d_6$) δ ppm 0.1 (d, J=4.8 Hz, 2 H) 0.4 (dd, J=8.0, 1.6 Hz, 2 H) 0.8 (dd, J=14.7, 6.8 Hz, 6 H) 1.6 (m, 2 H) 1.9 (m, 1 H) 2.8 (s, 3 H) 3.1 (m, 2 H) 3.4 (s, 3 H) 3.6 (m, 1 H) 7.1 (d, J=7.3 Hz, 1 H) 7.4 (m, 1 H) 7.5 (m, 1 H) 7.8 (dd, J=10.2, 8.7 Hz, 4 H) 7.9 (m, 2 H) 8.0 (d, J=8.8 Hz, 2 H) 8.3 (d, J=10.1 Hz, 1 H) 10.5 (s, 1 H)

Step 2: According to the procedure of Example 20, Step 5, L-2-(4'-{[4-(2-cyclopropyl-ethyl)-3-methyl-benzofuran-2-carbonyl]-amino}-biphenyl-4-sulfonylamino)-3-methyl-butyric acid methyl ester was hydrolyzed to give L-2-(4'-{[4-(2-cyclopropyl-ethyl)-3-methyl-benzofuran-2-carbonyl]-amino}-biphenyl-4-sulfonylamino)-3-methyl-butyric acid in quantitative yield. $^1$H NMR (400 MHz, DMSO-$d_6$) δ ppm 0.1 (d, J=5.6 Hz, 2 H) 0.4 (d, J=8.1 Hz, 2 H) 0.8 (m, 6 H) 1.6 (m, 2 H) 2.0 (dd, J=13.4,7.8 Hz, 1 H) 2.8 (s, 3 H) 3.1 (m, 1 H) 3.6 (m, 3 H) 7.1 (d, J=7.8 Hz, 1 H) 7.4 (m, 1 H) 7.5 (m, 1 H) 7.8 (d, J=8.6 Hz, 2 H) 7.9 (m, 4 H) 8.0 (d, J=8.6 Hz, 2 H) 8.0 (d, J=10.4 Hz, 1 H) 10.5 (s, 1 H).

Example 25

L-2-(4'-{[4-(3-Methoxy-Z-propenyl)-3-methyl-benzofuran-2-carbonyl]-amino}-biphenyl-4-sulfonylamino)-3-methyl-butyric acid

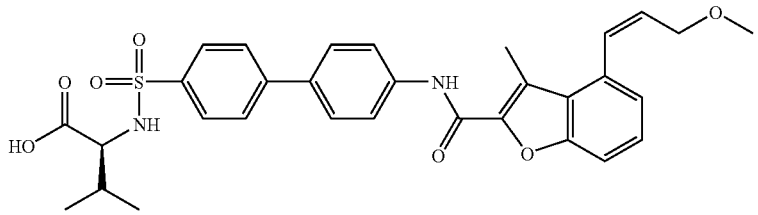

Step 1: To a solution of the product of Example 22, L-2-(4'-{[4-(3-methoxy-prop-1-ynyl)-3-methyl-benzofuran-2-carbonyl]-amino}-biphenyl-4-sulfonylamino)-3-methyl-butyric acid methyl ester (132 mg, 0.22 mmol), in 10 mL of toluene under nitrogen was added Pd/CaCO₃ (poisoned with lead, 34 mg). A balloon of hydrogen was attached to the reaction mixture. After 24 h the reaction was filtered through celite, and the filtrate was concentrated in vacuo. The crude product was purified using preparative HPLC to give L-2-(4'-{[4-(3-methoxy-Z-propenyl)-3-methyl-benzofuran-2-carbonyl]-amino}-biphenyl-4-sulfonylamino)-3-methyl-butyric acid methyl ester in 38% yield. $^1$H NMR (400 MHz, DMSO-$d_6$) δ ppm 0.8 (dd, J=14.7, 6.8 Hz, 6 H) 1.9 (dd, 1 H) 2.7 (s, 3 H) 3.2 (s, 3 H) 3.4 (s, 1 H) 4.1 (m, J=6.3, 1.5 Hz, 2 H) 6.0 (m, 1 H) 7.1 (d, J=7.3 Hz, 1 H) 7.2 (d, J=12.4 Hz, 1 H) 7.5 (d, 1 H) 7.6 (d, J=8.1 Hz, 1 H) 7.8 t, J=8.8 Hz, 4 H) 7.9 (d, J=8.8 Hz, 2 H) 8.0 (d, J=9.1 Hz, 2 H) 8.3 (s, 1 H) 10.6 (s, 1 H).

Step 2: According to the procedure of Example 20, Step 5, L-2-(4'-{[4-(3-methoxy-Z-propenyl)-3-methyl-benzofuran-2-carbonyl]-amino}-biphenyl-4-sulfonylamino)-3-methyl-butyric acid methyl ester was hydrolyzed to provide L-2-(4'-{[4-(3-methoxy-Z-propenyl)-3-methyl-benzofuran-2-carbonyl]-amino}-biphenyl-4-sulfonylamino)-3-methyl-butyric acid in 100% yield. $^1$H NMR (400 MHz, DMSO-$d_6$) δ ppm 0.8 (dd, J=12.8, 6.7 Hz, 6 H) 2.0 (dd, J=13.3, 6.4 Hz, 1 H) 2.7 (s, 3 H) 3.2 (s, 3 H) 4.1 (d, J=7.8 Hz, 2 H) 6.0 (m, 1 H) 7.1 (d, J=7.8 Hz, 1 H) 7.2 (d, J=10.4 Hz, 1 H) 7.5 (m, 1 H) 7.6 (d, J=7.6 Hz, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.6 (s, 1 H).

Example 26

L-2-(4'-{[4-(3-Hydroxy-prop-1-ynyl)-3-methyl-benzofuran-2-carbonyl]-amino}-biphenyl-4-sulfonylamino)-3-methyl-butyric acid

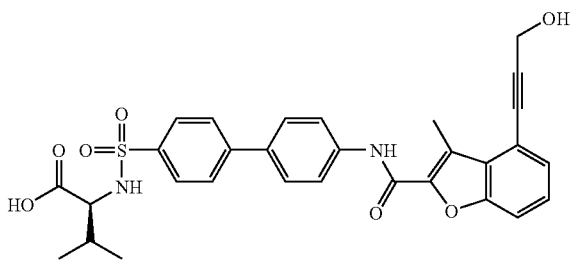

Step 1: According to the procedure of Example 22, Step 1, 4-(3-hydroxy-prop-1-ynyl)-3-methyl-benzofuran-2-carboxylic acid ethyl ester was prepared from propargyl alcohol and 3-methyl-4-trifluoromethanesulfonyloxy-benzofuran-2-carboxylic acid ethyl ester in 38% yield. $^1$H NMR (400 MHz, DMSO-$d_6$) δ ppm 1.4 (t, J=7.1 Hz, 3 H) 2.8 (s, 3 H) 4.4 (m, 4 H) 5.4 (t, J=6.1 Hz, 1 H) 7.4 (dd, J=7.6, 0.8 Hz, 1 H) 7.5 (m, 1 H) 7.7 (dd, J=8.3, 0.8 Hz, 1 H).

Step 2: According to the procedure of Example 20, Step 3, hydrolysis of 4-(3-hydroxy-prop-1-ynyl)-3-methyl-benzofuran-2-carboxylic acid ethyl ester provided 4-(3-hydroxy-prop-1-ynyl)-3-methyl-benzofuran-2-carboxylic acid in quantitative yield. $^1$H NMR (400 MHz, DMSO-$d_6$) δ ppm 2.8 (s, 3 H) 4.4 (d, J=6.1 Hz, 2 H) 5.4 (t, J=5.9 Hz, 1 H) 7.4 (dd, J=7.5, 0.9 Hz, 1 H) 7.5 (m, 1 H) 7.7 (dd, J=8.3, 1.0 Hz, 1 H).

Step 3: According to the procedure of Example 21, Step 3, coupling of L-2-(4'-amino-biphenyl-4-sulfonylamino)-3-methyl-butyric acid methyl ester with 4-(3-hydroxy-prop-1-ynyl)-3-methyl-benzofuran-2-carboxylic acid provided L-2-(4'-{[4-(3-hydroxy-prop-1-ynyl)-3-methyl-benzofuran-2-carbonyl]-amino}-biphenyl-4-sulfonylamino)-3-methyl-butyric acid methyl ester in 51% yield. $^1$H NMR (400 MHz, DMSO-$d_6$) δ ppm 0.8 (dd, J=14.7, 6.8 Hz, 6 H) 1.9 (m, 1 H) 2.8 (s, 3 H) 3.6 (dd, J=9.3, 7.1 Hz, 1 H) 4.4 (d, J=6.1 Hz, 2 H) 5.4 (m, 1 H) 7.4 (m, 1 H) 7.5 (m, 1 H) 7.7 (dd, J=8.3, 0.8 Hz, 1 H) 7.8 (t, J=8.6 Hz, 4 H) 7.9 (m, 2 H) 8.0 (d, J=8.8 Hz, 2 H) 8.3 (d, J=9.3 Hz, 1 H) 10.6 (s, 1 H).

Step 4: According to the procedure of Example 20, Step 5, hydrolysis of L-2-(4'-{[4-3-hydroxy-prop-1-ynyl)-3-methyl-benzofuran-2-carbonyl]-amino}-biphenyl-4-sulfonylamino)-3-methyl-butyric acid methyl ester provided L-2-(4'-{[4-(3-hydroxy-prop-1-ynyl)-3-methyl-benzofuran-2-carbonyl]-amino}-biphenyl-4-sulfonylamino)-3-methyl-butyric acid in quantitative yield. $^1$H NMR (400 MHz, DMSO-$d_6$) δ ppm 0.8 (dd, J=13.0, 6.7 Hz, 6 H) 1.9 (m, 1 H) 2.8 (s, 3 H) 3.5 (m, 1 H) 4.4 (d, J=5.8 Hz, 2 H) 5.4 (t, J=6.1 Hz, 1 H) 7.4 (dd, J=7.6, 1.0 Hz, 1 H) 7.5 (m, 1 H) 7.7 (dd, J=8.3, 1.0 Hz, 1 H) 7.8 (d, J=8.8 Hz, 2 H) 7.9 (m, 4 H) 8.0 (d, J=9.1 Hz, 2 H) 8.0 (d, J=7.8 Hz, 1 H) 10.6 (s, 1 H).

Example 27

L-2-(4'-{[4-(3-Hydroxy-propyl)-3-methyl-benzofuran-2-carbonyl]-amino}-biphenyl-4-sulfonylamino)-3-methyl-butyric acid

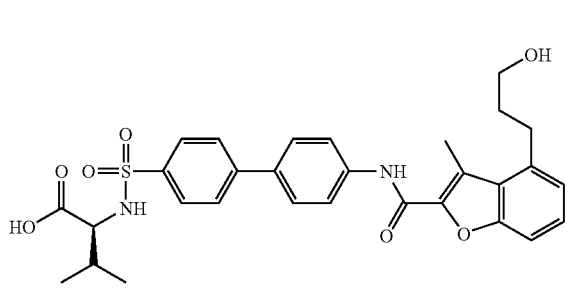

Step 1: The product of Example 26, Step 1, 4-(3-hydroxy-prop-1-ynyl)-3-methyl-benzofuran-2-carboxylic acid ethyl ester, was hydrogenated to give 4-(3-hydroxy-propyl)-3-methyl-benzofuran-2-carboxylic acid ethyl ester according to the procedure of Example 24, Step 1, in quantitative yield. $^1$H NMR (400 MHz, CDCl$_3$) δ ppm 1.3 (t, J=5.2 Hz, 1 H) 1.4 (t, J=7.1 Hz, 3 H) 2.0 (m, 2 H) 2.8 (s, 3 H) 3.1 (m, 2 H) 3.8 (m, 2 H) 4.5 (q, J=7.2 Hz, 2 H) 7.1 (dd, J=7.2, 0.9 Hz, 1 H) 7.3 (m, 1 H) 7.4 (m, 1 H).

Step 2: Hydrolysis of 4-(3-hydroxy-propyl)-3-methyl-benzofuran-2-carboxylic acid ethyl ester was carried out according to the procedure of Example 20, Step 3, to provide 4-(3-hydroxy-propyl)-3-methyl-benzofuran-2-carboxylic acid in quantitative yield. $^1$H NMR (400 MHz, DMSO-d$_6$) δ ppm 1.8 (m, 2 H) 2.7 (s, 3 H) 3.0 (m, 2 H) 3.5 (m, 2 H) 4.6 (t, J=5.1 Hz, 1 H) 7.1 (dd, J=7.1, 1.0 Hz, 1 H) 7.4 (m, 1 H) 7.4 (m, 1 H).

Step 3: Amide coupling of L-2-(4'-amino-biphenyl-4-sulfonylamino)-3-methyl-butyric acid methyl ester with 4-(3-hydroxy-propyl)-3-methyl-benzofuran-2-carboxylic acid according to the procedure of Example 21, Step 3, provided L-2-(4'-{[4-(3-hydroxy-propyl)-3-methyl-benzofuran-2-carbonyl]-amino}-biphenyl-4-sulfonylamino)-3-methyl-butyric acid methyl ester in 100% yield. $^1$H NMR (400 MHz, CDCl$_3$) δ ppm 0.9 (dd, J=32.1, 6.8 Hz, 6 H) 2.0 (m, 3 H) 2.9 (s, 3 H) 3.1 (m, 2 H) 3.4 (s, 3 H) 3.8 (m, 3 H) 5.1 (d, J=10.1 Hz, 1 H) 7.1 (m, 1 H) 7.4 (m, 1 H) 7.6 (d, J=8.6 Hz, 2 H) 7.7 (d, J=8.8 Hz, 2 H) 7.9 (dd, J=16.7, 8.6 Hz, 4 H) 8.5 (s, 1 H).

Step 4: Hydrolysis of L-2-(4'-{[4-(3-hydroxy-propyl)-3-methyl-benzofuran-2-carbonyl]-amino}-biphenyl-4-sulfonylamino)-3-methyl-butyric acid methyl ester according to the procedure of Example 20, Step 5, provided L-2-(4'-{[4-(3-hydroxy-propyl)-3-methyl-benzofuran-2-carbonyl]-amino}-biphenyl-4-sulfonylamino)-3-methyl-butyric acid in quantitative yield. $^1$H NMR (400 MHz, DMSO-d$_6$) δ ppm 0.8 (dd, J=12.55, 6.7 Hz, 6 H) 1.8 (m, 2 H) 2.0 (m, 1 H) 2.8 (s, 3 H) 3.1 (m, 2 H) 3.5 (m, 2 H) 3.6 (dd, J=9.3, 6.1 Hz, 1 H) 4.6 (s, 1 H) 7.1 (d, J=7.3 Hz, 1 H) 7.4 (m, 1 H) 7.5 (d, J=8.3 Hz, 1 H) 7.8 (d, J=8.8 Hz, 2 H) 7.9 (m, 4 H) 8.0 (d, J=8.8 Hz, 2 H) 8.1 (d, J=9.1 Hz, 1 H) 10.5 (s, 1 H).

Example 28

L-3-Methyl-2-(4'-{[3-methyl-4-(4-methyl-pent-1-ynyl)-benzofuran-2-carbonyl]-amino}-biphenyl-4-sulfonylamino)-butyric acid

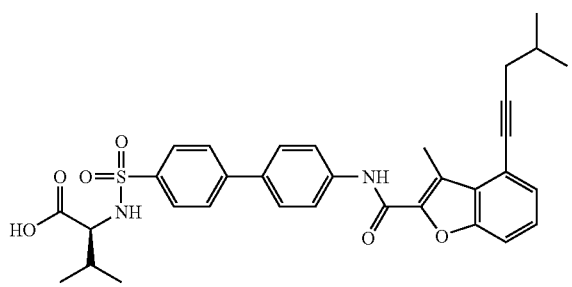

Step 1: According to the procedure of Example 22, Step 1, 3-methyl-4-(4-methyl-pent-1-ynyl)-benzofuran-2-carboxylic acid ethyl ester was prepared from 4-methyl-pent-1-yne and 3-methyl-4-trifluoromethanesulfonyloxy-benzofuran-2-carboxylic acid ethyl ester in 81% yield. $^1$H NMR (400 MHz, DMSO-d$_6$) δ ppm 1.0 (s, 3 H) 1.0 (s, 3 H) 1.3 (t, J=7.1 Hz, 3 H) 1.9 (m, 1 H) 2.4 (d, J=6.6 Hz, 2 H) 2.8 (s, 3 H) 4.4 (q, J=7.1 Hz, 2 H) 7.4 (dd, J=7.6, 1.0 Hz, 1 H) 7.5 (m, 1 H) 7.7 (dd, J=8.3, 1.0 Hz, 1 H).

Step 2: Hydrolysis of 3-methyl-4-(4-methyl-pent-1-ynyl)-benzofuran-2-carboxylic acid ethyl ester was carried out according to the procedure of Example 20, Step 3, to provide 3-methyl-4-(4-methyl-pent-1-ynyl)-benzofuran-2-carboxylic acid in quantitative yield. $^1$H NMR (400 MHz, DMSO-d$_6$) δ ppm 1.0 (d, J=6.6 Hz, 6 H) 1.9 (m, 1 H) 2.4 (d, J=6.6 Hz, 2 H) 2.8 (s, 3 H) 7.3 (dd, J=7.5, 0.9 Hz, 1 H) 7.4 (m, 1 H) 7.6 (dd, J=8.3, 1.0 Hz, 1 H) 13.5 (s, 1 H).

Step 3: Amide coupling of L-2-(4'-amino-biphenyl-4-sulfonylamino)-3-methyl-butyric acid methyl ester with 3-methyl-4-(4-methyl-pent-1-ynyl)-benzofuran-2-carboxylic acid was carried out according to the procedure of Example 21, Step 3, to provide L-3-methyl-2-(4'-{[3-methyl-4-(4-methyl-pent-1-ynyl)-benzofuran-2-carbonyl]-amino}-biphenyl-4-sulfonylamino)-butyric acid methyl ester in 42% yield. $^1$H NMR (400 MHz, DMSO-d$_6$) δ ppm 0.8 (dd, J=14.7, 6.8 Hz, 6 H) 1.1 (d, J=6.6 Hz, 6 H) 1.9 (m, 2 H) 2.5 (d, J=6.6 Hz, 2 H) 2.8 (s, 3 H) 3.4 (s, 3 H) 3.6 (dd, J=9.0, 6.9 Hz, 1 H) 7.4 (d, J=7.3 Hz, 1 H) 7.5 (m, 1 H) 7.7 (dd, J=8.3, 1.0 Hz, 1 H) 7.8 (m, 4 H) 7.9 (m, 2 H) 8.0 (d, J=8.8 Hz, 2 H) 8.3 (d, J=9.3 Hz, 1 H) 10.6 (s, 1 H).

Step 4: Hydrolysis of L-3-methyl-2-(4'-{[3-methyl-4-(4-methyl-pent-1-ynyl)-benzofuran-2-carbonyl]-amino}-biphenyl-4-sulfonylamino)-butyric acid methyl ester was carried out according to the procedure of Example 20, Step 5 to provide L-3-methyl-2-(4'-{[3-methyl-4-(4-methyl-pent-1-ynyl)-benzofuran-2-carbonyl]-amino}-biphenyl-4-sulfonylamino)-butyric acid in quantitative yield. $^1$H NMR (400 MHz, DMSO-d$_6$) δ ppm 0.8 (dd, J=12.9, 6.8 Hz, 6 H) 1.1 (d, J=6.8 Hz, 6 H) 1.9 (m, 2 H) 2.5 (d, J=6.6 Hz, 2 H) 2.8 (s, 3 H) 3.5 (m, 1 H) 7.4 (d, J=7.3 Hz, 1 H) 7.5 (m, 1 H) 7.7 (d, J=8.1 Hz, 1 H) 7.8 (d, J=8.8 Hz, 2 H) 7.9 (m, 4 H) 8.0 (d, J=8.8 Hz, 2 H) 8.0 (d, J=9.1 Hz, 1 H) 10.6 (s, 1 H).

Example 29

L-3-Methyl-2-(4'-{[3-methyl-4-(4-methyl-pentyl)-benzofuran-2-carbonyl]-amino}-biphenyl-4-sulfonylamino)-butyric acid

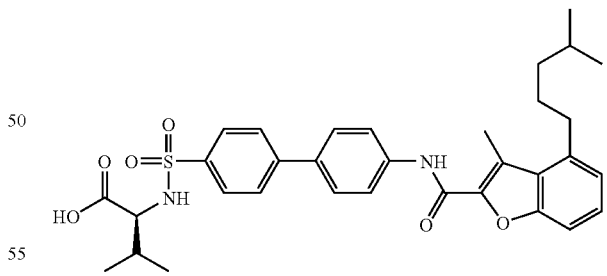

Step 1: Hydrogenation of the product of Example 28, Step 1, L-3-methyl-2-(4'-{[3-methyl-4-(4-methyl-pent-1-ynyl)-benzofuran-2-carbonyl]-amino}-biphenyl-4-sulfonylamino)-butyric acid methyl ester, was carried out according to Example 24, Step 1 to provide L-3-methyl-2-(4'-{[3-methyl-4-(4-methyl-pentyl)-benzofuran-2-carbonyl]-amino}-biphenyl-4-sulfonylamino)-butyric acid methyl ester in quantitative yield. $^1$H NMR (400 MHz, DMSO-d$_6$) δ ppm 0.8 (dd, J=14.9, 6.8 Hz, 6 H) 0.9 (m, J=6.6 Hz, 6 H) 1.3 (m, 2 H) 1.6 (m, 3 H) 1.9 (m, 1 H) 2.8 (s, 3 H) 3.0 (m, 2 H) 3.3 (s, 3 H)

3.6 (t, J=6.8 Hz, 1 H) 7.1 (d, J=7.3 Hz, 1 H) 7.4 (m, 1 H) 7.5 (m, 1 H) 7.8 (dd, J=10.0, 8.7 Hz, 4 H) 7.9 (m, 2 H) 8.0 (d, J=9.1 Hz, 2 H) 8.3 (d, J=8.6 Hz, 1 H) 10.5 (s, 1 H).

Step 2: Hydrolysis of L-3-methyl-2-(4'-{[3-methyl-4-(4-methyl-pentyl)-benzofuran-2-carbonyl]-amino}-biphenyl-4-sulfonylamino)-butyric acid methyl ester according to the procedure of Example 20, Step 5 provided L-3-methyl-2-(4'-{[3-methyl-4-(4-methyl-pentyl)-benzofuran-2-carbonyl]-amino}-biphenyl-4-sulfonylamino)-butyric acid in quantitative yield. $^1$H NMR (400 MHz, DMSO-$d_6$) δ ppm 0.8 (dd, J=12.6, 6.8 Hz, 6 H) 0.9 (d, J=6.6 Hz, 6 H) 1.3 (m, 2 H) 1.6 (m, 3 H) 1.9 (m, 1 H) 2.8 (s, 3 H) 3.0 (d, 2 H) 3.6 (dd, J=9.3, 6.1 Hz, 1 H) 7.1 (d, J=6.8 Hz, 1 H) 7.4 (m, 1 H) 7.5 (m, 1 H) 7.8 (d, J=8.8 Hz, 2 H) 7.9 (m, 4 H) 8.0 (d, J=8.8 Hz, 2 H) 8.1 (d, J=9.6 Hz, 1 H) 10.5 (s, 1 H).

Example 30

L-2-(4'-{[4-(3-Methoxy-propyl)-3-methyl-benzofuran-2-carbonyl]-amino}-biphenyl-4-sulfonylamino)-3-methyl-butyric acid

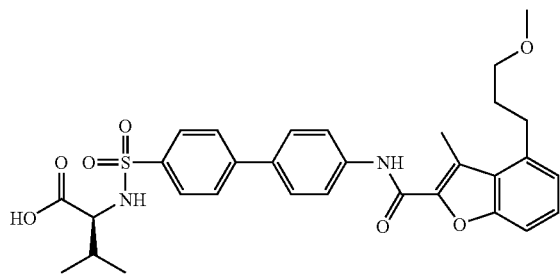

Step 1: Hydrogenation of the product of Example 22, Step 3, L-2-(4'-{[4-(3-methoxy-prop-1-ynyl)-3-methyl-benzofuran-2-carbonyl]-amino}-biphenyl-4-sulfonylamino)-3-methyl-butyric acid methyl ester according to the procedure of Example 24, Step 1 provided L-2-(4'-{[4-(3-methoxy-propyl)-3-methyl-benzofuran-2-carbonyl]-amino}-biphenyl-4-sulfonylamino)-3-methyl-butyric acid methyl ester in quantitative yield. $^1$H NMR (400 MHz, DMSO-$d_6$) δ ppm 0.8 (dd, J=14.8, 6.7 Hz, 6 H) 1.9 (m, 3 H) 2.8 (s, 3 H) 3.1 (m, 2 H) 3.3 (s, 3 H) 3.4 (s, 3 H) 3.4 (m, J=6.2, 6.2 Hz, 2 H) 3.6 (dd, J=9.3, 7.1 Hz, 1 H) 7.1 (d, J=6.6 Hz, 1 H) 7.4 (m, 1 H) 7.5 (m, 1 H) 7.8 (dd, J=10.0, 8.7 Hz, 4 H) 7.9 (m, 2 H) 8.0 (d, J=8.8 Hz, 2 H) 8.3 (d, J=9.3 Hz, 1 H) 10.5 (s, 1 H).

Step 2: Hydrolysis of L-2-(4'-{[4-(3-methoxy-propyl)-3-methyl-benzofuran-2-carbonyl]-amino}-biphenyl-4-sulfonylamino)-3-methyl-butyric acid methyl ester according to the procedure of Example 20, Step 5 provided L-2-(4'-{[4-(3-methoxy-propyl)-3-methyl-benzofuran-2-carbonyl]-amino}-biphenyl-4-sulfonylamino)-3-methyl-butyric acid in quantitative yield. $^1$H NMR (400 MHz, DMSO-$d_6$) δ ppm 0.8 (dd, J=12.4, 6.8 Hz, 6 H) δ ppm1.9 (m, 2 H) 2.0 (m, 1 H) 2.8 (s, 3 H) 3.1 (m, 2 H) 3.3 (s, 3 H) 3.4 (t, J=6.2 Hz, 2 H) 3.6 (dd, J=9.3, 6.1 Hz, 1 H) 7.1 (d, J=7.6 Hz, 1 H) 7.4 (dd, J=8.3, 7.3 Hz, 1 H) 7.5 (m, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.5 (s, 1 H).

Example 31

L-2-(4'-{[4-(3-Dimethylamino-prop-1-ynyl)-3-methyl-benzofuran-2-carbonyl]-amino}-biphenyl-4-sulfonylamino)-3-methyl-butyric acid

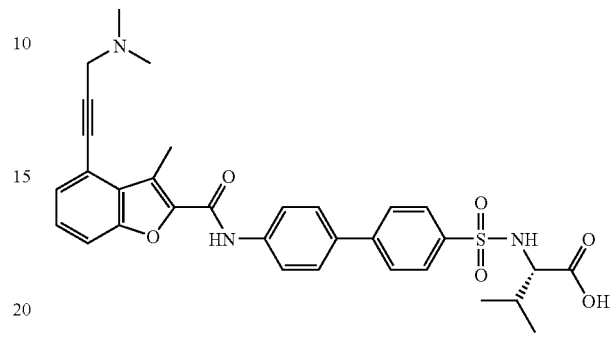

Step 1: To the product of Example 20, Step 1, 3-methyl-4-trifluoromethanesulfonyloxy-benzofuran-2-carboxylic acid ethyl ester (900 mg, 2.56 mmol, 1 eq), under nitrogen was added 1-dimethylamino-2-propyne (425 mg, 5.11 mmol, 2 eq), PdCl$_2$(PPh$_3$)$_2$ (90 mg, 0.13 mmol, 0.05 eq), and triethylamine (1.4 mL, 10.23 mmol, 4 eq), in 25 mL of toluene. The reaction mixture was heated at reflux for 16 h until the reaction was complete by TLC. After work up and column chromatography (0-10% MeOH/dichloromethane), 4-(3-dimethylamino-prop-1-ynyl)-3-methyl-benzofuran-2-carboxylic acid ethyl ester was obtained in 65% yield (474 mg). $^1$H NMR (400 MHz, DMSO-$d_6$) δ ppm 1.4 (t, J=7.1 Hz, 3 H) 2.3 (s, 6 H) 2.8 (s, 3 H) 3.6 (s, 2 H) 4.4 (q, J=7.1 Hz, 2 H) 7.4 (dd, J=7.3, 1.0 Hz, 1 H) 7.5 (m, 1 H) 7.7 (dd, J=8.2, 0.9 Hz, 1 H).

Step 2: Hydrolysis 4-(3-dimethylamino-prop-1-ynyl)-3-methyl-benzofuran-2-carboxylic acid ethyl ester according to the procedure of Example 20, Step 3, provided 4-(3-dimethylamino-prop-1-ynyl)-3-methyl-benzofuran-2-carboxylic acid in 70% yield. $^1$H NMR (400 MHz, DMSO-$d_6$) δ ppm 2.8 (s, 3 H) 2.9 (s, 6 H) 4.4 (s, 2 H) 7.5 (m, 2 H) 7.8 (m, 1 H).

Step 3: Coupling of 4-(3-dimethylamino-prop-1-ynyl)-3-methyl-benzofuran-2-carboxylic acid with L-2-(4'-amino-biphenyl-4-sulfonylamino)-3-methyl-butyric acid methyl ester according to the procedure of Example 21, Step 3, provided L-2-(4'-{[4-(3-dimethylamino-prop-1-ynyl)-3-methyl-benzofuran-2-carbonyl]-amino}-biphenyl-4-sulfonylamino)-3-methyl-butyric acid methyl ester in 60% yield. $^1$H NMR (400 MHz, DMSO-$d_6$) δ ppm 0.8 (dd, J=14.8, 6.7 Hz, 6 H) 1.9 (m, 1 H) 2.9 (s, 3 H) 2.9 (s, 6 H) 3.4 (s, 3 H) 3.6 (dd, J=9.3, 7.1 Hz, 1 H) 4.4 (s, 2 H) 7.6 (m, 2 H) 7.8 (t, J=8.3 Hz, 5 H) 7.9. (m, 2 H) 7.9 (m, 2 H) 8.0 (d, J=8.8 Hz, 1 H).

Step 4: Hydrolysis of L-2-(4'-{[4-(3-dimethylamino-prop-1-ynyl)-3-methyl-benzofuran-2-carbonyl]-amino}-biphenyl-4-sulfonylamino)-3-methyl-butyric acid methyl ester according to the procedure of Example 20, Step 5, provided L-2-(4'-{[4-(3-dimethylamino-prop-1-ynyl)-3-methyl-benzofuran-2-carbonyl]-amino}-biphenyl-4-sulfonylamino)-3-methyl-butyric acid in quantitative yield. $^1$H NMR (400 MHz, DMSO-$d_6$) δ ppm 0.8 (dd, J=12.4, 6.8 Hz, 6 H) 2.0 (m, 1 H) 2.9 (s, 3 H) 2.9 (s, 6 H) 3.6 (dd, J=9.3, 6.1 Hz, 1 H) 4.4 (s, 2 H) 7.6 (m, 2 H) 7.8 (m, 7 H) 8.0 (d, J=8.8 Hz, 2 H) 8.1 (d, J=9.6 Hz, 1 H) 10.7 (s, 1 H) 12.6 (s, 1 H).

Example 32

L-2-(4'-{[4-(3-Dimethylamino-propyl)-3-methyl-benzofuran-2-carbonyl]-amino}-biphenyl-4-sulfonylamino)-3-methyl-butyric acid

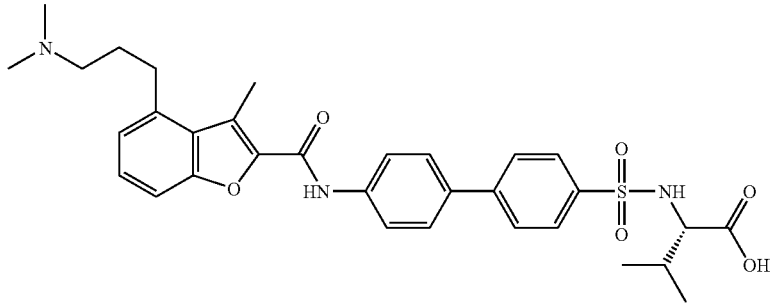

Step 1: To a solution of the product of Example 31, Step 3, L-2-(4'-{[4-(3-dimethylamino-prop-1-ynyl)-3-methyl-benzofuran-2-carbonyl]-amino}-biphenyl-4-sulfonylamino)-3-methyl-butyric acid methyl ester (200 mg, 0.33 mmol) in 5 mL of dichloromethane, was added 5% Pd/C (66 mg) and the reaction was stirred at room temperature under 1 atm of hydrogen for 72 h. The reaction mixture was filtered through celite, and the filtrate was concentrated in vacuo to provide the crude product which was purified by prep-HPLC to give L-2-(4'-{[4-(3-dimethylamino-propyl)-3-methyl-benzofuran-2-carbonyl]-amino}-biphenyl-4-sulfonylamino)-3-methyl-butyric acid methyl ester in 50% yield. $^1$H NMR (400 MHz, DMSO-$d_6$) δ ppm 0.8 (dd, J=14.9, 6.8 Hz, 6 H) 1.8 (dd, 2 H) 1.9 (m, 1 H) 2.2 (s, 6 H) 2.4 (m, 2 H) 2.8 (s, 3 H) 3.0 (m, 2 H) 3.3 (s, 3 H) 3.6 (dd, J=9.3, 7.1 Hz, 1 H) 7.1 (d, J=7.3 Hz, 1 H) 7.4 (m, 1 H) 7.5 (m, 1 H) 7.8 (dd, J=9.9, 8.8 Hz, 4 H) 7.9 (m, 2 H) 8.0 (d, J=8.8 Hz, 2 H) 8.3 (d, J=9.3 Hz, 1 H) 10.5 (s, 1 H).

Step 2: Hydrolysis of L-2-(4'-{[4-(3-dimethylamino-propyl)-3-methyl-benzofuran-2-carbonyl]-amino}-biphenyl-4-sulfonylamino)-3-methyl-butyric acid methyl ester according to the procedure of Example 20, Step 4, provided L-2-(4'-{[4-(3-dimethylamino-propyl)-3-methyl-benzofuran-2-carbonyl]-amino}-biphenyl-4-sulfonylamino)-3-methyl-butyric acid in quantitative yield. $^1$H NMR (400 MHz, DMSO-$d_6$) δ ppm 0.8 (dd, J=12.4, 6.8 Hz, 6 H) 2.0 (m, 1 H) 2.1 (m, 2 H) 2.8 (d, J=4.5 Hz, 6 H) 2.8 (s, 3 H) 3.1 (m, 2 H) 3.2 (m, 2 H) 3.6 (dd, J=9.3, 6.1 Hz, 1 H) 7.2 (d, J=7.6 Hz, 1 H) 7.5 (m, 1 H) 7.6 (m, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.5 (s, 1 H) 10.6 (s, 1 H).

Example 33

L-2-{4'-[(4-Ethynyl-3-methyl-benzofuran-2-carbonyl)-amino]-biphenyl-4-sulfonylamino}-3-methyl-butyric acid

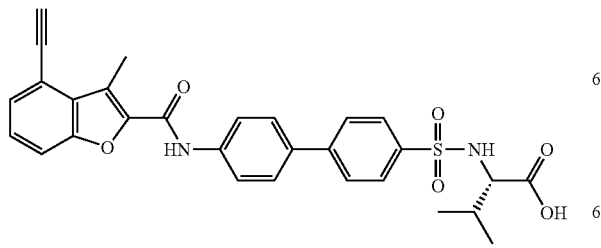

Step 1: Coupling of the product of Example 20, Step 1, 3-methyl-4-trifluoromethanesulfonyloxy-benzofuran-2-carboxylic acid ethyl ester, with (trimethylsilyl)acetylene according to the procedure of Example 31, Step 1, provided 3-methyl-4-trimethylsilanylethynyl-benzofuran-2-carboxylic acid ethyl ester in 41% yield after purification using flash chromatography (1-5% ethyl acetate/hexane).

Step 2: Hydrolysis 3-methyl-4-trimethylsilanylethynyl-benzofuran-2-carboxylic acid ethyl ester according to the procedure of Example 20, Step 3, provided 4-ethynyl-3-methyl-benzofuran-2-carboxylic acid in 73% yield.

Step 3: Coupling of 4-ethynyl-3-methyl-benzofuran-2-carboxylic acid with L-2-(4'-amino-biphenyl-4-sulfonylamino)-3-methyl-butyric acid methyl ester according to the procedure of Example 21, Step 3, provided L-2-{4'-[(4-ethynyl-3-methyl-benzofuran-2-carbonyl)-amino]-biphenyl-4-sulfonylamino}-3-methyl-butyric acid methyl ester in 96% yield. $^1$H NMR (400 MHz, DMSO-$d_6$) δ ppm 0.8 (dd, J=14.9, 6.8 Hz, 6 H) 1.9 (m, 1 H) 2.8 (s, 3 H) 3.4 (s, 3 H) 3.6 (dd, J=9.3, 7.1 Hz, 1 H) 4.6 (s, 1 H) 7.5 (m, 2 H) 7.8 (m, 5 H) 7.9 (m, 2 H) 8.0 (d, J=9.1 Hz, 2 H) 8.3 (d, J=9.3 Hz, 1 H) 10.6 (s, 1 H).

Step 4: Hydrolysis of L-2-{4'-[(4-ethynyl-3-methyl-benzofuran-2-carbonyl)-amino]-biphenyl-4-sulfonylamino}-3-methyl-butyric acid methyl ester according to the procedure of Example 20, Step 4, provided L-2-{4'-[(4-ethynyl-3-methyl-benzofuran-2-carbonyl)-amino]-biphenyl-4-sulfonylamino}-3-methyl-butyric acid in quantitative yield. $^1$H NMR (400 MHz, DMSO-$d_6$) δ ppm 0.8 (dd, J=12.6, 6.8 Hz, 6 H) 2.0 (m, 1 H) 2.8 (s, 3 H) 3.6 (dd, J=9.3, 6.1 Hz, 1 H) 4.6 (s, 1 H) 7.5 (m, 2 H) 7.8 (m, 3 H) 7.9 (m, 4 H) 8.0 (d, J=8.8 Hz, 2 H) 8.1 (d, J=9.3 Hz 1 H) 10.6 (s, 1 H) 12.6 (s, 1 H).

Example 34

L-2-(4'-{[4-(3,3-Dimethyl-but-1-ynyl)-3-methyl-benzofuran-2-carbonyl]-amino}-biphenyl-4-sulfonylamino)-3-methyl-butyric acid

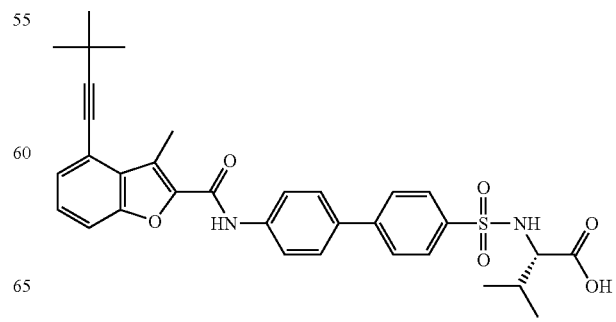

Step 1: Coupling of the product of Example 20, Step 1, 3-methyl-4-trifluoromethanesulfonyloxy-benzofuran-2-carboxylic acid ethyl ester, with 3,3-dimethyl-1-butyne according to the procedure of Example 31, Step 1, provided 4-(3,3-dimethyl-but-1-ynyl)-3-methyl-benzofuran-2-carboxylic acid ethyl ester in 58% yield after purification via flash chromatography eluting with 1-5% ethyl acetate/hexanes. $^1$H NMR (400 MHz, DMSO-$d_6$) δ ppm 1.3 (s, 12 H) 2.8 (s, 3 H) 4.4 (q, J=7.2 Hz, 2 H) 7.3 (dd, J=7.5, 0.9 Hz, 1 H) 7.4 (dd, J=8.3, 7.6 Hz, 1 H) 7.6 (m, 1 H).

Step 2: Hydrolysis 4-(3,3-dimethyl-but-1-ynyl)-3-methyl-benzofuran-2-carboxylic acid ethyl ester according to the procedure of Example 20, Step 3, provided 4-(3,3-dimethyl-but-1-ynyl)-3-methyl-benzofuran-2-carboxylic acid in 80% yield.

Step 3: Coupling of 4-(3,3-dimethyl-but-1-ynyl)-3-methyl-benzofuran-2-carboxylic acid with L-2-(4'-amino-biphenyl-4-sulfonylamino)-3-methyl-butyric acid methyl ester according to the procedure of Example 21, Step 3, provided L-2-(4'-{[4-(3,3-dimethyl-but-1-ynyl)-3-methyl-benzofuran-2-carbonyl]-amino}-biphenyl-4-sulfonyl amino)-3-methyl-butyric acid methyl ester in 52% yield. $^1$H NMR (400 MHz, DMSO-$d_6$) δ ppm 0.8 (dd, J=14.8, 6.7 Hz, 6 H) 1.4 (s, 9 H) 1.9 (m, 1 H) 2.8 (s, 3 H) 3.3 (s, 3 H) 3.6 (dd, J=9.3, 7.1 Hz, 1 H) 7.3 (d, J=7.3 Hz, 1 H) 7.5 (m, 1 H) 7.7 (d, J=9.1 Hz, 1 H) 7.8 (t, J=8.8 Hz, 4 H) 7.9 (m, 2 H) 8.0 (d, J=8.8 Hz, 2 H) 8.3 (d, J=9.3 Hz, 1 H) 10.6 (s, 1 H).

Step 4: Hydrolysis of L-2-(4'-{[4-(3,3-dimethyl-but-1-ynyl)-3-methyl-benzofuran-2-carbonyl]-amino}-biphenyl-4-sulfonylamino)-3-methyl-butyric acid methyl ester according to the procedure of Example 20, Step 5, provided L-2-(4'-{[4-(3,3-dimethyl-but-1-ynyl)-3-methyl-benzofuran-2-carbonyl]-amino}-biphenyl-4-sulfonylamino)-3-methyl-butyric acid in quantitative yield. $^1$H NMR (400 MHz, DMSO-$d_6$) δ ppm 0.8 (dd, J=12.6, 6.8 Hz, 6 H) 1.4 (s, 9 H) 2.0 (m, 1 H) 2.8 (s, 3 H) 3.6 (dd, J=9.3, 6.1 Hz, 1 H) 7.3 (dd, J=7.5, 0.9 Hz, 1 H) 7.5 (m, 1 H) 7.7 (dd, J=8.3, 1.0 Hz, 1 H) 7.8 (d, J=8.8 Hz, 2 H) 7.9 (m, 4 H) 8.0 (d, J=9.1 Hz, 2 H) 8.1 (d, J=9.3 Hz, 1 H) 10.6 (s, 1 H) 12.6 (s, 1 H).

Example 35

L-3-Methyl-2-(4'-{[3-methyl-4-(3-methyl-isoxazol-5-yl)-benzofuran-2-carbonyl]-amino}-biphenyl-4-sulfonylamino)-butyric acid

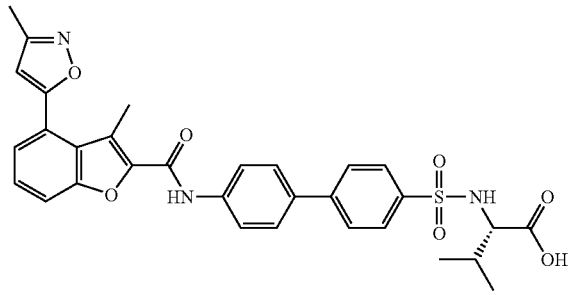

Step 1: To the product of Example 33, Step 1, 3-methyl-4-trimethylsilanylethynyl-benzofuran-2-carboxylic acid ethyl ester (1.5 g, 4.99 mmol, 1 eq), in THF (10 mL) under argon, was added tetrabutylammonium fluoride (1.0 M in THF, 6 mL, 5.99 mmol, 1.2 eq.) and the reaction was stirred at ambient temperature for 45 minutes. After work-up and flash column chromatography, 4-ethynyl-3-methyl-benzofuran-2-carboxylic acid ethyl ester was obtained in 35% yield. $^1$H NMR (400 MHz, DMSO-$d_6$) δ ppm 1.4 (t, J=7.1 Hz, 3 H) 2.8 (s, 3 H) 4.4 (m, J=7.1, 7.1, 7.1 Hz, 2 H) 4.6 (s, 1 H) 7.5 (m, 2 H) 7.7 (dd, J=7.7, 1.4 Hz, 1 H).

Step 2: To a solution of 4-ethynyl-3-methyl-benzofuran-2-carboxylic acid ethyl ester (228 mg, 0.99 mmol, 1 eq.) in acetonitrile (5 mL) under argon, was added di-tert-butyl dicarbonate (327 mg, 1.5 mmol, 1.5 eq.), and 4-(dimethylamino)pyridine (12 mg, 0.1 mmol, 0.1 eq.). Nitroethane (79 uL, 1.1 mmol, and 1.1 eq.) in acetonitrile (5 mL) was added drop-wise to the reaction mixture, and the reaction was stirred at room temperature for 72 hours. After work-up and flash column chromatography, 3-methyl-4-(3-methyl-isoxazol-5-yl)-benzofuran-2-carboxylic acid ethyl ester was obtained in 25% yield. $^1$H NMR (400 MHz, DMSO-$d_6$) δ ppm 1.4 (t, J=7.1 Hz, 3 H) 2.3 (s, 3 H) 2.4 (s, 3 H) 4.4 (q, J=7.1 Hz, 2 H) 6.8 (s, 1 H) 7.5 (dd, J=7.5, 0.9 Hz, 1 H) 7.6 (m, 1 H) 7.9 (dd, J=8.5, 0.9 Hz, 1 H).

Step 3: Hydrolysis of 3-methyl-4-(3-methyl-isoxazol-5-yl)-benzofuran-2-carboxylic acid ethyl ester according to the procedure of Example 20, Step 3, provided 3-methyl-4-(3-methyl-isoxazol-5-yl)-benzofuran-2-carboxylic acid in quantitative yield. $^1$H NMR (400 MHz, DMSO-$d_6$) δ ppm 2.3 (s, 3 H) 2.4 (s, 3 H) 6.8 (s, 1 H) 7.5 (d, J=8.3 Hz, 1 H) 7.6 (m, 1 H) 7.9 (d, J=9.1 Hz, 1 H).

Step 4: Coupling of 3-methyl-4-(3-methyl-isoxazol-5-yl)-benzofuran-2-carboxylic acid with L-2-(4'-amino-biphenyl-4-sulfonylamino)-3-methyl-butyric acid methyl ester according to the procedure of Example 21, Step 3, provided L-3-methyl-2-(4'-{[3-methyl-4-(3-methyl-isoxazol-5-yl)-benzofuran-2-carbonyl]-amino}-biphenyl-4-sulfonylamino)-butyric acid methyl ester in 52% yield. $^1$H NMR (400 MHz, DMSO-$d_6$) δ ppm 0.8 (dd, J=14.7, 6.8 Hz, 6 H) 1.9 (m, 1 H) 2.4 (s, 3 H) 2.5 (s, 3 H) 3.4 (s, 3 H) 3.6 (dd, J=9.3, 7.1 Hz, 1 H) 6.8 (s, 1 H) 7.5 (d, J=7.6 Hz, 1 H) 7.7 (m, 1 H) 7.8 (dd, J=8.5, 6.4 Hz, 4 H) 7.9 (m, 3 H) 8.0 (d, J=8.8 Hz, 2 H) 8.3 (d, J=9.1 Hz, 1 H) 10.7 (s, 1 H).

Step 5: Hydrolysis of L-3-methyl-2-(4'-{[3-methyl-4-(3-methyl-isoxazol-5-yl)-benzofuran-2-carbonyl]-amino}-biphenyl-4-sulfonylamino)-butyric acid methyl ester according to the procedure of Example 20, Step 5, provided L-3-methyl-2-(4'-{[3-methyl-4-(3-methyl-isoxazol-5-yl)-benzofuran-2-carbonyl]-amino}-biphenyl-4-sulfonylamino)-butyric acid in 38% yield after purification by preparative HPLC. $^1$H NMR (400 MHz, DMSO-$d_6$) δ ppm 0.8 (dd, J=12.4, 6.8 Hz, 6 H) 2.0 (m, 1 H) 2.4 (s, 3 H) 2.5 (s, 3 H) 3.6 (dd, J=9.3, 5.8 Hz, 1 H) 6.8 (s, 1 H) 7.5 (dd, J=7.6, 1.0 Hz, 1 H) 7.7 (dd, J=8.3, 7.3 Hz, 1 H) 7.8 (m, 4 H) 7.9 (m, 3 H) 8.0 (d, J=8.8 Hz, 2 H) 8.1 (d, J=9.3 Hz, 1 H) 10.7 (s, 1 H).

Example 36

L-2-{4'-[(4-Methanesulfonylamino-3-methyl-benzofuran-2-carbonyl)-amino]-biphenyl-4-sulfonylamino}-3-methyl-butyric acid

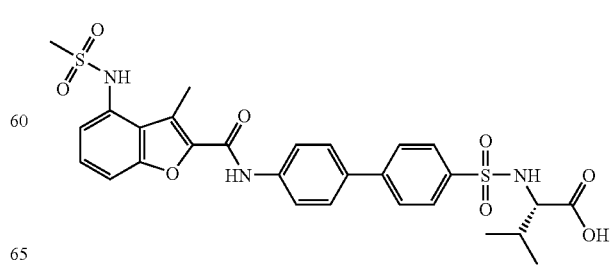

Step 1: To the product of Example 20, Step 1, 3-methyl-4-trifluoromethanesulfonyloxy-benzofuran-2-carboxylic acid ethyl ester (800 mg, 2.27 mmol), in 25 mL of toluene were added methane sulfonamide (650 mg, 6.82 mmol, 3 eq), Pd$_2$(dba)$_3$ (208 mg, 0.23 mmol, 0.1 eq), biphenyl-2-yl-di-tert-butyl-phosphine (68 mg, 0.23 mmol, 0.1 eq), and tribasic potassium phosphate (965 mg, 4.55 mmol, 2 eq) under nitrogen and the resulting mixture was heated at reflux for 3 h. After work up and trituration, 4-methanesulfonylamino-3-methyl-benzofuran-2-carboxylic acid ethyl ester was obtained in 67% yield (450 mg). $^1$H NMR (400 MHz, DMSO-d$_6$) δ ppm 1.3 (t, J=7.1 Hz, 3 H) 2.7 (s, 3 H) 3.1 (s, 3 H) 4.4 (q, J=7.1 Hz, 2 H) 7.3 (dd, J=7.7, 0.9 Hz, 1 H) 7.5 (dd, J=8.3, 7.6 Hz, 1 H) 7.6 (m, 1 H) 9.5 (s, 1 H).

Step 2: According to the procedure of Example 20, Step 3, 4-methanesulfonylamino-3-methyl-benzofuran-2-carboxylic acid ethyl ester was hydrolyzed to provide 4-methanesulfonylamino-3-methyl-benzofuran-2-carboxylic acid in 92% yield. $^1$H NMR (400 MHz, DMSO-d$_6$) δ ppm 2.7 (s, 3 H) 3.1 (s, 3 H) 7.2 (dd, J=7.8, 0.8 Hz, 1 H) 7.5 (dd, J=8.3, 7.6 Hz, 1 H) 7.6 (m, 1 H) 9.5 (s, 1 H).

Step 3: According to the procedure of example 21, Step 3, 4-methanesulfonylamino-3-methyl-benzofuran-2-carboxylic acid was coupled with L-2-(4'-amino-biphenyl-4-sulfonylamino)-3-methyl-butyric acid methyl ester to provide L-2-{4'-[(4-methanesulfonylamino-3-methyl-benzofuran-2-carbonyl)-amino]-biphenyl-4-sulfonylamino}-3-methyl-butyric acid methyl ester in 23% yield. $^1$H NMR (400 MHz, DMSO-d$_6$) δ ppm 0.8 (dd, J=14.8,6.7 Hz, 6 H) 1.9 (m, 1 H) 2.8 (s, 3 H) 3.1 (s, 3 H) 3.3 (s, 3 H) 3.6 (dd, J=9.3, 7.1 Hz, 1 H) 7.3 (d, J=7.8 Hz, 1 H) 7.5 (m, 1 H) 7.6 (d, J=9.1 Hz, 1 H) 7.8 (t, J=8.6 Hz, 4 H) 7.9 (m, 2 H) 8.0 (d, J=8.8 Hz, 2 H) 8.3 (d, J=9.3 Hz, 1 H) 9.5 (s, 1 H) 10.6 (s, 1 H).

Step 4: According to the procedure of example 20, Step 5, L-2-{4'-[(4-methanesulfonylamino-3-methyl-benzofuran-2-carbonyl)-amino]-biphenyl-4-sulfonylamino}-3-methyl-butyric acid methyl ester was hydrolyzed to L-2-{4'-[(4-methanesulfonylamino-3-methyl-benzofuran-2-carbonyl)-amino]-biphenyl-4-sulfonylamino}-3-methyl-butyric acid in quantitative yield. $^1$H NMR (400 MHz, DMSO-d$_6$) δ ppm 0.8 (dd, J=12.6, 6.8 Hz, 6 H) 2.0 (m, 1 H) 2.8 (s, 3 H) 3.1 (s, 3 H) 3.6 (dd, J=9.3, 5.8 Hz, 1 H) 7.3 (dd, J=7.7, 0.9 Hz, 1 H) 7.5 (m, 1 H) 7.6 (m, 1 H) 7.8 (d, J=8.8 Hz, 2 H) 7.9 (m, 4 H) 8.0 (d, J=8.8 Hz, 2 H) 8.1 (d, J=9.3 Hz, 1 H) 9.5 (s, 1 H) 10.6 (s, 1 H) 12.6 (s, 1 H).

Example 37

L-2-(4'-{[4-(Methanesulfonyl-methyl-animo)-3-methyl-benzofuran-2-carbonyl]-amino}-biphenyl-4-sulfonylamino)-3-methyl-butyric acid

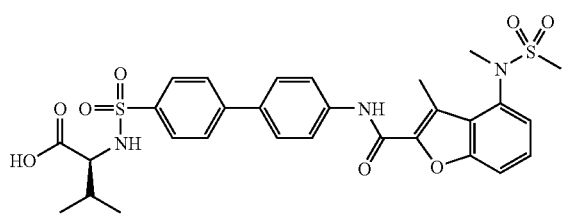

Step 1: To a mixture of the product of Example 36, Step 1, 4-methanesulfonylamino-3-methyl-benzofuran-2-carboxylic acid ethyl ester (438 mg, 1.47 mmol, 1 eq) and K$_2$CO$_3$ (430 mg, 3.11 mmol, 2.1 eq) in 4 mL of DMF under nitrogen was added 0.18 mL of iodomethane (2.89 mmol, 2 eq). The reaction mixture was sealed and heated to 80° C. for 18 h. After cooling to room temperature and work up, 4-(methanesulfonyl-methyl-amino)-3-methyl-benzofuran-2-carboxylic acid ethyl ester was obtained in pure form without further purification (100% yield). $^1$H NMR (400 MHz, CDCl$_3$) δ ppm 1.4 (t, J=7.1 Hz, 3 H) 2.8 (s, 3 H) 3.0 (s, 3 H) 3.4 (s, 3 H) 4.5 (q, J=7.1 Hz, 2 H) 7.2 (dd, J=7.6, 0.8 Hz, 1 H) 7.4 (m, 1 H) 7.6 (m, 1 H).

Step 2: According to the procedure of Example 20, Step 3, hydrolysis of 4-(methanesulfonyl-methyl-amino)-3-methyl-benzofuran-2-carboxylic acid ethyl ester provided 4-(methanesulfonyl-methyl-amino)-3-methyl-benzofuran-2-carboxylic acid in quantitative yield. $^1$H NMR (400 MHz, DMSO-d$_6$) δ ppm 2.7 (s, 3 H) 3.1 (s, 3 H) 3.3 (s, 3 H) 7.5 (m, 2 H) 7.7 (dd, J=8.2, 1.1 Hz, 1 H).

Step 3: According to the procedure of Example 21, Step 3, coupling of 4-(methanesulfonyl-methyl-amino)-3-methyl-benzofuran-2-carboxylic acid with L-2-(4'-amino-biphenyl-4-sulfonylamino)-3-methyl-butyric acid methyl ester provided L-2-(4'-{[4-(methanesulfonyl-methyl-amino)-3-methyl-benzofuran-2-carbonyl]-amino}-biphenyl-4-sulfonylamino)-3-methyl-butyric acid methyl ester in 100% yield. $^1$H NMR (400 MHz, DMSO-d$_6$) δ ppm 0.8 (dd, J=14.9, 6.8 Hz, 6 H) 1.9 (m, 1 H) 2.7 (d, J=0.5 Hz, 3 H) 2.8 (s, 3 H) 2.9 (s, 3 H) 3.1 (s, 3 H) 3.6 (dd, J=9.3, 7.1 Hz, 1 H) 7.6 (m, 2 H) 7.7 (m, 1 H) 7.8 (dd, J=8.7, 7.2 Hz, 4 H) 7.9 (m, 2 H) 8.0 (m, 3 H) 8.3 (d, J=9.3 Hz, 1 H) 10.6 (s, 1 H).

Step 4: According to the procedure of Example 20, Step 5, hydrolysis of L-2-(4'-{[4-(methanesulfonyl-methyl-amino)-3-methyl-benzofuran-2-carbonyl]-amino}-biphenyl-4-sulfonylamino)-3-methyl-butyric acid methyl ester provided L-2-(4'-{[4-(methanesulfonyl-methyl-amino)-3-methyl-benzofuran-2-carbonyl]-amino}-biphenyl-4-sulfonylamino)-3-methyl-butyric acid in 100% yield. $^1$H NMR (400 MHz, DMSO-d$_6$) δ ppm 0.8 (dd, J=12.6, 6.8 Hz, 6 H) 1.9 (m, 1 H) 2.7 (s, 3 H) 3.1 (s, 3 H) 3.3 (s, 3 H) 3.6 (dd, J=9.5, 6.2 Hz, 1 H) 7.6 (m, 2 H) 7.7 (m, 1 H) 7.8 (d, J=8.8 Hz, 2 H) 7.9 (m, 4 H) 8.0 (d, J=8.8 Hz, 2 H) 8.1 (d, J=9.6 Hz, 1 H) 10.6 (s, 1 H)

Example 38

L-3-Hydroxy-2-(4-{5-[(4-methanesulfonylamino-3-methyl-benzofuran-2-carbonyl)-amino]-pyridin-2-yl}-benzenesulfonylamino)-butyric acid

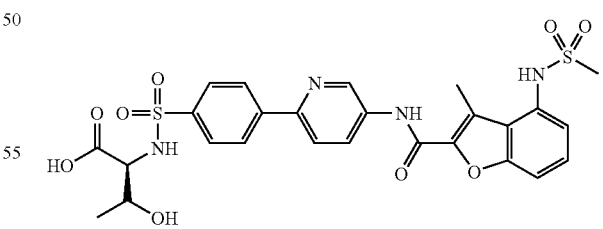

Step 1: To a mixture of L-2-amino-3-tert-butoxy-butyric acid methyl ester hydrochloric salt (4.87 g, 21.6 mmol, 1 eq) and 4-bromo-benzenesulfonyl chloride (5.51 g, 21.6 mmol, 1 eq) in 50 mL of dichloromethane at 0° C. under nitrogen was added N,N-diisopropylethylamine (7.5 mL, 43.1 mmol, 2 eq) dropwise. The ice bath was removed and the reaction was allowed to react at room temperature for 1 h. After work up and trituration with hexanes, L-2-(4-bromo-benzenesulfonylamino)-3-tert-butoxy-butyric acid methyl ester was obtained in 88% yield (7.77 g). $^1$H NMR (400 MHz, DMSO-d$_6$) δ ppm 1.0 (s, 9 H) 1.0 (s, 3 H) 3.4 (s, 3 H) 3.8 (dd, J=9.7, 3.4 Hz, 1 H) 4.0 (dd, J=6.2, 3.7 Hz, 1 H) 7.7 (d, J=8.8 Hz, 2 H) 7.8 (m, 2 H) 8.2 (d, J=9.6 Hz, 1 H)

Step 2: To a mixture of L-2-(4-bromo-benzenesulfonylamino)-3-tert-butoxy-butyric acid methyl ester (811 mg, 2 mmol, 1 eq), bis(pinacolato)diboron (1.55 g, 6.1 mmol, 2.05 eq), and KOAc (622 mg, 6.34 mmol, 3.17 eq) under nitrogen in 45 mL of DMSO was added PdCl$_2$(dppf) CH$_2$Cl$_2$ (110 mg, 0.13 mmol, 0.065 eq). The reaction mixture was heated to 80° C. for 18 h. After work up and column chromatography, L-3-tert-butoxy-2-[4-(4,4,5,5-tetramethyl-[1,3,2]dioxaborolan-2-yl)-benzenesulfonylamino]-butyric acid methyl ester was obtained in 77% yield (696 mg). $^1$H NMR (400 MHz, DMSO-d$_6$) δ ppm 1.0 (s, 9 H) 1.3 (s, 12 H) 3.4 (s, 3 H) 3.8 (dd, J=9.7, 3.7 Hz, 1 H) 3.9 (dd, J=6.2, 3.7 Hz, 1 H) 7.8 (m, 4 H) 8.1 (d, J=9.9 Hz, 1 H).

Step 3: A mixture of L-3-tert-butoxy-2-[4-(4,4,5,5-tetramethyl-[1,3,2]dioxaborolan-2-yl)-benzenesulfonylamino]-butyric acid methyl ester (696 mg, 1.53 mmol, 1 eq), 2-bromo-5-nitropyridine (932 mg, 4.59 mmol, 3 eq), Pd(PPh$_3$)$_4$ (88 mg, 0.076 mmol, 0.05 eq), and K$_2$CO$_3$ (423 mg, 3.06 mmol, 2 eq) in 10 mL of 1,2-dimethoxyethane and 5 mL of water was heated to 90° C. under nitrogen. After 3 h, the reaction was complete and subjected to work up and column chromatography (20% ethyl acetate/hexane) to give L-3-tert-butoxy-2-[4-(5-nitro-pyridin-2-yl)-benzenesulfonylamino]-butyric acid methyl ester in 81% yield (557 mg). $^1$H NMR (400 MHz, DMSO-d$_6$) δ ppm 1.0 (s, 12 H) 3.4 (s, 3 H) 3.9 (dd, J=9.9, 3.5 Hz, 1 H) 4.0 (m, 1 H) 8.0 (d, J=8.6 Hz, 2 H) 8.2 (d, J=9.9 Hz, 1 H) 8.4 (m, 3 H) 8.7 (dd, J=8.8, 2.8 Hz, 1 H) 9.5 (d, J=2.5 Hz, 1 H).

Step 4: To 550 mg of L-3-tert-butoxy-2-[4-(5-nitro-pyridin-2-yl)-benzenesulfonylamino]-butyric acid methyl ester in 10 mL of THF under a nitrogen atmosphere was added 125 mg of 5% Pd/C. A hydrogen balloon was introduced to the reaction mixture. After 24 h the mixture was worked up to give L-2-[4-(5-amino-pyridin-2-yl)-benzenesulfonylamino]-3-tert-butoxy-butyric acid methyl ester in quantitative yield. $^1$H NMR (400 MHz, DMSO-d$_6$) δ ppm 1.0 (s, 9 H) 1.0 (s, 3 H) 3.4 (s, 3 H) 3.8 (dd, J=9.7, 3.7 Hz, 1 H) 3.9 (dd, J=6.2, 3.7 Hz, 1 H) 5.7 (s, 2 H) 7.8 (t, J=9.0 Hz, 3 H) 8.0 (d, J=9.6 Hz, 1 H) 8.1 (m, 3 H)

Step 5: Amide coupling of the product of Example 36, Step 2, 4-methanesulfonylamino-3-methyl-benzofuran-2-carboxylic acid, with L-2-[4-(5-amino-pyridin-2-yl)-benzenesulfonylamino]-3-tert-butoxy-butyric acid methyl ester according to the procedure of Example 21, Step 3, provided L-3-tert-butoxy-2-(4-{5-[(4-methanesulfonylamino-3-methyl-benzofuran-2-carbonyl)-amino]-pyridin-2-yl}-benzenesulfonylamino)-butyric acid methyl ester in 42% yield. $^1$H NMR (400 MHz, DMSO-d$_6$) δ ppm 1.0 (s, 9 H) 1.0 (s, 3 H) 2.8 (s, 3 H) 3.1 (s, 3 H) 3.4 (s, 3 H) 3.9 (dd, J=9.7, 3.7 Hz, 1 H) 4.0 (dd, J=6.2, 3.7 Hz, 1 H) 7.3 (dd, J=7.8, 0.8 Hz, 1 H) 7.5 (m, 1 H) 7.7 (dd, J=8.3, 0.8 Hz, 1 H) 7.9 (d, J=8.6 Hz, 2 H) 8.1 (m, 2 H) 8.3 (d, J=8.8 Hz, 2 H) 8.4 (dd, J=8.7, 2.7 Hz, 1 H) 9.1 (d, J=3.0 Hz, 1 H) 9.6 (s, 1 H) 10.8 (s, 1 H).

Step 6: To 100 mg of L-3-tert-butoxy-2-(4-{5-[(4-methanesulfonylamino-3-methyl-benzofuran-2-carbonyl)-amino]-pyridin-2-yl}-benzenesulfonylamino)-butyric acid methyl ester in 8 mL of dichloroethane was added 0.5 mL of trifluoroacetic acid. After 1.5 h the solvent was removed in vacuo. To the crude residue was added THF (8 mL), MeOH (3 mL), and 1 N LiOH (4.5 mL). The reaction mixture was stirred at room temperature until the starting material was consumed (~1-2 days). The reaction mixture was then acidified with 1N hydrochloric acid to pH 4. The resulting mixture was extracted with ethyl acetate. The combined organic layers were concentrated in vacuo, and the crude residue was recrystallized to give 3-hydroxy-2-(4-{5-[(4-methanesulfonylamino-3-methyl-benzofuran-2-carbonyl)-amino]-pyridin-2-yl}-benzenesulfonylamino)-butyric acid in 72% yield. $^1$H NMR (400 MHz, DMSO-d$_6$) δ ppm 1.0 (s, 9 H) 1.0 (s, 3 H) 2.8 (s, 3 H) 3.1 (s, 3 H) 3.4 (s, 3 H) 3.9 (dd, J=9.7, 3.7 Hz, 1 H) 4.0 (dd, J=6.2, 3.7 Hz, 1 H) 7.3 (dd, J=7.8, 0.8 Hz, 1 H) 7.5 (m, 1 H) 7.7 (dd, J=8.3, 0.8 Hz, 1 H) 7.9 (d, J=8.6 Hz, 2 H) 8.1 (m, 2 H) 8.3 (d, J=8.8 Hz, 2 H) 8.4 (dd, J=8.7, 2.7 Hz, 1 H) 9.1 (d, J=3.0 Hz, 1 H) 9.6 (s, 1 H) 10.8 (s, 1 H)

Example 39

L-2-(4-{5-[(4-Methanesulfonylamino-3-methyl-benzofuran-2-carbonyl)-amino]-pyridin-2-yl}-benzenesulfonylamino)-3-methyl-butyric acid

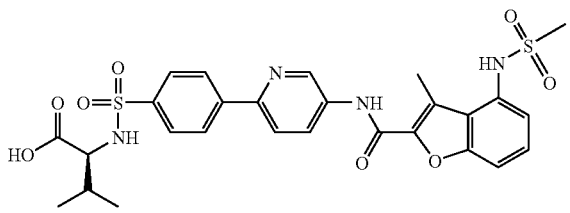

Step 1: L-3-Methyl-2-[4-(4,4,5,5-tetramethyl-[1,3,2]dioxaborolan-2-yl)-benzenesulfonylamino]-butyric acid methyl ester was prepared according to the procedure of Example 38, Step 2, from L-2-(4-bromo-benzenesulfonylamino)-3-methyl-butyric acid methyl ester and bis(pinacolato)diboron in 90% yield. $^1$H NMR (400 MHz, DMSO-d$_6$) δ ppm 0.8 (dd, J=9.0, 6.7 Hz, 6 H) 1.3 (s, 12 H) 1.9 (m, 1 H) 3.4 and (s, 3 H) 3.5 (dd, J=9.2, 6.9 Hz, 1 H) 7.8 (d, J=8.6 Hz, 2 H) 7.8 (m, 2 H) 8.3 (d, J=9.3 Hz, 1 H).

Step 2: L-3-Methyl-2-[4-(5-nitro-pyridin-2-yl)-benzenesulfonylamino]-butyric acid methyl ester was prepared according to the procedure of Example 36, Step 3, from L-3-methyl-2-[4-(4,4,5,5-tetramethyl-[1,3,2]dioxaborolan-2-yl)-benzenesulfonylamino]-butyric acid methyl ester and 2-bromo-5-nitropyridine in 78% yield. $^1$H NMR (400 MHz, CDCl$_3$) δ ppm 0.9 (dd, J=36.1, 6.8 Hz, 6 H) 2.1 (m, 1 H) 3.5 (s, 3 H) 3.8 (dd, J=10.0, 4.9 Hz, 1 H) 5.2 (d, J=9.9 Hz, 1 H) 8.0 (dd, J=8.7, 1.9 Hz, 3 H) 8.2 (d, J=8.8 Hz, 2 H) 8.6 (dd, J=8.7, 2.7 Hz, 1 H) 9.5 (d, J=3.3 Hz, 1 H).

Step 3: Hydrogenation of L-3-methyl-2-[4-(5-nitro-pyridin-2-yl)-benzenesulfonylamino]-butyric acid methyl ester according to the procedure of Example 36, Step 4, provided L-2-[4-(5-amino-pyridin-2-yl)-benzenesulfonylamino]-3-methyl-butyric acid methyl ester in quantitative yield. $^1$H NMR (400 MHz, DMSO-d$_6$) δ ppm 0.8 (dd, J=12.9, 6.8 Hz, 6 H) 1.9 (m, 1 H) 3.3 (s, 3 H) 3.5 (dd, J=9.3, 7.1 Hz, 1 H) 5.7 (s, 2 H) 7.0 (dd, J=8.6, 2.8 Hz, 1 H) 7.7 (m, 3 H) 8.1 (m, 3 H) 8.2 (d, J=9.3 Hz, 1 H).

Step 4: Amide coupling of 4-methanesulfonylamino-3-methyl-benzofuran-2-carboxylic acid with L-2-[4-(5-amino-pyridin-2-yl)-benzenesulfonylamino]-3-methyl-butyric acid methyl ester according to the procedure of Example 21, Step 3, provided L-2-(4-{5-[(4-Methanesulfonylamino-3-methyl-benzofuran-2-carbonyl)-amino]-pyridin-2-yl}-benzenesulfonylamino)-3-methyl-butyric acid methyl ester in 22% yield. $^1$H NMR (400 MHz, DMSO-d$_6$) δ ppm 0.8 (dd, J=12.5, 6.7 Hz, 6 H) 1.9 (m, 1 H) 2.8 (s, 3 H) 3.1 (s, 3 H) 3.3 (s, 3 H) 3.6 (dd, J=9.3, 7.1 Hz, 1 H) 7.3 (d, J=7.6 Hz, 1 H) 7.5 (m, 1 H) 7.7 (d, J=7.6 Hz, 1 H) 7.8 (d, J=8.6 Hz, 2 H) 8.1 (d, J=8.8 Hz, 1 H) 8.3 (d, J=8.8 Hz, 2 H) 8.3 (d, J=9.3 Hz, 1 H) 8.4 (dd, J=8.8, 2.5 Hz, 1 H) 9.1 (dd, J=2.0 Hz, 1 H) 9.6 (s, 1 H) 10.8 (s, 1 H).

Step 5: Hydrolysis of L-2-(4-{5-[(4-methanesulfonylamino-3-methyl-benzofuran-2-carbonyl)-amino]-pyridin-2-yl}-benzenesulfonylamino)-3-methyl-butyric acid methyl ester according to the procedure of Example 20, Step 5, provided L-2-(4-{5-[(4-methanesulfonylamino-3-methyl-benzofuran-2-carbonyl)-amino]-pyridin-2-yl}-benzenesulfonylamino)-3-methyl-butyric acid in quantitative yield. $^1$H NMR (400 MHz, DMSO-$d_6$) δ ppm 0.8 (dd, J=13.4, 6.8 Hz, 6 H) 2.0 (m, 1 H) 2.8 (s, 3 H) 3.1 (s, 3 H) 3.6 (dd, J=9.3, 5.8 Hz, 1 H) 7.3 (d, J=7.6 Hz, 1 H) 7.5 (m, 1 H) 7.7 (d, J=7.3 Hz, 1 H) 7.9 (d, J=8.8 Hz, 2 H) 8.1 (dd, J=9.0, 3.2 Hz, 2 H) 8.3 (d, J=8.6 Hz, 2 H) 8.4 (dd, J=8.7, 2.4 Hz, 1 H) 9.1 (d, J=2/5 Hz, 1 H) 9.6 (s, 1 H) 10.8 (s, 1 H).

Example 40

L-2-(4-{5-[(4-Cyano-3-methyl-benzofuran-2-carbonyl)-amino]-pyridin-2-yl}-benzenesulfonylamino)-3-methyl-butyric acid

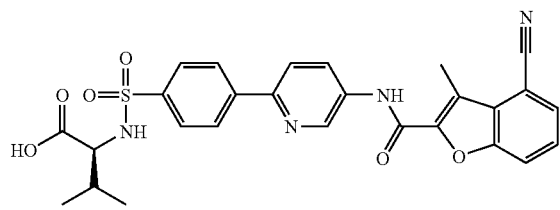

Step 1: Amide coupling of the product of Example 20, Step 3, 4-cyano-3-methyl-benzofuran-2-carboxylic acid, with L-2-[4-(5-amino-pyridin-2-yl)-benzenesulfonylamino]-3-methyl-butyric acid methyl ester, the product of Example 39, Step 3, was carried according to the procedure of Example 21, Step 3, to give L-2-(4-{5-[(4-cyano-3-methyl-benzofuran-2-carbonyl)-amino]-pyridin-2-yl}-benzenesulfonylamino)-3-methyl-butyric acid methyl ester in 57% yield. $^1$H NMR (400 MHz, DMSO-$d_6$) δ ppm 0.8 (dd, J=12.4, 6.8 Hz, 6 H) 1.9 (m, 1 H) 2.8 (s, 3 H) 3.4 (s, 3 H) 3.6 (dd, J=9.3, 7.1 Hz, 1 H) 7.7 (dd, J=8.3, 7.6 Hz, 1 H) 7.8 (d, J=8.8 Hz, 2 H) 7.9 (dd, J=7.5, 0.9 Hz, 1 H) 8.1 (m, 2 H) 8.3 (d, J=8.8 Hz, 2 H) 8.3 (d, J=9.3 Hz, 1 H) 8.4 (dd, J=8.8, 2.5 Hz, 1 H) 9.1 (d, J=1.8 Hz, 1 H) 11.0 (s, 1 H).

Step 2: Hydrolysis of L-2-(4-{5-[(4-cyano-3-methyl-benzofuran-2-carbonyl)-amino]-pyridin-2-yl}-benzenesulfonylamino)-3-methyl-butyric acid methyl ester according to the procedure of Example 20, Step 5, provided L-2-(4-{5-[(4-cyano-3-methyl-benzofuran-2-carbonyl)-amino]-pyridin-2-yl}-benzenesulfonylamino)-3-methyl-butyric acid in quantitative yield. $^1$H NMR (400 MHz, DMSO-$d_6$) δ ppm 0.8 (dd, J=13.1, 6.8 Hz, 6 H) 1.9 (m, 1 H) 2.8 (s, 3 H) 3.6 (dd, J=9.3, 6.3 Hz, 1 H) 7.7 (dd, J=8.3, 7.6 Hz, 1 H) 7.9 (d, J=8.6 Hz, 2 H) 7.9 (dd, J=7.6, 0.8 Hz, 1 H) 8.1 (m, 3 H) 8.3 (d, J=8.8 Hz, 2 H) 8.4 (dd, J=8.8, 2.5 Hz, 1 H) 9.1 (dd, J=2.5, 0.8 Hz, 1 H) 11.0 (s, 1 H).

Example 41

D-2-{4-[(4-Methanesulfonylamino-3-methyl-benzofuran-2-carbonyl)-amino]-biphenyl-4-sulfonylamino}-3-methyl-butyric acid

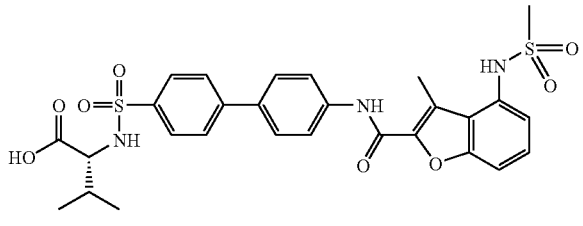

Step 1: Suzuki coupling of D-2-(4-bromo-benzenesulfonylamino)-3-methyl-butyric acid methyl ester with 4-(4,4,5,5-tetramethyl-[1,3,2]dioxaborolan-2-yl)-phenylamine was carried out according to Example 38, Step 3 to give D-2-(4'-amino-biphenyl-4-sulfonylamino)-3-methyl-butyric acid methyl ester in 88% yield. $^1$H NMR (400 MHz, DMSO-$d_6$) δ ppm 0.8 (dd, J=15.2, 6.8 Hz, 6 H) 1.9 (m, 1 H) 3.3 (s, 3 H) 3.5 (dd, J=9.3, 7.1 Hz, 1 H) 5.4 (s, 2 H) 6.7 (d, J=8.6 Hz, 2 H) 7.5 (d, J=8.6 Hz, 2 H) 7.7 (d, J=4.5 Hz, 4 H) 8.2 (d, J=9.3 Hz, 1 H).

Step 2: Amide coupling of D-2-(4'-amino-biphenyl-4-sulfonylamino)-3-methyl-butyric acid methyl ester with 4-methanesulfonylamino-3-methyl-benzofuran-2-carboxylic acid was carried out according to Example 21, Step 3 to give D-2-{4'-[(4-methanesulfonylamino-3-methyl-benzofuran-2-carbonyl)-amino]-biphenyl-4-sulfonylamino}-3-methyl-butyric acid methyl ester 58% yield. $^1$H NMR (400 MHz, DMSO-$d_6$) δ ppm 0.8 (dd, J=14.8, 6.7 Hz, 6 H) 1.9 (m, 1 H) 2.8 (s, 3 H) 3.1 (s, 3 H) 3.3 (s, 3 H) 3.6 (dd, J=9.3, 7.3 Hz, 1 H) 7.3 (d, J=7.8 Hz, 1 H) 7.5 (m, 1 H) 7.6 (d, J=8.8 Hz, 2 H) 7.8 (t, J=8.3 Hz, 4 H) 7.9 (m, 2 H) 8.0 (d, J=8.8 Hz, 2 H) 8.3 (d, J=9.3 Hz, 1 H) 9.5 (s, 1 H) 10.6 (s, 1 H)

Step 3: Hydrolysis of D-2-{4'-[(4-methanesulfonylamino-3-methyl-benzofuran-2-carbonyl)-amino]-biphenyl-4-sulfonylamino}-3-methyl-butyric acid methyl ester was carried out according to Example 20, Step 5 in quantitative yield. $^1$H NMR (400 MHz, DMSO-$d_6$) δ ppm 0.8 (dd, J=12.9, 6.8 Hz, 6 H) 1.9 (m, 1 H) 2.8 (s, 3 H) 3.1 (s, 3 H) 3.6 (dd, J=9.5, 5.9 Hz, 1 H) 7.3 (d, J=7.8 Hz, 1 H) 7.5 (m, 1 H) 7.6 (m, 1 H) 7.8 (d, J=8.6 Hz, 2 H) 7.9 (m, 4 H) 8.0 (d, J=8.8 Hz, 2 H) 8.1 (d, J=9.3 Hz, 1 H) 9.5 (s, 1 H) 10.6 (s, 1 H)

Example 42

L-2-({4'-[(4-Cyano-3-methyl-benzofuran-2-carbonyl)-amino]-biphenyl-4-sulfonyl}-methyl-amino)-3-methyl-butyric acid

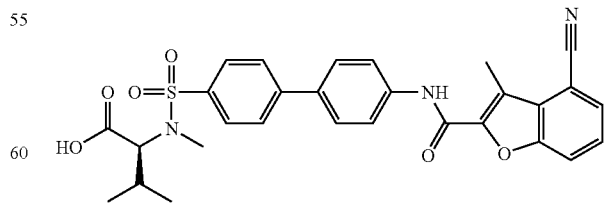

Step 1: L-3-Methyl-2-(4'-nitro-biphenyl-4-sulfonylamino)-butyric acid methyl ester was prepared from 4'-nitro-biphenyl-4-sulfonyl chloride and 2-amino-3-methyl-butyric acid methyl ester hydrochloride acid salt according to Example 38, Step 1. ¹H NMR (400 MHz, DMSO-d₆) δ ppm 0.8 (dd, J=13.4, 6.8 Hz, 6 H) 1.9 (m, 1 H) 3.3 (s, 3 H) 3.6 (dd, J=9.3, 7.1 Hz, 1 H) 7.9 (d, J=8.6 Hz, 2 H) 8.0 (dd, J=15.8, 9.0 Hz, 4 H) 8.3 (d, J=8.8 Hz, 2 H) 8.4 (d, J=9.3 Hz, 1 H).

Step 2: To a mixture of L-3-methyl-2-(4'-nitro-biphenyl-4-sulfonylamino)-butyric acid methyl ester (1.05 g, 2.7 mmol, 1 eq) and K₂CO₃ (1.1 g, 8 mmol, 3 eq) in 8 mL of DMF was added iodomethane (0.25 mL, 4.0 mmol, 1.5 eq) under nitrogen. After 12 h, the mixture was worked-up to give L-3-methyl-2-[methyl-(4'-nitro-biphenyl-4-sulfonyl)-amino]-butyric acid methyl ester in 94% yield (1.023 g). ¹H NMR (400 MHz, DMSO-d₆) δ ppm 0.9 (dd, J=8.8, 6.6 Hz, 6 H) 2.1 (m, 1 H) 2.8 (s, 3 H) 3.3 (s, 3 H) 4.0 (d, J=10.6 Hz, 1 H) 7.9 (d, J=8.8 Hz, 2 H) 8.0 (m, 4 H) 8.4 (d, J=9.1 Hz, 2 H).

Step 3: Hydrogenation of L-3-methyl-2-[methyl-(4'-nitro-biphenyl-4-sulfonyl)-amino]-butyric acid methyl ester was carried out according to Example 38, Step 4 to give L-2-[(4'-amino-biphenyl-4-sulfonyl)-methyl-amino]-3-methyl-butyric acid methyl ester in quantitative yield. ¹H NMR (400 MHz, DMSO-d₆) δ ppm 0.9 (dd, J=10.4, 6.6 Hz, 6 H) 2.0 (dd, 1 H) 2.8 (s, 3 H) 3.4 (s, 3 H) 4.0 (d, J=7.1 Hz, 1 H) 5.4 (s, 2 H) 6.7 (d, J=8.6 Hz, 2 H) 7.5 (d, J=8.6 Hz, 2 H) 7.7 (d, J=8.8 Hz, 2 H) 7.8 (m, 2 H).

Step 4: Amide coupling of L-2-[(4'-amino-biphenyl-4-sulfonyl)-methyl-amino]-3-methyl-butyric acid methyl ester with 4-cyano-3-methyl-benzofuran-2-carboxylic acid (Example 20, Step 3) in 75% yield. ¹H NMR (400 MHz, DMSO-d₆) δ ppm 0.9 (dd, J=10.6, 6.6 Hz, 6 H) 2.1 (dd, 1 H) 2.8 (s, 3 H) 2.8 (s, 3 H) 3.4 (s, 3 H) 4.0 (d, J=10.6 Hz, 1 H) 7.7 (dd, J=8.6, 7.6 Hz, 1 H) 7.8 (dd, J=8.7, 3.2 Hz, 4 H) 7.9 (m, 3 H) 8.0 (d, J=8.8 Hz, 2 H) 8.1 (dd, J=8.5, 0.9 Hz, 1 H) 10.8 (s, 1 H).

Step 5: Hydrolysis of L-2-({4'-[(4-cyano-3-methyl-benzofuran-2-carbonyl)-amino]-biphenyl-4-sulfonyl}-methyl-amino)-3-methyl-butyric acid methyl ester was carried out according to Example 20, Step 5 to give L-2-({4'-[(4-cyano-3-methyl-benzofuran-2-carbonyl)-amino]-biphenyl-4-sulfonyl}-methyl-amino)-3-methyl-butyric acid in quantitative yield. ¹H NMR (400 MHz, DMSO-d₆) δ ppm 0.9 (dd, J=21.3, 6.7 Hz, 6 H) 2.0 (m, 1 H) 2.8 (d, J=10.1 Hz, 6 H) 4.0 (d, J=10.6 Hz, 1 H) 7.7 (dd, J=8.3, 7.6 Hz, 1 H) 7.8 (t, J=8.8 Hz, 4 H) 7.9 (m, 3 H) 8.0 (d, J=8.8 Hz, 2 H) 8.1 (dd, J=8.5, 0.9 Hz, 1 H) 10.8 (s, 1 H).

Examples 43A and B (L-3-Methyl-2-{4'-[(3-methyl-4-methylcarbamoyl-benzofuran-2-carbonyl)-amino]-biphenyl-4-sulfonylamino}-butyric acid triethylamine salt and 2-{4'-[(4-Dimethylcarbamoyl-3-methyl-benzofuran-2-carbonyl)-amino]-biphenyl-4-sulfonylamino}-3-methyl-butyric acid triethylamine salt

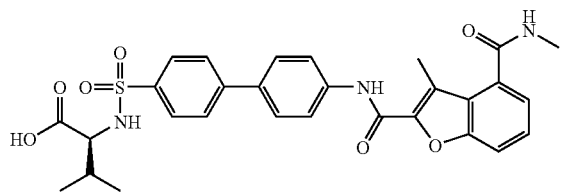

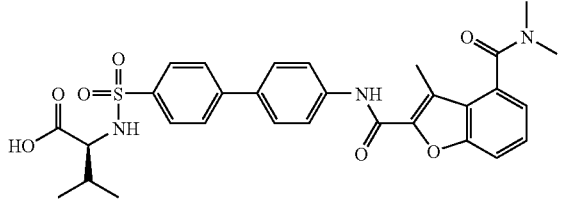

Step 1: To 213 mg of 4-cyano-3-methyl-benzofuran-2-carboxylic acid ethyl ester (Example 20, Step 2) in 6 mL of ethanol and 6 mL of DMSO was added 3 mL of Na₂CO₃ (3M), followed by 3 mL of H₂O₂ (30% in water). After 24 h of reaction, the mixture was worked up to give 4-carbamoyl-3-methyl-benzofuran-2-carboxylic acid ethyl ester in quantitative yield. ¹H NMR (400 MHz, DMSO-d₆) δ ppm 1.4 (t, J=7.1 Hz, 3 H) 2.6 (s, 3 H) 4.4 (q, J=7.1 Hz, 2 H) 7.4 (dd, J=7.3, 1.0 Hz, 1 H) 7.5 (dd, J=8.3, 7.3 Hz, 1 H) 7.7 (s, 1 H) 7.8 (m, 1 H) 8.0 (s, 1 H).

Step 2: To 200 mg of 4-carbamoyl-3-methyl-benzofuran-2-carboxylic acid ethyl ester (0.81 mmol, 1 eq.) in 5 mL of DMF was added 50 mg of NaH (60% in mineral oil, 1.25 mmol, 1.5 eq) under nitrogen. After 30 min of reaction, iodomethane (0.053 mL, 0.85 mmol, 1 eq) was added to the reaction. The mixture was then heated to 50° C. for 12 h. After work up and column chromatography, a mixture of 3-methyl-4-methylcarbamoyl-benzofuran-2-carboxylic acid ethyl ester and 4-dimethylcarbamoyl-3-methyl-benzofuran-2-carboxylic acid ethyl ester was obtained (76 mg). ¹H NMR (400 MHz, DMSO-d₆) δ ppm 1.3 (t, J=7.1 Hz, 3 H) 2.8 (d, J=4.5 Hz, 6 H) 4.4 (q, J=7.2 Hz, 2 H) 7.3 (dd, J=7.3, 1.0 Hz, 1 H) 7.5 (dd, J=8.3, 7.3 Hz, 1 H) 7.8 (dd, J=8.5, 0.9 Hz, 1 H).

Step 3: Hydrolysis of the mixture of 3-methyl-4-methylcarbamoyl-benzofuran-2-carboxylic acid ethyl ester and 4-dimethylcarbamoyl-3-methyl-benzofuran-2-carboxylic acid ethyl ester was carried out according to Example 20, Step 3. The mixture of 3-methyl-4-methylcarbamoyl-benzofuran-2-carboxylic acid and 4-dimethylcarbamoyl-3-methyl-benzofuran-2-carboxylic acid obtained was used for the next reaction without purification. ¹H NMR (400 MHz, DMSO-d₆) δ ppm 2.8 (d, J=4.8 Hz, 6 H) 7.3 (d, J=7.3, 0.8 Hz, 1 H) 7.5 (dd, J=8.5, 7.5 Hz, 1 H) 7.7 (dd, J=8.5, 0.9 Hz, 1 H).

Step 4: Amide coupling using material from Step 3 and L-2-(4'-amino-biphenyl-4-sulfonylamino)-3-methyl-butyric acid methyl ester was carried out according to Example: 21, Step 3. After column chromatography, a mixture of two products was obtained. ¹H NMR (400 MHz, DMSO-d₆) δ ppm 0.8 (dd, J=14.7, 6.8 Hz, 6 H) 1.9 (m, 1 H) 2.6 (s, 3 H) 2.8 (d, J=4.5 Hz, 3 H) 3.4 (s, 3 H) 3.6 (m, 1 H) 7.4 (dd, J=7.3, 1.0 Hz, 1 H) 7.5 (dd, J=8.3, 7.6 Hz, 1 H) 7.8 (m, 5 H) 7.9 (m, 2 H) 8.0 (d, J=8.8 Hz, 1 H) 8.3 (d, J=9.3 Hz, 1 H) 8.5 (d, J=4.5 Hz, 1 H) 10.6 (s, 1 H).

Step 5: Hydrolysis of the above mixture was carried out according to the procedure of Example 20, Step 5. Final purification using preparative HPLC (triethylamine as additive to improve compound solubility) provided 40 mg of (L-3-methyl-2-{4'-[(3-methyl-4-methylcarbamoyl-benzofuran-2-carbonyl)-amino]-biphenyl-4-sulfonylamino}-butyric acid triethylamine salt (43A) and 12 mg of 2-{4'-[(4-dimethylcarbamoyl-3-methyl-benzofuran-2-carbonyl)-amino]-biphenyl-4-sulfonylamino}-3-methyl-butyric acid triethylamine salt (43B). 43A ¹H NMR (400 MHz, DMSO-d₆) δ ppm 0.8 (dd, J=33.9, 6.8 Hz, 6 H) 2.0 (m, 1 H) 2.6 (s, 3 H) 2.8 (d, J=4.8 Hz, 3 H) 7.4 (d, J=7.3 Hz, 1 H) 7.5 (m, 1 H) 7.8 (m, 7 H) 8.0 (d, J=8.8 Hz, 2 H) 8.5 (d, J=4.5 Hz, 1 H) 10.6 (s, 1 H).

43B $^1$H NMR (400 MHz, DMSO-d$_6$) δ ppm 0.8 (dd, J=28.3, 6.8 Hz, 6 H) 2.0 (dd, J=11.9, 7.1 Hz, 1 H) 2.5 (s, 3 H) 2.8 (s, 3 H) 3.1 (s, 3 H) 7.2 (d, J=7.1 Hz, 1 H) 7.6 (m, 1 H) 7.8 (m, 7 H) 8.0 (d, J=8.8 Hz, 2 H) 10.6 (s, 1 H).

Example 44

L-2-{4'-[(4,6-Dimethoxy-3,7-dimethyl-benzofuran-2-carbonyl)-amino]-biphenyl-4-sulfonylamino}-3-methyl-butyric acid

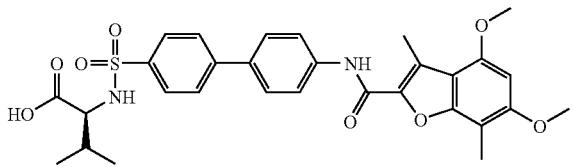

Step 1: Amide coupling of 4,6-dimethoxy-3,7-dimethyl-benzofuran-2-carboxylic acid with L-2-(4'-amino-biphenyl-4-sulfonylamino)-3-methyl-butyric acid methyl ester was carried out according to Example 21, Step 3, to provide 2-{4'-[(4,6-dimethoxy-3,7-dimethyl-benzofuran-2-carbonyl)-amino]-biphenyl-4-sulfonylamino}-3-methyl-butyric acid methyl ester in 74% yield. $^1$H NMR (400 MHz, DMSO-d$_6$) δ ppm 0.8 (dd, J=14.3, 6.7 Hz, 6 H) 1.9 (dd, J=13.8, 6.9 Hz, 1 H) 2.3 (s, 3 H) 2.7 (s, 3 H) 3.4 (s, 3 H) 3.6 (m, 1 H) 3.9 (d, J=8.1 Hz, 6H) 6.6 (s, 1 H) 7.8 (m, 4 H) 7.9 (m, 2 H) 7.9 (d, J=9.1 Hz, 2 H) 8.3 (d, J=9.1 Hz, 1 H) 10.1 (s, 1 H).

Step 2: Hydrolysis of 2-{4'-[(4,6-dimethoxy-3,7-dimethyl-benzofuran-2-carbonyl)-amino]-biphenyl-4-sulfonylamino}-3-methyl-butyric acid methyl ester was carried out according to Example 20, Step 5 to provide 2-{4'-[(4,6-dimethoxy-3,7-dimethyl-benzofuran-2-carbonyl)-amino]-biphenyl-4-sulfonylamino}-3-methyl-butyric acid in quantitative yield. $^1$H NMR (400 MHz, DMSO-d$_6$) δ ppm 0.8 (dd, J=14.1, 6.8 Hz, 6 H) 2.0 (dd, J=13.3, 6.4 Hz, 1 H) 2.3 (s, 3 H) 2.7 (s, 3 H) 3.4 (s, 1 H) 3.9 (m, J=8.1 Hz, 6 H) 6.6 (s, 1 H) 7.8 (m, J=8.8 Hz, 2 H) 7.8 (d, J=8.8 Hz, 2 H) 7.9 (m, 2 H) 7.9 (d, J=8.8 Hz, 2 H) 10.1 (s, 1 H).

Example 45

2-{4'-[(5-Bromo-3-methyl-benzofuran-2-carbonyl)-amino]-biphenyl-4-sulfonylamino}-3-methyl-butyric acid

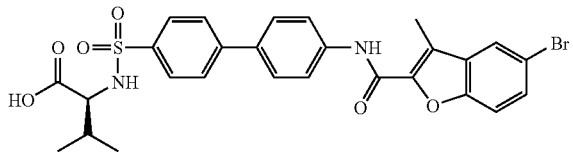

Step 1: To a mixture of 1-(5-bromo-2-hydroxy-phenyl)-ethanone (2.1 g, 9.8 mmol, 1 eq) and K$_2$CO$_3$ (2.4 g, 17.4 mmol, 1.8 eq) in 15 mL of DMF was added 1.3 mL of bromo-acetic acid ethyl ester (11.7 mmol, 1.2 eq) under nitrogen. After 12 h, the mixture was worked up and crude compound recrystallized to give (2-acetyl-4-bromo-phenoxy)-acetic acid ethyl ester in 97% yield (2.87 g). $^1$H NMR (400 MHz, CDCl$_3$) δ ppm 1.3 (t, J=7.1 Hz, 3 H) 2.7 (s, 3 H) 4.3 (q, J=7.1 Hz, 2 H) 4.7 (s, 2 H) 6.7 (d, J=8.8 Hz, 1 H) 7.5 (dd, J=8.8, 2.8 Hz, 1 H) 7.9 (d, J=2.8 Hz, 1 H).

Step 2: A mixture of (2-acetyl-4-bromo-phenoxy)-acetic acid ethyl ester (2.87 g, 9.5 mmol, 1 eq) and sodium ethoxide (0.65 g, 9.5 mmol, 1 eq) in 100 mL of ethanol under nitrogen was heated to 75° C. for 3 h. After work up followed by column chromatography (20% MeOH/dichloromethane), 5-bromo-3-methyl-benzofuran-2-carboxylic acid was obtained in 72% yield (1.74 g). $^1$H NMR (400 MHz, CD$_3$OD) δ ppm 2.5 (s, 3 H) 7.5 (d, J=8.8 Hz, 1 H) 7.6 (m, 1 H) 7.9 (d, J=2.0 Hz, 1 H).

Step 3: Amide coupling of 5-bromo-3-methyl-benzofuran-2-carboxylic acid with L-2-(4'-amino-biphenyl-4-sulfonylamino)-3-methyl-butyric acid methyl ester was carried out according to Example 21, Step 3 provided L-2-{4'-[(5-bromo-3-methyl-benzofuran-2-carbonyl)-amino]-biphenyl-4-sulfonylamino}-3-methyl-butyric acid methyl ester in 50% yield. $^1$H NMR (400 MHz, DMSO-d$_6$) δ ppm 0.8 (dd, J=14.8, 6.7 Hz, 6 H) 1.9 (m, 1 H) 2.6 (s, 3 H) 3.3 (s, 3 H) 3.6 (dd, J=9.3, 7.1 Hz, 1 H) 7.7 (d, J=1.3 Hz, 2 H) 7.8 (t, J=8.6 Hz, 4 H) 7.9 (m, 2 H) 8.0 (d, J=8.8 Hz, 2 H) 8.1 (t, J=1.4 Hz, 1 H) 8.3 (d, J=9.3 Hz, 1 H) 10.6 (s, 1 H).

Step 4: Hydrolysis of L-2-{4'-[(5-bromo-3-methyl-benzofuran-2-carbonyl)-amino]-biphenyl-4-sulfonylamino}-3-methyl-butyric acid methyl ester according to Example 20, Step 5 provided L-2-{4'-[(5-bromo-3-methyl-benzofuran-2-carbonyl)-amino]-biphenyl-4-sulfonylamino}-3-methyl-butyric acid in quantitative yield. $^1$H NMR (400 MHz, CD$_3$OD) δ ppm 1.1 (dd, J=24.0, 6.8 Hz, 6 H) 2.2 (m, 1 H) 2.8 (s, 3 H) 3.9 (d, J=5.8 Hz, 1 H) 7.8 (m 2 H) 7.9 (d, J=8.8 Hz, 2 H) 8.0 (d, J=8.8 Hz, 2 H) 8.1 (m, 5 H) 10.4 (s, 1 H).

Example 46

L-2-{4'-[(4-Carbamoyl-3-methyl-benzofuran-2-carbonyl)-amino]-biphenyl-4-sulfonylamino}-3-methyl-butyric acid

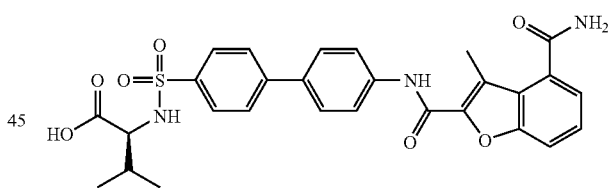

Step 1: To a solution of the product of Example 20, L-2-{4'-[(4-cyano-3-methyl-benzofuran-2-carbonyl)-amino]-biphenyl-4-sulfonylamino}-3-methyl-butyric acid methyl ester (128 mg), in a mixture of MeOH (6 mL) and DMSO (4 mL) was added 3 mL of Na$_2$CO$_3$ (3M) and 3 mL of hydrogen peroxide (30% in water). The reaction was complete in 12 h. After work up, L-2-{4'-[(4-carbamoyl-3-methyl-benzofuran-2-carbonyl)-amino]-biphenyl-4-sulfonylamino}-3-methyl-butyric acid methyl ester was obtained in quantitative yield. $^1$H NMR (400 MHz, DMSO-d$_6$) δ ppm 0.8 (dd, J=14.7, 6.8 Hz, 6 H) 1.9 (m, 1 H) 2.6 (s, 3 H) 3.6 (dd, J=9.3, 7.1 Hz, 1 H) 7.4 (dd, J=7.3, 0.8 Hz, 1 H) 7.5 (dd, J=8.3, 7.3 Hz, 1 H) 7.7 (s, 1 H) 7.8 (m, 5 H) 7.9 (m, 2 H) 8.0 (d, J=9.1 Hz, 2 H) 8.0 (s, 1 H) 8.3 (m, J=9.3 Hz, 1 H) 10.6 (s, 1 H).

Step 2: Hydrolysis of L-2-{4'-[(4-carbamoyl-3-methyl-benzofuran-2-carbonyl)-amino]-biphenyl-4-sulfonylamino}-3-methyl-butyric acid methyl ester was carried out according to Example 20, Step 5 to provide L-2-{4'-[(4-carbamoyl-3-methyl-benzofuran-2-carbonyl)-amino]-biphenyl-4-sulfonylamino}-3-methyl-butyric acid in quantitative yield. $^1$H NMR (400 MHz, DMSO-$d_6$) δ ppm 0.8 (dd, J=12.6, 6.8 Hz, 6 H) 1.9 (m, 1 H) 2.6 (s, 3 H) 3.6 (m, 1 H) 7.4 (d, J=7.3 Hz, 1 H) 7.5 (m, 1 H) 7.7 (s, 1 H) 7.8 (m, 5 H) 7.9 (m, 2 H) 8.0 (d, J=8.8 Hz, 2 H) (m, 2 H) 10.6 (s, 1 H).

Example 47

L-2-(4'-{[4-(Cyclopropanecarbonyl-amino)-3-methyl-benzofuran-2-carbonyl]-amino}-biphenyl-4-sulfonylamino)-3-methyl-butyric acid

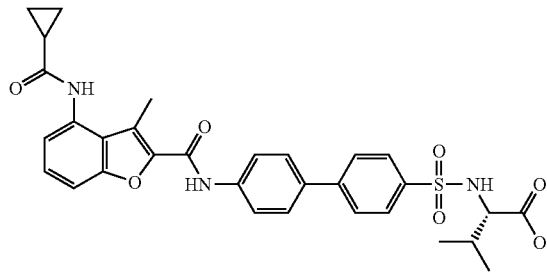

Step 1: To 3-methyl-4-trifluoromethanesulfonyloxy-benzofuran-2-carboxylic acid ethyl ester (300 mg, 0.85 mmol, 1 eq, prepared according to Example 20, Step 1) in 8 mL of dioxane under nitrogen were added cyclopropyl carboxamide (87 mg, 1.02 mmol, 1.2 eq), Pd$_2$(dba)$_3$ (16 mg, 0.017 mmol, 0.02 eq), 4,5-bis(diphenylphosphino)-9,9-dimethylxanthene (30 mg, 0.051 mmol, 0.06 eq), and cesium carbonate (390 mg, 1.19 mmol, 1.4 eq). The reaction mixture was heated at reflux for 72 h. After work up and column chromatography (dichloromethane/hexanes), 4-(cyclopropanecarbonyl-amino)-3-methyl-benzofuran-2-carboxylic acid ethyl ester was obtained in 98% yield (238 mg). $^1$H NMR (400 MHz, DMSO-$d_6$) δ ppm 0.8 (m, 4 H) 1.3 (t, J=7.1 Hz, 3 H) 1.8 (s, 1 H) 2.6 (s, 3 H) 4.4 (q, J=7.2 Hz, 2 H) 7.2 (d, J=7.1 Hz, 1 H) 7.5 (m, 1 H) 7.5 (m, 1 H) 10.1 (s, 1 H).

Step 2: Hydrolysis of 4-(cyclopropanecarbonyl-amino)-3-methyl-benzofuran-2-carboxylic acid ethyl ester was done according to Example 20, Step 3 to provide 4-(cyclopropanecarbonyl-amino)-3-methyl-benzofuran-2-carboxylic acid in 40% yield. $^1$H NMR (400 MHz, DMSO-$d_6$) δ ppm 0.8 (d, J=5.3 Hz, 4 H) 1.9 (s, 1 H) 2.6 (s, 3 H) 7.2 (d, J=7.6 Hz, 1 H) 7.5 (m, 2 H) 10.1 (s, 1 H) 13.4 (s, 1 H).

Step 3: To a mixture of 4-(cyclopropanecarbonyl-amino)-3-methyl-benzofuran-2-carboxylic acid (83 mg, 0.32 mmol, 1 eq), L-2-(4'-amino-biphenyl-4-sulfonylamino)-3-methyl-butyric acid methyl ester (116 mg, 0.32 mmol, 1 eq) and benzotriazol-1-yloxytris(dimethylamino)phosphonium hexafluorophosphate (BOP, 170 mg, 0.38 mmol, 1.2 eq) in 3 mL DMF under nitrogen was added 0.07 mL of N,N-diisopropylethylamine (0.38 mmol, 1.2 eq). The reaction mixture was stirred at room temperature for 18 h. The desired product precipitated out upon the addition of ethyl acetate, and was collected via filtration, washed with 1N HCl, saturated aqueous Na$_2$SO$_4$, and hexanes. L-2-(4'-{[4-cyclopropanecarbonyl-amino)-3-methyl-benzofuran-2-carbonyl]-amino}-biphenyl-4-sulfonylamino)-3-methyl-butyric acid methyl ester was obtained in 26% yield (50 mg). $^1$H NMR (400 MHz, DMSO-$d_6$) δ ppm 0.8 (dd, J=14.1, 7.3 Hz, 10 H) 1.9 (m, 2 H) 2.7 (s, 3 H) 3.3 (s, 3 H) 3.6 (dd, J=9.3, 7.1 Hz, 1 H) 7.2 (d, J=7.6 Hz, 1 H) 7.5 (t, J=8.1 Hz, 1 H) 7.5 (m, 1 H) 7.8 (m, 4 H) 7.9 (m, 2 H) 8. 0(d, J=8.6 Hz, 2 H) 8.3 (d, J=9.3 Hz, 1 H) 10.1 (s, 1 H) 10.6 (s, 1 H).

Step 4: Hydrolysis of L-2-(4'-{[4-(cyclopropanecarbonyl-amino)-3-methyl-benzofuran-2-carbonyl]-amino}-biphenyl-4-sulfonylamino)-3-methyl-butyric acid methyl ester was done according to Example 20, Step 5 to give L-2-(4'-{[4-(cyclopropanecarbonyl-amino)-3-methyl-benzofuran-2-carbonyl]-amino}-biphenyl-4-sulfonylamino)-3-methyl-butyric acid in quantitative yield. $^1$H NMR (400 MHz, DMSO-$d_6$) δ ppm 0.8 (m, 10 H) 1.9 (s, 1 H) 2.0 (m, 1 H) 2.7 (s, 3 H) 3.5 (dd, J=9.5, 6.2 Hz, 1 H) 7.2 (d, J=7.6 Hz, 1 H) 7.5 (m, 1 H) 7.5 (m, 1 H) 7.8 (d, J=8.8 Hz, 2 H) 7.9 (m, 4 H) 8.0 (d, J=8.8 Hz, 2 H) 8.0 (d, J=9.6 Hz, 1 H) 10.1 (s, 1 H) 10.6 (s, 1 H).

Example 48

L-2-{4'-[(4-Acetylamino-3-methyl-benzofuran-2-carbonyl)-amino]-biphenyl-4-sulfonylamino}-3-methyl-butyric acid

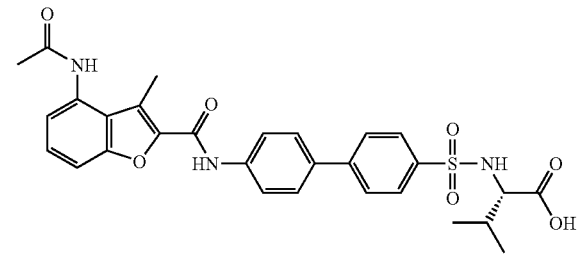

Step 1: Coupling of 3-methyl-4-trifluoromethanesulfonyloxy-benzofuran-2-carboxylic acid ethyl ester (Example 20, Step 1) with acetamide to give 4-acetylamino-3-methyl-benzofuran-2-carboxylic acid ethyl ester, was done according to Example 47, Step 1 to provide 4-acetylamino-3-methyl-benzofuran-2-carboxylic acid ethyl ester in quantitative yield. $^1$H NMR (400 MHz, DMSO-$d_6$) δ ppm 1.3 (t, J=7.2 Hz, 3 H) 2.1 (s, 3 H) 2.6 (s, 3 H) 4.4 (q, J=7.1 Hz, 2 H) 7.2 (d, J=8.1 Hz, 1 H) 7.5 (m, 2 H) 9.8 (s, 1 H).

Step 2: Hydrolysis of 4-acetylamino-3-methyl-benzofuran-2-carboxylic acid ethyl ester to 4-Acetylamino-3-methyl-benzofuran-2-carboxylic acid was done according to Example: 20, Step 3 to provide 4-acetylamino-3-methyl-benzofuran-2-carboxylic acid in quantitative yield. $^1$H NMR (400 MHz, DMSO-$d_6$) δ ppm 2.1 (s, 3 H) 2.6 (s, 3 H) 7.2 (d, J=7.3 Hz, 1 H) 7.5 (m, 2 H) 9.8 (s, 1 H) 13.4 (s, 1 H).

Step 3: Coupling of 4-acetylamino-3-methyl-benzofuran-2-carboxylic acid with L-2-(4'-amino-biphenyl-4-sulfonylamino)-3-methyl-butyric acid methyl ester was done according to Example 47, Step 3 to provide L-2-{4'-[(4-acetylamino-3-methyl-benzofuran-2-carbonyl)-amino]-biphenyl-4-sulfonylamino}-3-methyl-butyric acid methyl ester in 50% yield. $^1$H NMR (400 MHz, DMSO-$d_6$) δ ppm 0.8 (dd, J=14.8, 6.7 Hz, 6 H) 1.9 (m, 1 H) 2.1 (s, 3 H) 2.7 (s, 3 H) 3.3 (s, 3 H) 3.6 (dd, J=9.3, 7.3 Hz, 1 H) 7.2 (d, J=7.8 Hz, 1 H) 7.5 (m, 1 H) 7.5 (m, 1 H) 7.8 (m, 4 H) 7.9 (d, J=8.8 Hz, 2 H) 8.0 (d, J=8.8 Hz, 2 H) 8.3 (d, J=9.3 Hz, 1 H) 9.8 (s, 1 H) 10.6 (s, 1 H)

Step 4: Hydrolysis of L-2-{4'-[(4-acetylamino-3-methyl-benzofuran-2-carbonyl)-amino]-biphenyl-4-sulfonylamino}-3-methyl-butyric acid methyl ester was done according to Example 20, Step 5 to provide L-2-{4'-[(4-acetylamino-3-methyl-benzofuran-2-carbonyl)-amino]-biphenyl-4-sulfonylamino}-3-methyl-butyric acid in quantitative yield. $^1$H NMR (400 MHz, DMSO-$d_6$) δ ppm 0.8 (dd, J=12.5, 6.7 Hz, 6 H) 2.0 (m, 1 H) 2.1 (s, 3 H) 2.7 (s, 3 H) 3.6 (dd, J=9.3, 6.1 Hz, 1 H) 7.2 (d, J=7.6 Hz, 1 H) 7.5 (m, 1 H) 7.5 (m, 1 H) 7.8 (d, J=8.8 Hz, 2 H) 7.9 (m, 4 H) 8.0 (d, J=9.1 Hz, 2 H) 8.1 (d, J=9.3 Hz, 1 H) 9.8 (s, 1 H) 10.6 (s, 1 H) 12.6 (s, 1 H).

Example 49

L-3-Methyl-2-{4'-[(3-methyl-4-propionylamino-benzofuran-2-carbonyl)-amino]-biphenyl-4-sulfonylamino}-butyric acid

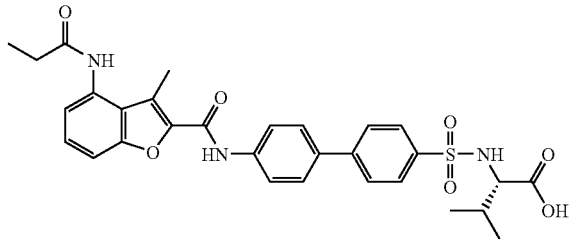

Step 1: Coupling of 3-methyl-4-trifluoromethanesulfonyloxy-benzofuran-2-carboxylic acid ethyl ester (Example 20, Step 1) with propionamide to give 3-methyl-4-propionylamino-benzofuran-2-carboxylic acid ethyl ester was done according to Example 47, Step 1 in quantitative yield. $^1$H NMR (400 MHz, DMSO-$d_6$) δ ppm 1.1 (t, J=7.6 Hz, 3 H) 1.3 (t, J=7.2 Hz, 3 H) 2.4 (q, J=7.5 Hz, 2 H) 2.6 (s, 3 H) 4.4 (q, J=7.2 Hz, 2 H) 7.2 (d, J=7.3 Hz, 1 H) 7.5 (m, 1 H) 7.5 (m, 1 H) 9.8 (s, 1 H).

Step 2: Hydrolysis of 3-methyl-4-propionylamino-benzofuran-2-carboxylic acid ethyl ester to 3-methyl-4-propionylamino-benzofuran-2-carboxylic acid was done according to Example 20, Step 3, in quantitative yield. $^1$H NMR (400 MHz, DMSO-$d_6$) δ ppm 1.1 (t, J=7.3 Hz, 3 H) 2.4 (q, J=8.0 Hz, 2 H) 2.6 (s, 3 H) 7.2 (d, J=7.3 Hz, 1 H) 7.5 (m, 2 H) 9.7 (s, 1 H) 13.5 (s, 1 H).

Step 3: Coupling of 3-methyl-4-propionylamino-benzofuran-2-carboxylic acid with L-2-(4'-amino-biphenyl-4-sulfonylamino)-3-methyl-butyric acid methyl was done according to Example 47, Step 3, to provide ester L-3-methyl-2-{4'-[(3-methyl-4-propionylamino-benzofuran-2-carbonyl)-amino]-biphenyl-4-sulfonylamino}-butyric acid methyl ester in 67% yield. $^1$H NMR (400 MHz, DMSO-$d_6$) δ ppm 0.8 (dd, J=14.8, 6.7 Hz, 6 H) 1.1 (t, J=7.6 Hz, 3 H) 1.9 (m, 1 H) 2.4 (q, J=7.5 Hz, 2 H) 2.7 (s, 3 H) 3.3 (s, 3 H) 3.6 (dd, J=9.3, 7.1 Hz, 1 H) 7.2 (d, J=7.6 Hz, 1 H) 7.5 (m, 1 H) 7.5 (m, 1 H) 7.8 (m, 4 H) 7.9 (m, 2 H) 8.0 (d, J=9.1 Hz, 2 H) 8.3 (d, J=9.3 Hz, 1 H) 9.7 (s, 1 H) 10.6 (s, 1 H).

Step 4: Hydrolysis of L-3-methyl-2-{4'-[(3-methyl-4-propionylamino-benzofuran-2-carbonyl)-amino]-biphenyl-4-sulfonylamino}-butyric acid methyl ester was done according to Example 20, Step 5, to provide L-3-methyl-2-{4'-[(3-methyl-4-propionylamino-benzofuran-2-carbonyl)-amino]-biphenyl-4-sulfonylamino}-butyric acid in quantitative yield. $^1$H NMR (400 MHz, DMSO-$d_6$) δ ppm 0.8 (dd, J=12.6, 6.8 Hz, 6 H) 1.1 (t, J=7.5 Hz, 3 H) 2.0 (m, 1 H) 2.4 (q, J=7.6 Hz, 2 H) 2.7 (s, 3 H) 3.6 (dd, J=9.3, 6.1 Hz, 1 H) 7.2 (d, J=7.6 Hz, 1 H) 7.5 (m, 1 H) 7.5 (m, 1 H) 7.8 (d, J=8.8 Hz, 2 H) 7.9 (m, 4 H) 8.0 (d, J=8.8 Hz, 2 H) 8.1 (d, J=9.3 Hz, 1 H) 9.7 (s, 1 H) 10.6 (s, 1 H) 12.6 (s, 1 H).

Example 50

L-2-{4'-[(4-Isobutyrylamino-3-methyl-benzofuran-2-carbonyl)-amino]-biphenyl-4-sulfonylamino}-3-methyl-butyric acid

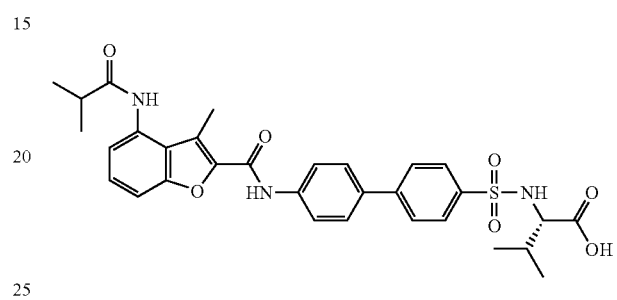

Step 1: Coupling of 3-methyl-4-trifluoromethanesulfonyloxy-benzofuran-2-carboxylic acid ethyl ester (Example 20, Step 1) with isobutyramide to give 4-isobutyrylamino-3-methyl-benzofuran-2-carboxylic acid ethyl ester, was done according to Example 47, Step 1 in 95% yield. $^1$H NMR (400 MHz, DMSO-$d_6$) δ ppm 1.2 (d, J=6.8 Hz, 6 H) 1.3 (t, J=7.1 Hz, 3 H) 2.6 (s, 3 H) 2.7 (m, 1 H) 4.4 (q, J=7.1 Hz, 2 H) 7.2 (d, J=7.6 Hz, 1 H) 7.5 (m, 1 H) 9.7 (s, 1 H).

Step 2: Hydrolysis 4-isobutyrylamino-3-methyl-benzofuran-2-carboxylic acid ethyl ester to 4-isobutyrylamino-3-methyl-benzofuran-2-carboxylic acid was done according to Example20, Step 3, in 71% yield. $^1$H NMR (400 MHz, DMSO-$d_6$) δ ppm 1.2 (d, J=6.8 Hz, 6 H) 2.6 (s, 3 H) 2.7 (m, 1 H) 7.2 (dd, J=7.6, 0.5 Hz, 1 H) 7.5 (m, 2 H) 9.7 (s, 1 H).

Step 3: Coupling of 4-isobutyrylamino-3-methyl-benzofuran-2-carboxylic acid with L-2-(4'-amino-biphenyl-4-sulfonylamino)-3-methyl-butyric acid methyl ester to obtain L-2-{4'-[(4-Isobutyrylamino-3-methyl-benzofuran-2-carbonyl)-amino]-biphenyl-4-sulfonylamino}-3-methyl-butyric acid methyl ester was done according to Example 47, Step 3 in 84% yield. $^1$H NMR (400 MHz, DMSO-$d_6$) ppm 0.8 (dd, J=12.4, 6.8 Hz, 6 H) 2.0 (m, 1 H) 2.4 (s, 3 H) 2.5 (s, 3 H) 3.6 (dd, J=9.3, 5.8 Hz, 1 H) 6.8 (s, 1 H) 7.5 (dd, J=7.6, 1.0 Hz, 1 H) 7.7 (dd, J=8.3, 7.3 Hz, 1 H) 7.8 (m, 4 H) 7.9 (m, 3 H) 8.0 (d, J=8.8 Hz, 2 H) 8.1 (d, J=9.3 Hz, 1 H) 10.7 (s, 1 H).

Step 4: Hydrolysis of L-2-{4'-[(4-isobutyrylamino-3-methyl-benzofuran-2-carbonyl)-amino]-biphenyl-4-sulfonylamino}-3-methyl-butyric acid methyl ester to L-2-{4'-[(4-isobutyrylamino-3-methyl-benzofuran-2-carbonyl)-amino]-biphenyl-4-sulfonylamino}-3-methyl-butyric acid was done according to Example 20, Step 5 in quantitative yield. $^1$H NMR (400 MHz, DMSO-$d_6$) δ ppm 0.8 (dd, J=12.6, 6.8 Hz, 6 H) 1.2 (d, J=6.8 Hz, 6 H) 2.0 (m, 1 H) 2.7 (s, 4 H) 3.6 (dd, J=9.3, 6.1 Hz, 1 H) 7.2 (d, J=7.6 Hz, 1 H) 7.5 (m, 1 H) 7.5 (m, 2 H) 7.8 (d, J=8.8 Hz, 2 H) 7.9 (m, 4 H) 8.0 (d, J=8.8 Hz, 2 H) 8.1 (d, J=9.3 Hz, 1 H) 10.6 (s, 1 H) 12.6 (s, 1 H).

Example 51

L-2-{4'-[(4-Cyclopropylmethoxy-3-methyl-benzofuran-2-carbonyl)-amino]-biphenyl-4-sulfonylamino}-3-methyl-butyric acid

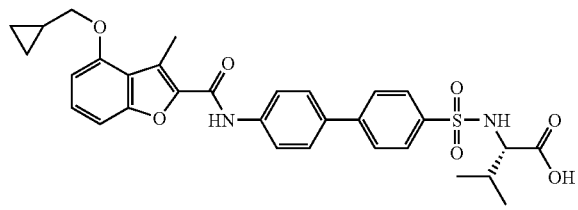

Step 1: To 4-hydroxy-3-methyl-benzofuran-2-carboxylic acid ethyl ester (300 mg, 1.36 mmol, 1 eq) under nitrogen was added potassium carbonate (377 mg, 2.73 mmol, 2 eq), 5 mL of DMF and bromomethylcyclopropane (145 uL, 1.50 mmol, 1.1 eq) and the reaction was stirred at room temperature for 16 h. After work-up and flash column chromatography, 4-cyclopropylmethoxy-3-methyl-benzofuran-2-carboxylic acid ethyl ester was obtained in 94% yield (350 mg). $^1$H NMR (400 MHz, DMSO-$d_6$) δ ppm 0.4 (m, 2 H) 0.6 (m, 2 H) 1.3 (m, 1 H) 1.3 (d, J=14.4 Hz, 3 H) 2.7 (d, 3 H) 4.0 (d, J=6.8 Hz, 2 H) 4.3 (q, J=7.1 Hz, 2 H) 6.8 (dd, J=8.1, 0.5 Hz, 1 H) 7.2 (dd, J=8.3, 0.5 Hz, 1 H) 7.4 (t, J=8.2 Hz, 1 H).

Step 2: Hydrolysis 4-cyclopropylmethoxy-3-methyl-benzofuran-2-carboxylic acid ethyl ester to 4-cyclopropylmethoxy-3-methyl-benzofuran-2-carboxylic acid was done according to Example 20, Step 3 in 96% yield. $^1$H NMR (400 MHz, DMSO-$d_6$) δ ppm 0.4 (m, 2 H) 0.6 (m, 2 H) 1.3 (m, 1 H) 2.7 (s, 3 H) 4.0 (d, J=6.8 Hz, 2 H) 6.8 (d, J=8.1 Hz, 1 H) 7.2 (dd, J=8.5, 0.6 Hz, 1 H) 7.4 (m, 1 H) 13.3 (s, 1 H).

Step 3: Coupling of 4-cyclopropylmethoxy-3-methyl-benzofuran-2-carboxylic acid with L-2-(4'-amino-biphenyl-4-sulfonylamino)-3-methyl-butyric acid methyl ester to obtain L-2-{4'-[(4-cyclopropylmethoxy-3-methyl-benzofuran-2-carbonyl)-amino]-biphenyl-4-sulfonylamino}-3-methyl-butyric acid methyl ester was done according to Example 47, Step 3 in quantitative yield. $^1$H NMR (400 MHz, DMSO-$d_6$) δ ppm 0.4 (m, 2 H) 0.6 (m, 2 H) 0.8 (dd, J=14.8, 6.7 Hz, 6 H) 1.3 (m, 1 H) 1.9 (m, 1 H) 2.8 (s, 3 H) 3.3 (s, 3 H) 3.6 (dd, J=9.3, 7.1 Hz, 1 H) 4.0 (d, J=6.6 Hz, 2 H) 6.8 (d, J=8.6 Hz, 1 H) 7.2 (d, J=7.8 Hz, 1 H) 7.4 (m, 1 H) 7.8 (dd, J=12.0, 8.7 Hz, 4 H) 7.9 (m, 2 H) 8.0 (d, J=8.8 Hz, 2 H) 8.3 (d, J=9.3 Hz, 1 H) 10.5 (s, 1 H).

Step 4: Hydrolysis of L-2-{4'-[(4-cyclopropylmethoxy-3-methyl-benzofuran-2-carbonyl)-amino]-biphenyl-4-sulfonylamino}-3-methyl-butyric acid methyl ester to obtain L-2-{4'-[(4-cyclopropylmethoxy-3-methyl-benzofuran-2-carbonyl)-amino]-biphenyl-4-sulfonylamino}-3-methyl-butyric acid was done according to Example 20, Step 5, in quantitative yield. The product was purified by recrystalization from ethyl acetate/hexanes. $^1$H NMR (400 MHz, DMSO-$d_6$) δ ppm 0.4 (d, J=4.8 Hz, 2 H) 0.6 (d, J=8.1 Hz, 2 H) 0.8 (dd, J=12.5, 6.7 Hz, 6 H) 1.3 (m, 1 H) 2.0 (m, 1 H) 2.8 (s, 3 H) 3.6 (dd, J=9.5, 6.2 Hz, 1 H) 4.0 (d, J=6.8 Hz, 2 H) 6.8 (d, J=8.3 Hz, 1 H) 7.2 (d, J=8.3 Hz, 1 H) 7.4 (t, J=8.1 Hz, 1 H) 7.8 (d, J=8.6 Hz, 2 H) 7.9 (m, 4 H) 8.0 (d, J=8.8 Hz, 2 H) 8.1 (d, J=9.1 Hz, 1 H) 10.5 (s, 1 H) 12.6 (s, 1 H).

Example 52

L-2-{4'-[(1H-Benzoimidazole-2-carbonyl)-amino]-biphenyl-4-sulfonylamino}-3-methyl-butyric acid

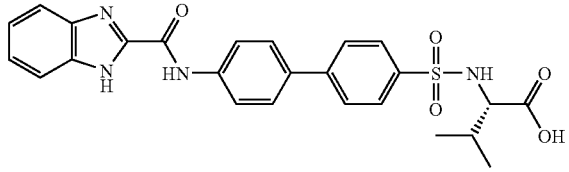

Step 1: Coupling of commercially available 1H-benzoimidazole-2-carboxylic acid with L-2-(4'-amino-biphenyl-4-sulfonylamino)-3-methyl-butyric acid methyl ester to obtain L-2-{4'-[(1H-benzoimidazole-2-carbonyl)-amino]-biphenyl-4-sulfonylamino}-3-methyl-butyric acid methyl ester was done according to Example 47, Step 3 in 37% yield. $^1$H NMR (400 MHz, DMSO-$d_6$) δ ppm 0.8 (dd, J=15.0, 6.7 Hz, 6 H) 1.9 (m, 1 H) 3.3 (s, 3 H) 3.6 (dd, J=9.5, 7.2 Hz, 1 H) 7.4 (m, 2 H) 7.6 (d, J=8.1 Hz, 1 H) 7.8 (m, 5 H) 7.9 (m, 2 H) 8.1 (d, J=8.8 Hz, 2 H) 8.3 (d, J=9.3 Hz, 1 H) 11.1 (s, 1 H) 13.5 (s, 1 H).

Step 2: Hydrolysis of L-2-{4'-[(1H-benzoimidazole-2-carbonyl)-amino]-biphenyl-4-sulfonylamino}-3-methyl-butyric acid methyl ester to obtain L-2-{4'-[(1H-benzoimidazole-2-carbonyl)-amino]-biphenyl-4-sulfonylamino}-3-methyl-butyric acid was done according to Example 20, Step 5 in quantitative yield. $^1$H NMR (400 MHz, DMSO-$d_6$) δ ppm 0.8 (dd, J=12.9, 6.8 Hz, 6 H) 2.0 (m, 1 H) 3.6 (dd, J=9.5, 5.9 Hz, 1 H) 7.4 (d, J=6.6 Hz, 2 H) 7.8 (m, 8 H) 8.1 (dd, J=11.1, 9.1 Hz, 3 H) 11.1 (s, 1 H) 12.6 (s, 1 H) 13.5 (s, 1 H).

Example 53

L-2-{4'-[(4-sec-Butoxy-3-methyl-benzofuran-2-carbonyl)-amino]-biphenyl-4-sulfonylamino}-3-methyl-butyric acid

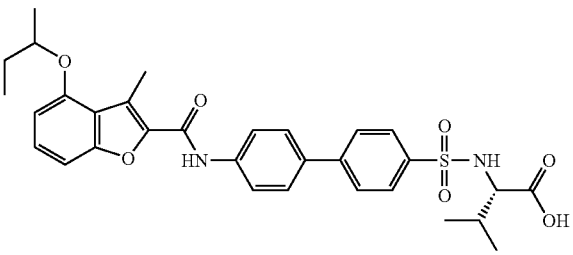

Step 1: Alkylation of 4-hydroxy-3-methyl-benzofuran-2-carboxylic acid ethyl ester with 2-bromobutane to give 4-sec-butoxy-3-methyl-benzofuran-2-carboxylic acid ethyl ester was done according to Example 51, Step 1, in 80% yield. $^1$H NMR (400 MHz, DMSO-$d_6$) δ ppm 1.0 (t, J=7.5 Hz, 3 H) 1.3 (m, 6 H) 1.7 (m, 2 H) 2.7 (s, 3 H) 4.3 (q, J=7.1 Hz, 2 H) 4.6 (m, 1 H) 6.8 (d, J=8.1 Hz, 1 H) 7.2 (dd, J=8.3, 0.5 Hz, 1 H) 7.4 (t, J=8.2 Hz, 1 H).

Step 2: Hydrolysis of 4-sec-butoxy-3-methyl-benzofuran-2-carboxylic acid ethyl ester to 4-sec-butoxy-3-methyl-benzofuran-2-carboxylic acid was done according to Example 20, Step 3 in quantitative yield. $^1$H NMR (400 MHz, DMSO-$d_6$) δ ppm 1.0 (t, J=7.5 Hz, 3 H) 1.3 (d, J=6.1 Hz, 3 H) 1.7 (m, 2 H) 2.7 (s, 3 H) 4.6 (m, 1 H) 6.8 (d, J=8.1 Hz, 1 H) 7.1 (m, 1 H) 7.4 (t, J=8.2 Hz, 1 H).

Step 3: Coupling of 4-sec-butoxy-3-methyl-benzofuran-2-carboxylic acid with L-2-(4'-amino-biphenyl-4-sulfonylamino)-3-methyl-butyric acid methyl ester to obtain L-2-{4'-[(4-sec-butoxy-3-methyl-benzofuran-2-carbonyl)-amino]-biphenyl-4-sulfonylamino}-3-methyl-butyric acid methyl ester was done according to Example 47, Step 3 in quantitative yield. $^1$H NMR (400 MHz, DMSO-$d_6$) δ ppm 0.8 (dd, J=14.7, 6.8 Hz, 6 H) 1.0 (t, J=7.5 Hz, 3 H) 1.3 (d, J=6.1 Hz, 3 H) 1.7 (m, 2 H) 1.9 (m, 1 H) 2.7 (s, 3 H) 3.3 (s, 3 H) 3.6 (dd, J=8.7, 7.7 Hz, 1 H) 4.6 (d, 1 H) 6.9 (d, J=8.3 Hz, 1 H) 7.2 (d, J=8.1 Hz, 1 H) 7.4 (t, J=8.2 Hz, 1 H) 7.8 (dd, J=12.3, 8.7 Hz, 4 H) 7.9 (m, 2 H) 8.0 (d, J=8.8 Hz, 2 H) 8.3 (d, J=9.3 Hz, 1 H) 10.5 (s, 1 H).

Step 4: Hydrolysis of L-2-{4'-[(4-sec-butoxy-3-methyl-benzofuran-2-carbonyl)-amino]-biphenyl-4-sulfonylamino}-3-methyl-butyric acid methyl ester to L-2-{4'-[(4-sec-butoxy-3-methyl-benzofuran-2-carbonyl)-amino]-biphenyl-4-sulfonylamino}-3-methyl-butyric acid was done according to Example 20, Step 5, in quantitative yield. $^1$H NMR (400 MHz, DMSO-$d_6$) δ ppm 0.8 (dd, J=12.6, 6.8 Hz, 6 H) 1.0 (t, J=7.5 Hz, 3 H) 1.3 (d, J=6.1 Hz, 3 H) 1.7 (m, 2 H) 2.0 (m, 1 H) 2.7 (s, 3 H) 3.6 (dd, J=9.3, 6.1 Hz, 1 H) 4.6 (q, J=6.1 Hz, 1 H) 6.9 (d, J=8.1 Hz, 1 H) 7.2 (d, J=8.1 Hz, 1 H) 7.4 (t, J=8.2 Hz, 1 H) 7.8 (d, J=8.8 Hz, 2 H) 7.9 (m, 4 H) 8.0 (d, J=9.1 Hz, 2 H) 8.1 (d, J=9.3 Hz, 1 H) 10.5 (s, 1 H) 12.6 (s, 1 H).

Example 54

L-3-Methyl-2-{4'-[(3-phenyl-benzofuran-2-carbonyl)-amino]-biphenyl-4-sulfonylamino}-butyric acid

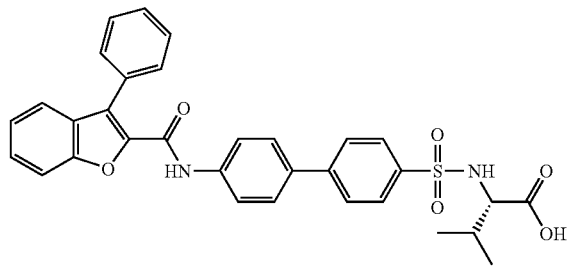

Step 1: Coupling of 3-phenyl-benzofuran-2-carboxylic acid with L-2-(4'-amino-biphenyl-4-sulfonylamino)-3-methyl-butyric acid methyl ester to obtain L-3-methyl-2-{4'-[(3-phenyl-benzofuran-2-carbonyl)-amino]-biphenyl-4-sulfonylamino}-butyric acid methyl ester was done according to Example 47, Step 3, in 83% yield. $^1$H NMR (400 MHz, DMSO-$d_6$) δ ppm 0.8 (dd, J=14.5, 6.7 Hz, 6 H) 1.9 (m, 1 H) 3.3 (s, 3 H) 3.6 (dd, J=9.3, 7.1 Hz, 1 H) 7.5 (m, 4 H) 7.6 (m, 1 H) 7.7 (m, 3 H) 7.8 (m, 5 H) 7.9 (m, 4 H) 8.3 (d, J=9.3 Hz, 1 H) 10.7 (s, 1 H).

Step 2: Hydrolysis of L-3-methyl-2-{4'-[(3-phenyl-benzofuran-2-carbonyl)-amino]-biphenyl-4-sulfonylamino}-butyric acid methyl ester to L-3-methyl-2-{4'-[(3-phenyl-benzofuran-2-carbonyl)-amino]-biphenyl-4-sulfonylamino}-butyric acid was done according to Example 20, Step 5, in quantitative yield. $^1$H NMR (400 MHz, DMSO-$d_6$) δ ppm 0.8 (dd, J=12.6, 6.8 Hz, 6 H) 1.9 (m, 1 H) 3.6 (dd, J=9.3, 6.1 Hz, 1 H) 7.5 (m, 2 H) 7.5 (m 2 H) 7.6 (m, 1 H) 7.7 (m, 3 H) 7.8 (d, J=8.8 Hz, 2 H) 7.8 (m, 5 H) 7.9 (d, J=8.8 Hz, 2 H) 8.1 (d, J=9.3 Hz, 1 H) 10.7 (s, 1 H) 12.6 (s, 1 H).

Example 55

L-2-(4'-{[4-(Acetyl-methyl-amino)-3-methyl-benzofuran-2-carbonyl]-amino}-biphenyl-4-sulfonylamino)-3-methyl-butyric acid

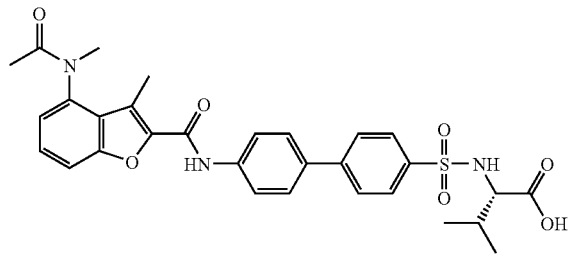

Step 1: To 4-acetylamino-3-methyl-benzofuran-2-carboxylic acid ethyl ester (300 mg, 1.15 mmol, 1 eq, prepared according to Example 48, Step 1) under nitrogen was added 5 mL of DMF, iodomethane (79 uL, 1.26 mmol, 1.1 eq), and sodium hydride (60%, 51 mg, 1.26 mmol, 1.1 eq). The reaction mixture was stirred at room temperature for 4 h. After work up and flash column chromatography (5-40% ethyl acetate/hexanes), 4-(acetyl-methyl-amino)-3-methyl-benzofuran-2-carboxylic acid ethyl ester was obtained in 35% yield (112 mg). $^1$H NMR (400 MHz, DMSO-$d_6$) δ ppm 1.3 (t, J=7.2 Hz, 3 H) 1.7 (s, 3 H) 2.5 (s, 3 H) 3.2 (s, 3 H) 4.4 (m, 2 H) 7.3 (dd, J=7.6, 0.8 Hz, 1 H) 7.6 (dd, J=8.5, 7.7 Hz, 1 H) 7.8 (dd, J=8.5, 0.9 Hz, 1 H).

Step 2: Hydrolysis of 4-(acetyl-methyl-amino)-3-methyl-benzofuran-2-carboxylic acid ethyl ester to 4-(acetyl-methyl-amino)-3-methyl-benzofuran-2-carboxylic acid was done according to Example 20, Step 3, in 55% yield. $^1$H NMR (400 MHz, DMSO-$d_6$) δ ppm 1.7 (s, 3 H) 2.5 (s, 3 H) 3.2 (s, 3 H) 7.3 (dd, J=7.7, 0.9 Hz, 1 H) 7.6 (dd, J=8.6, 7.6 Hz, 1 H) 7.7 (m, 1 H) 13.6 (s, 1 H).

Step 3: Coupling of 4-(acetyl-methyl-amino)-3-methyl-benzofuran-2-carboxylic acid with L-2-(4'-amino-biphenyl-4-sulfonylamino)-3-methyl-butyric acid methyl ester to obtain L-2-(4'-{[4-(acetyl-methyl-amino)-3-methyl-benzofuran-2-carbonyl]-amino}-biphenyl-4-sulfonylamino)-3-methyl-butyric acid methyl ester was done according to Example 47, Step 3, in 85% yield. $^1$H NMR (400 MHz, DMSO-$d_6$) δ ppm 0.8 (dd, J=14.7, 6.8 Hz, 6 H) 1.7 (s, 3 H) 1.9 (m, 1 H) 2.5 (s, 3 H) 3.2 (s, 3 H) 3.3 (s, 3 H) 3.6 (dd, J=9.3, 7.1 Hz, 1 H) 7.3 (m, 1 H) 7.6 (m, 1 H) 7.8 (m, 5 H) 7.9 (m, 2 H) 8.0 (d, J=8.8 Hz, 2 H) 8.3 (d, J=9.3 Hz, 1 H) 10.7 (s, 1 H).

Step 4: Hydrolysis of L-2-(4'-{[4-(acetyl-methyl-amino)-3-methyl-benzofuran-2-carbonyl]-amino}-biphenyl-4-sulfonylamino)-3-methyl-butyric acid methyl ester to obtain L-2-(4'-{[4-(acetyl-methyl-amino)-3-methyl-benzofuran-2-carbonyl]-amino}-biphenyl-4-sulfonylamino)-3-methyl-butyric acid was done according to 20, Step 5, in quantitative yield. The product was purified via trituration with ethyl acetate. $^1$H NMR (400 MHz, DMSO-$d_6$) δ ppm 0.8 (dd, J=12.6, 6.8 Hz, 6 H) 1.7 (s, 3 H) 1.9 (m, 1 H) 2.5 (s, 3 H) 3.2 (s, 3.6 (dd, J=9.1, 6.1 Hz, 1 H) 7.3 (dd, J=7.6, 0.8 Hz, 1 H) 7.6 (m, 1 H) 7.8 (m, 3 H) 7.9 (m, 4 H) 8.0 (d, J=8.8 Hz, 2 H) 8.1 (d, J=9.3 Hz, 1 H) 10.7 (s, 1 H) 12.6 (s, 1 H).

Example 56

L-3-Methyl-2-(4'-{[3-methyl-4-(2H-tetrazol-5-yl)-benzofuran-2-carbonyl]-amino}-biphenyl-4-sulfonylamino)-butyric acid

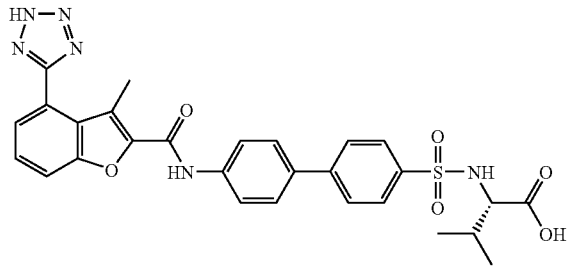

Step 1: To L-2-{4'-[(4-cyano-3-methyl-benzofuran-2-carbonyl)-amino]-biphenyl-4-sulfonylamino}-3-methyl-butyric acid methyl ester (45 mg, 0.082 mmol, Example 20, Step 4) was added trimethylsilyl azide (40 uL, 0.03 mmol, 3.65 eq), dibutyltin oxide (10 mg, cat.) and 1 mL of toluene, then the reaction was heated at 120° C. in a pressure tube for 72 h. L-3-Methyl-2-(4'-{[3-methyl-4-(2H-tetrazol-5-yl)-benzofuran-2-carbonyl]-amino}-biphenyl-4-sulfonylamino)-butyric acid methyl ester was obtained and used in crude form. $^1$H NMR (400 MHz, DMSO-$d_6$) ppm 0.8 (m, J=14.8, 6.7 Hz, 6 H) 1.9 (m, 1 H) 2.4 (s, 3 H) 3.4 (s, 3 H) 3.6 (dd, J=9.3, 7.1 Hz, 1 H) 7.6 (dd, J=7.6, 1.0 Hz, 1 H) 7.7 (dd, J=8.3, 7.3 Hz, 1 H) 7.8 (dd, J=8.6, 5.6 Hz, 4 H) 7.9 (dd, 3 H) 8.0 (d, J=8.8 Hz, 2 H) 8.3 (d, J=9.3 Hz, 1 H) 10.7 (s, 1 H).

Step 2: Hydrolysis of L-3-methyl-2-(4'-{[3-methyl-4-(2H-tetrazol-5-yl-benzofuran-2-carbonyl]-amino}-biphenyl-4-sulfonylamino)-butyric acid methyl ester to obtain L-3-methyl-2-(4'-{[3-methyl-4-(2H-tetrazol-5-yl)-benzofuran-2-carbonyl]-amino}-biphenyl-4-sulfonylamino)-butyric acid was done according to Example 20, Step 5, in quantitative yield. The product was purified via prep-HPLC. $^1$H NMR (400 MHz, DMSO-$d_6$) δ ppm 0.8 (dd, J=20.7, 6.8 Hz, 6 H) 2.0 (m, 1 H) 2.5 (s, 3 H) 3.5 (s, 1 H) 7.5 (m, 2 H) 7.6 (m, J=7.3, 2.0 Hz, 1 H) 7.8 (d, J=8.8 Hz, 2 H) 7.8 (m, 4 H) 8.0 (d, J=8.8 Hz, 2 H) 10.5 (s, 1 H).

Example 57

L-2-(4'-{[4-(3,3-Dimethyl-butyl)-3-methyl-benzofuran-2-carbonyl]-amino}-biphenyl-4-sulfonylamino)-3-methyl-butyric acid

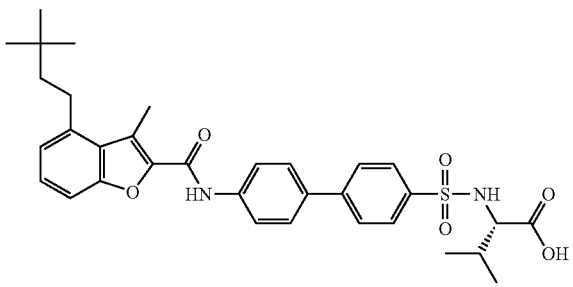

Step 1: L-2-(4'-{[4-(3,3-dimethyl-but-1-ynyl)-3-methyl-benzofuran-2-carbonyl]-amino}-biphenyl-4-sulfonylamino)-3-methyl-butyric acid methyl ester (65 mg, 0.11 mmol, prepared according to Example 34, Step 3) was reduced to L-2-(4'-{[4-(3,3-dimethyl-butyl)-3-methyl-benzofuran-2-carbonyl]-amino}-biphenyl-4-sulfonylamino)-3-methyl-butyric acid methyl ester following the procedure of Example 32, Step 1. $^1$H NMR (400 MHz, DMSO-$d_6$) δ ppm 0.8 (dd, J=14.7, 6.8 Hz, 6 H) 1.0 (s, 9 H) 1.5 (m, 2 H) 1.9 (m, 1 H) 2.8 (s, 3 H) 3.0 (m, 2 H) 3.4 (s, 3 H) 3.6 (dd, J=9.5, 7.2 Hz, 1 H) 7.1 (dd, J=7.5, 0.9 Hz, 1 H) 7.4 (dd, J=8.3, 7.3 Hz, 1 H) 7.5 (m, 1 H) 7.8 (dd, J=11.2, 8.7 Hz, 4 H) 7.9 (m, 2 H) 8.0 (d, J=8.8 Hz, 2 H) 8.3 (d, J=9.6 Hz, 1 H) 10.5 (s, 1 H)

Step 2: Hydrolysis of L-2-(4'-{[4-(3,3-dimethyl-butyl)-3-methyl-benzofuran-2-carbonyl]-amino}-biphenyl-4-sulfonylamino)-3-methyl-butyric acid methyl ester to obtain L-2-(4'-{[4-(3,3-dimethyl-butyl)-3-methyl-benzofuran-2-carbonyl]-amino}-biphenyl-4-sulfonylamino)-3-methyl-butyric acid was done according to Example 20, Step 5, in quantitative yield. The product was purified via prep-HPLC. $^1$H NMR (400 MHz, DMSO-$d_6$) δ ppm 0.8 (dd, J=13.4, 6.8 Hz, 6 H) 1.0 (s, 9 H) 1.5 (m, 2 H) 2.0 (m, 1 H) 2.8 (s, 3 H) 3.0 (m, 2 H) 3.5 (s, 1 H) 7.1 (d, J=7.3 Hz, 1 H) 7.4 (m, 1 H) 7.5 (m, 1 H) 7.8 (d, J=8.8 Hz, 2 H) 7.9 (m, 4 H) 8.0 (d, J=8.8 Hz, 3 H) 10.5 (s, 1 H).

Example 58

L-2-{4'-[(3-Ethyl-benzofuran-2-carbonyl)-amino]-biphenyl-4-sulfonylamino}-3-methyl-butyric acid

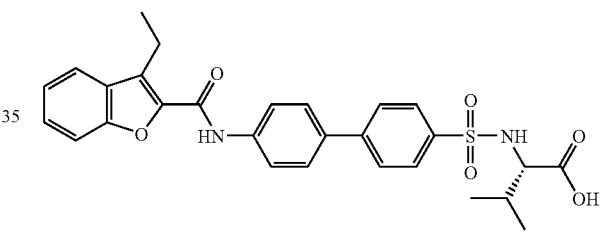

Step 1: (2-Propionyl-phenoxy)-acetic acid methyl ester (432 mg, 1.94 mmol, 1 eq.) was added to a solution of sodium methoxide (105 mg, 0.94 mmol, 1 eq.) in methanol (10 mL) and the reaction was heated at 60° C. for 4 h. The reaction was acidified using 1N HCl, diluted with water, extracted twice with ethyl acetate, and the combined organic layers were washed with saturated aqueous NaHCO$_3$. The aqueous layers were extracted with ethyl acetate. The organic layers were combined, dried over magnesium sulfate, and concentrated in vacuo. 3-Ethyl-benzofuran-2-carboxylic acid methyl ester is obtained in 38% yield after flash column chromatography purification (1-5% ethyl acetate/hexanes). $^1$H NMR (400 MHz, DMSO-$d_6$) δ ppm 1.2 (t, J=7.6 Hz, 3 H) 3.1 (q, J=7.6 Hz, 2 H) 3.9 (s, 3 H) 7.4 (m, 1 H) 7.5 (m, 1 H) 7.7 (m, 1 H) 7.9 (dd, J=7.8, 0.8 Hz, 1 H).

Step 2: Hydrolysis of 3-ethyl-benzofuran-2-carboxylic acid methyl ester to 3-ethyl-benzofuran-2-carboxylic acid was done according to Example 20, Step 3, in 98% yield. $^1$H NMR (400 MHz, CD$_3$OD) δ ppm 1.2 (d, J=7.6 Hz, 3 H) 3.0 (q, J=7.4 Hz, 2 H) 7.2 (m, 1 H) 7.4 (m, 1 H) 7.4 (m, 1 H) 7.6 (m, 1 H).

Step 3: Coupling of 3-ethyl-benzofuran-2-carboxylic acid with L-2-(4'-amino-biphenyl-4-sulfonylamino)-3-methyl-butyric acid methyl ester to obtain L-2-{4'-[(3-ethyl-benzofuran-2-carbonyl)-amino]-biphenyl-4-sulfonylamino}-3-methyl-butyric acid methyl ester was done according to Example 47, Step 3 in 85% yield. $^1$H NMR (400 MHz, DMSO-$d_6$) δ ppm 0.8 (dd, J=14.7, 6.8 Hz, 6 H) 1.3 (t, J=7.6 Hz, 3 H) 1.9 (m, 1 H) 3.2 (q, J=7.7 Hz, 2 H) 3.4 (s, 3 H) 3.6 (dd, J=9.3, 7.1 Hz, 1 H) 7.4 (m, 1 H) 7.5 (m, 1 H) 7.7 (d, J=9.1 Hz, 1 H) 7.8 (dd, J=10.5, 8.7 Hz, 4 H) 7.9 (d, J=7.3 Hz, 1 H) 7.9 (m, 2 H) 8.0 (d, J=8.8 Hz, 2 H) 8.3 (d, J=9.6 Hz, 1 H) 10.6 (s, 1 H).

Step 4: Hydrolysis of L-2-{4'-[(3-ethyl-benzofuran-2-carbonyl)-amino]-biphenyl-4-sulfonylamino}-3-methyl-butyric acid methyl ester to obtain L-2-{4'-[(3-ethyl-benzofuran-2-carbonyl)-amino]-biphenyl-4-sulfonylamino}-3-methyl-butyric acid was done according to Example 20, Step 5, in quantitative yield. The product was purified by trituration with 25% ethyl acetate/hexane. $^1$H NMR (400 MHz, DMSO-$d_6$) δ ppm 0.8 (dd, J=16.9, 6.8 Hz, 6 H) 1.3 (t, J=7.5 Hz, 3 H) 2.0 (m, 1 H) 3.2 (q, J=7.7 Hz, 2 H) 3.5 (s, 1 H) 7.4 (m, 1 H) 7.5 (m, 1 H) 7.7 (d, J=8.3 Hz, 1 H) 7.8 (m, 7 H) 8.0 (d, J=8.8 Hz, 2 H) 10.6 (s, 1 H).

Example 59

L-2-{4'-[(4-tert-Butoxycarbonylamino-3-methyl-benzofuran-2-carbonyl)-amino]-biphenyl-4-sulfonylamino}-3-methyl-butyric acid

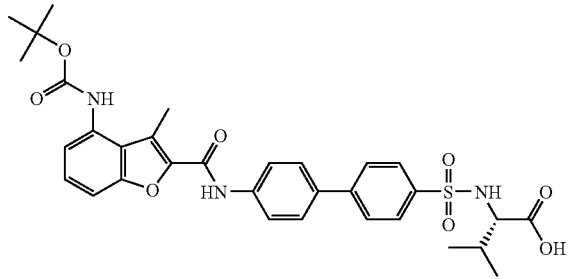

Step 1: Coupling of 3-methyl-4-trifluoromethanesulfonyloxy-benzofuran-2-carboxylic acid ethyl ester to tert-butyl carbamate to give 4-tert-butoxycarbonylamino-3-methyl-benzofuran-2-carboxylic acid ethyl ester, was done according to Example 47, Step 1 in 60% yield. $^1$H NMR (400 MHz, DMSO-$d_6$) δ ppm 1.3 (t, J=7.1 Hz, 3 H) 1.5 (s, 9 H) 2.6 (s, 3 H) 4.4 (q, J=7.1 Hz, 2 H) 7.1 (d, J=7.6 Hz, 1 H) 7.5 (m, 2 H) 9.1 (s, 1 H).

Step 2: Hydrolysis of 4-tert-butoxycarbonylamino-3-methyl-benzofuran-2-carboxylic acid ethyl ester to give 4-tert-butoxycarbonylamino-3-methyl-benzofuran-2-carboxylic acid was done according to Example 20, Step 3. Yield: 98%. $^1$H NMR (400 MHz, CD$_3$OD) δ ppm 1.4 (s, 9 H) 2.6 (s, 3 H) 7.1 (m, 1 H) 7.3 (m, 2 H) 8.7 (s, 1 H).

Step 3: Coupling of 4-tert-butoxycarbonylamino-3-methyl-benzofuran-2-carboxylic acid with L-2-(4'-amino-biphenyl-4-sulfonylamino)-3-methyl-butyric acid methyl ester to give L-2-{4'-[(4-tert-butoxycarbonylamino-3-methyl-benzofuran-2-carbonyl)-amino]-biphenyl-4-sulfonylamino}-3-methyl-butyric acid methyl ester was done according to Example 47, Step 3 in 85% yield. $^1$H NMR (400 MHz, DMSO-$d_6$) δ ppm 0.8 (dd, J=14.8, 6.7 Hz, 6 H) 1.5 (dd, 9 H) 1.9 (m, 1 H) 2.7 (s, 3 H) 3.3 (s, 3 H) 3.6 (dd, J=9.3, 7.1 Hz, 1 H) 7.2 (dd, J=7.6 Hz, 1 H) 7.4 (m, 1 H) 7.5 (m, 1 H) 7.8 (dd, J=10.2, 8.7 Hz, 4 H) 7.9 (m, 2 H) 8.0 (d, J=9.1 Hz, 2 H) 8.3 (d, J=9.3 Hz, 1 H) 9.1 (s, 1 H) 10.5 (s, 1 H).

Step 4: Hydrolysis of L-2-{4'-[(4-tert-butoxycarbonylamino-3-methyl-benzofuran-2-carbonyl)-amino]-biphenyl-4-sulfonylamino}-3-methyl-butyric acid methyl ester to obtain L-2-{4'-[(4-tert-butoxycarbonylamino-3-methyl-benzofuran-2-carbonyl)-amino]-biphenyl-4-sulfonylamino}-3-methyl-butyric acid was done according to Example 20, Step 5, in quantitative yield. The product was purified by trituration with 25% ethyl acetate/hexane. $^1$H NMR (400 MHz, DMSO-$d_6$) δ ppm 0.8 (dd, J=13.6, 6.8 Hz, 6 H) 1.5 (s, 9 H) 2.0 (m, 1 H) 2.7 (s, 3 H) 3.5 (m, 1 H) 7.2 (d, J=7.6 Hz, 1 H) 7.4 (m, 1 H) 7.5 (m, 1 H) 7.8 (d, J=8.8 Hz, 2 H) 7.9 (m, 4 H) 8.0 (d, J=9.1 Hz, 3 H) 9.1 (s, 1 H) 10.5 (s, 1 H).

Example 60

L-3-Methyl-2-{4'-[(3-methyl-4-methylamino-benzofuran-2-carbonyl)-amino]-biphenyl-4-sulfonylamino}-butyric acid

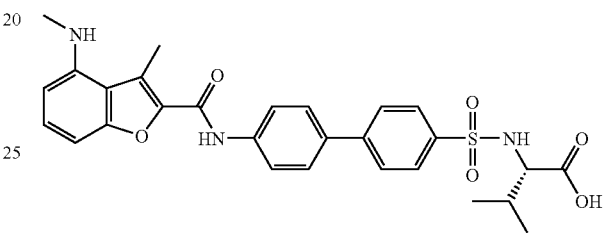

Step 1: To 4-tert-butoxycarbonylamino-3-methyl-benzofuran-2-carboxylic acid ethyl ester (624 mg, 1.95 mmol, prepared according to Example 59, Step 1) was added 1,2-dichloroethane (12 mL) and trifluoroacetic acid (TFA, 6 mL). The reaction was stirred at room temperature for 2 hours. Solvent was removed in vacuo to provide 4-amino-3-methyl-benzofuran-2-carboxylic acid ethyl ester in quantitative yield. $^1$H NMR (400 MHz, DMSO-$d_6$) δ ppm 1.3 (t, J=7.1 Hz, 3 H) 2.7 (s, 3 H) 4.3 (q, J=7.1 Hz, 2 H) 6.5 (dd, J=7.8, 0.8 Hz, 1 H) 6.8 (d, J=8.3 Hz, 1 H) 7.2 (t, J=8.1 Hz, 1 H).

Step 2: To 4-amino-3-methyl-benzofuran-2-carboxylic acid ethyl ester (500 mg, 2.28 mmol, 1 eq.) was added iodomethane (310 uL, 6.16 mmol, 2.7 eq.), sodium carbonate (314 mg, 2.96 mmol, 1.3 eq.), and ethanol (10 mL) and reaction was heated at reflux for 16 hours. 3-Methyl-4-methylamino-benzofuran-2-carboxylic acid ethyl ester was obtained in 17% yield after flash column chromatography, eluting with ethyl acetate/hexanes. (90 mg) $^1$H NMR (400 MHz, DMSO-$d_6$) δ ppm 1.3 (t, J=7.1 Hz, 3 H) 2.7 (s, 3 H) 4.3 (q, J=7.1 Hz, 2 H) 6.5 (dd, J=7.8, 0.8 Hz, 1 H) 6.8 (d, J=8.3 Hz, 1 H) 7.2 (t, J=8.1 Hz, 1 H).

Step 3: Hydrolysis of 3-methyl-4-methylamino-benzofuran-2-carboxylic acid ethyl ester to give 3-methyl-4-methylamino-benzofuran-2-carboxylic acid was done according to Example 20, Step 3, in quantitative yield. $^1$H NMR (400 MHz, DMSO-$d_6$) δ ppm 2.7 (s, 3 H) 2.8 (d, J=4.3 Hz, 3 H) 5.7 (d, J=4.8 Hz, 1 H) 6.3 (d, J=7.8 Hz, 1 H) 6.8 (dd, J=8.3, 0.8 Hz, 1 H) 7.2 (t, J=8.1 Hz, 1 H) 13.1 (s, 1 H).

Step 4: Coupling of 3-methyl-4-methylamino-benzofuran-2-carboxylic acid with L-2-(4'-amino-biphenyl-4-sulfonylamino)-3-methyl-butyric acid methyl ester to obtain L-3-methyl-2-{4'-[(3-methyl-4-methylamino-benzofuran-2-carbonyl)-amino]-biphenyl-4-sulfonylamino}-butyric acid methyl ester was done according to Example 47, Step 3, in 33% yield. $^1$H NMR (400 MHz, DMSO-$d_6$) δ ppm 1.2 (t, J=7.6 Hz, 3 H) 3.1 (q, J=7.6 Hz, 2 H) 3.9 (s, 3 H) 7.4 (m, 1 H) 7.5 (m, 1 H) 7.7 (m, 1 H) 7.9 (dd, J=7.8, 0.8 Hz, 1 H).

Step 5: Hydrolysis of L-3-methyl-2-{4'-[(3-methyl-4-methylamino-benzofuran-2-carbonyl)-amino]-biphenyl-4-sulfonylamino}-butyric acid methyl ester to obtain L-3-methyl-2-{4'-[(3-methyl-4-methylamino-benzofuran-2-carbonyl)-amino]-biphenyl-4-sulfonylamino}-butyric acid was done according to Example 20, Step 5, in quantitative yield. $^1$H NMR (400 MHz, DMSO-d$_6$) δ ppm 0.8 (dd, J=12.5, 6.7 Hz, 6 H) 2.0 (m, 1 H) 2.8 (m, 6 H) 3.6 (dd, J=9.3, 6.1 Hz, 1 H) 5.7 (d, J=4.5 Hz, 1 H) 6.3 (d, J=7.8 Hz, 1 H) 6.9 (d, J=7.8 Hz, 1 H) 7.3 (t, J=8.1 Hz, 1 H) 7.8 (d, J=8.8 Hz, 2 H) 7.8 (m, 4 H) 8.0 (d, J=8.8 Hz, 2 H) 8.1 (d, J=9.3 Hz, 1 H) 10.4 (s, 1 H).

Example 61

L-2-{4'-[(4-Amino-3-methyl-benzofuran-2-carbonyl)-amino]-biphenyl-4-sulfonylamino}-3-methyl-butyric acid

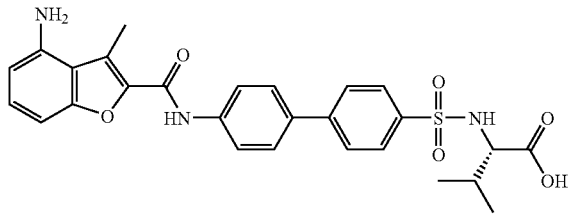

To L-2-{4'-[(4-tert-butoxycarbonylamino-3-methyl-benzofuran-2-carbonyl)-amino]-biphenyl-4-sulfonylamino}-3-methyl-butyric acid (84 mg, prepared according to Example 59, Step 4), 1,2-dichloroethane (2 mL) and TFA (1 mL) were added, and stirred at room temperature for 3 hours. The solvent was removed in vacuo to give L-2-{4'-[(4-amino-3-methyl-benzofuran-2-carbonyl)-amino]-biphenyl-4-sulfonylamino}-3-methyl-butyric acid in quantitative yield. NMR: $^1$H NMR (400 MHz, DMSO-d$_6$) δ ppm 0.8 (dd, J=12.6, 6.8 Hz, 6 H) 1.9 (m, 1 H) 2.8 (s, 3 H) 3.6 (dd, J=9.3, 6.1 Hz, 1 H) 5.5 (s, 2 H) 6.5 (dd, J=8.0, 0.6 Hz, 1 H) 6.8 (d, J=8.8 Hz, 1 H) 7.1 (t, J=8.1 Hz, 1 H) 7.8 (d, J=8.8 Hz, 2 H) 7.8 (m, 4 H) 8.0 (d, J=9.1 Hz, 2 H) 8.1 (d, J=9.3 Hz, 1 H) 10.3 (s, 1 H).

Example 62

L-2-{4'-[(4-Dimethylamino-3-methyl-benzofuran-2-carbonyl)-amino]-biphenyl-4-sulfonylamino}-3-methyl-butyric acid

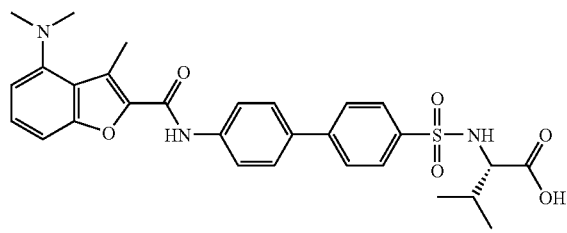

Step 1: To 4-amino-3-methyl-benzofuran-2-carboxylic acid ethyl ester (500 mg, 2.28 mmol, 1 eq. prepared according to Example 60, Step 1), ethanol (8 mL), iodomethane (500 uL, 7.98 mmol, 3.5 eq.), and potassium carbonate (946 mg, 6.84 mmol, 3 eq.) were added under argon in a sealed tube and the mixture was heated at 80° C. for 16 hours. After work-up and flash column chromatography, 4-dimethylamino-3-methyl-benzofuran-2-carboxylic acid ethyl ester was obtained in 44% yield. $^1$H NMR (400 MHz, DMSO-d$_6$) δ ppm 1.3 (t, J=7.2 Hz, 3 H) 2.7 (t, 3 H) 2.8 (s, 6 H) 4.3 (m, J=7.1, 7.1, 7.1 Hz, 2 H) 6.9 (dd, J=7.8, 0.8 Hz, 1 H) 7.3 (dd, J=8.3, 1.0 Hz, 1 H) 7.4 (m, 1 H).

Step 2: Hydrolysis of 4-dimethylamino-3-methyl-benzofuran-2-carboxylic acid ethyl ester to give 4-dimethylamino-3-methyl-benzofuran-2-carboxylic acid was done according to Example 20, Step 3, in quantitative yield. $^1$H NMR (400 MHz, DMSO-d$_6$) δ ppm 2.7 (s, 3 H) 2.8 (s, 6 H) 6.9 (d, J=7.6 Hz, 1 H) 7.2 (d, J=7.6 Hz, 1 H) 7.4 (t, J=8.1 Hz, 1 H) 13.2 (s, 1 H).

Step 3: Coupling of 4-dimethylamino-3-methyl-benzofuran-2-carboxylic acid with L-2-(4'-amino-biphenyl-4-sulfonylamino)-3-methyl-butyric acid methyl ester to obtain L-2-{4'-[(4-dimethylamino-3-methyl-benzofuran-2-carbonyl)-amino]-biphenyl-4-sulfonylamino}-3-methyl-butyric acid methyl ester was done according to Example 47, Step 3, in quantitative yield.

Step 4: Hydrolysis of L-2-{4'-[(4-dimethylamino-3-methyl-benzofuran-2-carbonyl)-amino]-biphenyl-4-sulfonylamino}-3-methyl-butyric acid methyl ester to L-2-{4'-[(4-dimethylamino-3-methyl-benzofuran-2-carbonyl)-amino]-biphenyl-4-sulfonylamino}-3-methyl-butyric acid was done according to Example 20, Step 5. Purification by preparative HPLC gave the desired product in 50% yield. $^1$H NMR (400 MHz, DMSO-d$_6$) δ ppm 0.8 (dd, J=12.6, 6.8 Hz, 6 H) 2.0 (m, 1 H) 2.8 (m, 9 H) 3.6 (dd, J=9.3, 5.8 Hz, 1 H) 6.9 (dd, J=7.8, 0.8 Hz, 1 H) 7.3 (dd, J=8.3, 0.8 Hz, 1 H) 7.4 (m, 1 H) 7.8 (d, J=8.8 Hz, 2 H) 7.9 (m, 4 H) 8.0 (d, J=8.8 Hz, 2 H) 8.0 (d, J=9.1 Hz, 1 H) 10.5 (s, 1 H).

Example 63

L-3-Methyl-2-{4'-[(3-methyl-4-pyrrolidin-1-yl-benzofuran-2-carbonyl)-amino]-biphenyl-4-sulfonylamino}-butyric acid

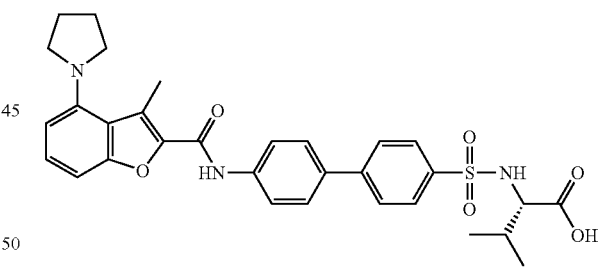

Step 1: To 4-amino-3-methyl-benzofuran-2-carboxylic acid ethyl ester (500 mg, 2.28 mmol, 1 eq., prepared according to Example 60, Step 1) were added toluene (3 mL), 1,4-dibromobutane(272 uL, 2.28 mmol, 1 eq.), and N,N-diisopropylethylamine (953 uL, 5.47 mmol, 2.4 eq.) under argon in a sealed tube and the mixture was heated at 110° C. for 16 hours. After work-up and flash column chromatography, 3-methyl-4-pyrrolidin-1-yl-benzofuran-2-carboxylic acid ethyl ester was obtained in 48% yield. $^1$H NMR (400 MHz, DMSO-d$_6$) δ ppm 1.3 (t, J=7.1 Hz, 3 H) 1.9 (m, 4 H) 2.7 (s, 3 H) 3.1 (m, 4 H) 4.3 (q, J=7.1 Hz, 2 H) 6.8 (dd, J=8.0, 0.6 Hz, 1 H) 7.2 (dd, J=8.3, 0.8 Hz, 1 H) 7.3 (m, 1 H).

Step 2: Hydrolysis of 3-methyl-4-pyrrolidin-1-yl-benzofuran-2-carboxylic acid ethyl ester to give 3-methyl-4-pyrrolidin-1-yl-benzofuran-2-carboxylic acid was done according to Example 20, Step 3, in 73% yield. ¹H NMR (400 MHz, DMSO-d₆) δ ppm 1.9 (m, 4 H) 2.7 (s, 3 H) 3.1 (m, 4 H) 6.8 (dd, J=7.8, 0.8 Hz, 1 H) 7.2 (dd, J=8.1, 0.8 Hz, 1 H) 7.3 (m, 1 H)

Step 3: Coupling of 3-methyl-4-pyrrolidin-1-yl-benzofuran-2-carboxylic acid with L-2-(4'-amino-biphenyl-4-sulfonylamino)-3-methyl-butyric acid methyl ester to obtain L-3-Methyl-2-{4'-[(3-methyl-4-pyrrolidin-1-yl-benzofuran-2-carbonyl)-amino]-biphenyl-4-sulfonylamino}-butyric acid methyl ester was done according to Example 47, Step 3, in 27% yield. ¹H NMR (400 MHz, DMSO-d₆) δ ppm 0.8 (m, 6 H) 1.9 (s, 5 H) 2.8 (d, J=1.5 Hz, 3 H) 3.2 (s, 4 H) 3.4 (d, J=1.5 Hz, 3 H) 3.6 (t, J=8.0 Hz, 1 H) 6.9 (d, J=7.8 Hz, 1 H) 7.2 (dd, J=9.3, 1.3 Hz, 1 H) 7.4 (m, 1 H) 7.8 (m, 4 H) 7.9 (m, 2 H) 8.0 (dd, J=8.6, 1.5 Hz, 2 H) 8.3 (d, J=9.6 Hz, 1 H) 10.4 (s, 1 H).

Step 4: Hydrolysis of L-3-methyl-2-{4'-[(3-methyl-4-pyrrolidin-1-yl-benzofuran-2-carbonyl)-amino]-biphenyl-4-sulfonylamino}-butyric acid methyl ester to L-3-methyl-2-{4'-[(3-methyl-4-pyrrolidin-1-yl-benzofuran-2-carbonyl)-amino]-biphenyl-4-sulfonylamino}-butyric acid was done according to Example 20, Step 5, in quantitative yield. ¹H NMR (400 MHz, DMSO-d₆) δ ppm 0.8 (dd, J=45.5, 6.8 Hz, 6 H) 1.9 (m, 4 H) 2.0 (m, 1 H) 2.8 (s, 3 H) 2.9 (d, J=2.8 Hz, 1 H) 3.2 (m, 4 H) 6.9 (dd, J=7.8, 0.8 Hz, 1 H) 7.2 (dd, J=8.1, 0.8 Hz, 1 H) 7.4 (m, 1 H) 7.8 (m, 6 H) 8.0 (d, J=8.8 Hz, 2 H) 8.5 (s, 1 H) 10.4 (s, 1 H).

Example 64

L-2-({4'-[(4-Methanesulfonylamino-3-methyl-benzofuran-2-carbonyl)-amino]-biphenyl-4-sulfonyl}-methyl-amino)-3-methyl-butyric acid

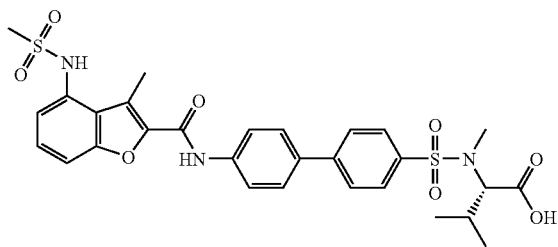

Step 1: Coupling of 4-methanesulfonylamino-3-methyl-benzofuran-2-carboxylic acid (prepared according to Example 36, Step 2) with L-2-[(4'-amino-biphenyl-4-sulfonyl)-methyl-amino]-3-methyl-butyric acid methyl ester to obtain L-2-({4'-[(4-methanesulfonylamino-3-methyl-benzofuran-2-carbonyl)-amino]-biphenyl-4-sulfonyl}-methyl-amino)-3-methyl-butyric acid methyl ester was done according to Example 47, Step 3, in 43% yield. The product was purified by prep-HPLC.

Step 2: Hydrolysis of L-2-({4'-[(4-methanesulfonylamino-3-methyl-benzofuran-2-carbonyl)-amino]-biphenyl-4-sulfonyl}-methyl-amino)-3-methyl-butyric acid methyl ester to L-2-(({4'-[(4-methanesulfonylamino-3-methyl-benzofuran-2-carbonyl)-amino]-biphenyl-4-sulfonyl}-methyl-amino)-3-methyl-butyric acid was done according to Example 20, Step 5, in quantitative yield. ¹H NMR (400 MHz, DMSO-d₆) δ ppm 0.9 (dd, J=21.0, 6.6 Hz, 6 H) 2.0 (m, 1 H) 2.8 (s, 3 H) 2.8 (s, 3 H) 3.1 (s, 3 H) 4.0 (d, J=10.4 Hz, 1 H) 7.3 (dd, J=7.7, 0.9 Hz, 1 H) 7.5 (m, 1 H) 7.6 (m, 1 H) 7.8 (dd, J=13.3, 8.7 Hz, 4 H) 7.9 (m, 2 H) 8.0 (d, J=8.8 Hz, 2 H) 9.5 (s, 1 H) 10.6 (s, 1 H).

Example 65

L-3-Hydroxy-2-{4'-[(4-methanesulfonylamino-3-methyl-benzofuran-2-carbonyl)-amino]-biphenyl-4-sulfonylamino}-butyric acid

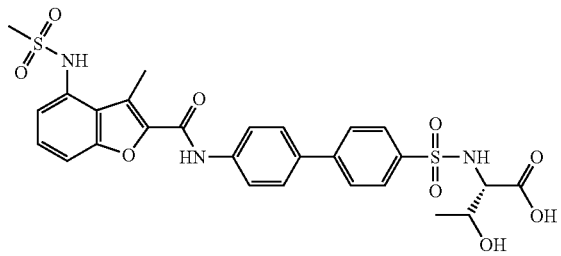

Step 1: L-2-(4'-Amino-biphenyl-4-sulfonylamino)-3-tert-butoxy-butyric acid methyl ester was prepared according to the procedure of Example 39, Steps 1-3, using O-t-butyl-threonine methyl ester and 4-(4,4,5,5-tetramethyl-[1,3,2]dioxaborolan-2-yl)-phenylamine. Coupling of 4-methanesulfonylamino-3-methyl-benzofuran-2-carboxylic acid (prepared according to Example 36, Step 2) with L-2-(4'-amino-biphenyl-4-sulfonylamino)-3-tert-butoxy-butyric acid methyl ester to obtain L-3-tert-butoxy-2-{4'-[(4-methanesulfonylamino-3-methyl-benzofuran-2-carbonyl)-amino]-biphenyl-4-sulfonylamino}-butyric acid methyl ester was done according to Example 47, Step 3, in 38% yield. ¹H NMR (400 MHz, DMSO-d₆) δ ppm 1.0 (m, 12 H) 2.8 (s, 3 H) 3.1 (s, 3 H) 3.4 (s, 3 H) 3.8 (dd, J=9.7, 3.7 Hz, 1 H) 4.0 (dd, J=10.2, 6.4 Hz, 1 H) 7.3 (d, J=7.6 Hz, 1 H) 7.5 (m, 1 H) 7.6 (d, J=8.3 Hz, 1 H) 7.8 (d, J=8.8 Hz, 2 H) 7.9 (m, 4 H) 8.0 (d, J=8.8 Hz, 2 H) 8.0 (d, J=9.9 Hz, 1 H) 9.5 (s, 1 H) 10.6 (s, 1 H).

Step 2: Deprotection of L-3-tert-butoxy-2-{4'-[(4-methanesulfonylamino-3-methyl-benzofuran-2-carbonyl)-amino]-biphenyl-4-sulfonylamino}-butyric acid methyl ester to obtain L-3-hydroxy-2-{4'-[(4-methanesulfonylamino-3-methyl-benzofuran-2-carbonyl)-amino]-biphenyl-4-sulfonylamino}-butyric acid methyl ester was done according to Example 61, Step 1, in quantitative yield. ¹H NMR (400 MHz, DMSO-d₆) δ ppm 1.0 (d, J=6.3 Hz, 3 H) 2.8 (s, 3 H) 3.1 (s, 3 H) 3.4 (s, 3 H) 3.8 (dd, J=9.3, 4.0 Hz, 1 H) 4.0 (m, 1 H) 7.3 (d, J=7.6 Hz, 1 H) 7.5 (m, 1 H) 7.6 (d, J=7.6 Hz, 1 H) 7.8 (d, J=8.8 Hz, 2 H) 7.9 (m, 4 H) 8.0 (d, J=8.8 Hz, 2 H) 8.0 (d, J=9.1 Hz, 1 H) 9.5 (s, 1 H) 10.6 (s, 1 H).

Step 3: Hydrolysis of L-3-hydroxy-2-{4'-[(4-methanesulfonylamino-3-methyl-benzofuran-2-carbonyl)-amino]-biphenyl-4-sulfonylamino}-butyric acid methyl ester to L-3-hydroxy-2-{4'-[(4-methanesulfonylamino-3-methyl-benzofuran-2-carbonyl)-amino]-biphenyl-4-sulfonylamino}-butyric acid was done according to Example 20, Step 5, in quantitative yield. ¹H NMR (400 MHz, DMSO-d₆) δ ppm 1.0 (d, J=6.3 Hz, 3 H) 2.8 (s, 3 H) 3.1 (s, 3 H) 3.7 (dd, J=9.3, 3.5 Hz, 1 H) 4.0 (s, 1 H) 4.8 (d, J=5.3 Hz, 1 H) 7.3 (d, J=7.8 Hz, 1 H) 7.5 (m, 1 H) 7.6 (d, J=8.3 Hz, 1 H) 7.7 (d, J=9.3 Hz, 1 H) 7.8 (d, J=8.8 Hz, 2 H) 7.9 (s, 4 H) 8.0 (d, J=8.8 Hz, 2 H) 9.5 (s, 1 H) 10.6 (s, 1 H).

Example 66

(S)-3-Methyl-2-(4'-{[4-methyl-2-(4-trifluoromethyl-phenyl)-thiazole-5-carbonyl]-amino}-biphenyl-4-sulfonylamino)-butyric acid

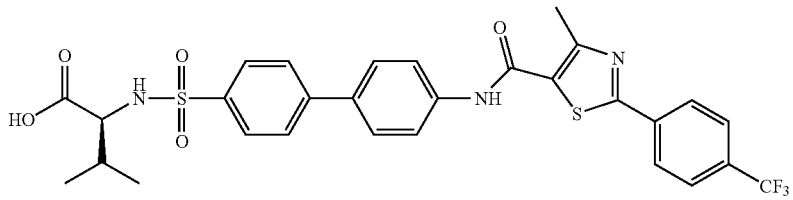

Step 1. Coupling of the 4-methyl-2-(4-trifluoromethyl-phenyl)-thiazole-5-carboxylic acid (commercially available) with L-2-(4'-amino-biphenyl-4-sulfonylamino)-3-methyl-butyric acid methyl ester was carried out according to the procedure described in Example 21, Step 3. The (S)-3-methyl-2-(4'-{[4-methyl-2-(4-trifluoromethyl-phenyl)-thiazole-5-carbonyl]-amino}-biphenyl-4-sulfonylamino)-butyric acid methyl ester was obtained as a white solid in 75% yield.

Step 2. Hydrolysis of (S)-3-methyl-2-(4'-{[4-methyl-2-(4-trifluoromethyl-phenyl)-thiazole-5-carbonyl]-amino}-biphenyl-4-sulfonylamino)-butyric acid methyl ester according to the procedure described in Example 20, Step 5, afforded (S)-3-methyl-2-(4'-{[4-methyl-2-(4-trifluoromethyl-phenyl)-thiazole-5-carbonyl]-amino}-biphenyl-4-sulfonylamino)-butyric acid as a white solid. MS: calc'd for [M+H]$^+$: 618.67. found:618.17.

Example 67

L-3-Methyl-2-(4'-{[3-methyl-4-(2,2,2-trifluoro-acetylamino)-benzofuran-2-carbonyl]-amino}-biphenyl-4-sulfonylamino)-butyric acid

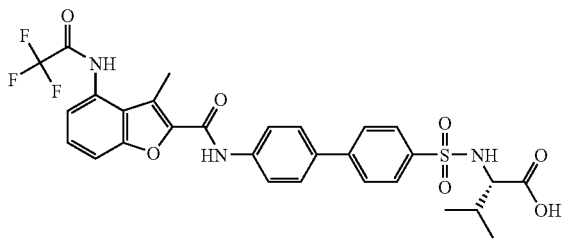

Step 1: Coupling of 3-methyl-4-(2,2,2-trifluoro-acetylamino)-benzofuran-2-carboxylic acid with L-2-(4'-amino-biphenyl-4-sulfonylamino)-3-methyl-butyric acid methyl ester to obtain L-3-methyl-2-(4'-{[3-methyl-4-(2,2,2-trifluoro-acetylamino)-benzofuran-2-carbonyl]-amino}-biphenyl-4-sulfonylamino)-butyric acid methyl ester was done according to Example 47, Step 3, in 61% yield. $^1$H NMR (400 MHz, DMSO-d$_6$) δ 0.8 (dd, J=14.7, 6.6 Hz, 6 H) 1.9 (m, 1 H) 2.6 (s, 3 H) 3.4 (s, 3 H) 3.6 (dd, J=9.5, 7.2 Hz, 1 H) 7.3 (d, J=7.8 Hz, 1 H) 7.6 (m, 1 H) 7.7 (d, J=8.3 Hz, 1 H) 7.8 (m, 4 H) 7.9 (m, 2 H) 8.0 (d, J=8.8 Hz, 2 H) 8.3 (d, J=9.3 Hz, 1 H) 10.6 (s, 1 H) 11.5 (s, 1 H).

Step 2: Hydrolysis of L-3-methyl-2-(4'-{[3-methyl-4-(2,2,2-trifluoro-acetylamino)-benzofuran-2-carbonyl]-amino}-biphenyl-4-sulfonylamino)-butyric acid methyl ester to L-3-methyl-2-(4'-{[3-methyl-4-(2,2,2-trifluoro-acetylamino)-benzofuran-2-carbonyl]-amino}-biphenyl-4-sulfonylamino)-butyric acid was done according to Example 20, Step 5, in 25% yield. The product was purified via prep-HPLC. $^1$H NMR (400 MHz, DMSO-d$_6$) δ ppm 0.8 (dd, J=13.4, 6.8 Hz, 6 H) 2.0 (m, 1 H) 2.6 (s, 3 H) 3.5 (m, 1 H) 7.3 (d, J=7.8 Hz, 1 H) 7.6 (m, 1 H) 7.7 (d, J=7.6 Hz, 1 H) 7.8 (d, J=8.8 Hz, 2 H) 7.9 (m, 4 H) 8.0 (d, J=9.1 Hz, 2 H) 8.0 (d, J=8.6 Hz, 1 H) 10.6 (s, 1 H).

Example 68

L-2-{4'-[(4-Ethanesulfonylamino-3-methyl-benzofuran-2-carbonyl)-amino]-biphenyl-4-sulfonylamino}-3-methyl-butyric acid

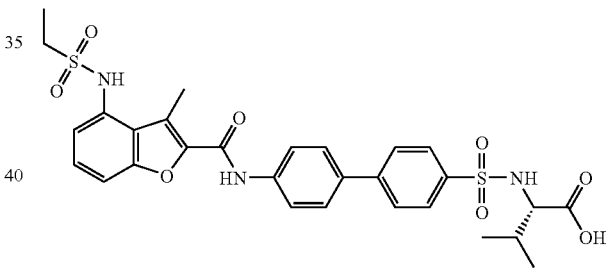

Step 1: To 4-amino-3-methyl-benzofuran-2-carboxylic acid ethyl ester (563 mg, 2.57 mmol, 1 eq., prepared according to Example 60, Step 1), CH$_2$Cl$_2$ (12 mL) was added under argon and the reaction was cooled to <0° C. Then ethanesulfonyl chloride (243 uL, 2.57 mmol, 1 eq.), and pyridine (623 uL, 7.70 mmol, 3 eq.) were added and the reaction was stirred while slowly warming to room temperature. After work-up and flash column chromatography, 4-ethanesulfonylamino-3-methyl-benzofuran-2-carboxylic acid ethyl ester was obtained in 69% yield. $^1$H NMR (400 MHz, DMSO-d$_6$) δ ppm 1.3 (m, 6 H) 2.8 (s, 3 H) 3.2 (q, J=7.3 Hz, 2 H) 4.4 (m, J=7.1, 7.1, 7.1 Hz, 2 H) 7.2 (d, J=7.6 Hz, 1 H) 7.5 (m, 1 H) 7.6 (m, 1 H) 9.6 (s, 1 H).

Step 2: Hydrolysis 4-ethanesulfonylamino-3-methyl-benzofuran-2-carboxylic acid ethyl ester to give 4-ethanesulfonylamino-3-methyl-benzofuran-2-carboxylic acid was done according to Example 20, Step 3, in quantitative yield. $^1$H NMR (400 MHz, DMSO-d$_6$) δ ppm 1.3 (t, J=7.3 Hz, 3 H) 2.7 (s, 3 H) 3.2 (q, J=7.3 Hz, 2 H) 7.2 (d, J=7.6 Hz) 7.5 (m, 1 H) 7.6 (d, J=8.3 Hz, 1 H) 9.5 (s, 1 H).

Step 3: Coupling of 4-ethanesulfonylamino-3-methyl-benzofuran-2-carboxylic acid with L-2-(4'-amino-biphenyl-4- sulfonylamino)-3-methyl-butyric acid methyl ester to L-2-{4'-[(4-ethanesulfonylamino-3-methyl-benzofuran-2-carbonyl)-amino]-biphenyl-4-sulfonylamino}-3-methyl-butyric acid methyl ester was done according to Example 47, Step 3, in quantitative yield. $^1$H NMR (400 MHz, DMSO-d$_6$) δ ppm 0.8 (dd, J=14.8, 6.7 Hz, 6 H) 1.9 (dd, J=12.9, 7.8 Hz, 1 H) 2.8 (s, 3 H) 3.6 (dd, J=9.5, 7.2 Hz, 1 H) 7.2 (d, J=7.6 Hz, 1 H) 7.5 (m, 1 H) 7.6 (d, J=7.8 Hz, 1 H) 7.8 (t, J=8.5 Hz, 4 H) 7.9 (m, 2 H) 8.0 (d, J=8.8 Hz, 2 H) 8.3 (d, J=9.6 Hz, 1 H) 9.6 (s, 1 H) 10.6 (s, 1 H).

Step 4: Hydrolysis of L-2-{4'-[(4-ethanesulfonylamino-3-methyl-benzofuran-2-carbonyl)-amino]-biphenyl-4-sulfonylamino}-3-methyl-butyric acid methyl ester to L-2-{4'-[(4-ethanesulfonylamino-3-methyl-benzofuran-2-carbonyl)-amino]-biphenyl-4-sulfonylamino}-3-methyl-butyric acid was done according to Example 20, Step 5, in 71% yield. $^1$H NMR (400 MHz, DMSO-d$_6$) δ ppm 0.8 (dd, J=13.1, 6.8 Hz, 6 H) 1.3 (t, J=7.5 Hz, 3 H) 2.0 (m, 1 H) 2.8 (s, 3 H) 3.2 (q, J=7.3 Hz, 2 H) 3.6 (dd, J=9.0, 5.9 Hz, 1 H) 7.2 (d, J=7.8 Hz, 1 H) 7.5 (m, 1 H) 7.6 (d, J=7.6 Hz, 1 H) 7.8 (d, J=8.8 Hz, 2 H) 7.9 (m, 4 H) 8.0 (d, J=9.1 Hz, 2 H) 8.1 (d, J=9.9 Hz, 1 H) 9.6 (s, 1 H) 10.6 (s, 1 H).

Example 69

L-3-Methyl-2-(4'-{[3-methyl-4-(propane-2-sulfonylamino)-benzofuran-2-carbonyl]-amino}-biphenyl-4-sulfonylamino)-butyric acid

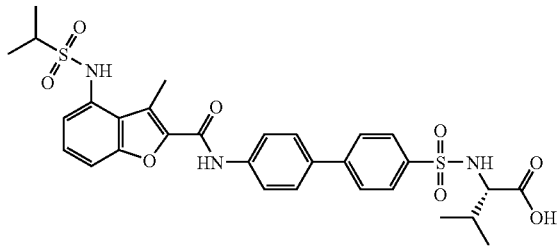

Step 1: To a mixture of 6 mL of dichloromethane and 11 mL of ammonium hydroxide at room temperature was added 500 uL of isopropylsulfonyl chloride (4.5 mmol). After stirring overnight the reaction was extracted with dichloromethane, the organic layer was dried over magnesium sulfate, filtered and concentrated in vacuo to give isopropylsulfonamide (121 mg) in 22% yield. $^1$H NMR (400 MHz, CDCl$_3$) δ ppm 1.4 (d, J=6.8 Hz, 6 H) 3.2 (m, 1 H) 4.4 (s, 2 H).

Step 2: Coupling of isopropylsulfonamide with 3-methyl-4-trifluoromethanesulfonyloxy-benzofuran-2-carboxylic acid ethyl ester was carried out according to Example 36, Step 1 to give 3-methyl-4-(propane-2-sulfonylamino)-benzofuran-2-carboxylic acid ethyl ester in 23% yield. $^1$H NMR (400 MHz, CDCl$_3$) δ ppm 1.4 (t, J=6.4 Hz, 9 H) 2.9 (t, 3 H) 3.5 (m, 1 H) 4.5 (q, J=7.1 Hz, 2 H) 6.6 (s, 1 H) 7.4 (m, 3 H).

Step 3: Hydrolysis of 3-methyl-4-(propane-2-sulfonylamino)-benzofuran-2-carboxylic acid ethyl ester was done according to Example 20, Step 3, to give 3-methyl-4-(propane-2-sulfonylamino)-benzofuran-2-carboxylic acid in quantitative yield. $^1$H NMR (400 MHz, DMSO-d$_6$) δ ppm 1.3 (d, J=6.8 Hz, 6 H) 2.8 (s, 3 H) 3.4 (m, 1 H) 7.2 (d, J=7.8 Hz, 1 H) 7.5 (m, 1 H) 7.6 (d, J=7.8 Hz, 1 H) 9.5 (s, 1 H).

Step 4: Amide coupling of 3-methyl-4-(propane-2-sulfonylamino)-benzofuran-2-carboxylic acid with L-2-(4'-amino-biphenyl-4-sulfonylamino)-3-methyl-butyric acid methyl ester was done according to Example 21, Step 3, to provide L-3-methyl-2-(4'-{[3-methyl-4-(propane-2-sulfonylamino)-benzofuran-2-carbonyl]-amino}-biphenyl-4-sulfonylamino)-butyric acid methyl ester in 88% yield. $^1$H NMR (400 MHz, DMSO-d$_6$) δ ppm 0.8 (dd, J=14.8, 6.7 Hz, 6 H) 1.3 (d, J=6.6 Hz, 6 H) 1.9 (m, 1 H) 2.8 (s, 3 H) 3.3 (s, 3 H) 3.4 (m, 1 H) 3.6 (dd, J=9.3, 7.1 Hz, 1 H) 7.2 (d, J=7.8 Hz, 1 H) 7.5 (m, 1 H) 7.6 (d, J=8.3 Hz, 1 H) 7.8 (t, J=8.7 Hz, 4 H) 7.9 (m, 2 H) 8.0 (d, J=8.8 Hz, 2 H) 8.1 (s, 1 H) 8.3 (d, J=9.6 Hz, 1 H) 9.5 (s, 1 H).

Step 5: Hydrolysis of L-3-methyl-2-(4'-{[3-methyl-4-(propane-2-sulfonylamino)-benzofuran-2-carbonyl]-amino}-biphenyl-4-sulfonylamino)-butyric acid methyl ester was carried out according to Example 20, Step 5, to give L-3-methyl-2-(4'-{[3-methyl-4-(propane-2-sulfonylamino)-benzofuran-2-carbonyl]-amino}-biphenyl-4-sulfonylamino)-butyric acid in quantitative yield. $^1$H NMR (400 MHz, DMSO-d$_6$) δ ppm 0.8 (dd, J=12.9, 6.8 Hz, 6 H) 1.3 (d, J=6.8 Hz, 6 H) 2.0 (m, 1 H) 2.8 (s, 3 H) 3.4 (m, 1 H) 3.6 (dd, J=9.3, 6.1 Hz, 1 H) 7.2 (d, J=7.8 Hz, 1 H) 7.5 (m, 1 H) 7.6 (d, J=7.8 Hz, 1 H) 7.8 (d, J=8.8 Hz, 2 H) 7.9 (m, 4 H) 8.0 (d, J=9.1 Hz, 2 H) 8.1 (d, J=9.6 Hz, 1 H) 9.5 (s, 1 H) 10.6 (s, 1 H).

Example 70

L-2-(4'-{[4-(Ethanesulfonyl-methyl-amino)-3-methyl-benzofuran-2-carbonyl]-amino}-biphenyl-4-sulfonylamino)-3-methyl-butyric acid

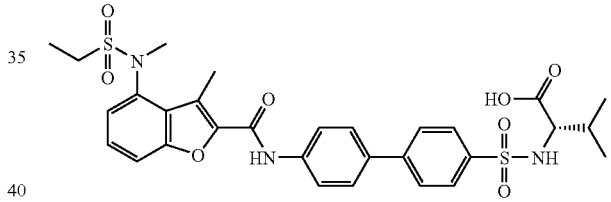

Step 1: 4-Ethanesulfonylamino-3-methyl-benzofuran-2-carboxylic acid ethyl ester (prepared according to Example 68, Step 1) was alkylated with iodomethane according to Example 60, Step 2, to give 4-(ethanesulfonyl-methyl-amino)-3-methyl-benzofuran-2-carboxylic acid ethyl ester. $^1$H NMR (400 MHz, DMSO-d$_6$) δ ppm 1.3 (m, 9 H) 2.7 (s, 3 H) 3.3 (s, 2 H) 4.4 (q, J=7.1 Hz, 2 H) 7.5 (dd, J=7.7, 0.9 Hz, 1 H) 7.6 (m, 1 H) 7.7 (m, 1 H).

Step 2: Hydrolysis of 4-(ethanesulfonyl-methyl-amino)-3-methyl-benzofuran-2-carboxylic acid ethyl ester to give 4-(ethanesulfonyl-methyl-amino)-3-methyl-benzofuran-2-carboxylic acid was done according to Example 20, Step 3 in 92% yield. $^1$H NMR (400 MHz, DMSO-d$_6$) δ ppm 1.3 (t, J=7.1 Hz, 3 H) 1.5 (s, 9 H) 2.6 (s, 3 H) 4.4 (q, J=7.1 Hz, 2 H) 7.1 (d, J=7.6 Hz, 1 H) 7.4 (m, 1 H) 7.5 (m, 1 H) 9.1 (s, 1 H).

Step 3: Coupling of 4-(ethanesulfonyl-methyl-amino)-3-methyl-benzofuran-2-carboxylic acid with L-2-(4'-amino-biphenyl-4-sulfonylamino)-3-methyl-butyric acid methyl ester to give L-2-(4'-{[4-(ethanesulfonyl-methyl-amino)-3-methyl-benzofuran-2-carbonyl]-amino}-biphenyl-4-sulfonylamino)-3-methyl-butyric acid methyl ester was done according to Example 47, Step 3, in 88% yield. $^1$H NMR (400 MHz, DMSO-d$_6$) δ ppm 0.8 (dd, J=14.9, 6.8 Hz, 6 H) 1.2 (t, J=7.1 Hz, 3 H) 1.3 (t, J=7.5 Hz, 3 H) 1.9 (m, 1 H) 2.0 (s, 3 H) 2.8 (s, 3 H) 3.6 (dd, J=9.3, 7.1 Hz, 1 H) 4.0 (q, J=7.2 Hz, 2 H) 7.5 (m, 2 H) 7.7 (dd, J=8.1, 1.0 Hz, 1 H) 7.8 (dd, J=8.7, 7.5 Hz, 4 H) 7.9 (m, 2 H) 8.0 (d, J=8.8 Hz, 2 H) 8.3 (d, J=9.3 Hz, 1 H) 10.6 (s, 1 H).

Step 4: Hydrolysis of L-2-(4'-{[4-(ethanesulfonyl-methyl-amino)-3-methyl-benzofuran-2-carbonyl]-amino}-biphenyl-4-sulfonylamino)-3-methyl-butyric acid methyl ester to L-2-(4'-{[4-(ethanesulfonyl-methyl-amino)-3-methyl-benzofuran-2-carbonyl]-amino}-biphenyl-4-sulfonylamino)-3-methyl-butyric acid was done according to Example 20, Step 5, in 90% yield. $^1$H NMR (400 MHz, DMSO-$d_6$) δ ppm 0.8 (dd, J=12.6, 6.8 Hz, 6 H) 1.3 (t, J=7.3 Hz, 3 H) 2.0 (m, 1 H) 2.8 (s, 3 H) 3.3 (s, 2 H) 3.6 (dd, J=9.5, 5.9 Hz, 1 H) 5.8 (s, 3 H) 7.5 (dd, J=7.6, 1.0 Hz, 1 H) 7.6 (m, 1 H) 7.7 (m, 1 H) 7.8 (d, J=8.8 Hz, 2 H) 7.9 (m, 4 H) 8.0 (d, J=9.1 Hz, 2 H) 8.1 (d, J=9.3 Hz, 1 H) 10.6 (s, 1 H).

Example 71

L-2-{4'-[(4-Benzenesulfonylamino-3-methyl-benzofuran-2-carbonyl)-amino]-biphenyl-4-sulfonylamino}-3-methyl-butyric acid

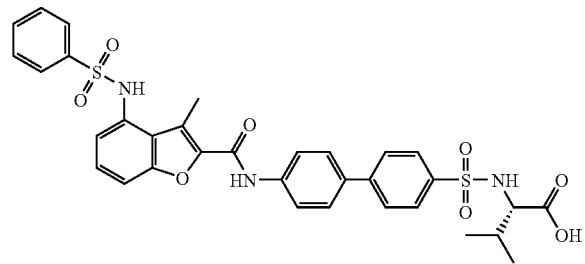

Step 1: 4-Benzenesulfonylamino-3-methyl-benzofuran-2-carboxylic acid ethyl ester was prepared from 4-amino-3-methyl-benzofuran-2-carboxylic acid ethyl ester (Example 60, Step 1), and benzenesulfonyl chloride according to the procedure of Example 68, Step 1. Yield: 83%. $^1$H NMR (400 MHz, DMSO-$d_6$) δ ppm 1.3 (t, J=7.2 Hz, 3 H) 2.6 (s, 3 H) 4.4 (q, J=7.1 Hz, 2 H) 6.6 (d, J=7.8 Hz, 1 H) 7.3 (m, 1 H) 7.6 (t, J=7.8 Hz, 3 H) 7.7 (m, 3 H) 10.1 (s, 1 H).

Step 2: Hydrolysis of 4-benzenesulfonylamino-3-methyl-benzofuran-2-carboxylic acid ethyl ester to give 4-benzenesulfonylamino-3-methyl-benzofuran-2-carboxylic acid was done according to Example 20, Step 3. Yield: 94%. $^1$H NMR (400 MHz, DMSO-$d_6$) δ ppm 2.6 (s, 3 H) 6.6 (d, J=7.6 Hz, 1 H) 7.3 (m, 1 H) 7.6 (m, 3 H) 7.7 (d, J=8.1 Hz, 3 H) 10.0 (s, 1 H) 13.5 (s, 1 H).

Step 3: Coupling of 4-benzenesulfonylamino-3-methyl-benzofuran-2-carboxylic acid with L-2-(4'-amino-biphenyl-4-sulfonylamino)-3-methyl-butyric acid methyl ester to obtain L-2-{4'-[(4-benzenesulfonylamino-3-methyl-benzofuran-2-carbonyl)-amino]-biphenyl-4-sulfonylamino}-3-methyl-butyric acid methyl ester was done according to Example 21, Step 3. Yield: 70%. $^1$H NMR (400 MHz, DMSO-$d_6$) δ ppm 0.8 (dd, J=14.7, 6.8 Hz, 6 H) 1.9 (m, 1 H) 2.7 (s, 3 H) 3.3 (s, 3 H) 3.6 (dd, J=9.5, 7.2 Hz, 1 H) 6.6 (d, J=7.6 Hz, 1 H) 7.3 (m, 1 H) 7.6 (m, 3 H) 7.7 (m, 3 H) 7.8 (t, J=9.0 Hz, 4 H) 7.9 (m, 2 H) 8.0 (d, J=8.8 Hz, 2 H) 8.3 (d, J=9.3 Hz, 1 H) 10.1 (s, 1 H) 10.6 (s, 1 H).

Step 4: Hydrolysis of L-2-{4'-[(4-benzenesulfonylamino-3-methyl-benzofuran-2-carbonyl)-amino]-biphenyl-4-sulfonylamino}-3-methyl-butyric acid methyl ester to obtain L-2-{4'-[(4-benzenesulfonylamino-3-methyl-benzofuran-2-carbonyl)-amino]-biphenyl-4-sulfonylamino}-3-methyl-butyric acid was done according to Example 20, Step 5, and the product was purified by ethyl acetate trituration. Yield: 50%. $^1$H NMR (400 MHz, DMSO-$d_6$) δ ppm 0.8 (dd, J=12.9, 6.8 Hz, 6 H) 1.9 (m, 1 H) 2.7 (s, 3 H) 3.6 (dd, J=9.3, 6.1 Hz, 1 H) 6.6 (d, J=8.1 Hz, 1 H) 7.3 (m, 1 H) 7.6 (m, 3 H) 7.7 (m, 3 H) 7.8 (d, J=8.8 Hz, 2 H) 7.9 (m, 4 H) 8.0 (d, J=8.8 Hz, 2 H) 8.1 (d, J=9.3 Hz, 1 H) 10.1 (s, 1 H) 10.6 (s, 1 H).

Example 72

L-3-Methyl-2-(4'-{[3-methyl-4-(thiophene-2-sulfonylamino)-benzofuran-2-carbonyl]-amino}-biphenyl-4-sulfonylamino)-butyric acid

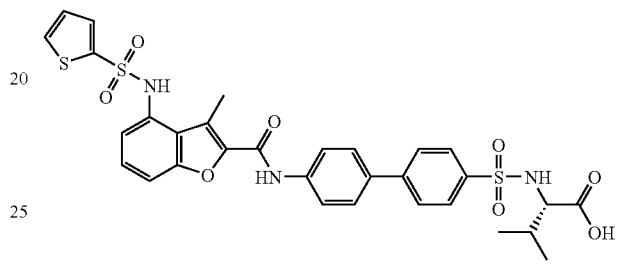

Step 1: 3-Methyl-4-(thiophene-2-sulfonylamino)-benzofuran-2-carboxylic acid ethyl ester was prepared from 4-amino-3-methyl-benzofuran-2-carboxylic acid ethyl ester (Example 60, Step 1), and 2-thiophenesulfonyl chloride according to the procedure of Example 68, Step 1. Yield: 68%. $^1$H NMR (400 MHz, DMSO-$d_6$) δ ppm 1.3 (t, J=7.1 Hz, 3 H) 2.6 (s, 3 H) 4.4 (q, J=7.1 Hz, 2 H) 6.7 (dd, J=7.8, 0.8 Hz, 1 H) 7.2 (dd, J=4.9, 3.7 Hz, 1 H) 7.4 (m, 2 H) 7.6 (dd, J=8.3, 0.8 Hz, 1 H) 8.0 (dd, J=4.9, 1.4 Hz, 1 H) 10.2 (s, 1 H)

Step 2: Hydrolysis of 3-methyl-4-(thiophene-2-sulfonylamino)-benzofuran-2-carboxylic acid ethyl ester to give 3-methyl-4-(thiophene-2-sulfonylamino)-benzofuran-2-carboxylic acid was done according to Example 20, Step 3. Yield: 92%. $^1$H NMR (400 MHz, DMSO-$d_6$) δ ppm 2.6 (s, 3 H) 6.7 (dd, J=7.7, 0.9 Hz, 1 H) 7.2 (dd, J=5.1, 3.8 Hz, 1 H) 7.4 (m, 1 H) 7.5 (dd, J=3.7, 1.4 Hz, 1 H) 7.6 (dd, J=8.3, 0.8 Hz, 1 H) 8.0 (dd, J=5.1, 1.3 Hz, 1 H) 10.2 (s, 1 H) 13.5 (s, 1 H)

Step 3: Coupling of 3-methyl-4-(thiophene-2-sulfonylamino)-benzofuran-2-carboxylic acid with L-2-(4'-amino-biphenyl-4-sulfonylamino)-3-methyl-butyric acid methyl ester to obtain L-3-methyl-2-(4'-{[3-methyl-4-(thiophene-2-sulfonylamino)-benzofuran-2-carbonyl]-amino}-biphenyl-4-sulfonylamino)-butyric acid methyl ester was done according to Example 47, Step 3. Yield: quantitative. $^1$H NMR (400 MHz, DMSO-$d_6$) δ ppm 0.8 (dd, J=14.8, 6.7 Hz, 6 H) 1.9 (dd, J=13.6, 6.8 Hz, 1 H) 2.7 (s, 3 H) 3.3 (s, 3 H) 3.6 (dd, J=9.3, 7.1 Hz, 1 H) 6.8 (dd, J=7.8, 0.8 Hz, 1 H) 7.2 (dd, J=4.8, 3.8 Hz, 1 H) 7.4 (m, 1 H) 7.5 (dd, J=3.8, 1.3 Hz, 1 H) 7.6 (d, J=7.8 Hz, 1 H) 7.8 (t, J=9.0 Hz, 4 H) 7.9 (m, 2 H) 8.0 (m, 3 H) 8.3 (d, J=9.3 Hz, 1 H) 10.2 (s, 1 H) 10.6 (s, 1 H).

Step 4: Hydrolysis of L-3-methyl-2-(4'-{[3-methyl-4-(thiophene-2-sulfonylamino)-benzofuran-2-carbonyl]-amino}-biphenyl-4-sulfonylamino)-butyric acid methyl ester to obtain L-3-methyl-2-(4'-{[3-methyl-4-(thiophene-2-sulfonylamino)-benzofuran-2-carbonyl]-amino}-biphenyl-4-sulfonylamino)-butyric acid was done according to Example 20, Step 5, and the product was purified by ethyl acetate trituration. Yield: 78%. $^1$H NMR (400 MHz, DMSO-$d_6$) δ ppm 0.8 (dd, J=12.8, 6.7 Hz, 6 H) 1.9 (m, 1 H) 2.7 (s, 3 H) 3.6 (dd, J=9.3, 6.1 Hz, 1 H) 6.8 (d, J=7.8 Hz, 1 H) 7.2 (dd, J=5.1, 3.8 Hz, 1 H) 7.4 (m, 1 H) 7.5 (dd, J=3.8, 1.3 Hz, 1 H) 7.6 (dd, J=8.1 Hz, 1 H) 7.8 (d, J=8.8 Hz, 2 H) 7.9 (m, 4 H) 8.0 (m, 3 H) 8.1 (d, J=9.1 Hz, 1 H) 10.2 (s, 1 H) 10.6 (s, 1 H).

Example 73

L-2-(4'-{[4-(1,1-Dioxo-1λ⁶-isothiazolidin-2-yl)-3-methyl-benzofuran-2-carbonyl]-amino}-biphenyl-4-sulfonylamino)-3-methyl-butyric acid

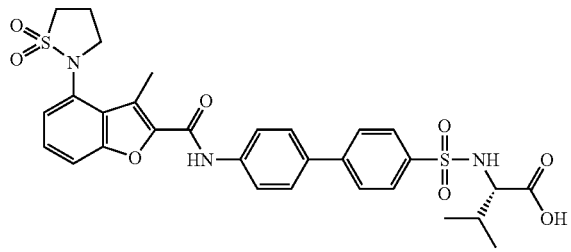

Step 1: 4-(3-Chloro-propane-1-sulfonylamino)-3-methyl-benzofuran-2-carboxylic acid ethyl ester was prepared from 4-amino-3-methyl-benzofuran-2-carboxylic acid ethyl ester (Example 60, Step 1), and 3-chloropropanesulfonyl chloride according to the procedure of Example 68, Step 1. Yield: 70%. ¹H NMR (400 MHz, DMSO-d₆) δ ppm 1.4 (m, 3 H) 2.2 (m, 2 H) 2.8 (s, 3 H) 3.3 (m, 2 H) 3.8 (t, J=6.4 Hz, 2 H) 4.4 (q, J=7.2 Hz, 2 H) 7.2 (d, J=7.3 Hz, 1 H) 7.5 (m, 1 H) 7.7 (m, 1 H) 9.7 (s, 1 H).

Step 2: To 4-(3-chloro-propane-1-sulfonylamino)-3-methyl-benzofuran-2-carboxylic acid ethyl ester (246 mg, 0.68 mmol, 1 eq.) in THF (10 mL) cooled to <0° C. was added sodium hydride (60%, 30 mg, 0.75 mmol, 1.1 eq.). The reaction was allowed to slowly warm to room temperature, then transferred to a pressure tube and heated at 74° C. for 16 hours. After work-up and flash column chromatography, 4-(1,1-dioxo-1λ⁶-isothiazolidin-2-yl)-3-methyl-benzofuran-2-carboxylic acid ethyl ester was obtained. Yield: 64%. ¹H NMR (400 MHz, DMSO-d₆) δ ppm 1.3 (t, J=7.1 Hz, 3 H) 2.5 (m, 2 H) 2.7 (s, 3 H) 3.5 (m, 2 H) 3.7 (dd, J=6.8 Hz, 2 H) 4.4 (q, J=7.1 Hz, 2 H) 7.4 (dd, J=7.8, 0.8 Hz, 1 H) 7.6 (m, 1 H) 7.7 (dd, J=8.3, 0.8 Hz, 1 H).

Step 3: Hydrolysis of 4-(1,1-dioxo-1λ⁶-isothiazolidin-2-yl)-3-methyl-benzofuran-2-carboxylic acid ethyl ester to give 4-(1,1-dioxo-1λ⁶-isothiazolidin-2-yl)-3-methyl-benzofuran-2-carboxylic acid was done according to Example 20, Step 3, to give 4-(1,1-dioxo-1λ⁶-isothiazolidin-2-yl)-3-methyl-benzofuran-2-carboxylic acid. Yield: 94%. ¹H NMR (400 MHz, DMSO-d₆) δ ppm 2.5 (dd, J=14.7, 7.6 Hz, 2 H) 2.7 (s, 3 H) 3.5 (m, 2 H) 3.7 (t, J=6.8 Hz, 2 H) 7.4 (m, 1 H) 7.6 (m, 1 H) 7.7 (d, J=8.6 Hz, 1 H).

Step 3: Coupling of 4-(1,1-dioxo-1λ⁶-isothiazolidin-2-yl)-3-methyl-benzofuran-2-carboxylic acid with L-2-(4'-amino-biphenyl-4-sulfonylamino)-3-methyl-butyric acid methyl ester to obtain L-2-(4'-{[4-(1,1-dioxo-1λ⁶-isothiazolidin-2-yl)-3-methyl-benzofuran-2-carbonyl]-amino}-biphenyl-4-sulfonylamino)-3-methyl-butyric acid methyl ester was done according to Example 47, Step 3. Yield: 89%. ¹H NMR (400 MHz, DMSO-d₆) δ ppm 0.8 (dd, J=14.7, 6.8 Hz, 6 H) 1.9 (m, 1 H) 2.8 (s, 3 H) 3.3 (s, 3 H) 3.5 (m, 2 H) 3.6 (dd, J=9.5, 7.2 Hz, 1 H) 3.8 (t, J=6.8 Hz, 2 H) 7.5 (dd, J=7.8, 0.8 Hz, 1 H) 7.6 (m, 1 H) 7.8 (m, 5 H) 7.9 (m, 2 H) 8.0 (d, J=8.8 Hz, 2 H) 8.3 (d, J=9.3 Hz, 1 H) 10.6 (s, 1 H).

Step 4: Hydrolysis of L-2-(4'-{[4-(1,1-dioxo-1λ⁶-isothiazolidin-2-yl)-3-methyl-benzofuran-2-carbonyl]-amino}-biphenyl-4-sulfonylamino)-3-methyl-butyric acid methyl ester to obtain L-2-(4'-{[4-(1,1-dioxo-1λ⁶-isothiazolidin-2-yl)-3-methyl-benzofuran-2-carbonyl]-amino}-biphenyl-4-sulfonylamino)-3-methyl-butyric acid was done according to Example 20, Step 5, and the product was purified by ethyl acetate trituration. Yield: 67%. ¹H NMR (400 MHz, DMSO-d₆) δ ppm 0.8 (dd, J=12.9, 6.8 Hz, 6 H) 1.9 (m, 1 H) 2.8 (s, 3 H) 3.5 (m, 2 H) 3.6 (dd, J=9.3, 5.8 Hz, 1 H) 3.8 (t, J=6.8 Hz, 2 H) 7.5 (dd, J=7.7, 0.9 Hz, 1 H) 7.6 (m, 1 H) 7.7 (dd, J=8.2, 0.9 Hz, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.6 (s, 1 H).

Example 74

D-3-Methyl-2-{4'-[(3-methyl-benzofuran-2-carbonyl)-amino]-biphenyl-4-sulfonylamino}-butyric acid

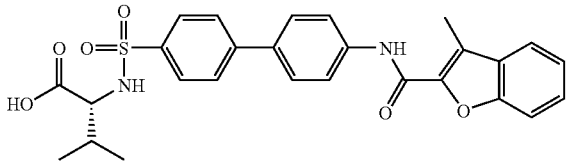

Step 1: Amide coupling of 3-methyl-benzofuran-2-carboxylic acid with 4-(4,4,5,5-tetramethyl-[1,3,2]dioxaborolan-2-yl)-phenylamine was done according to Example 20, Step 4, to give 3-methyl-benzofuran-2-carboxylic acid [4-(4,4,5,5-tetramethyl-[1,3,2]dioxaborolan-2-yl)-phenyl]-amide in 55% yield. ¹H NMR (400 MHz, DMSO-d₆) δ ppm 1.3 (s, 12 H) 2.6 (s, 3 H) 7.4 (m, 1 H) 7.5 (m, 1 H) 7.7 (m, 3 H) 7.8 (d, J=7.3 Hz, 1 H) 7.9 (d, J=8.6 Hz, 2 H) 10.5 (s, 1 H).

Step 2: To H-D-Val-OtBu—HCl (22.5 g, 0.107 mol, 1 eq.) in 400 mL of dichloromethane under argon, cooled using an ice-ethanol bath, was added 4-bromobenzene sulfonyl chloride (27.4 g, 0.107 mol, 1 eq.). Then N,N-diisopropylethylamine (43 mL, 0.247 mol, 2.3 eq.) was added via an addition funnel, and the reaction was stirred for 3 hours with slow warming to room temperature. After work-up, D-2-(4-bromo-benzenesulfonylamino)-3-methyl-butyric acid tert-butyl ester was obtained in 94% yield. ¹H NMR (400 MHz, DMSO-d₆) δ ppm 0.8 (dd, J=11.4, 6.8 Hz, 6 H) 1.2 (s, 9 H) 1.9 (m, 1 H) 3.5 (dd, J=9.5, 6.2 Hz, 1 H) 7.7 (d, J=8.8 Hz, 2 H) 7.8 (m, 2 H) 8.2 (d, J=9.6 Hz, 1 H).

Step 3: Suzuki coupling of 3-methyl-benzofuran-2-carboxylic acid [4-(4,4,5,5-tetramethyl-[1,3,2]dioxaborolan-2-yl)-phenyl]-amide with D-2-(4-bromo-benzenesulfonylamino)-3-methyl-butyric acid tert-butyl ester was carried out according to Example 38, Step 3, to give D-3-methyl-2-{4'-[(3-methyl-benzofuran-2-carbonyl)-amino]-biphenyl-4-sulfonylamino}-butyric acid tert-butyl ester in 66% yield. ¹H NMR (400 MHz, CDCl₃) δ ppm 0.9 (d, J=6.8 Hz, 3 H) 1.0 (d, J=6.8 Hz, 3 H) 1.2 (s, 9 H) 2.1 (m, 1 H) 2.7 (s, 3 H) 3.7 (dd, J=10.0, 4.4 Hz, 1 H) 5.1 (d, J=9.9 Hz, 1 H) 7.4 (m, 1 H) 7.5 (m, 1 H) 7.5 (m, 1 H) 7.6 (d, J=8.6 Hz, 2 H) 7.7 (d, J=8.6 Hz, 3 H) 7.8 (d, J=8.8 Hz, 2 H) 7.9 (d, J=8.6 Hz, 2 H) 8.5 (s, 1 H).

Step 4: Removal of t-butyl ester of D-3-methyl-2-{4'-[(3-methyl-benzofuran-2-carbonyl)-amino]-biphenyl-4-sulfonylamino}-butyric acid tert-butyl ester was done according to Example 1, Step 3, in quantitative yield. ¹H NMR (400 MHz, CD₃OD) δ ppm 0.8 (dd, J=24.1, 6.7 Hz, 6 H) 1.9 (m, 1 H) 2.6 (s, 3 H) 3.6 (d, J=5.8 Hz, 1 H) 7.3 (t, J=7.6 Hz, 1 H) 7.4 (m, 1 H) 7.5 (d, J=8.3 Hz, 1 H) 7.6 (m, 3 H) 7.7 (d, J=8.3 Hz, 2 H) 7.8 (m, 4 H) 10.1 (s, 1 H).

Example 75

D-2-{4'-[(Benzofuran-2-carbonyl)-methyl-amino]-biphenyl-4-sulfonylamino}-3-methyl-butyric acid

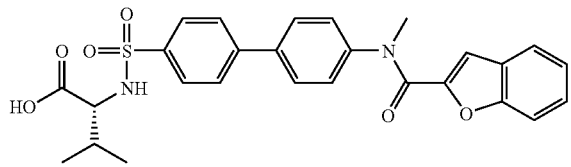

Step 1: Amide coupling of benzofuran-2-carboxylic acid with 4-(4,4,5,5-tetramethyl-[1,3,2]dioxaborolan-2-yl)-phenylamine was done according to Example 20, Step 4 to give benzofuran-2-carboxylic acid [4-(4,4,5,5-tetramethyl-[1,3,2]dioxaborolan-2-yl)-phenyl]-amide in 83% yield. $^1$H NMR (400 MHz, DMSO-d$_6$) δ ppm 1.3 (s, 12 H) 7.4 (m, 1 H) 7.5 (m, 1 H) 7.7 (d, J=8.3 Hz, 2 H) 7.7 (dd, J=8.5, 0.9 Hz, 1 H) 7.8 (m, 4 H) 10.6 (s, 1 H)

Step 2: To a solution of benzofuran-2-carboxylic acid [4-(4,4,5,5-tetramethyl-[1,3,2]dioxaborolan-2-yl)-phenyl]-amide (195 mg, 0.54 mmol, 1 eq) in 3.5 mL of DMF under nitrogen atmosphere was added NaH (60% in mineral oil, 23 mg, 0.58 mmol, 1.1 eq). After 30 min of reaction, iodomethane (0.05 mL, 0.8 mmol, 1.5 eq) was added and the reaction was allowed to go for 12 h. After work up and column chromatography, benzofuran-2-carboxylic acid methyl-[4-(4,4,5,5-tetramethyl-[1,3,2]dioxaborolan-2-yl)-phenyl]-amide (83 mg) was obtained in 41% yield. $^1$H NMR (400 MHz, Benzene-d$_6$) δ ppm 1.3 (s, 12 H) 3.4 (s, 3 H) 6.9 (d, J=0.8 Hz, 1 H) 7.0 (m, 4 H) 7.2 (m, 2 H) 8.1 (d, J=8.3 Hz, 2 H).

Step 3: Suzuki coupling of benzofuran-2-carboxylic acid methyl-[4-(4,4,5,5-tetramethyl-[1,3,2]dioxaborolan-2-yl)-phenyl]-amide with D-2-(4-bromo-benzenesulfonylamino)-3-methyl-butyric acid tert-butyl ester was carried out according to Example 38, Step 3 to give D-2-{4'-[(benzofuran-2-carbonyl)-methyl-amino]-biphenyl-4-sulfonylamino}-3-methyl-butyric acid tert-butyl ester in 77% yield. $^1$H NMR (400 MHz, CD$_3$OD) δ ppm 0.8 (m, 6 H) 1.1 (s, 9 H) 1.9 (m, 1 H) 3.4 (s, 3 H) 3.5 (d, J=5.8 Hz, 1 H) 6.6 (s, 1 H) 7.1 (m, 1 H) 7.2 (m, 2 H) 7.3 (d, J=8.8 Hz, 2 H) 7.4 (d, J=7.8 Hz, 1 H) 7.6 (d, J=8.8 Hz, 2 H) 7.7 (d, J=8.6 Hz, 2 H) 7.8 (m, 2 H).

Step 4: Removal of t-butyl ester was done according to Example 1, Step 3, in quantitative yield. $^1$H NMR (400 MHz, DMSO-d$_6$) δ ppm 0.8 (dd, J=12.1, 6.8 Hz, 6 H) 1.9 (m, 1 H) 3.5 (dd, J=9.3, 6.1 Hz, 1 H) 5.1 (s, 2 H) 7.1 (d, J=8.8 Hz, 2 H) 7.5 (m, 1 H) 7.6 (d, J=7.6 Hz, 1 H) 7.7 (d, J=8.8 Hz, 2 H) 7.8 (s, 4 H) 7.9 (dd, J=7.8, 1.3 Hz, 1 H) 8.0 (d, J=9.3 Hz, 1 H).

Example 76

4-{5-[(Benzofuran-2-carbonyl)-amino]-pyridin-2-yl}-benzenesulfonyl-L-valine

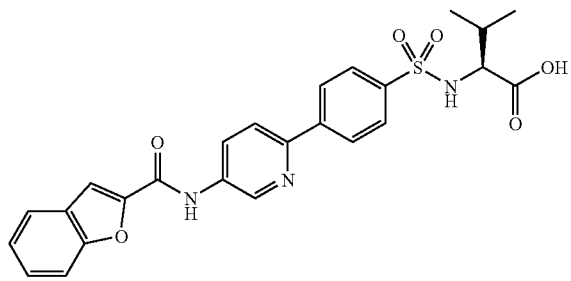

Step 1: 4-Bromo-benzenesulfonyl-L-valine-t-butyl ester, prepared from L-valine-t-butyl ester and 4-bromobenzenesulfonyl chloride according to the procedure of Example 38, Step 1, (10.2 mmol) was dissolved in DMSO (40 mL). To the solution was added PdCl$_2$(dppf) (0.51 mmol), KOAc (30.6 mmol), bis(pinacolato)diboron (13.3 mmol), and dppf (0.51 mmol). The reaction mixture was de-gassed and stirred overnight at 75° C. The mixture was diluted with EtOAc and washed with brine (3×). The organic layer was separated and dried over anhydrous sodium sulfate, filtered and concentrated. The crude product was purified by flash chromatography to afford 1.57 g of 4-(4,4,5,5-tetramethyl-[1,3,2]dioxaborolan-2-yl)-benzenesulfonyl]-L-valine-t-butyl ester.

Step 2: The ester from Step 1 (0.45 mmol) was dissolved in 1,4-dioxane (2 mL). To the solution was added Pd(PPh$_3$)$_4$ (0.022 mmol), K$_3$PO$_4$ (0.90 mmol), and 2-bromo-5-nitro-pyridine (0.48 mmol). After degassing, the mixture was stirred at 80° C. for 16 h. The mixture was diluted with ethyl acetate and washed with brine (3×). The organic layer was separated and dried over anhydrous sodium sulfate, and then concentrated. The crude product was purified by flash chromatography to afford 4-(5-nitro-pyridin-2-yl)-benzenesulfonyl-L-valine-t-butyl ester in 56% yield.

Steps 3-6: The nitro group of the product was reduced to the amino group using the procedure for Example 2, Step 4. The resulting product was acylated with benzofuran-2-carbonyl chloride using the same procedure as that for N-({4'-[(1-benzofuran-2-ylcarbonyl)amino]-1,1'-biphenyl-4-yl}sulfonyl fluoride to give 4-{5-[(benzofuran-2-carbonyl)-amino]-pyridin-2-yl}-benzenesulfonyl-L-valine-t-butyl ester. The tert-butyl group was removed using the procedure of Example 1, Step 3 to give 4-{5-[(benzofuran-2-carbonyl)-amino]-pyridin-2-yl}-benzenesulfonyl-L-valine. LCMS MH$^+$ (m/z) 494. $^1$H NMR (300 MHz, CDCl$_3$/CD$_3$OD): δ 9.0 ppm (d, 1H, J=2.5 Hz), 8.45 ppm (dd, 1H, J$_1$=8.6 Hz, J$_2$=2.6 Hz), 8.08-7.93 ppm (dm, 4H), 7.85 ppm (d, 1H, J=9.0 Hz), 7.77-7.62 ppm (m, 3H), 7.54-7.48 ppm (m, 1H), 7.39-7.33 ppm (m, 1H), 4.43 ppm (s, 1H), 3.75 ppm (d, 1H, J=5.2 Hz), 2.17 ppm (m, 1H), 1.01 ppm (d, 3H, J=6.0 Hz), 0.92 ppm (d, 3H, J=6.0 Hz).

Example 77

N-({4'-[(1-benzofuran-2-ylcarbonyl)amino]-1,1'-biphenyl-4-yl}sulfonyl)-N-methyl-D-valine

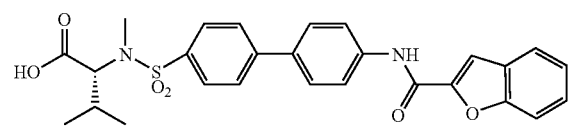

Step 1: To 0.117 g of D-valine in 2.5 mL dioxane and 2.5 mL of water, cooled in an ice bath, was added 0.31 g of 4'-nitro-1,1'-biphenyl-4-sulfonyl chloride, followed by 0.4 mL of triethylamine, The reaction was then stirred at room temperature overnight. After concentrating the reaction mixture in vacuo, the residue was extracted with ethyl acetate and 1N HCl. The organic layer was washed with water and brine, dried over Na$_2$SO$_4$, filtered and concentrated in vacuo to provide 0.35 g of N-[(4'-nitro-1,1'-biphenyl-4-yl)sulfonyl]-D-valine as a solid. Yield 74.5%. m.p. 165-167° C.; MS: 377.0 (M−H)$^-$.

Step 2: To 0.25 g of N-[(4'-nitro-1,1'-biphenyl-4-yl)sulfonyl]-D-valine and 0.40 g of potassium carbonate was added 0.16 mL of iodomethane and the reaction was stirred overnight. After concentrating the reaction mixture in vacuo the residue was extracted with dichloromethane and washed with water. The organic layer was washed with brine, dried over Na$_2$SO$_4$, filtered and concentrated in vacuo to provide 0.27 g of methyl N-methyl-N-[(4'-nitro-1,1'-biphenyl-4-yl)sulfonyl]-D-valinate. Yield ~100%. m.p. 117-118° C.; MS: 406 (M$^{+/-}$).

Step 3: To 0.22 g of methyl N-methyl-N-[(4'-nitro-1,1'-biphenyl-4-yl)sulfonyl]-D-valinate in 8 mL of ethyl acetate was added 1.21 g of tin (II) chloride dihydrate and the reaction was stirred at room temperature overnight. To the reaction was added ~8 mL of 2N sodium carbonate to adjust the pH to ~8-9. The reaction was then filtered through celite. The filtrate washed with water and brine, dried over Na$_2$SO$_4$, filtered, and concentrated to provide 0.19 g of as methyl N-[(4'-amino-1,1'-biphenyl-4-yl)sulfonyl]-N-methyl-D-valinate as an oil. Yield 95%. MS:377.2 (M+H)$^+$.

Step 4: To 0.11 g of methyl N-[(4'-amino-1,1'-biphenyl-4-yl)sulfonyl]-N-methyl-D-valinate in 4 mL dichloromethane cooled in ice bath, was added 0.058 g of 2-benzofurancarbonyl chloride, and N,N-diisopropylethylamine (0.15 mL) was dropped in. The reaction was stirred at room temperature overnight and then diluted with dichloromethane. The organic layer was washed with water, 5% HCl, and brine, dried over sodium sulfate, filtered, concentrated, and purified by column chromatography eluting with hexane:ethyl acetate (2:1) to provide 0.13 g of methyl N-({4'-[(1-benzofuran-2-ylcarbonyl)amino]-1,1'-biphenyl-4-yl}sulfonyl)-N-methyl-D-valinate. Yield 86.6%. m.p. 67-69° C. MS: 521.3 (M+H)$^+$.

Step 5: To 0.13 g of methyl N-({4'-[(1-benzofuran-2-ylcarbonyl)amino]-1,1'-biphenyl-4-yl}sulfonyl)-N-methyl-D-valinate in 12 mL ethyl acetate was added 0.67 g of lithium iodide and the mixture was refluxed overnight. The reaction was diluted with ethyl acetate and 1N HCl. The organic layer was washed with water, sodium thiosulfate solution, water and brine, dried over Na$_2$SO$_4$, filtered, and concentrated to provide 0.099 g of N-({4'-[(1-benzofuran-2-ylcarbonyl)amino]-1,1'-biphenyl-4-yl}sulfonyl)-N-methyl-D-valine. Yield 77.9%. m.p. 239-241° C.; MS 505.1(M−H)$^−$.

Example 78

N-({4'-[(1-Benzofuran-2-ylcarbonyl)amino]-1,1'-biphenyl-4-yl}sulfonyl)-N-methyl-L-valine

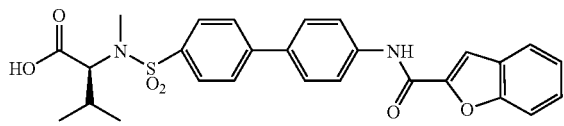

According to the same general method as Example 77, 0.2 g of L-valine methyl ester hydrochloride provided 0.13 g of N-({4'-[(1-benzofuran-2-ylcarbonyl)amino]-1,1'-biphenyl-4-yl}sulfonyl)-N-methyl-L-valine. Yield 77.6%. m.p. 237-239° C.; MS 505.0(M−H)$^−$.

Example 79

N-({4'-[(1-Benzofuran-2-ylcarbonyl)amino]-1,1'-biphenyl-4-yl}sulfonyl)-N-methylglycine

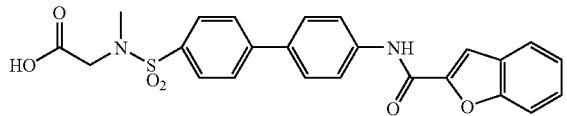

According to the same general method as Example 77, 0.14 g of sarcosine methyl ester hydrochloride provided 0.1 g of N-({4'-[(1-benzofuran-2-ylcarbonyl)amino]-1,1'-biphenyl-4-yl}sulfonyl)-N-methylglycine. m.p. 226-228° C.; MS 463.1 (M−H)$^−$.

Example 80

(S)-2-{4'-[(1,3-Dimethyl-1H-thieno[2,3-c]pyrazole-5-carbonyl)-amino]-biphenyl-4-sulfonylamino}-3-methyl-butyric acid

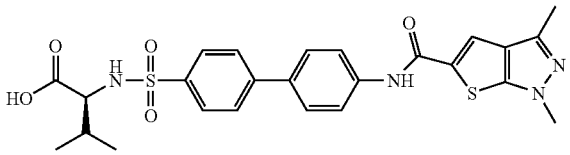

Step 1. Coupling of 1,3-dimethyl-1H-thieno[2,3-c]pyrazole-5-carboxylic acid (commercially available) with L-2-(4'-amino-biphenyl-4-sulfonylamino)-3-methyl-butyric acid methyl ester was carried out according to the procedure described in Example 21, Step 3. The (S)-2-{4'-[(1,3-dimethyl-1H-thieno[2,3-c]pyrazole-5-carbonyl)-amino]-biphenyl-4-sulfonylamino}-3-methyl-butyric acid methyl ester was obtained as a white solid in 75% yield.

Step 2. Hydrolysis of (S)-2-{4'-[(1,3-dimethyl-1H-thieno[2,3-c]pyrazole-5-carbonyl)-amino]-biphenyl-4-sulfonylamino}-3-methyl-butyric acid methyl ester according to the procedure described in Example 20, Step 5 afforded (S)-2-{4'-[(1,3-dimethyl-1H-thieno[2,3-c]pyrazole-5-carbonyl)-amino]-biphenyl-4-sulfonylamino}-3-methyl-butyric acid as a white solid. MS: calc'd for {M+H}$^+$: 527.64. found: 527.21.

Example 81

N-({4'-[(1-Benzofuran-2-ylcarbonyl)amino]-1,1'-biphenyl-4-yl}sulfonyl)-N-(pyridin-3-ylmethyl)-L-valine

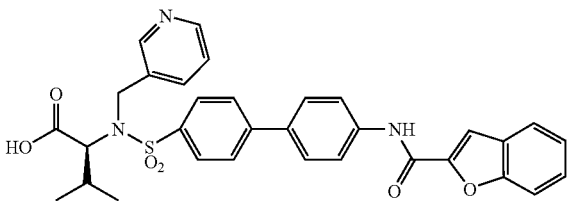

According to the general procedure of Example 77, starting with L-valine and alkylating with 3-picolyl chloride hydrochloride in Step 2, N-({4'-[(1-benzofuran-2-ylcarbonyl)amino]-1,1'-biphenyl-4-yl}sulfonyl)-N-(pyridin-3-ylmethyl)-L-valine was obtained. m.p. 261-262° C.; MS 584.2 (M+H)$^+$.

Example 82

N-({4'-[(1-Benzofuran-2-ylcarbonyl)amino]-1,1'-biphenyl-4-yl}sulfonyl)-N-(2-morpholin-4-ylethyl)-L-valine

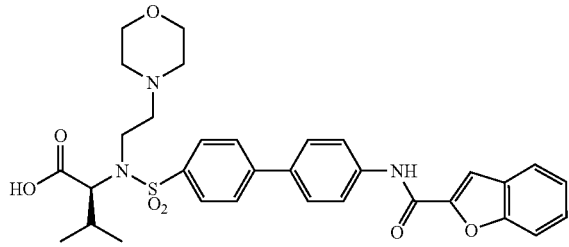

According to the general procedure of Example 77, starting with L-valine and alkylating with 4-(2-chloroethyl)morpholine hydrochloride in Step 2, N-({4'-[(1-benzofuran-2-ylcarbonyl)amino]-1,1'-biphenyl-4-yl}sulfonyl)-N-(2-morpholin-4-ylethyl)-L-valine was obtained. m.p. 181-185° C.; MS 606.3 (M+H)$^+$.

Example 83

N-[(4'-{[(3-Methyl-1-benzofuran-2-yl)carbonyl]amino}-1,1'-biphenyl-4-yl)sulfonyl]-L-valine

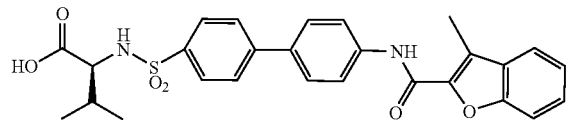

According to the general procedure of Example 2A, starting with L-valine methyl ester and acylating L-2-(4'-aminobiphenyl-4-sulfonylamino)-3-methyl-butyric acid methyl ester with 3-methylbenzofuran-2-carbonyl chloride in Step 5, N-[(4'-{[(3-methyl-1-benzofuran-2-yl)carbonyl]amino}-1,1'-biphenyl-4-yl)sulfonyl]-L-valine was obtained. m.p. 264-266° C.; MS 505.2 (M−H)$^-$.

Example 84

N-[(4'-{[(5-Bromo-1-benzofuran-2-yl)carbonyl]amino}-1,1'-biphenyl-4-yl)sulfonyl]-L-valine

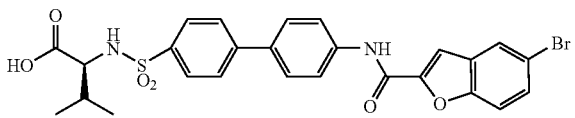

According to the general procedure of Example 2A, starting with L-valine methyl ester and acylating L-2-(4'-aminobiphenyl-4-sulfonylamino)-3-methyl-butyric acid methyl ester with 5-bromobenzofuran-2-carbonyl chloride in Step 5, N-[(4'-{[(5-bromo-1-benzofuran-2-yl)carbonyl]amino}-1,1'-biphenyl-4-yl)sulfonyl]-L-valine was obtained. m.p. 263-265° C.; MS 569.0 (M−H)$^-$.

Example 85

N-[(4'-{[(4-Methyl-3,4,5,6-tetrahydrofuro[4,3,2-ef][3]benzazepin-2-yl)carbonyl]amino}-1,1'-biphenyl-4-yl)sulfonyl]-L-valine

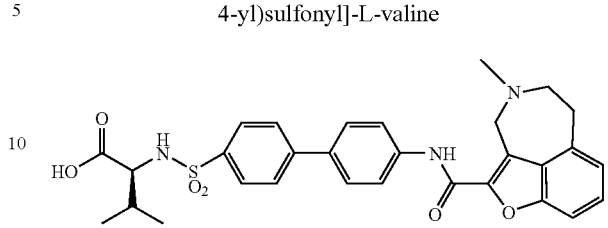

According to the general procedure of Example 2A, starting with L-valine methyl ester and acylating L-2-(4'-aminobiphenyl-4-sulfonylamino)-3-methyl-butyric acid methyl ester with 3,4,5,6-tetrahydro-4-methylfuro[4,3,2-ef][3]benzazepine-2-carbonyl chloride in Step 5, N-[(4'-{[(4-methyl-3,4,5,6-tetrahydrofuro[4,3,2-ef][3]benzazepin-2-yl)carbonyl]amino}-1,1'-biphenyl-4-yl)sulfonyl]-L-valine was obtained. m.p. >300° C.; MS 562.3 (M+H)$^+$.

Example 86

N-[(4'-{[(5-Ethyl-4-methoxy-3-methyl-1-benzofuran-2-yl)carbonyl]amino}-1,1'-biphenyl-4-yl)sulfonyl]-L-valine

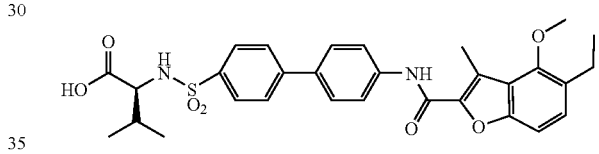

Step 1: To a solution of 2.0 g (11.1 mmol) of 2,6-dihydroxy-3-ethyl-acetophenone in 21 mL of acetone was added 2.45 g (17.8 mmol) of potassium carbonate and 1.35 mL (12.2 mmol) of ethyl bromoacetate. The resulting mixture was refluxed for 3.5 h and then cooled to room temperature and filtered. The filtrate was diluted with water, acidified with 1N HCl and extracted with ethyl acetate. The combined organics were washed with water and brine, dried over magnesium sulfate, filtered and concentrated in vacuo. The residue was chromatographed on silica gel eluting with ethyl acetate/hexanes (1:10) to provide 2.1 g of ethyl (2-acetyl-4-ethyl-3-hydroxyphenoxy)acetate.

Step 2: To a solution of 1.92 g (7.22 mmol) of ethyl (2-acetyl-4-ethyl-3-hydroxyphenoxy)acetate in 35 mL of absolute ethanol was added 0.54 g (7.94 mmol) of sodium ethoxide. The reaction was heated at reflux for 3 h and then cooled to room temperature, acidified with 1N HCl, and concentrated in vacuo. The residue was diluted with water and extracted with ethyl acetate. The organics were washed with water and brine, dried over magnesium sulfate, filtered and concentrated in vacuo. The residue was chromatographed on silica gel eluting with ethyl acetate/heaxnes (1:9) to provide 0.9 g of ethyl 3-methyl-4-hydroxy-5-ethylbenzofuran-2-carboxylate.

Step 3: To a solution of 0.25 g (1.01 mmol) of ethyl 3-methyl-4-hydroxy-5-ethylbenzofuran-2-carboxylate in 3.0 mL of DMF was added 0.417 g (3 eq) of potassium carbonate and 0.63 mL (10 eq) of iodomethane and the reaction was stirred at room temperature for 14 h. The reaction was then diluted with ether and water. The organic layer was washed with water, dried over magnesium sulfate, filtered and concentrated in vacuo. The residue was chromatographed on silica gel eluting with ethyl acetate/hexanes (1:10) to provide 0.24 g of ethyl 3-methyl -4-methoxy-5-ethylbenzofuran-2-carboxylate.

Step 4: To a solution of 0.22 g (0.82 mmol) of ethyl 2-methyl-,3-methoxy-4-ethylbenzofuran-2-carboxylate in 4.1 mL of methanol and 4.1 mL of THF was added 4.1 mL of 1N sodium hydroxide solution. The reaction was stirred for 12 h at room temperature and then acidified with 1N HCl and extracted with ethyl acetate. The combined organic layers were washed with water and brine, dried over magnesium sulfate, filtered and concentrated in vacuo to provide 0.201 g of 3-methyl-4-methoxy-5-ethylbenzofuran-2-carboxylic acid.

Step 5: To 0.094 g of 3-methyl-4-methoxy-5-ethylbenzofuran-2-carboxylic acid, 0.27 g of benzotriazole-1-yloxytri(pyrrolidinophosphonium)hexafluorophosphate and 0.145 g of L-2-(4'-amino-biphenyl-4-sulfonylamino)-3-methyl-butyric acid methyl ester (Example 2A, Step 4), in 1.5 mL DMF, cooled in an ice bath, was added N,N-diisopropylethylamine and the resulting mixture was stirred at 0° C. for 5 minutes. The reaction was allowed to warm to room temperature and stirred overnight. The reaction mixture was concentrated in vacuo, and the residue was extracted with dichloromethane and water. The organic layer was washed with water and brine, dried over Na$_2$SO$_4$, filtered, concentrated in vacuo, and purified by column chromatography eluting with hexane: ethyl acetate (3:2) to provide 0.17 g of methyl N-[(4'-{[(5-ethyl-4-methoxy-3-methyl-1-benzofuran-2-yl)carbonyl]amino}-1,1'-biphenyl-4-yl)sulfonyl]-L-valinate. Yield 73.9%. m.p. 170-172° C.; MS: 579.3 (M+H)$^+$.

Step 6: According to the procedure of Example 2A, Step 6, 0.16 g of methyl N-[(4'-{[(5-ethyl-4-methoxy-3-methyl-1-benzofuran-2-yl)carbonyl]amino}-1,1'-biphenyl-4-yl)sulfonyl]-L-valinate provided 0.11 g of N-[(4'-{[(5-ethyl-4-methoxy-3-methyl-1-benzofuran-2-yl)carbonyl]amino}-1,1'-biphenyl-4-yl)sulfonyl]-L-valine. Yield 70.5%. m.p. 225-228° C.; MS 565.3 (M+H)$^+$.

Example 87

N-[(4'-{[(4-Ethyl-3-methyl-1-benzofuran-2-yl)carbonyl]amino}-1,1'-biphenyl-4-yl)sulfonyl]-L-valine

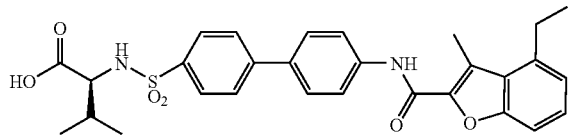

Step 1: To a solution of 2.48 g (7.05 mmol) of 3-methyl-4-trifluoromethanesulfonyloxy-benzofuran-2-carboxylic acid ethyl ester (Example 20, Step 2) in 30 mL of DMF was added 2.16 mL (7.40 mmol) of vinyl tributyltin, 0.898 g (21.1 mmol) of lithium chloride and 0.247 g (0.352 mmol) of tetrakis(triphenylphosphine)palladium(0). The reaction was heated to 90° C. for 3 h and then cooled to room temperature. The reaction was diluted with water and extracted with ether. The combined organics were washed with water and brine, dried over magnesium sulfate, filtered and concentrated in vacuo. The residue was chromatographed on silica gel eluting with ethyl acetate/hexanes (1:25) to provide 1.22 g of 3-methyl-4-vinylbenzofuran-2-carboxylic acid ethyl ester.

Step 2: To a solution of 0.40 g (1.74 mmol) of 3-methyl-4-vinylbenzofuran-2-carboxylic acid ethyl ester in 25 mL of ethyl acetate under nitrogen was added 0.050 g of 10% palladium on carbon. The reaction was shaken on a Parr hydrogenator under 40 psi of hydrogen for 4 h. The reaction was then filtered through a pad of celite. The celite was washed with an additional 150 mL of ethyl acetate and the filtrate was concentrated in vacuo. The residue was chromatographed on silica gel eluting with ethyl acetate/hexanes (1:30) to provide 0.395 of 3-methyl-4-ethylbenzofuran-2-carboxylic acid ethyl ester.

Step 3: To a solution of 0.380 g (1.64 mmol) of 3-methyl-4-ethylbenzofuran-2-carboxylicacid ethyl ester in 8 mL of methanol and 8 mL of THF was added 8.2 mL of 1N sodium hydroxide solution and the reaction was stirred for 14 h at room temperature and then acidified with 1N HCl and extracted with ethyl acetate. The combined organic layers were washed with water and brine, dried over magnesium sulfate, filtered and concentrated in vacuo to provide 0.321 g of 3-methyl-4-ethylbenzofuran-2-carboxylic acid.

Step 4: According to the procedure of Example 86, Step 5, 0.082 g of 3-methyl-4-ethylbenzofuran-2-carboxylic acid and 0.15 g of L-2-(4'-amino-biphenyl-4-sulfonylamino)-3-methyl-butyric acid methyl ester provided 0.19 g of methyl N-[(4'-{[(4-ethyl-3-methyl-1-benzofuran-2-yl)carbonyl]amino}-1,1'-biphenyl-4-yl)sulfonyl]-L-valinate. Yield 86.3%. m.p. 183-185° C.; MS: 549.2 (M+H)$^+$.

Step 5: According to the procedure of Example 2A, Step 6, 0.16 g of methyl N-[(4'-{[(4-ethyl-3-methyl-1-benzofuran-2-yl)carbonyl]amino}-1,1'-biphenyl-4-yl)sulfonyl]-L-valinate provided 0.075 g of N-[(4'-{[(4-ethyl-3-methyl-1-benzofuran-2-yl)carbonyl]amino}-1,1'-biphenyl-4-yl)sulfonyl]-L-valine. Yield 48.1%. m.p. 239-241° C.; MS 535.3 (M+H)$^+$.

Example 88

N-[(4'-{[(5-Ethyl-4-isopropoxy-3-methyl-1-benzofuran-2-yl)carbonyl]amino}-1,1'-biphenyl-4-yl)sulfonyl]-L-valine

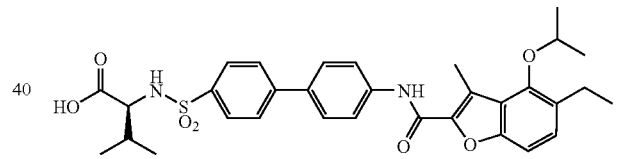

Step 1: According to the procedure of Example 86, Step 3 0.200 g (0.81 mmol) of 3-methyl-4-hydroxy-5-ethylbenzofuran carboxylic acid ethyl ester (Example 86, Step 2) and 0.379 mL (4.03 mmol) of 2-bromopropane gave 0.211 g of 5-ethyl-4-isopropoxy-3-methylbenzofuran-2-carboxylic acid ethyl ester after chromatography on silica gel eluting with ethyl acetate/hexanes (1:20).

Step 2: According to the procedure of Example 86, Step 4, 0.170 g (0.586 mmol) of 5-ethyl-4-isopropoxy-3-methyl-1-benzofuran-2-carboxylic acid ethyl ester provided 0.142 g of 5-ethyl-4-isopropoxy-3-methylbenzofuran-2-carboxylic acid, purified by washing with hexanes.

Step 3: According to the procedure of Example 86, Step 5, 0.052 g (0.2 mmol) of 5-ethyl-4-isopropoxy-3-methylbenzofuran-2-carboxylic acid and 0.073 g of L-2-(4'-amino-biphenyl-4-sulfonylamino)-3-methyl-butyric acid methyl ester provided 0.11 g of methyl N-[(4'-{[(5-ethyl-4-isopropoxy-3-methyl-1-benzofuran-2-yl)carbonyl]amino}-1,1'-biphenyl-4-yl)sulfonyl]-L-valinate. Yield 89.3%. m.p. 182-184° C.; MS: 607.3 (M+H)$^+$.

Step 4: According to the procedure of Example 2A, Step 6, 0.055 g of methyl N-[(4'-{[(5-ethyl-4-isopropoxy-3-methyl-1-benzofuran-2-yl)carbonyl]amino}-1,1'-biphenyl-4-yl)sulfonyl]-L-valinate provided 0.053 g of N-[(4'-{[(5-ethyl-4-isopropoxy-3-methyl-1-benzofuran-2-yl)carbonyl]amino}-1,1'-biphenyl-4-yl)sulfonyl]-L-valine. Yield ~100%. m.p. 159-162° C.; MS 591.3 (M–H)⁻.

Example 89

N-{[4'-({[4-(Benzyloxy)-5-ethyl-3-methyl-1-benzofuran-2-yl]carbonyl}amino)-1,1'-biphenyl-4-yl]sulfonyl}-L-valine

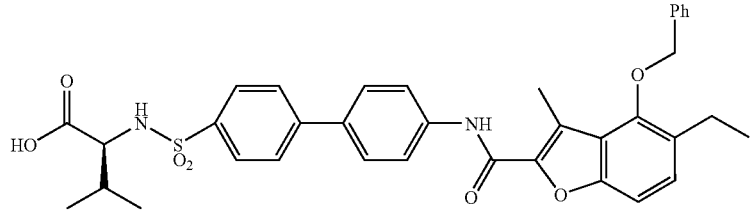

Step 1: According to the procedure of Example 86, Step 3, 0.250 g (1.01 mmol) of 3-methyl-4-hydroxy-5-ethylbenzofuran carboxylic acid ethyl ester (Example 86, Step 2) and 0.599 mL (5.04 mmol) of benzyl bromide gave 0.341 g of 5-ethyl-4-benzyloxy-3-methylbenzofuran-2-carboxylic acid ethyl ester after chromatography on silica gel eluting with ethyl acetate/hexanes (1:20).

Step 2: According to the procedure of Example 86, Step 4, 0.307 g (0.908 mmol) of 5-ethyl-4-benzyloxy-3-methyl-1-benzofuran-2-carboxylic acid ethyl ester provided 0.219 g of 5-ethyl-4-benzyloxy-3-methylbenzofuran-2-carboxylic acid, purified by washing with hexanes.

Step 3: According to the procedure of Example 86, Step 5, 0.155 g (0.5 mmol) of 5-ethyl-4-benzyloxy-3-methylbenzofuran-2-carboxylic acid and 0.18 g of L-2-(4'-amino-biphenyl-4-sulfonylamino)-3-methyl-butyric acid methyl ester provided 0.21 g of methyl N-{[4'-({[4-(benzyloxy)-5-ethyl-3-methyl-1-benzofuran-2-yl]carbonyl}amino)-1,1'-biphenyl-4-yl]sulfonyl}-L-valinate. Yield 63.6%. m.p. 191-193° C.; MS: 655.2 (M+H)⁺.

Step 4: According to the procedure of Example 2A, Step 6, 0.06 g of methyl N-{[4'-({[4-(benzyloxy)-5-ethyl-3-methyl-1-benzofuran-2-yl]carbonyl}amino)-1,1'-biphenyl-4-yl]sulfonyl}-L-valinate provided 0.054 g of N-{[4'-({[4-(benzyloxy)-5-ethyl-3-methyl-1-benzofuran-2-yl]carbonyl}amino)-1,1'-biphenyl-4-yl]sulfonyl}-L-valine. Yield 86%. m.p. 224-226° C.; MS 639.2 (M–H)⁻.

Example 90

N-[(4'-{[(5-Ethyl-4-hydroxy-3-methyl-1-benzofuran-2-yl)carbonyl]amino}-1,1'-biphenyl-4-yl)sulfonyl]-L-valine

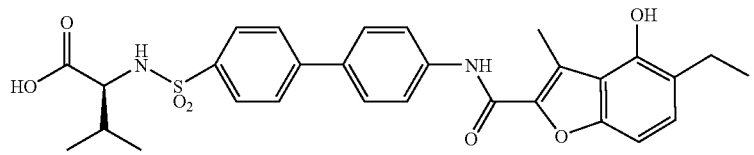

Step 1: To 0.1 g (0.15 mmol) of methyl N-{[4'-({[4-(benzyloxy)-5-ethyl-3-methyl-1-benzofuran-2-yl]carbonyl}amino)-1,1'-biphenyl-4-yl]sulfonyl}-L-valinate from Example 89, dissolved in 20 mL of methanol and 10 mL of THF was added 0.2 g of 10% palladium on active carbon and the mixture was hydrogenated in a Parr hydrogenator at 40 psi for 4 hours. The reaction mixture was then filtered through celite and the celite pad was washed with with methanol. The filtrate was concentrated in vacuo to provide 0.11 g of methyl N-[(4'-{[(5-ethyl-4-hydroxy-3-methyl-1-benzofuran-2-yl)carbonyl]amino}-1,1'-biphenyl-4-yl)sulfonyl]-L-valinate. Yield ~100%, m.p. 75-80° C. MS: 565.2 (M+H)⁺.

Step 2: According to the procedure of Example 2A, Step 6, 0.098 g of methyl N-[(4'-{[(5-ethyl-4-hydroxy-3-methyl-1-benzofuran-2-yl)carbonyl]amino}-1,1'-biphenyl-4-yl)sulfonyl]-L-valinate provided 0.054 g of N-[(4'-{[(5-ethyl-4-hydroxy-3-methyl-1-benzofuran-2-yl)carbonyl]amino}-1,1'-biphenyl-4-yl)sulfonyl]-L-valine. Yield 56.8%. m.p. 122-125° C.; MS 549.2 (M–H)⁻.

Example 91

N-{[4'-({[4-(2,2-Dimethyl-1,3-dioxolan-4-yl)-3-methyl-1-benzofuran-2-yl]carbonyl}amino)-1,1'-biphenyl-4-yl]sulfonyl}-L-valine

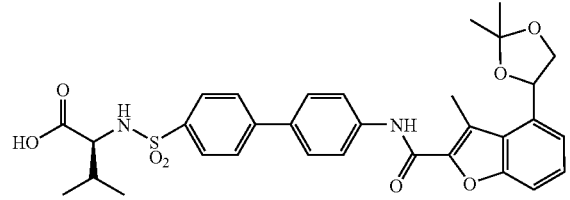

Step 1: To a solution of 0.146 g (1.25 mmol) of N-methylmorpholine N-oxide in 1 mL of THF and 3 mL of water was added 0.272 mL of osmium tetroxide (2.5 weight % in t-butanol, 0.022 mmol) followed by 0.250 g (0.087 mmol) of 3-methyl-4-vinylbenzofuran-2-carboxylic acid ethyl ester (Example 87, Step 1) dissolved in 1 mL of THF. The reaction was stirred for 2 h at room temperature and then quenched with excess aqueous sodium hydrosulfite solution. The resulting mixture was extracted with ethyl acetate, and the combined organics were washed with water and brine, dried over magnesium sulfate, filtered and concentrated in vacuo. The residue was chromatographed on silica gel eluting with ethyl acetate/hexanes (1:1) to provide 0.202 g of 4-(1,2-dihydroxyethyl)-3-methylbenzofuran-2-carboxylic acid ethyl ester.

Step 2: To a solution of 0.150 g (0.568 mmol) of 4-(1,2-dihydroxyethyl)-3-methylbenzofuran-2-carboxylic acid ethyl ester dissolved in 5 mL of acetone was added 0.010 g of p-toluenesulfonic acid and the reaction was stirred at room temperature overnight. Saturated sodium bicarbonate was added and the acetone was removed in vacuo. The residue was extracted with ether, the organics were dried over sodium sulfate, filtered and concentrated in vacuo. The residue was chromatographed on silica gel eluting with ethyl acetate/hexanes (1:5) to provide 0.172 g of 4-(2,2-dimethyl-1,3-dioxolan-4-yl)-3-methylbenzofuran-2-carboxylic acid ethyl ester.

Step 3: According to the procedure of Example 86, Step 4, 0.172 g (0.566 mmol) of 4-(2,2-dimethyl-1,3-dioxolan-4-yl)-3-methylbenzofuran-2-carboxylic acid ethyl ester provided 0.147 g of 4-(2,2-dimethyl-1,3-dioxolan-4-yl)-3-methylbenzofuran-2-carboxylic acid as a white solid after purification by washing with ether/hexanes (1:1).

Step 4: According to the procedure of Example 86, Step 5, 0.116 g (0.41 mmol) of 4-(2,2-dimethyl-1,3-dioxolan-4-yl)-3-methylbenzofuran-2-carboxylic acid and 0.18 g of L-2-(4'-amino-biphenyl-4-sulfonylamino)-3-methyl-butyric acid methyl ester provided 0.18 g of methyl N-{[4'-({[4-(2,2-dimethyl-1,3-dioxolan-4-yl)-3-methyl-1-benzofuran-2-yl]carbonyl}amino)-1,1'-biphenyl-4-yl]sulfonyl}-L-valinate. Yield 89.4%. m.p. 192-194° C.; MS: 619.3 (M–H)⁻.

Step 5: According to the procedure of Example 2A, Step 6, 0.157 g of methyl N-{[4'-({[4-(2,2-dimethyl-1,3-dioxolan-4-yl)-3-methyl-1-benzofuran-2-yl]carbonyl}amino)-1,1'-biphenyl-4-yl]sulfonyl}-L-valinate provided 0.084 g of N-{[4'-({[4-(2,2-dimethyl-1,3-dioxolan-4-yl)-3-methyl-1-benzofuran-2-yl]carbonyl}amino)-1,1'-biphenyl-4-yl]sulfonyl}-L-valine. Yield 54.9%. m.p. 240° C.(d). MS 605.2 (M–H)⁻.

Example 92

N-{[4'-({[4-(Hydroxymethyl)-3-methyl-1-benzofuran-2-yl]carbonyl}amino)-1,1'-biphenyl-4-yl]sulfonyl}-L-valine

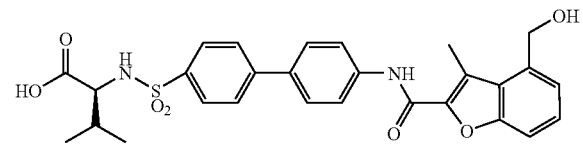

Step 1: To a solution of 0.250 g (1.087 mmol) of 3-methyl-4-vinylbenzofuran-2-carboxylic acid ethyl ester (Example 87, Step 1) in 7.5 mL of dioxane and 2.5 mL of water was added 0.272 mL of 2.5 weight % osmium tetroxide in t-butanol (0.022 mmol) and the reaction was stirred for 10 minutes at room temperature, turning yellow-brown in color. Sodium periodate (0.488 g, 2.282 mmol) was then added in several portions over 30 minutes and a white precipitate formed. The reaction was stirred at room temperature for 2 h and then diluted with water and extracted with ethyl acetate. The combined organics were washed with water and brine, dried over magnesium sulfate, filtered and concentrated in vacuo. The residue was chromatographed on silica gel eluting with ethyl acetate/hexanes (1:10) to provide 0.225 g of 4-carbonyl-3-methylbenzofuran-2-carboxylic acid ethyl ester.

Step 2: To a solution of 0.123 g (0.530 mmol) of 4-carbonyl-3-methylbenzofuran-2-carboxylic acid ethyl ester in 10 mL of ethanol was added 0.019 g (0.505 mmol) of sodium borohydride. The reaction was stirred at room temperature for 2 h and than diluted wuth water and extracted with ethyl acetate. The combined organics were washed with water and brine, dried over magnesium sulfate, filtered and concentrated in vacuo. The residue was chromatographed on silica gel eluting with ethyl acetate/hexanes (1:3) to provide 0.113 g of 4-hydroxymethyl-3-methylbenzofuran-2-carboxylic acid ethyl ester.

Step 3: To a solution of 0.220 g (0.940 mmol) of 4-hydroxymethyl-3-methylbenzofuran-2-carboxylic acid ethyl ester in 5 mL of DMF was added 0.156 g (1.034 mmol) of t-butyldimethylsilyl chloride and 0.160 g (2.350 mmol) of imidazole and the reaction was stirred at room temperature for 14 h. The reaction mixture was diluted with water and extracted with ether. The combined organics were washed with water and brine, dried over magnesium sulfate, filtered and concentrated in vacuo. The residue was chromatographed on silica gel eluting with ethyl acetate/hexanes (1:10) to provide 0.315 g of 4-tert-butyl(dimethyl)silyloxymethyl-3-methylbenzofuran-2-carboxylic acid ethyl ester.

Step 4: According to the procedure of Example 86, Step 4, 0.277 g (0.796 mmol) of 4-tert-butyl(dimethyl)silyloxymethyl-3-methylbenzofuran-2-carboxylic acid ethyl ester provided 0.054 g of 4-tert-butyl(dimethyl)silyloxymethyl-3-methylbenzofuran-2-carboxylic acid after chromatography on silica gel eluting with ethyl acetate/hexanes (1:3).

Step 5: According to the procedure of Example 86, Step 5, 0.115 g of 4-({[tert-butyl(dimethyl)silyl]oxy}methyl)-3-methyl-1-benzofuran-2-carboxylic acid and 0.13 g of L-2-(4'-amino-biphenyl-4-sulfonylamino)-3-methyl-butyric acid methyl ester provided 0.20 g of methyl N-{[4'-({[4-({[tert-butyl(dimethyl)silyl]oxy}methyl)-3-methyl-1-benzofuran-2-yl]carbonyl}amino)-1,1'-biphenyl-4-yl]sulfonyl}-L-valinate. Yield 84.5%. m.p. 204-206° C.; MS: 663.4 (M–H)⁻.

Step 6: According to the procedure of Example 2A, Step 6, 0.18 g of methyl N-{[4'-({[4-({[tert-butyl(dimethyl)silyl]oxy}methyl)-3-methyl-1-benzofuran-2-yl]carbonyl}amino)-1,1'-biphenyl-4-yl]sulfonyl}-L-valinate provided 0.13 g of N-{[4'-({[4-(hydroxymethyl)-3-methyl-1-benzofuran-2-yl]carbonyl}amino)-1,1'-biphenyl-4-yl]sulfonyl}-L-valine. Yield 73.3%. m.p. 272° C.(d). MS 535.12 (M–H)⁻.

Example 93

N-[(4'-{[(3,4-Dimethyl-1-benzofuran-2-yl)carbonyl]amino}-1,1'-biphenyl-4-yl)sulfonyl]-L-valine

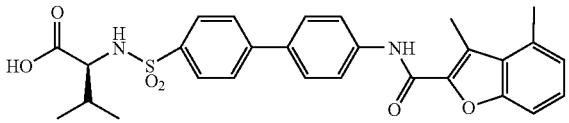

Step 1: To a solution of 0.200 g (0.855 mmol) 4-hydroxymethyl-3-methylbenzofuran-2-carboxylic acid ethyl ester (Example 92, Step 2) in 5 mL of THF was added 0.336 g (1.28 mmol) of triphenylphosphine and 0.355 g (1.07 mmol) of carbon tetrabromide. The reaction was stirred at room temperature for 1 h and then concentrated in vacuo. The residue was diluted ith 20 mL of ether and filtered. The filtrate was concentrated in vacuo and chromatographed on silica gel eluting with ethyl acetate/hexanes (1:10) to provide 0.196 g of 4-bromomethyl-3-methylbenzofuran-2-carboxylic acid ethyl ester.

Step 2: To a solution of 0.291 g (0.98 mmol) of 4-bromomethyl-3-methylbenzofuran-2-carboxylic acid ethyl ester in 5 mL of DMSO was added 0.074 g (1.96 mmol) of sodium borohydride and the reaction was stirred at room temperature for 2 h. The reaction was diluted with water and extracted with ether. The organics were washed with water and brine, filtered and concentrated in vacuo. The residue was chromatographed on silica gel eluting with ethyl acetate/hexanes (1:10) to provide 0.209 g of 4-methyl-3-methylbenzofuran-2-carboxylic acid ethyl ester.

Step 3: According to the procedure of Example 86, Step 4, 0.206 g (0.95 mmol) of 4-methyl-3-methylbenzofuran-2-carboxylic acid ethyl ester provided 0.175 g of 4-methyl-3-methylbenzofuran-2-carboxylic acid.

Step 4: According to the procedure of Example 86, Step 5, 0.067 g of 4-methyl-3-methylbenzofuran-2-carboxylic acid and 0.13 g of L-2-(4'-amino-biphenyl-4-sulfonylamino)-3-methyl-butyric acid methyl ester provided 0.14 g of methyl N-[(4'-{[(3,4-dimethyl-1-benzofuran-2-yl)carbonyl]amino}-1,1'-biphenyl-4-yl)sulfonyl]-L-valinate. Yield 53.8%. m.p. 199-200° C.; MS: 535.1 (M+H)$^+$.

Step 5: According to the procedure of Example 2A, Step 6, 0.12 g of methyl N-[(4'-{[(3,4-dimethyl-1-benzofuran-2-yl)carbonyl]amino}-1,1'-biphenyl-4-yl)sulfonyl]-L-valinate provided 0.12 g of N-[(4'-{[(3,4-dimethyl-1-benzofuran-2-yl)carbonyl]amino}-1,1'-biphenyl-4-yl)sulfonyl]-L-valine. Yield ~100%. m.p. 250-252° C.; MS 519.2 (M−H)$^−$.

Example 94

N-[(4'-{[(4-Acetyl-3-methyl-1-benzofuran-2-yl)carbonyl]amino}-1,1'-biphenyl-4-yl)sulfonyl]-L-valine

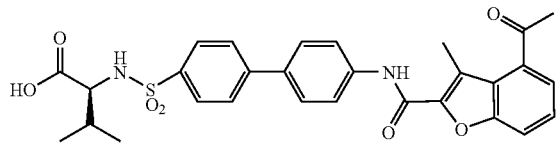

Step 1: To a solution of 2.061 g (5.86 mmol) of 3-methyl-4-trifluoromethanesulfonyloxy-benzofuran-2-carboxylic acid ethyl ester (Example 20, Step 2) in 26 mL of DMF was added 3.0 mL of butyl vinyl ether, 1.6 mL of triethylamine, 0.077 g of palladium acetate, and 0.139 g of 1,3-bis(diphenylphosphino)propane. The resulting mixture was heated to 60° C. for 24 h and then cooled tor room temperature. The mixture was diluted with water and extracted with ether. The organics were washed with water and brine, filtered and concentrated in vacuo. The residue was filtered through a pad of silica gel eluting with ethyl acetate/hexanes (1:10) to provide a mixture of 4-acetyl-3-methylbenzofuran-2-carboxylic acid ethyl ester and ethyl 4-(1-butoxyvinyl)-3-methyl-1-benzofuran-2-carboxylate. The mixture was dissolved in 12.9 mL of acetic acid and 8.6 mL of 3N HCl and stirred at room temperature for 1 h. The reaction was diluted with water and extracted with ether. The organics were washed with water and brine, filtered and concentrated in vacuo. The residue was filtered through a pad of silica gel eluting with ethyl acetate/hexanes (1:20) to provide 1.16 g of 4-acetyl-3-methylbenzofuran-2-carboxylic acid ethyl ester.

Step 2: According to the procedure of Example 86, Step 4, 0.200 g of 4-acetyl-3-methylbenzofuran-2-carboxylic acid ethyl ester provided 0.165 g of 4-acetyl-3-methylbenzofuran-2-carboxylic acid.

Step 3: According to the procedure of Example 86, Step 5, 0.165 g of 4-acetyl-3-methyl-1-benzofuran-2-carboxylic acid and 0.27 g of L-2-(4'-amino-biphenyl-4-sulfonylamino)-3-methyl-butyric acid methyl ester provided 0.20 g of methyl N-[(4'-{[(4-acetyl-3-methyl-1-benzofuran-2-yl)carbonyl]amino}-1,1'-biphenyl-4-yl)sulfonyl]-L-valinate. Yield 47.6%. m.p. 197-199° C. MS: 535.1 (M+H)$^+$.

Step 4: According to the procedure of Example 2A, Step 6, 0.23 g of methyl N-[(4'-{[(4-acetyl-3-methyl-1-benzofuran-2-yl)carbonyl]amino}-1,1'-biphenyl-4-yl)sulfonyl]-L-valinate provided 0.11 g of N-[(4'-{[(4-acetyl-3-methyl-1-benzofuran-2-yl)carbonyl]amino}-1,1'-biphenyl-4-yl)sulfonyl]-L-valine. Yield 50.1%. m.p. 228-235° C.; MS: 547.2 (M−H)$^−$.

Example 95

N-{[4'-({[4-(1-Hydroxyethyl)-3-methyl-1-benzofuran-2-yl]carbonyl}amino)-1,1'-biphenyl-4-yl]sulfonyl}-L-valine

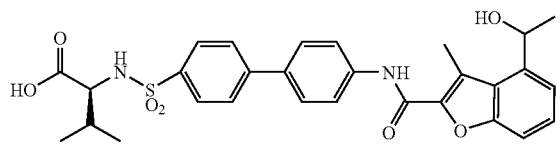

To a solution of 0.05 g of N-[(4'-{[(4-acetyl-3-methyl-1-benzofuran-2-yl)carbonyl]amino}-1,1'-biphenyl-4-yl)sulfonyl]-L-valine, the product of Example 94, Step 3, in 18 mL of ethanol was added 0.01 g of sodium borohydride and the reaction was stirred at room temperature for 2 hours. The reaction was quenched with 1N HCl, adjusting to ~pH3. The reaction mixture was concentrated in vacuo and the residue was then extracted with ethyl acetate. The organic layer was washed with water, brine, dried over Na$_2$SO$_4$, filtered, and concentrated to provide 0.037 g of N-{[4'-({[4-(1-hydroxyethyl)-3-methyl-1-benzofuran-2-yl]carbonyl}amino)-1,1'-biphenyl-4-yl]sulfonyl}-L-valine. Yield 74%. m.p. 148° C.(d); MS: 549.1(M−H)$^−$.

Example 96

N-[(4'-{[(3-methyl-4-vinyl-1-benzofuran-2-yl)carbonyl]amino}-1,1'-biphenyl-4-yl)sulfonyl]-L-valine

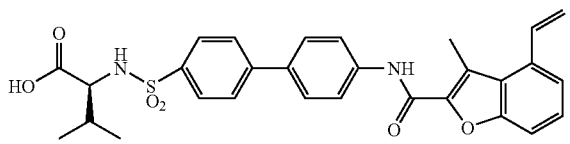

Step 1: According to the procedure of Example 86, Step 4, 0.300 g (1.304 mmol) of 3-methyl-4-vinyl-benzofuran-2-carboxylic acid ethyl ester (Example 87, Step 1) provided 0.256 g of 3-methyl-4-vinyl-benzofuran-2-carboxylic acid after chromatography on silica gel eluting with ethyl acetate/hexanes (1:3).

Step 2: According to the procedure of Example 86, Step 5, 0.081 g of 3-methyl-4-vinyl-benzofuran-2-carboxylic acid and 0.15 g of L-2-(4'-amino-biphenyl-4-sulfonylamino)-3-methyl-butyric acid methyl ester provided 0.18 g of methyl N-[(4'-{[(3-methyl-4-vinyl-1-benzofuran-2-yl)carbonyl]amino}-1,1'-biphenyl-4-yl)sulfonyl]-L-valinate. Yield 82%. m.p. 185° C. (d); MS: 547.3 (M+H)⁺.

Step 3: According to the procedure of Example 2A, Step 6, 0.16 g of methyl N-[(4'-{[(3-methyl-4-vinyl-1-benzofuran-2-yl)carbonyl]amino}-1,1'-biphenyl-4-yl)sulfonyl]-L-valinate provided 0.065 g of N-[(4'-{[(3-methyl-4-vinyl-1-benzofuran-2-yl)carbonyl]amino}-1,1'-biphenyl-4-yl)sulfonyl]-L-valine. Yield 42%. m.p. 285° C. (d); MS 531.2 (M−H)⁻.

Example 97

N-{[4'-({[4-(1,2-dihydroxyethyl)-3-methyl-1-benzofuran-2-yl]carbonyl}amino)-1,1'-biphenyl-4-yl]sulfonyl}-L-valine

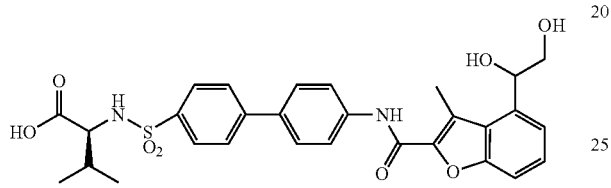

Step 1: To a solution of N-methyl morpholine-N-oxide (50% wt solution in water, 0.103 g, 0.44 mmol) in THF and water (1 mL/0.3 mL) was added 0.096 mL (0.38 mmol) of osmium tetroxide (2.5 wt % in t-butanol). To that solution was quickly added 0.21 g (0.38 mmol) of methyl N-[(4'-{[(3-methyl-4-vinyl-1-benzofuran-2-yl)carbonyl]amino}-1,1'-biphenyl-4-yl)sulfonyl]-L-valinate (Example 96, Step 2). The reaction was stirred at room temperature for 2 hours and then quenched with excess sodium hydrosulfite in water. The reaction mixture was extracted with ethyl acetate and water. The organic layer was washed with water and brine, dried over Na₂SO₄, filtered, and concentrated to provide 0.19 g of methyl N-{[4'-({[4-(1,2-dihydroxyethyl)-3-methyl-1-benzofuran-2-yl]carbonyl}amino)-1,1'-biphenyl-4-yl]sulfonyl}-L-valinate. Yield 85.2%. m.p. 90-95° C. MS: 581.2 (M+H)⁺.

Step 2: According to the procedure of Example 2A, Step 6, 0.18 g of methyl N-{[4'-({[4-(1,2-dihydroxyethyl)-3-methyl-1-benzofuran-2-yl]carbonyl}amino)-1,1'-biphenyl-4-yl]sulfonyl}-L-valinate provided 0.11 g of N-{[4'-({[4-(1,2-dihydroxyethyl)-3-methyl-1-benzofuran-2-yl]carbonyl}amino)-1,1'-biphenyl-4-yl]sulfonyl}-L-valine. Yield 61.9%. m.p. 165° C. (d). MS 565.3 (M−H)⁻.

Example 98

N-methyl-N-[(4'-{[(3-methyl-4-vinyl-1-benzofuran-2-yl)carbonyl]amino}-1,1'-biphenyl-4-yl)sulfonyl]-L-valine

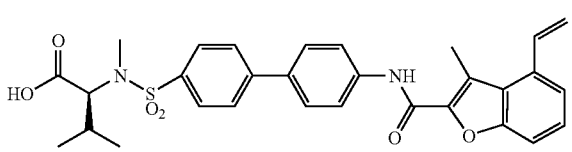

Step 1: To a solution of 0.077 g (0.14 mmol) of the product of Example 96, Step 2, methyl N-[(4'-{[(3-methyl-4-vinyl-1-benzofuran-2-yl)carbonyl]amino}-1,1'-biphenyl-4-yl)sulfonyl]-L-valinate, in 1 mL of DMF, 0.05 g of potassium carbonate were added, followed by 0.018 mL of iodomethane. The reaction was stirred at room temperature overnight. The reaction mixture was concentrated in vacuo and the residue was extracted with dichloromethane. The organic layer was washed with water and brine, dried over Na₂SO₄, filtered, and concentrated to provide 0.1 g of methyl N-methyl-N-[(4'-{[(3-methyl-4-vinyl-1-benzofuran-2-yl)carbonyl]amino}-1,1'-biphenyl-4-yl)sulfonyl]-L-valinate. Yield 63.4%. MS: 561 (M+H)⁺.

Step 2: According to the procedure of Example 2A, Step 6, 0.05 g of methyl N-methyl-N-[(4'-{[(3-methyl-4-vinyl-1-benzofuran-2-yl)carbonyl]amino}-1,1'-biphenyl-4-yl)sulfonyl]-L-valinate provided 0.033 g of N-methyl-N-[(4'-{[(3-methyl-4-vinyl-1-benzofuran-2-yl)carbonyl]amino}-1,1'-biphenyl-4-yl)sulfonyl]-L-valine. MS: 547.2 (M+H)⁺.

Example 99

N-{[4'-({[4-(1,2-dihydroxyethyl)-3-methyl-1-benzofuran-2-yl]carbonyl}amino)-1,1'-biphenyl-4-yl]sulfonyl}-N-methyl-L-valine

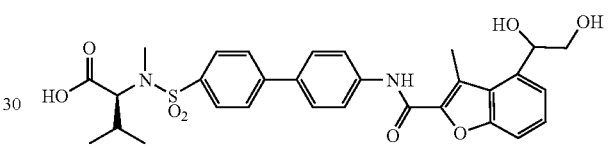

Step 1: According to the procedure of Example 97, Step 1, 0.14 g (025 mmol) of methyl N-methyl-N-[(4'-{[(3-methyl-4-vinyl-1-benzofuran-2-yl)carbonyl]amino}-1,1'-biphenyl-4-yl)sulfonyl]-L-valinate was oxidized to provide 0.09 g of methyl N-{[4'-({[4-(1,2-dihydroxyethyl)-3-methyl-1-benzofuran-2-yl]carbonyl}amino)-1,1'-biphenyl-4-yl]sulfonyl}-N-methyl-L-valinate. Yield 60.8%. m.p. 182-185° C.; MS: 595.3 (M+H)⁺.

Step 2: According to the procedure of Example 2A, Step 6, 0.07 g of methyl N-{[4'-({[4-(1,2-dihydroxyethyl)-3-methyl-1-benzofuran-2-yl]carbonyl}amino)-1,1'-biphenyl-4-yl]sulfonyl}-N-methyl-L-valinate provided 0.049 g of N-{[4'-({[4-(1,2-dihydroxyethyl)-3-methyl-1-benzofuran-2-yl]carbonyl}amino)-1,1'-biphenyl-4-yl]sulfonyl}-N-methyl-L-valine. Yield 71.9%. m.p. 222-225° C.; MS: 579.1 (M−H)⁻.

Example 100

N-{[4'-({[4-(methoxymethyl)-3-methyl-1-benzofuran-2-yl]carbonyl}amino)-1,1'-biphenyl-4-yl]sulfonyl}-L-valine

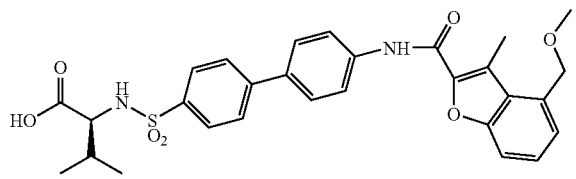

Step 1: To a solution of 0.19 g (0.81 mmole) of ethyl 4-(hydroxymethyl)-3-methyl-1-benzofuran-2-carboxylate (Example 92, Step 2) in 2 mL of chloroform was added silver (II) oxide (0.34 g, 1.46 mmol, 1.8 eq) and 2 mL of iodomethane and the mixture was heated in sealed tube at ~55° C. for 4.5 days. The reaction was filtered and concentrated in vacuo to provide 0.20 g of ethyl 4-(methoxymethyl)-3-methyl-1-benzofuran-2-carboxylate. Yield: ~93.8% m.p. 45-47° C.; MS: 249.1(M+H)+.

Step 2: According to the procedure of Example 86, Step 4, 0.21 g (0.85 mmole) of ethyl 4-(methoxymethyl)-3-methyl-1-benzofuran-2-carboxylate provides 0.18 g of 4-(methoxymethyl)-3-methyl-1-benzofuran-2-carboxylic acid. Yield: 100% m.p. 164-166° C.; MS: 219.0 (M−H)−.

Step 3: According to the procedure of (Example 86, Step 5) 0.066 g (0.3 mmole) of 4-(methoxymethyl)-3-methyl-1-benzofuran-2-carboxylic acid and 0.109 g (0.3 mmole) of methyl N-[(4'-amino-1,1'-biphenyl-4-yl)sulfonyl]-L-valinate, after purification by column chromatograph eluting with hexane/ethyl acetate (1:1) provided 0.12 g of methyl N-{[4'-({[4-(methoxymethyl)-3-methyl-1-benzofuran-2-yl]carbonyl}amino)-1,1'-biphenyl-4-yl]sulfonyl}-L-valine. Yield: 71.0% m.p. 144-146° C.; MS: 565.3 (M+H)+.

Step 4: According to the procedure of (Example 2A, Step 6), 0.09 g of methyl N-{[4'-({[4-(methoxymethyl)-3-methyl-1-benzofuran-2-yl]carbonyl}amino)-1,1'-biphenyl-4-yl]sulfonyl}-L-valine provided 0.076 g of N-{[4'-({[4-(methoxymethyl)-3-methyl-1-benzofuran-2-yl]carbonyl}amino)-1,1'-biphenyl-4-yl]sulfonyl}-L-valine. Yield: 86.3% m.p. 227-230° C.; MS: 551.2 (M−H)−.

Example 101

N-{[4'-({[4-(1-methoxyethyl)-3-methyl-1-benzofuran-2-yl]carbonyl}amino)-1,1'-biphenyl-4-yl]sulfonyl}-L-valine

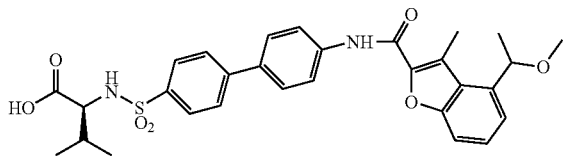

Step 1: According to the procedure of Example 92, Step 2, 1.065 (4.33 mmol) of 4-acetyl-3-methylbenzofuran-2-carboxylic acid ethyl ester (Example 94, Step 1) provided 0.75 g of ethyl 4-(1-hydroxyethyl)-3-methyl-1-benzofuran-2-carboxylate.

Step 2: According to the procedure of (Example 100, Step 1), 0.21 g of ethyl 4-(1-hydroxyethyl)-3-methyl-1-benzofuran-2-carboxylate after heating with iodomethane for 8 days provided 0.22 g of ethyl 4-(1-methoxyethyl)-3-methyl-1-benzofuran-2-carboxylate. Yield: ~100% m.p. 67-69° C.; MS: 263.2 (M+H)+.

Step 3: According to the procedure of (Example 86, Step 4), 0.17 g of ethyl 4-(1-methoxyethyl)-3-methyl-1-benzofuran-2-carboxylate provided 0.15 g of 4-(1-methoxyethyl)-3-methyl-1-benzofuran-2-carboxylic acid. Yield 100% m.p. 113-115° C.; MS: 233.1 (M−H)−.

Step 4: According to the procedure of (Example 86, Step 5), 0.09 g (0.4 mmole) of 4-(1-methoxyethyl)-3-methyl-1-benzofuran-2-carboxylic acid and 0.15 g (0.4 mmole) of N-[(4'-amino-1,1'-biphenyl-4-yl)sulfonyl]-L-valinate, after purification by column chromatography eluting with hexane/ethyl acetate (1:1) provided 0.19 g of methyl N-{[4'-({[4-(1-methoxyethyl)-3-methyl-1-benzofuran-2-yl]carbonyl}amino)-1,1'-biphenyl-4-yl]sulfonyl}-L-valinate. Yield 82.6% m.p. 186-188° C.; MS: 579.3(M+H)+.

Step 5: According to the procedure of (Example 2A, Step 6)), 0.16 g of methyl N-{[4'-({[4-(1-methoxyethyl)-3-methyl-1-benzofuran-2-yl]carbonyl}amino)-1,1'-biphenyl-4-yl]sulfonyl}-L-valinate provided 0.12 g of N-{[4'-({[4-(1-methoxyethyl)-3-methyl-1-benzofuran-2-yl]carbonyl}amino)-1,1'-biphenyl-4-yl]sulfonyl}-L-valine. Yield 76.9% m.p. 97° C.(d); MS: 563.3 (M−H)−.

Example 102

N-{[4'-({[4-(2-methoxyethyl)-3-methyl-1-benzofuran-2-yl]carbonyl}amino)-1,1'-biphenyl-4-yl]sulfonyl}-L-valinate

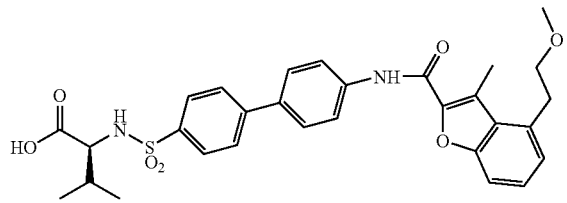

Step 1: To a solution of 0.35 g (1.5 mmol) of 3-methyl-4-vinyl-1-benzofuran-2-carboxylate (Example 87, Step 1) in 3 mL of THF, cooled in an ice bath, was added 1 mL (1 mmol) of borane-THF complex (1.0M solution in THF). The reaction was stirred at room temperature for 2 hours. The reaction was cooled in an ice bath and 1.5 mL of water was added. Next 0.61 g of sodium percarbonate was added in one portion. The reaction was heated at ~50° C. for 1 hour, then cooled to room temperature. Water was added and the resulting mixture was extracted with ethyl acetate. The organic layer washed with water and brine, dried over sodium sulfate, filtered, and concentrated in vacuo. The residue was chromatographed on silica gel eluting with hexane/ethyl acetate (2:1) to provide 0.20 g of ethyl 4-(2-hydroxyethyl)-3-methyl-1-benzofuran-2-carboxylate. Yield 54%. m.p. 88-90° C.; MS 249.1 (M+H)+.

Step 2: According to the procedure of (Example 100, Step 1), 0.16 g (0.65 mmol) of ethyl 4-(2-hydroxyethyl)-3-methyl-1-benzofuran-2-carboxylate was heated at ~55° C. for 7 days to provide 0.17 g of ethyl 4-(2-methoxyethyl)-3-methyl-1-benzofuran-2-carboxylate. Yield ~100%; MS: 263.1 (M+H)+.

Step 3: According to the procedure of (Example 86, Step 4), 0.16 g of ethyl 4-(2-methoxyethyl)-3-methyl-1-benzofuran-2-carboxylate provided 0.14 g of 4-(2-methoxyethyl)-3-methyl-1-benzofuran-2-carboxylic acid. Yield 100%; m.p. 138-140° C.; M: 233.1 (M−H)−.

Step 4: According to the procedure of (Example 86, Step 5), 0.13 g (0.56 mmol) of 4-(2-methoxyethyl)-3-methyl-1-benzofuran-2-carboxylic acid and 0.20 g (0.56 mmol) of N-[(4'-amino-1,1'-biphenyl-4-yl)sulfonyl]-L-valinate, after purification by column chromatography eluting with hexane/ethyl acetate (1:1) provided 0.21 g of methyl N-{[4'-({[4-(2-methoxyethyl)-3-methyl-1-benzofuran-2-yl]carbonyl}amino)-1,1'-biphenyl-4-yl]sulfonyl}-L-valinate. Yield 66% m.p. 67-70° C.; MS: 579.1(M+H)+.

Step 5: According to the procedure of (Example 2A, Step 6), 0.16 g of methyl N-{[4'-({[4-(2-methoxyethyl)-3-methyl-1-benzofuran-2-yl]carbonyl}amino)-1,1'-biphenyl-4-yl]sulfonyl}-L-valinate provided 0.144 g of N-{[4'-({[4-(2-methoxyethyl)-3-methyl-1-benzofuran-2-yl]carbonyl}amino)-1,1'-biphenyl-4-yl]sulfonyl}-L-valine. Yield 93%; m.p. 100-110° C.; MS: 563.2(M–H)⁻.

Example 103

N-[(4'-{[(4-Isopropoxy-1-benzofuran-2-yl)carbonyl]amino}-1,1'-biphenyl-4-yl)sulfonyl]-L-valine

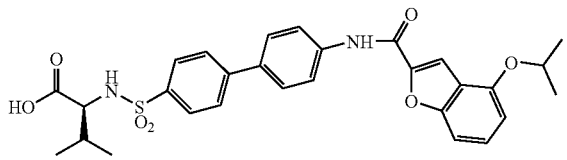

Step 1: To a solution of 0.41 g (2.13 mmol) of 4-hydroxy-2-benzofurancarboxylic acid methyl ester in 7 mL of DMF was added 0.80 mL (8.54 mmol) of 2-bromopropane and 1.18 g (8.54 mmol) of potassium carbonate. The reaction was stirred at room temperature overnight. The reaction mixture was concentrated in vacuo, and the residue was extracted with ethyl acetate. The organic layer washed with water and brine, dried over sodium sulfate, filtered, and concentrated in vacuo to provide 0.49 g of methyl 4-isopropoxy-1-benzofuran-2-carboxylate. Yield ~100%; m.p. 43-45° C.; MS: 235.1 (M+H)⁺.

Step 2: To 0.15 g (0.62 mmole) of 4-isopropoxy-1-benzofuran-2-carboxylate in 2.5 mL of methanol and 2.5 mL of THF was added 3 mL of 1N sodium hydroxide solution. The solution was stirred at room temperature for 45 minutes. The reaction mixture was concentrated in vacuo, the residue was diluted with water and neutralized with 1N HCl to pH ~3-4, and then extracted with ethyl acetate. The organic layer was washed with water and brine, dried over sodium sulfate, filtered, and concentrated in vacuo to give 0.13 g of 4-isopropoxy-1-benzofuran-2-carboxylic acid. Yield 94%. m.p. 148-150° C. MS: 219.1(M–H)⁻.

Step 3: According to the procedure of (Example 86, Step 5), 0.11 g (0.5 mmol) of 4-isopropoxy-1-benzofuran-2-carboxylic acid and 0.18 g (0.5 mmol) of N-[(4'-amino-1,1'-biphenyl-4-yl)sulfonyl]-L-valinate, after purification by column chromatography eluting with hexane/ethyl acetate (1:1) provided 0.14 g of methyl N-[(4'-{[(4-isopropoxy-1-benzofuran-2-yl)carbonyl]amino}-1,1'-biphenyl-4-yl)sulfonyl]-L-valinate. Yield 52%; m.p. 226-229° C.; MS: 563.3(M–H)⁻.

Step 4: According to the procedure of (Example 2A, Step 6), 0.14 g of methyl N-[(4'-{[(4-isopropoxy-1-benzofuran-2-yl)carbonyl]amino}-1,1'-biphenyl-4-yl)sulfonyl]-L-valinate provided 0.07 g of N-[(4'-{[(4-isopropoxy-1-benzofuran-2-yl)carbonyl]amino}-1,1'-biphenyl-4-yl)sulfonyl]-L-valine. Yield 50%; m.p. 132° C.(d); MS: 549.2 (M–H)⁻.

Example 104

N-[(4'-{[(5-methoxy-1-benzofuran-2-yl)carbonyl]amino}-1,1'-biphenyl-4-yl)sulfonyl]-L-valine

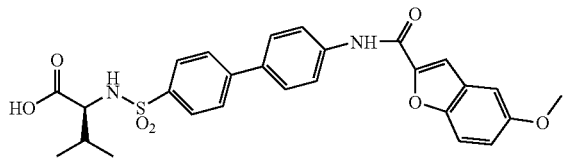

Step 1: According to the procedure of (Example 86, Step 5), 0.24 g (0.6 mmol) of 5-methoxy-2-benzofurancarboxylic acid and 0.44 g (0.6 mmol) of N-[(4'-amino-1,1'-biphenyl-4-yl)sulfonyl]-L-valinate, after purification by column chromatography eluting with hexane/ethyl acetate (1:1) provided 0.33 g of methyl N-[(4'-{[(5-methoxy-1-benzofuran-2-yl)carbonyl]amino}-1,1'-biphenyl-4-yl)sulfonyl]-L-valinate. Yield: 53%; m.p. 234-235° C.; MS: 537.3 (M+H)⁺.

Step 2: According to the procedure of (Example 2A, Step 6), 0.31 g of methyl N-[(4'-{[(5-methoxy-1-benzofuran-2-yl)carbonyl]amino}-1,1'-biphenyl-4-yl)sulfonyl-L-valinate provided 0.17 g of N-[(4'-{[(5-methoxy-1-benzofuran-2-yl)carbonyl]amino}-1,1'-biphenyl-4-yl)sulfonyl]-L-valine. Yield 53% m.p. 257-259° C.; MS: 521.2 (M–H)⁻.

Example 105

(S)-2-{4'-[(4-Methoxy-3-methyl-benzofuran-2-carbonyl)-amino]-biphenyl-4-sulfonylamino}-3-methyl-butyric acid

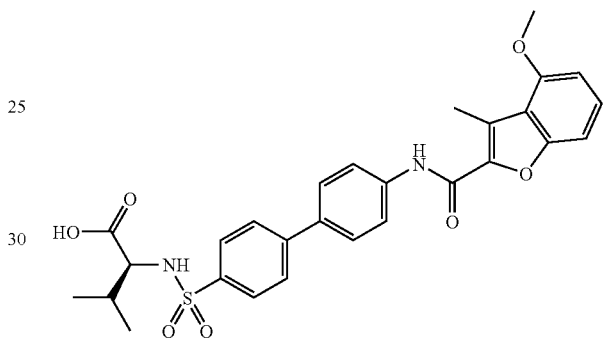

Step 1: 4-Hydroxy-3-methyl-benzofuran-2-carboxylic acid ethyl ester (200 mg) was mixed with iodomethane (0.5 mL), K₂CO₃ (200 mg) and 2 mL of DMF. The mixture was stirred at room temperature overnight. The mixture was mixed with brine and extracted with ethyl acetate, and the combined ethyl acetate layers were washed with brine. Removal of the solvent gave the crude product that was purified by column chromatographt to give 162 mg (76% yield) of 4-methoxy-3-methyl-benzofuran-2-carboxylic acid ethyl ester as amber colored oil.

Step 2: To 150 mg of 4-methoxy-3-methyl-benzofuran-2-carboxylic acid ethyl ester dissolved in 1 mL of THF was added 3 mL of LiOH solution (3.6 g LiOH/50 mL MeOH/50 mL H₂O). The mixture was stirred at room temperature overnight. The solvents were removed under vacuum and the residue was dissolved in 5 mL of water. The solution was acidified and the resulting suspension was filtered. The solid product was dried under vacuum to give 120 mg (91% yield) of 4-methoxy-3-methyl-benzofuran-2-carboxylic acid as white solid.

Step 3: To 110 mg (0.53 mmol) of 4-methoxy-3-methyl-benzofuran-2-carboxylic acid was added 2 mL of oxalyl chloride and the resulting mixture was refluxed for 4 h in the presence of a catalytic amount of DMF, then the excess oxalyl chloride was removed under vacuum. The residue was dissolved in 2 mL of dichloromethane and was added to a mixture of 232 mg (0.64 mmol) of (S)-2-(4'-amino-biphenyl-4-sulfonylamino)-3-methyl-butyric acid methyl ester and 2 mL of pyridine in an ice/water bath. The mixture was stirred at room temperature overnight. All the solvents were removed under vacuum. Column chromatography on silica gel gave 95 mg (33% yield) of (S)-2-{4'-[(4-methoxy-3-methyl-benzofuran-2-carbonyl)-amino]-biphenyl-4-sulfonylamino}-3-methyl-butyric acid methyl ester as off white solid.

Step 4: To a solution of 80 mg of (S)-2-{4'-[(4-methoxy-3-methyl-benzofuran-2-carbonyl)-amino]-biphenyl-4-sulfonylamino}-3-methyl-butyric acid methyl ester dissolved in 1 mL of THF was added 3 mL of LiOH solution (3.6 g LiOH/50 mL MeOH/50 mL H$_2$O). The mixture was stirred at room temperature for 4 days. The solvents were removed under vacuum and the residue was dissolved in 5 mL of water. The solution was acidified and the resulting suspension was filtered. The solid product was dried under vacuum and triturated with acetonitrile to give 63 mg (81% yield) of (S)-2-{4'-[(4-methoxy-3-methyl-benzofuran-2-carbonyl)-amino]-biphenyl-4-sulfonylamino}-3-methyl-butyric acid, obtained as white solid. $^1$H NMR (400 MHz, DMSO-d$_6$) δ ppm 0.8 (dd, J=12.5, 6.7 Hz, 6 H) 2.0 (m, 1 H) 2.7 (s, 3 H) 3.6 (dd, J=9.3, 5.8 Hz, 1 H) 3.9 (s, 3 H) 6.9 (d, J=8.1 Hz, 1 H) 7.2 (d, J=7.8 Hz, 1 H) 7.4 (t, J=8.2 Hz, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.5 (s, 1 H) 12.6 (s, 1 H).

Example 106

(S)-2-{4'-[(4-ethoxy-3-methyl-benzofuran-2-carbonyl)-amino]-biphenyl-4-sulfonylamino}-3-methyl-butyric acid

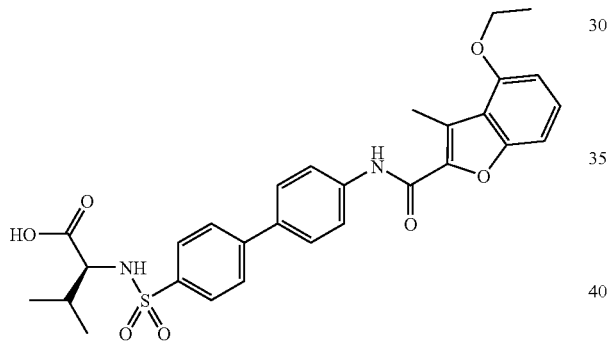

Step 1: 4-Hydroxy-3-methyl-benzofuran-2-carboxylic acid ethyl ester (200 mg) was mixed with ethyl iodide (0.5 mL), K$_2$CO$_3$ (200 mg) and 2 mL of DMF. The mixture was stirred at room temperature overnight. The mixture was washed with brine and extracted with ethyl acetate. The combined ethyl acetate layers were washed with brine. Removal of the solvent under vacuum gave the crude product, which was purified by column chromatography to give 175 mg (77% yield) of 4-ethoxy-3-methyl-benzofuran-2-carboxylic acid ethyl ester as white solid.

Step 2: To a solution of 160 mg of 4-ethoxy-3-methyl-benzofuran-2-carboxylic acid ethyl ester dissolved in 1 mL of THF was added 3 mL of LiOH solution (3.6 g LiOH/50 mL MeOH/50 mL H$_2$O). The mixture was stirred at room temperature overnight. The solvents were removed under vacuum and the residue was dissolved in 5 mL of water. The solution was acidified and the resulting suspension was filtered. The solid product was dried under vacuum to give 130 mg (92% yield) of 4-ethoxy-3-methyl-benzofuran-2-carboxylic acid was obtained as white solid.

Step 3: A solution of 115 mg (0.46 mmol) of 4-ethoxy-3-methyl-benzofuran-2-carboxylic acid in 2 mL of oxalyl chloride was refluxed for 4 h in the presence of a catalytic amount of DMF, then the excess oxalyl chloride was removed under vacuum. The residue was dissolved in 2 mL of dichloromethane and was added to a mixture of 201 mg (0.56 mmol) of (S)-2-(4'-amino-biphenyl-4-sulfonylamino)-3-methyl-butyric acid methyl ester, and 2 mL of pyridine in an ice/water bath. The mixture was stirred at room temperature overnight. All the solvents were then removed under vacuum. Column chromatography with silica gel gave 237 mg (93% yield) of (S)-2-{4'-[(4-ethoxy-3-methyl-benzofuran-2-carbonyl)-amino]-biphenyl-4-sulfonylamino}-3-methyl-butyric acid methyl ester as an off white solid.

Step 4: To 100 mg of (S)-2-{4'-[(4-ethoxy-3-methyl-benzofuran-2-carbonyl)-amino]-biphenyl-4-sulfonylamino}-3-methyl-butyric acid methyl ester dissolved in 1 mL of THF was added 3 mL of LiOH solution (3.6 g LiOH/50 mL MeOH/50 mL H$_2$O). The mixture was stirred at room temperature for 4 days. The solvents were removed under vacuum and the residue was dissolved in 5 mL of water. The solution was acidified and the resulting suspension was filtered. The solid product was dried under vacuum and triturated with acetonitrile to give 89 mg (91% yield) of (S)-2-{4'-[(4-ethoxy-3-methyl-benzofuran-2-carbonyl)-amino]-biphenyl-4-sulfonylamino}-3-methyl-butyric acid as a white solid. $^1$H NMR (400 MHz, DMSO-d$_6$) δ ppm 0.8 (dd, J=12.6, 6.6 Hz, 6 H) 1.4 (t, J=6.9 Hz, 3 H) 2.0 (m, 1 H) 2.7 (s, 3 H) 3.6 (m, 1 H) 4.2 (q, J=6.9 Hz, 2 H) 6.8 (d, J=8.3 Hz, 1 H) 7.2 (d, J=8.3 Hz, 1 H) 7.4 (t, J=8.2 Hz, 1 H) 7.8 (d, J=8.8 Hz, 2 H) 7.9 (m, 4 H) 8.0 (d, J=8.8 Hz, 2 H) 8.1 (d, J=9.1 Hz, 1 H) 10.5 (s, 1 H) 12.6 (s, 1 H).

Example 107

(S)-3-Methyl-2-{4'-[(3-methyl-4-propoxy-benzofuran-2-carbonyl)-amino]-biphenyl-4-sulfonylamino}-butyric acid

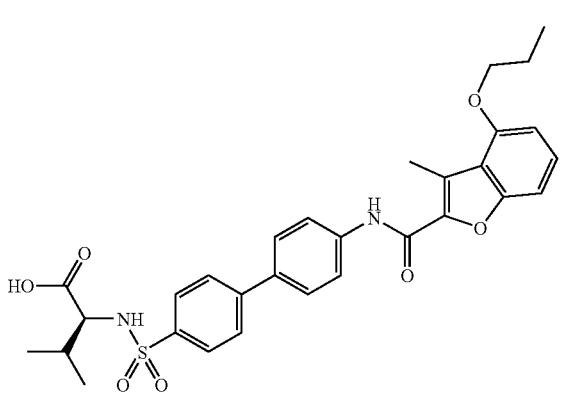

Step 1: 4-Hydroxy-3-methyl-benzofuran-2-carboxylic acid ethyl ester (200 mg) was mixed with iodopropane (0.5 mL), K$_2$CO$_3$ (200 mg) and 2 mL of DMF. The mixture was stirred at room temperature overnight. The mixture was washed with brine and extracted with ethyl acetate. The combined ethyl acetate layers were washed with brine. Removal of the solvent gave the crude product, which was purified by column chromatography to give 176 mg of 3-methyl-4-propoxy-benzofuran-2-carboxylic acid ethyl ester as white solid.

Step 2: To a solution of 160 mg of 4-propoxy-3-methyl-benzofuran-2-carboxylic acid ethyl ester dissolved in 1 mL of THF was added 3 mL of LiOH solution (3.6 g LiOH/50 mL MeOH/50 mL H$_2$O). The mixture was stirred at room temperature overnight. The solvents were removed under vacuum and the residue was dissolved in 5 mL of water. The solution was acidified and the resulting suspension was filtered. The solid product was dried under vacuum to give 124 mg (87% yield) of 4-propoxy-3-methyl-benzofuran-2-carboxylic acid, obtained as white solid.

Step 3: A solution of 110 mg (0.47 mmol) of 4-ethoxy-3-methyl-benzofuran-2-carboxylic acid in 4 mL of oxalyl chloride was refluxed for 4 h in the presence of a catalytic amount of DMF. The excess oxalyl chloride was then removed under vacuum. The residue was dissolved in 2 mL of dichloromethane and was added to a mixture of 204 mg (0.56 mmol) of (S)-2-(4'-amino-biphenyl-4-sulfonylamino)-3-methyl-butyric acid methyl ester, and 2 mL of pyridine in an ice/water bath. The mixture was stirred at room temperature overnight. All the solvents were removed under vacuum. Column chromatography on silica gel gave 152 mg (57% yield) of (S)-2-{4'-[(3-methyl-4-propoxy-benzofuran-2-carbonyl)-amino]-biphenyl-4-sulfonylamino}-3-methyl-butyric acid methyl ester as a white solid.

Step 4: To 100 mg of (S)-2-{4'-[(4-ethoxy-3-methyl-benzofuran-2-carbonyl)-amino]-biphenyl-4-sulfonylamino}-3-methyl-butyric acid methyl ester dissolved in 1 mL of THF was added 3 mL of LiOH solution (3.6 g LiOH/50 mL MeOH/50 mL $H_2O$). The mixture was stirred at room temperature for 4 days. The solvents were removed under vacuum and the residue was dissolved in 5 mL of water. The solution was acidified and the resulting suspension was filtered. The solid product was dried under vacuum to give 84 mg (86% yield) of (S)-3-methyl-2-{4'-[(3-methyl-4-propoxy-benzofuran-2-carbonyl)-amino]-biphenyl-4-sulfonylamino}-butyric acid, obtained as white solid. $^1$H NMR (400 MHz, DMSO-$d_6$) δ ppm 0.8 (dd, J=12.9, 6.8 Hz, 6 H) 1.1 (t, J=7.3 Hz, 3 H) 1.8 (m, 2 H) 2.0 (m, 1 H) 2.8 (s, 3 H) 3.6 (dd, J=9.1, 6.1 Hz, 1 H) 4.1 (t, J=6.2 Hz, 2 H) 6.8 (d, J=8.1 Hz, 1 H) 7.2 (d, J=8.1 Hz, 1 H) 7.4 (t, J=8.2 Hz, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.5 (s, 1 H) 12.6 (s, 1 H).

Example 108

(S)-2-{4'-[(4-Isopropoxy-3-methyl-benzofuran-2-carbonyl)-amino]-biphenyl-4-sulfonylamino}-3-methyl-butyric acid

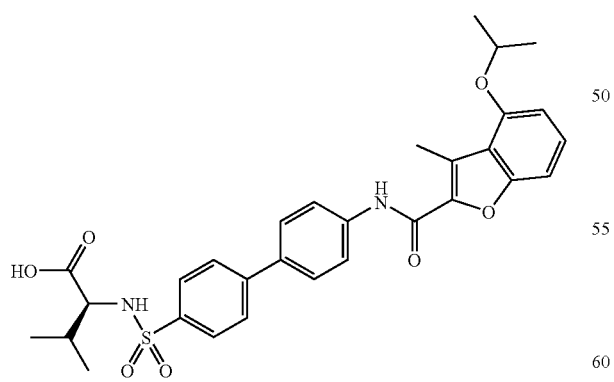

Step 1: To 4-hydroxy-3-methyl-benzofuran-2-carboxylic acid tert-butyl ester (200 mg, 0.8 mmol) in 4 mL of DMF was added 2-bromopropane (0.5 mL), and $K_2CO_3$ (200 mg). The mixture was stirred at room temperature overnight. The mixture was washed with brine and extracted with ethyl acetate. The combined ethyl acetate layers were washed with brine. Removal of the solvent gave 176 mg of 3-methyl-4-isopropoxy-benzofuran-2-carboxylic acid tert-butyl ester as colorless crystals.

Step 2: To 220 mg of 4-isopropoxy-3-methyl-benzofuran-2-carboxylic acid tert-butyl ester was added 3 mL of TFA/dichloromethane (1:1). The solution was stirred at room temperature for 3 h. The solvents were removed under vacuum and the residue was triturated with acetonitrile. Filtration of the precipitate gave 210 mg of 4-isopropoxy-3-methyl-benzofuran-2-carboxylic acid as a white solid.

Step 3: To 200 mg (0.91 mmol) 4-isopropoxy-3-methyl-benzofuran-2-carboxylic acid in 4 mL of DMF was added 329 mg (1 eq) of (S)-2-(4'-amino-biphenyl-4-sulfonylamino)-3-methyl-butyric acid methyl ester, 482 mg (1.2 eq) of BOP, and 0.19 mL of N,N-diisopropylethylamine. The mixture was stirred at room temperature overnight. Brine was added, and the mixture was extracted with ethyl acetate. The combined organic layers were washed with brine and water. Removal of the solvent in vacuo gave the crude product, which was purified by column chromatography on silica gel to give 395 mg (69% yield) of (S)-2-{4'-[(4-Isopropoxy-3-methyl-benzofuran-2-carbonyl)-amino]-biphenyl-4-sulfonylamino}-3-methyl-butyric acid methyl ester as colorless oil.

Step 4: To 370 mg (S)-2-{4'-[(4-isopropoxy-3-methyl-benzofuran-2-carbonyl)-amino]-biphenyl-4-sulfonylamino}-3-methyl-butyric acid methyl ester dissolved in 2 mL of THF was added 3 mL of LiOH solution (3.6 g LiOH/50 mL MeOH/50 mL $H_2O$). The mixture was stirred at room temperature for 6 days. The solvents were removed under vacuum and the residue was dissolved in 5 mL of water. The solution was acidified and the resulting suspension was filtered. The solid product was dried under vacuum to give 286 mg of (S)-2-{4'-[(4-isopropoxy-3-methyl-benzofuran-2-carbonyl)-amino]-biphenyl-4-sulfonylamino}-3-methyl-butyric acid, obtained as white solid. $^1$H NMR (400 MHz, DMSO-$d_6$) δ ppm 0.8 (dd, J=13.5, 6.7 Hz, 6 H) 1.4 (d, J=6.1 Hz, 6 H) 1.9 (m, 1 H) 2.7 (s, 3 H) 3.5 (t, J=7.2 Hz, 1 H) 4.8 (m, 1 H) 6.9 (d, J=8.6 Hz, 1 H) 7.2 (d, J=8.6 Hz, 1 H) 7.4 (t, J=8.2 Hz, 1 H) 7.8 (d, J=8.8 Hz, 2 H) 7.8 (m, 4 H) 8.0 (m, 3 H) 10.5 (s, 1 H).

Example 109

(S)-3-Methyl-2-{4'-[(3-methyl-4-phenyl-benzofuran-2-carbonyl)-amino]-biphenyl-4-sulfonylamino}-butyric acid

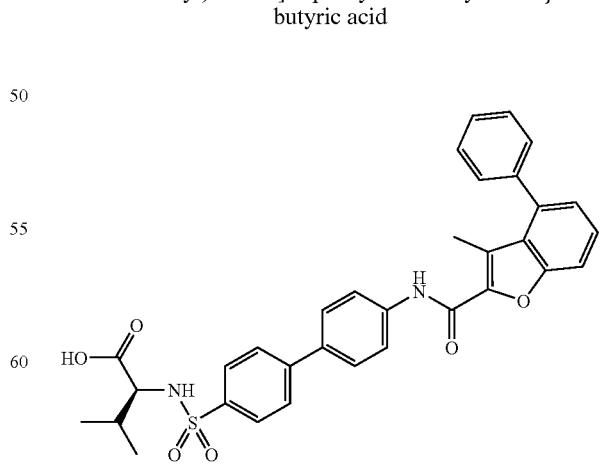

Step 1: To 4-hydroxy-3-methyl-benzofuran-2-carboxylic acid tert-butyl ester (100 mg, 0.4 mmol) was added N,N- diisopropylethylamine (130 mg, 1 mmol) and 2 mL of dichloromethane. The solution was cooled to <−10° C. Trifluoromethanesulfonic anhydride (0.1 mL, 0.6 mmol) was added dropwise. The reaction mixture was stirred at −10° C. for 2 h and was then poured into water. The mixture was extracted with dichloromethane and the combined organic layers were washed with water and dried over sodium sulfate. Removal of the solvent gave 145 mg (95% yield) of 3-methyl-4-trifluoromethanesulfonyloxy-benzofuran-2-carboxylic acid tert-butyl ester.

Step 2: 3-Methyl-4-trifluoromethanesulfonyloxy-benzofuran-2-carboxylic acid tert-butyl ester (85 mg, 0.25 mmol) was mixed with $K_2CO_3$ (68 mg, 0.5 mmol), phenylboronic acid (31 mg, 0.25 mmol), Pd(Ph$_3$)$_4$ (14 mg, 0.01 mmol), 1 mL of 1,2-dimethoxyethane and 2 drops of water. The mixture was heated and stirred in an 85° C. oil bath for 2 h. The reaction mixture was poured into water and was extracted with ethyl acetate. The organic extract was washed with water and dried over sodium sulfate. Filtration followed by removal of the solvent in vacuo gave the crude product (71 mg), which was purified by column chromatography to give 53 mg (77% yield) of 3-methyl-4-phenyl-benzofuran-2-carboxylic acid tert-butyl ester, obtained as white solid.

Step 3: 3-Methyl-4-phenyl-benzofuran-2-carboxylic acid tert-butyl ester was dissolved in 2 mL of TFA/dichloromethane (1:1). The solution was stirred at room temperature for 3 h. The solvents were removed under vacuum and the residue was triturated with ether. Filtration gave 66 mg of 3-methyl-4-phenyl-benzofuran-2-carboxylic acid as white solid.

Step 4: To 60 mg (0.24 mmol) 3-methyl-4-phenyl-benzofuran-2-carboxylic acid was added 1 mL of oxalyl chloride and the mixture was refluxed for 1 h in the presence of a catalytic amount of DMF, then the excess oxalyl chloride was removed under vacuum. The residue was dissolved in 1 mL of dichloromethane and was added to a mixture of 129 mg (0.36 mmol) of (S)-2-(4'-amino-biphenyl-4-sulfonylamino)-3-methyl-butyric acid methyl ester, 87 mg (0.714 mmol) of 4-(dimethylamino)pyridine and 2 mL of in an ice/water bath. The mixture was stirred at room temperature overnight. All the solvents were removed under vacuum. Column chromatography on silica gel gave 41 mg (29% yield) of (S)-3-methyl-2-{4'-[(3-methyl-4-phenyl-benzofuran-2-carbonyl)-amino]-biphenyl-4-sulfonylamino}-butyric acid methyl ester as white solid.

Step 5: To 38 mg of (S)-3-methyl-2-{4'-[(3-methyl-4-phenyl-benzofuran-2-carbonyl)-amino]-biphenyl-4-sulfonylamino}-butyric acid methyl ester dissolved in 0.5 mL of THF was added 2 mL of LiOH solution (3.6 g LiOH/50 mL MeOH/50 mL H$_2$O). The mixture was stirred at room temperature for 4 days. The solvents were removed under vacuum and the residue was dissolved in 5 mL of water. The solution was acidified and the resulting suspension was filtered. The solid product was dried under vacuum to give 12 mg of (S)-3-methyl-2-{4'-[(3-methyl-4-phenyl-benzofuran-2-carbonyl)-amino]-biphenyl-4-sulfonylamino}-butyric acid, obtained as pale brown solid. $^1$H NMR (400 MHz, DMSO-d$_6$) δ ppm 0.8 (dd, J=13.6, 6.8 Hz, 6 H) 2.0 (m, 1 H) 2.2 (s, 3 H) 3.5 (m, 1 H) 7.2 (dd, J=7.3, 1.0 Hz, 1 H) 7.5 (m, 5 H) 7.6 (dd, J=8.3, 7.3 Hz, 1 H) 7.7 (dd, J=8.3, 1.0 Hz, 1 H) 7.8 (d, J=8.8 Hz, 2 H) 7.8 (m, 4 H) 8.0 (m, 3 H) 10.6 (s, 1 H).

Example 110

(S)-3-Methyl-2-(4'-{[3-methyl-4-(3-nitro-phenyl)-benzofuran-2-carbonyl]-amino}-biphenyl-4-sulfonylamino)-butyric acid

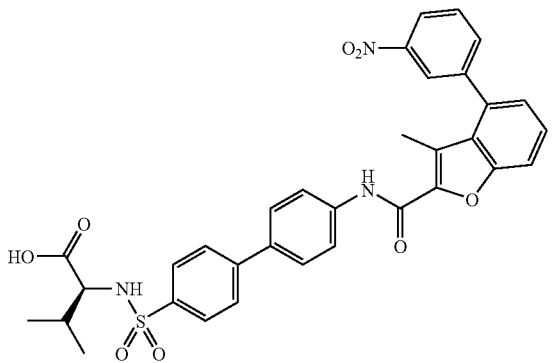

Step 1: To 4-hydroxy-3-methyl-benzofuran-2-carboxylic acid tert-butyl ester (100 mg, 0.4 mmol) was added N,N-diisopropylethylamine (130 mg, 1 mmol) and 2 mL of dichloromethane. The solution was cooled to <−10° C. Trifluoromethanesulfonic anhydride (0.1 mL, 0.6 mmol) was added dropwise. The reaction mixture was stirred at −10° C. for 2 h and was poured into water. The mixture was extracted with dichloromethane and the combined organic layers were washed with water and dried over sodium sulfate. Removal of the solvent gave 145 mg (95% yield) of 3-methyl-4-trifluoromethanesulfonyloxy-benzofuran-2-carboxylic acid tert-butyl ester.

Step 2: 3-Methyl-4-trifluoromethanesulfonyloxy-benzofuran-2-carboxylic acid tert-butyl ester (380 mg, 1 mmol) was mixed with $K_2CO_3$ (280 mg, 2 mmol), 3-nitro-phenylboronic acid (334 mg, 2 mmol), Pd(Ph$_3$)$_4$ (115 mg, 0.1 mmol), 4 mL of 1,2-dimethoxyethane and 5 drops of water. The mixture was heated and stirred in an 85° C. oil bath for 3 h. The reaction mixture was poured into water and was extracted with ethyl acetate. The organic extract was washed with water and dried over sodium sulfate. Removal of solvent gave the crude product, which was purified by column chromatography to give 310 mg (88% yield) of 3-methyl-4-(3-nitro-phenyl)-benzofuran-2-carboxylic acid tert-butyl ester, obtained as white solid.

Step 3: To 300 mg of 3-methyl-4-(3-nitro-phenyl)-benzofuran-2-carboxylic acid tert-butyl ester was added 4 mL of TFA/dichloromethane (1:1). The solution was stirred at room temperature for 5 h. The solvents were removed under vacuum and the residue was triturated with ether. Filtration gave 232 mg (92% yield) of 3-methyl-4-(3-nitro-phenyl)-benzofuran-2-carboxylic acid as white solid.

Step 4: To 100 mg (0.34 mmol) of 3-methyl-4-(3-nitro-phenyl)-benzofuran-2-carboxylic acid was added 2 mL of oxalyl chloride and the resulting mixture was refluxed for 2 h in the presence of a catalytic amount of DMF, then the excess oxalyl chloride was removed under vacuum. The residue was dissolved in 1 mL of dichloromethane and was added to a mixture of 183 mg (0.5 mmol) of (S)-2-(4'-amino-biphenyl-4-sulfonylamino)-3-methyl-butyric acid methyl ester and 2 mL of pyridine in an ice/water bath. The mixture was stirred at room temperature overnight. All the solvents were removed under vacuum. Column chromatography on silica gel gave 41 mg of (S)-3-methyl-2-(4'-{[3-methyl-4-(3-nitro-phenyl)- benzofuran-2-carbonyl]-amino}-biphenyl-4-sulfonylamino)-butyric acid methyl ester as white solid.

Step 5: To 41 mg of (S)-3-methyl-2-(4'-{[3-methyl-4-(3-nitro-phenyl)-benzofuran-2-carbonyl]-amino}-biphenyl-4-sulfonylamino)-butyric acid methyl ester dissolved in 0.5 mL of THF was added 2 mL of LiOH solution (3.6 g LiOH/50 mL MeOH/50 mL H$_2$O). The mixture was stirred at room temperature for 4 days. The solvents were removed under vacuum and the residue was dissolved in 5 mL of water. The solution was acidified and the resulting suspension was filtered. The solid product was dried under vacuum to give 29 mg of (S)-3-methyl-2-(4'-{[3-methyl-4-(3-nitro-phenyl)-benzofuran-2-carbonyl]-amino}-biphenyl-4-sulfonylamino)-butyric acid, obtained as pale brown solid. $^1$H NMR (400 MHz, DMSO-d$_6$) δ ppm 0.8 (dd, J=12.4, 6.8 Hz, 6 H) 1.9 (m, 1 H) 2.2 (s, 3 H) 3.6 (dd, J=9.3, 6.1 Hz, 1 H) 7.3 (dd, J=7.3, 0.8 Hz, 1 H) 7.6 (dd, J=8.3, 7.3 Hz, 1 H) 7.8 (m, 8 H) 8.0 (d, J=8.8 Hz, 3 H) 8.1 (d, J=9.3 Hz, 1 H) 8.3 (t, J=1.9 Hz, 1 H) 8.3 (m, 1 H) 10.6 (s, 1 H) 12.6 (s, 1 H).

Example 111

(S)-3-methyl-2-{4'-[(3-methyl-4-pyridin-3-yl-benzofuran-2-carbonyl)-amino]-biphenyl-4-sulfonylamino}-butyric acid

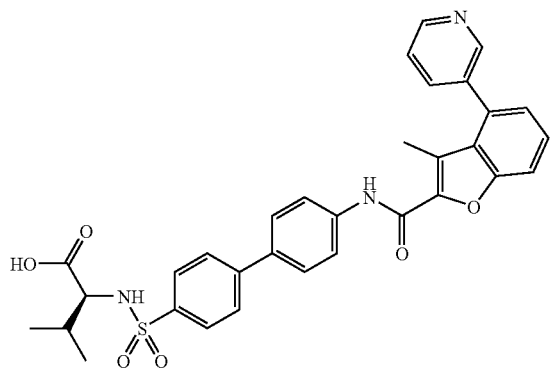

Step 1: To 4-hydroxy-3-methyl-benzofuran-2-carboxylic acid tert-butyl ester (100 mg, 0.4 mmol) was added N,N-diisopropylethylamine (130 mg, 1 mmol) and 2 mL of dichloromethane. The solution was cooled to <−10° C. Trifluoromethanesulfonic anhydride (0.1 mL, 0.6 mmol) was added dropwise. The reaction mixture was stirred at −10° C. for 2 h and was then poured into water. The mixture was extracted with dichloromethane and the combined organic layers were washed with water and dried over sodium sulfate. Removal of the solvent gave 145 mg (95% yield) of 3-methyl-4-trifluoromethanesulfonyloxy-benzofuran-2-carboxylic acid tert-butyl ester.

Step 2: To 3-methyl-4-trifluoromethanesulfonyloxy-benzofuran-2-carboxylic acid tert-butyl ester (285 mg, 0.75 mmol) in 3 mL of 1,2-dimethoxyethane was added K$_2$CO$_3$ (363 mg, 3.5 eq), pyridine-3-boronic acid (138 mg, 1.13 mmol), Pd(Ph$_3$)$_4$ (43 mg, 0.05 eq), and 0.5 mL of water. The mixture was heated and stirred in an 85° C. oil bath for 3 h. The reaction mixture was poured into water and was extracted with ethyl acetate. The organic extract was washed with water and dried over sodium sulfate. Removal of the solvent in vacuo gave the crude product, which was purified by column chromatography to give 202 mg of 3-methyl-4-pyridin-3-yl-benzofuran-2-carboxylic acid tert-butyl ester, obtained as white solid.

Step 3: To 185 mg of 3-methyl-4-pyridin-3-yl-benzofuran-2-carboxylic acid tert-butyl ester was added 4 mL of TFA/dichloromethane (1:1). The solution was stirred at room temperature for 5 h. The solvents were removed under vacuum and the residue was triturated with ether. Filtration gave 136 mg of desired of 3-methyl-4-pyridin-3-yl-benzofuran-2-carboxylic acid as white solid.

Step 4: To 3-methyl-4-pyridin-3-yl-benzofuran-2-carboxylic acid (123 mg, 0.49 mmol) in 4 mL of DMF was added (S)-2-(4'-amino-biphenyl-4-sulfonylamino)-3-methyl-butyric acid methyl ester (352 mg, 0.97 mmol), BOP (429 mg, 0.97 mmol), and N,N-diisopropylethylamine (0.17 mL, 0.97 mmol). The mixture was stirred at room temperature overnight. The reaction mixture was poured into brine, and extracted with ethyl acetate. The combined organic solution was washed with brine and water. Removal of solvent in vacuo gave the crude product, which was purified by column chromatography on silica gel to give 115 mg of (S)-3-methyl-2-{4'-[(3-methyl-4-pyridin-3-yl-benzofuran-2-carbonyl)-amino]-biphenyl-4-sulfonylamino}-butyric acid methyl ester, obtained as white solid.

Step 5: To 100 mg of (S)-3-methyl-2-{4'-[(3-methyl-4-pyridin-3-yl-benzofuran-2-carbonyl)-amino]-biphenyl-4-sulfonylamino}-butyric acid methyl ester was dissolved in 1 mL of THF was added 3 mL of LiOH solution (3.6 g LiOH/50 mL MeOH/50 mL H$_2$O). The mixture was stirred at room temperature for 4 days. The solvents were removed under vacuum and the residue was dissolved in 5 mL of water. The pH of the solution was adjusted to 7 and the resulting suspension was filtered. The solid product was dried under vacuum to give 75 mg of (S)-3-methyl-2-{4'-[(3-methyl-4-pyridin-3-yl-benzofuran-2-carbonyl)-amino]-biphenyl-4-sulfonylamino}-butyric acid, obtained as white solid. $^1$H NMR (400 MHz, DMSO-d$_6$) δ ppm 0.8 (dd, J=12.6, 6.8 Hz, 6 H) 2.0 (m, 1 H) 2.2 (s, 3 H) 3.6 (dd, J=9.3 Hz, 1 H) 7.3 (dd, J=7.3, 1.0 Hz, 1 H) 7.5 (m, 1 H) 7.6 (dd, J=8.3, 7.6 Hz, 1 H) 7.8 (m, 3 H) 7.9 (m, 4 H) 7.9 (m, 1 H) 8.0 (d, J=8.8 Hz, 2 H) 8.1 (d, J=9.1 Hz, 1 H) 8.7 (m, 2 H) 10.6 (s, 1 H) 12.6 (s, 1 H).

Example 112

(S)-3-Methyl-2-{4'-[(3-methyl-4-pyridin-4-yl-benzofuran-2-carbonyl)-amino]-biphenyl-4-sulfonylamino}-butyric acid

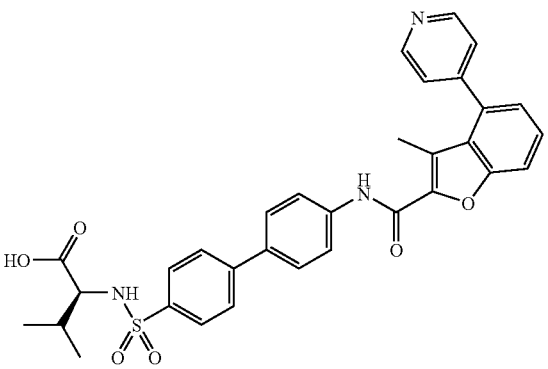

Step 1: To 4-hydroxy-3-methyl-benzofuran-2-carboxylic acid tert-butyl ester (100 mg, 0.4 mmol) was added N,N- diisopropylethylamine (130 mg, 1 mmol) and 2 mL of dichloromethane. The solution was cooled to <−10° C. Trifluoromethanesulfonic anhydride (0.1 mL, 0.6 mmol) was added dropwise. The reaction mixture was stirred at −10° C. for 2 h and was then poured into water. The mixture was extracted with dichloromethane and the combined organic solution was washed with water and dried over sodium sulfate. Removal of the solvent gave 145 mg (95% yield) of 3-methyl-4-trifluoromethanesulfonyloxy-benzofuran-2-carboxylic acid tert-butyl ester.

Step 2: 3-Methyl-4-trifluoromethanesulfonyloxy-benzofuran-2-carboxylic acid tert-butyl ester (258 mg, 0.68 mmol) was mixed with $K_2CO_3$ (207 mg, 2.2 eq), pyridine-4-boronic acid (110 mg, 1.3 eq), $Pd(Ph_3)_4$ (43 mg, 0.05 eq), 3 mL of 1,2-dimethoxyethane and 0.5 mL of water. The mixture was heated and stirred in an 85° C. oil bath for 5 h. The reaction mixture was poured into water and was extracted with ethyl acetate. The organic extract was washed with water and dried over sodium sulfate. Removal of solvent gave the crude product, which was purified by column chromatography to give 156 mg of 3-methyl-4-pyridin-4-yl-benzofuran-2-carboxylic acid tert-butyl ester, obtained as white solid.

Step 3: To 141 mg of 3-methyl-4-pyridin-3-yl-benzofuran-2-carboxylic acid tert-butyl ester was added 4 mL of TFA/dichloromethane (1:1). The solution was stirred at room temperature for 5 h. The solvents were removed under vacuum and the residue was triturated with ether. Filtration gave 98 mg of 3-methyl-4-pyridin-4-yl-benzofuran-2-carboxylic acid as a white solid.

Step 4: To 3-methyl-4-pyridin-4-yl-benzofuran-2-carboxylic acid (88 mg, 0.35 mmol) in 4 mL of DMF was added (S)-2-(4'-amino-biphenyl-4-sulfonylamino)-3-methyl-butyric acid methyl ester (252 mg, 0.7 mmol), BOP (307 mg, 0.7 mmol), and N,N-diisopropylethylamine (0.12 mL, 0.7 mmol). The mixture was stirred at room temperature overnight. The reaction mixture was poured into brine, and extracted with ethyl acetate. The combined organic solution was washed with brine and water. Removal of the solvent in vacuo gave the crude product, which was purified by column chromatography on silica gel to give 172 mg of (S)-3-methyl-2-{4'-[(3-methyl-4-pyridin-4-yl-benzofuran-2-carbonyl)-amino]-biphenyl-4-sulfonylamino}-butyric acid methyl ester, obtained as white solid.

Step 5: To 160 mg of (S)-3-methyl-2-{4'-[(3-methyl-4-pyridin-4-yl-benzofuran-2-carbonyl)-amino]-biphenyl-4-sulfonylamino}-butyric acid methyl ester was added 1 mL of THF and 3 mL of LiOH solution (3.6 g LiOH/50 mL MeOH/50 mL $H_2O$). The mixture was stirred at room temperature for 4 days. The solvents were removed under vacuum and the residue was dissolved in 5 mL of water. The pH of the solution was adjusted to 7 and the resulting suspension was filtered. The solid product was dried under vacuum to give 132 mg of (S)-3-methyl-2-{4'-[(3-methyl-4-pyridin-4-yl-benzofuran-2-carbonyl)-amino]-biphenyl-4-sulfonylamino}-butyric acid, obtained as white solid. $^1$H NMR (400 MHz, DMSO-$d_6$) δ ppm 0.8 (dd, J=21.5, 6.8 Hz, 6 H) 2.0 (m, 1 H) 2.2 (s, 3 H) 3.4 (s, 1 H) 7.3 (dd, J=7.3, 1.0 Hz, 1 H) 7.5 (m, 2 H) 7.6 (dd, J=8.3, 7.3 Hz, 1 H) 7.8 (m, 5 H) 7.9 (m, 2 H) 8.0 (d, J=8.8 Hz, 2 H) 8.7 (m, 2 H) 10.6 (s, 1 H).

Example 113

(S)-2-{4'-[(4-Furan-3-yl-3-methyl-benzofuran-2-carbonyl)-amino]-biphenyl-4-sulfonylamino}-3-methyl-butyric acid

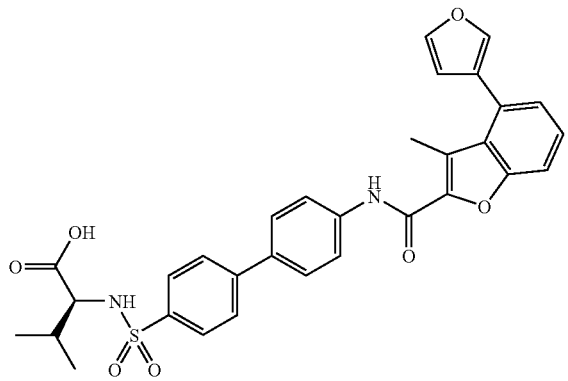

Step 1: To 4-hydroxy-3-methyl-benzofuran-2-carboxylic acid tert-butyl ester (100 mg, 0.4 mmol) was added N,N-diisopropylethylamine (130 mg, 1 mmol) and 2 mL of dichloromethane. The solution was cooled to <−10° C. Trifluoromethanesulfonic anhydride (0.1 mL, 0.6 mmol) was added dropwise. The reaction mixture was stirred at −10° C. for 2 h and was then poured into water. The mixture was extracted with dichloromethane and the combined organic layers were washed with water and dried over sodium sulfate. Removal of the solvent gave 145 mg (95% yield) of 3-methyl-4-trifluoromethanesulfonyloxy-benzofuran-2-carboxylic acid tert-butyl ester.

Step 2: 3-Methyl-4-trifluoromethanesulfonyloxy-benzofuran-2-carboxylic acid tert-butyl ester (285 mg, 0.75 mmol) was mixed with $K_2CO_3$ (207 mg, 2.2 eq), furan-3-boronic acid (101 mg, 1.2 eq), $Pd(Ph_3)_4$ (43 mg, 0.05 eq), 3 mL of 1,2-dimethoxyethane and 0.5 mL of water. The mixture was heated and stirred in a 85° C. oil bath for 2 h. The reaction mixture was poured into water and was extracted with ethyl acetate. The organic extract was washed with water and dried over sodium sulfate. Removal of the solvent in vacuo gave the crude product, which was purified by column chromatography to give 153 mg of 4-furan-3-yl-3-methyl-benzofuran-2-carboxylic acid tert-butyl ester, obtained as white solid.

Step 3: To 174 mg of 4-furan-3-yl-3-methyl-benzofuran-2-carboxylic acid tert-butyl ester was added 4 mL of TFA/dichloromethane (1:1). The solution was stirred at room temperature for 2 h. The solvents were removed under vacuum and the residue was triturated with ether. Filtration gave 124 mg of of 4-furan-3-yl-3-methyl-benzofuran-2-carboxylic acid as a white solid.

Step 4: To 4-furan-3-yl-3-methyl-benzofuran-2-carboxylic acid (114 mg, 0.47 mmol) was added (S)-2-(4'-amino-biphenyl-4-sulfonylamino)-3-methyl-butyric acid methyl ester (170 mg, 0.47 mmol), BOP (249 mg, 1.2 eq), N,N-diisopropylethylamine (0.1 mL, 1.2 eq) and 4 mL of DMF. The mixture was stirred at room temperature overnight. The reaction mixture was poured into brine, and extracted with ethyl acetate. The combined organic solution was washed with brine and water. Removal of the solvent gave the crude product, which was purified by column chromatography on silica gel to give 258 mg of (S)-2-{4'-[(4-furan-3-yl-3-methyl-benzofuran-2-carbonyl)-amino]-biphenyl-4-sulfony-lamino}-3-methyl-butyric acid methyl ester, obtained as white solid.

Step 5: To 240 mg of (S)-2-{4'-[(4-furan-3-yl-3-methyl-benzofuran-2-carbonyl)-amino]-biphenyl-4-sulfonylamino}-3-methyl-butyric acid methyl ester was added 2 mL of THF and 4 mL of LiOH solution (3.6 g LiOH/50 mL MeOH/50 mL H$_2$O). The mixture was stirred at room temperature for 4 days. The solvents were removed under vacuum and the residue was dissolved in 5 mL of water. The solution was acidified to pH2 and the resulting suspension was filtered. The solid product was dried under vacuum to give 171 mg of (S)-2-{4'-[(4-furan-3-yl-3-methyl-benzofuran-2-carbonyl)-amino]-biphenyl-4-sulfonylamino}-3-methyl-butyric acid was obtained as white solid. $^1$H NMR (400 MHz, DMSO-d$_6$) δ ppm 0.8 (dd, J=13.1, 6.8 Hz, 6 H) 2.4 (s, 3 H) 3.5 (m, 1 H) 6.8 (dd, J=1.9, 0.9 Hz, 1 H) 7.2 (dd, J=7.3, 1.0 Hz, 1 H) 7.5 (dd, J=7.6 Hz, 1 H) 7.7 (dd, J=8.5, 0.9 Hz, 1 H) 7.8 (d, J=8.8 Hz, 2 H) 7.8 (m, 4 H) 7.9 (m, 2 H) 7.9 (dd, J=1.5, 0.8 Hz, 1 H) 8.0 (m, 3 H) 10.6 (s, 1 H) 12.6 (s, 1 H).

Example 114

(S)-3-methyl-2-{4'-[(3-methyl-4-morpholin-4-yl-benzofuran-2-carbonyl)-amino]-biphenyl-4-sulfonylamino}-butyric acid

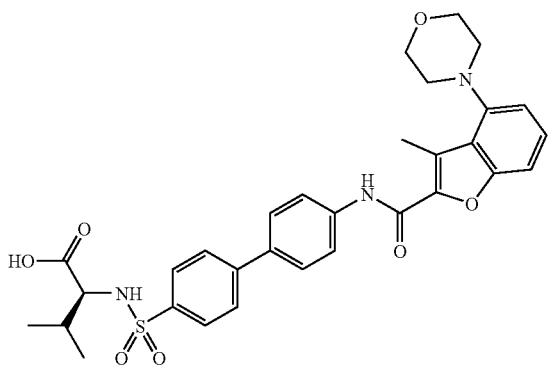

Step 1: To 4-hydroxy-3-methyl-benzofuran-2-carboxylic acid tert-butyl ester (100 mg, 0.4 mmol) was added N,N-diisopropylethylamine (130 mg, 1 mmol) and 2 mL of dichloromethane. The solution was cooled to <−10°C. Trifluoromethanesulfonic anhydride (0.1 mL, 0.6 mmol) was added dropwise. The reaction mixture was stirred at −10°C. for 2 h and was then poured into water. The mixture was extracted with dichloromethane and the combined organic layers were washed with water and dried over sodium sulfate. Removal of the solvent gave 145 mg (95% yield) of 3-methyl-4-trifluoromethanesulfonyloxy-benzofuran-2-carboxylic acid tert-butyl ester.

Step 2: To 3-methyl-4-trifluoromethanesulfonyloxy-benzofuran-2-carboxylic acid tert-butyl ester (190 mg, 0.5 mmol) was added K$_3$PO$_4$ (159 mg, 0.75 mmol), morpholine (52 mg, 0.6 mmol), Pd(OAc)$_2$ (10 mg) and 4 mL of dioxane. The mixture was heated and stirred in an 85° C. oil bath overnight. The reaction mixture was poured into water and was extracted with ethyl acetate. The organic extract was washed with water and dried over sodium sulfate. Removal of the solvent in vacuo gave the crude product, which was purified by column chromatography to give 96 mg of 3-methyl-4-morpholin-4-yl-benzofuran-2-carboxylic acid tert-butyl ester, obtained as white solid.

Step 3: To 140 mg 3-methyl-4-morpholin-4-yl-benzofuran-2-carboxylic acid tert-butyl ester was added 4 mL of TFA/dichloromethane (1:1). The solution was stirred at room temperature for 5 h. The solvents were removed under vacuum and the residue was triturated with ether. Filtration gave 107 mg of 3-methyl-4-morpholin-4-yl-benzofuran-2-carboxylic acid as a white solid.

Step 4: To 3-methyl-4-morpholin-4-yl-benzofuran-2-carboxylic acid (97 mg, 0.37 mmol) was added (S)-2-(4'-amino-biphenyl-4-sulfonylamino)-3-methyl-butyric acid methyl ester (268 mg, 0.74 mmol), BOP (327 mg, 0.74 mmol), N,N-diisopropylethylamine (0.13 mL, 0.74 mmol) and 4 mL of DMF. The mixture was stirred at room temperature overnight. The reaction mixture was poured into brine, and extracted with ethyl acetate. The combined organic solution was washed with brine and water. Removal of the solvent in vacuo gave the crude product, which was purified by column chromatography on silica gel to give 184 mg of (S)-3-methyl-2-{4'-[(3-methyl-4-morpholin-4-yl-benzofuran-2-carbonyl)-amino]-biphenyl-4-sulfonylamino}-butyric acid methyl ester, obtained as an off-white solid.

Step 5: To 160 mg of (S)-3-methyl-2-{4'-[(3-methyl-4-morpholin-4-yl-benzofuran-2-carbonyl)-amino]-biphenyl-4-sulfonylamino}-butyric acid methyl ester was added 1 mL of THF and 3 mL of LiOH solution (3.6 g LiOH/50 mL MeOH/50 mL H$_2$O). The mixture was stirred at room temperature for 4 days. The solvents were removed under vacuum and the residue was dissolved in 5 mL of water. The solution was acidified and the resulting suspension was filtered. The solid product was dried under vacuum to give 150 mg of (S)-3-methyl-2-{4'-[(3-methyl-4-morpholin-4-yl-benzofuran-2-carbonyl)-amino]-biphenyl-4-sulfonylamino}-butyric acid, obtained as an off-white solid. $^1$H NMR (400 MHz, DMSO-d$_6$) δ ppm 0.8 (dd, J=14.1, 6.8 Hz, 6 H) 2.0 (dd, J=12.1, 6.8 Hz, 1 H) 2.8 (s, 3 H) 3.0 (m, 4 H) 3.5 (m, 1 H) 3.8 (m, 4 H) 7.0 (d, J=7.8 Hz, 1 H) 7.4 (d, J=8.3 Hz, 1 H) 7.4 (m, 1 H) 7.8 (d, J=8.6 Hz, 2 H) 7.8 (m, 4 H) 8.0 (d, J=9.1 Hz, 3 H) 10.5 (s, 1 H).

Example 115

(S)-2-{4'-[(5-Chloro-4-isopropoxy-3-methyl-benzofuran-2-carbonyl)-amino]-biphenyl-4-sulfonylamino}-3-methyl-butyric acid

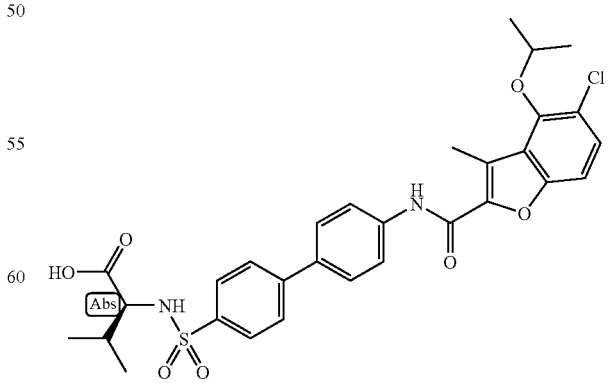

Step 1: To 4-hydroxy-3-methyl-benzofuran-2-carboxylic acid ethyl ester (0.5 g, 2.27 mmol) was added 5 mL of carbon tetrachloride, and the mixture was cooled with an ethanol/ice bath while 1 equivalent of N-chlorosuccinimide was added in small poroom temperatureions. After stirring at −10° C. for 3 h, the reaction mixture was filtered and the filtrate was loaded onto a silica column and chromatographed to give 259 mg (48% yield) of 5-chloro-4-hydroxy-3-methyl-benzofuran-2-carboxylic acid ethyl ester as an off-white solid.

Step 2: To 5-chloro-4-hydroxy-3-methyl-benzofuran-2-carboxylic acid ethyl ester (110 mg) was added 2 mL of isopropylbromide, 150 mg of $K_2CO_3$ and 4 mL of DMF. The mixture was stirred at room temperature overnight. The mixture was washed with brine and extracted with ethyl acetate. The combined ethyl acetate layers were washed with brine. Removal of the solvent in vacuo gave 134 mg of 5-chloro-4-isopropoxy-3-methyl-benzofuran-2-carboxylic acid ethyl ester as a thick colorless oil (100% yield).

Step 3: To 110 mg of 5-chloro-4-isopropoxy-3-methyl-benzofuran-2-carboxylic acid ethyl ester was added 1 mL of THF and 3 mL of LiOH solution (3.6 g LiOH/50 mL MeOH/50 mL $H_2O$) was added. The mixture was stirred at room temperature overnight. The solvents were removed under vacuum and the residue was dissolved in 5 mL of water. The solution was acidified and resulting suspension was filtered. The solid product was dried under vacuum to give 94 mg (94% yield) of 5-chloro-4-isopropoxy-3-methyl-benzofuran-2-carboxylic acid.

Step 4: To 80 mg of 5-chloro-4-isopropoxy-3-methyl-benzofuran-2-carboxylic acid was added 121 mg of (S)-2-(4'-amino-biphenyl-4-sulfonylamino)-3-methyl-butyric acid tert-butyl ester, 159 mg of BOP, 46 mg of N,N-diisopropyl-ethylamine and 4 mL of DMF. The mixture was stirred at room temperature for 48 h. The mixture was addedbrine and was extracted with ethyl acetate. The combined ethyl acetate solution was washed with brine. Removal of the solvent and purification of the residue by column chromatography on silica gel gave 178 mg (98% yield) of (S)-2-{4'-[(5-chloro-4-isopropoxy-3-methyl-benzofuran-2-carbonyl)-amino]-biphenyl-4-sulfonylamino}-3-methyl-butyric acid tert-butyl ester as a colorless semi-solid.

Step 5: To 160 mg of (S)-2-{4'-[(5-chloro-4-isopropoxy-3-methyl-benzofuran-2-carbonyl)-amino]-biphenyl-4-sulfonylamino}-3-methyl-butyric acid tert-butyl ester was added 3 mL of TFA/dichloromethane (1:1) and the solution was stirred at room temperature for 9 h. When the reaction was done, the solvents were removed under vacuum and the residue was triturated with acetonitrile. The mixture was freeze-dried to yield 120 mg (77% yield) of (S)-2-{4'-[(5-chloro-4-isopropoxy-3-methyl-benzofuran-2-carbonyl)-amino]-biphenyl-4-sulfonylamino}-3-methyl-butyric acid as a white solid. $^1$H NMR (400 MHz, DMSO-$d_6$) δ ppm 0.8 (dd, J=12.4, 6.8 Hz, 6 H) 1.3 (d, J=6.1 Hz, 6 H) 1.9 (m, 1 H) 2.7 (s, 3 H) 3.6 (dd, J=9.3, 6.1 Hz, 1 H) 4.7 (m, 1 H) 7.5 (d, J=8.8 Hz, 1 H) 7.6 (m, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.6 (s, 1 H) 12.6 (s, 1 H).

Example 116

(S)-2-{4'-[(5-Chloro-4-methoxy-3-methyl-benzofuran-2-carbonyl)-amino]-biphenyl-4-sulfonylamino}-3-methyl-butyric acid

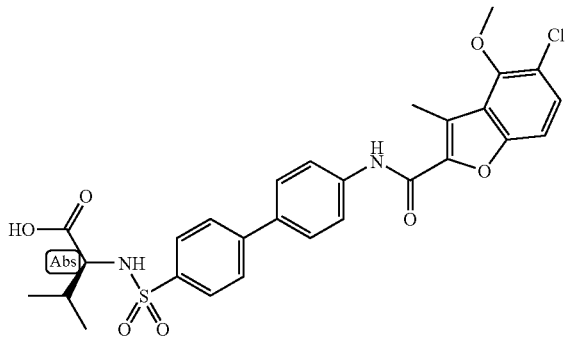

Step 1: To 4-hydroxy-3-methyl-benzofuran-2-carboxylic acid ethyl ester 0.5 g (2.27 mmol) was added 5 mL of carbon tetrachloride, and the mixture was cooled with an ethanol/ice bath while 1 equivalent of N-chlorosuccinimide was added in small portions. After stirring at −10° C. for 3 h, the reaction mixture was filtered and the filtrate was loaded onto a silica gel column. Chromatography gave 259 mg (48% yield) of 5-chloro-4-hydroxy-3-methyl-benzofuran-2-carboxylic acid ethyl ester as an off-white solid.

Step 2: To 5-chloro-4-hydroxy-3-methyl-benzofuran-2-carboxylic acid ethyl ester (120 mg, 0.47 mmol) was added 0.3 mL (4.7 mmol) of iodomethane, 130 mg (2 eq) of $K_2CO_3$ and 4 mL of DMF. The mixture was stirred at room temperature overnight. The mixture was washed with brine and extracted with ethyl acetate. The combined organic solution was washed with brine and water. Removal of the solvent in vacuo gavel 19 mg (94% yield) of 5-chloro-4-methoxy-3-methyl-benzofuran-2-carboxylic acid ethyl ester as a white solid.

Step 3: To 105 mg of 5-chloro-4-methoxy-3-methyl-benzofuran-2-carboxylic acid ethyl ester was added 1 mL of THF and 3 mL of LiOH solution (3.6 g LiOH/50 mL MeOH/50 mL $H_2O$). The mixture was stirred at room temperature overnight. The solvents were removed under vacuum and the residue was dissolved in 5 mL of water. The solution was acidified and the resulting suspension was filtered. The solid product was triturated with dichloromethane and dried under vacuum to give 82 mg (87% yield) of 5-chloro-4-methoxy-3-methyl-benzofuran-2-carboxylic acid.

Step 4: To 80 mg (0.33 mmol) of 5-chloro-4-methoxy-3-methyl-benzofuran-2-carboxylic acid was added 2 mL of oxalyl chloride and the mixture refluxed for 2 h, then stirred room temperature overnight. The excess oxalyl chloride was removed under vacuum. The residue was dissolved in 2 mL of dichloromethane and was added to a mixture of 181 mg (0.5 mmol) of (S)-2-(4'-amino-biphenyl-4-sulfonylamino)-3-methyl-butyric acid methyl ester and 1 mL of pyridine in an ice/water bath. The mixture was stirred at 0° C. overnight. The reaction mixture was diluted with dichloromethane and was washed with 2N HCl, and water. Removal of the solvent in vacuo gave the crude product which was purified by column chromatography to give 168 mg (86% yield) of (S)-2-{4'-[(5- chloro-4-methoxy-3-methyl-benzofuran-2-carbonyl)-amino]-biphenyl-4-sulfonylamino}-3-methyl-butyric acid methyl ester as a white solid.

Step 5: To 100 mg of (S)-2-{4'-[(5-chloro-4-methoxy-3-methyl-benzofuran-2-carbonyl)-amino]-biphenyl-4-sulfonylamino}-3-methyl-butyric acid methyl ester was added 2 mL of THF and 2 mL of LiOH solution (3.6 g LiOH/50 mL MeOH/50 mL H$_2$O) was added. The mixture was stirred at room temperature for 3 days. The solvents were removed under vacuum and the residue was dissolved in 5 mL of water. The solution was acidified and the resulting suspension was filtered. The solid product was dried under vacuum to give 60 mg (62% yield) of (S)-2-{4'-[(5-chloro-4-methoxy-3-methyl-benzofuran-2-carbonyl)-amino]-biphenyl-4-sulfonylamino}-3-methyl-butyric acid. $^1$H NMR (400 MHz, DMSO-d$_6$) δ ppm 0.8 (dd, J=12.4, 6.8 Hz, 6 H) 2.0 (dd, J=13.1, 6.6 Hz, 1 H) 2.7 (s, 3 H) 3.6 (dd, J=9.3, 6.1 Hz, 1 H) 3.9 (s, 3 H) 7.5 (d, J=8.6 Hz, 1 H) 7.6 (m, 1 H) 7.8 (d, J=8.8 Hz, 2 H) 7.9 (m, 4 H) 8.0 (d, J=8.8 Hz, 2 H) 8.1 (d, J=9.3 Hz, 1 H) 10.6 (s, 1 H) 12.6 (s, 1 H).

Example 117

(S)-2-{4'-[(5,7-Dichloro-4-methoxy-3-methyl-benzofuran-2-carbonyl)-amino]-biphenyl-4-sulfonylamino}-3-methyl-butyric acid

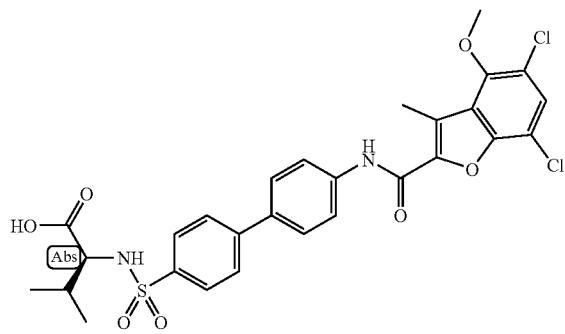

Step 1: To 4-hydroxy-3-methyl-benzofuran-2-carboxylic acid ethyl ester (0.5 g, 2.27 mmol) was added 5 mL of carbon tetrachloride, carbon tetrachloride, and the mixture was cooled with an ethanol/ice bath while 1 equivalent of N-chlorosuccinimide was added in small portions. After stirring at −10° C. for 3 h, the reaction mixture was filtered and the filtrate was loaded onto a silica gel column. Chromatography gave 190 mg (30% yield) of 5,7-dichloro-4-hydroxy-3-methyl-benzofuran-2-carboxylic acid ethyl ester as an off-white solid.

Step 2: To 120 mg of 5,7-dichloro-4-hydroxy-3-methyl-benzofuran-2-carboxylic acid ethyl ester was added 1 mL of iodomethane, 200 mg of K$_2$CO$_3$ and 4 mL of DMF. The mixture was stirred at room temperature overnight. The mixture was washed with brine and extracted with ethyl acetate. The combined ethyl acetate solution was washed with brine. Removal of the solvent in vacuo gave 125 mg (99% yield) of 5,7-dichloro-4-methoxy-3-methyl-benzofuran-2-carboxylic acid ethyl ester as off-white solid.

Step 3: To 110 mg of 5,7-dichloro-4-methoxy-3-methyl-benzofuran-2-carboxylic acid ethyl ester was added 1 mL of THF and 3 mL of LiOH solution (3.6 g LiOH/50 mL MeOH/50 mL H$_2$O). The mixture was stirred at room temperature overnight. The solvents were removed under vacuum and the residue was dissolved in 5 mL of water. The solution was acidified and the resulting suspension was filtered. The solid product was dried under vacuum to give 96 mg (96% yield) of 5,7-dichloro-4-methoxy-3-methyl-benzofuran-2-carboxylic acid, obtained as a white solid.

Step 4: To 80 mg of 5,7-dichloro-4-methoxy-3-methyl-benzofuran-2-carboxylic acid was added 120 mg of (S)-2-(4'-amino-biphenyl-4-sulfonylamino)-3-methyl-butyric acid tert-butyl ester, 154 mg of BOP, 50 mg of N,N-diisopropylethylamine and 4 mL of DMF. The mixture was stirred at room temperature for 48 h. The mixture was washed with brine and was extracted with ethyl acetate. The combined ethyl acetate layers were washed with brine. Removal of the solvent in vacuo and purification of the residue by column chromatography on silica gel gave 110 mg (60% yield) of (S)-2-{4'-[(5,7-dichloro-4-methoxy-3-methyl-benzofuran-2-carbonyl)-amino]-biphenyl-4-sulfonylamino}-3-methyl-butyric acid tert-butyl ester as an off-white solid.

Step 5: To 102 mg of (S)-2-{4'-[(5,7-dichloro-4-methoxy-3-methyl-benzofuran-2-carbonyl)-amino]-biphenyl-4-sulfonylamino}-3-methyl-butyric acid tert-butyl ester was added 3 mL of TFA/dichloromethane (1:1) and the solution was stirred at room temperature for 3 h. When the reaction was done, the solvents were removed under vacuum and the residue was triturated with ether/chloroform. Filtration of the suspension gave 67 mg (72% yield) of (S)-2-{4'-[(5,7-dichloro-4-methoxy-3-methyl-benzofuran-2-carbonyl)-amino]-biphenyl-4-sulfonylamino}-3-methyl-butyric acid as a white solid. $^1$H NMR (400 MHz, DMSO-d$_6$) δ ppm 0.8 (dd, J=12.4, 6.8 Hz, 6 H) 1.9 (m, 1 H) 2.7 (s, 3 H) 3.6 (dd, J=9.3, 6.1 Hz, 1 H) 3.9 (s, 3 H) 7.8 (m, 5 H) 7.9 (m, 2 H) 7.9 (d, J=8.6 Hz, 2 H) 8.1 (d, J=9.6 Hz, 1 H) 10.6 (s, 1 H) 12.6 (s, 1 H).

Example 118

(S)-2-{4'-[(5-bromo-4-methoxy-3-methyl-benzofuran-2-carbonyl)-amino]-biphenyl-4-sulfonylamino}-3-methyl-butyric acid

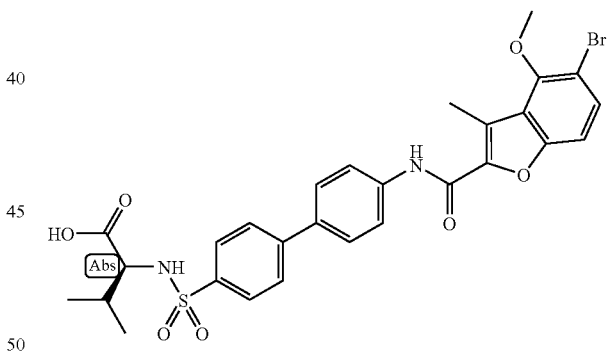

Step 1: To 200 mg (0.81 mmol) of 4-hydroxy-3-methyl-benzofuran-2-carboxylic acid tert-butyl ester was added 2 mL of carbon tetrachloride. The mixture was cooled with water/ice bath while 1 equivalent of N-bromosuccinimide was added in small portions. After stirring at 0° C. for 6 h, the reaction mixture was filtered and the filtrate was loaded onto a column and purified by column chromatography to give 225 mg (85% yield) of 5-bromo-4-hydroxy-3-methyl-benzofuran-2-carboxylic acid tert-butyl ester as a white solid.

Step 2: To 220 mg (0.67 mmol) of 5-bromo-4-hydroxy-3-methyl-benzofuran-2-carboxylic acid tert-butyl ester was added 0.42 mL (6.7 mmol) of iodomethane, 185 mg (1.34 mmol) of K$_2$CO$_3$ and 2 mL of DMF. The mixture was stirred at room temperature overnight. The mixture was washed with brine and extracted with ethyl acetate. The combined ethyl acetate layers were washed with brine. Removal of the solvent gave 230 mg (100% yield) of 5-bromo-4-methoxy-3-methyl-benzofuran-2-carboxylic acid tert-butyl ester as a colorless oil.

Step 3: To 220 mg of 5-bromo-4-methoxy-3-methyl-benzofuran-2-carboxylic acid tert-butyl ester was added 3 mL of TFA/dichloromethane (1:1) and the solution was stirred at room temperature for 10 h. When the reaction was done, the solvents were removed by vacuum and the residue was triturated with hexane/dichloromethane. Filtration of the suspension gave 141 mg (77% yield) of 5-bromo-4-methoxy-3-methyl-benzofuran-2-carboxylic acid as a white solid.

Step 4: To 40 mg (0.14 mmol) of 5-bromo-4-methoxy-3-methyl-benzofuran-2-carboxylic acid was added 0.5 mL of oxalyl chloride and the mixture was refluxed for 2 h, then the excess oxalyl chloride was removed by vacuum. The residue was dissolved in 0.5 mL of dichloromethane and was added to a mixture of 92 mg (0.25 mmol) of (S)-2-(4'-amino-biphenyl-4-sulfonylamino)-3-methyl-butyric acid methyl ester, 34 mg (0.28 mmol) of 4-(dimethylamino)pyridine and 1 mL of dichloromethane in an ice/water bath. The mixture was stirred at 0° C. for overnight. The mixture was diluted with dichloromethane and was washed with 2N HCl, and water. Removal of the solvent from the organic solution gave 20 mg (23% yield) of (S)-2-{4'-[(5-bromo-4-methoxy-3-methyl-benzofuran-2-carbonyl)-amino]-biphenyl-4-sulfonylamino}-3-methyl-butyric acid methyl ester as an off-white solid.

Step 5: To 18 mg of (S)-2-{4'-[(5-bromo-4-methoxy-3-methyl-benzofuran-2-carbonyl)-amino]-biphenyl-4-sulfonylamino}-3-methyl-butyric acid methyl ester was added 0.5 mL of THF and 0.5 mL of LiOH solution (3.6 g LiOH/50 mL MeOH/50 mL $H_2O$). The mixture was stirred at room temperature for 6 days. The solvents were removed under vacuum and the residue was dissolved in 5 mL of water. The solution was acidified and the resulting suspension was filtered. The solid product was dried under vacuum to give 8 mg (39% yield) of (S)-2-{4'-[(5-bromo-4-methoxy-3-methyl-benzofuran-2-carbonyl)-amino]-biphenyl-4-sulfonylamino}-3-methyl-butyric acid. $^1$H NMR (400 MHz, DMSO-$d_6$) δ ppm 0.8 (dd, J=12.9, 6.8 Hz, 6 H) 2.0 (m, 1 H) 2.7 (s, 3 H) 3.6 (dd, J=9.0, 5.9 Hz, 1 H) 3.9 (s, 3 H) 7.5 (d, J=8.8 Hz, 1 H) 7.7 (d, J=8.8 Hz, 1 H) 7.8 (d, J=8.6 Hz, 2 H) 7.9 (m, 4 H) 8.0 (d, J=8.8 Hz, 2 H) 8.1 (d, J=9.1 Hz, 1 H) 10.6 (s, 1 H) 12.6 (s, 1 H).

Example 119

(R)-2-{4'-[(5-Bromo-4-methoxy-3-methyl-benzofuran-2-carbonyl)-amino]-biphenyl-4-sulfonylamino}-3-methyl-butyric acid

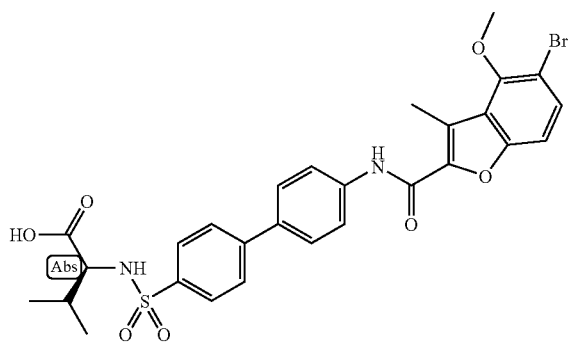

Step 1: To 2 g (0.81 mmol) of 4-hydroxy-3-methyl-benzofuran-2-carboxylic acid ethyl ester was added 20 mL of carbon tetrachloride, and the mixture was cooled with a water/ice bath while 1 equivalent of N-bromosuccinimide was added in small portions. After stirring at 0° C. for 3 h, the reaction mixture was filtered and the filtrate was loaded onto a column and purified by column chromatography to give 1.6 mg (59% yield) of 5-bromo-4-hydroxy-3-methyl-benzofuran-2-carboxylic acid ethyl ester as a white solid.

Step 2: To 200 mg (0.67 mmol) of 5-bromo-4-hydroxy-3-methyl-benzofuran-2-carboxylic acid ethyl ester was added 0.5 mL of iodomethane, 200 mg of $K_2CO_3$ and 2 mL of DMF. The mixture was stirred at room temperature overnight. The mixture was washed with brine and extracted with ethyl acetate. The combined ethyl acetate layers were washed with brine. Removal of the solvent in vacuo gave 185 mg (88% yield) of 5-bromo-4-methoxy-3-methyl-benzofuran-2-carboxylic acid ethyl ester as a white solid.

Step 3: To 170 mg of 5-bromo-4-methoxy-3-methyl-benzofuran-2-carboxylic acid ethyl ester was added 1 mL of THF and 3 mL of LiOH solution (3.6 g LiOH/50 mL MeOH/50 mL $H_2O$). The mixture was stirred at room temperature overnight. The solvents were removed under vacuum and the residue was dissolved in 5 mL of water. The solution was acidified and the resulting suspension was filtered. The solid product was dried under vacuum to give 156 mg (100% yield) of 5-bromo-4-methoxy-3-methyl-benzofuran-2-carboxylic acid, obtained as a white solid.

Step 4: To 75 mg (0.263 mmol) of 5-bromoo-4-methoxy-3-methyl-benzofuran-2-carboxylic acid was added 2 mL of oxalyl chloride and the mixture was refluxed for 2 h in the presence of a catalytic amount of DMF, then the excess oxalyl chloride was removed by vacuum. The residue was dissolved in 0.5 mL of dichloromethane and was added to a mixture of 143 mg (0.39 mmol) of (R)-2-(4'-amino-biphenyl-4-sulfonylamino)-3-methyl-butyric acid methyl ester, 2 mL of pyridine in an ice/water bath. The mixture was stirred at room temperature overnight. The solvent was removed under vacuum. Column chromatography on silica gel gave 89 mg (54% yield) of (R)-2-{4'-[(5-bromo-4-methoxy-3-methyl-benzofuran-2-carbonyl)-amino]-biphenyl-4-sulfonylamino}-3-methyl-butyric acid methyl ester as an off-white solid.

Step 5: To 89 mg of (R)-2-{4'-[(5-bromo-4-methoxy-3-methyl-benzofuran-2-carbonyl)-amino]-biphenyl-4-sulfonylamino}-3-methyl-butyric acid methyl ester was added 1 mL of THF and 3 mL of LiOH solution (3.6 g LiOH/50 mL MeOH/50 mL $H_2O$). The mixture was stirred at room temperature for 4 days. The solvents were removed under vacuum and the residue was dissolved in 5 mL of water. The solution was acidified and the resulting suspension was filtered. The solid product was dried under vacuum and triturated with 0.5 mL of chloroform to give 49 mg (56% yield) of (R)-2-{4'-[(5-bromo-4-methoxy-3-methyl-benzofuran-2-carbonyl)-amino]-biphenyl-4-sulfonylamino}-3-methyl-butyric acid. $^1$H NMR (400 MHz, DMSO-$d_6$) δ ppm 0.8 (dd, J=12.4, 6.8 Hz, 6 H) 2.0 (m, 1 H) 2.7 (s, 3 H) 3.6 (dd, J=9.3, 6.1 Hz, 1 H) 3.9 (s, 3 H) 7.7 (d, J=8.8 Hz, 1 H) 7.8 (d, J=8.8 Hz, 2 H) 7.9 (m, 4 H) 8.0 (d, J=8.8 Hz, 2 H) 8.1 (d, J=9.3 Hz, 1 H) 8.3 (s, 1 H) 10.6 (s, 1 H) 12.6 (s, 1 H).

Example 120

(S)-2-{4'-[(5-Iodo-4-methoxy-3-methyl-benzofuran-2-carbonyl)-amino]-biphenyl-4-sulfonylamino}-3-methyl-butyric acid

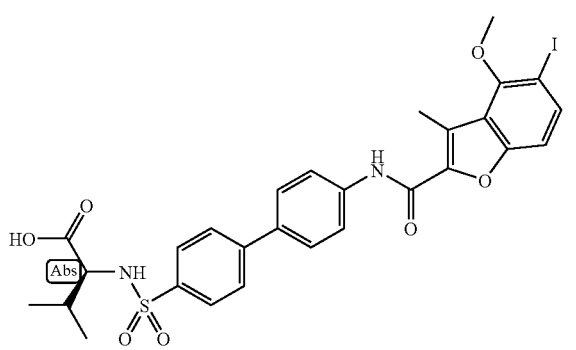

Step 1: To 4.4 g (17.7 mmol) of 4-hydroxy-3-methyl-benzofuran-2-carboxylic acid tert-butyl ester was added 40 mL of carbon tetrachloride, the mixture was cooled with an water/ice bath while 1 equivalent of N-iodosuccinimide was added in small portions. After stirring at 0° C. for 3 h, the reaction mixture was loaded onto a column and purified by column chromatography to give 2.55 g mg (38% yield) of 5-iodo-4-hydroxy-3-methyl-benzofuran-2-carboxylic acid tert-butyl ester as a white solid.

Step 2: To 748 mg (2 mmol) of 5-iodo-4-hydroxy-3-methyl-benzofuran-2-carboxylic acid tert-butyl ester was added 1.42 g (10 mmol) of iodomethane, 553 mg (4 mmol) of $K_2CO_3$ and 10 mL of DMF. The mixture was stirred at room temperature overnight. The reaction mixture was washed with brine and extracted with ethyl acetate. The combined ethyl acetate layers were washed with brine. Removal of the solvent in vacuo gave 790 mg (100% yield) 5-iodo-4-methoxy-3-methyl-benzofuran-2-carboxylic acid tert-butyl ester as a pale brown oil.

Step 3: To 140 mg (0.36 mmol) of 5-iodo-4-methoxy-3-methyl-benzofuran-2-carboxylic acid tert-butyl ester was added 3 mL of TFA/dichloromethane (1:1) and the solution was stirred at room temperature for 2.5 h. When the reaction was done, the solvents were removed by vacuum and the residue was triturated with hexane/dichloromethane. Filtration of the suspension gave 120 mg (100% yield) of 5-iodo-4-methoxy-3-methyl-benzofuran-2-carboxylic acid as a white solid.

Step 4: To 110 mg (0.33 mmol) of 5-iodo-4-methoxy-3-methyl-benzofuran-2-carboxylic acid was added 132 mg (1.1 eq) of (S)-2-(4'-amino-biphenyl-4-sulfonylamino)-3-methyl-butyric acid methyl ester, BOP (34 mg, 1.2 eq), N,N-diisopropylethylamine (52 mg, 1.2 eq) and 4 mL of DMF. The mixture was stirred at room temperature for 48 h. Brine was added and the mixture was extracted with ethyl acetate. The combined organic solution was washed with 2N HCl and water. Concentration of the organics in vacuo gave the crude product which was purified by column chromatography on silica gel to give 106 mg (47% yield) of (S)-2-{4'-[(5-iodo-4-methoxy-3-methyl-benzofuran-2-carbonyl)-amino]-biphenyl-4-sulfonylamino}-3-methyl-butyric acid methyl ester was obtained as an off-white solid.

Step 5: To 96 mg of (S)-2-{4'-[(5-iodo-4-methoxy-3-methyl-benzofuran-2-carbonyl)-amino]-biphenyl-4-sulfonylamino}-3-methyl-butyric acid methyl ester was added 0.5 mL of THF and 2 mL of LiOH solution (3.6 g LiOH/50 mL MeOH/50 mL $H_2O$. The mixture was stirred at room temperature for 3 days. The solvents were removed under vacuum and the residue was dissolved in 5 mL of water. The solution was acidified and the resulting suspension was filtered. The solid product was dried under vacuum to give 60 mg (63% yield) of (S)-2-{4'-[(S-iodo-4-methoxy-3-methyl-benzofuran-2-carbonyl)-amino]-biphenyl-4-sulfonylamino}-3-methyl-butyric acid. $^1$H NMR (400 MHz, DMSO-$d_6$) δ ppm 0.8 (dd, J=13.9, 6.8 Hz, 6 H) 2.0 (m, 1 H) 2.7 (s, 3 H) 3.5 (m, 1 H) 3.9 (s, 3 H) 7.3 (d, J=8.6 Hz, 1 H) 7.8 (d, J=8.8 Hz, 2 H) 7.9 (m, 5 H) 8.0 (d, J=9.1 Hz, 3 H) 10.6 (s, 1 H).

Example 121

(S)-2-{4'-[(5-Acetyl-4-methoxy-3-methyl-benzofuran-2-carbonyl)-amino]-biphenyl-4-sulfonylamino}-3-methyl-butyric acid

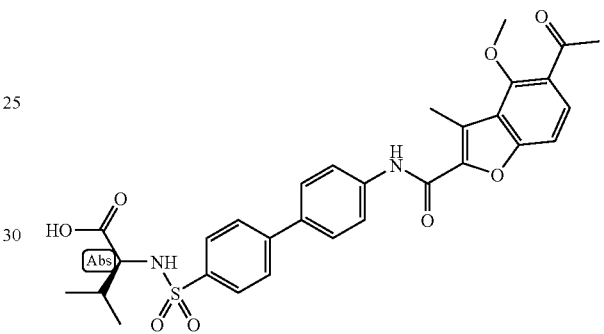

Step 1: To 4-hydroxy-3-methyl-benzofuran-2-carboxylic acid tert-butyl ester (300 mg, 1.21 mmol) was added iodomethane (0.75 mL, 10 eq), $K_2CO_3$ (332 mg, 2.4 mmol) and 2 mL of DMF. The mixture was stirred at room temperature overnight. The mixture was washed with brine and extracted with ethyl acetate. The combined ethyl acetate solution was washed with brine. Removal of the solvent gave 312 mg (98% yield) of 4-methoxy-3-methyl-benzofuran-2-carboxylic acid tert-butyl ester as an amber colored oil.

Step 2: To 4-methoxy-3-methyl-benzofuran-2-carboxylic acid tert-butyl ester (310 mg, 1.18 mmol) dissolved in 9 mL of chlorobenzene was added acetyl chloride (0.3 mL, 3.6 eq). The solution was cooled to <0° C. while titanium tetrachloride (0.61 mL, 4.8 eq) was added dropwise. The reaction mixture was stirred at 0° C. and below for 6 h and then heated in an 85° C. oil bath for 3.5 h. The reaction mixture was poured into ice/water, and the mixture was extracted with ethyl acetate. The combined organic solution was washed with 2N HCl and water. Removal of the solvents in vacuo gave 167 mg (57% yield) of 5-acetyl-4-methoxy-3-methyl-benzofuran-2-carboxylic acid.

Step 3: To 75 mg (0.3 mmol) of 5-acetyl-4-methoxy-3-methyl-benzofuran-2-carboxylic acid was added 1 mL of oxalyl chloride and the mixture was refluxed for 2.5 h in the presence of a catalytic amount of DMF, then the excess oxalyl chloride was removed under vacuum. The residue was dissolved in 1 mL of dichloromethane and was added to a mixture of 163 mg (0.46 mmol) of (S)-2-(4'-amino-biphenyl-4-sulfonylamino)-3-methyl-butyric acid methyl ester and 2 mL of pyridine in an ice/water bath. The mixture was stirred at room temperature overnight. All the solvents were removed under vacuum. Column chromatography on silica gel gave 54 mg (31% yield) of (S)-2-{4'-[(5-acetyl-4-methoxy-3-methyl-benzofuran-2-carbonyl)-amino]-biphenyl-4-sulfonylamino}-3-methyl-butyric acid methyl ester as an off-white solid.

Step 4: To (S)-2-{4'-[(5-acetyl-4-methoxy-3-methyl-benzofuran-2-carbonyl)-amino]-biphenyl-4-sulfonylamino}-3-methyl-butyric acid methyl ester (89 mg) was added 1 mL of THF and 3 mL of LiOH solution (3.6 g LiOH/50 mL MeOH/50 mL H$_2$O). The mixture was stirred at room temperature for 2 days. The solvents were removed under vacuum and the residue was triturated with 4 mL of 2N HCl and filtered. The solid product was dried under vacuum to give 54 mg of (S)-2-{4'-[(5-acetyl-4-methoxy-3-methyl-benzofuran-2-carbonyl)-amino]-biphenyl-4-sulfonylamino}-3-methyl-butyric acid was obtained as an off-white solid. $^1$H NMR (400 MHz, DMSO-d$_6$) δ ppm 0.8 (dd, J=12.9, 6.8 Hz, 6 H) 2.0 (m, 1 H) 2.7 (s, 3 H) 2.9 (s, 3 H) 3.6 (dd, J=9.3, 6.1 Hz, 1 H) 4.0 (s, 3 H) 7.0 (d, J=8.8 Hz, 1 H) 7.8 (m, 4 H) 7.9 (m, 4 H) 8.0 (d, J=8.6 Hz, 1 H) 8.1 (d, J=9.3 Hz, 1 H) 10.3 (s, 1 H) 12.6 (s, 1 H).

Example 122

(S)-2-(4'-{[5-(1-Chloro-vinyl)-4-methoxy-3-methyl-benzofuran-2-carbonyl]-amino}-biphenyl-4-sulfonylamino)-3-methyl-butyric acid

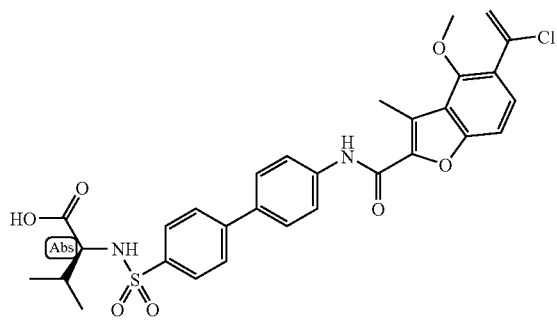

Step 1: To 4-hydroxy-3-methyl-benzofuran-2-carboxylic acid tert-butyl ester (300 mg, 1.21 mmol) was added iodomethane (0.75 mL, 10 eq), K$_2$CO$_3$ (332 mg, 2.4 mmol) and 2 mL of DMF. The mixture was stirred at room temperature overnight. The mixture was washed with brine and extracted with ethyl acetate. The combined ethyl acetate solution was washed with brine. Removal of the solvent gave 312 mg (98% yield) of 4-methoxy-3-methyl-benzofuran-2-carboxylic acid tert-butyl ester as an amber colored oil.

Step 2: To 4-methoxy-3-methyl-benzofuran-2-carboxylic acid tert-butyl ester (310 mg, 1.18 mmol) dissolved in 9 mL of chlorobenzene was added acetyl chloride (0.3 mL, 3.6 eq). The solution was cooled to <0° C. while titanium tetrachloride (0.61 mL, 4.8 eq) was added dropwise. The reaction mixture was stirred at 0° C. and below for 6 h and then heated in an 85° C. oil bath for 3.5 h. The reaction mixture was poured into ice/water, and the mixture was extracted with ethyl acetate. The combined organic solution was washed with 2N HCl and water. Removal of the solvents gave 167 mg (57% yield) of 5-acetyl-4-methoxy-3-methyl-benzofuran-2-carboxylic acid.

Step 3: To 75 mg (0.3 mmol) of 5-acetyl-4-methoxy-3-methyl-benzofuran-2-carboxylic acid was added 1 mL of oxalyl chloride and the mixture was refluxed for 2.5 h in the presence of a catalytic amount of DMF, then the excess oxalyl chloride was removed under vacuum. The residue was dissolved in 1 mL of dichloromethane and was added to a mixture of 163 mg (0.46 mmol) of (S)-2-(4'-amino-biphenyl-4-sulfonylamino)-3-methyl-butyric acid methyl ester and 2 mL of pyridine in an ice/water bath. The mixture was stirred at room temperature overnight. All the solvents were removed under vacuum. Column chromatography on silica gel gave 36 mg (20% yield) of (S)-2-(4'-{[5-(1-chloro-vinyl)-4-methoxy-3-methyl-benzofuran-2-carbonyl]-amino}-biphenyl-4-sulfonylamino)-3-methyl-butyric acid methyl ester as an off-white solid.

Step 4: To (S)-2-(4'-{[5-(1-chloro-vinyl)-4-methoxy-3-methyl-benzofuran-2-carbonyl]-amino}-biphenyl-4-sulfonylamino)-3-methyl-butyric acid methyl ester (29 mg) was added 0.5 mL of THF and 2 mL of LiOH solution (3.6 g LiOH/50 mL MeOH/50 mL H$_2$O). The mixture was stirred at room temperature for 3 days. The solvents were removed under vacuum and the residue was triturated with 2 mL of 2N HCl and filtered. The solid product was dried under vacuum. 23 mg of desired (S)-2-(4'-{[5-(1-chloro-vinyl)-4-methoxy-3-methyl-benzofuran-2-carbonyl]-amino}-biphenyl-4-sulfonylamino)-3-methyl-butyric acid, obtained as an off-white solid. $^1$H NMR (400 MHz, DMSO-d$_6$) δ ppm 0.8 (dd, J=12.9, 6.8 Hz, 6 H) 2.0 (m, 1 H) 2.7 (s, 3 H) 3.6 (dd, J=9.3, 6.1 Hz, 1 H) 4.0 (s, 3 H) 5.9 (d, J=2.3 Hz, 1 H) 6.7 (d, J=2.3 Hz, 1 H) 7.0 (d, J=8.6 Hz, 1 H) 7.7 (d, J=8.6 Hz, 1 H) 7.8 (m, 8 H) 8.1 (d, 1 H) 10.3 (s, 1 H) 12.6 (s, 1 H).

Example 123

(S)-2-{4'-[(5-Acetyl-4-hydroxy-3-methyl-benzofuran-2-carbonyl)-amino]-biphenyl-4-sulfonylamino}-3-methyl-butyric acid

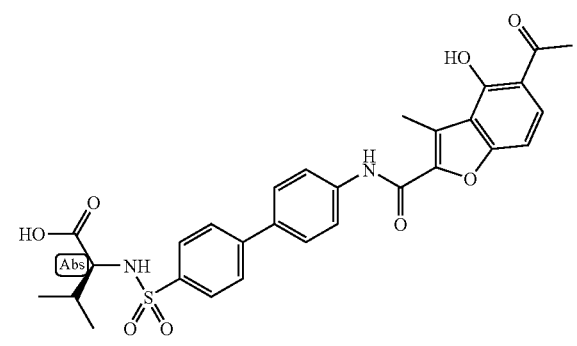

Step 1. To 4-hydroxy-3-methyl-benzofuran-2-carboxylic acid ethyl ester 0.5 g (2.27 mmol) was added 15 mL of chlorobenzene, 0.27 g (3.4 mmol) of acetyl chloride and 0.63 mL (5.7 mmol) of titanium tetrachloride. The mixture was sealed in a pressure tube and the tube was placed in 95° C. oil bath for 5 h with stirring. The reaction mixture was washed with 0.5N HCl and was extracted with ethyl acetate. Removal of the solvents gave the crude product, which was purified by column chromatography to give 0.33 g (59% yield) of 5-acetyl-4-hydroxy-3-methyl-benzofuran-2-carboxylic acid ethyl ester as a white solid.

Step 2. To 100 mg of 5-acetyl-4-hydroxy-3-methyl-benzofuran-2-carboxylic acid ethyl ester was added 1 mL of THF and 3 mL of LiOH solution (3.6 g LiOH/50 mL MeOH/50 mL H$_2$O). The mixture was stirred at room temperature overnight. The solvents were removed under vacuum and the residue was dissolved in 5 mL of water. The solution was acidified and resulting suspension was filtered. The solid product was dried under vacuum to give 82 mg (92% yield) of 5-bromo-4-methoxy-3-methyl-benzofuran-2-carboxylic acid.

Step 3: To 70 mg (0.3 mmol) of 5-acetyl-4-hydroxy-3-methyl-benzofuran-2-carboxylic acid ethyl ester was added 115 mg (2 eq) EDCI, 109 mg (1 eq) of (S)-2-(4'-amino-biphenyl-4-sulfonylamino)-3-methyl-butyric acid methyl ester and 2 mL of DMF. The mixture was stirred at 65° C. overnight. The reaction mixture was poured into brine, and extracted with dichloromethane. The organic solution was washed with 2N HCl and water. Removal of the solvents under vacuum gave crude product, which was purified by column chromatography on silica gel to give 20 mg (10% yield) of (S)-2-{4'-[(5-acetyl-4-hydroxy-3-methyl-benzofuran-2-carbonyl)-amino]-biphenyl-4-sulfonylamino}-3-methyl-butyric acid methyl ester as a white solid.

Step 4: To (S)-2-{4'-[(5-acetyl-4-hydroxy-3-methyl-benzofuran-2-carbonyl)-amino]-biphenyl-4-sulfonylamino}-3-methyl-butyric acid methyl ester (15 mg) was added 0.5 mL of THF and 2 mL of LiOH solution (3.6 g LiOH/50 mL MeOH/50 mL H$_2$O). The mixture was stirred at room temperature for 4 days. The solvents were removed under vacuum and 2 mL of water was added. The aqueous solution was acidified and the resulting solid was collected through filtration to give 7 mg of (S)-2-{4'-[(5-acetyl-4-hydroxy-3-methyl-benzofuran-2-carbonyl)-amino]-biphenyl-4-sulfonylamino}-3-methyl-butyric acid as an off-white solid. $^1$H NMR (400 MHz, DMSO-d$_6$) δ ppm 0.8 (dd, J=12.4, 6.8 Hz, 6 H) 1.9 (m, 1 H) 2.7 (s, 3 H) 2.8 (s, 3 H) 3.6 (dd, J=9.3, 6.1 Hz, 1 H) 7.3 (d, J=9.1 Hz, 1 H) 7.8 (d, J=8.8 Hz, 2 H) 7.9 (m, 4 H) 8.0 (d, J=8.8 Hz, 2 H) 8.1 (dd, J=9.1, 3.8 Hz, 2 H) 10.5 (s, 1 H) 13.7 (s, 1 H).

Example 124

(S)-2-{4'-[(5-Cyano-4-methoxy-3-methyl-benzofuran-2-carbonyl)-amino]-biphenyl-4-sulfonylamino}-3-methyl-butyric acid

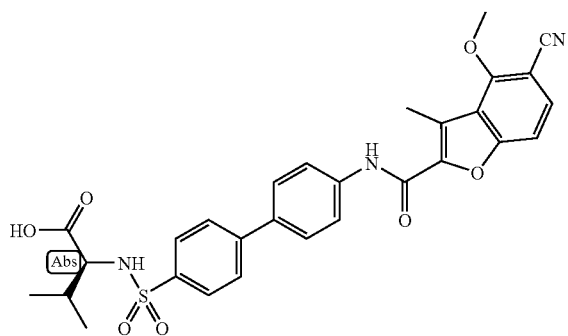

Step 1: To 4.4 g (17.7 mmol) of 4-hydroxy-3-methyl-benzofuran-2-carboxylic acid tert-butyl ester was added 40 mL of carbon tetrachloride, and the mixture was cooled with a water/ice bath while 1 equivalent of N-iodosuccinimide was added in small portions. After stirring at 0° C. for 3 h, the reaction mixture was loaded onto a column and purified by column chromatography to give 2.55 g mg (38% yield) of 5-iodo-4-hydroxy-3-methyl-benzofuran-2-carboxylic acid tert-butyl ester as a white solid.

Step 2: To 748 mg (2 mmol) of 5-iodo-4-hydroxy-3-methyl-benzofuran-2-carboxylic acid tert-butyl ester was added 1.42 g (10 mmol) of iodomethane, 553 mg (4 mmol) of K$_2$CO$_3$ and 10 mL of DMF. The mixture was stirred at room temperature overnight. The reaction mixture was washed with brine and extracted with ethyl acetate. The combined ethyl acetate layers were washed with brine. Removal of the solvent gave 790 mg (100% yield) of 5-iodo-4-methoxy-3-methyl-benzofuran-2-carboxylic acid tert-butyl ester as a pale brown oil.

Step 3. To 5-iodo-4-methoxy-3-methyl-benzofuran-2-carboxylic acid tert-butyl ester (490 mg, 1.26 mmol) was added 356 mg (3 mmol) of Zn(CN)$_2$, 140 mg of Pd(PPh$_3$)$_4$ and 4 mL of DMF. The mixture was stirred at 90° C. for 3 h. After cooling to room temperature the reaction mixture was loaded onto a silica gel column and was purified by column chromatography to give 260 mg (72% yield) of desired 5-cyano-4-methoxy-3-methyl-benzofuran-2-carboxylic acid tert-butyl ester was obtained as a white solid.

Step 4: To 150 mg of 5-cyano-4-methoxy-3-methyl-benzofuran-2-carboxylic acid tert-butyl ester was added 4 mL of TFA/dichloromethane (1:1) and the solution was stirred at room temperature for 3 h. When the reaction was done, the solvents were removed under vacuum and the residue was triturated with hexane/dichloromethane. Filtration of the suspension gave 121 mg (100% yield) of 5-cyano-4-methoxy-3-methyl-benzofuran-2-carboxylic acid as a white solid.

Step 5: To 110 mg (0.48 mmol) of 5-cyano-4-methoxy-3-methyl-benzofuran-2-carboxylic acid was added 207 mg (1.2 eq) of (S)-2-(4'-amino-biphenyl-4-sulfonylamino)-3-methyl-butyric acid methyl ester, BOP (252 mg, 1.2 eq), N,N-diisopropylethylamine (74 mg,1.2 eq) and 4 mL of DMF. The mixture was stirred at room temperature for 48 h. Brine was added and the mixture was extracted with ethyl acetate. The combined organic solution was washed with 2N HCl and water. Concentration of the organics in vacuo gave crude product, which was purified by column chromatography on silica gel to give 89 mg (32% yield) of (S)-2-{4'-[(5-cyano-4-methoxy-3-methyl-benzofuran-2-carbonyl)-amino]-biphenyl-4-sulfonylamino}-3-methyl-butyric acid methyl ester as an off-white solid.

Step 6: To 70 mg of (S)-2-{4'-[(5-cyano-4-methoxy-3-methyl-benzofuran-2-carbonyl)-amino]-biphenyl-4-sulfonylamino}-3-methyl-butyric acid methyl ester was added 1.5 mL of THF and 2 mL of LiOH solution (3.6 g LiOH/50 mL MeOH/50 mL H$_2$O). The mixture was stirred at room temperature for 3 days. The solvents were removed under vacuum and the residue was dissolved in 5 mL of water. The solution was acidified and the resulting suspension was filtered. The solid product was dried under vacuum to give 42 mg (61% yield) of (S)-2-{4'-[(5-cyano-4-methoxy-3-methyl-benzofuran-2-carbonyl)-amino]-biphenyl-4-sulfonylamino}-3-methyl-butyric acid. $^1$H NMR (400 MHz, DMSO-d$_6$) δ ppm 0.8 (dd, J=12.6, 6.8 Hz, 6 H) 2.0 (m, 1 H) 2.7 (s, 3 H) 3.6 (dd, J=9.5, 5.9 Hz, 1 H) 4.2 (s, 3 H) 7.6 (d, J=8.6 Hz, 1 H) 7.8 (m, 7 H) 8.0 (d, J=8.8 Hz, 2 H) 8.1 (d, J=9.1 Hz, 1 H) 10.7 (s, 1 H).

Example 125

(S)-2-{4'-[(5-Methyl-4-methoxy-3-methyl-benzofuran-2-carbonyl)-amino]-biphenyl-4-sulfonylamino}-3-methyl-butyric acid

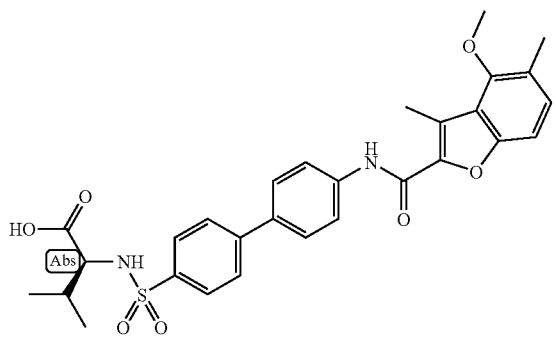

Step 1: To 1.24 g (5 mmol) of 4-hydroxy-benzofuran-2-acid tert-butyl ester was added 9.5 g of magnesium methoxide/methanol solution (6-10 weight %) and 25 mL of toluene. The mixture was heated at reflux for 45 minutes. Methanol was distilled off. An additional 10 mL of toluene was then added for further distillation to ensure the complete removal of the methanol. 2.4 g of paraformaldehyde was added in small portions over 35 min. The reaction mixture was stirred at 130° C. for another 30 min. The reaction mixture was washed with 2N HCl, and extracted with ethyl acetate. Removal of the solvents gave the crude product which was purified by column chromatography to give 440 mg of 5-formyl-4-hydroxy-3-methyl-benzofuran-2-carboxylic acid tert-butyl ester.

Step 2: To 5-formyl-4-hydroxy-3-methyl-benzofuran-2-carboxylic acid tert-butyl ester (430 mg, 1.56 mmol) was added 8 mL of THF, and sodium cyanoborohydride (117 mg, 1.87 mmol) was added in one portion. The solution was stirred at room temperature for 1 h and then placed in a 65° C. oil bath overnight. The solvent was removed under vacuum and water was added. The mixture was extracted with ethyl acetate. Removal of the solvent gave the crude product, which was purified by column chromatography to give 70 mg of 4-hydroxy-3,5-dimethyl-benzofuran-2-carboxylic acid tert-butyl ester as a white solid.

Step 3. To 80 mg of 4-hydroxy-3,5-dimethyl-benzofuran-2-carboxylic acid tert-butyl ester was added 1 mL of iodomethane, 80 mg of $K_2CO_3$ and 1 mL of DMF. The mixture was stirred at room temperature overnight. The reaction mixture was washed with brine and extracted with ethyl acetate. The combined ethyl acetate solution was washed with brine. Removal of the solvent gave 82 mg of 4-methoxy-3,5-dimethyl-benzofuran-2-carboxylic acid tert-butyl ester as a pale yellow solid.

Step 4: To 80 mg of 4-methoxy-3,5-dimethyl-benzofuran-2-carboxylic acid tert-butyl ester was added 2 mL of TFA/dichloromethane (1:1) and the solution was stirred at room temperature for 3 h. When the reaction was done, the solvents were removed under vacuum and the residue was triturated with hexane/dichloromethane. Filtration of the suspension gave 55 mg of 4-methoxy-3,5-dimethyl-benzofuran-2-carboxylic acid as a pale brown solid.

Step 5: To 45 mg (0.2 mmol) of 4-methoxy-3,5-dimethyl-benzofuran-2-carboxylic acid was added 124 mg (1.5 eq) of (S)-2-(4'-amino-biphenyl-4-sulfonylamino)-3-methyl-butyric acid tert-butyl ester, BOP (106 mg, 1.2 eq), N,N-diisopropylethylamine (31 mg, 1.2 eq) and 2 mL of DMF. The mixture was stirred at room temperature for 24 h. Brine was added and the mixture was extracted with ethyl acetate. The combined organic solution was washed with 2N HCl and water. Removal of the solvent from the organic solution gave the crude product, which was purified by column chromatography on silica gel to give 89 mg of (S)-2-{4'-[(4-methoxy-3,5-dimethyl-benzofuran-2-carbonyl)-amino]-biphenyl-4-sulfonylamino}-3-methyl-butyric acid tert-butyl ester as an off-white solid.

Step 6: To 80 mg of (S)-2-{4'-[(4-methoxy-3,5-dimethyl-benzofuran-2-carbonyl)-amino]-biphenyl-4-sulfonylamino}-3-methyl-butyric acid tert-butyl ester was added 2 mL of TFA/dichloromethane (1:1) and the solution was stirred at room temperature for 3 h. When the reaction was done, the solvent was removed under vacuum and the residue was triturated with acetonitrile. Filtration of the suspension gave 64 mg of (S)-2-{4'-[(4-methoxy-3,5-dimethyl-benzofuran-2-carbonyl)-amino]-biphenyl-4-sulfonylamino}-3-methyl-butyric acid as a white solid. $^1$H NMR (400 MHz, DMSO-$d_6$) δ ppm 0.8 (dd, J=12.4, 6.8 Hz, 6 H) 2.0 (m, 1 H) 2.3 (s, 3 H) 2.7 (s, 3 H) 3.6 (dd, J=9.3, 5.8 Hz, 1 H) 3.8 (s, 3 H) 7.4 (m, 2 H) 7.8 (d, J=8.8 Hz, 2 H) 7.9 (m, 4 H) 8.0 (d, J=8.8 Hz, 2 H) 8.1 (d, J=9.3 Hz, 1 H) 10.5 (s, 1 H).

Example 126

(S)-2-{4'-[(5-Hydroxymethyl-4-methoxy-3-methyl-benzofuran-2-carbonyl)-amino]-biphenyl-4-sulfonylamino}-3-methyl-butyric acid

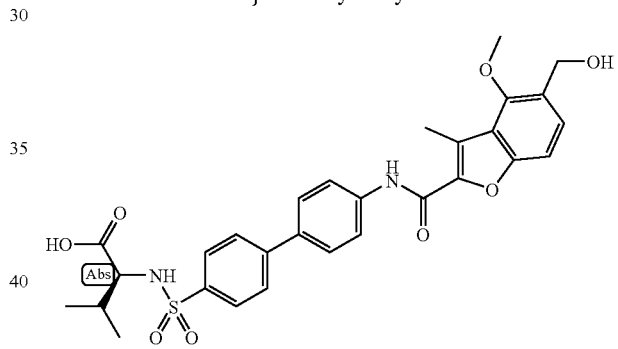

Step 1: To 1.24 g (5 mmol) of 4-hydroxy-benzofuran-2-acid tert-butyl ester was added 9.5 g of magnesium methoxide/methanol solution (6-10 weight %) and 25 mL of toluene. The mixture was heated at reflux for 45 minutes. Methanol was distilled off. An additional 10 mL of toluene was then added for further distillation to ensure the complete removal of the methanol. Next, 2.4 g of paraformaldehyde was added in small portions over 35 min. The reaction mixture was stirred at 130° C. for another 30 min. The reaction mixture was washed with 2N HCl, and extracted with ethyl acetate. Removal of the solvents gave the crude product which was purified by column chromatography to give 440 mg of 5-formyl-4-hydroxy-3-methyl-benzofuran-2-carboxylic acid tert-butyl ester.

Step 2: To 5-formyl-4-hydroxy-3-methyl-benzofuran-2-carboxylic acid tert-butyl ester (430 mg, 1.56 mmol) was added 8 mL of THF, followed by sodium cyanoborohydride (117 mg, 1.87 mmol) in one portion. The solution was stirred at room temperature for 1 h and then placed in a 65° C. oil bath overnight. The solvent was removed under vacuum and water was added. The mixture was extracted with ethyl acetate. Removal of the solvent gave the crude product, which was purified by column chromatography to give 200 mg of 4-hydroxy-5-hydroxymethyl-3-methyl-benzofuran-2-carboxylic acid tert-butyl ester was obtained as a yellow semi-solid.

Step 3. To 190 mg of 4-hydroxy-5-hydroxymethyl-3-methyl-benzofuran-2-carboxylic acid tert-butyl ester was added 1 mL of iodomethane, 200 mg of $K_2CO_3$ and 3 mL of DMF. The mixture was stirred at room temperature overnight. The reaction mixture was washed with brine and extracted with ethyl acetate. The combined ethyl acetate solution was washed with brine. Removal of the solvent gave 200 mg of 4-methoxy-5-hydroxymethyl-3-methyl-benzofuran-2-carboxylic acid tert-butyl ester as a pale yellow oil.

Step 4: To 190 mg of 4-methoxy-5-hydroxymethyl-3-methyl-benzofuran-2-carboxylic acid tert-butyl ester was added 4 mL of TFA/dichloromethane (1:1) and the solution was stirred at room temperature for 3 h. When the reaction was done, the solvents were removed under vacuum and the residue was triturated with acetonitrile. Filtration of the suspension gave 184 mg of 4-methoxy-3-methyl-5-(2,2,2-trifluoro-acetoxymethyl)-benzofuran-2-carboxylic acid as a white solid.

Step 5: To 100 mg (0.42 mmol) of 4-methoxy-3-methyl-5-(2,2,2-trifluoro-acetoxymethyl)-benzofuran-2-carboxylic acid was added 256 mg (1.5 eq) of (S)-2-(4'-amino-biphenyl-4-sulfonylamino)-3-methyl-butyric acid tert-butyl ester, BOP (185 mg, 1 eq), N,N-diisopropylethylamine (54 mg, 1 eq) and 4 mL of DMF. The mixture was stirred at room temperature for 48 h. Brine was added and the mixture was extracted with ethyl acetate. The combined organic solution was washed with 2N HCl and water. Removal of the solvent from the organic solution gave the crude product, which was purified by column chromatography on silica gel to give 89 mg of (S)-2-{4'-[(5-hydroxymethyl-4-methoxy-3-methyl-benzofuran-2-carbonyl)-amino]-biphenyl-4-sulfonylamino}-3-methyl-butyric acid tert-butyl ester as an off white solid.

Step 6: To 81 mg of (S)-2-{4'-[(5-hydroxymethyl-4-methoxy-3-methyl-benzofuran-2-carbonyl)-amino]-biphenyl-4-sulfonylamino}-3-methyl-butyric acid tert-butyl ester was added 2 mL of TFA/dichloromethane (1:1) and the solution was stirred at room temperature for 3 h. When the reaction was done, the solvents were removed under vacuum and the residue was triturated with acetonitrile/water. Filtration of the suspension gave mixture of (S)-2-(4'-{[4-methoxy-3-methyl-5-(2,2,2-trifluoro-acetoxymethyl)-benzofuran-2-carbonyl]-amino}-biphenyl-4-sulfonylamino)-3-methyl-butyric acid and (S)-2-{4'-[(5-hydroxymethyl-4-methoxy-3-methyl-benzofuran-2-carbonyl)-amino]-biphenyl-4-sulfonylamino}-3-methyl-butyric acid. To the mixture was added 1 mL of THF and 2 mL of LiOH solution (3.6 g of LiOH/50 mL of MeOH/50 mL of water). The solution was stirred at room temperature overnight. The solvents were removed under vacuum and the residue was dissolved in 3 mL of water. The solution was acidified and the resulting suspension was filtered. The solid product was dried under vacuum to give 68 mg of (S)-2-{4'-[(5-hydroxymethyl-4-methoxy-3-methyl-benzofuran-2-carbonyl)-amino]-biphenyl-4-sulfonylamino}-3-methyl-butyric acid as an off-white solid. $^1$H NMR (400 MHz, DMSO-d$_6$) δ ppm 0.8 (dd, J=12.6, 6.8 Hz, 6 H) 2.0 (m, 1 H) 2.8 (s, 3 H) 3.6 (dd, J=9.1, 6.1 Hz, 1 H) 3.9 (s, 3 H) 4.6 (d, J=5.3 Hz, 2 H) 5.2 (t, J=5.6 Hz, 1 H) 7.5 (d, J=8.6 Hz, 1 H) 7.6 (d, J=8.6 Hz, 1 H) 7.8 (d, J=8.8 Hz, 2 H) 7.9 (m, 4 H) 8.0 (d, J=9.1 Hz, 2 H) 8.1 (d, J=9.1 Hz, 1 H) 10.5 (s, 1 H) 12.6 (s, 1 H).

Example 127

(S)-3-Methyl-2-{4'-[(benzooxazole-2-carbonyl)-amino]-biphenyl-4-sulfonylamino}-butyric acid

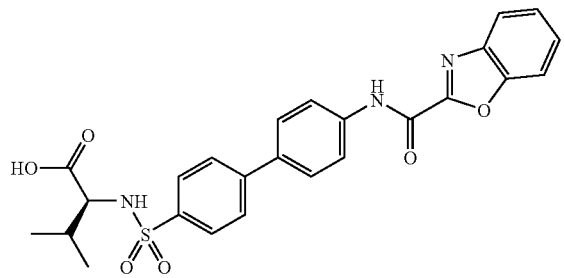

Step 1: To 2-aminophenol (437 mg, 4 mmol) was added ethyl triethoxyacetate (3.5 g, 4 eq). The mixture was stirred at 110° C. overnight. The reaction mixture was cooled and triturated with hexane. Filtration gave 516 mg of benzoxazole-2-carboxylic acid ethyl ester as a white solid.

Step 2: To benzoxazole-2-carboxylic acid ethyl ester (437 mg, 4 mmol) was added 2 mL of THF and 4 mL of NaOH solution (2N in MeOH). The reaction mixture was stirred at room temperature overnight. The suspension was filtered and the solid was dried under vacuum to give 160 mg of benzoxazole-2-carboxylic acid sodium salt as an off-white solid.

Step 3: To benzooxazole-2-carboxylic acid sodium salt (161 mg, 1 mmol) was added (S)-2-(4'-amino-biphenyl-4-sulfonylamino)-3-methyl-butyric acid tert-butyl ester (405 mg, 1 eq), BOP (550 mg, 1.2 eq), N,N-diisopropylethylamine (155 mg, 1.2 eq) and 4 mL of DMF. The mixture was stirred at room temperature overnight. The reaction mixture was poured into brine, and extracted with ethyl acetate. The combined organic layers were washed with brine and water. Removal of solvent gave the crude product, which was purified by column chromatography on silica gel to give 126 mg of (S)-3-methyl-2-{4'-[(benzoxazole-2-carbonyl)-amino]-biphenyl-4-sulfonylamino}-butyric acid tert-butyl ester as a white solid.

Step 4: To (S)-3-methyl-2-{4'-[(benzoxazole-2-carbonyl)-amino]-biphenyl-4-sulfonylamino}-butyric acid tert-butyl ester was added 4 mL of TFA/CH$_2$Cl$_2$ (1:1). The solution was stirred at room temperature for 3 h. The solvents were removed under vacuum and the residue was triturated with ether. Filtration gave 90 mg of (S)-3-methyl-2-{4'-[(benzooxazole-2-carbonyl)-amino]-biphenyl-4-sulfonylamino}-butyric acid as a white solid. $^1$H NMR (400 MHz, DMSO-d$_6$) δ ppm 0.8 (dd, J=12.6, 6.8 Hz, 6 H) 1.9 (m, 1 H) 3.6 (dd, J=9.3, 6.1 Hz, 1 H) 7.6 (m, 1 H) 7.6 (m, 1 H) 7.8 (m, 6 H) 8.0 (m, 2 H) 8.1 (m, 3 H) 11.4 (s, 1 H).

Example 128

(S)-3-Methyl-2-{4'-[(4-methyl-benzooxazole-2-carbonyl)-amino]-biphenyl-4-sulfonylamino}-butyric acid

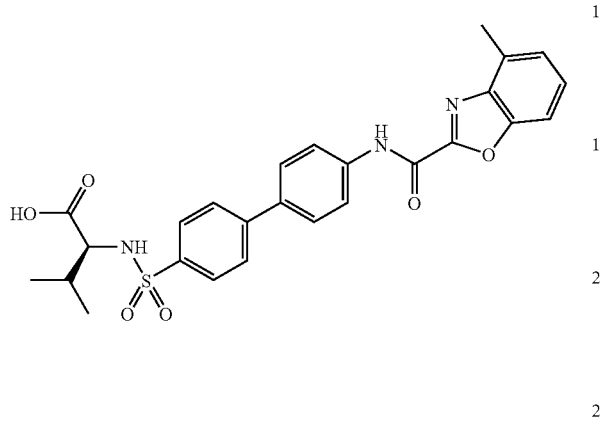

Step 1: To 2-amino-3-methylphenol (1 g, 8.1 mmol) was added ethyl triethoxyacetate (5.4 g, 3 eq). The mixture was stirred at 110° C. overnight. The reaction mixture was cooled and triturated with hexane. Filtration gave 1.36 g of 4-methyl-benzooxazole-2-carboxylic acid ethyl ester as a white solid.

Step 2: To 4-methyl-benzooxazole-2-carboxylic acid ethyl ester (140 mg) was added 2 mL of THF, and 0.93 mL (2 eq) of NaOH solution (2N in MeOH). The reaction mixture was stirred at room temperature overnight. The suspension was filtered and the solid was dried under vacuum to give 200 mg (100%) of 4-methyl-benzooxazole-2-carboxylic acid sodium salt as an off-white solid.

Step 3: To 4-methyl-benzooxazole-2-carboxylic acid sodium salt (180 mg, 0.93 mmol) was added (S)-2-(4'-amino-biphenyl-4-sulfonylamino)-3-methyl-butyric acid tert-butyl ester (450 mg, 1.2 eq), BOP (490 mg, 1.2 eq), N,N-diisopropylethylamine (144 mg, 1.2 eq) and 4 mL of DMF. The mixture was stirred at room temperature overnight. The reaction mixture was poured into brine, and extracted with ethyl acetate. The combined organic solution was washed with brine and water. Removal of the solvent in vacuo gave the crude product, which was purified by column chromatography on silica gel to give 158 mg of (S)-3-methyl-2-{4'-[(4-methyl-benzooxazole-2-carbonyl)-amino]-biphenyl-4-sulfonylamino}-butyric acid tert-butyl ester as a white solid.

Step 4: To (S)-3-methyl-2-{4'-[(4-methyl-benzooxazole-2-carbonyl)-amino]-biphenyl-4-sulfonylamino}-butyric acid tert-butyl ester (135 mg) was added 4 mL of TFA/CH$_2$Cl$_2$ (1:1). The solution was stirred at room temperature for 3 h. The solvents were removed under vacuum and the residue was triturated with ether. Filtration gave 140 mg of (S)-3-methyl-2-{4'-[(4-methyl-benzooxazole-2-carbonyl)-amino]-biphenyl-4-sulfonylamino}-butyric acid as white solid. $^1$H NMR (400 MHz, DMSO-d$_6$) δ ppm 0.8 (dd, J=12.4, 6.8 Hz, 6 H) 2.0 (m, 1 H) 2.7 (s, 3 H) 3.6 (dd, J=9.3, 6.1 Hz, 1 H) 7.4 (d, J=8.3 Hz, 1 H) 7.5 (m, 1 H) 7.7 (d, J=8.3 Hz, 1 H) 7.8 (m, 6 H) 8.1 (t, J=8.8 Hz, 3 H) 11.3 (s, 1 H).

Example 129

(S)-3-Methyl-2-{4'-[(5-methyl-benzooxazole-2-carbonyl)-amino]-biphenyl-4-sulfonylamino}-butyric acid

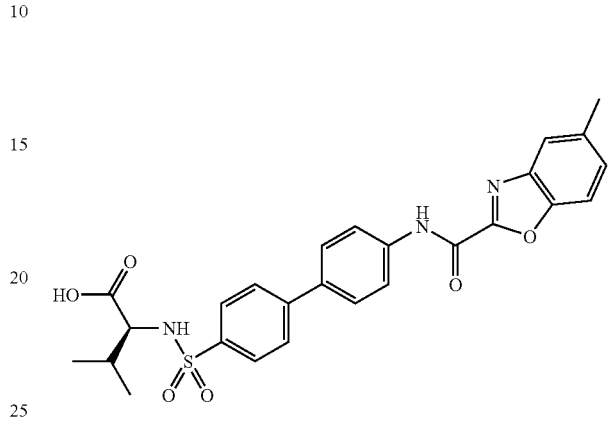

Step 1: To 2-amino-4-methylphenol (1 g, 8.1 mmol) was added ethyl triethoxyacetate (5.4 g, 3 eq). The mixture was stirred at 110° C. overnight. The reaction mixture was cooled and triturated with hexane. Filtration gave 850 mg (91%) of 5-methyl-benzooxazole-2-carboxylic acid ethyl ester as a white solid.

Step 2: To 5-methyl-benzooxazole-2-carboxylic acid ethyl ester (170 mg) was added 2 mL of THF, and 0.83 mL (2 eq) of sodium hydroxide solution (2N in MeOH). The reaction mixture was stirred at room temperature overnight. The suspension was filtered and the solid was dried under vacuum to give 144 mg of 5-methyl-benzooxazole-2-carboxylic acid sodium salt as an off-white solid.

Step 3: To 5-methyl-benzooxazole-2-carboxylic acid sodium salt (130 mg, 0.83 mmol) was added (S)-2-(4'-amino-biphenyl-4-sulfonylamino)-3-methyl-butyric acid tert-butyl ester (400 mg, 1.2 eq), BOP (430 mg, 1.2 eq), N,N-diisopropylethylamine (126 mg, 1.2 eq) and 4 mL of DMF. The mixture was stirred at room temperature overnight. The reaction mixture was poured into brine, and extracted with ethyl acetate. The combined organic solution was washed with brine and water. Removal of solvent gave the crude product, which was purified by column chromatography on silica gel to give 60 mg of (S)-3-methyl-2-{4'-[(5-methyl-benzooxazole-2-carbonyl)-amino]-biphenyl-4-sulfonylamino}-butyric acid tert-butyl ester was obtained as a white solid.

Step 4: To (S)-3-methyl-2-{4'-[(5-methyl-benzooxazole-2-carbonyl)-amino]-biphenyl-4-sulfonylamino}-butyric acid tert-butyl ester (30 mg) was added 2 mL of TFA/CH$_2$Cl$_2$ (1:1). The solution was stirred at room temperature for 3 h. The solvents were removed under vacuum and the residue was triturated with ether. Filtration gave 14 mg of (S)-3-methyl-2-{4'-[(5-methyl-benzooxazole-2-carbonyl)-amino]-biphenyl-4-sulfonylamino}-butyric acid as a white solid. $^1$H NMR (400 MHz, DMSO-d$_6$) δ ppm 0.76-0.93 (m, 6 H) 1.84-2.07 (m, 6 H) 3.56 (dd, 1 H) 7.70-7.95 (m, 8 H) 7.98-8.14 (m, 3 H) 11.32-11.41 (m, 1 H).

Example 130

(S)-3-Methyl-2-{4'-[(5-chloro-benzothiazole-2-carbonyl)-amino]-biphenyl-4-sulfonylamino}-butyric acid

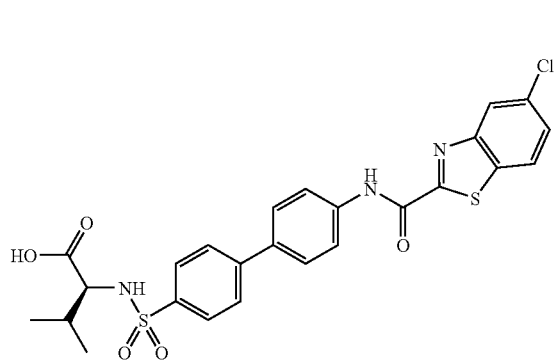

Step 1: To 2-amino-4-chloro-benzenethiol (1 g) was added ethyl triethoxyacetate (3 eq). The mixture was stirred at 110° C. overnight. The reaction mixture was cooled and triturated with hexane. Filtration gave 392 mg of 5-chloro-benzothiazole-2-carboxylic acid ethyl ester as a white solid.

Step 2: To 5-chloro-benzothiazole-2-carboxylic acid ethyl ester (200 mg, 0.83 mmol) was added 3 mL of THF, and 0.83 mL (2 eq) of NaOH solution (2N in MeOH). The reaction mixture was stirred at room temperature overnight. The suspension was filtered and the solid was dried under vacuum to give 170 mg of 5-chloro-benzothiazole-2-carboxylic acid sodium salt as an off-white solid.

Step 3: To 5-chloro-benzothiazole-2-carboxylic acid sodium salt (150 mg, 0.64 mmol) was added (S)-2-(4'-amino-biphenyl-4-sulfonylamino)-3-methyl-butyric acid tert-butyl ester (310 mg, 1.2 eq), BOP (340 mg, 1.2 eq), N,N-diisopropylethylamine (99 mg, 1.2 eq) and 4 mL of DMF. The mixture was stirred at room temperature overnight. The reaction mixture was poured into brine, and extracted with ethyl acetate. The combined organic solution was washed with brine and water. Removal of solvent gave the crude product, which was purified by column chromatography on silica gel to give 136 mg of (S)-3-methyl-2-{4'-[(5-chloro-benzothiazole-2-carbonyl)-amino]-biphenyl-4-sulfonylamino}-butyric acid tert-butyl ester was obtained as a white solid.

Step 4: To (S)-3-methyl-2-{4'-[(5-chloro-benzothiazole-2-carbonyl)-amino]-biphenyl-4-sulfonylamino}-butyric acid tert-butyl ester (30 mg) was added 3 mL of TFA/CH$_2$Cl$_2$ (1:1). The solution was stirred at room temperature for 3 h. The solvents were removed under vacuum and the residue was triturated with ether. Filtration gave 105 mg of (S)-3-methyl-2-{4'-[(5-chloro-benzothiazole-2-carbonyl)-amino]-biphenyl-4-sulfonylamino}-butyric acid as yellow solid. $^1$H NMR (400 MHz, DMSO-d$_6$) δ ppm 0.79-0.88 (m, 6 H) 1.85-2.07 (m, 1 H) 3.56 (dd, 1 H) 7.70 (dd, 1 H) 7.76-7.94 (m, 6 H) 8.03-8.12 (m, 3 H) 8.26 (d, 1 H) 8.35 (d, 1 H) 11.36-11.40 (m, 1 H).

Example 131

(S)-3-Methyl-2-{4'-[(5-trifluoromethyl-benzothiazole-2-carbonyl)-amino]-biphenyl-4-sulfonylamino}-butyric acid

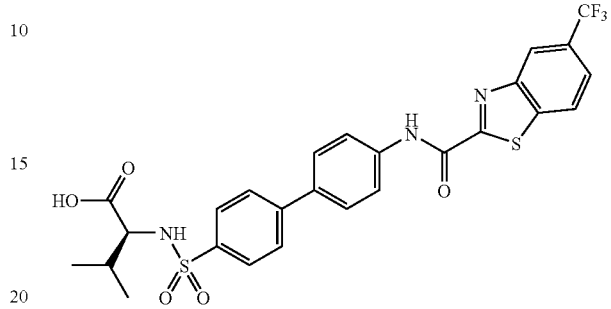

Step 1: To 2-amino-4-trifluoromethyl-benzenethiol (0.7 g) was added ethyl triethoxyacetate (3 eq). The mixture was stirred at 110° C. overnight. The reaction mixture was cooled and triturated with hexane. Filtration gave 460 mg of 5-trifluoromethyl-benzothiazole-2-carboxylic acid ethyl ester as a white solid.

Step 2: To 5-trifluoromethyl-benzothiazole-2-carboxylic acid ethyl ester (200 mg, 0.73 mmol) was added 3 mL of THF, and 0.73 mL (2 eq) of NaOH solution (2N in MeOH). The reaction mixture was stirred at room temperature overnight. The suspension was filtered and the solid was dried under vacuum to give 270 mg of 5-trifluoromethyl-benzothiazole-2-carboxylic acid sodium salt as an off-white solid.

Step 3: To 5-trifluoromethyl-benzothiazole-2-carboxylic acid sodium salt (260 mg, 0.97 mmol) was added (S)-2-(4'-amino-biphenyl-4-sulfonylamino)-3-methyl-butyric acid tert-butyl ester (469 mg, 1.2 eq), BOP (515 mg, 1.2 eq) and 5 mL of DMF. The mixture was stirred at room temperature overnight. The reaction mixture was poured into brine, and extracted with ethyl acetate. The combined organic layers were washed with brine and water. Removal of solvent gave the crude product, which was purified by column chromatography on silica gel to give 230 mg of (S)-3-methyl-2-{4'-[(5-trifluoromethyl-benzothiazole-2-carbonyl)-amino]-biphenyl-4-sulfonylamino}-butyric acid tert-butyl ester as a white solid.

Step 4: To (S)-3-methyl-2-{4'-[(5-trifluoromethyl-benzothiazole-2-carbonyl)-amino]-biphenyl-4-sulfonylamino}-butyric acid tert-butyl ester (210 mg) was added 3 mL of TFA/CH$_2$Cl$_2$ (1:1). The solution was stirred at room temperature for 3 h. The solvents were removed under vacuum and the residue was triturated with ether. Filtration gave 181 mg of (S)-3-methyl-2-{4'-[(5-trifluoromethyl-benzothiazole-2-carbonyl)-amino]-biphenyl-4-sulfonylamino}-butyric acid as a yellow solid. $^1$H NMR (400 MHz, DMSO-D$_6$) δ ppm 0.83 (dd, J=12.63, 6.82 Hz, 6 H) 1.92-2.00 (m, 1 H) 3.56 (dd, J=9.35, 6.06 Hz, 1 H) 7.80-7.86 (m, 4 H) 7.88-7.92 (m, 2 H) 7.97 (dd, J=8.59, 1.52 Hz, 1 H) 8.05-8.07 (m, 1 H) 8.09 (d, J=2.78 Hz, 1 H) 8.49 (s, 1 H) 8.57 (d, J=8.59 Hz, 1 H) 11.41 (s, 1 H).

Example 132

D-3-Methyl-benzofuran-2-carboxylic acid 4'-(1-carboxy-2-methyl-propylsulfamoyl)-3,5-dimethyl-biphenyl-4-yl ester

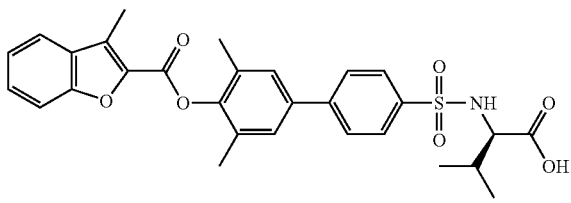

Step 1: To 3-methyl-benzofuran-2-carboxylic acid (500 mg, 2.84 mmol, 1 eq) in 5 mL of dichloromethane under argon was added 2,6-dimethyl-4-(4,4,5,5-tetramethyl-[1,3,2]dioxaborolan-2-yl)-phenol (704 mg, 2.84 mmol, 1 eq.), 1,3-dicyclohexylcarbodiimide (1.17 g, 5.68 mmol, 2 eq.), and 4-(dimethylamino)pyridine (173 mg, 1.42 mmol, 0.5 eq.). The resulting mixture was stirred at room temperature for 6 h. The reaction was then diluted with water and extracted with ethyl acetate. The organics were washed with brine, dried over magnesium sulfate, filtered and concentrated in vacuo. The residue was purified using flash column chromatography on silica gel to provide 3-methyl-benzofuran-2-carboxylic acid 2,6-dimethyl-4-(4,4,5,5-tetramethyl-[1,3,2]dioxaborolan-2-yl)-phenyl ester in 28% yield. $^1$H NMR (400 MHz, DMSO-$d_6$) δ ppm 1.3 (s, 12 H) 2.2 (s, 6 H) 2.7 (s, 3 H) 7.4 (m, 1 H) 7.5 (s, 2 H) 7.6 (m, 1 H) 7.8 (d, J=8.3 Hz, 1 H) 7.9 (m, 1 H).

Step 2: To 3-methyl-benzofuran-2-carboxylic acid 2,6-dimethyl-4-(4,4,5,5-tetramethyl-[1,3,2]dioxaborolan-2-yl)-phenyl ester (310 mg, 0.76 mmol, 1 eq.), D-2-(4-bromo-benzenesulfonylamino)-3-methyl-butyric acid tert-butyl ester (300 mg, 0.76 mmol, 1 eq., Example 74, step 2), tetrakis(triphenylphosphine)palladium(0) (44 mg, 0.0387 mmol, 0.05 eq.), and ethylene glycol dimethyl ether (10 mL) were added under argon and stirred for 10 minutes. Then potassium carbonate (211 mg, 1.53 mmol, 2 eq.) in water (4 mL) was added. The reaction was heated at reflux for 16 h. After aqueous work-up and ethyl acetate extraction, purification using flash column chromatography provided D-3-methyl-benzofuran-2-carboxylic acid 4'-(1-tert-butoxycarbonyl-2-methyl-propylsulfamoyl)-3,5-dimethyl-biphenyl-4-yl ester in 69% yield. $^1$H NMR (400 MHz, DMSO-$d_6$) δ ppm 0.9 (m, 6 H) 1.2 (s, 9 H) 1.9 (m, 1 H) 2.2 (s, 6 H) 2.7 (s, 3 H) 3.5 (dd, J=9.9, 6.3 Hz, 1 H) 7.4 (t, J=7.6 Hz, 1 H) 7.6 (s, 2 H) 7.6 (t, J=7.7 Hz, 1 H) 7.8 (d, J=8.3 Hz, 1 H) 7.9 (m, 5 H) 8.2 (d, J=9.6 Hz, 1 H).

Step 3: To D-3-methyl-benzofuran-2-carboxylic acid 4'-(1-tert-butoxycarbonyl-2-methyl-propylsulfamoyl)-3,5-dimethyl-biphenyl-4-yl ester in dichloroethane (6 mL) was added TFA (3 mL), and the reaction was stirred at room temperature for 2 hours. After work-up, D-3-methyl-benzofuran-2-carboxylic acid 4'-(1-carboxy-2-methyl-propylsulfamoyl)-3,5-dimethyl-biphenyl-4-yl ester was obtained in quantitative yield. $^1$H NMR (400 MHz, DMSO-$d_6$) δ ppm 0.8 (dd, J=12.4, 6.8 Hz, 6 H) 2.0 (m, 1 H) 2.2 (s, 6 H) 2.7 (s, 3 H) 3.6 (dd, J=9.3, 6.1 Hz, 1 H) 7.4 (m, 1 H) 7.6 (s, 2 H) 7.6 (m, 1 H) 7.8 (d, J=8.3 Hz, 1 H) 7.9 (m, 5 H) 8.1 (d, J=9.3 Hz, 1 H).

Example 133

D-Benzofuran-2-carboxylic acid 4'-(1-carboxy-2-methyl-propylsulfamoyl)-3,5-dimethyl-biphenyl-4-yl ester

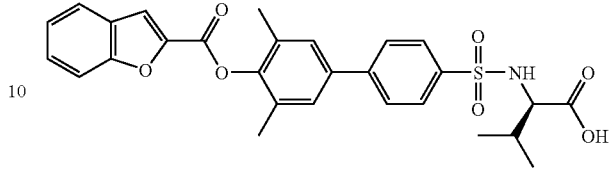

Step 1: Coupling of benzofuran-2-carboxylic acid with 2,6-dimethyl-4-(4,4,5,5-tetramethyl-[1,3,2]dioxaborolan-2-yl)-phenol to obtain benzofuran-2-carboxylic acid 2,6-dimethyl-4-(4,4,5,5-tetramethyl-[1,3,2]dioxaborolan-2-yl)-phenyl ester was done according to Example 132, Step 1 to provide benzofuran-2-carboxylic acid 2,6-dimethyl-4-(4,4,5,5-tetramethyl-[1,3,2]dioxaborolan-2-yl)-phenyl ester in 50% yield. $^1$H NMR (400 MHz, DMSO-$d_6$) δ ppm 1.3 (s, 12 H) 2.2 (s, 6 H) 7.4 (m, 1 H) 7.5 (s, 2 H) 7.6 (m, 1 H) 7.8 (dd, J=8.3, 0.8 Hz, 1 H) 7.9 (m, 1 H) 8.1 (d, J=1.0 Hz, 1 H).

Step 2: Coupling of benzofuran-2-carboxylic acid 2,6-dimethyl-4-(4,4,5,5-tetramethyl-[1,3,2]dioxaborolan-2-yl)-phenyl ester with D-2-(4-bromo-benzenesulfonylamino)-3-methyl-butyric acid tert-butyl ester to obtain D-benzofuran-2-carboxylic acid 4'-(1-tert-butoxycarbonyl-2-methyl-propylsulfamoyl)-3,5-dimethyl-biphenyl-4-yl ester was done according to Example 132, Step 2 to provide D-benzofuran-2-carboxylic acid 4'-(1-tert-butoxycarbonyl-2-methyl-propylsulfamoyl)-3,5-dimethyl-biphenyl-4-yl ester in 81% yield. $^1$H NMR (400 MHz, DMSO-$d_6$) δ ppm 0.9 (m, 6 H) 1.2 (s, 9 H) 1.9 (m, 1 H) 2.2 (s, 6 H) 3.5 (dd, J=9.7, 6.4 Hz, 1 H) 7.4 (t, J=7.6 Hz, 1 H) 7.6 (s, 2 H) 7.6 (m, 1 H) 7.9 (m, 6 H) 8.2 (t, J=4.8 Hz, 2 H).

Step 3: Deprotection of D-benzofuran-2-carboxylic acid 4'-(1-tert-butoxycarbonyl-2-methyl-propylsulfamoyl)-3,5-dimethyl-biphenyl-4-yl ester to provide D-benzofuran-2-carboxylic acid 4'-(1-carboxy-2-methyl-propylsulfamoyl)-3,5-dimethyl-biphenyl-4-yl ester was done according to Example 132, Step 3, in quantitative yield. $^1$H NMR (400 MHz, DMSO-$d_6$) δ ppm 0.8 (dd, J=12.4, 6.8 Hz, 6 H) 2.0 (m, 1 H) 2.2 (s, 6 H) 3.6 (dd, J=9.3, 5.8 Hz, 1 H) 7.4 (m, 1 H) 7.6 (m, 3 H) 7.9 (m, 6 H) 8.1 (d, J=9.3 Hz, 1 H) 8.2 (s, 1 H) 12.6 (s, 1 H).

Example 134

D-3-Methyl-benzofuran-2-carboxylic acid 4'-(1-carboxy-2-methyl-propylsulfamoyl)-biphenyl-4-yl ester

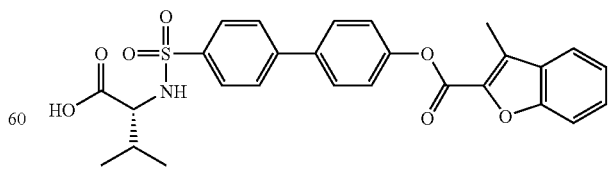

Step 1: Coupling of D-2-(4-bromo-benzenesulfonylamino)-3-methyl-butyric acid tert-butyl ester (Example 74, Step 2) with 4-(4,4,5,5-tetramethyl-1,2,3-dioxaborolan-2-yl)phenol was done according to Example 132, Step 2, to provide D-2-(4'-hydroxy-biphenyl-4-sulfonylamino)-3-methyl-butyric acid tert-butyl ester in quantitative yield. $^1$H NMR (400 MHz, DMSO-d$_6$) δ ppm 0.8 (dd, J=8.2, 6.9 Hz, 6 H) 1.2 (s, 9 H) 1.9 (m, 1 H) 3.5 (dd, J=9.6, 6.3 Hz, 1 H) 6.9 (d, J=8.6 Hz, 2 H) 7.5 (m, J=8.8 Hz, 2 H) 7.8 (d, J=2.3 Hz, 4 H) 8.1 (d, J=9.9 Hz, 1 H) 9.7 (s, 1 H).

Step 2: A mixture of D-2-(4'-hydroxy-biphenyl-4-sulfonylamino)-3-methyl-butyric acid tert-butyl ester (305 mg, 0.75 mmol, 1 eq), 3-methyl-benzofuran-2-carboxylic acid (131 mg, 0.74 mmol, 1 eq), 4-(dimethylamino)pyridine (95 mg, 0.77 mol, 1 eq), and 1,3-dicyclohexylcarbodiimide (DCC, 240 mg, 1.17 mmol, 1.6 eq) in 5 mL of dichloromethane under nitrogen atmosphere was stirred at room temperature for 3.5 h. After aqueous work-up, and extraction with ethyl acetate, column chromatography (10% ethyl acetate/hexane) provided D-3-methyl-benzofuran-2-carboxylic acid 4'-(1-tert-butoxycarbonyl-2-methyl-propylsulfamoyl)-biphenyl-4-yl ester (300 mg) in 71% yield. $^1$H NMR (400 MHz, CDCl$_3$) δ ppm 0.9 (d, J=7.1 Hz, 3 H) 1.0 (d, J=6.8 Hz, 3 H) 1.2 (s, 9 H) 2.1 (m, 1 H) 2.7 (s, 3 H) 3.7 (dd, J=10.0, 4.4 Hz, 1 H) 5.1 (d, J=9.9 Hz, 1 H) 7.4 (m, 3 H) 7.5 (m, 1 H) 7.6 (t, J=8.0 Hz, 3 H) 7.7 (m, 3 H) 7.9 (d, J=8.3 Hz, 2 H).

Step 3: Deprotection of D-3-methyl-benzofuran-2-carboxylic acid 4'-(1-tert-butoxycarbonyl-2-methyl-propylsulfamoyl)-biphenyl-4-yl ester was done according to Example 132, Step 3. After 1 hr of reaction, solvent was removed and the product was further chased with toluene. The solid thus obtained was dissolved in minimum amount of acetonitrile. About same amount of water was added to the mixture. And the mixture was frozen using dry ice-acetone bath and subject to lyophilyzer solvent removal to give D-3-methyl-benzofuran-2-carboxylic acid 4'-(1-carboxy-2-methyl-propylsulfamoyl)-biphenyl-4-yl ester. $^1$H NMR (400 MHz, DMSO-d$_6$) δ ppm 0.8 (dd, J=12.1, 6.8 Hz, 6 H) 2.0 (m, 1 H) 2.7 (s, 3 H) 3.6 (dd, J=9.2, 5.9 Hz, 1 H) 7.4 (t, J=7.6 Hz, 1 H) 7.5 (d, J=8.8 Hz, 2 H) 7.6 (t, J=8.2 Hz, 1 H) 7.8 (d, J=8.3 Hz, 1 H) 7.9 (m, 7 H) 8.1 (d, J=9.3 Hz, 1 H).

Example 135

Benzofuran-2-carboxylic acid 4'-(1-carboxy-2-methyl-propylsulfamoyl)-biphenyl-4-yl ester

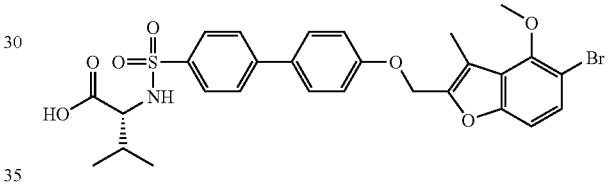

Step 1: To benzofuran-2-carboxylic acid (0.401 g, 2.47 mmol, 1 equiv.) dissolved in dry dichloromethane (50 mL) was added dicyclohexylcarbidiimide (1.019 g, 4.94 mmol, 2 equiv) and the mixture was stirred under nitrogen for 15 minutes. Then 2-(4'-hydroxy-biphenyl-4-sulfonylamino)-3-methyl-butyric acid tert-butyl ester (1.0 g, 2.47 mmol, 1 equiv., Example 134, Step 1) was introduced to the reaction mixture, followed by the addition of 4-dimethylamino pyridine (0.050 g, 0.41 mmol). The mixture was allowed to stir at room temperature overnight. The reaction mixture was then diluted with dichloromethane, washed with water and brine. The organic layer was dried over magnesium sulfate and the solvent was concentrated in vacuo. The residue was dissolved in ethyl acetate and purified by column chromatography on silica gel eluting with 20% ethyl acetate/hexane to afford 325 mg of benzofuran-2-carboxylic acid 4'-(1-tert-butoxycarbonyl-2-methyl-propylsulfamoyl)-biphenyl-4-yl ester in 31% yield. $^1$H NMR (400 MHz, CDCl$_3$) δ ppm 0.87 (d, J=6.82 Hz, 3 H) 1.03 (d, J=6.82 Hz, 3 H) 1.21 (s, 9 H) 2.07 (m, 1 H) 3.68 (dd, J=9.85, 4.55 Hz, 1 H) 5.15 (d, J=9.85 Hz, 1 H) 7.37 (m, 3 H) 7.53 (t, J=7.83 Hz, 1 H) 7.66 (m, 5 H) 7.77 (m, 2 H) 7.92 (d, J=8.34 Hz, 2 H).

Step 2: Benzofuran-2-carboxylic acid 4'-(1-tert-butoxycarbonyl-2-methyl-propylsulfamoyl)-biphenyl-4-yl ester (325 mg) provided 214 mg of benzofuran-2-carboxylic acid 4'-(1-carboxy-2-methyl-propylsulfamoyl)-biphenyl-4-yl ester (76% yield) according to the procedure of Example 132, Step 3, after column chromatography eluting with 5-20% methanol/ethyl acetate. $^1$H NMR (400 MHz, DMSO-d$_6$) δ ppm 0.80 (d, J=6.57 Hz, 3 H) 0.87 (d, J=6.82 Hz, 3 H) 2.04 (m, 1 H) 3.24 (m, 1 H) 7.43 (t, J=7.58 Hz, 1 H) 7.49 (d, J=8.84 Hz, 2 H) 7.60 (t, J=7.96 Hz, 1 H) 7.70 (d, J=9.85 Hz, 1 H) 7.85 (m, 7 H) 8.08 (s, 1 H).

Example 136

D-2-[4'-(5-Bromo-4-methoxy-3-methyl-benzofuran-2-ylmethoxy)-biphenyl-4-sulfonylamino]-3-methyl-butyricacid

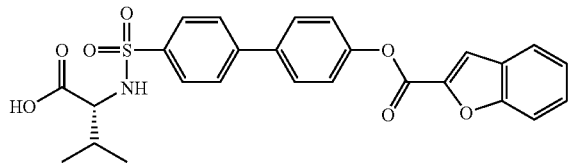

Step 1: A solution of 5-bromo-4-methoxy-3-methyl-benzofuran-2-carboxylic acid (286 mg, 1.0 mmol, 1 eq, Example 119, Step 3)) in 5 mL of THF under a nitrogen atmosphere was placed in a water bath. To this solution, 1.4 mL of BH$_3$.THF (1.0 M in THF, 1.4 mmol, 1.4 eq) was added dropwise. After 24 h the reaction mixture was quenched with water, and extracted with ethyl acetate. The organic layer was washed with water, saturated sodium carbonate and brine. The organic layer was dried over magnesium sulfate, filtered, and concentrated in vacuo to give (5-bromo-4-methoxy-3-methyl-benzofuran-2-yl)-methanol (220 mg) in 81% yield. $^1$H NMR (400 MHz, CDCl$_3$) δ ppm 2.4 (s, 3 H) 3.9 (s, 3 H) 4.7 (s, 2 H) 7.1 (d, J=8.6 Hz, 1 H) 7.4 (d, J=8.8 Hz, 1 H).

Step 2: To a solution of (5-bromo-4-methoxy-3-methyl-benzofuran-2-yl)-methanol in 7 mL of dichloromethane was added 0.5 mL of thionyl chloride at room temperature. After 2 h the reaction was concentrated in vacuo, diluted with ethyl acetate and washed with water. The organics were dried over magnesium sulfate, filtered and concentrated in vacuo to give 216 mg (92%) of 5-bromo-2-chloromethyl-4-methoxy-3-methyl-benzofuran. $^1$H NMR (400 MHz, CDC$_3$) δ ppm 2.4 (s, 3 H) 3.9 (s, 3 H) 4.7 (s, 2 H) 7.1 (d, J=8.8 Hz, 1 H) 7.4 (d, J=8.6 Hz, 1 H).

Step 3: A mixture of D-2-(4'-hydroxy-biphenyl-4-sulfonylamino)-3-methyl-butyric acid methyl ester (155 mg, 0.43 mmol, 1 eq), 5-bromo-2-chloromethyl-4-methoxy-3-methyl-benzofuran (120 mg, 0.42 mmol, 1 eq), and K$_2$CO$_3$ (137 mg, 0.99 mmol, 2.4 eq) in 8 mL of DMF was heated to 90° C. for 18 h. After work up and column chromatography eluting with 20% ethyl acetate/hexane, D-2-[4'-(5-bromo-4-methoxy-3-methyl-benzofuran-2-ylmethoxy)-biphenyl-4-sulfonylamino]-3-methyl-butyric acid methyl ester (102 mg) was obtained in 40% yield. $^1$H NMR (400 MHz, CDCl$_3$) δ ppm 0.9 (dd, J=31.8, 6.8 Hz, 6 H) 2.1 (m, 1 H) 2.5 (s, 3 H) 3.4 (s, 3 H) 3.8 (dd, J=10.2, 5.2 Hz, 1 H) 3.9 (s, 3 H) 5.1 (d, J=10.1 Hz, 1 H) 5.2 (s, 2 H) 7.1 (dd, J=12.6, 8.8 Hz, 3 H) 7.4 (d, J=8.6 Hz, 1 H) 7.6 (d, J=8.8 Hz, 2 H) 7.7 (d, J=8.6 Hz, 2 H) 7.9 (d, J=8.6 Hz, 2 H).

Step 4: Hydrolysis of D-2-[4'-(5-bromo-4-methoxy-3-methyl-benzofuran-2-ylmethoxy)-biphenyl-4-sulfonylamino]-3-methyl-butyric acid methyl ester was carried out according to Example 20, Step 5, in quantitative yield. $^1$H NMR (400 MHz, DMSO-d$_6$) δ ppm 0.8 (dd, J=12.1, 6.8 Hz, 6 H) 2.0 (m, 1 H) 2.4 (s, 3 H) 3.5 (dd, J=9.2, 5.9 Hz, 1 H) 3.9 (s, 3 H) 5.3 (s, 2 H) 7.2 (d, J=8.8 Hz, 2 H) 7.4 (d, J=8.8 Hz, 1 H) 7.5 (d, J=8.8 Hz, 1 H) 7.7 (d, J=9.1 Hz, 2 H) 7.8 (d, J=3.0 Hz, 4 H) 8.0 (d, J=9.3 Hz, 1 H).

Example 137

D-2-[4'-(Benzothiazol-2-ylmethoxy)-biphenyl-4-sulfonylamino]-3-methyl-butyric acid

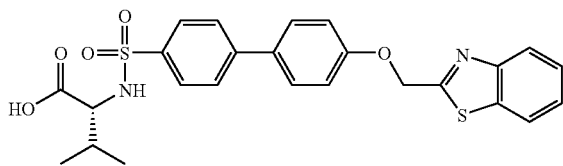

Step 1: Alkylation of 2-bromomethyl-benzothiazole with D-2-(4'-hydroxy-biphenyl-4-sulfonylamino)-3-methyl-butyric acid methyl ester was carried out according to Example 136, Step 3, to give D-2-[4'-(benzothiazol-2-ylmethoxy)-biphenyl-4-sulfonylamino]-3-methyl-butyric acid methyl ester in 20% yield. $^1$H NMR (400 MHz, DMSO-d$_6$) δ ppm 0.8 (dd, J=15.0, 6.7 Hz, 6 H) 1.9 (m, 1 H) 3.6 (dd, J=9.5, 7.2 Hz, 1 H) 5.7 (s, 2 H) 7.2 (m, J=8.8 Hz, 2 H) 7.5 (m, 1 H) 7.6 (m, 1 H) 7.7 (m, 4 H) 7.8 (m, 2 H) 8.0 (d, J=7.3 Hz, 1 H) 8.1 (d, J=7.8 Hz, 1 H) 8.3 (d, J=9.6 Hz, 1 H).

Step 2: Hydrolysis of D-$^2$-[4'-(benzothiazol-2-ylmethoxy)-biphenyl-4-sulfonylamino]-3-methyl-butyric acid methyl ester was carried out according to Example 20, Step 5, in quantitative yield. $^1$H NMR (400 MHz, DMSO-d$_6$) δ ppm 0.8 (dd, J=12.4, 6.8 Hz, 6 H) 1.9 (m, 1 H) 3.5 (dd, J=9.3, 5.8 Hz, 1 H) 5.7 (s, 2 H) 7.2 (d, J=8.8 Hz, 2 H) 7.5 (m, 1 H) 7.6 (m, 1 H) 7.7 (d, J=8.8 Hz, 2 H) 7.8 (d, J=2.3 Hz, 4 H) 8.0 (dd, J=9.1, 4.5 Hz, 2 H) 8.1 (d, J=8.6 Hz, 1 H).

Example 138

D-3-Methyl-2-[4'-(1-methyl-1H-benzoimidazol-2-ylmethoxy)-biphenyl-4-sulfonylamino]-butyric acid

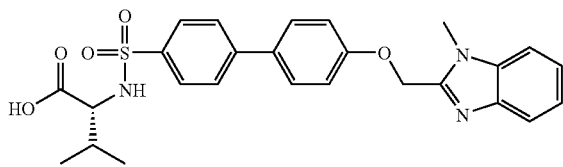

Step 1: To 432 mg of 1-methyl-1H-benzoimidazole-2-carbaldehyde (2.7 mmol, 1 eq) dissolved in a mixture of THF (10 mL) and methanol (10 mL) was added 340 mg of sodium borohydride (9.0 mmol, 3.33 eq) in several portions. After 12 h the reaction mixture was quenched with water and extracted with ethyl acetate. The organics were washed with brine, dried over sodium sulfate, filtered and concentrated in vacuo to give (1-methyl-1H-benzoimidazol-2-yl)-methanol in quantitative yield. $^1$H NMR (400 MHz, DMSO-d$_6$) δ ppm 3.8 (s, 3 H) 4.7 (d, J=5.6 Hz, 2 H) 5.6 (t, J=5.7 Hz, 1 H) 7.2 (m, 1 H) 7.2 (m, 1 H) 7.5 (m, 1 H) 7.6 (m, 1 H).

Step 2: Conversion of (1-methyl-1H-benzoimidazol-2-yl)-methanol into 2-chloromethyl-1-methyl-1H-benzoimidazole was carried out according to Example 136, Step 2 in 48% yield. $^1$H NMR (400 MHz, CDCl$_3$) δ ppm 3.9 (s, 3 H) 4.9 (s, 2 H) 7.3 (m, 3 H) 7.8 (m, 1 H).

Step 3: Alkylation of 2-chloromethyl-1-methyl-1H-benzoimidazole with D-2-(4'-hydroxy-biphenyl-4-sulfonylamino)-3-methyl-butyric acid methyl ester was carried out according to Example 136, Step 3, to give D-3-methyl-2-[4'-(1-methyl-1H-benzoimidazol-2-ylmethoxy)-biphenyl-4-sulfonylamino]-butyric acid methyl ester in 28% yield. $^1$H NMR (400 MHz, DMSO-d$_6$) δ ppm 0.8 (dd, J=15.4, 6.8 Hz, 6 H) 1.9 (m, 1 H) 3.3 (s, 3 H) 3.6 (dd, J=9.5, 7.2 Hz, 1 H) 3.9 (s, 3 H) 5.5 (s, 2 H) 7.3 (m, 4 H) 7.6 (d, J=7.1 Hz, 1 H) 7.7 (d, J=7.8 Hz, 1 H) 7.7 (m, 4 H) 7.8 (m, 2 H) 8.3 (d, J=9.6 Hz, 1 H).

Step 4: Hydrolysis of D-3-methyl-2-[4'-(1-methyl-1H-benzoimidazol-2-ylmethoxy)-biphenyl-4-sulfonylamino]-butyric acid methyl ester was carried out according to Example 20, Step 5, in quantitative yield. $^1$H NMR (400 MHz, DMSO-d$_6$) δ ppm 0.8 (dd, J=11.9, 6.8 Hz, 6 H) 1.9 (m, 1 H) 3.5 (dd, J=9.3, 6.1 Hz, 1 H) 4.0 (s, 3 H) 5.7 (s, 2 H) 7.3 (d, J=9.1 Hz, 2 H) 7.5 (m, 2 H) 7.8 (m, 8 H) 8.1 (d, J=9.1 Hz, 1 H).

Example 139

D-3-Methyl-2-[4'-(3-methyl-benzofuran-2-ylmethoxy)-biphenyl-4-sulfonylamino]-butyric acid

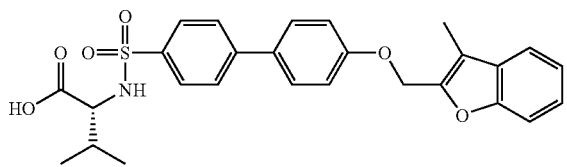

Step 1: A solution of 3-methyl-benzofuran-2-carboxylic acid (2.0 g, 11.4 mmol, 1 eq) in 60 mL of THF under nitrogen was placed in water bath. Then 30 mL of BH$_3$.THF (1.0 M in THF, 30 mmol, 2.6 eq) was added dropwise. The reaction mixture was allowed to stir at room temperature for 12 h. Then the reaction was quenched with methanol (10 mL). Solvent was removed in vacuo and the residue was subjected to column chromatography eluting with 20% ethyl acetate/hexane to give (3-methyl-benzofuran-2-yl)-methanol (1.6 g) in 87% yield. $^1$H NMR (400 MHz, DMSO-d$_6$) δ ppm 2.2 (s, 3 H) 4.5 (d, J=5.8 Hz, 2 H) 5.3 (t, J=5.8 Hz, 1 H) 7.3 (m, 2 H) 7.5 (m, 1 H) 7.6 (m, 1 H).

Step 2: To a solution of (3-methyl-benzofuran-2-yl)-methanol (1.12 g, 6.9 mmol) in 12 mL of dichloromethane was added 2.8 mL of thionyl chloride. The color of the reaction turned from pink initially to light yellow. After 2 h the reaction was worked up and 2-chloromethyl-3-methyl-benzofuran was obtained in quantitative yield. ¹H NMR (400 MHz, CDCl₃) δ ppm 2.3 (s, 3 H) 4.7 (s, 2 H) 7.2 (m, 1 H) 7.3 (m, 1 H) 7.5 (m, 1 H).

Step 3: Alkylation of 2-chloromethyl-3-methyl-benzofuran with 4-(4,4,5,5-tetramethyl-[1,3,2]dioxaborolan-2-yl)-phenol was carried out according to Example 136, Step 3, to give 3-methyl-2-[4-(4,4,5,5-tetramethyl-[1,3,2]dioxaborolan-2-yl)-phenoxymethyl]-benzofuran in 44% yield. ¹H NMR (400 MHz, CDCl₃) δ ppm 1.3 (s, 12 H) 2.3 (s, 3 H) 5.2 (s, 2 H) 7.0 (d, J=8.6 Hz, 2 H) 7.3 (m, 2 H) 7.5 (dd, J=21.6, 7.7 Hz, 2 H) 7.8 (d, J=8.8 Hz, 2 H).

Step 4: Suzuki coupling of D-2-(4-bromo-benzenesulfonylamino)-3-methyl-butyric acid methyl ester with 3-methyl-2-[4-(4,4,5,5-tetramethyl-[1,3,2]dioxaborolan-2-yl)-phenoxymethyl]-benzofuran was carried out according to Example 38, Step 3, in 75% yield. ¹H NMR (400 MHz, CD₃OD) δ ppm 0.8 (d, J=6.8 Hz, 6 H) 1.9 (m, 1 H) 2.2 (s, 3 H) 3.2 (s, 3 H) 3.5 (d, J=6.6 Hz, 1 H) 5.1 (s, 2 H) 7.0 (m, J=9.1 Hz, 2 H) 7.1 (m, 1 H) 7.2 (m, 1 H) 7.3 (m, 1 H) 7.4 (m, 1 H) 7.5 (d, J=9.1 Hz, 2 H) 7.6 (d, J=8.8 Hz, 2 H) 7.7 (m, 2 H).

Step 5: Hydrolysis of D-3-methyl-2-[4'-(3-methyl-benzofuran-2-ylmethoxy)-biphenyl-4-sulfonylamino]-butyric acid methyl ester was carried out according to Example 20, Step 5 in quantitative yield. 1H NM (400 MHz, CD₃OD) δ ppm 0.8 (dd, J=30.3, 6.8 Hz, 6 H) 2.0 (m, 1 H) 2.2 (s, 3 H) 3.5 (d, J=5.3 Hz, 1 H) 5.1 (s, 2 H) 7.1 (d, J=9.1 Hz, 2 H) 7.1 (m, 1 H) 7.2 (m, 1 H) 7.3 (d, J=8.3 Hz, 1 H) 7.5 (d, J=8.3 Hz, 1 H) 7.5 (d, J=9.1 Hz, 3 H) 7.6 (d, J=8.6 Hz, 2 H) 7.8 (d, J=8.8 Hz, 2 H).

Example 140

D-2-[4'-(Benzofuran-2-ylmethoxy)-3'-methoxy-biphenyl-4-sulfonylamino]-3-methyl-butyric acid

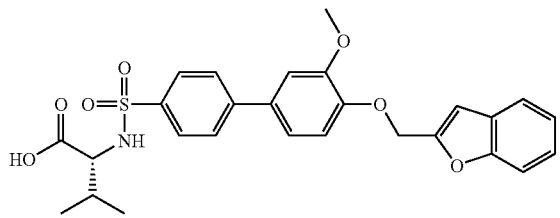

Step 1: To benzofuran-2-carbaldehyde (4 g, 27.4 mmol, 1 eq.), THF (50 mL) and methanol (50 mL) were added, under argon, and the reaction was cooled using an ice-salt bath. Then sodium borohydride (3.11 g, 82.1 mmol, 3 eq.) was added in several portions, and the reaction was allowed to warm slowly to room temperature for 1 hour. After work-up, benzofuran-2-yl-methanol was obtained in quantitative yield. ¹H NMR (400 MHz, DMSO-d₆) δ ppm 4.6 (d, J=5.8 Hz, 2 H) 5.5 (t, J=5.9 Hz, 1 H) 6.8 (s, 1 H) 7.3 (m, 2 H) 7.6 (m, 2 H).

Step 2: Alkylation of 2-bromomethyl-benzofuran with 2-methoxy-4-(4,4,5,5-tetramethyl-[1,3,2]dioxaborolan-2-yl)-phenol was carried out according to Example 136, Step 3, to give 2-[2-methoxy-4-(4,4,5,5-tetramethyl-[1,3,2]dioxaborolan-2-yl)-phenoxymethyl]-benzofuran in 29% yield. ¹H NMR (400 MHz, CDCl₃) δ ppm 1.3 (s, 12 H) 3.9 (s, 3 H) 5.3 (s, 2 H) 6.8 (d, J=0.8 Hz, 1 H) 7.0 (d, J=8.1 Hz, 1 H) 7.2 (m, 1 H) 7.3 (m, 1 H) 7.4 (dd, J=8.0, 1.4 Hz, 1 H) 7.5 (dd, J=8.1, 0.8 Hz, 1 H) 7.5 (dd, J=8.0, 1.1 Hz, 1 H).

Step 3: Suzuki coupling of D-2-(4-bromo-benzenesulfonylamino)-3-methyl-butyric acid methyl ester with 2-[2-methoxy-4-(4,4,5,5-tetramethyl-[1,3,2]dioxaborolan-2-yl)-phenoxymethyl]-benzofuran was carried out according to Example 38, Step 3, to provide 2-[4'-(benzofuran-2-ylmethoxy)-3'-methoxy-biphenyl-4-sulfonylamino]-3-methyl-butyric acid methyl ester in 53% yield. ¹H NMR (400 MHz, DMSO-d₆) δ ppm 0.8 (dd, J=14.1, 6.8 Hz, 6 H) 1.9 (m, 1 H) 3.6 (dd, J=9.2, 6.9 Hz, 1 H) 3.9 (s, 3 H) 5.3 (s, 2 H) 7.1 (s, 1 H) 7.3 (m, 5 H) 7.6 (d, J=8.3 Hz, 1 H) 7.7 (d, J=8.6 Hz, 1 H) 7.8 (d, J=8.6 Hz, 2 H) 7.9 (m, 2 H) 8.3 (d, J=9.3 Hz, 1 H).

Step 4: Hydrolysis of 2-[4'-(benzofuran-2-ylmethoxy)-3'-methoxy-biphenyl-4-sulfonylamino]-3-methyl-butyric acid methyl ester was carried out according to Example 20, Step 5, to provide 2-[4'-(benzofuran-2-ylmethoxy)-3'-methoxy-biphenyl-4-sulfonylamino]-3-methyl-butyric acid in quantitative yield. ¹H NMR (400 MHz, DMSO-d₆) δ pm 0.8 (dd, J=12.1, 6.8 Hz, 6 H) 1.9 (m, 1 H) 3.5 (dd, J=9.3, 6.1 Hz, 1 H) 3.9 (s, 3 H) 5.3 (s, 2 H) 7.1 (s, 1 H) 7.3 (m, 5 H) 7.6 (d, J=8.3 Hz, 1 H) 7.7 (d, J=6.3 Hz, 1 H) 7.8 (d, J=8.6 Hz, 2 H) 7.9 (m, 2 H) 8.0 (d, J=9.3 Hz, 1 H).

Example 141

D-2-[4'-(Benzofuran-2-ylmethoxy)-biphenyl-4-sulfonylamino]-3-methyl-butyric acid

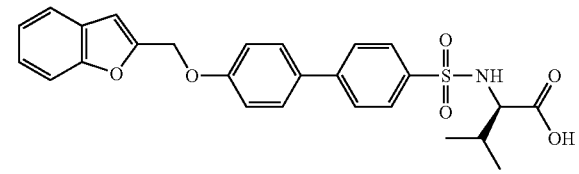

Step 1: To benzofuran-2-yl-methanol (4.3 g, 29.0 mmol, 1 eq., Example 140, Step 1), dichloromethane (200 mL) was added and the solution was cooled using an ice-ethanol bath. Then carbon tetrabromide (10.6 g, 31.9 mmol, 1.1 eq.) and 1,3-bis(diphenylphosphino)-propane (6.6 g, 16.0 mmol, 0.55 eq.) were added under argon, and the reaction was allowed to slowly warm to room temperature for 2.5 hours. After work-up and flash column chromatography, 2-bromomethyl-benzofuran was obtained in quantitative yield. ¹H NMR (400 MHz, DMSO-d₆) δ ppm 4.9 (s, 2 H) 7.0 (dd, J=5.3, 0.5 Hz, 1 H) 7.3 (dd, 1 H) 7.4 (m, 1 H) 7.6 (m, 2 H).

Step 2: To 2-bromomethyl-benzofuran (1.5 g, 7.1 mmol, 1 eq.), 4-(4,4,5,5-tetramethyl-[1,3,2]dioxaborolan-2-yl)-phenol (1.56 g, 7.1 mmol, 1 eq.), potassium carbonate (1.96 g, 14.2 mmol, 2 eq.), and acetonitrile (50 mL) were added under argon and the reaction was heated at 70° C. for 16 hours. After work-up and flash column chromatography, 2-[4-(4,4,5,5-tetramethyl-[1,3,2]dioxaborolan-2-yl)-phenoxymethyl]-benzofuran was obtained in 63% yield. ¹H NMR (400 MHz, DMSO-d₆) δ ppm 1.3 (s, 12 H) 5.3 (s, 2 H) 7.1 (m, 3 H) 7.3 (m, 1 H) 7.3 (m, 1 H) 7.6 (m, 4 H).

Step 3: Coupling of 2-[4-(4,4,5,5-tetramethyl-[1,3,2]dioxaborolan-2-yl)-phenoxymethyl]-benzofuran with D-2-(4-bromo-benzenesulfonylamino)-3-methyl-butyric acid tert-butyl ester was done according to Example 132, Step 2, to provide a 33% yield of D-2-[4'-(benzofuran-2-ylmethoxy)-biphenyl-4-sulfonylamino]-3-methyl-butyric acid tert-butyl ester. ¹H NMR (400 MHz, DMSO-d₆) δ ppm 0.8 (dd, J=8.3, 7.1 Hz, 6 H) 1.2 (s, 9 H) 1.9 (m, 1 H) 3.5 (dd, J=9.7, 6.2 Hz, 1 H) 5.3 (s, 2 H) 7.1 (s, 1 H) 7.2 (d, J=8.6 Hz, 2 H) 7.3 (m, 1 H) 7.3 (m, 1 H) 7.6 (dd, J=8.2, 0.6 Hz, 1 H) 7.7 (m, 3 H) 7.8 (d, J=3.3 Hz, 4 H) 8.1 (d, J=9.9 Hz, 1 H).

Step 4: To D-2-[4'-(benzofuran-2-ylmethoxy)-biphenyl-4-sulfonylamino]-3-methyl-butyric acid tert-butyl ester (126 mg, 0.23 mmol, 1 eq.) in acetonitrile (10 mL) under argon were added cerium chloride heptahydrate (175 mg, 0.47 mmol, 2 eq.), and potassium iodide (51 mg, 0.30 mmol, 1.3 eq.) and the reaction was heated at 70° C. for 16 hours. After work-up and flash column chromatography, D-2-[4'-(benzofuran-2-ylmethoxy)-biphenyl-4-sulfonylamino]-3-methyl-butyric acid was obtained in 25% yield. $^1$H NMR (400 MHz, DMSO-$d_6$) δ ppm 0.8 (dd, J=12.5, 6.7 Hz, 6 H) 2.0 (m, 1 H) 3.5 (dd, J=9.2, 5.9 Hz, 1 H) 5.3 (s, 2 H) 7.1 (s, 1 H) 7.2 (d, J=8.8 Hz, 2 H) 7.3 (dd, J=8.1, 0.8 Hz, 1 H) 7.3 (m, 1 H) 7.6 (d, J=8.1 Hz, 1 H) 7.7 (m, 1 H) 7.7 (d, J=8.8 Hz, 2 H) 7.8 (d, 4 H) 8.0 (d, J=9.3 Hz, 1 H).

Example 142

L-2-[4'-(5-Chloro-4-methoxy-3-methyl benzofuran-2-ylmethoxy)-biphenyl-4-sulfonylamino]-3-methyl butyric acid

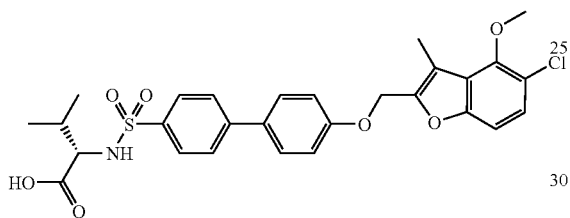

Step 1: To 0.31 g (1.3 mmol) 5-chloro-4-methoxy-3-methyl-benzofuran-2-carboxylic acid (Example 116, Step 3) in 10 mL of THF under nitrogen was added 1.0M BH$_3$/THF solution (1.8 mL; 1.8 mmol; 1.4 eq). The reaction was stirred overnight and then quenched cautiously with water and extracted twice with ethyl acetate. The combined organic layers were washed with 1N sodium hydroxide and then brine, dried over magnesium sulfate, filtered and concentrated in vacuo to give (5-chloro-4-methoxy-3-methyl benzofuran-2-yl)-methanol as a white crystalline solid (0.29 g; 99% yield).

Step 2: To a 0° C. solution of (5-chloro-4-methoxy-3-methyl benzofuran-2-yl)-methanol (0.29 g; 1.3 mmol) in dichloromethane (5 mL) was added neat phosphorus tribromide (0.18 mL; 0.52 g; 1.9 mmol; 1.5 eq) and pyridine (3 drops). The ice bath was removed and the reaction was allowed to warm to room temperature overnight. Additional phosphorus tribromide (0.09 mL; 0.26 g; 0.95 mmol; 0.75 eq) was added and stirring continued at room temperature. After two hours, the reaction was quenched with ice and extracted twice with ethyl acetate. The combined organic layers were washed with water and saturated sodium bicarbonate, followed by drying over magnesium sulfate, filtration and concentration in vacuo to give essentially pure 2-bromomethyl-5-chloro-4-methoxy-3-methyl benzofuran (0.37 g; 99%).

Step 3: To a flask charged with L-2-(4'-hydroxy-biphenyl-4-sulfonylamino)-3-methyl butyric acid methyl ester (0.49 g; 1.3 mmol; 1.05 eq) and 2-bromomethyl-5-chloro-4-methoxy-3-methyl benzofuran (0.37 g; 1.2 mmol; 1 eq) was added reagent grade acetone (20 mL) and solid potassium carbonate (0.18 g; 1.2 mmol; 1 eq). After stirring at room temperature for 12 h, the acetone was removed in vacuo and the residue was diluted with water. The resulting mixture was extracted twice with ethyl acetate and the combined organic layers were washed successively with water, 1N sodium hydroxide, and brine, dried over magnesium sulfate, filtered and concentrated in vacuo to give the crude product as a tan solid. This was chromatographed on silica gel, eluting with 20% to 30% ethyl acetate/hexanes to give L-2-[4'-(5-chloro-4-methoxy-3-methyl benzofuran-2-ylmethoxy)-biphenyl-4-sulfonylamino]-3-methyl butyric acid methyl ester as an off-white solid (0.41 g; 57%).

Step 4: To a solution of L-2-[4'-(5-chloro-4-methoxy-3-methyl benzofuran-2-ylmethoxy)-biphenyl-4-sulfonylamino]-3-methyl butyric acid methyl ester (0.41 g; 0.72 mmol) dissolved in 1:1 methanol/THF (10 mL) was added 7.2 mL of 1N sodium hydroxide (7.2 mmol; 10 eq) and the resulting solution was stirred at room temperature overnight. The organic solvents were removed in a stream of nitrogen and the aqueous layer was acidified to pH~3 with concentrated HCl and extracted twice with ethyl acetate. The organic layers were dried over magnesium sulafate, filtered and concentrated in vacuo the to provide L-2-[4'-(5-chloro-4-methoxy-3-methyl benzofuran-2-ylmethoxy)-biphenyl-4-sulfonylamino]-3-methyl butyric acid as an off-white solid (0.32 g; 79% yield). Mass Spec: M–H$^-$=556.1, 558.1

Example 143

L-2-[4'-(5-Cyano-4-methoxy-3-methyl benzofuran-2-ylmethoxy)-biphenyl-4-sulfonylamino]-3-methyl butyric acid

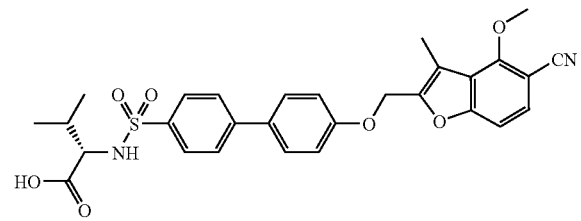

Step 1: A suspension of (5-bromo-4-methoxy-3-methyl benzofuran-2-yl)-methanol (0.31 g; 1.1 mmol, Example 136, Step 1) and CuCN (0.21 g; 2.3 mmol; 2 eq) in N-methylpyrrolidinone (1.5 mL) was subjected to microwave radiation at 200° C. for 10 minutes. The reaction was diluted with water and ethyl acetate (10 mL each) and filtered. The layers were separated and the aqueous phase was washed with a second portion of ethyl acetate. The combined organic layers were washed twice with water and once with brine. After drying over magnesium sulfate, filtration and concentration in vacuo gave the crude product. Chromatography on silica gel, eluting with 20% to 30% ethyl acetate/hexanes gave pure 2-hydroxymethyl-4-methoxy-3-methyl benzofuran-5-carbonitrile (0.17 g; 67% yield).

Step 2: A solution of 2-hydroxymethyl-4-methoxy-3-methyl benzofuran-5-carbonitrile (0.17 g; 0.76 mmol) in dichloromethane (5 mL) was cooled to 0° C. To this solution was added, successively, neat phosphorus tribromide (0.11 mL; 0.32 g; 1.2 mmol; 1.5 eq) and pyridine (2 drops). The ice bath was removed and the reaction was allowed to come to room temperature overnight with stirring. After quenching with ice, the crude product was isolated by ethyl acetate extraction. The organic layer was washed with saturated sodium bicarbonate, then dried over magnesium sulfate, filtered and concentrated in vacuo to give 2-bromomethyl-4-methoxy-3-methyl benzofuran-5-carbonitrile (0.20 g; 95% yield).

Step 3: To a vial charged with L-2-(4'-hydroxy-biphenyl-4-sulfonylamino)-3-methyl butyric acid methyl ester (0.28 g; 0.76 mmol; 1.05 eq) and 2-bromomethyl-4-methoxy-3-methyl benzofuran-5-carbonitrile (0.20 g; 0.72 mmol; 1 eq) was added reagent grade acetone (5 mL) and solid cesium carbonate (0.23 g; 0.72 mmol; 1 eq). The reaction proceeded overnight and was concentrated in vacuo when TLC indicated the consumption of starting materials. The residue was diluted with water and extracted twice with ethyl acetate. The combined organic layers were washed with water, 1N sodium hydroxide and brine, then dried over magnesium sulfate, filtered and concentrated in vacuo to give the crude ether as a tan solid. This was chromatographed on silica gel, eluting with 20% to 30% ethyl acetate/hexanes, followed by one recrystallization from ethyl acetate/hexanes to give L-2-[4'-(5-cyano-4-methoxy-3-methyl benzofuran-2-ylmethoxy)-biphenyl-4-sulfonylamino]-3-methyl butyric acid methyl ester as a white crystalline solid (0.28 g; 68%).

Step 4: To a solution of L-2-[4'-(5-cyano-4-methoxy-3-methyl benzofuran-2-ylmethoxy)-biphenyl-4-sulfonylamino]-3-methyl butyric acid methyl ester (0.16 g; 0.28 mmol) dissolved in 1:1 methanol/THF (5 mL) was added 1 N sodium hydroxide solution (3 mL; 3.0 mmol; 10 eq) and the reaction was stirred overnight at room temperature. The temperature was then raised to 40° C. for 4 h whereupon the organic solvent was removed in a stream of nitrogen and the resulting aqueous residue was acidified to pH~3 with concentrated HCl. This was then extracted with ethyl acetate (2×) and the combined organic layers were dried over magnesium sulfate, filtered and concentrated in vacuo to give pure L-2-[4'-(5-cyano-4-methoxy-3-methyl benzofuran-2-ylmethoxy)-biphenyl-4-sulfonylamino]-3-methyl butyric acid as an off-white solid. (0.20 g; 73% yield). Mass Spec: M-H⁻=547.1

Example 144

N-{[4'-(2-Furoyloxy)-1,1'-biphenyl-4-yl]sulfonyl}-D-valine

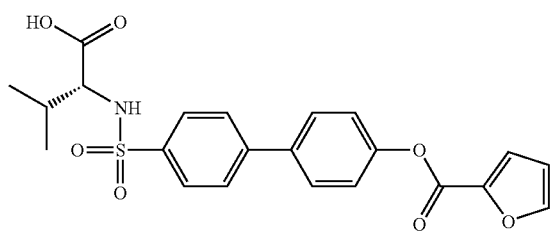

According to the procedure of Example 134, furan-2-carbonyl chloride provided N-{[4'-(2-furoyloxy)-1,1'-biphenyl-4-yl]sulfonyl}-D-valine. $^1$H NMR (400 MHz, DMSO-d$_6$) δ ppm 0.82 (d, J=6.82 Hz, 3 H) 0.85 (d, J=6.82 Hz, 3 H) 1.96 (m, 1 H) 3.57 (dd, J=9.35, 6.06 Hz, 1 H) 6.83 (dd, J=3.54, 1.77 Hz, 1 H) 7.42 (d, J=8.84 Hz, 2 H) 7.61 (dd, J=3.66, 0.88 Hz, 1 H) 7.86 (m, 6 H) 8.09 (d, J=9.35 Hz, 1 H) 8.13 (dd, J=1.77, 0.76 Hz, 1 H).

Example 145

N-{[4'-(3-Furoyloxy)-1,1'-biphenyl-4-yl]sulfonyl}-D-valine

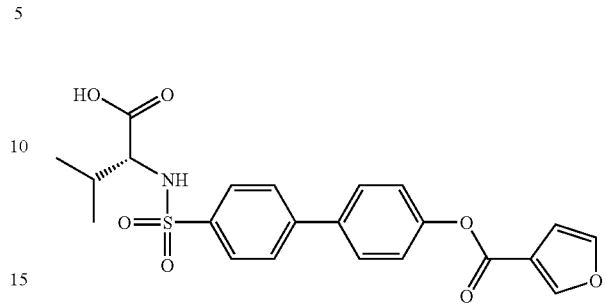

According to the procedure of Example 134, furan 3-carbonyl chloride provided N-{[4'-(3-furoyloxy)-1,1'-biphenyl-4-yl]sulfonyl}-D-valine. $^1$H NMR (400 MHz, CD$_3$OD) δ ppm 0.82 (d, J=6.82 Hz, 3 H) 0.88 (d, J=6.82 Hz, 3 H) 1.96 (m, 1 H) 3.59 (d, J=5.56 Hz, 1 H) 6.81 (s, 1 H) 7.23 (d, J=8.84 Hz, 2 H) 7.59 (d, J=2.02 Hz, 1 H) 7.66 (d, J=8.84 Hz, 2 H) 7.70 (d, J=8.84 Hz, 2 H) 7.83 (d, J=8.59 Hz, 2 H) 8.30 (d, J=0.76 Hz, 1 H).

Example 146

L-2-[4'-(4-Ethyl-3-methyl benzofuran-2-ylmethoxy)-biphenyl-4-sulfonylamino]-3-methyl butyric acid

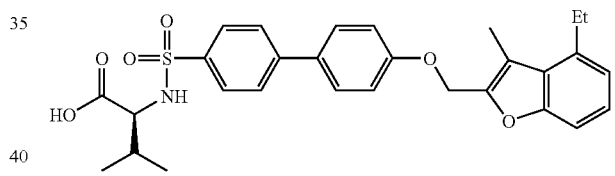

Step 1: To 3-methyl-4-ethylbenzofuran-2-carboxylic acid ethyl ester (0.795 g, 3.43 mmol) in tetrahydrofuran (20 mL) cooled at 0° C. was added diisopropylaluminium hydride (13.7 mL, of a 1.0M solution in toluene) dropwise. After stirring for 1 hour methanol (10 mL) was added followed by saturated aqueous sodium potassium tartrate (10 mL). The resulting mixture was stirred for 15 minutes and was then thrice extracted with ethyl acetate. The combined organic extracts were dried over sodium sulfate, filtered, reduced to dryness and the resulting residue was subjected to silica gel gradient flash chromatography (hexanes/ethyl acetate 10:1-3:1) which furnished 0.6124 g (94%) of 4-ethyl-3-methyl-benzofuran-2-yl)-methanol as a white solid. MS (ES) m/z: 190.1 (M⁺).

Step 2: To a solution of 4-ethyl-3-methyl-benzofuran-2-yl)-methanol (77 mg, 0.403 mmol) in dichloromethane (4 mL) at 0° C. was added pyridine (0.1 mL) followed by phosphorous tribromide (0.057 mL, 0.604 mmol). The cooling bath was removed and the solution was stirred for 1 hour at room temperature. After recooling to 0° C. the reaction was quenched by the addition of ice chips. The mixture was extracted with ethyl acetate and the combined organic layers were washed with saturated aqueous sodium bicarbonate and saturated aqueous sodium bromide. The solution was dried over sodium sulfate, filtered and reduced to dryness to provide 83 mg (82%) of 4-ethyl-3-methyl-2-bromomethyl-benzofuran as a white solid.

Step 3: To a solution of L-2-(4'-hydroxy-biphenyl-4-sulfonylamino)-3-methyl butyric acid methyl ester (165 mg, 0.454 mmol) in DMF (3 mL) was added cesium carbonate (444 mg, 1.362 mmol). After 10 minutes 4-ethyl-3-methyl-2-bromomethyl-benzofuran (82 mg, 0.324 mmol) in dimethylformamide (3 mL) was added dropwise. After 1 hour water (30 mL) was added and the solution was extracted with ethyl acetate. Combined organic extracts were dried over sodium sulfate, filtered, reduced to dryness and the resulting residue was subjected to silica gel gradient flash chromatography (hexanes/ethyl acetate 20:1-3:1) which furnished 89 mg (51%) of L-2-[4'-(4-ethyl-3-methyl benzofuran-2-ylmethoxy)-biphenyl-4-sulfonylamino]-3-methyl butyric acid methyl ester as a white solid. MS (ES) m/z: 536.2 (M+H)$^+$, 1071.4 (2M+H).

Step 4: To a solution of L-2-[4'-(4-ethyl-3-methyl benzofuran-2-ylmethoxy)-biphenyl-4-sulfonylamino]-3-methyl butyric acid methyl ester (70 mg, 0.131 mmol) in tetrahydrofuran (6 mL), methanol (4 mL), water (2 mL) was added lithium hydroxide (125 mg, 5.23 mmol). After stirring for 2.5 days at room temperature hydrochloric acid (5.23 mL, 1 N solution) was added followed by ethyl acetate (50 mL). The layers were separated and the organic phase was washed with water, dried over sodium sulfate, filtered and reduced to dryness. The solid material was recrystallized from a minimum amount of boiling isopropanol to furnish which furnished 54 mg (79%) of L-2-[4'-(4-ethyl-3-methyl benzofuran-2-ylmethoxy)-biphenyl-4-sulfonylamino]-3-methyl butyric acid as a white solid. MS (ES) m/z: 520.1 (M−H)$^−$, 1041.4 (2M−H).

Example 147

N-[(4'-{[4-(3-methoxypropyl)-3-methyl-1-benzofuran-2-yl]methoxy}-1,1'-biphenyl-4-yl)sulfonyl]-L-valine

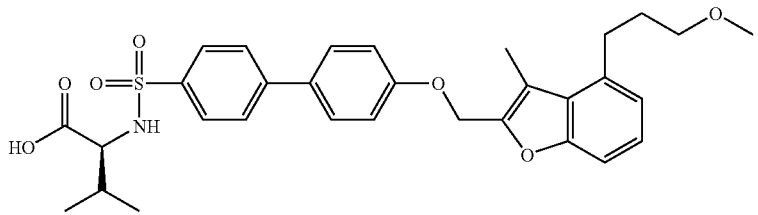

Step 1: A mixture of 4-(3-methoxy-prop-1-ynyl)-3-methyl-benzofuran-2-carboxylic acid ethyl ester (2.6566 g, 0.00977 mol, Example 22, Step 1) and 10% palladium on activated carbon (705 mg) and tetrahydrofuran (60 mL) was stirred under a hydrogen atmosphere (balloon) for 20 hours. After filtering the mixture through a celite pad the resulting solution was reduced to dryness furnishing 2.46 g (91%) of of 4-(3-methoxy-propyl)-3-methyl-benzofuran-2-carboxylic acid ethyl ester as a clear oil. MS (ES) m/z: 277.1 (M+H)$^+$, 553.3 (2M+H).

Step 2: To a solution of 4-(3-methoxy-propyl)-3-methyl-benzofuran-2-carboxylic acid ethyl ester (2.213 g, 8.018 mol) in tetrahydrofuran (25 mL) and methanol (9 mL) at room temperature was added 1N LiOH (16.838 mL). The resulting yellow solution was stirred at room temperature for 2.5 hours, neutralized with 1N HCl and was then partitioned between ethyl acetate and water. The organic layer was dried over sodium sulfate, filtered and reduced to dryness furnishing 1.98 g (98%) of 4-(3-methoxy-propyl)-3-methyl-benzofuran-2-carboxylic acid as a white solid. MS (ES) m/z: 249.11214 (M+H)$^+$, 497.21700 (2M+H).

Step 3: To 4-(3-methoxy-propyl)-3-methyl-benzofuran-2-carboxylic acid (0.2354 g, 0.853 mmol) in tetrahydrofuran (10 mL) cooled at 0° C. was added diisopropylaluminium hydride (3.41 mL, of a 1.0M solution in toluene) dropwise. After stirring for 1 hour methanol (5 mL) was added followed by saturated aqueous sodium potassium tartrate (5 mL). The resulting mixture was stirred for 15 minutes and was then thrice extracted with ethyl acetate. Combined organic extracts were dried over sodium sulfate, filtered, reduced to dryness and the resulting residue was subjected to silica gel gradient flash chromatography (hexanes/ ethyl acetate 10:1-3:1) which furnished 0.192 g (96%) of [4-(3-methoxypropyl)-3-methyl-1-benzofuran-2-yl]methanol as a white solid. MS (ES) m/z: 234.1 (M$^+$).

Step 4: To a solution of [4-(3-methoxypropyl)-3-methyl-1-benzofuran-2-yl]methanol (181 mg, 0.774 mmol) in dichloromethane (4 mL) at 0° C. was added pyridine (0.1 mL) followed by phosphorous tribromide (0.109 mL, 1.16 mmol). The cooling bath was removed and the solution was stirred for 1 hour at room temperature. After recooling to 0° C. the reaction was quenched by the addition of ice chips. The mixture was extracted with ethyl acetate and the combined organic layers were washed with saturated aqueous sodium bicarbonate and saturated aqueous sodium bromide. The solution was dried over sodium sulfate, filtered and reduced to dryness to furnish 188 mg (82%) of the [4-(3-methoxypropyl)-3-methyl-2-bromomethyl-1-benzofuran, which was directly carried on to the next step.

Step 5: To a solution of L-2-(4'-hydroxy-biphenyl-4-sulfonylamino)-3-methyl butyric acid methyl ester (240 mg, 0.66 mmol) in acetone (5 mL) was added cesium carbonate (206 mg, 0.633 mmol). After 10 minutes [4-(3-methoxypropyl)-3-methyl-2-bromomethyl-1-benzofuran (188 mg, 0.633 mmol), in acetone (5 mL) was added dropwise. After 1 hour water (20 mL) was added and the solution was extracted with ethyl acetate. Combined organic extracts were dried over sodium sulfate, filtered, reduced to dryness and the resulting residue was subjected to silica gel gradient flash chromatography (hexanes/ethyl acetate 20:1-3:1) which furnished 210 mg (57%) of methyl N-[(4'-{[4-(3-methoxypropyl)-3-methyl-1-benzofuran-2-yl]methoxy}-1,1'-biphenyl-4-yl)sulfonyl]-L-valinate as a white solid. MS (ES) m/z: 580.2 (M+H).

Step 6: To a solution of methyl N-[(4'-{[4-(3-methoxypropyl)-3-methyl-1-benzofuran-2-yl]methoxy}-1,1'-biphenyl-4-yl)sulfonyl]-L-valinate (192 mg, 0.331 mmol) in tetrahydrofuran (12 mL), methanol (8 mL), water (4 mL) was added lithium hydroxide (317 mg, 13.25 mmol). After stirring for 2.5 days at room temperature hydrochloric acid (13.25 mL, 1

N solution) was added followed by ethyl acetate (80 mL). The layers were separated and the organic phase was washed with water, dried over sodium sulfate, filtered and reduced to dryness. The solid material was recrystallized from a minimum amount of boiling isopropanol to furnish which furnished 171 mg (91%) of N-[(4'-{[4-(3-methoxypropyl)-3-methyl-1-benzofuran-2-yl]methoxy}-1,1'-biphenyl-4-yl)sulfonyl]-L-valine as a white solid. MS (ES) m/z: 564.2 (M–H), 1129.4 (2M–H).

Example 148

N-({4'-[(5-Bromo-4-methoxy-3-methyl-1-benzofuran-2-yl)methoxy]-1,1'-biphenyl-4- yl}sulfonyl)-L-valine

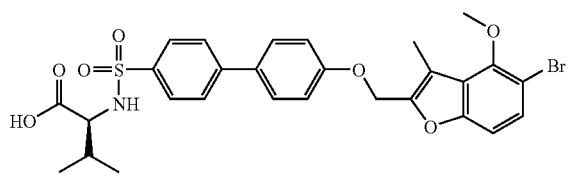

According to the procedure of Example 136 N-({4'-[(5-bromo-4-methoxy-3-methyl-1-benzofuran-2-yl)methoxy]-1,1'-biphenyl-4-yl}sulfonyl)-L-valine was obtained starting from 5-bromo-2-chloromethyl-4-methoxy-3-methyl-benzofuran and of L-2-(4'-hydroxy-biphenyl-4-sulfonylamino)-3-methyl butyric acid methyl ester. m.p. 198-200° C.; MS: 600.0 (M–H)⁻.

Example 149

N-({4'-[(5-Bromo-4-isopropoxy-3-methyl-1-benzofuran-2-yl)methoxy]-1,1'-biphenyl-4-yl}sulfonyl)-D-valine

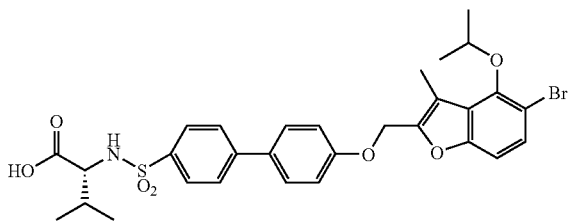

Step 1: To 0.50 g (1.7 mmole) of ethyl 5-bromo-4-hydroxy-3-methyl-1-benzofuran-2-carboxylate (Example 119, Step 1) in 7 mL DMF was added 0.51 g (3.75 mmole) of potassium carbonate and 0.48 mL (3 mmole) of 2-bromopropane and the reaction was stirred at room temperature overnight. The solvent was concentrated in vacuo, and the residue was extracted with ethyl acetate and water. The organic layer washed with water and brine, dried over sodium sulfate, filtered, and concentrated to provide 0.58 g of ethyl 5-bromo-4-isopropoxy-3-methyl-1-benzofuran-2-carboxylate. Yield: 100%; m.p. 48-50° C.; MS: 341.0 (M+H)⁺.

Step 2: To 0.58 g (1.7 mmole) of ethyl 5-bromo-4-isopropoxy-3-methyl-1-benzofuran-2-carboxylate in 15 mL of THF and 15 mL MeOH was added 8.5 mL of 1NaOH and the reaction was stirred at room temperature for 1 hour. The solvent was concentrated in vacuo, the residue was neutralized with 1N HCl and extracted with ethyl acetate. The organic layer was washed with water and brine, dried over sodium sulfate, filtered, and concentrated to provide 0.46 g of 5-bromo-4-isopropoxy-3-methyl-1-benzofuran-2-carboxylic acid. Yield 86.8%; m.p. 182-184° C.; MS 311.0 (M–H)⁻.

Step 3: A solution of 5-bromo-4-isopropoxy-3-methyl-1-benzofuran-2-carboxylic acid (0.43 g 1.37 mmole) in 25 mL of THF under nitrogen was placed in a water bath. To this solution was added 2 mL of BH₃.THF (1.0M in THF, 2.06 mmole, 1.4 eq) dropwise. After 24 hours, The mixture was quenched with water, the solvent was concentrated in vacuo, and the residue was extracted with ethyl acetate. The organic layer washed with water, saturated sodium carbonate and brine, dried over sodium sulfate, filtered, and concentrated to provide 0.33 g of (5-bromo-4-isopropoxy-3-methyl-1-benzofuran-2-yl) methanol. Yield 80.5%; EA: Theory C: 52.15: H, 5.05. Found C: 52.26; H: 4.80.

Step 4: To a solution of (5-bromo-4-isopropoxy-3-methyl-1-benzofuran-2-yl) methanol (0.3 g, 1 mmole) in 10 mL dichloromethane was added 0.73 mL of thionyl chloride and the reaction was stirred at room temperature for 2 hours. The solvent was concentrated in vacuo, the residue was added toluene to provide 0.33 g of 5-bromo-4-isopropoxy-3-methyl-2-chloromethyl-1-benzofuran.

Step 5: A mixture of the above chloro compound (0.31 g, 1.03 mmole), methyl N-[(4'-hydroxy-1,1'-biphenyl-4-yl)sulfonyl]-D-valinate (0.37 g, 0.98 mmole) and potassium carbonate (0.34 g, 2.45 mmole) in 20 mL DMF were heated on an oil bath (~90° C.) for 18 hours. The solvent was concentrated in vacuo, and the residue was extracted with ethyl acetate. The organic layer washed with water and brine, dried over sodium sulfate, filtered, and concentrated to provide 0.61 g of the crude product. After column chromatography eluting with hexane/ethyl acetate (2:1) 0.13 g of methyl N-({4'-[(5-bromo-4-isopropoxy-3-methyl-1-benzofuran-2-yl)methoxy]-1,1'- biphenyl-4-yl}sulfonyl)-D-valinate was obtained. Yield 20.6%; m.p. 154-156° C.; MS: 661(M+NH₄)⁺.

Step 6: According to the procedure of Example 136, Step 4, 0.11 g of methyl N-({4'-[(5-bromo-4-isopropoxy-3-methyl-1-benzofuran-2-yl)methoxy]-1,1'-biphenyl-4-yl}sulfonyl)-D-valinate provided 0.1 g of N-({4'-[(5-bromo-4-isopropoxy-3-methyl-1-benzofuran-2-yl)methoxy]-1,1'-biphenyl-4-yl}sulfonyl)-D-valine. Yield ~100%; m.p. 137-140° C.; MS: 628 (M–H)⁻.

Example 150

N-[(4'-{[(5-bromo-4-methoxy-3-methyl-1-benzofuran-2-yl)methyl]amino}-1,1'-biphenyl-4-yl)sulfonyl]-L-valine

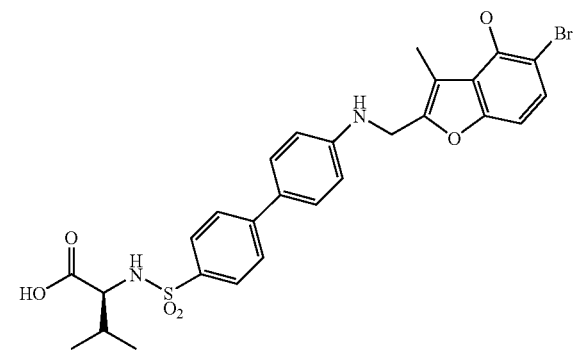

Step 1: To a solution of 0.21 g (0.77 mmole) of 5-bromo-4-methoxy-3-methyl-1-benzofuran-2-yl) methanol (Example 136, Step 1) in 6 mL of dichloromethane, 0.36 g (0.85 mmole, 1.1 eq) of Dess Martin periodinane was added. The reaction was stirred at room temperature for 2 hours and then diluted with 15 mL of ether. To the reaction was added 5 mL of 1NaOH and the mixture was stirred for 30 minutes. The reaction was diluted with ether and water. The organic layer was washed with water and brine, dried over sodium sulfate, filtered and concentrated to provide 0.19 g of 5-bromo-4-methoxy-3-methyl-1-benzofuran-2-carbaldehyde. Yield 90.4%; m.p. 81-82° C.; MS: 268.9 (M+H)$^+$.

Step 2: To 0.14 g (0.52 mmole) of 5-bromo-4-methoxy-3-methyl-1-benzofuran-2-carbaldehyde and 0.20 g (0.55 mmole) of L-2-(4'-amino-biphenyl-4-sulfonylamino)-3-methyl-butyric acid methyl ester in 8 mL dichloromethane was added 0.15 g (0.68 mmole) of sodium triacetoxyborohydride and the mixture was stirred at room temperature for 1.5 h. The reaction was diluted with ethyl acetate, and then neutralized with 1N NaOH to pH~8. The organic layer was washed with water and brine, dried over sodium sulfate, filtered and concentrated. After chromatography on silica gel eluting with hexane: ethyl acetate (2:1) 0.21 g of methyl N-[(4'-{[(5-bromo-4-methoxy-3-methyl-1-benzofuran-2-yl)methyl]amino}-1,1'-biphenyl-4-yl)sulfonyl]-L-valinate was obtained. Yield 66.7%; m.p. 144-146° C.; MS: 615.2 (M+H)$^+$.

Step 3: According to the procedure of Example 136, Step 4, 0.22 g of methyl N-[(4'-{[(5-bromo-4-methoxy-3-methyl-1-benzofuran-2-yl)methyl]amino}-1,1'-biphenyl-4-yl)sulfonyl]-L-valinate provided 0.20 g of N-[(4'-{[(5-bromo-4-methoxy-3-methyl-1-benzofuran-2-yl)methyl]amino}-1,1'-biphenyl-4-yl)sulfonyl]-L-valine. Yield 90.9%; m.p. 194-198° C.; MS 601.0 (M+H)$^+$.

Example 151

L-2-{4'-[(Benzothiazole-2-carbonyl)-amino]-biphenyl-4-sulfonylamino}-3-methyl-butyric acid

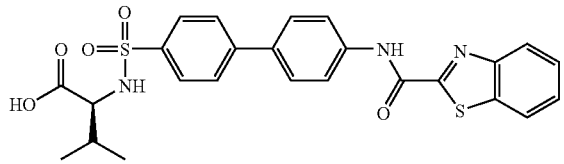

Step 1. To an oven-dried flask was added L-2-(4'-amino-biphenyl-4-sulfonylamino)-3-methyl-butyric acid methyl ester (0.552 g), anhydrous methylene chloride (10 mL), and N,N-diisopropylethylamine (2.0 equiv.). The solution was cooled with an ice bath before the addition of 2-benzothioxazolecarboxylic acid chloride (1.0 equiv.), prepared according to a literature procedure: Romero, et al *J. Med. Chem.* 1993, 37, 999. The reaction was allowed to stir at 0° C. for 4 h after which it was judged complete. Water was added, and the resulting mixture was extracted with $CH_2Cl_2$ (2×15 mL). The organic layers were combined, dried over magnesium sulfate, and evaporated under reduced pressure to afford L-2-{4'-[(benzothiazole-2-carbonyl)-amino]-biphenyl-4-sulfonylamino}-3-methyl-butyric acid methyl ester as a white solid in quantitative yield.

Step 2. Hydrolysis of L-2-{4'-[(benzothiazole-2-carbonyl)-amino]-biphenyl-4-sulfonylamino}-3-methyl-butyric acid methyl ester according to the procedure described in Example 20, Step 5 afforded the final product L-2-{4'-[(benzothiazole-2-carbonyl)-amino]-biphenyl-4-sulfonylamino}-3-methyl-butyric acid as a white solid. $^1$H NMR (400 MHz, DMSO-d$_6$) δ ppm 0.8 (dd, J=13.3, 6.7 Hz, 6 H) 2.0 (m, 1 H) 3.6 (t, J=6.6 Hz, 1 H) 7.7 (m, 2 H) 7.8 (m, 4 H) 7.9 (m, 2 H) 8.1 (d, J=8.8 Hz, 3 H) 8.3 (dd, J=17.9, 7.8 Hz, 2 H) 11.3 (s, 1 H) 12.6 (s, 1 H).

Example 152

D-2-{4'-[(Benzothiazole-2-carbonyl)-amino]-biphenyl-4-sulfonylamino}-3-methyl-butyric acid

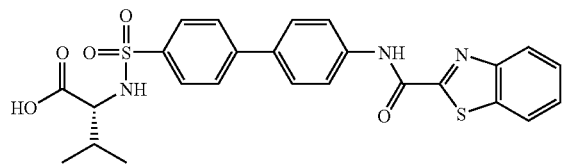

Step 1. To an oven-dried flask was added D-2-(4'-amino-biphenyl-4-sulfonylamino)-3-methyl-butyric acid methyl ester (0.552 g), anhydrous methylene chloride (10 mL), and N,N-diisopropylethylamine (2.0 equiv.). The solution was cooled with an ice bath before the addition of 2-benzothiazolecarboxylic acid chloride (1.0 equiv). The reaction was allowed to stir at 0° C. for 4 h after which it was judged complete. Water was added and the resulting mixture was extracted with dichloromethane (2×15 mL). The organic layer was combined, dried over magenesium sulfate, and evaporated under reduced pressure to afford D-2-{4'-[(benzothiazole-2-carbonyl)-amino]-biphenyl-4-sulfonylamino}-3-methyl-butyric acid methyl ester as a white solid in quantitative yield.

Step 2. Hydrolysis of D-2-{4'-[(benzothiazole-2-carbonyl)-amino]-biphenyl-4-sulfonylamino}-3-methyl-butyric acid methyl ester according to the procedure described in Example 20, Step 5 afforded D-2-{4'-[(benzothiazole-2-carbonyl)-amino]-biphenyl-4-sulfonylamino}-3-methyl-butyric acid as a white solid. $^1$H NMR (400 MHz, DMSO-d$_6$) δ ppm 0.8 (dd, J=12.9, 6.8 Hz, 6 H) 2.0 (m, 1 H) 3.6 (dd, J=9.3, 6.1 Hz, 1 H) 7.7 (m, 2 H) 7.9 (m, 6 H) 8.1 (m, 3 H) 8.3 (m, 2 H) 11.3 (s, 1 H) 12.6 (s, 1 H).

Example 153

L-3-Methyl-2-{4'-[(naphtho[2,1-b]furan-2-carbonyl)-amino]-biphenyl-4-sulfonylamino}-butyric acid

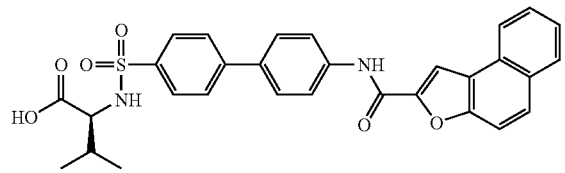

Step 1: Coupling of naphtho[2,1-b]furan-2-carboxylic acid (Emmont & Livingstone, *J. Chem. Soc.* 1957, 3144) with L-2-(4'-amino-biphenyl-4-sulfonylamino)-3-methyl-butyric acid t-butyl ester was carried out according to the procedure described in Example 21, Step 3. The L-3-methyl-2-{4'-[(naphtho[2,1-b]furan-2-carbonyl)-amino]-biphenyl-4-sulfonylamino}-butyric acid t-butyl ester was obtained as a white solid in 75% yield.

Step 2: Removal of the t-butyl group was conducted using 40% TFA in methylene chloride at ambient temperature in 4 hours. The L-3-methyl-2-{4'-[(naphtho[2,1-b]furan-2-carbonyl)-amino]-biphenyl-4-sulfonylamino}-butyric acid was isolated as a white solid in 90% yield. $^1$H NMR (400 MHz, DMSO-$d_6$) δ ppm 0.8 (dd, J=12.9, 6.8 Hz, 6 H) 2.0 (m, 1 H) 3.6 (dd, J=9.1, 6.1 Hz, 1 H) 7.7 (m, 2 H) 8.0 (m, 11 H) 8.4 (m, 2 H) 10.8 (s, 1 H).

Example 154

L-3-Methyl-2-{4'-[(1-methyl-naphtho[2,1-b]furan-2-carbonyl)-amino]-biphenyl-4-sulfonylamino}-butyric acid

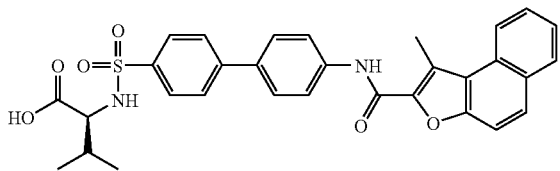

Step 1: Coupling of 1-methyl-naphtho[2,1-b]furan-2-carboxylic acid (prepared according to Emmont & Livingstone, *J. Chem. Soc.* 1957, 3144) with L-2-(4'-amino-biphenyl-4-sulfonylamino)-3-methyl-butyric acid t-butyl ester was carried out according to the procedure described in Example 21, Step 3. The L-3-methyl-2-{4'-[(1-methyl-naphtho[2,1-b]furan-2-carbonyl)-amino]-biphenyl-4-sulfonylamino}-butyric acid t-butyl ester was obtained as a white solid.

Step 2: Removal of the t-butyl group was conducted using 40% TFA in methylene chloride at room temperature in 4 hours. The L-3-methyl-2-{4'-[(1-methyl-naphtho[2,1-b]furan-2-carbonyl)-amino]-biphenyl-4-sulfonylamino}-butyric acid was isolated as a white solid in 90% yield. $^1$H NMR (400 MHz, DMSO-$d^6$) δ ppm 0.8 (dd, J=13.4, 6.8 Hz, 6 H) 2.0 (m, 1 H) 3.1 (s, 3 H) 3.6 (d, J=6.1 Hz, 1 H) 7.6 (m, 1 H) 7.7 (m, 1 H) 7.8 (m, 7 H) 8.0 (m, 3 H) 8.1 (d, J=8.1 Hz, 1 H) 8.5 (d, J=8.1 Hz, 1 H) 10.6 (s, 1 H).

Example 155

L-3-Methyl-2-{4'-[(3-methyl-4-phenoxy-benzofuran-2-carbonyl)-amino]-biphenyl-4-sulfonylamino}-butyric acid

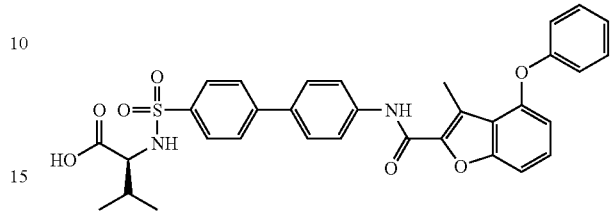

Step 1: 3-Methyl-4-phenoxy-benzofuran-2-carboxylic acid ethyl ester was prepared from phenylboronic acid and 4-hydroxy-3-meythyl-benzofuran-2-carboxylic acid ethyl ester in the presence of copper (II) acetate according to the procedure of Evans, et al. *Tetrahedron Lett.* 1998, 39, 2937, in 50% yield.

Step 2: Hydrolysis of 3-methyl-4-phenoxy-benzofuran-2-carboxylic acid ethyl ester was carried out according to Example 20, Step 3, affording 3-methyl-4-phenoxy-benzofuran-2-carboxylic acid as a white solid in 75% yield.

Step 3: Coupling of 3-methyl-4-phenoxy-benzofuran-2-carboxylic acid with L-2-(4'-amino-biphenyl-4-sulfonylamino)-3-methyl-butyric acid t-butyl ester was carried out according to the procedure described in Example 21, Step 3. The L-3-methyl-2-{4'-[(3-methyl-4-phenoxy-benzofuran-2-carbonyl)-amino]-biphenyl-4-sulfonylamino}-butyric acid methyl ester was obtained as a white solid.

Step 4: Hydrolysis of L-3-methyl-2-{4'-[(3-methyl-4-phenoxy-benzofuran-2-carbonyl)-amino]-biphenyl-4-sulfonylamino}-butyric acid methyl ester was carried out according the Example 20, Step 5, to afford L-3-methyl-2-{4'-[(3-methyl-4-phenoxy-benzofuran-2-carbonyl)-amino]-biphenyl-4-sulfonylamino}-butyric acid as a white solid. $^1$H NMR (400 MHz, DMSO-$d_6$) δ ppm 0.8 (dd, J=12.5, 6.7 Hz, 6 H) 2.0 (m, 1 H) 2.6 (s, 3 H) 3.6 (dd, J=9.3, 6.1 Hz, 1 H) 6.8 (dd, J=5.7, 2.9 Hz, 1 H) 7.1 (dd, J=8.7, 1.1 Hz, 2 H) 7.2 (m, 1 H) 7.5 (m, 4 H) 7.8 (d, J=8.8 Hz, 2 H) 7.9 (m, 4 H) 8.0 (d, J=8.8 Hz, 2 H) 8.1 (d, J=9.3 Hz, 1 H) 10.6 (s, 1 H).

Example 156

L-2-(4'-{[4-(1-Methoxycarbonyl-1-methyl-ethoxy)-3-methyl-benzofuran-2-carbonyl]-amino}-biphenyl-4-sulfonylamino)-3-methyl-butyric acid

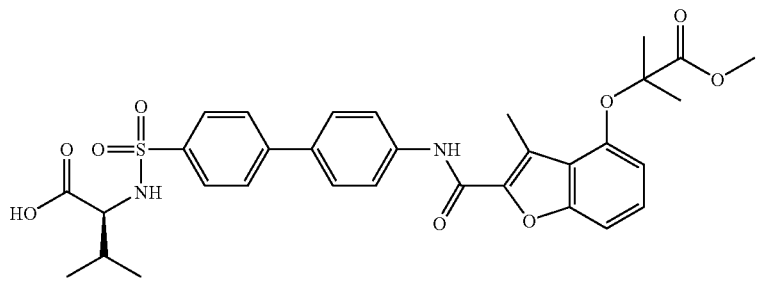

Step 1: A solution of 2,6-dihydroxyacetophenone (35.37 g, 0.23 moles), potassium carbonate (51.4 g, 0.37 moles), and t-butyl bromoacetate (28.4 mL, 0.23 moles) in 440 mL of acetone was heated at reflux for 1.5 hours. It was then cooled to room temperature and filtered. The filter cake was washed with acetone and the combined mother liquors were concentrated in vacuo. (2-Acetyl-3-hydroxy-phenoxy)-acetic acid tert-butyl ester was isolated as thick yellow oil, which was used directly used for the next step.

Step 2: The (2-acetyl-3-hydroxy-phenoxy)-acetic acid tert-butyl ester was dissolved in DMF, and heated to 110-130° C. in the presence of potassium carbonate for 4 hours. The resulting suspension was slowly poured into cold water. The product precipitated out and was collected by filtration. Recrystalyzation in toluene afforded 34.26 g of the desired 4-hydroxy-3-methyl-benzofuran-2-carboxylic acid tert-butyl ester as pale yellow solid (60% overall yield).

Step 3: 4-(1-Ethylperoxycarbonyl-1-methyl-ethoxy)-3-methyl-benzofuran-2-carboxylic acid t-butyl ester compound was prepared from 4-hydroxy-3-methyl-benzofuran-2-carboxylic acid tert-butyl ester according to the procedure of Bencze, et. al, *Tetrahedron* 1970, 26, 5407, as a white solid.

Step 4: Removal of the t-butyl group from 4-hydroxy-3-methyl-benzofuran-2-carboxylic acid tert-butyl ester was carried out using 40% TFA in methylene chloride at room temperature for 4 hours. The monoacid, 4-(1-ethylperoxycarbonyl-1-methyl-ethoxy)-3-methyl-benzofuran-2-carboxylic acid, was isolated as a white solid in 40% overall yield.

Step 5: Coupling of 4-(1-ethylperoxycarbonyl-1-methyl-ethoxy)-3-methyl-benzofuran-2-carboxylic acid with L-2-(4'-amino-biphenyl-4-sulfonylamino)-3-methyl-butyric acid t-butyl ester was carried out according to the procedure described in Example 21, Step 3. The L-2-(4'-{[4-(1-methoxycarbonyl-1-methyl-ethoxy)-3-methyl-benzofuran-2-carbonyl]-amino}-biphenyl-4-sulfonylamino)-3-methyl-butyric acid t-butyl ester was obtained as a thick oil.

Step 6: Removal of the t-butyl group from L-2-(4'-{[4-(1-methoxycarbonyl-1-methyl-ethoxy)-3-methyl-benzofuran-2-carbonyl]-amino}-biphenyl-4-sulfonylamino)-3-methyl-butyric acid t-butyl ester according to the procedure described in Step 2 afforded L-2-(4'-{[4-(1-methoxycarbonyl-1-methyl-ethoxy)-3-methyl-benzofuran-2-carbonyl]-amino}-biphenyl-4-sulfonylamino)-3-methyl-butyric acid as a white solid. $^1$H NMR (400 MHz, CDCl$_3$) δ ppm 0.9 (dd, J=46.6, 6.7 Hz, 6 H) 1.7 (s, 6 H) 2.1 (m, 1 H) 2.9 (s, 3 H) 3.8 (s, 3 H) 3.8 (dd, J 9.9, 4.5 Hz, 1 H) 5.1 (d, J=9.9 Hz, 1 H) 6.4 (d, J=8.1 Hz, 1 H) 7.1 (d, J=8.3 Hz, 1 H) 7.6 (dd, J=29.1, 8.6 Hz, 4 H) 7.8 (dd, J=20.5, 8.8 Hz, 4 H) 8.4 (s, 1 H).

Example 157

L-2-{4'-[(4-Ethoxycarbonylmethoxy-3-methyl-benzofuran-2-carbonyl)-amino]-biphenyl-4-sulfonylamino}-3-methyl-butyric acid

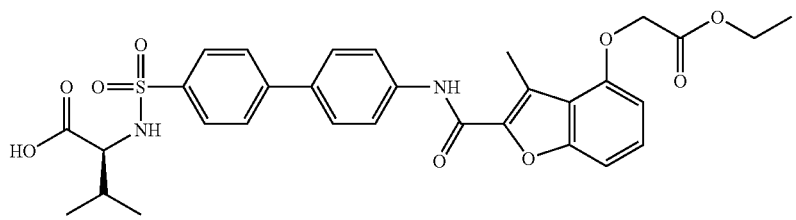

Step 1: To a round bottom flask with a stir bar was added 4-hydroxy-3-methyl-benzofuran-2 carboxylic acid t-butyl ester (1 mmol), ethyl 2-bromoacetate (1.1 eq.) potassium carbonate (5 equiv.), and 10 mL of DMF. The reaction mixture was stirred overnight and then slowly added dropwise to water (10 mL) with stirring. The resulting mixture was extracted with ethyl acetate (2×20 mL), brine (20 mL), dried over magenesium sulfate. Filtration and evaporation of the solvent gave 4-ethoxycarbonylmethoxy-3-methyl-benzofuran-2-carboxylic acid tert-butyl ester as a thick oil in 90% yield.

Step 2: The above 4-ethoxycarbonylmethoxy-3-methyl-benzofuran-2-carboxylic acid tert-butyl ester was dissolved into a 40% TFA/methylene chloride solution, and stirred at room temperature for 4 hours. Evaporation of solvent gave 4-ethoxycarbonylmethoxy-3-methyl-benzofuran-2-carboxylic acid in quantitative yield.

Step 3: Coupling of 4-ethoxycarbonylmethoxy-3-methyl-benzofuran-2-carboxylic acid with L-2-(4'-amino-biphenyl-4-sulfonylamino)-3-methyl-butyric acid t-butyl ester was carried out according to the procedure described in Example 21, Step 3. The L-2-{4'-[(4-ethoxycarbonylmethoxy-3-methyl-benzofuran-2-carbonyl)-amino]-biphenyl-4-sulfonylamino}-3-methyl-butyric acid t-butyl ester was obtained as a thick oil.

Step 4: Removal of the t-butyl group of L-2-{4'-[(4-ethoxycarbonylmethoxy-3-methyl-benzofuran-2-carbonyl)-amino]-biphenyl-4-sulfonylamino}-3-methyl-butyric acid t-butyl ester according to the procedure described in Step 2 afforded L-2-{4'-[(4-ethoxycarbonylmethoxy-3-methyl-benzofuran-2-carbonyl)-amino]-biphenyl-4-sulfonylamino}-3-methyl-butyric acid as a white solid. $^1$H NMR (400 MHz, CDCl$_3$) δ ppm 0.9 (dd, J=45.0, 6.8 Hz, 6 H) 1.3 (t, J=7.1 Hz, 3 H) 2.1 (m, 1 H) 2.9 (s, 3 H) 3.8 (dd, J=9.9, 4.8 Hz, 1 H) 4.3 (q, J=7.1 Hz, 2 H) 4.7 (s, 2 H) 5.5 (d, J=10.1 Hz, 1 H) 6.5 (d, J=7.8 Hz, 1 H) 7.1 (d, J=7.8 Hz, 1 H) 7.3 (m, 1 H) 7.5 (dd, J=25.5, 8.6 Hz, 4 H) 7.8 (dd, J=24.5, 8.6 Hz, 4 H) 8.3 (s, 1 H).

Example 158

L-2-{4'-[(4-Methoxycarbonylmethoxy-3-methyl-benzofuran-2-carbonyl)-amino]-biphenyl-4-sulfonylamino}-3-methyl-butyric acid

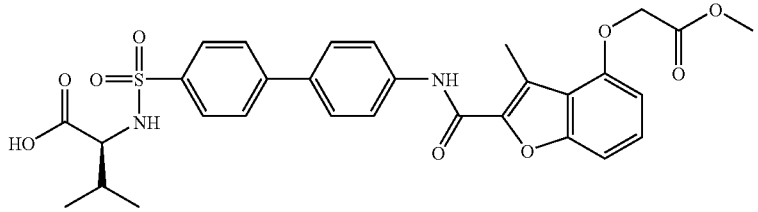

Step 1: To a round-bottom flask with stir bar was added 4-hydroxy-3-methyl-benzofuran-2 carboxylic acid t-butyl ester (1 mmole), methyl 2-bromoacetate (1.1 eq.) potassium carbonate (5 equiv.) and 10 mL of DMF. The reaction mixture was stirred overnight and then slowly added dropwise to water (10 mL) with stirring. The resulting mixture was extracted with ethyl acetate (2×20 mL), brine (20 mL), dried over magenesium sulfate. Filtration and evaporation of solvent gave 4-methoxycarbonylmethoxy-3-methyl-benzofuran-2-carboxylic acid tert-butyl ester as a thick oil in 92% yield.

Step 2: The above 4-methoxycarbonylmethoxy-3-methyl-benzofuran-2-carboxylic acid tert-butyl ester was dissolved into a 40% TFA/methylene chloride solution, and stirred at room temperature for 4 hours. Evaporation of the solvent gave 4-methoxycarbonylmethoxy-3-methyl-benzofuran-2-carboxylic acid in quantitative yield.

Step 3: Coupling of 4-methoxycarbonylmethoxy-3-methyl-benzofuran-2-carboxylic acid with L-2-(4'-amino-biphenyl-4-sulfonylamino)-3-methyl-butyric acid t-butyl ester was carried out according to the procedure described in Example 21, Step 3. The L-2-{4'-[(4-methoxycarbonylmethoxy-3-methyl-benzofuran-2-carbonyl)-amino]-biphenyl-4-sulfonylamino}-3-methyl-butyric acid t-butyl ester was obtained as a thick oil.

Step 4: Removal of the t-butyl group of L-2-{4'-[(4-methoxycarbonylmethoxy-3-methyl-benzofuran-2-carbonyl)-amino]-biphenyl-4-sulfonylamino}-3-methyl-butyric acid t-butyl ester according to the procedure described in Step 2. afforded L-2-{4'-[(4-methoxycarbonylmethoxy-3-methyl-benzofuran-2-carbonyl)-amino]-biphenyl-4-sulfonylamino}-3-methyl-butyric acid as a white solid. $^1$H NMR (400 MHz, CDCl$_3$) δ ppm 0.9 (dd, J=45.0, 6.8 Hz, 6 H) 2.1 (m, 1 H) 2.8 (s, 3 H) 3.8 (m, 4 H) 4.7 (s, 2 H) 5.5 (d, J=10.1 Hz, 1 H) 7.8 (m, 4 H) 8.3 (s, 1 H).

Example 159

L-2-{4'-[(4-Carboxymethoxy-3-methyl-benzofuran-2-carbonyl)-amino]-biphenyl-4-sulfonylamino}-3-methyl-butyric acid

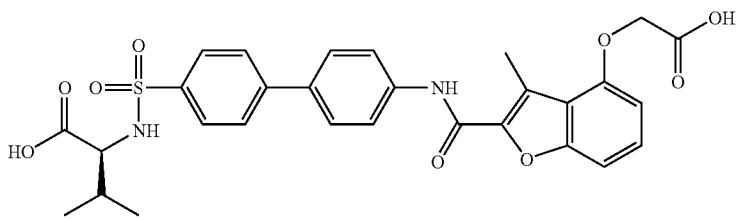

Hydrolysis of L-2-{4'-[(4-methoxycarbonylmethoxy-3-methyl-benzofuran-2-carbonyl)-amino]-biphenyl-4-sulfonylamino}-3-methyl-butyric acid (Example 158) according to the procedure of Example 20, Step 5, afforded L-2-{4'-[(4-carboxymethoxy-3-methyl-benzofuran-2-carbonyl)-amino]-biphenyl-4-sulfonylamino}-3-methyl-butyric acid as a white solid. $^1$H NMR (400 MHz, CD$_3$OD) δ ppm 0.8 (dd, J=23.6, 6.7 Hz, 6 H) 1.9 (m, 1 H) 2.7 (s, 3 H) 3.6 (d, J=5.8 Hz, 1 H) 4.7 (s, 2 H) 6.6 (d, J=8.1 Hz, 1 H) 7.1 (d, J=8.3 Hz, 1 H) 7.3 (t, J=8.2 Hz, 1 H) 7.6 (d, J=8.8 Hz, 2 H) 7.7 (d, J=8.6 Hz, 2 H) 7.8 (m, 4 H) 9.9 (s, 1 H).

Example 160

L-3-Methyl-2-(4'-{[3-methyl-4-(pyridin-3-yl-methoxy)-benzofuran-2-carbonyl]-amino}-biphenyl-4-sulfonylamino)-butyric acid

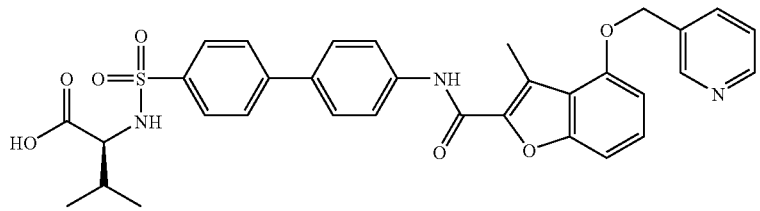

Step 1: To a round bottom flask with stir bar was added 4-hydroxy-3-methyl-benzofuran-2 carboxylic acid t-butyl ester (1 mmol), 3-picolyl chloride (1.1 equiv.) potassium carbonate (5 equiv.) and 10 mL DMF. The reaction mixture was stirred overnight and then slowly added dropwise to water (10 mL) with stirring. The resulting mixture was extracted with ethyl acetate (2×20 mL), brine (20 mL), dried over magenesium sulfate. Filtration and evaporation of solvent afforded 3-methyl-4-(pyridin-3-ylmethoxy)-benzofuran-2-carboxylic acid t-butyl ester as a thick oil in 90% yield.

Step 2. The 3-methyl-4-(pyridin-3-ylmethoxy)-benzofuran-2-carboxylic acid t-butyl ester was dissolved into a 40% TFA/methylene chloride solution, and stirred at room temperature for 4 hours. Evaporation of the solvent gave 3-methyl-4-(pyridin-3-ylmethoxy)-benzofuran-2-carboxylic acid in quantitative yield.

Step 3: Coupling of 3-methyl-4-(pyridin-3-ylmethoxy)-benzofuran-2-carboxylic acid with L-2-(4'-amino-biphenyl-4-sulfonylamino)-3-methyl-butyric acid t-butyl ester was carried out according to the procedure described in Example 21, Step 3. The penultimate L-3-methyl-2-(4'-{[3-methyl-4-(pyridin-3-ylmethoxy)-benzofuran-2-carbonyl]-amino}-biphenyl-4-sulfonylamino)-butyric acid t-butyl ester was obtained as a white solid.

Step 4: Removal of the t-butyl group according to the procedure described in Step 2 afforded L-3-methyl-2-(4'-{[3-methyl-4-(pyridin-3-ylmethoxy)-benzofuran-2-carbonyl]-amino}-biphenyl-4-sulfonylamino)-butyric acid as a white solid. $^1$H NMR (400 MHz, CD$_3$OD) δ ppm 0.9 (dd, J=24.0, 6.8 Hz, 6 H) 2.1 (m, 1 H) 2.8 (s, 3 H) 3.7 (d, J=5.6 Hz, 1 H) 5.5 (s, 2 H) 6.9 (d, J=8.1 Hz, 1 H) 7.3 (d, J=8.3 Hz, 1 H) 7.4 (t, J=8.2 Hz, 1 H) 7.7 (d, J=8.8 Hz, 2 H) 7.7 (d, J=8.6 Hz, 2 H) 7.9 (m, 4 H) 8.1 (dd, J=8.2, 5.7 Hz, 1 H) 8.7 (d, J=7.8 Hz, 1 H) 8.8 (d, J=4.0 Hz, 1 H) 9.0 (s, 1 H).

Example 161

L-2-{4'-[(4-Hydroxy-3-methyl-benzofuran-2-carbonyl)-amino]-biphenyl-4-sulfonylamino}-3-methyl-butyric acid

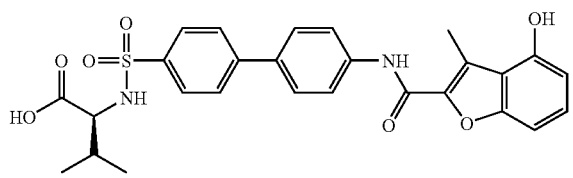

Step 1. 4-Hydroxy-3-methyl-benzofuran-2-carboxylic acid tert-butyl ester (Example 156, Step 2) was dissolved in a 40% TFA/methylene chloride solution at room temperature for 4 hours. 4-Hydroxy-3-methyl-benzofuran-2-carboxylic acid was isolated as a white powder by evaporation of the solvent.

Step 2. Coupling of 4-hydroxy-3-methyl-benzofuran-2-carboxylic acid with L-2-(4'-amino-biphenyl-4-sulfonylamino)-3-methyl-butyric acid t-butyl ester was carried out according to the procedure described in Example 21, Step 3. The L-2-{4'-[(4-hydroxy-3-methyl-benzofuran-2-carbonyl)-amino]-biphenyl-4-sulfonylamino}-3-methyl-butyric acid t-butyl ester was obtained as a white solid.

Step 3. Removal of the t-butyl group from L-2-{4'-[(4-hydroxy-3-methyl-benzofuran-2-carbonyl)-amino]-biphenyl-4-sulfonylamino}-3-methyl-butyric acid t-butyl ester to form L-2-{4'-[(4-hydroxy-3-methyl-benzofuran-2-carbonyl)-amino]-biphenyl-4-sulfonylamino}-3-methyl-butyric acid was carried out according to Step 1. The final product was isolated as a gray powder. $^1$H NMR (400 MHz, CD$_3$OD) δ ppm 0.8 (dd, J=23.5, 6.8 Hz, 6 H) 1.9 (m, 1 H) 2.7 (s, 3 H) 3.5 (d, J=5.6 Hz, 1 H) 6.5 (d, J=7.8 Hz, 1 H) 6.9 (d, J=8.8 Hz, 1 H) 7.1 (m, 1 H) 7.6 (d, J=8.8 Hz, 2 H) 7.6 (d, J=8.8 Hz, 2 H) 7.7 (dd, J=13.8, 8.7 Hz, 4 H).

Example 162

L-2-(4-{5-[(1-Ethyl-1H-benzimidazole-2-carbonyl)-amino]-pyridin-2-yl}-benzenesulfonylamino)-3-methyl-butyric acid

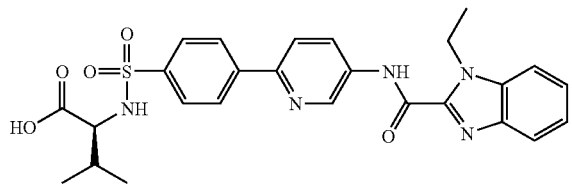

Step 1: To a solution containing 2-methylbenzimidazole (10 mmol) in DMF (100 mL) at 0° C. was slowly added sodium hydride (1.3 equiv.). Gas evolution was observed. After completion of the addition, the resulting suspension was stirred at room temperature for 30 min., and then cooled to 0° C. Ethyl iodide was then added slowly, and the reaction mixture was stirred at room temperature for 4 hr. The reaction mixture was poured into water and extracted with ethyl acetate (2×100 mL). The organic layers were combined, washed with brine (50 mL), and dried over Mg$_2$SO$_4$. Filtration and evaporation of solvents gave the product as a thick oil.

Step 2. Oxidation of the 1-ethyl-2-methylbenzimidazole to the corresponding aldehyde using selenium dioxide was conducted according to a literature procedure (Werner et al. *Tetrahedron,* 1995, 51, 4779). 1-Ethyl-1H-benzimidazole-2-carboxaldehyde was isolated as a yellow oil in overall 52% yield.

Step 3. Oxidation of 1-ethyl-1H-benzimidazole-2-carboxaldehyde to the corresponding carboxylic acid was conducted according to a similar literature procedure (Burtner & Cusic *J. Am. Chem. Soc.* 1943, 65, 265). The 1-ethyl-1H-benzimidazole-2-carboxylic acid was isolated as a white solid in 80% yield.

Step 4. Coupling of the 1-ethyl-1H-benzimidazole-2-carboxylic acid with L-2-(4'-amino-biphenyl-4-sulfonylamino)-3-methyl-butyric acid t-butyl ester was carried out according to the procedure described in Example 21, Step 3. The L-2-(4-{5-[(1-ethyl-1H-benzimidazole-2-carbonyl)-amino]-pyridin-2-yl}-benzenesulfonylamino)-3-methyl-butyric acid t-butyl ester was obtained as a white solid.

Step 5. Removal of the t-butyl group of L-2-(4-{5-[(1-ethyl-1H-benzimidazole-2-carbonyl)-amino]-pyridin-2-yl}-benzenesulfonylamino)-3-methyl-butyric acid t-butyl ester was carried out using 40% TFA in methylene chloride. The L-2-(4-{5-[(1-ethyl-1H-benzimidazole-2-carbonyl)-amino]-pyridin-2-yl}-benzenesulfonylamino)-3-methyl-butyric acid t-butyl ester was isolated as pale brown solid. $^1$H NMR (400 MHz, CD$_3$OD) δ ppm 0.9 (dd, J=23.7, 6.8 Hz, 6 H) 1.5 (t, J=7.2 Hz, 3 H) 2.1 (m, 1 H) 3.7 (d, J=5.6 Hz, 1 H) 4.8 (m, 2 H) 5.5 (s, 1 H) 7.5 (m, 2 H) 7.7 (m, 3 H) 7.8 (m, 3 H) 7.9 (m, 4 H).

Example 163

N-({4'-[(1,2,3-thiadiazol-4-ylcarbonyl)amino]-1,1'-biphenyl-4-yl}sulfonyl)-L-valine

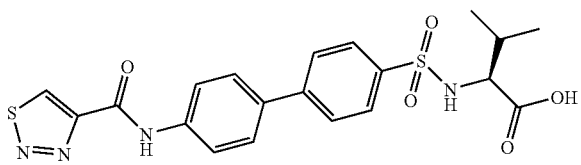

N-({4'-[(1,2,3-thiadiazol-4-ylcarbonyl)amino]-1,1'-biphenyl-4-yl}sulfonyl)-L-valine was prepared from Fmoc-L-Val-Wang resin and 1,2,3-thiadiazole-4-carboxylic acid using the same precedure as for Example 4. LCMS MH+ (m/z) 461. $^1$H NMR (300 MHz, DMSO-$d_6$): δ 10.96 ppm (s, 1H), 9.67 ppm (s, 1H), 7.84 ppm (d, 2H, J=8.7 Hz), 7.68-7.60 ppm (m, 6H) 3.36 ppm (d, 1H J=6.0 Hz), 1.75 ppm (m, 1H), 0.63 ppm (m, 6H).

Example 164

Example D-2-[4'-(Benzofuran-2-sulfonylmethyl)-biphenyl-4-sulfonylamino]-3-methyl-butyric acid

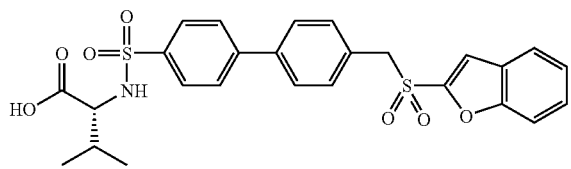

Step 1: A mixture of 2-[1,2,3]thiadiazol-4-yl-phenol (241 mg, 1.35 mmol, 1 eq, prepared according to M. A. Abramov, W. Dehaen, B. D'hooge, M. L. Petrov, S. Smeets, S. Toppet and M. Voets Tetrahedron, 2000, 56, 3933-3940), 2-(4-bromomethyl-phenyl)-4,4,5,5-tetramethyl-[1,3,2]dioxaborolane (406 mg, 1.37 mmol, 1 eq), and potassium carbonate (396 mg, 2.87 mmol, 1.9 eq) was dissolved in 8 mL of acetonitrile and heated to 90° C. under a nitrogen atmosphere. After the reaction was complete as monitored by TLC, the mixture was filtered and the solvent removed in vacuo. The resulting crude material was chromatographed on silica gel eluting with 20% ethyl acetate/hexane to give 2-[4-(4,4,5,5-tetramethyl-[1,3,2]dioxaborolan-2-yl)-benzylsulfanyl]-benzofuran (198 mg) in 40% yield. $^1$H NMR (400 MHz, CDCl$_3$) δ ppm 1.3 (s, 12 H) 4.1 (s, 2 H) 6.6 (d, J=1.0 Hz, 1 H) 7.2 (m, 4 H) 7.4 (d, J=7.8 Hz, 2 H) 7.7 (d, J=8.1 Hz, 2 H).

Step 2: Suzuki coupling of D-2-(4-bromo-benzenesulfonylamino)-3-methyl-butyric acid methyl ester with 2-[4-(4,4,5,5-tetramethyl-[1,3,2]dioxaborolan-2-yl)-benzylsulfanyl]-benzofuran was carried out according to Example 38, Step 3, to give D-2-[4'-(benzofuran-2-ylsulfanylmethyl)-biphenyl-4-sulfonylamino]-3-methyl-butyric acid methyl ester in 54% yield. $^1$H NMR (400 MHz, Benzene-$d_6$) δ ppm 0.7 (d, J=6.8 Hz, 3 H) 0.9 (d, J=6.8 Hz, 3 H) 1.9 (m, 1 H) 3.0 (s, 3 H) 4.0 (m, 3 H) 5.0 (d, J=10.1 Hz, 1 H) 6.6 (d, J=1.0 Hz, 1 H) 7.1 (m, 4 H) 7.3 (m, 6 H) 7.3 (s, 1 H) 7.4 (m, 1 H).

Step 3: A solution of D-2-[4'-(benzofuran-2-ylsulfanylmethyl)-biphenyl-4-sulfonylamino]-3-methyl-butyric acid methyl ester (75 mg, 0.15 mmol, 1 eq) in 4 mL of THF was placed in an ice bath. m-Chloroperoxybenzoic acid (125 mg of 77%, 0.55 mmol, 3.7 eq) in 3 mL of THF was added dropwise. After 10 minutes at 0° C. the ice bath was removed and the reaction was let go for 12 h. After work up and column chromatography eluting with 20% ethyl acetate/hexane, D-2-[4'-(benzofuran-2-sulfonylmethyl)-biphenyl-4-sulfonylamino]-3-methyl-butyric acid methyl ester (56 mg) was obtained in 70% yield. $^1$H NMR (400 MHz, CDCl$_3$) δ ppm 0.9 (dd, J=33.3, 6.8 Hz, 6 H) 2.0 (m, 1 H) 3.4 (s, 3 H) 3.8 (dd, J=10.1, 5.3 Hz, 1 H) 4.6 (s, 2 H) 5.1 (d, J=10.1 Hz, 1 H) 7.4 (m, 4 H) 7.5 (m, 3 H) 7.6 (m, 1 H) 7.7 (m, 3 H) 7.9 (d, J=8.8 Hz, 2 H).

Step 4: Hydrolysis of D-2-[4'-(benzofuran-2-sulfonylmethyl)-biphenyl-4-sulfonylamino]-3-methyl-butyric acid methyl ester was carried out according to Example 20, Step 5, in quantitative yield. $^1$H NMR (400 MHz, DMSO-$d_6$) δ ppm 0.8 (dd, J=12.1, 6.8 Hz, 6 H) 1.9 (m, 1 H) 3.5 (dd, J=9.3, 6.1 Hz, 1 H) 5.0 (s, 2 H) 7.4 (d, J=8.3 Hz, 2 H) 7.4 (m, 1 H) 7.6 (m, 1 H) 7.7 (d, J=1.0 Hz, 1 H) 7.7 (d, J=8.3 Hz, 2 H) 7.8 (m, 6 H) 8.1 (d, J=9.1 Hz, 1 H).

Example 165

Example D-2-[4'-(Benzofuran-2-sulfinylmethyl)-biphenyl-4-sulfonylamino]-3-methyl-butyric acid

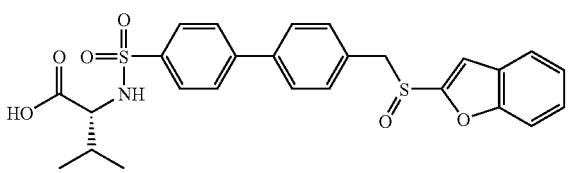

Step 1: A solution of D-2-[4'-(benzofuran-2-ylsulfanylmethyl)-biphenyl-4-sulfonylamino]-3-methyl-butyric acid methyl ester (190 mg, 0.37 mmol, 1 eq, prepared according to Example 164, Step 2) in 5 mL of dichloromethane was placed in an ice bath. m-Chloroperoxybenzoic acid (88 mg of 77%, 0.39 mmol, 1.05 eq) in 3 mL of dichloromethane was added dropwise. After 45 minutes, the reaction was worked up washing with saturated sodiumcarbonate solution. The organic layer was dried over magnesium sulfate and the solvent was removed in vacuo. The crude product was chromatographed eluting with 25% ethyl acetate/hexane to give D-2-[4'-(benzofuran-2-sulfinylmethyl)-biphenyl-4-sulfonylamino]-3-methyl-butyric acid methyl ester in 83% yield. $^1$H NMR (400 MHz, CDCl$_3$) δ ppm 0.9 (dd, J=33.2, 6.7 Hz, 6 H) 2.0 (m, 1 H) 3.4 (s, 3 H) 3.8 (dd, J=10.1, 5.1 Hz, 1 H) 4.5 (m, 2 H) 5.1 (d, J=10.1 Hz, 1 H) 7.1 (s, 1 H) 7.3 (s, 2 H) 7.3 (dd, J=8.2, 7.2 Hz, 1 H) 7.5 (m, 3 H) 7.6 (m, 4 H) 7.9 (d, J=8.6 Hz, 2 H).

Step 2: Hydrolysis of D-2-[4'-(benzofuran-2-sulfinylmethyl)-biphenyl-4-sulfonylamino]-3-methyl-butyric acid methyl ester was carried out according to Example 20, Step 5 in quantitative yield. $^1$H NMR (400 MHz, DMSO-$d_6$) δ ppm 0.8 (dd, J=12.0, 6.7 Hz, 6 H) 1.9 (m, 1 H) 3.5 (dd, J=9.3, 6.1 Hz, 1 H) 4.7 (m, 2 H) 7.4 (m, 3 H) 7.5 (m, 2 H) 7.7 (d, J=8.3 Hz, 2 H) 7.8 (m, 6 H) 8.1 (d, J=9.6 Hz, 1 H) 12.6 (s, 1 H).

Example 166

(S)-2-(4'-{[3-(4-Chloro-phenyl)-isoxazole-5-carbonyl]-amino}-biphenyl-4-sulfonylamino)-3-methyl-butyric acid

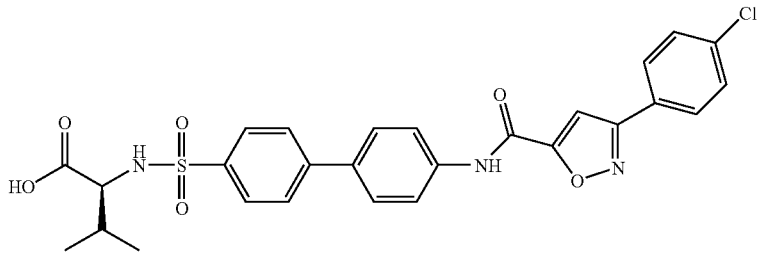

Step 1. Coupling of the 3-(4-chloro-phenyl)-isoxazole-5-carboxylic acid (commercially available) with L-2-(4'-amino-biphenyl-4-sulfonylamino)-3-methyl-butyric acid methyl ester was carried out according to the procedure described in Example 21, Step 3. The (S)-2-(4'-{[3-(4-chloro-phenyl)-isoxazole-5-carbonyl]-amino}-biphenyl-4-sulfonylamino)-3-methyl-butyric acid methyl ester was obtained as a white solid in 70% yield.

Step 2. Hydrolysis of the (S)-2-(4'-{[3-(4-chloro-phenyl)-isoxazole-5-carbonyl]-amino}-biphenyl-4-sulfonylamino)-3-methyl-butyric acid methyl ester according to the procedure described in Example 20, Step 5 afforded (S)-2-(4'-{[3-(4-chloro-phenyl)-isoxazole-5-carbonyl]-amino}-biphenyl-4-sulfonylamino)-3-methyl-butyric acid as a white solid. MS: calc'd for [M−H]⁻: 553.02. found: 552.36.

Example 167

(S)-3-Methyl-2-{4'-[(1-methyl-3-phenyl-1H-thieno[2,3-c]pyrazole-5-carbonyl)-amino]-biphenyl-4-sulfonylamino}-butyric acid

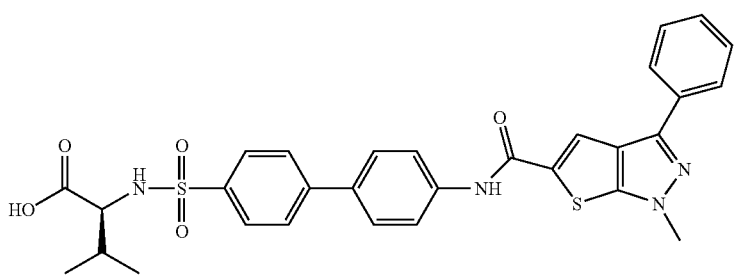

Step 1. Coupling of the 1-methyl-3-phenyl-1H-thieno[2,3-c]pyrazole-5-carboxylic acid (commercially available) with L-2-(4'-amino-biphenyl-4-sulfonylamino)-3-methyl-butyric acid methyl ester was carried out according to the procedure described in Example 21, Step 3. The (S)-3-methyl-2-{4'-[(1-methyl-3-phenyl-1H-thieno[2,3-c]pyrazole-5-carbonyl)-amino]-biphenyl-4-sulfonylamino}-butyric acid methyl ester was obtained as a white solid in 72% yield.

Step 2. Hydrolysis of (S)-3-methyl-2-{4'-[(1-methyl-3-phenyl-1H-thieno[2,3-c]pyrazole-5-carbonyl)-amino]-biphenyl-4-sulfonylamino}-butyric acid methyl ester according to the procedure described in Example 20, Step 5 afforded (S)-3-methyl-2-{4'-[(1-methyl-3-phenyl-1H-thieno[2,3-c]pyrazole-5-carbonyl)-amino]-biphenyl-4-sulfonylamino}-butyric acid as a white solid. MS: calc'd for [M+H]⁺: 589.71. found: 589.16.

Example 168

(S)-3-Methyl-2-{4'-[(5-methyl-1-phenyl-1H-pyrazole-3-carbonyl)-amino]-biphenyl-4-sulfonylamino}-butyric acid

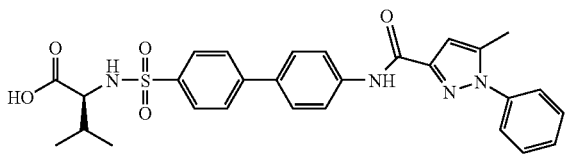

Step 1. Coupling of the 5-methyl-1-phenyl-1H-pyrazole-3-carboxylic acid (commercially available) with L-2-(4'-amino-biphenyl-4-sulfonylamino)-3-methyl-butyric acid methyl ester was carried out according to the procedure described in Example 21, Step 3. The (S)-3-methyl-2-{4'-[(5-methyl-1-phenyl-1H-pyrazole-3-carbonyl)-amino]-biphenyl-4-sulfonylamino}-butyric acid methyl ester was obtained as a white solid in 72% yield.

Step 2. Hydrolysis of the (S)-3-methyl-2-{4'-[(5-methyl-1-phenyl-1H-pyrazole-3-carbonyl)-amino]-biphenyl-4-sulfonylamino}-butyric acid methyl ester according to the procedure described in Example 20, Step 5 afforded (S)-3-methyl-2-{4'-[(5-methyl-1-phenyl-1H-pyrazole-3- carbonyl)-amino]-biphenyl-4-sulfonylamino}-butyric acid as a white solid. MS: calc'd for [M+H]⁺: 533.62. found: 533.19.

Example 169

(S)-3-Methyl-2-{4'-[(2-pyridin-4-yl-thiazole-4-carbonyl)-amino]-biphenyl-4-sulfonylamino}-butyric acid

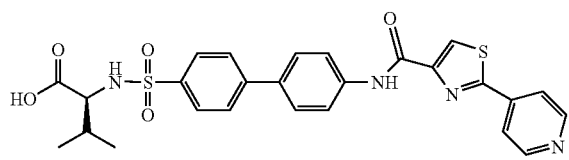

Step 1. Coupling of the 2-pyridin-4-yl-thiazole-4-carboxylic acid (commercially available) with L-2-(4'-amino-biphenyl-4-sulfonylamino)-3-methyl-butyric acid methyl ester was carried out according to the procedure described in Example 21, Step 3. The (S)-3-methyl-2-{4'-[(2-pyridin-4-yl-thiazole-4-carbonyl)-amino]-biphenyl-4-sulfonylamino}-butyric acid methyl ester was obtained as a white solid in 79% yield.

Step 2. Hydrolysis of (S)-3-methyl-2-{4'-[(2-pyridin-4-yl-thiazole-4-carbonyl)-amino]-biphenyl-4-sulfonylamino}-butyric acid methyl ester according to the procedure described in Example 20, Step 5 afforded (S)-3-methyl-2-{4'-[(2-pyridin-4-yl-thiazole-4-carbonyl)-amino]-biphenyl-4-sulfonylamino}-butyric acid as a white solid. MS: calc'd for [M−H]⁻: 535.64. found: 535.70.

Example 170

(S)-3-Methyl-2-[4'-(thiophene-2-sulfonylamino)-biphenyl-4-sulfonylamino]-butyric acid

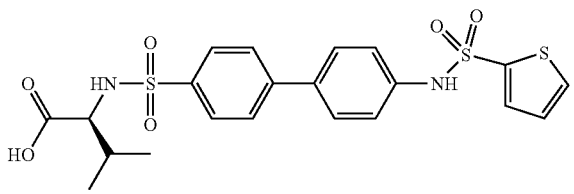

(S)-3-Methyl-2-[4'-(thiophene-2-sulfonylamino)-biphenyl-4-sulfonylamino]-butyric acid was prepared according to the procedure of Example 166, using 2-thiophenesulfonyl chloride. HRMS: calc'd for [M+H]⁺: 495.071. Found: 495.071.

Example 171

(R)-3-Methyl-2-[4'-(thiophene-2-sulfonylamino)-biphenyl-4-sulfonylamino]-butyric acid

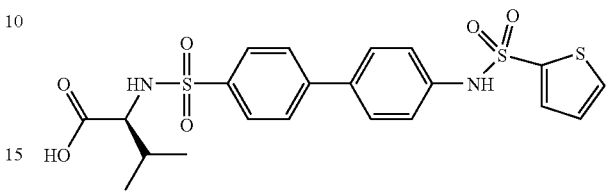

(R)-3-Methyl-2-[4'-(thiophene-2-sulfonylamino)-biphenyl-4-sulfonylamino]-butyric acid was prepared according to the procedure of Example 166, using 2-thiophenesulfonyl chloride. MS: calc'd for [M−H]⁻: 493.1. Found: 493.5.

Example 172

(R)-2-{4'-[(Furan-2-carbonyl)-amino]-biphenyl-4-sulfonylamino}-3-methyl-butyric acid

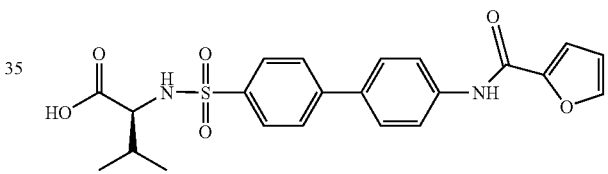

(R)-2-{4'-[(Furan-2-carbonyl)-amino]-biphenyl-4-sulfonylamino}-3-methyl-butyric acid was prepared according to the procedure of Example 166, using 2-furoyl chloride. MS: calc'd for [M−H]⁻: 441.1. Found: 441.5.

Example 173

(R)-3-Methyl-2-{4'-[(thiophene-2-carbonyl)-amino]-biphenyl-4-sulfonylamino}-butyric acid

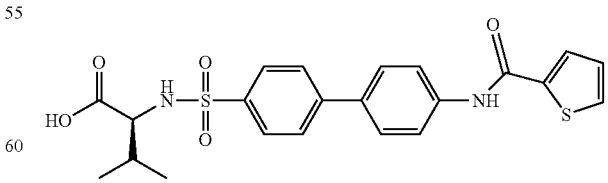

(R)-3-Methyl-2-{4'-[(thiophene-2-carbonyl)-amino]-biphenyl-4-sulfonylamino}-butyric acid was prepared according to the procedure of Example 166, using 2-thiophenecarbonyl chloride. MS: calc'd for [M−H]⁻: 457.1. Found: 457.5.

Example 174

(S)-3-Methyl-2-{4'-[(thiophene-2-carbonyl)-amino]-biphenyl-4-sulfonylamino}-butyric acid

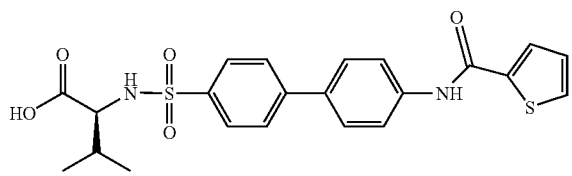

(S)-3-Methyl-2-{4'-[(thiophene-2-carbonyl)-amino]-biphenyl-4-sulfonylamino}-butyric acid was prepared according to the procedure of Example 166, using 2-thiophenecarbonyl chloride. MS: calc'd for [M−H]⁻: 457.1. Found: 457.5.

Example 175

(S)-2-{4'-[(Furan-2-carbonyl)-amino]-biphenyl-4-sulfonylamino}-3-methyl-butyric acid

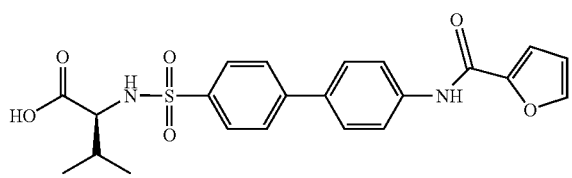

(S)-2-{4'-[(Furan-2-carbonyl)-amino]-biphenyl-4-sulfonylamino}-3-methyl-butyric acid was prepared according to the procedure of Example 166, using 2-furoyl chloride. MS: calc'd for [M−H]⁻: 441.1. Found: 441.6.

Example 176

(S)-2-{4'-[(4-Dimethylcarbamoylmethoxy-3-methyl-benzofuran-2-carbonyl)-amino]-biphenyl-4-sulfonylamino}-3-methyl-butyric acid Step 1: To a round bottom flask with a stir bar was added 4-hydroxy-3-methyl-benzofuran-2 carboxylic acid t-butyl ester (1 mmol), α-bromo-N,N-dimethylacetamide (1.1 eq.) potassium carbonate (5 equiv.), and 10 ml of DMF. The reaction mixture was stirred overnight and then slowly added dropwise to water (10 ml) with stirring. The resulting mixture was extracted with ethyl acetate (2×20 ml), washed with brine (20 ml), dried over MgSO₄. Filtration and evaporation of the solvent gave 4-dimethylcarbamoylmethoxy-3-methyl-benzofuran-2-carboxylic acid tert-butyl ester as a thick oil in 90% yield.

Step 2. The above 4-dimethylcarbamoylmethoxy-3-methyl-benzofuran-2-carboxylic acid tert-butyl ester was dissolved into a 40% TFA/methylene chloride solution, and stirred at room temperature for four hours. Evaporation of solvent gave 4-dimethylcarbamoylmethoxy-3-methyl-benzofuran-2-carboxylic acid in quantitative yield.

Step 3: Coupling of 4-dimethylcarbamoylmethoxy-3-methyl-benzofuran-2-carboxylic acid with L-2-(4'-amino-biphenyl-4-sulfonylamino)-3-methyl-butyric acid t-butyl ester was carried out according to the procedure described in Example 21, Step 3. The (S)-2-{4'-[(4-dimethylcarbamoylmethoxy-3-methyl-benzofuran-2-carbonyl)-amino]-biphenyl-4-sulfonylamino}-3-methyl-butyric acid t-butyl ester was obtained as a thick oil.

Step 4: Removal of the t-butyl group from (S)-2-{4'-[(4-dimethylcarbamoylmethoxy-3-methyl-benzofuran-2-carbonyl)-amino]-biphenyl-4-sulfonylamino}-3-methyl-butyric acid t-butyl ester according to the procedure described in Step 2 afforded (S)-2-{4'-[(4-dimethylcarbamoylmethoxy-3-methyl-benzofuran-2-carbonyl)-amino]-biphenyl-4-sulfonylamino}-3-methyl-butyric acid as a white solid. MS: calc'd for [M+H]⁺: 608.68. Found: 608.30.

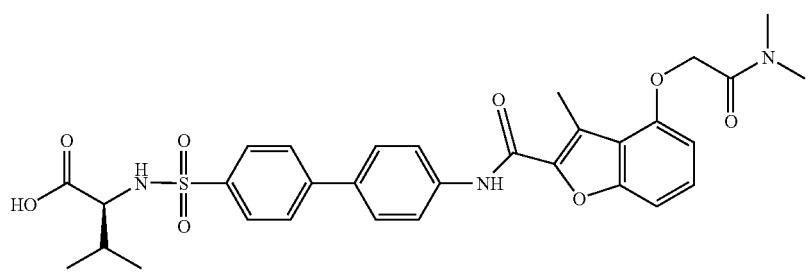

Example 177

(S)-2-(4'-{[4-(2-tert-Butoxycarbonylamino-ethoxy)-3-methyl-benzofuran-2-carbonyl]-amino}-biphenyl-4-sulfonylamino)-3-methyl-butyric acid

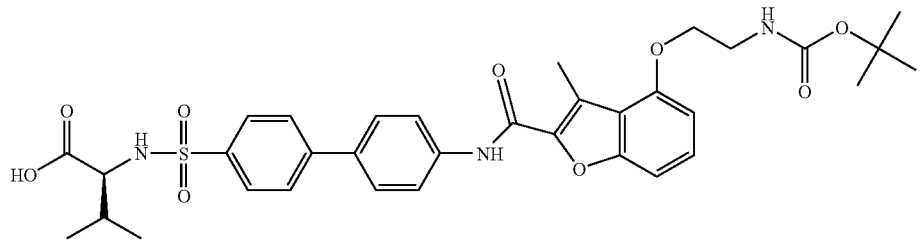

Step 1: Preparation of the 4-(2-tert-butoxycarbonylamino-ethoxy)-3-methyl-benzofuran-2-carboxylic acid ethyl ester was done according to the procedure described in Example 176, Step 1, using (2-bromoethyl)carbamic acid tert-butyl ester as a white solid in 90% yield.

Step 2. Hydrolysis of 4-(2-tert-butoxycarbonylamino-ethoxy)-3-methyl-benzofuran-2-carboxylic acid ethyl with LiOH was done according to the procedure described in Example 20, Step 3, to give 4-(2-tert-butoxycarbonylamino-ethoxy)-3-methyl-benzofuran-2-carboxylic acid as a white solid.

Step 3: Coupling of 4-(2-tert-butoxycarbonylamino-ethoxy)-3-methyl-benzofuran-2-carboxylic acid with L-2-(4'-amino-biphenyl-4-sulfonylamino)-3-methyl-butyric acid methyl ester was carried out according to the procedure described in Example 21, Step 3, to give (S)-2-(4'-{[4-(2-tert-butoxycarbonylamino-ethoxy)-3-methyl-benzofuran-2-carbonyl]-amino)}-biphenyl-4-sulfonylamino)-3-methyl-butyric acid methyl ester as a white solid.

Step 4: Hydrolysis of (S)-2-(4'-{[4-(2-tert-butoxycarbonylamino-ethoxy)-3-methyl-benzofuran-2-carbonyl]-amino}-biphenyl-4-sulfonylamino)-3-methyl-butyric acid methyl ester with LiOH according to the procedure described in Example 20, Step 5 afforded (S)-2-(4'-{[4-(2-tert-butoxycarbonylamino-ethoxy)-3-methyl-benzofuran-2-carbonyl]-amino}-biphenyl-4-sulfonylamino)-3-methyl-butyric acid as a white solid. MS: calc'd for [M−H]⁻: 664.77. Found: 664.61.

Example 178

(S)-3-Methyl-2-(4'-{[3-methyl-4-(pyridin-2-yl-methoxy)-benzofuran-2-carbonyl]-amino}-biphenyl-4-sulfonylamino)-butyric acid

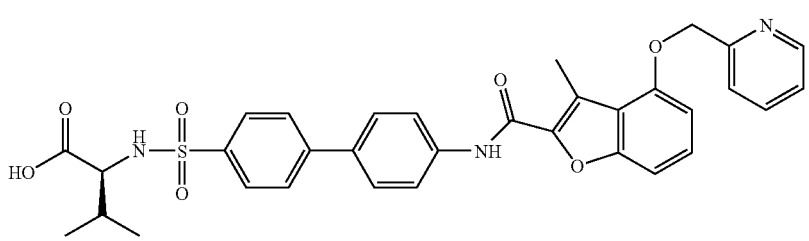

This compound was prepared according to a procedure similar to that described in Example 160, using 2-picolyl chloride. MS: calc'd for {M+H}⁺: 614.69. Found: 614.22.

Example 179

(S)-3-Methyl-2-(4'-{[3-methyl-4-(pyridin-4-yl-methoxy)-benzofuran-2-carbonyl]-amino}-biphenyl-4-sulfonylamino)-butyric acid

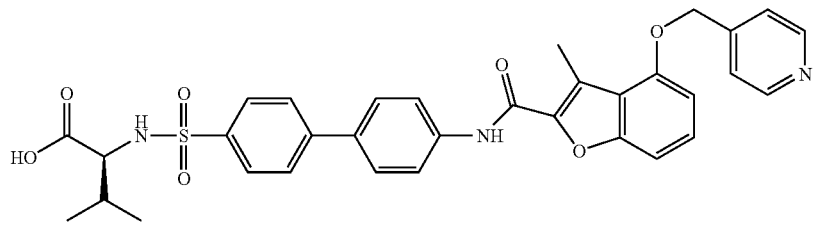

This compound was prepared according to a procedure similar to that described in Example 160, using 4-picolyl chloride. MS: calc'd for {M+H}⁺: 614.69. Found: 614.26.

Example 180

(S)-2-{4'-[(4-Carbamoylmethoxy-3-methyl-benzofuran-2-carbonyl)-amino]-biphenyl-4-sulfonylamino}-3-methyl-butyric acid

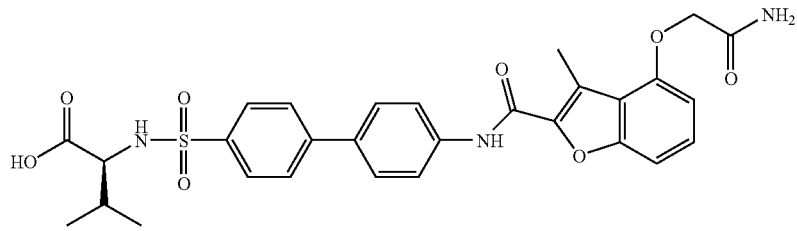

This compound was prepared according to a procedure similar to that described in Example 176, starting from 2-bromoacetamide. MS: calc'd for {M+H}⁺: 580.63. Found: 580.32.

Example 181

(S)-2-(4'-{[4-(2-Amino-ethoxy)-3-methyl-benzofuran-2-carbonyl]-amino}-biphenyl-4-sulfonylamino)-3-methyl-butyric acid

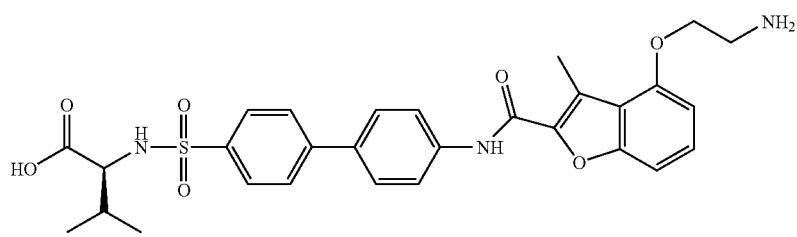

The product of Example 177, (S)-2-(4'-{[4-(2-tert-butoxy-carbonylamino-ethoxy)-3-methyl-benzofuran-2-carbonyl]-amino}-biphenyl-4-sulfonylamino)-3-methyl-butyric acid, was treated with 40% TFA/methylene chloride solution at ambient temperature for four hours to afford (S)-2-(4'-{[4-(2-amino-ethoxy)-3-methyl-benzofuran-2-carbonyl]-amino}-biphenyl-4-sulfonylamino)-3-methyl-butyric acid as a brown solid (TFA salt). MS: calc'd for {M−H}⁻: 564.65. Found: 564.51.

Example 182

(S)-2-(4'-{[4-(2-Dimethylamino-ethoxy)-3-methyl-benzofuran-2-carbonyl]-amino}-biphenyl-4-sulfonylamino)-3-methyl-butyric acid

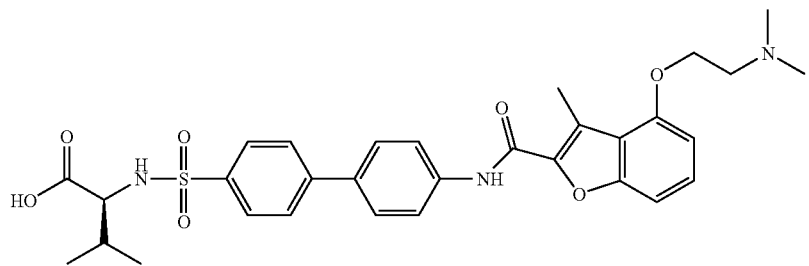

Step 1. To a solution of 4-hydroxy-3-methyl-benzofuran-2 carboxylic acid t-butyl ester was dissolved in THF (30 ml/g) under nitrogen was added N,N-dimethylethanolamine and triphenylphosphine, followed by the dropwise addition of diisopropylcarbodiimide. The resulting mixture was allowed to stir overnight. The crude product was isolated by concentrating the reaction mixture in vacuo.

Step 2. The tert-butyl ester from Step 1 was dissolved into a 40% TFA/methylene chloride solution, and stirred at room temperature for four hours. Evaporation of solvent gave 4-(2-dimethylamino-ethoxy)-3-methyl-benzofuran-2-carboxylic acid as a white solid in quantitative yield.

Step 3. Coupling of the 4-(2-dimethylamino-ethoxy)-3-methyl-benzofuran-2-carboxylic acid with L-2-(4'-amino-biphenyl-4-sulfonylamino)-3-methyl-butyric acid methyl ester was carried out according to the procedure described in Example 21, Step 3 to give L-2-(4'-{[4-(2-dimethylamino-ethoxy)-3-methyl-benzofuran-2-carbonyl]-amino}-biphenyl-4-sulfonylamino)-3-methyl-butyric acid methyl ester as a white solid in 65% yield.

Step 4. Hydrolysis of L-2-(4'-{[4-(2-dimethylamino-ethoxy)-3-methyl-benzofuran-2-carbonyl]-amino}-biphenyl-4-sulfonylamino)-3-methyl-butyric acid methyl ester according to the procedure described in Example 20, Step 5 afforded L-2-(4'-{[4-(2-dimethylamino-ethoxy)-3-methyl-benzofuran-2-carbonyl]-amino}-biphenyl-4-sulfonylamino)-3-methyl-butyric acid as a white solid. MS: calc'd for {M+H}⁺: 594.70. Found: 594.29.

Examples 183-193

Step 1: To a solution of (4'-amino-biphenyl-4-sulfonyl)-L-valine methyl ester (0.055 mmol, 20 mg) and the carboxylic acid (0.75 mmol) in THF was added diisopropylcarbodiimide (0.1 mmol, 12.6 mg) and the solution heated to 60° C. for 16 hours. After cooling to room temperature the solvent was removed. The crude product was used in the next step.

Step 2: To a solution of the product of Step 1 (0.55 mmol) in water/methanol (1:1) was added lithium hydroxide (0.15 mmol, 7 mg). The resulting solution was shaken at 50° C. overnight, and then concentrated in vacuo. The residue was dissolved in water/methanol/DMSO (1.5 mL) and purified by semi-preparative RP-HPLC (Gilson Preparative HPLC conditions: Gilson Preparative HPLC system; YMC Pro C18, 20 mm×50 mm ID, 5 uM column; 2 mL injection; Solvent A: 0.02% TFA/water; Solvent B: 0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.) Table 1 lists the acid used in Step 1 for Examples 183-193.

TABLE 1

| Ex. No. | Acid used in Step 1. | HPLC[1] Ret. Time | M-H |
|---|---|---|---|
| 183 | 5-chlorobenzofuran-2-carboxylic acid | 2.84 | 525 |
| 184 | 5-bromofuroic acid | 2.49 | 521 |
| 185 | 7-nitro-1H-indole-carboxylic acid | 2.67 | 535 |
| 186 | 2-(4-pyridyl)-1,3-thiazole-4-carboxylic acid | 2.31 | 535 |
| 187 | 5-(2-nitrophenyl)-2-furoic acid | 2.70 | 562 |
| 188 | 2-(2,3-dihydro-1,4-benzodioxin-2-yl)1,3-thiazole-4-carboxylic acid | 2.77 | 592 |
| 189 | 5-methyl-3-phenylisoxazole-carboxylic acid | 2.67 | 532 |
| 190 | 4-methyl-1,2,3-thiadiazole-5-carboxylic acid | 2.32 | 473 |
| 191 | 1-tert-butyl-3-methylpyrazole-5-carboxylic acid | 2.66 | 511 |
| 192 | 3-chlorobenzo[b]thiophene-2-carboxylic acid | 3.07 | 541 |
| 193 | 3-(2-chlorophenyl)-5-methyl-isoxazole-4-carboxylic acid | 2.73 | 566 |

[1]LCMS: Waters Xterra MS C18, 2 mm (i.d.) × 50 mm (length), 3.5 mm column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

Table 2 lists the chemical name for the compounds produced in Examples 183-193.

TABLE 2

| Ex. No. | CHEMICAL NAMES |
|---|---|
| 183 | N-[(4'-{[(5-chloro-1-benzofuran-2-yl)carbonyl]amino}-1,1'-biphenyl-4-yl)sulfonyl]-L-valine |
| 184 | N-({4'-[(5-bromo-2-furoyl)amino]-1,1'-biphenyl-4-yl}sulfonyl)-L-valine |
| 185 | N-[(4'-{[(7-nitro-1H-indol-2-yl)carbonyl]amino}-1,1'-biphenyl-4-yl)sulfonyl]-L-valine |
| 186 | N-[(4'-{[(2-pyridin-4-yl-1,3-thiazol-5-yl)carbonyl]amino}-1,1'-biphenyl-4-yl)sulfonyl]-L-valine |
| 187 | N-[(4'-{[5-(2-nitrophenyl)-2-furoyl]amino}-1,1'-biphenyl-4-yl)sulfonyl]-L-valine |
| 188 | N-{[4'-({[2-(2,3-dihydro-1,4-benzodioxin-2-yl)-1,3-thiazol-4-yl]carbonyl}amino)-1,1'-biphenyl-4-yl]sulfonyl}-L-valine |
| 189 | N-[(4'-{[(5-methyl-3-phenylisoxazol-4-yl)carbonyl]amino}-1,1'-biphenyl-4-yl)sulfonyl]-L-valine |
| 190 | N-[(4'-{[(4-methyl-1,2,3-thiadiazol-5-yl)carbonyl]amino}-1,1'-biphenyl-4-yl)sulfonyl]-L-valine |
| 191 | N-[(4'-{[(1-tert-butyl-3-methyl-1H-pyrazol-5-yl)carbonyl]amino}-1,1'-biphenyl-4-yl)sulfonyl]-L-valine |
| 192 | N-[(4'-{[(3-chloro-1-benzothien-2-yl)carbonyl]amino}-1,1'-biphenyl-4-yl)sulfonyl]-L-valine |
| 193 | N-{[4'-({[3-(2-chlorophenyl)-5-methylisoxazol-4-yl]carbonyl}amino)-1,1'-biphenyl-4-yl]sulfonyl}-L-valine |

Examples 194-247

N-({4'-[(1-benzofuran-2-ylcarbonyl)amino]-1,1'-biphenyl-4-yl}sulfonyl)-D-alanine

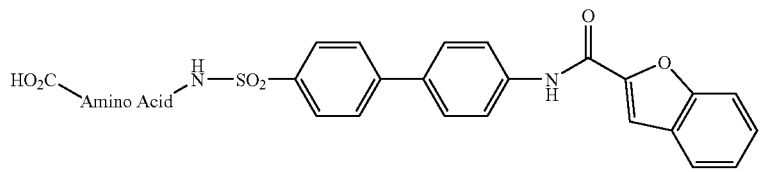

Step 1. Biphenyl (46.3 g, 0.3 mol) was dissolved in 500 ml of chloroform. The solution was cooled in an ice/water bath. Chlorosulfonic acid (19.9 ml, 1 eq) was added dropwise over 30 min. The ice/water bath was removed and the reaction mixture was stirred at room temperature overnight. The reaction mixture was filtered and the solid was washed with CHCl₃ to provide 41.2 g of biphenyl-4-sulfonic acid as a white solid.

Step 2. Biphenyl-4-sulfonic acid (30 g) was mixed with trifluoroacetic acid and a suspension was formed. The mixture was cooled to −5° C. Fuming nitric acid (12.8 ml) was added dropwise over 30 min. The reaction mixture was stirred at 0° C. for 2 h. The chloroform was removed in vacuo and the residue was recrystallized from acetic acid to provide 15 g of 4'-nitro-biphenyl-4-sulfonic acid, obtained as white crystals.

Step 3. 4'-Nitro-biphenyl-4-sulfonic acid (1.12 g, 4 mmol) was mixed with tin (II) chloride (5.2 g, 32 mmol) and 40 ml of THF. The mixture was refluxed overnight. The reaction mixture was poured into 80 ml of water and stirred at room temperature for 8 h. The mixture was filtered and the solid was dried under vacuum to provide 0.73 g (73%) of 4'-amino-biphenyl-4-sulfonic acid, obtained as an off-white solid.

Step 4. Benzofuran-2-carboxylic acid (310 mg, 1.9 mmol) was mixed with 3 ml of oxalyl chloride and refluxed for 1 h in the presence of a catalytic amount of DMF, then the excess oxalyl chloride was removed by vacuum. The residue was dissolved in 4 ml of dichloromethane and was added to a mixture of 400 mg (1.6 mmol) of 4'-amino-biphenyl-4-sulfonic acid, N,N-diisopropylethylamine (0.92 ml, 4 eq) and 4 ml of THF in an ice/water bath. The mixture was stirred at room temperature for 4 h. The reaction mixture was mixed with 2N HCl and in the process a suspension formed. The solid was collected by centrifugation and was washed with chloroform and 2N HCl to provide 540 mg of 4'-[(benzofuran-2-carbonyl)-amino]-biphenyl-4-sulfonic acid, obtained as pale brown solid.

Step 5. To 75 ml of DMF cooled to −20° C., oxalyl chloride (6.7 ml, 76 mmol) was carefully added dropwise. A white suspension was formed and the fumes generated were removed by blowing N₂ through the flask. A solution of 4'-[(benzofuran-2-carbonyl)-amino]-biphenyl-4-sulfonic acid (15 g, 38 mmol) in 100 ml DMF was added slowly and the temperature was maintained <0° C. After the addition was complete, the reaction mixture was warmed to room temperature and was stirred at room temperature for 3 h. The reaction mixture was poured into 4L ice/water, and the suspension was filtered. The solid was collected and dried under vacuum to provide 7.3 g of 4'-[(benzofuran-2-carbonyl)-amino]-biphenyl-4-sulfonyl chloride, obtained as off-white solid.

Step 6: To a solution of D-alanine (0.15 mmol, 14 mg) in water (0.5 mL) and DMF (0.1 mL) was added N,N-diisopropylethylamine (52 uL, 0.3 mmol) and 4'-[(benzofuran-2-carbonyl)-amino]-biphenyl-4-sulfonyl chloride (0.1 mmol, 41 mg) as a solution in acetonitrile (0.4 mL). The resulting solution was shaken at room temperature for 4 hours and purified by semi-preparative RP-HPLC (Gilson Preparative HPLC conditions: Gilson Preparative HPLC system; YMC Pro C18, 20 mm×50 mm ID, 5 uM column; 2 mL injection; Solvent A: 0.02% TFA/water; Solvent B: 0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.) to provide N-({4'-[(1-benzofuran-2-ylcarbonyl)amino]-1,1'-biphenyl-4-yl}sulfonyl)-D-alanine.

Using essentially the same procedures as outlined for Example 194, Step 6, and utilizing the appropriate amino acid, the compounds of Examples 195-247, shown in Table 3, were prepared and purified by preparative reverse phase HPLC².

TABLE 3

| Ex. No. | Amino acid | HPLC[2] Ret. Time | M-H |
|---|---|---|---|
| 194 | D-alanine | 2.46 | 463.01 |
| 195 | L-valine | 2.63 | 491.16 |
| 196 | D-valine | 2.63 | 491.16 |
| 197 | L-norvaline | 2.64 | 491.16 |
| 198 | D-norvaline | 2.64 | 491.16 |
| 199 | L-aspartic acid | 2.3 | 507.03 |
| 200 | D-astartic acid | 2.41 | 507.1 |
| 201 | L-glutamic acid | 2.21 | 520.14 |
| 202 | D-glutamic acid | 2.2 | 520.13 |
| 203 | L-histidine | 1.93 | 529.15 |
| 204 | D-histidine | 1.9 | 529.17 |
| 205 | L-isoleucine | 2.73 | 505.19 |
| 206 | D-isoleucine | 2.76 | 505.19 |
| 207 | L-leucine | 2.76 | 505.2 |
| 208 | D-leucine | 2.74 | 505.2 |
| 209 | L-norleucine | 2.77 | 505.18 |
| 210 | D-norleucine | 2.74 | 505.18 |
| 211 | L-phenylalanine | 2.77 | 539.15 |
| 212 | D-phenylalanine | 2.77 | 539.16 |
| 213 | L-proline | 2.56 | 489.14 |
| 214 | D-proline | 2.57 | 489.13 |
| 215 | L-tryptophan | 2.7 | 578.14 |
| 216 | D-tryptophan | 2.7 | 578.15 |
| 217 | N-methylglycine | 2.59 | 463.14 |
| 218 | 2-methylalamine | 2.5 | 477.1 |
| 219 | N-methyl-L-alanine | 2.63 | 477.15 |
| 220 | 1-aminocyclopentanecarboxylic acid | 2.63 | 503.15 |
| 221 | N-methylvaline | 2.73 | 505.1 |
| 222 | 3-methyl-L-valine | 2.73 | 505.12 |
| 223 | 2-methylleucine | 2.87 | 519.17 |
| 224 | D-glutamic acid | 2.3 | 521.12 |
| 225 | D-phenylglycine | 2.71 | 525.13 |
| 226 | 2-thienylglycine | 2.64 | 531.09 |
| 227 | L-glutamic acid-gamma-methyl ester | 2.5 | 535.13 |
| 228 | 3-phenylpropanoic acid | 2.66 | 539.15 |
| 229 | L-homophenylalanine | 2.84 | 553.13 |
| 230 | L-tyrosine | 2.5 | 555.14 |
| 231 | D-tyrosine | 2.47 | 555.14 |
| 232 | L-aspartic acid beta-t-butylester | 2.76 | 563.16 |
| 233 | D-aspartic acid beta-t-butylester | 2.78 | 563.16 |
| 234 | 2-aminoindan-2-carboxylic acid | 2.89 | 565.16 |
| 235 | O-methyl-L-tyrosine | 2.73 | 569.15 |
| 236 | N-methylindole-5-glycine | 2.73 | 578.17 |
| 237 | benzothiophene-5-glycine | 2.8 | 581.1 |
| 238 | 4-nitro-L-phenylalanine | 2.7 | 584.12 |
| 239 | 3-(2-naphthyl)alanine | 2.93 | 589.16 |
| 240 | beta-methylphenylalanine | 2.84 | 553.14 |
| 241 | N-methyl-L-tryptophan | 2.86 | 592.16 |
| 242 | L-glutamic acid-gamma-anilide | 2.63 | 596.17 |
| 243 | 4,4,4,4',4',4'-hexafluorovaline | 2.76 | 599.1 |
| 244 | 4-amino-L-phenylalanine | 2.21 | 554.16 |
| 245 | D-glutamic acid-5-benzyl ester | 2.86 | 611.18 |
| 246 | 1-benzyl-L-histidine | 2.24 | 619.17 |
| 247 | O-benzyl-L-tyrosine | 3.07 | 645.19 |

[2]LCMS: Waters Xterra MS C18, 2 mm (i.d.) × 50 mm (length), 3.5 mm column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

Table 4 lists the chemical names of the compounds produced in Examples 194-247.

TABLE 4

| Ex. No. | CHEMICAL NAMES |
|---|---|
| 194 | N-({4'-[(1-benzofuran-2-ylcarbonyl)amino]-1,1'-biphenyl-4-yl}sulfonyl)-D-alanine |
| 195 | N-({4'-[(1-benzofuran-2-ylcarbonyl)amino]-1,1'-biphenyl-4-yl}sulfonyl)-L-valine |
| 196 | N-({4'-[(1-benzofuran-2-ylcarbonyl)amino]-1,1'-biphenyl-4-yl}sulfonyl)-D-valine |
| 197 | N-({4'-[(1-benzofuran-2-ylcarbonyl)amino]-1,1'-biphenyl-4-yl}sulfonyl)-L-norvaline |
| 198 | N-({4'-[(1-benzofuran-2-ylcarbonyl)amino]-1,1'-biphenyl-4-yl}sulfonyl)-D-norvaline |
| 199 | N-({4'-[(1-benzofuran-2-ylcarbonyl)amino]-1,1'-biphenyl-4-yl}sulfonyl)-L-aspartic acid |
| 200 | N-({4'-[(1-benzofuran-2-ylcarbonyl)amino]-1,1'-biphenyl-4-yl}sulfonyl)-D-aspartic acid |
| 201 | N~2~-({4'-[(1-benzofuran-2-ylcarbonyl)amino]-1,1'-biphenyl-4-yl}sulfonyl)-L-glutamine |
| 202 | N~2~-({4'-[(1-benzofuran-2-ylcarbonyl)amino]-1,1'-biphenyl-4-yl}sulfonyl)-D-glutamine |
| 203 | N-({4'-[(1-benzofuran-2-ylcarbonyl)amino]-1,1'-biphenyl-4-yl}sulfonyl)-L-histidine |
| 204 | N-({4'-[(1-benzofuran-2-ylcarbonyl)amino]-1,1'-biphenyl-4-yl}sulfonyl)-D-histidine |
| 205 | N-({4'-[(1-benzofuran-2-ylcarbonyl)amino]-1,1'-biphenyl-4-yl}sulfonyl)-L-isoleucine |
| 206 | N-({4'-[(1-benzofuran-2-ylcarbonyl)amino]-1,1'-biphenyl-4-yl}sulfonyl)-D-isoleucine |
| 207 | N-({4'-[(1-benzofuran-2-ylcarbonyl)amino]-1,1'-biphenyl-4-yl}sulfonyl)-L-leucine |
| 208 | N-({4'-[(1-benzofuran-2-ylcarbonyl)amino]-1,1'-biphenyl-4-yl}sulfonyl)-D-leucine |
| 209 | N-({4'-[(1-benzofuran-2-ylcarbonyl)amino]-1,1'-biphenyl-4-yl}sulfonyl)-L-norleucine |
| 210 | N-({4'-[(1-benzofuran-2-ylcarbonyl)amino]-1,1'-biphenyl-4-yl}sulfonyl)-D-norleucine |
| 211 | N-({4'-[(1-benzofuran-2-ylcarbonyl)amino]-1,1'-biphenyl-4-yl}sulfonyl)-L-phenylalanine |
| 212 | N-({4'-[(1-benzofuran-2-ylcarbonyl)amino]-1,1'-biphenyl-4-yl}sulfonyl)-D-phenylalanine |
| 213 | 1-({4'-[(1-benzofuran-2-ylcarbonyl)amino]-1,1'-biphenyl-4-yl}sulfonyl)-L-proline |
| 214 | 1-({4'-[(1-benzofuran-2-ylcarbonyl)amino]-1,1'-biphenyl-4-yl}sulfonyl)-D-proline |
| 215 | N-({4'-[(1-benzofuran-2-ylcarbonyl)amino]-1,1'-biphenyl-4-yl}sulfonyl)-L-tryptophan |
| 216 | N-({4'-[(1-benzofuran-2-ylcarbonyl)amino]-1,1'-biphenyl-4-yl}sulfonyl)-D-tryptophan |
| 217 | N-({4'-[(1-benzofuran-2-ylcarbonyl)amino]-1,1'-biphenyl-4-yl}sulfonyl)-N-methylglycine |
| 218 | N-({4'-[(1-benzofuran-2-ylcarbonyl)amino]-1,1'-biphenyl-4-yl}sulfonyl)-2-methylalanine |
| 219 | N-({4'-[(1-benzofuran-2-ylcarbonyl)amino]-1,1'-biphenyl-4-yl}sulfonyl)-N-methyl-L-alanine |
| 220 | 1-[({4'-[(1-benzofuran-2-ylcarbonyl)amino]-1,1'-biphenyl-4-yl}sulfonyl)amino]cyclopentanecarboxylic acid |
| 221 | N-({4'-[(1-benzofuran-2-ylcarbonyl)amino]-1,1'-biphenyl-4-yl}sulfonyl)-N-methylvaline |
| 222 | N-({4'-[(1-benzofuran-2-ylcarbonyl)amino]-1,1'-biphenyl-4-yl}sulfonyl)-3-methyl-L-valine |
| 223 | N-({4'-[(1-benzofuran-2-ylcarbonyl)amino]-1,1'-biphenyl-4-yl}sulfonyl)-2-methylleucine |
| 224 | N-({4'-[(1-benzofuran-2-ylcarbonyl)amino]-1,1'-biphenyl-4-yl}sulfonyl)-D-glutamic acid |
| 225 | (2R)-[({4'-[(1-benzofuran-2-ylcarbonyl)amino-1,1'-biphenyl-4-yl}sulfonyl)amino](phenyl)acetic acid |
| 226 | [({4'-[(1-benzofuran-2-ylcarbonyl)amino]-1,1'-biphenyl-4-yl}sulfonyl)amino](thien-2-yl)acetic acid |
| 227 | (2S)-2-[({4'-[(1-benzofuran-2-ylcarbonyl)amino-1,1'-biphenyl-4-yl}sulfonyl)amino]-5-methoxy-5-oxopentanoic acid(non-preferred name) |
| 228 | 3-[({4'-[(1-benzofuran-2-ylcarbonyl)amino]-1,1'-biphenyl-4-yl}sulfonyl)amino]-3-phenylpropanoic acid |
| 229 | 2-[({4'-[(1-benzofuran-2-ylcarbonyl)amino]-1,1'-biphenyl-4-yl}sulfonyl)amino]-4-phenylbutanoic acid |
| 230 | N-({4'-[(1-benzofuran-2-ylcarbonyl)amino]-1,1'-biphenyl-4-yl}sulfonyl)-L-tyrosine |

TABLE 4-continued

| Ex. No. | CHEMICAL NAMES |
|---|---|
| 231 | N-({4'-[(1-benzofuran-2-ylcarbonyl)amino]-1,1'-biphenyl-4-yl}sulfonyl)-D-tyrosine |
| 232 | (2S)-2-[({4'-[(1-benzofuran-2-ylcarbonyl)amino]-1,1'-biphenyl-4-yl}sulfonyl)amino]-4-tert-butoxy-4-oxobutanoic acid(non-preferred name) |
| 233 | (2R)-2-[({4'-[(1-benzofuran-2-ylcarbonyl)amino]-1,1'-biphenyl-4-yl}sulfonyl)amino]-4-tert-butoxy-4-oxobutanoic acid(non-preferred name) |
| 234 | (2S)-[({4'-[(1-benzofuran-2-ylcarbonyl)amino]-1,1'-biphenyl-4-yl}sulfonyl)amino](2,3-dihydro-1H-inden-2-yl)acetic acid |
| 235 | N-({4'-[(1-benzofuran-2-ylcarbonyl)amino]-1,1'-biphenyl-4-yl}sulfonyl)-O-methyl-L-tyrosine |
| 236 | [({4'-[(1-benzofuran-2-ylcarbonyl)amino]-1,1'-biphenyl-4-yl}sulfonyl)amino](1-methyl-1H-indol-5-yl)acetic acid |
| 237 | [({4'-[(1-benzofuran-2-ylcarbonyl)amino]-1,1'-biphenyl-4-yl}sulfonyl)amino](1-benzothien-5-yl)acetic acid |
| 238 | N-({4'-[(1-benzofuran-2-ylcarbonyl)amino]-1,1'-biphenyl-4-yl}sulfonyl)-4-nitro-L-phenylalanine |
| 239 | N-({4'-[(1-benzofuran-2-ylcarbonyl)amino]-1,1'-biphenyl-4-yl}sulfonyl)-3-(2-naphthyl)alanine |
| 240 | N-({4'-[(1-benzofuran-2-ylcarbonyl)amino]-1,1'-biphenyl-4-yl}sulfonyl)-beta-methylphenylalanine |
| 241 | N-({4'-[(1-benzofuran-2-ylcarbonyl)amino]-1,1'-biphenyl-4-yl}sulfonyl)-N-methyl-L-tryptophan |
| 242 | N~2~-({4'-[(1-benzofuran-2-ylcarbonyl)amino]-1,1'-biphenyl-4-yl}sulfonyl)-N~5~-phenylglutamine |
| 243 | N-({4'-[(1-benzofuran-2-ylcarbonyl)amino]-1,1'-biphenyl-4-yl}sulfonyl)-4,4,4,4',4',4'-hexafluorovaline |
| 244 | 4-amino-N-({4'-[(1-benzofuran-2-ylcarbonyl)amino]-1,1'-biphenyl-4-yl}sulfonyl)-L-phenylalanine |
| 245 | (2R)-2-[({4'-[(1-benzofuran-2-ylcarbonyl)amino]-1,1'-biphenyl-4-yl}sulfonyl)amino]-5-(benzyloxy)-5-oxopentanoic acid(non-preferred name) |
| 246 | N-({4'-[(1-benzofuran-2-ylcarbonyl)amino]-1,1'-biphenyl-4-yl}sulfonyl)-1-benzyl-L-histidine |
| 247 | N-({4'-[(1-benzofuran-2-ylcarbonyl)amino]-1,1'-biphenyl-4-yl}sulfonyl)-O-benzyl-L-tyrosine |

Example 248

Activity

The activity of the compounds of the invention was assessed through in vitro assays of enzyme inhibition, using MMP-1, MMP-2, MMP-7, MMP-9, MMP-12, MMP-13, and Aggrecanase-1. Inhibitory potencies of some of the compounds of the invention are shown in the Table 5 below. Values are given as $IC_{50}$s in nanomolar, or as percent inhibition at a concentration given in micromolar.

a. In-vitro Fluorescence Assay of MMP-1 Activity:

A continuous assay was used in which the substrate is a synthetic peptide containing a fluorescent group (7-methoxycoumarin; Mca) which is quenched by energy transfer to a 2,4-dinitrophenyl group. When the peptide was cleaved by MMP, a large increase in fluorescence was observed. The source of enzyme in the assay was the recombinant human catalytic domain of MMP-1 prepared at Wyeth-Research in Cambridge. The substrate used was Mca-PQGL-(3-[2,4-dinitrophenyl]-L-2,3-diaminopropionyl)-AR-OH (denoted as Wammp-5, custom synthesized by AnaSpec, Inc.). The assay buffer consisted of 50 mM Hepes (pH 7.4), 100 mM NaCl, 5 mM $CaCl_2$, and 0.005% Brij-35. Each well of black polystyrene 96-well plates contained a 200 µL reaction mixture consisting of assay buffer, purified MMP (final concentration of 25 ng/ml, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point (IC50) for the curve. That is, y is halfway between the lower and upper asymptotes when x=c. b is the slope factor or Hill coefficient.

b. In-vitro Fluorescence Assay of MMP-2 Activity:

A continuous assay was used in which the substrate is a synthetic peptide containing a fluorescent group (7-methoxycoumarin; Mca) which is quenched by energy transfer to a 2,4-dinitrophenyl group. When the peptide was cleaved by MMP, a large increase in fluorescence was observed. The source of enzyme in the assay was the recombinant human MMP-2 (66 kDa) purchased from Oncogene Research Products (catalog number PF023 from Calbiochem). The substrate used was Mca-PQGL-(3-[2,4-dinitrophenyl]-L-2,3-diaminopropionyl)-AR-OH (denoted as Wammp-5, custom synthesized by AnaSpec, Inc.). The assay buffer consisted of 50 mM Hepes (pH 7.4), 100 mM NaCl, 5 mM $CaCl_2$, and 0.005% Brij-35. Each well of black polystyrene 96-well plates contained a 200 µL reaction mixture consisting of assay buffer, MMP (final concentration of 25 ng/ml, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point (IC50) for the curve. That is, y is halfway between the lower and upper asymptotes when x=c. b is the slope factor or Hill coefficient.

c. In-vitro Fluorescence Assay of MMP-13 Activity:

A continuous assay was used in which the substrate is a synthetic peptide containing a fluorescent group (7-methoxycoumarin; Mca) which is quenched by energy transfer to a 2,4-dinitrophenyl group. When the peptide was cleaved by MMP, a large increase in fluorescence was observed. The source of enzyme in the assay was the recombinant human catalytic domain of MMP-13 (165 amino acids, residues 104-268, 19 kDa) prepared at Wyeth-Research in Cambridge. The substrate used was Mca-PQGL-(3-[2,4-dinitrophenyl]-L-2,3-diaminopropionyl)-AR-OH (denoted as Wammp-5, custom synthesized by AnaSpec, Inc.). The assay buffer consisted of 50 mM Hepes (pH 7.4), 100 mM NaCl, 5 mM $CaCl_2$, and 0.005% Brij-35. Each well of black polystyrene 96-well plates contained a 200 µL reaction mixture consisting of assay buffer, purified MMP (final concentration of 0.5 nM, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point (IC50) for the curve. That is, y is halfway between the lower and upper asymptotes when x=c. b is the slope factor or Hill coefficient.

d. In-vitro Fluorescence Assay of MMP-14 Activity:

A continuous assay was used in which the substrate is a synthetic peptide containing a fluorescent group (7-methoxycoumarin; Mca) which is quenched by energy transfer to a 2,4-dinitrophenyl group. When the peptide was cleaved by MMP, a large increase in fluorescence was observed. The source of enzyme in the assay was the recombinant human catalytic domain of MMP-14 (177 amino acids corresponding to Tyr89-Gly265 of mature human enzyme; 20 kDa) purchased from Chemicon International, Inc. (catalog number CC 1041). The substrate used was Mca-PQGL-(3-[2,4-dinitrophenyl]-L-2,3-diaminopropionyl)-AR-OH (denoted as Wammp-5, custom synthesized by AnaSpec, Inc.). The assay buffer consisted of 50 mM Hepes (pH 7.4), 100 mM NaCl, 5 mM $CaCl_2$, and 0.005% Brij-35. Each well of black polystyrene 96-well plates contained a 200 µL reaction mixture consisting of assay buffer, MMP (final concentration of 25 ng/ml, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point (IC50) for the curve. That is, y is halfway between the lower and upper asymptotes when x=c. b is the slope factor or Hill coefficient.

e. MMP-7 Activity Assay:

A continuous assay was used in which the substrate is a synthetic peptide containing a fluorescent group (7-methoxycoumarin; Mca) that is quenched by energy transfer to a 2,4-dinitrophenyl group. When the peptide is cleaved by a MMP, a large increase in fluorescence is observed. Active, recombinant human MMP-7 was purchased from Calbiochem (catalog #444270; expressed in *E. coli,* 19 kDa). The substrate used was Mca-PLGL-(3-[2,4-dinitrophenyl]-L-2,3-diaminopropionyl)-AR-$NH_2$ (purchased from Bachem or AnaSpec, Inc; first described by Knight, C. G., Willenbrock, F., and Murphy, G. *FEBS Lett.* (1992) 296, 263-266). The concentration of the substrate stock was spectrophotometrically determined using the extinction coefficient at 410 nm of 7500 $M^{-1}cm^{-1}$. The assay buffer (pH 7.4) consisted of 50 mM Hepes, 100 mM NaCl, 5 mM $CaCl_2$, and 0.005% Brij-35. Each well of black polystyrene 96-well plates contained a reaction consisting of assay buffer, purified MMP (final concentration of 1.0 nM, prepared by dilution with assay buffer), and varied concentrations of inhibitor (prepared by serial dilution in DMSO in 96-well polypropylene plates). The plates were then incubated at room temperature for 30 minutes. The enzymatic reactions were initiated by adding substrate to a final concentration of 15 µM and were mixed by pipetting up and down. The final DMSO concentration in the assay was 10% and the final, total assay volume was 200 µl. The initial rate of the cleavage reaction was determined at room temperature with a fluorescence plate reader (excitation at 325 nm with a 12 nm bandwidth and emission at 395 nm with a 12 nm bandwidth) immediately after substrate addition. Plots of the inhibitor concentration vs. the initial cleavage rate were fit to the following equation in order to determine $IC_{50}$ values: $y=V_{max}*(1-(x^n/(K^n+x^n)))$, whereby x=inhibitor concentration, y=initial rate, $V_{max}$=initial rate in the absence of inhibitor, n=slope factor, and $K=IC_{50}$ for the inhibition curve.

f. MMP-9 Activity Assay:

Active, recombinant human MMP-9 (83 kDa) was purchased from Calbiochem (catalog #PF024). The assay procedure was identical to that described for MMP-7 except the final enzyme concentration was 0.5-1.0 nM and the final substrate concentration was 20 µM.

g. In vitro Fluorescence Assay of MMP-12 Activity:

A continuous, assay was used in which the substrate is a synthetic peptide containing a fluorescent group (7-methoxycoumarin; Mca) which is quenched by energy transfer to a 2,4-dinitrophenyl group. When the peptide is cleaved by a MMP, a large increase in fluorescence is observed. The source of enzyme in the assay was the recombinant human MMP-12 (19 kDa; "A280" form) purified at Wyeth Research (Biological Chemistry, Cambridge). The substrate used was Mca-PLGL-(3-[2,4-dinitrophenyl]-L-2,3-diaminopropionyl)-AR-$NH_2$ (purchased from Bachem or AnaSpec, Inc; first described by Knight, C. G., Willenbrock, F., and Murphy, G. *FEBS Lett.* (1992) 296, 263-266). The concentration of the substrate stock was spectrophotometrically determined using the extinction coefficient at 410 nm of 7500 $M^{-1}cm^{-1}$. The assay buffer (pH 7.4) consisted of 50 mM Hepes, 100 mM NaCl, 5 mM $CaCl_2$, and 0.005% Brij-35. Each well of black polystyrene 96-well plates contained a reaction consisting of assay buffer, purified MMP (final concentration of 1.5 nM, prepared by dilution with assay buffer), and varied concentrations of inhibitor (prepared by serial dilution in DMSO in 96-well polypropylene plates). The plates were then incubated at room temperature for 30 minutes. The enzymatic reactions were initiated by adding substrate to a final concentration of 20 µM and they were mixed by pipetting up and down. The final DMSO concentration in the assay was 10% and the final, total assay volume was 200 µl. The initial rate of the cleavage reaction was determined at room temperature with a fluorescence plate reader (excitation at 325 nm with a 12 nm bandwidth and emission at 395 nm with a 12 nm bandwidth) immediately after substrate addition.

Plots of the inhibitor concentration vs. the initial cleavage rate were fit to the following equation: $y=V_{max}*(1-(x^n/(K^n+x^n)))$, whereby x=inhibitor concentration, y=initial rate, $V_{max}$=initial rate in the absence of inhibitor, n=slope factor, and K=$IC_{50}$ for the inhibition curve.

h. Aggrecanase-1 FRET Assay:

The following protocol was used:

Fluorimeter was started and temperature set to 30° C., about 30 min before setting up the assay. The following reagents are used:

Buffer: 50 mM HEPES, pH 7.5, 100 mM NaCl, 5 mM $CaCl_2$, 0.1% CHAPS, 5% glycerol.

rAgg1: 5 µg/ml (final concentration in the assay):

Substrate: WAAG-3R (MWT=1645.8, Anaspec, stored at 4° C.). Make a stock at 2 mg/ml in 100% DMSO. Measure the absorbance at 354 nm ($\epsilon=18172$ $M^{-1}$ $cm^{-1}$) to determine the exact concentration. Dilute to 62.5 µM in buffer. Store unused 100% DMSO stock at –80° C. Final concentration of substrate in the assay is 25 µM. This concentration is much less than the $K_m$ ($K_m$=1.1+/–0.2 mM as determined by Jin and Cowling)

Inhibitors. Make up inhibitors at 10× starting concentration in 100% DMSO. Perform serial dilutions (in duplicate) across the nunc plate in 100% DMSO;

Dilution plates: Nunc, polypropylene low binding (Nalgene)

Assay plate: Fluoronunc (Nalgene)

Fluorimeter: GeminiXS (Molecular Devices).;

The assay is performed as follows: The plates are set up so that the final column (12) is used for controls. Total reaction volume is 100 µl. Each compound is assayed in duplicate, so 4 compounds are screened per plate.

1) Add buffer to the entire 96-well plate (30 ρl/well).
2) Dilute rAgg1 to 25 µg/ml buffer just prior to addition on the plate. Add 20 µl/well to all wells. Mix 6 times.
3) Add 10 µl/well of 10× inhibitors from the working plate, except column 12. Mix 6 times. To wells 12A-F, add 10× controls (see reference compounds below).
4) To wells 12G-H add 10 µl 100% DMSO.
5) Incubate for 10-15 min at 30° C.
6) Add 40 µl/well of 62.5 µM WAAG-3R substrate. Mix 6 times.

The reaction is monitored for 30-40 min at 30° C. λex: 340 nm and λ em: 420 nm). The fluorescence is linear during this time and the slope of the line (Vmax/sec) represents the initial reaction rate, v. The maximal rate of cleavage of substrate is determined in the absence of inhibitor. The percent inhibition of activity in the presence of inhibitor is calculated as follows:

$$\% \text{ inhibition} = (1 - v(\text{Rate, } RFU/\text{sec})/\text{Maximal Rate}(RFU/\text{sec})) * 100$$

The IC50 was obtained by fitting the initial rate, v, or % inhibition at each concentration of inhibitor to the following equation in Excel.

$$y=(a-d)/(1+C/IC_{50})^n)+d$$

This model describes a sigmoidal curve with an adjustable baseline, a. y is the % inhibition or initial rate of reaction, C is the concentration of inhibitor under test. a is the limiting response as C approaches zero. As C increases without bound y tends toward its lower limit, d. y is halfway between the lower and upper asymptotes when C=$IC_{50}$. n is the Hill coefficient. The sign of n is positive when the response increases with increasing dose and is negative when the response decreases with increasing dose (inhibition).

Table 5 lists the activities for the compounds of Examples 1-179. All values are $IC_{40}$s in nanomolar, or % inhibition at a concentration (uM).

TABLE 5

| Example | MMP-1 | MMP-2 | MMP-7 | MMP-9 | MMP-12 | MMP-13 | MMP-14 | AGG-1 |
|---|---|---|---|---|---|---|---|---|
| 1 | | 47 | | | | 35 | 13900 | |
| 2 | >3500 | 6.5 | 19 | 1100 | 14 | 1.6 | 2200 | |
| 3 | | 19 | | | | 35 | 5600 | |
| 4 | | 4.1 | | | | 0.3 | | |
| 5 | | | | | | 10.4 | | |
| 6 | | 3.3 | | | | 0.7 | | |
| 7 | | | | | | 1.5 | | |
| 8 | | 3.9 | | | | 0.4 | | |
| 9 | | 4.0 | | | | 1.3 | | |
| 10 | | 19 | | | | 3.4 | | |
| 11 | | 16 | | | | 2.3 | | |
| 12 | | 149 | | | | 6.2 | | |
| 13 | | 62 | | | | 3.5 | | |
| 14 | | 916 | | | | 11 | | |
| 15 | | 10 | | | | 2.5 | | |
| 16 | | | | | | | | |
| 17 | | 37 | | | | 8.1 | | |
| 18 | | 8.4 | | | | 2.2 | | |
| 19 | | | | | | | | |
| 20 | 24000 | 581 | | | 33 | 3.7 | 5450 | |
| 21 | | 15000 | | | 175 | 9.5 | | |
| 22 | | 1940 | | | 137 | 12 | | |
| 23 | | 3000 | | | | 21 | | |

TABLE 5-continued

| Example | MMP-1 | MMP-2 | MMP-7 | MMP-9 | MMP-12 | MMP-13 | MMP-14 | AGG-1 |
|---|---|---|---|---|---|---|---|---|
| 24 | | 8000 | | | | 24 | | |
| 25 | | 6320 | | | | 14 | | |
| 26 | | 3380 | | | | 6.2 | | |
| 27 | | 4410 | | | | 7.1 | | |
| 28 | | 6640 | | | | 47 | | |
| 29 | | 9320 | | | | 37 | | |
| 30 | >18000 | 4000 | 6000 | 1500 | 85 | 11 | 26200 | 14000 |
| 31 | | 1450 | | | 155 | 16 | | |
| 32 | | 3150 | | | | 21 | | |
| 33 | | 595 | | | | 6.1 | | |
| 34 | | 2500 | | | | 152 | | |
| 35 | | 50% at 3.5 uM | | | | 9.9 | | |
| 36 | | 2250 | | | 126 | 11 | | |
| 37 | | 2340 | | | | 16 | | |
| 38 | | 8890 | | | | 28 | | |
| 39 | | 7500 | | | | 30 | | |
| 40 | | 2840 | | | | 16.2 | | |
| 41 | | 1460 | | | | 8.5 | | |
| 42 | | 1590 | | | | 41 | | |
| 43A | | 6720 | | | | 22 | | |
| 43B | | 7770 | | | | 18 | | |
| 44 | | | | | | 286 | | |
| 45 | | 81 | | | | 3.0 | | |
| 46 | 20200 | 1000 | | | 187 | 14 | 24800 | |
| 47 | | 4290 | | | 438 | 32 | | |
| 48 | | 3810 | | | 226 | 25 | | |
| 49 | | 5770 | | | | 35 | | |
| 50 | | 7710 | | | | 45 | | |
| 51 | | 7110 | | | 187 | 11 | | |
| 52 | | 0.4 | | | | 0.4 | | |
| 53 | | 10000 | 2600 | >4000 | | 17 | | |
| 54 | | | | | | 220 | | |
| 55 | | 2380 | | | | 20 | | |
| 56 | | 13300 | | | | 13 | | |
| 57 | | 7000 | | | | 93 | | |
| 58 | | 1770 | | | | 56 | | |
| 59 | | 3270 | | | | 32 | | |
| 60 | | 886 | | | | 8.0 | | |
| 61 | | 323 | | | | 4.3 | | |
| 62 | | 5110 | | | | 6.5 | | |
| 63 | | 5000 | | | | 28 | | |
| 64 | | 6940 | | | | 63 | | |
| 65 | | 2470 | | | | 10.9 | | |
| 66 | | | | | | 121 | | |
| 67 | | 5750 | | | | 20 | | |
| 68 | | 1650 | | | | 12 | | |
| 69 | | 2340 | | | | 16 | | |
| 70 | | 3470 | | | | 14 | | |
| 71 | | 6020 | | | | 8.1 | | |
| 72 | | 3980 | | | | 8.5 | | |
| 73 | | 4770 | | | | 11.9 | | |
| 74 | 28300 | 93 | | | | 13 | 29 | |
| 75 | | | | | | | | 42000 |
| 76 | | | | | | 3.1 | | |
| 77 | 15000 | 6.0 | | | | 5.7 | 7110 | |
| 78 | | | | | | 5600 | | |
| 79 | 500000 | 35 | | | | 40 | 24000 | |
| 80 | | 4350 | | | 51 | 43 | | |
| 81 | | | | | | 323 | | |
| 82 | >10000 | 30 | | | | 18 | >60000 | |
| 83 | 24300 | 259 | | | | 5.9 | 12400 | |
| 84 | | 0.9 | | | | 0.6 | | |
| 85 | | | | | | 294 | | |
| 86 | | 2500 | | | | 3.8 | | |
| 87 | | 1410 | | | | 2.3 | | |
| 88 | | 7000 | | | | 27 | | |
| 89 | | 4340 | | | | 67 | | |
| 90 | | 1760 | | | | 7.1 | | |
| 91 | | 2230 | | | | 6.9 | | |
| 92 | | 3760 | | | | 25 | | |
| 93 | | 1150 | | | | 4.8 | | |
| 94 | | 673 | | | | 4.5 | | |
| 95 | | 2070 | | | | 8.4 | | |
| 96 | | 625 | | | | 4.4 | | |
| 97 | | 2860 | | | | 14 | | |

TABLE 5-continued

| Example | MMP-1 | MMP-2 | MMP-7 | MMP-9 | MMP-12 | MMP-13 | MMP-14 | AGG-1 |
|---|---|---|---|---|---|---|---|---|
| 98 | | 890 | | | | 84.1 | | |
| 99 | | 13200 | | | | 70 | | |
| 100 | | 2399 | | | | 2.6 | | |
| 101 | | 2000 | | | | 5.8 | | |
| 102 | | 1520 | | | | 5.7 | | |
| 103 | | 78.4 | | | | 3.9 | | |
| 104 | | 1.5 | | | | 0.7 | | |
| 105 | | 1050 | | | 60 | 9.5 | | |
| 106 | | 3590 | | | 121 | 7.4 | | |
| 107 | | 4220 | | | | 11 | | |
| 108 | | 4290 | | | | 13 | | |
| 109 | 11000 | 3650 | | | | 15 | 7000 | |
| 110 | 49600 | 2400 | | | | 17 | 20000 | |
| 111 | 22000 | 1340 | | | 84 | 4.0 | 7310 | |
| 112 | | 2670 | | | | 8.5 | | |
| 113 | | 2060 | | | | 6.4 | | |
| 114 | | 1630 | | | | 32 | | |
| 115 | | 3010 | | | | 11 | | |
| 116 | 34100 | 1490 | | | 50 | 1.9 | 12400 | |
| 117 | | 20000 | | | | 199 | | |
| 118 | 30000 | 1700 | | | | 2.3 | 14600 | |
| 119 | | 688 | | | | 3.4 | | |
| 120 | | 1370 | | | | 2.1 | | |
| 121 | | | | | | 1020 | | |
| 122 | | | | | | 222 | | |
| 123 | | 63 | | | | 3.2 | | |
| 124 | | 522 | | | | 3.0 | | |
| 125 | | 1610 | | | | 4.9 | | |
| 126 | | | | | | | | |
| 127 | | 47 | | | | 0.8 | | |
| 128 | | 59.5 | | | | 2.8 | | |
| 129 | | 116 | | | 1.9 | 0.8 | | |
| 130 | | 25.9 | | | | 2 | | |
| 131 | | 149 | | | | 17 | | |
| 132 | | 346 | | | | 14 | 100000 | 2200 |
| 133 | 100000 | 64 | | | | 5.2 | 12000 | 800 |
| 134 | 10000 | 17 | | | | 1.2 | 6250 | 113 |
| 135 | 20000 | 0.7 | | | | 0.5 | 2000 | 345 |
| 136 | 400000 | 135 | 1100 | >7000 | 20 | 1.8 | 5000 | 430 |
| 137 | | 23.9 | | | | 4.6 | 49% at 1.6 uM | 2500 |
| 138 | | 1120 | | | | 89.3 | | |
| 139 | | 28 | | | | 4.4 | 3500 | |
| 140 | | | | | | | | |
| 141 | | 2.5 | | | | 1.1 | 500 | |
| 142 | | 130 | | | | 2.1 | | |
| 143 | | 64 | | | | 1.2 | | |
| 144 | | | | | | | | 11600 |
| 145 | | | | | | | | 8600 |
| 146 | | 207 | | | | 1.2 | | |
| 147 | | | | | | 1.9 | | |
| 148 | | 136 | | | | 1.4 | | 400 |
| 149 | | 375 | | | | 7.9 | | |
| 150 | | 198 | | | | 8.1 | | |
| 151 | 70000 | 4.5 | | | 11 | 0.4 | 35000 | |
| 152 | | 2.3 | | | 1.1 | 0.7 | | |
| 153 | 40000 | 14 | | | | 0.5 | 17000 | |
| 154 | | 60 | | | | 1.7 | | |
| 155 | 25000 | 5000 | | | 508 | 19 | 8000 | |
| 156 | | 6200 | | | | 25 | | |
| 157 | | 2050 | | | | 8.8 | | |
| 158 | | 1840 | | | | 8.7 | | |
| 159 | | 3520 | | | | 8.5 | | |
| 160 | | 4550 | | | | 9.5 | | |
| 161 | | 379 | | | | 6.1 | | |
| 162 | | 2610 | | | | 85 | | |
| 163 | | 2 | | | | 11 | | |
| 164 | 500000 | 5.6 | | | | 1.1 | 1430 | 12700 |
| 165 | | 5.6 | | | 4.6 | 1.2 | 2120 | 20000 |
| 166 | | 5.8 | | | | 3.1 | | |
| 167 | 90000 | 9300 | | | 97 | 12 | 11000 | |
| 168 | 60000 | 1290 | | | | 99 | 36000 | |
| 169 | 40400 | 1190 | | | | 75 | 40000 | |
| 170 | | | | | | 2870 | | |
| 171 | | | | | | 1090 | | 60% at 150 uM |

TABLE 5-continued

| Example | MMP-1 | MMP-2 | MMP-7 | MMP-9 | MMP-12 | MMP-13 | MMP-14 | AGG-1 |
|---------|-------|-------|-------|-------|--------|--------|--------|-------|
| 172 | 18500 | 6.9 | | | | 29 | 8920 | 43000 |
| 173 | | | | | | 115 | | 25400 |
| 174 | 7400 | 61 | | | | 25 | 6130 | |
| 175 | 3090 | 5.7 | | | | 11 | 2910 | |
| 176 | | 4340 | | | | 20 | | |
| 177 | | 3000 | | | | 15 | | |
| 178 | | 3320 | | | | 13 | | |
| 179 | | 4000 | | | | 7.1 | | |

The disclosures of each patent, patent application, and publication cited or described in this document are hereby incorporated herein by reference, in their entireties.

Various modifications of the invention, in addition to those described herein, will be apparent to those skilled in the art from the foregoing description. Such modifications are also intended to fall within the scope of the appended claims.

What is claimed is:

1. A compound the formula 1:

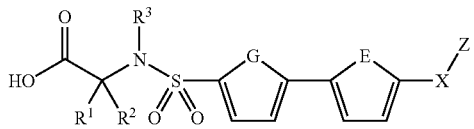

wherein:
$R^1$ and $R^2$ are, independently, H, CH(OH)$R^4$, phenyl, benzofuranyl, or $C_1$-$C_6$ alkyl, with the proviso that when $R^1$ or $R^2$ is CH(OH)$R^4$, then Z is substituted with NR$^4$SO$_2$R$^5$, SO$_2$NR$^4$R$^5$, benzofuranyl, or $C_3$-$C_6$ cycloalkyl;
$R^3$ is H or $C_1$-$C_6$ alkyl;
$R^4$ and $R^5$ are, independently with respect to each occurrence, a bond to the other, H, $C_1$-$C_6$ alkyl, or phenyl;
G and E are, independently, C($R^6$)=C($R^6$);
$R^6$ is, independently with respect to each occurrence, H, halogen, NR$^4$R$^5$, N[(CH$_2$)$_2$]$_2$O, N[(CH$_2$)$_2$]$_2$NR$^4$, NR$^4$SO$_2$R$^5$, NR$^4$C(=O)R$^5$, NHC(=O)OR$^4$, NO$_2$, SO$_2$NR$^4$R$^5$, SO$_2$R$^4$, OR$^4$, C(=O)R$^4$, COOR$^4$, CONR$^4$R$^5$, CN, phenyl, benzofuranyl, $C_1$-$C_6$ alkyl, $C_2$-$C_6$ alkenyl, or $C_2$-$C_6$ alkynyl;
X is N($R^3$)C(=O), OC(=O), OS(O)$_2$, NHSO$_2$, OCH$_2$, CH$_2$S(O), or CH$_2$S(O)$_2$; and

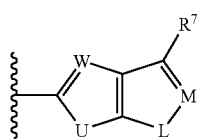

Z is
wherein:
U is O;
W is C($R^6$);
M is C($R^6$);
L is C($R^6$)=C($R^6$);
$R^7$ is a bond to $R^6$, H, halogen, NR$^4$R$^5$, N[(CH$_2$)$_2$]$_2$O, N[(CH$_2$)$_2$]$_2$NR$^4$, NHSO$_2$R$^4$, NR$^4$C(=O)R$^5$, NHC (=O)OR$^4$, NO$_2$, SO$_2$NR$^4$R$^5$, SO$_2$R$^4$, OR$^4$, C(=O)R$^4$, COOR$^4$, CONR$^4$R$^5$, CN, phenyl, benzofuranyl, $C_1$-$C_6$ alkyl, $C_2$-$C_6$ alkenyl, or $C_2$-$C_6$ alkynyl, each optionally substituted with NR$^4$R$^5$, N[(CH$_2$)$_2$]$_2$O, N[(CH$_2$)$_2$]$_2$NR$^4$, NHSO$_2$R$^4$, NR$^4$C(=O)R$^5$, NHC(=O)OR$^4$, NO$_2$, SO$_2$NR$^4$R$^5$, SO$_2$R$^4$, OR$^8$, C(=O)R$^4$, COOR$^4$, CONR$^4$R$^5$, CN, cycloalkyl, phenyl, or benzofuranyl; and
$R^8$ is H, phenyl, benzofuranyl, or $C_1$-$C_6$ alkyl, optionally substituted with NR$^4$R$^5$, N[(CH$_2$)$_2$]$_2$O, N[(CH$_2$)$_2$]$_2$NR$^4$, NR$^4$SO$_2$R$^5$, NR$^4$C(=O)R$^5$, NHC(=O)OR$^4$, NO$_2$, SO$_2$NR$^4$R$^5$, SO$_2$R$^4$, C(=O)R$^4$, COOR$^4$, CONR$^4$R$^5$, CN, cycloalkyl, phenyl or benzofuranyl;
or a pharmaceutically acceptable salt thereof.

2. The compound of claim 1 wherein $R^1$ is substituted with halogen CO$_2$R$^4$, C(=O)NR$^4$R$^5$, phenyl, or benzofuranyl.

3. The compound of claim 1 wherein $R^3$ is substituted with NR$^4$R$^5$, N[(CH$_2$)$_2$]$_2$O, N[(CH$_2$)$_2$]$_2$NR$^4$, NR$^4$SO$_2$R$^5$, NR$^4$C(=O)R$^5$, NHC(=O)OR$^4$, NO$_2$, SO$_2$NR$^4$R$^5$, SO$_2$R$^4$, OR$^4$, C(=O)R$^4$, COOR$^4$, CONR$^4$R$^5$, CN, cycloalkyl, phenyl, or benzofuranyl.

4. The compound of claim 1 wherein $R^6$ is each optionally substituted with NR$^4$R$^5$, N[(CH$_2$)$_2$]$_2$O, N[(CH$_2$)$_2$]$_2$NR$^4$, NR$^4$SO$_2$R$^5$, NR$^4$C(=O)R$^5$, NR$^4$C(=O)OR$^4$, NO$_2$, SO$_2$NR$^4$R$^5$, SO$_2$R$^4$, OR$^4$, C(=O)R$^4$, COOR$^4$, CONR$^4$R$^5$, CN, phenyl, or benzofuranyl.

5. The compound of claim 1 wherein:
$R^3$ is H;
X is NHC(=O), or OCH$_2$.

6. The compound of claim 5 wherein:
E is C(H)=C(H);
W is C(H), or C(CH$_3$);
M is C($R^9$), wherein $R^9$ is H, halogen, $C_1$-$C_6$ alkyl, or CN; and
L is C(H)=C(H).

7. The compound of claim 1 wherein at least one of $R^1$ or $R^2$ is $C_1$-$C_6$ alkyl.

8. The compound of claim 1 wherein $R^3$ is H.

9. The compound of claim 1 wherein $R^4$ and $R^5$ are each $C_1$-$C_6$ alkyl.

10. The compound of claim 1 wherein G and E are each C(H)=C(H).

11. The compound of claim 1 wherein W is C(H) or C(CH$_3$).

12. The compound of claim 1 wherein L is CH=CH.

13. The compound of claim 1 wherein $R^7$ is other than H.

14. The compound of claim 1 that is
N-({4'-[(1-benzofuran-2-ylcarbonyl)amino]-1,1'-biphenyl-4-yl}sulfonyl)glycine;
L-2-{4'-[(Benzofuran-2-carbonyl)-amino]-biphenyl-4-sulfonylamino}-3-methyl-butyric acid;
(4'-{[(5-chloro-1-benzofuran-2-yl)carbonyl]amino}-1,1'-biphenyl-4-yl)sulfonyl]-L-valine;

N-[(4'-{[(7-methoxy-1-benzofuran-2-yl)carbonyl]
amino}-1,1'-biphenyl-4-yl)sulfonyl]-L-valine;
N-[(4'-{[(5-nitro-1-benzofuran-2-yl)carbonyl]amino}-1,
1'-biphenyl-4-yl)sulfonyl]-L-valine;
N-[(4'-{[(5-amino-1-benzofuran-2-yl)carbonyl]amino}-
1,1'-biphenyl-4-yl)sulfonyl]-L-valine;
N-({4'-[({5-[(methylsulfonyl)amino]-1-benzofuran-2-
yl}carbonyl)amino]-1,1'-biphenyl-4-yl}sulfonyl)-L-
valine;
N-{[4'-({[5-(acetylamino)-1-benzofuran-2-yl]
carbonyl}amino)-1,1'-biphenyl-4-yl]sulfonyl}-L-va-
line;
4'-[(5-Benzenesulfonylamino-benzofuran-2-carbonyl)-
amino]-biphenyl-4-sulfonyl-L-valine;
N-[(4'-{[(4-methoxy-1-benzofuran-2-yl)carbonyl]
amino}-1,1'-biphenyl-4-yl)sulfonyl]-L-valine;
4'-[(4-Benzyloxy-benzofuran-2-carbonyl)-amino]-biphe-
nyl-4-sulfonyl-L-valine;
4'-{[4-(1-Carboxy-ethoxy)-benzofuran-2-carbonyl]-
amino}-biphenyl-4-sulfonyl-L-valine;
N-({4'-[(1-Benzofuran-2-ylcarbonyl)amino]-1,1'-biphe-
nyl-4-yl}sulfonyl)-L-Asparagine;
N-({4'-[(1-Benzofuran-2-ylcarbonyl)amino]-1,1'-biphe-
nyl-4-yl}sulfonyl)-L-leucine;
L-2-{4'-[(4-Cyano-3-methyl-benzofuran-2-carbonyl)-
amino]-biphenyl-4-sulfonylamino}-3-methyl-butyric
acid;
L-3-Methyl-2-{4'-[(3-methyl-4-prop-1-ynyl-benzofuran-
2-carbonyl)-amino]-biphenyl-4-sulfonylamino}-bu-
tyric acid;
L-2-(4'-{[4-(3-Methoxy-prop-1-ynyl)-3-methyl-benzofu-
ran-2-carbonyl]-amino}-biphenyl-4-sulfonylamino)-3-
methyl-butyric acid;
2-{4'-[(4-Cyclopropylethynyl-3-methyl-benzofuran-2-
carbonyl)-amino]-biphenyl-4-sulfonylamino}-3-me-
thyl-butyric acid;
L-2-(4'-{[4-(2-Cyclopropyl-ethyl)-3-methyl-benzofuran-
2-carbonyl]-amino}-biphenyl-4-sulfonylamino)-3-me-
thyl-butyric acid;
L-2-(4'-{[4-(3-Methoxy-Z-propenyl)-3-methyl-benzofu-
ran-2-carbonyl]-amino}-biphenyl-4-sulfonylamino)-3-
methyl-butyric acid;
L-2-(4'-{[4-(3-Hydroxy-prop-1-ynyl)-3-methyl-benzofu-
ran-2-carbonyl]-amino}-biphenyl-4-sulfonylamino)-3-
methyl-butyric acid;
L-2-(4'-{[4-(3-Hydroxy-propyl)-3-methyl-benzofuran-2-
carbonyl]-amino}-biphenyl-4-sulfonylamino)-3-me-
thyl-butyric acid;
L-3-Methyl-2-(4'-{[3-methyl-4-(4-methyl-pent-1-ynyl)-
benzofuran-2-carbonyl]-amino}-biphenyl-4-sulfony-
lamino)-butyric acid;
L-3-Methyl-2-(4'-{[3-methyl-4-(4-methyl-pentyl)-benzo-
furan-2-carbonyl]-amino}-biphenyl-4-sulfonylamino)-
butyric acid;
L-2-(4'-{[4-(3-Methoxy-propyl)-3-methyl-benzofuran-2-
carbonyl]-amino}-biphenyl-4-sulfonylamino)-3-me-
thyl-butyric acid;
L-2-(4'-{[4-(3-Dimethylamino-prop-1-ynyl)-3-methyl-
benzofuran-2-carbonyl]-amino}-biphenyl-4-sulfony-
lamino)-3-methyl-butyric acid;
L-2-(4'-{[4-(3-Dimethylamino-propyl)-3-methyl-benzo-
furan-2-carbonyl]-amino}-biphenyl-4-sulfonylamino)-
3-methyl-butyric acid;
L-2-{4'-[(4-Ethynyl-3-methyl-benzofuran-2-carbonyl)-
amino]-biphenyl-4-sulfonylamino}-3-methyl-butyric
acid;
L-2-(4'-{[4-(3,3-Dimethyl-but-1-ynyl)-3-methyl-benzo-
furan-2-carbonyl]-amino}-biphenyl-4-sulfonylamino)-
3-methyl-butyric acid;
L-2-{4'-[(4-Methanesulfonylamino-3-methyl-benzofu-
ran-2-carbonyl)-amino]-biphenyl-4-sulfonylamino}-3-
methyl-butyric acid;
L-2-(4'-{[4-(Methanesulfonyl-methyl-amino)-3-methyl-
benzofuran-2-carbonyl]-amino}-biphenyl-4-sulfony-
lamino)-3-methyl-butyric acid;
D-2-{4'-[(4-Methanesulfonylamino-3-methyl-benzofu-
ran-2-carbonyl)-amino]-biphenyl-4-sulfonylamino}-3-
methyl-butyric acid;
L-2-({4'-[(4-Cyano-3-methyl-benzofuran-2-carbonyl)-
amino]-biphenyl-4-sulfonyl}-methyl-amino)-3-me-
thyl-butyric acid;
(L-3-Methyl-2-{4'-[(3-methyl-4-methylcarbamoyl-ben-
zofuran-2-carbonyl)-amino]-biphenyl-4-sulfony-
lamino}-butyric acid triethylamine salt;
2-{4'-[(4-Dimethylcarbamoyl-3-methyl-benzofuran-2-
carbonyl)-amino]-biphenyl-4-sulfonylamino}-3-me-
thyl-butyric acid triethylamine salt;
L-2-{4'-[(4,6-Dimethoxy-3,7-dimethyl-benzofuran-2-
carbonyl)-amino]-biphenyl-4-sulfonylamino}-3-me-
thyl-butyric acid;
2-{4'-[(5-Bromo-3-methyl-benzofuran-2-carbonyl)-
amino]-biphenyl-4-sulfonylamino}-3-methyl-butyric
acid;
L-2-{4'-[(4-Carbamoyl-3-methyl-benzofuran-2-carbo-
nyl)-amino]-biphenyl-4-sulfonylamino}-3-methyl-bu-
tyric acid;
L-2-(4'-{[4-(Cyclopropanecarbonyl-amino)-3-methyl-
benzofuran-2-carbonyl]-amino}-biphenyl-4-sulfony-
lamino)-3-methyl-butyric acid;
L-2-{4'-[(4-Acetylamino-3-methyl-benzofuran-2-carbo-
nyl)-amino]-biphenyl-4-sulfonylamino}-3-methyl-bu-
tyric acid;
L-3-Methyl-2-{4'-[(3-methyl-4-propionylamino-benzo-
furan-2-carbonyl)-amino]-biphenyl-4-sulfonylamino}-
butyric acid;
L-2-{4'-[(4-Isobutyrylamino-3-methyl-benzofuran-2-car-
bonyl)-amino]-biphenyl-4-sulfonylamino}-3-methyl-
butyric acid;
L-2-{4'-[(4-Cyclopropylmethoxy-3-methyl-benzofuran-
2-carbonyl)-amino]-biphenyl-4-sulfonylamino}-3-me-
thyl-butyric acid;
L-2-{4'-[(4-sec-Butoxy-3-methyl-benzofuran-2-carbo-
nyl)-amino]-biphenyl-4-sulfonylamino}-3-methyl-bu-
tyric acid;
L-3-Methyl-2-{4'-[(3-phenyl-benzofuran-2-carbonyl)-
amino]-biphenyl-4-sulfonylamino}-butyric acid;
L-2-(4'-{[4-(Acetyl-methyl-amino)-3-methyl-benzofu-
ran-2-carbonyl]-amino}-biphenyl-4-sulfonylamino)-3-
methyl-butyric acid;
L-2-(4'-{[4-(3,3-Dimethyl-butyl)-3-methyl-benzofuran-
2-carbonyl]-amino}-biphenyl-4-sulfonylamino)-3-me-
thyl-butyric acid;
L-2-{4'-[(3-Ethyl-benzofuran-2-carbonyl)-amino]-biphe-
nyl-4-sulfonylamino}-3-methyl-butyric acid;
L-2-{4'-[(4-tert-Butoxycarbonylamino-3-methyl-benzo-
furan-2-carbonyl)-amino]-biphenyl-4-sulfonylamino}-
3-methyl-butyric acid;
L-3-Methyl-2-{4'-[(3-methyl-4-methylamino-benzofu-
ran-2-carbonyl)-amino]-biphenyl-4-sulfonylamino}-
butyric acid;
L-2-{4'-[(4-Amino-3-methyl-benzofuran-2-carbonyl)-
amino]-biphenyl-4-sulfonylamino}-3-methyl-butyric
acid;

L-2-{4'-[(4-Dimethylamino-3-methyl-benzofuran-2-carbonyl)-amino]-biphenyl-4-sulfonylamino}-3-methyl-butyric acid;
L-2-({4'-[(4-Methanesulfonylamino-3-methyl-benzofuran-2-carbonyl)-amino]-biphenyl-4-sulfonyl}-methyl-amino)-3-methyl-butyric acid;
L-3-Hydroxy-2-{4'-[(4-methanesulfonylamino-3-methyl-benzofuran-2-carbonyl)-amino]-biphenyl-4-sulfonylamino}-butyric acid;
L-3-Methyl-2-(4'-{[3-methyl-4-(2,2,2-trifluoro-acetylamino)-benzofuran-2-carbonyl]-amino}-biphenyl-4-sulfonylamino)-butyric acid;
L-2-{4'-[(4-Ethanesulfonylamino-3-methyl-benzofuran-2-carbonyl)-amino]-biphenyl-4-sulfonylamino}-3-methyl-butyric acid;
L-3-Methyl-2-(4'-{[3-methyl-4-(propane-2-sulfonylamino)-benzofuran-2-carbonyl]-amino}-biphenyl-4-sulfonylamino)-butyric acid;
L-2-(4'-{[4-(Ethanesulfonyl-methyl-amino)-3-methyl-benzofuran-2-carbonyl]-amino}-biphenyl-4-sulfonylamino)-3-methyl-butyric acid;
L-2-{4'-[(4-Benzenesulfonylamino-3-methyl-benzofuran-2-carbonyl)-amino]-biphenyl-4-sulfonylamino}-3-methyl-butyric acid;
D-3-Methyl-2-{4'-[(3-methyl-benzofuran-2-carbonyl)-amino]-biphenyl-4-sulfonylamino}-butyric acid;
D-2-{4'-[(Benzofuran-2-carbonyl)-methyl-amino]-biphenyl-4-sulfonylamino}-3-methyl-butyric acid;
N-({4'-[(1-benzofuran-2-ylcarbonyl)amino]-1,1'-biphenyl-4-yl}sulfonyl)-N-methyl-D-valine;
N-({4'-[(1-Benzofuran-2-ylcarbonyl)amino]-1,1'-biphenyl-4-yl}sulfonyl)-N-methyl-L-valine;
N-({4'-[(1-Benzofuran-2-ylcarbonyl)amino]-1,1'-biphenyl-4-yl}sulfonyl)-N-methylglycine;
N-[(4'-{[(3-Methyl-1-benzofuran-2-yl)carbonyl]amino}-1,1'-biphenyl-4-yl)sulfonyl]-L-valine;
N-[(4'-{[(5-Bromo-1-benzofuran-2-yl)carbonyl]amino}-1,1'-biphenyl-4-yl)sulfonyl]-L-valine;
N-[(4'-{[(5-Ethyl-4-methoxy-3-methyl-1-benzofuran-2-yl)carbonyl]amino}-1,1'-biphenyl-4-yl)sulfonyl]-L-valine;
N-[(4'-{[(4-Ethyl-3-methyl-1-benzofuran-2-yl)carbonyl]amino}-1,1'-biphenyl-4-yl)sulfonyl]-L-valine;
N-[(4'-{[(5-Ethyl-4-isopropoxy-3-methyl-1-benzofuran-2-yl)carbonyl]amino}-1,1'-biphenyl-4-yl)sulfonyl]-L-valine;
N-{[4'-({[4-(Benzyloxy)-5-ethyl-3-methyl-1-benzofuran-2-yl]carbonyl}amino)-1,1'-biphenyl-4-yl]sulfonyl}-L-valine;
N-[(4'-{[(5-Ethyl-4-hydroxy-3-methyl-1-benzofuran-2-yl)carbonyl]amino}-1,1'-biphenyl-4-yl)sulfonyl]-L-valine;
N-{[4'-({[4-(Hydroxymethyl)-3-methyl-1-benzofuran-2-yl]carbonyl}amino)-1,1'-biphenyl-4-yl]sulfonyl}-L-valine;
N-[(4'-{[(3,4-Dimethyl-1-benzofuran-2-yl)carbonyl]amino}-1,1'-biphenyl-4-yl)sulfonyl]-L-valine;
N-[(4'-{[(4-Acetyl-3-methyl-1-benzofuran-2-yl)carbonyl]amino}-1,1'-biphenyl-4-yl)sulfonyl]-L-valine;
N-{[4'-({[4-(1-Hydroxyethyl)-3-methyl-1-benzofuran-2-yl]carbonyl}amino)-1,1'-biphenyl-4-yl]sulfonyl}-L-valine;
N-[(4'-{[(3-methyl-4-vinyl-1-benzofuran-2-yl)carbonyl]amino}-1,1'-biphenyl-4-yl)sulfonyl]-L-valine;
N-{[4'-({[4-(1,2-dihydroxyethyl)-3-methyl-1-benzofuran-2-yl]carbonyl}amino)-1,1'-biphenyl-4-yl]sulfonyl}-L-valine;
N-methyl-N-[(4'-{[(3-methyl-4-vinyl-1-benzofuran-2-yl)carbonyl]amino}-1,1'-biphenyl-4-yl)sulfonyl]-L-valine;
N-{[4'-({[4-(1,2-dihydroxyethyl)-3-methyl-1-benzofuran-2-yl]carbonyl}amino)-1,1'-biphenyl-4-yl]sulfonyl}-N-methyl-L-valine;
N-{[4'-({[4-(methoxymethyl)-3-methyl-1-benzofuran-2-yl]carbonyl}amino)-1,1'-biphenyl-4-yl]sulfonyl}-L-valine;
N-{[4'-({[4-(1-methoxyethyl)-3-methyl-1-benzofuran-2-yl]carbonyl}amino)-1,1'-biphenyl-4-yl]sulfonyl}-L-valine;
N-{[4'-({[4-(2-methoxyethyl)-3-methyl-1-benzofuran-2-yl]carbonyl}amino)-1,1'-biphenyl-4-yl]sulfonyl}-L-valinate;
N-[(4'-{[(4-Isopropoxy-1-benzofuran-2-yl)carbonyl]amino}-1,1'-biphenyl-4-yl)sulfonyl]-L-valine;
N-[(4'-{[(5-methoxy-1-benzofuran-2-yl)carbonyl]amino}-1,1'-biphenyl-4-yl)sulfonyl]-L-valine;
(S)-2-{4'-[(4-Methoxy-3-methyl-benzofuran-2-carbonyl)-amino]-biphenyl-4-sulfonylamino}-3-methyl-butyric acid;
(S)-2-{4'-[(4-ethoxy-3-methyl-benzofuran-2-carbonyl)-amino]-biphenyl-4-sulfonylamino}-3-methyl-butyric acid;
(S)-3-Methyl-2-{4'-[(3-methyl-4-propoxy-benzofuran-2-carbonyl)-amino]-biphenyl-4-sulfonylamino}-butyric acid;
(S)-2-{4'-[(4-Isopropoxy-3-methyl-benzofuran-2-carbonyl)-amino]-biphenyl-4-sulfonylamino}-3-methyl-butyric acid;
(S)-3-Methyl-2-{4'-[(3-methyl-4-phenyl-benzofuran-2-carbonyl)-amino]-biphenyl-4-sulfonylamino}-butyric acid;
(S)-3-Methyl-2-(4'-{[3-methyl-4-(3-nitro-phenyl)-benzofuran-2-carbonyl]-amino}-biphenyl-4-sulfonylamino)-butyric acid;
(S)-2-{4'-[(5-Chloro-4-isopropoxy-3-methyl-benzofuran-2-carbonyl)-amino]-biphenyl-4-sulfonylamino}-3-methyl-butyric acid;
(S)-2-{4'-[(5-Chloro-4-methoxy-3-methyl-benzofuran-2-carbonyl)-amino]-biphenyl-4-sulfonylamino}-3-methyl-butyric acid;
(S)-2-{4'-[(5,7-Dichloro-4-methoxy-3-methyl-benzofuran-2-carbonyl)-amino]-biphenyl-4-sulfonylamino}-3-methyl-butyric acid;
(S)-2-{4'-[(5-bromo-4-methoxy-3-methyl-benzofuran-2-carbonyl)-amino]-biphenyl-4-sulfonylamino}-3-methyl-butyric acid;
(R)-2-{4'-[(5-Bromo-4-methoxy-3-methyl-benzofuran-2-carbonyl)-amino]-biphenyl-4-sulfonylamino}-3-methyl-butyric acid;
(S)-2-{4'-[(5-Iodo-4-methoxy-3-methyl-benzofuran-2-carbonyl)-amino]-biphenyl-4-sulfonylamino}-3-methyl-butyric acid;
(S)-2-{4'-[(5-Acetyl-4-methoxy-3-methyl-benzofuran-2-carbonyl)-amino]-biphenyl-4-sulfonylamino}-3-methyl-butyric acid;
S)-2-(4'-{[5-(1-Chloro-vinyl)-4-methoxy-3-methyl-benzofuran-2-carbonyl]-amino}-biphenyl-4-sulfonylamino)-3-methyl-butyric acid;
(S)-2-{4'-[(5-Acetyl-4-hydroxy-3-methyl-benzofuran-2-carbonyl)-amino]-biphenyl-4-sulfonylamino}-3-methyl-butyric acid;
(S)-2-{4'-[(5-Cyano-4-methoxy-3-methyl-benzofuran-2-carbonyl)-amino]-biphenyl-4-sulfonylamino}-3-methyl-butyric acid;

(S)-2-{4'-[(5-Methyl-4-methoxy-3-methyl-benzofuran-2-carbonyl)-amino]-biphenyl-4-sulfonylamino}-3-methyl-butyric acid;
(S)-2-{4'-[(5-Hydroxymethyl-4-methoxy-3-methyl-benzofuran-2-carbonyl)-amino]-biphenyl-4-sulfonylamino}-3-methyl-butyric acid;
D-3-Methyl-benzofuran-2-carboxylic acid 4'-(1-carboxy-2-methyl-propylsulfamoyl)-3,5-dimethyl-biphenyl-4-yl ester;
D-Benzofuran-2-carboxylic acid 4'-(1-carboxy-2-methyl-propylsulfamoyl)-3,5-dimethyl-biphenyl-4-yl ester;
D-3-Methyl-benzofuran-2-carboxylic acid 4'-(1-carboxy-2-methyl-propylsulfamoyl)-biphenyl-4-yl ester;
Benzofuran-2-carboxylic acid 4'-(1-carboxy-2-methyl-propylsulfamoyl)-biphenyl-4-yl ester;
D-2-[4'-(5-Bromo-4-methoxy-3-methyl-benzofuran-2-ylmethoxy)-biphenyl-4-sulfonylamino]-3-methyl-butyricacid;
D-3-Methyl-2-[4'-(3-methyl-benzofuran-2-ylmethoxy)-biphenyl-4-sulfonylamino]-butyric acid;
D-2-[4'-(Benzofuran-2-ylmethoxy)-3'-methoxy-biphenyl-4-sulfonylamino]-3-methyl-butyric acid;
D-2-[4'-(Benzofuran-2-ylmethoxy)-biphenyl-4-sulfonylamino]-3-methyl-butyric acid;
L-2-[4'-(5-Chloro-4-methoxy-3-methyl benzofuran-2-ylmethoxy)-biphenyl-4-sulfonylamino]-3-methyl butyric acid;
L-2-[4'-(5-Cyano-4-methoxy-3-methyl benzofuran-2-ylmethoxy)-biphenyl-4-sulfonylamino]-3-methyl butyric acid;
L-2-[4'-(4-Ethyl-3-methyl benzofuran-2-ylmethoxy)-biphenyl-4-sulfonylamino]-3-methyl butyric acid;
N-[(4'-{[4-(3-methoxypropyl)-3-methyl-1-benzofuran-2-yl]methoxyl-}-1,1'-biphenyl-4-yl)sulfonyl]-L-valine;
N-({4'-[(5-Bromo-4-methoxy-3-methyl-1-benzofuran-2-yl)methoxy]-1,1'-biphenyl-4-yl}sulfonyl)-L-valine;
N-({4'-[(5-Bromo-4-isopropoxy-3-methyl-1-benzofuran-2-yl)methoxy]-1,1'-biphenyl-4-yl}sulfonyl)-D-valine;
N-[(4'-{[(5-bromo-4-methoxy-3-methyl-1-benzofuran-2-yl)methyl]amino}-1,1'-biphenyl-4-yl)sulfonyl]-L-valine;
L-3-Methyl-2-{4'-[(3-methyl-4-phenoxy-benzofuran-2-carbonyl)-amino]-biphenyl-4-sulfonylamino}-butyric acid;
L-2-(4'-{[4-(1-Methoxycarbonyl-1-methyl-ethoxy)-3-methyl-benzofuran-2-carbonyl]-amino}-biphenyl-4-sulfonylamino)-3-methyl-butyric acid;
L-2-{4'-[(4-Ethoxycarbonylmethoxy-3-methyl-benzofuran-2-carbonyl)-amino]-biphenyl-4-sulfonylamino}-3-methyl-butyric acid;
L-2-{4'-[(4-Methoxycarbonylmethoxy-3-methyl-benzofuran-2-carbonyl)-amino]-biphenyl-4-sulfonylamino}-3-methyl-butyric acid;
L-2-{4'-[(4-Carboxymethoxy-3-methyl-benzofuran-2-carbonyl)-amino]-biphenyl-4-sulfonylamino}-3-methyl-butyric acid;
L-2-{4'-[(4-Hydroxy-3-methyl-benzofuran-2-carbonyl)-amino]-biphenyl-4-sulfonylamino}-3-methyl-butyric acid;
D-2-[4'-(Benzofuran-2-sulfonylmethyl)-biphenyl-4-sulfonylamino]-3-methyl-butyric acid;
D-2-[4'-(Benzofuran-2-sulfinylmethyl)-biphenyl-4-sulfonylamino]-3-methyl-butyric acid;
(S)-2-{4'-[(4-Dimethylcarbamoylmethoxy-3-methyl-benzofuran-2-carbonyl)-amino]-biphenyl-4-sulfonylamino}-3-methyl-butyric acid;
(S)-2-(4'-{[4-(2-tert-Butoxycarbonylamino-ethoxy)-3-methyl-benzofuran-2-carbonyl]-amino}-biphenyl-4-sulfonylamino)-3-methyl-butyric acid;
(S)-2-{4'-[(4-Carbamoylmethoxy-3-methyl-benzofuran-2-carbonyl)-amino]-biphenyl-4-sulfonylamino}-3-methyl-butyric acid;
(S)-2-(4'-{[4-(2-Amino-ethoxy)-3-methyl-benzofuran-2-carbonyl]-amino}-biphenyl-4-sulfonylamino)-3-methyl-butyric acid;
(S)-2-(4'-{[4-(2-Dimethylamino-ethoxy)-3-methyl-benzofuran-2-carbonyl]-amino}-biphenyl-4-sulfonylamino)-3-methyl-butyric acid;
N-[(4'-{[(5-Chloro-1-benzofuran-2-yl)carbonyl]amino}-1,1'-biphenyl-4-yl)sulfonyl]-L-valine;
N-({4'-[(1-Benzofuran-2-ylcarbonyl)amino]-1,1'-biphenyl-4-yl}sulfonyl)-D-alanine;
N-({4'-[(1-Benzofuran-2-ylcarbonyl)amino]-1,1'-biphenyl-4-yl}sulfonyl)-L-valine;
N-({4'-[(1-Benzofuran-2-ylcarbonyl)amino]-1,1'-biphenyl-4-yl}sulfonyl)-D-valine;
N-({4'-[(1-Benzofuran-2-ylcarbonyl)amino]-1,1'-biphenyl-4-yl}sulfonyl)-L-norvaline;
N-({4'-[(1-Benzofuran-2-ylcarbonyl)amino]-1,1'-biphenyl-4-yl}sulfonyl)-D-norvaline;
N-({4'-[(1-Benzofuran-2-ylcarbonyl)amino]-1,1'-biphenyl-4-yl}sulfonyl)-L-aspartic acid;
N-({4'-[(1-Benzofuran-2-ylcarbonyl)amino]-1,1'-biphenyl-4-yl}sulfonyl)-D-aspartic acid;
N-2-({4'-[(1-Benzofuran-2-ylcarbonyl)amino]-1,1'-biphenyl-4-yl}sulfonyl)-L-glutamine;
N~2~-({4'-[(1-Benzofuran-2-ylcarbonyl)amino]-1,1'-biphenyl-4-yl}sulfonyl)-D-glutamine;
N-({4'-[(1-Benzofuran-2-ylcarbonyl)amino]-1,1'-biphenyl-4-yl}sulfonyl)-L-isoleucine;
N-({4'-[(1-Benzofuran-2-ylcarbonyl)amino]-1,1'-biphenyl-4-yl}sulfonyl)-D-isoleucine;
N-({4'-[(1-Benzofuran-2-ylcarbonyl)amino]-1,1'-biphenyl-4-yl}sulfonyl)-L-leucine;
N-({4'-[(1-Benzofuran-2-ylcarbonyl)amino]-1,1'-biphenyl-4-yl}sulfonyl)-D-leucine;
N-({4'-[(1-Benzofuran-2-ylcarbonyl)amino]-1,1'-biphenyl-4-yl}sulfonyl)-L-norleucine;
N-({4'-[(1-Benzofuran-2-ylcarbonyl)amino]-1,1'-biphenyl-4-yl}sulfonyl)-D-norleucine;
N-({4'-[(1-Benzofuran-2-ylcarbonyl)amino]-1,1'-biphenyl-4-yl}sulfonyl)-L-phenylalanine;
N-({4'-[(1-Benzofuran-2-ylcarbonyl)amino]-1,1'-biphenyl-4-yl}sulfonyl)-D-phenylalanine;
N-({4'-[(1-Benzofuran-2-ylcarbonyl)amino]-1,1'-biphenyl-4-yl}sulfonyl)-N-methylglycine;
N-({4'-[(1-Benzofuran-2-ylcarbonyl)amino]-1,1'-biphenyl-4-yl}sulfonyl)-2-methylalanine;
N-({4'-[(1-Benzofuran-2-ylcarbonyl)amino]-1,1'-biphenyl-4-yl}sulfonyl)-N-methyl-L-alanine;
1-[({4'-[(1-Benzofuran-2-ylcarbonyl)amino]-1,1'-biphenyl-4-yl}sulfonyl)amino]cyclopentanecarboxylic acid;
N-({4'-[(1-Benzofuran-2-ylcarbonyl)amino]-1,1'-biphenyl-4-yl}sulfonyl)-N-methylvaline;
N-({4'-[(1-Benzofuran-2-ylcarbonyl)amino]-1,1'-biphenyl-4-yl}sulfonyl)-3-methyl-L-valine;
N-({4'-[(1-Benzofuran-2-ylcarbonyl)amino]-1,1'-biphenyl-4-yl}sulfonyl)-2-methylleucine;
N-({4'-[(1-Benzofuran-2-ylcarbonyl)amino]-1,1'-biphenyl-4-yl}sulfonyl)-D-glutamic acid;
(2R)-[({4'-[(1-Benzofuran-2-ylcarbonyl)amino]-1,1'-biphenyl-4-yl}sulfonyl)amino](phenyl)acetic acid;

(2S)-2-[({4'-[(1-Benzofuran-2-ylcarbonyl)amino]-1,1'-biphenyl-4-yl}sulfonyl)amino]-5-methoxy-5-oxopentanoic acid;
3-[({4'-[(1-Benzofuran-2-ylcarbonyl)amino]-1,1'-biphenyl-4-yl}sulfonyl)amino]-3-phenylpropanoic acid;
2-[({4'-[(1-Benzofuran-2-ylcarbonyl)amino]-1,1'-biphenyl-4-yl}sulfonyl)amino]-4-phenylbutanoic acid;
N-({4'-[(1-Benzofuran-2-ylcarbonyl)amino]-1,1'-biphenyl-4-yl}sulfonyl)-L-tyrosine;
N-({4'-[(1-Benzofuran-2-ylcarbonyl)amino]-1,1'-biphenyl-4-yl}sulfonyl)-D-tyrosine;
(2S)-2-[({4'-[(1-Benzofuran-2-ylcarbonyl)amino]-1,1'-biphenyl-4-yl}sulfonyl)amino]-4-tert-butoxy-4-oxobutanoic acid;
(2R)-2-[({4'-[(1-Benzofuran-2-ylcarbonyl)amino]-1,1'-biphenyl-4-yl}sulfonyl)amino]-4-tert-butoxy-4-oxobutanoic acid;
N-({4'-[(1-Benzofuran-2-ylcarbonyl)amino]-1,1'-biphenyl-4-yl}sulfonyl)-O-methyl-L-tyrosine;
N-({4'-[(1-Benzofuran-2-ylcarbonyl)amino]-1,1'-biphenyl-4-yl}sulfonyl)-4-nitro-L-phenylalanine;
N-({4'-[(1-Benzofuran-2-ylcarbonyl)amino]-1,1'-biphenyl-4-yl}sulfonyl)-3-(2-naphthyl)alanine;
N-({4'-[(1-Benzofuran-2-ylcarbonyl)amino]-1,1'-biphenyl-4-yl}sulfonyl)-beta-methylphenylalanine;
N-2-({4'-[(1-Benzofuran-2-ylcarbonyl)amino]-1,1'-biphenyl-4-yl}sulfonyl)-N~5~-phenylglutamine;
N-({4'-[(1-Benzofuran-2-ylcarbonyl)amino]-1,1'-biphenyl-4-yl}sulfonyl)-4,4,4,4',4',4'-hexafluorovaline;
4-Amino-N-({4'-[(1-benzofuran-2-ylcarbonyl)amino]-1,1'-biphenyl-4-yl}sulfonyl)-L-phenylalanine;
(2R)-2-[({4'-[(1-Benzofuran-2-ylcarbonyl)amino]-1,1'-biphenyl-4-yl}sulfonyl)amino]-5-(benzyloxy)-5-oxopentanoic acid; or
N-({4'-[(1-Benzofuran-2-ylcarbonyl)amino]-1,1'-biphenyl-4-yl}sulfonyl)-O-benzyl-L-tyrosine; or
a pharmaceutically acceptable salt thereof.

15. The compound of claim 1 that is
L-2-(4'-{[4-(3-Methoxy-propyl)-3-methyl-benzofuran-2-carbonyl]-amino}-biphenyl-4-sulfonylamino)-3-methyl-butyric acid;
D-2-{4'-[(4-Methanesulfonylamino-3-methyl-benzofuran-2-carbonyl)-amino]-biphenyl-4-sulfonylamino}-3-methyl-butyric acid;
L-2-{4'-[(4-Cyclopropylmethoxy-3-methyl-benzofuran-2-carbonyl)-amino]-biphenyl-4-sulfonylamino}-3-methyl-butyric acid;
L-2-{4'-[(4-Dimethylamino-3-methyl-benzofuran-2-carbonyl)-amino]-biphenyl-4-sulfonylamino}-3-methyl-butyric acid;
L-2-{4'-[(4-Benzenesulfonylamino-3-methyl-benzofuran-2-carbonyl)-amino]-biphenyl-4-sulfonylamino}-3-methyl-butyric acid;
N-[(4'-{[(5-Ethyl-4-methoxy-3-methyl-1-benzofuran-2-yl)carbonyl]amino}-1,1'-biphenyl-4-yl)sulfonyl]-L-valine;
N-[(4'-{[(4-Ethyl-3-methyl-1-benzofuran-2-yl)carbonyl]amino}-1,1'-biphenyl-4-yl)sulfonyl]-L-valine;
N-[(4'-{[(5-Ethyl-4-hydroxy-3-methyl-1-benzofuran-2-yl)carbonyl]amino}-1,1'-biphenyl-4-yl)sulfonyl]-L-valine;
N-[(4'-{[(3,4-Dimethyl-1-benzofuran-2-yl)carbonyl]amino}-1,1'-biphenyl-4-yl)sulfonyl]-L-valine;
N-[(4'-{[(4-Acetyl-3-methyl-1-benzofuran-2-yl)carbonyl]amino}-1,1'-biphenyl-4-yl)sulfonyl]-L-valine;
N-{[4'-({[4-(1-Hydroxyethyl)-3-methyl-1-benzofuran-2-yl]carbonyl}amino)-1,1'-biphenyl-4-yl]sulfonyl}-L-valine;
N-[(4'-{[(3-methyl-4-vinyl-1-benzofuran-2-yl)carbonyl]amino}-1,1'-biphenyl-4-yl)sulfonyl]-L-valine;
N-{[4'-({[4-(methoxymethyl)-3-methyl-1-benzofuran-2-yl]carbonyl}amino)-1,1'-biphenyl-4-yl]sulfonyl}-L-valine;
N-{[4'-({[4-(1-methoxyethyl)-3-methyl-1-benzofuran-2-yl]carbonyl}amino)-1,1'-biphenyl-4-yl]sulfonyl}-L-valine;
N-{[4'-({[4-(2-methoxyethyl)-3-methyl-1-benzofuran-2-yl]carbonyl}amino)-1,1'-biphenyl-4-yl]sulfonyl}-L-valinate;
(S)-2-{4'-[(4-ethoxy-3-methyl-benzofuran-2-carbonyl)-amino]-biphenyl-4-sulfonylamino}-3-methyl-butyric acid;
(S)-2-{4'-[(5-Chloro-4-methoxy-3-methyl-benzofuran-2-carbonyl)-amino]-biphenyl-4-sulfonylamino}-3-methyl-butyric acid;
(S)-2-{4'-[(5-bromo-4-methoxy-3-methyl-benzofuran-2-carbonyl)-amino]-biphenyl-4-sulfonylamino}-3-methyl-butyric acid;
(R)-2-{4'-[(5-Bromo-4-methoxy-3-methyl-benzofuran-2-carbonyl)-amino]-biphenyl-4-sulfonylamino}-3-methyl-butyric acid;
(S)-2-{4'-[(5-Iodo-4-methoxy-3-methyl-benzofuran-2-carbonyl)-amino]-biphenyl-4-sulfonylamino}-3-methyl-butyric acid;
(S)-2-{4'-[(5-Cyano-4-methoxy-3-methyl-benzofuran-2-carbonyl)-amino]-biphenyl-4-sulfonylamino}-3-methyl-butyric acid;
(S)-2-{4'-[(5-Methyl-4-methoxy-3-methyl-benzofuran-2-carbonyl)-amino]-biphenyl-4-sulfonylamino}-3-methyl-butyric acid;
D-2-[4'-(5-Bromo-4-methoxy-3-methyl-benzofuran-2-ylmethoxy)-biphenyl-4-sulfonylamino]-3-methyl-butyric acid;
L-2-{4'-[(4-Ethoxycarbonylmethoxy-3-methyl-benzofuran-2-carbonyl)-amino]-biphenyl-4-sulfonylamino}-3-methyl-butyric acid;
L-2-{4'-[(4-Carboxymethoxy-3-methyl-benzofuran-2-carbonyl)-amino]-biphenyl-4-sulfonylamino}-3-methyl-butyric acid; or
a pharmaceutically acceptable salt thereof.

16. A composition comprising:
one or more compounds of claim 1; and
one or more pharmaceutically acceptable carriers.

* * * * *